US012480144B2

(12) United States Patent
Zhang et al.

(10) Patent No.: US 12,480,144 B2
(45) Date of Patent: Nov. 25, 2025

(54) CANNABINOID SYNTHASE VARIANTS AND METHODS FOR THEIR USE

(71) Applicant: GENOMATICA, INC., San Diego, CA (US)

(72) Inventors: Deqiang Zhang, San Diego, CA (US); Jamison Parker Huddleston, San Diego, CA (US); Joseph Roy Warner, San Diego, CA (US); Benjamin Matthew Griffin, San Diego, CA (US)

(73) Assignee: CREO INGREDIENTS, INC., Fort Worth, TX (US)

( * ) Notice: Subject to any disclaimer, the term of this patent is extended or adjusted under 35 U.S.C. 154(b) by 371 days.

(21) Appl. No.: 17/995,778

(22) PCT Filed: Apr. 13, 2021

(86) PCT No.: PCT/US2021/027125
§ 371 (c)(1),
(2) Date: Oct. 7, 2022

(87) PCT Pub. No.: WO2021/211611
PCT Pub. Date: Oct. 21, 2021

(65) Prior Publication Data

US 2023/0167468 A1 Jun. 1, 2023

Related U.S. Application Data

(60) Provisional application No. 63/139,171, filed on Jan. 19, 2021, provisional application No. 63/009,573, filed on Apr. 14, 2020.

(51) Int. Cl.

| | |
|---|---|
| ***C12N 9/10*** | (2006.01) |
| ***C12N 9/02*** | (2006.01) |
| ***C12P 7/22*** | (2006.01) |
| ***C12P 7/42*** | (2006.01) |
| ***C12P 17/06*** | (2006.01) |

(52) U.S. Cl.
CPC .............. *C12P 7/42* (2013.01); *C12N 9/0004* (2013.01); *C12P 7/22* (2013.01); *C12P 17/06* (2013.01); *C12Y 121/03007* (2015.07); *C12Y 121/03008* (2015.07)

(58) Field of Classification Search
CPC .... C12P 7/42; C12P 17/06; C12P 7/22; C12N 9/02
See application file for complete search history.

(56) References Cited

U.S. PATENT DOCUMENTS

| | | | | |
|---|---|---|---|---|
| 9,359,625 | B2 | 6/2016 | Winnicki et al. | |
| 9,526,715 | B1 | 12/2016 | Winnicki et al. | |
| 9,657,316 | B2 | 5/2017 | Burgard et al. | |
| 10,081,818 | B2 | 9/2018 | Peet et al. | |
| 11,920,166 | B2 * | 3/2024 | Botsch ................ | C12N 9/0004 |
| 2017/0211049 | A1 | 7/2017 | Page et al. | |

FOREIGN PATENT DOCUMENTS

| | | | |
|---|---|---|---|
| WO | 2018176055 | A2 | 9/2018 |
| WO | 2019/046941 | A1 | 3/2019 |
| WO | 2020069142 | A1 | 4/2020 |

OTHER PUBLICATIONS

Ahmad et al., "Probing protein stability and proteolytic resistance by loop scanning: A comprehensive mutational analysis," Protein Sci 21(3):433-446 (2012).
Allen et al., "Complex Variability within the THCA and CBDA Synthase Genes in *Cannabis* Species," J Forensic Investigation 4(1): 7 (2016).
Baker et al., "The tetrahydrocannabinol and tetrahydrocannabinolic acid content of cannabis products," J Pharm Pharmacol 33(1):369-372 (1981).
Cascini et al., "Highly Predictive Genetic Markers Distinguish Drug-Type from Fiber-Type *Cannabis sativa* L," Plants 8(11):496 (2019).
De Petrocellis et al., "Non-THC cannabinoids inhibit prostate carcinoma growth in vitro and in vivo: pro-apoptotic effects and underlying mechanisms," Br J Pharmacol 168(1):79-102 (2013).
Heard et al., "A General Method for Making Peptide Therapeutics Resistant to Serine Protease Degradation: Application to Dipeptidyl Peptidase IV Substrates," J Med Chem 56(21):8339-8351 (2013).
Kimple et al., "Overview of Affinity Tags for Protein Purification," Curr Protoc Protein Sci 73: Unit-9.9 (2013).

(Continued)

*Primary Examiner* — Tekchand Saidha
(74) *Attorney, Agent, or Firm* — MEDLER FERRO WOODHOUSE & MILLS PLLC

(57) ABSTRACT

The invention relates to a non-natural cannabinoid synthase comprising at least one amino acid variation as compared to a wild type cannabinoid synthase Δ9-tetrahydrocannabinolic acid synthase (THCAS), comprising three alpha helices (αA, αB and αC) where a disulfide bond is not formed between alpha helix αA and alpha helix αC, wherein the non-natural cannabinoid synthase catalyzes the oxidative cyclization of cannabigerolic acid (CBGA) into a cannabinoid. The invention further relates to a non-natural $\Delta^9$-tetrahydrocannabinolic acid synthase (THCAS), a non-natural cannabidiolic acid synthase (CBDAS), and a non-natural cannabichromenic acid synthase (CBCAS) comprising at least one amino acid variation as compared to a wild type THCAS, CBDAS, or CBCAS, respectively, comprising three alpha helices (αA, αB and αC) and wherein a disulfide bond is not formed between alpha helix αA and alpha helix αC. The invention also relates to a nucleic acid, expression construct, and engineered cell for making the non-natural THCAS, CBDAS, and/or CBCAS. Also provided are compositions comprising the non-natural THCAS, CBDAS, and/or CBCAS; isolated non-natural THCAS, CBDAS, and/or CBCAS enzymes; methods of making the isolated enzymes; cell extracts comprising cannabinoids; and methods of making cannabinoids.

15 Claims, 8 Drawing Sheets

Specification includes a Sequence Listing.

(56) References Cited

OTHER PUBLICATIONS

Laverty et al., "A physical and genetic map of *Cannabis sativa* identifies extensive rearrangements at the THC/CBD acid synthase loci," Genome Res 29(1): 146-156 (2019).
McPartland et al., "Affinity and Efficacy Studies of Tetrahydrocannabinolic Acid A at Cannabinoid Receptor Types One and Two," *Cannabis Cannabinoid Res* 2(1):87-95 (2017).
Moldzio et al., "Effects of cannabinoids Δ(9)-tetrahydrocannabinol, Δ(9)-tetrahydrocannabinolic acid and cannabidiol in MPP+ affected murine mesencephalic cultures," Phytomedicine 19:819-824 (2012).
Ruhaak et al., "Evaluation of the cyclooxygenase inhibiting effects of six major cannabinoids isolated from *Cannabis sativa*," Biol Pharm Bull 34(5):774-778 (2011).
Shoyama et al., "Structure and function of Δ1-tetrahydrocannabinolic acid (THCA) synthase, the enzyme controlling the psychoactivity of *Cannabis sativa*," J Mol Biol 423:96-105 (2012).
Sirikantaramas et al., "The gene controlling marijuana psychoactivity: molecular cloning and heterologous expression of Delta1-tetrahydrocannabinolic acid synthase from *Cannabis sativa* L," J Biol Chem 279:39767-39774 (2004).
Taura et al., "First direct evidence for the mechanism of .DELTA. 1-tetrahydrocannabinolic acid biosynthesis," J Am Chem Soc 117:9766-9767 (1995).
Taura et al., "Purification and Characterization of Cannabidiolic-acid Synthase from *Cannabis sativa* L.," J Biol Chem 271:17411-17416 (1996).
Taura et al., "Cannabidiolic-acid synthase, the chemotype-determining enzyme in the fiber-type *Cannabis sativa*," FEBS Lett 581(16): 2929-2934 (2007).
Verhoeckx et al., "Unheated Cannabis sativa extracts and its major compound THC-acid have potential immuno-modulating properties not mediated by CB1 and CB2 receptor coupled pathways," Int Immunopharmacol 6(4):656-665 (2006).
Yang et al., "Structural basis for olivetolic acid formation by apolyketide cyclase from*Cannabis sativa*," FEBS J 283(6):1088-1106 (2016).
Zager et al., "Gene Networks Underlying Cannabinoid and Terpenoid Accumulation in Cannabis," Plant Physiol 180: 1877-1897 (2019).
International Search Report and Written Opinion issued in PCT/US2021/027125, dated Aug. 17, 2021.
El Alaoui et al., "Affinity comparison of different THCA synthase to CBGA using modeling computational approaches," Bioinformation 10(1):033-038 (2014).
Shoyama et al., "Structure and Function of delta1-Tetrahydrocannabinolic Acid (THCA) Synthase, the Enzyme Controlling the Psychoactivity of *Cannabis sativa*," Journal of Molecular Biology 423:96-105 (2012).
Zirpel et al., "Elucidation of structure-function relationship of THCA and CBDA synthase from *Cannabis sativa* L.," Journal of Biotechnology 284:17-26 (2018).
De Marco et al., "Strategies for successful recombinant expression of disulfide bond-dependent proteins in *Escherichia coli*," Microbial Cell Factories 8:26 (2009).

* cited by examiner

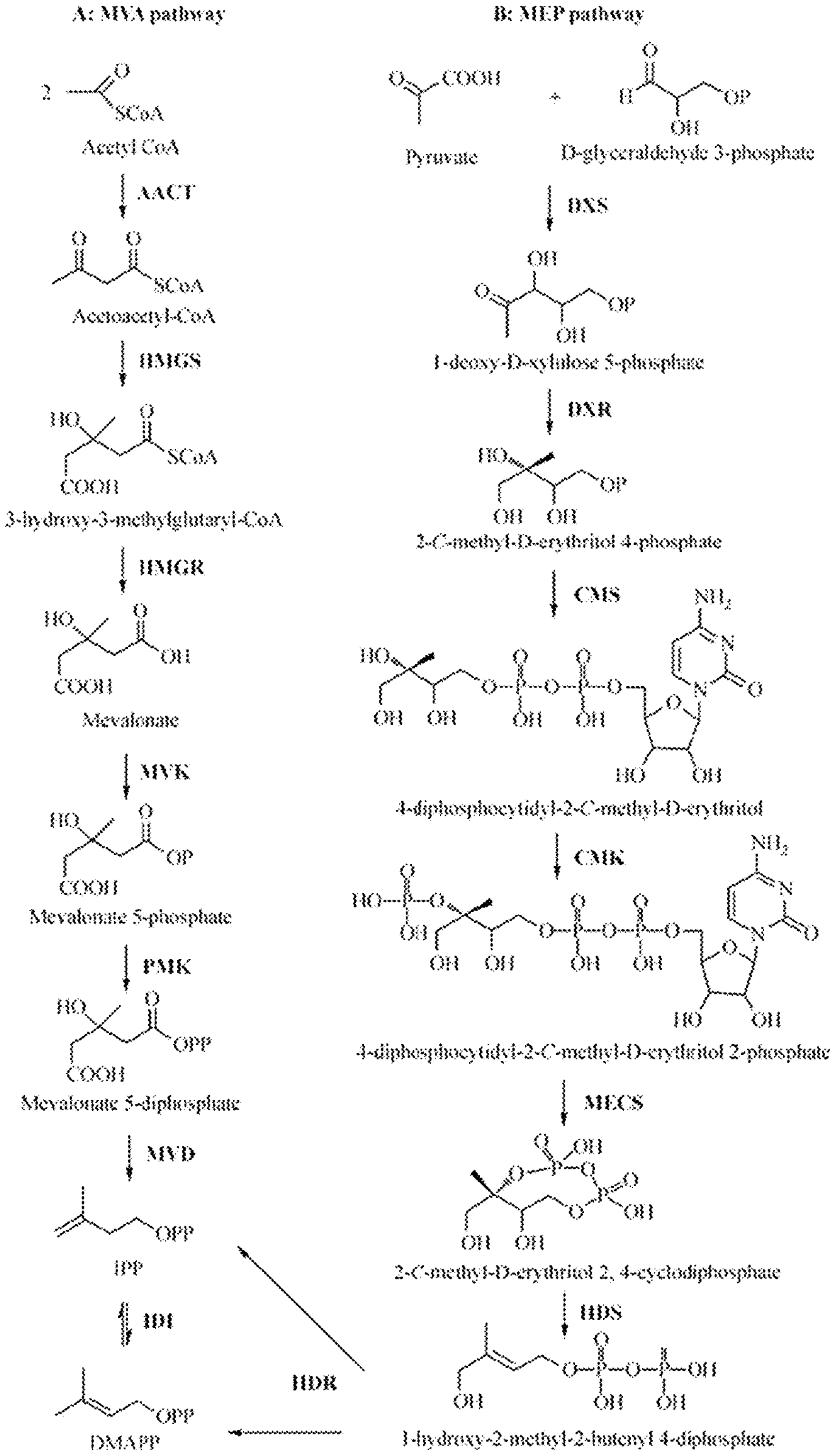

Acetyl CoA
Acetoacetyl-CoA
3-hydroxy-3-methylglutaryl-CoA
Mevalonate
Mevalonate 5-phosphate
Mevalonate 5-diphosphate
IPP
DMAPP
Pyruvate
D-glyceraldehyde 3-phosphate
1-deoxy-D-xylulose 5-phosphate
2-C-methyl-D-erythritol 4-phosphate
4-diphosphocytidyl-2-C-methyl-D-erythritol
4-diphosphocytidyl-2-C-methyl-D-erythritol 2-phosphate
2-C-methyl-D-erythritol 2, 4-cyclodiphosphate
1-hydroxy-2-methyl-2-butenyl 4-diphosphate

FIG. 8

```
1                                                          50
 SEQ1  ---------- ---------- ------MANP RENFLKCFSK HIPNNVANPK
 SEQ2  MNCSAFSFWF VCKIIFFFLS FHIQISIANP RENFLKCFSK HIPNNVANPK
SEQ78  ---------- ---------- -------ANP RENFLKCFSQ YIPNNATNLK
SEQ79  MKCSTFSFWF VCKIIFFFFS FNIQTSIANP RENFLKCFSQ YIPNNATNLK
SEQ80  ---------- ---------- -------ANP QENFLKCFSE YIPNNPANPK
SEQ81  MNCSTFSFWF VCKIIFFFLS FNIQISIANP QENFLKCFSE YIPNNPANPK
SEQ82  ---------- ---------- -------ANP RENFLKCFSK HIPNNVANPK
SEQ83  ---------- ---------- ------MANP RENFLKCFSQ YIPNNATNLK
SEQ84  ---------- ---------- ------MANP QENFLKCFSE YIPNNPANPK

       51                                                 100
 SEQ1  LVYTQHDQLY MSILNSTIQN LRFISDTTPK PLVIVTPSNN SHIQATILCS
 SEQ2  LVYTQHDQLY MSILNSTIQN LRFISDTTPK PLVIVTPSNN SHIQATILCS
SEQ78  LVYTQNNPLY MSVLNSTIHN LRFTSDTTPK PLVIVTPSHV SHIQGTILCS
SEQ79  LVYTQNNPLY MSVLNSTIHN LRFTSDTTPK PLVIVTPSHV SHIQGTILCS
SEQ80  FIYTQHDQLY MSVLNSTIQN LRFTSDTTPK PLVIVTPSNV SHIQASILCS
SEQ81  FIYTQHDQLY MSVLNSTIQN LRFTSDTTPK PLVIVTPSNV SHIQASILCS
SEQ82  LVYTQHDQLY MSILNSTIQN LRFISDTTPK PLVIVTPSNN SHIQATILCS
SEQ83  LVYTQNNPLY MSVLNSTIHN LRFTSDTTPK PLVIVTPSHV SHIQGTILCS
SEQ84  FIYTQHDQLY MSVLNSTIQN LRFTSDTTPK PLVIVTPSNV SHIQASILCS

       101                                                150
 SEQ1  KKVGLQIRTR SGGHDAEGMS YISQVPFVVV DLRNMHSIKI DVHSQTAWVE
 SEQ2  KKVGLQIRTR SGGHDAEGMS YISQVPFVVV DLRNMHSIKI DVHSQTAWVE
SEQ78  KKVGLQIRTR SGGHDSEGMS YISQVPFVIV DLRNMRSIKI DVHSQTAWVE
SEQ79  KKVGLQIRTR SGGHDSEGMS YISQVPFVIV DLRNMRSIKI DVHSQTAWVE
SEQ80  KKVGLQIRTR SGGHDAEGLS YISQVPFAIV DLRNMHTVKV DIHSQTAWVE
SEQ81  KKVGLQIRTR SGGHDAEGLS YISQVPFAIV DLRNMHTVKV DIHSQTAWVE
SEQ82  KKVGLQIRTR SGGHDAEGMS YISQVPFVVV DLRNMHSIKI DVHSQTAWVE
SEQ83  KKVGLQIRTR SGGHDSEGMS YISQVPFVIV DLRNMRSIKI DVHSQTAWVE
SEQ84  KKVGLQIRTR SGGHDAEGLS YISQVPFAIV DLRNMHTVKV DIHSQTAWVE

       151                                                200
 SEQ1  AGATLGEVYY WINEKNENLS FPGGYCPTVG VGGHFSGGGY GALMRNYGLA
 SEQ2  AGATLGEVYY WINEKNENLS FPGGYCPTVG VGGHFSGGGY GALMRNYGLA
SEQ78  AGATLGEVYY WVNEKNENLS LAAGYCPTVC AGGHFGGGGY GPLMRNYGLA
SEQ79  AGATLGEVYY WVNEKNENLS LAAGYCPTVC AGGHFGGGGY GPLMRNYGLA
SEQ80  AGATLGEVYY WINEMNENFS FPGGYCPTVG VGGHFSGGGY GALMRNYGLA
SEQ81  AGATLGEVYY WINEMNENFS FPGGYCPTVG VGGHFSGGGY GALMRNYGLA
SEQ82  AGATLGEVYY WINEKNENLS FPGGYCPTVG VGGHFSGGGY GALMRNYGLA
SEQ83  AGATLGEVYY WVNEKNENLS LAAGYCPTVC AGGHFGGGGY GPLMRNYGLA
SEQ84  AGATLGEVYY WINEMNENFS FPGGYCPTVG VGGHFSGGGY GALMRNYGLA

       201                                                250
 SEQ1  ADNIIDAHLV NVDGKVLDRK SMGEDLFWAI RGGGGENFGI IAAWKIKLVA
 SEQ2  ADNIIDAHLV NVDGKVLDRK SMGEDLFWAI RGGGGENFGI IAAWKIKLVD
SEQ78  ADNIIDAHLV NVHGKVLDRK SMGEDLFWAL RGGGAESFGI IVAWKIRLVA
SEQ79  ADNIIDAHLV NVHGKVLDRK SMGEDLFWAL RGGGAESFGI IVAWKIRLVA
SEQ80  ADNIIDAHLV NVDGKVLDRK SMGEDLFWAI RGGGGENFGI IAACKIKLVV
SEQ81  ADNIIDAHLV NVDGKVLDRK SMGEDLFWAI RGGGGENFGI IAACKIKLVV
SEQ82  ADNIIDAHLV NVDGKVLDRK SMGEDLFWAI RGGGGENFGI IAAWKIKLVA
SEQ83  ADNIIDAHLV NVHGKVLDRK SMGEDLFWAL RGGGAESFGI IVAWKIRLVA
SEQ84  ADNIIDAHLV NVDGKVLDRK SMGEDLFWAI RGGGGENFGI IAACKIKLVV
```

FIG. 11A

| | | | | | |
|---|---|---|---|---|---|
| 251 | | | | | 300 |
| SEQ1 | VPSKSTIFSV | KKNMEIHGLV | KLFNKWQNIA | YKYDKDLVLM | THFITKNITD |
| SEQ2 | VPSKSTIFSV | KKNMEIHGLV | KLFNKWQNIA | YKYDKDLVLM | THFITKNITD |
| SEQ78 | VP-KSTMFSV | KKIMEIHELV | KLVNKWQNIA | YKYDKDLLLM | THFITRNITD |
| SEQ79 | VP-KSTMFSV | KKIMEIHELV | KLVNKWQNIA | YKYDKDLLLM | THFITRNITD |
| SEQ80 | VPSKATIFSV | KKNMEIHGLV | KLFNKWQNIA | YKYDKDLMLT | THFRTRNITD |
| SEQ81 | VPSKATIFSV | KKNMEIHGLV | KLFNKWQNIA | YKYDKDLMLT | THFRTRNITD |
| SEQ82 | VPSKSTIFSV | KKNMEIHGLV | KLFNKWQNIA | YKYDKDLVLM | THFITKNITD |
| SEQ83 | VP-KSTMFSV | KKIMEIHELV | KLVNKWQNIA | YKYDKDLLLM | THFITRNITD |
| SEQ84 | VPSKATIFSV | KKNMEIHGLV | KLFNKWQNIA | YKYDKDLMLT | THFRTRNITD |

| | | | | | |
|---|---|---|---|---|---|
| | 301 | | | | 350 |
| SEQ1 | NHGKNKTTVH | GYFSSIFHGG | VDSLVDLMNK | SFPELGIKKT | DCKEFSWIDT |
| SEQ2 | NHGKNKTTVH | GYFSSIFHGG | VDSLVDLMNK | SFPELGIKKT | DCKEFSWIDT |
| SEQ78 | NQGKNKTAIH | TYFSSVFLGG | VDSLVDLMNK | SFPELGIKKT | DCRQLSWIDT |
| SEQ79 | NQGKNKTAIH | TYFSSVFLGG | VDSLVDLMNK | SFPELGIKKT | DCRQLSWIDT |
| SEQ80 | NHGKNKTTVH | GYFSSIFLGG | VDSLVDLMNK | SFPELGIKKT | DCKELSWIDT |
| SEQ81 | NHGKNKTTVH | GYFSSIFLGG | VDSLVDLMNK | SFPELGIKKT | DCKELSWIDT |
| SEQ82 | NHGKNKTTVH | GYFSSIFHGG | VDSLVDLMNK | SFPELGIKKT | DCKEFSWIDT |
| SEQ83 | NQGKNKTAIH | TYFSSVFLGG | VDSLVDLMNK | SFPELGIKKT | DCRQLSWIDT |
| SEQ84 | NHGKNKTTVH | GYFSSIFLGG | VDSLVDLMNK | SFPELGIKKT | DCKELSWIDT |

| | | | | | |
|---|---|---|---|---|---|
| | 351 | | | | 400 |
| SEQ1 | TIFYSGVVNF | NTANFKKEIL | LDRSAGKKTA | FSIKLDYVKK | PIPETAMVKI |
| SEQ2 | TIFYSGVVNF | NTANFKKEIL | LDRSAGKKTA | FSIKLDYVKK | PIPETAMVKI |
| SEQ78 | IIFYSGVVNY | DTDNFNKEIL | LDRSAGQNGA | FKIKLDYVKK | PIPESVFVQI |
| SEQ79 | IIFYSGVVNY | DTDNFNKEIL | LDRSAGQNGA | FKIKLDYVKK | PIPESVFVQI |
| SEQ80 | TIFYSGVVNY | NTANFKKEIL | LDRSAGKKTA | FSIKLDYVKK | LIPETAMVKI |
| SEQ81 | TIFYSGVVNY | NTANFKKEIL | LDRSAGKKTA | FSIKLDYVKK | LIPETAMVKI |
| SEQ82 | TIFYSGVVNF | NTANFKKEIL | LDRSAGKKTA | FSIKLDYVKK | PIPETAMVKI |
| SEQ83 | IIFYSGVVNY | DTDNFNKEIL | LDRSAGQNGA | FKIKLDYVKK | PIPESVFVQI |
| SEQ84 | TIFYSGVVNY | NTANFKKEIL | LDRSAGKKTA | FSIKLDYVKK | LIPETAMVKI |

| | | | | | |
|---|---|---|---|---|---|
| | 401 | | | | 450 |
| SEQ1 | LEKLYEEDVG | AGMYVLYPYG | GIMEEISESA | IPFPHRAGIM | YELWYTASWE |
| SEQ2 | LEKLYEEDVG | AGMYVLYPYG | GIMEEISESA | IPFPHRAGIM | YELWYTASWE |
| SEQ78 | LEKLYEEDIG | AGMYALYPYG | GIMDEISESA | IPFPHRAGIL | YELWYICSWE |
| SEQ79 | LEKLYEEDIG | AGMYALYPYG | GIMDEISESA | IPFPHRAGIL | YELWYICSWE |
| SEQ80 | LEKLYEEEVG | VGMYVLYPYG | GIMDEISESA | IPFPHRAGIM | YELWYTATWE |
| SEQ81 | LEKLYEEEVG | VGMYVLYPYG | GIMDEISESA | IPFPHRAGIM | YELWYTATWE |
| SEQ82 | LEKLYEEDVG | AGMYVLYPYG | GIMEEISESA | IPFPHRAGIM | YELWYTASWE |
| SEQ83 | LEKLYEEDIG | AGMYALYPYG | GIMDEISESA | IPFPHRAGIL | YELWYICSWE |
| SEQ84 | LEKLYEEEVG | VGMYVLYPYG | GIMDEISESA | IPFPHRAGIM | YELWYTATWE |

| | | | | | |
|---|---|---|---|---|---|
| | 451 | | | | 500 |
| SEQ1 | KQEDNEKHIN | WVRSVYNFTT | PYVSQNPRLA | YLNYRDLDLG | KTNHASPNNY |
| SEQ2 | KQEDNEKHIN | WVRSVYNFTT | PYVSQNPRLA | YLNYRDLDLG | KTNHASPNNY |
| SEQ78 | KQEDNEKHLN | WIRNIYNFMT | PYVSKNPRLA | YLNYRDLDIG | INDPKNPNNY |
| SEQ79 | KQEDNEKHLN | WIRNIYNFMT | PYVSKNPRLA | YLNYRDLDIG | INDPKNPNNY |
| SEQ80 | KQEDNEKHIN | WVRSVYNFTT | PYVSQNPRLA | YLNYRDLDLG | KTNPESPNNY |
| SEQ81 | KQEDNEKHIN | WVRSVYNFTT | PYVSQNPRLA | YLNYRDLDLG | KTNPESPNNY |
| SEQ82 | KQEDNEKHIN | WVRSVYNFTT | PYVSQNPRLA | YLNYRDLDLG | KTNHASPNNY |
| SEQ83 | KQEDNEKHLN | WIRNIYNFMT | PYVSKNPRLA | YLNYRDLDIG | INDPKNPNNY |
| SEQ84 | KQEDNEKHIN | WVRSVYNFTT | PYVSQNPRLA | YLNYRDLDLG | KTNPESPNNY |

FIG. 11B

| | | | | | | |
|---|---|---|---|---|---|---|
| 501 | | | | | 545 | |
| SEQ1 | TQARIWGEKY | FGKNFNRLVK | VKTKVDPNNF | FRNEQSIPPL | PPHHH | |
| SEQ2 | TQARIWGEKY | FGKNFNRLVK | VKTKVDPNNF | FRNEQSIPPL | PPHHH | |
| SEQ78 | TQARIWGEKY | FGKNFDRLVK | VKTLVDPNNF | FRNEQSIPPL | PRHRH | |
| SEQ79 | TQARIWGEKY | FGKNFDRLVK | VKTLVDPNNF | FRNEQSIPPL | PRHRH | |
| SEQ80 | TQARIWGEKY | FGKNFNRLVK | VKTKADPNNF | FRNEQSIPPL | PPRHH | |
| SEQ81 | TQARIWGEKY | FGKNFNRLVK | VKTKADPNNF | FRNEQSIPPL | PPRHH | |
| SEQ82 | TQARIWGEKY | FGKNFNRLVK | VKTKVDPNNF | FRNEQSIPPL | PPHHH | |
| SEQ83 | TQARIWGEKY | FGKNFDRLVK | VKTLVDPNNF | FRNEQSIPPL | PRHRH | |
| SEQ84 | TQARIWGEKY | FGKNFNRLVK | VKTKADPNNF | FRNEQSIPPL | PPRHH | |

FIG. 11C

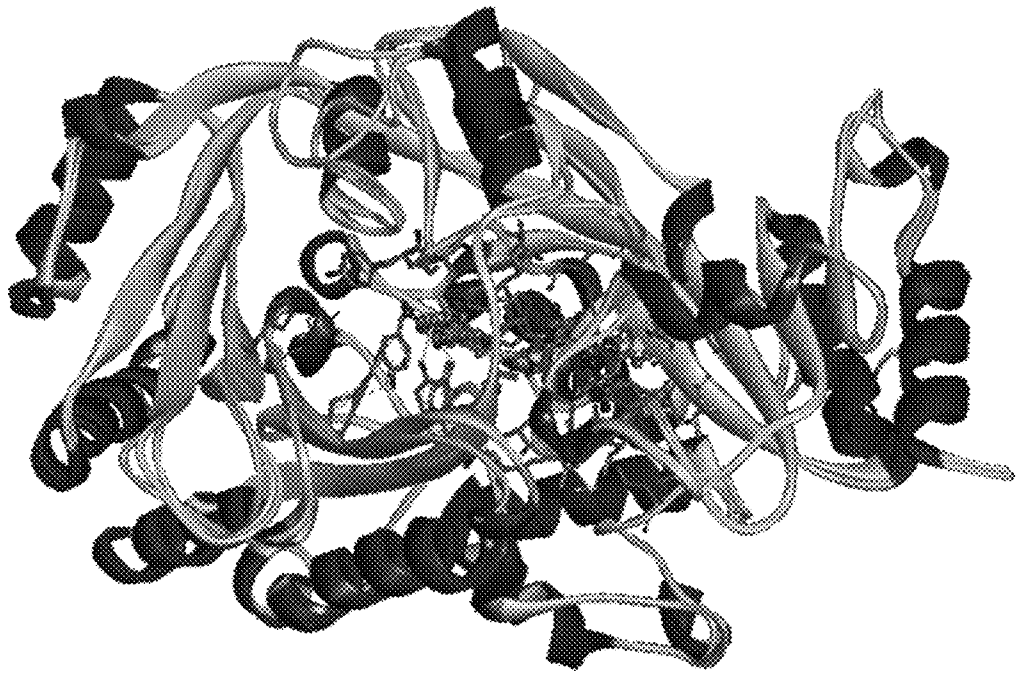

FIG. 12

SEQUENCE LISTING

<160> NUMBER OF SEQ ID NOS: 90

<210> SEQ ID NO 1
<211> LENGTH: 519
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Met Ala Asn Pro Arg Glu Asn Phe Leu Lys Cys Phe Ser Lys His Ile
1 5 10 15

Pro Asn Asn Val Ala Asn Pro Lys Leu Val Tyr Thr Gln His Asp Gln
20 25 30

-continued

```
Leu Tyr Met Ser Ile Leu Asn Ser Thr Ile Gln Asn Leu Arg Phe Ile
        35                  40                  45

Ser Asp Thr Thr Pro Lys Pro Leu Val Ile Val Thr Pro Ser Asn Asn
    50                  55                  60

Ser His Ile Gln Ala Thr Ile Leu Cys Ser Lys Lys Val Gly Leu Gln
65                  70                  75                  80

Ile Arg Thr Arg Ser Gly Gly His Asp Ala Glu Gly Met Ser Tyr Ile
                85                  90                  95

Ser Gln Val Pro Phe Val Val Val Asp Leu Arg Asn Met His Ser Ile
            100                 105                 110

Lys Ile Asp Val His Ser Gln Thr Ala Trp Val Glu Ala Gly Ala Thr
        115                 120                 125

Leu Gly Glu Val Tyr Tyr Trp Ile Asn Glu Lys Asn Glu Asn Leu Ser
    130                 135                 140

Phe Pro Gly Gly Tyr Cys Pro Thr Val Gly Val Gly Gly His Phe Ser
145                 150                 155                 160

Gly Gly Gly Tyr Gly Ala Leu Met Arg Asn Tyr Gly Leu Ala Ala Asp
                165                 170                 175

Asn Ile Ile Asp Ala His Leu Val Asn Val Asp Gly Lys Val Leu Asp
            180                 185                 190

Arg Lys Ser Met Gly Glu Asp Leu Phe Trp Ala Ile Arg Gly Gly Gly
        195                 200                 205

Gly Glu Asn Phe Gly Ile Ile Ala Ala Trp Lys Ile Lys Leu Val Ala
    210                 215                 220

Val Pro Ser Lys Ser Thr Ile Phe Ser Val Lys Lys Asn Met Glu Ile
225                 230                 235                 240

His Gly Leu Val Lys Leu Phe Asn Lys Trp Gln Asn Ile Ala Tyr Lys
                245                 250                 255

Tyr Asp Lys Asp Leu Val Leu Met Thr His Phe Ile Thr Lys Asn Ile
            260                 265                 270

Thr Asp Asn His Gly Lys Asn Lys Thr Thr Val His Gly Tyr Phe Ser
        275                 280                 285

Ser Ile Phe His Gly Gly Val Asp Ser Leu Val Asp Leu Met Asn Lys
    290                 295                 300

Ser Phe Pro Glu Leu Gly Ile Lys Lys Thr Asp Cys Lys Glu Phe Ser
305                 310                 315                 320

Trp Ile Asp Thr Thr Ile Phe Tyr Ser Gly Val Val Asn Phe Asn Thr
                325                 330                 335

Ala Asn Phe Lys Lys Glu Ile Leu Leu Asp Arg Ser Ala Gly Lys Lys
            340                 345                 350

Thr Ala Phe Ser Ile Lys Leu Asp Tyr Val Lys Lys Pro Ile Pro Glu
        355                 360                 365

Thr Ala Met Val Lys Ile Leu Glu Lys Leu Tyr Glu Glu Asp Val Gly
    370                 375                 380

Ala Gly Met Tyr Val Leu Tyr Pro Tyr Gly Gly Ile Met Glu Glu Ile
385                 390                 395                 400

Ser Glu Ser Ala Ile Pro Phe Pro His Arg Ala Gly Ile Met Tyr Glu
                405                 410                 415

Leu Trp Tyr Thr Ala Ser Trp Glu Lys Gln Glu Asp Asn Glu Lys His
            420                 425                 430

Ile Asn Trp Val Arg Ser Val Tyr Asn Phe Thr Thr Pro Tyr Val Ser
        435                 440                 445
```

-continued

Gln Asn Pro Arg Leu Ala Tyr Leu Asn Tyr Arg Asp Leu Asp Leu Gly
    450                 455                 460

Lys Thr Asn His Ala Ser Pro Asn Asn Tyr Thr Gln Ala Arg Ile Trp
465                 470                 475                 480

Gly Glu Lys Tyr Phe Gly Lys Asn Phe Asn Arg Leu Val Lys Val Lys
                485                 490                 495

Thr Lys Val Asp Pro Asn Asn Phe Phe Arg Asn Glu Gln Ser Ile Pro
            500                 505                 510

Pro Leu Pro Pro His His His
        515

<210> SEQ ID NO 2
<211> LENGTH: 545
<212> TYPE: PRT
<213> ORGANISM: Cannabis sativa

<400> SEQUENCE: 2

Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala Asn Pro Arg Glu
            20                  25                  30

Asn Phe Leu Lys Cys Phe Ser Lys His Ile Pro Asn Asn Val Ala Asn
        35                  40                  45

Pro Lys Leu Val Tyr Thr Gln His Asp Gln Leu Tyr Met Ser Ile Leu
    50                  55                  60

Asn Ser Thr Ile Gln Asn Leu Arg Phe Ile Ser Asp Thr Thr Pro Lys
65                  70                  75                  80

Pro Leu Val Ile Val Thr Pro Ser Asn Asn Ser His Ile Gln Ala Thr
                85                  90                  95

Ile Leu Cys Ser Lys Lys Val Gly Leu Gln Ile Arg Thr Arg Ser Gly
            100                 105                 110

Gly His Asp Ala Glu Gly Met Ser Tyr Ile Ser Gln Val Pro Phe Val
        115                 120                 125

Val Val Asp Leu Arg Asn Met His Ser Ile Lys Ile Asp Val His Ser
    130                 135                 140

Gln Thr Ala Trp Val Glu Ala Gly Ala Thr Leu Gly Glu Val Tyr Tyr
145                 150                 155                 160

Trp Ile Asn Glu Lys Asn Glu Asn Leu Ser Phe Pro Gly Gly Tyr Cys
                165                 170                 175

Pro Thr Val Gly Val Gly Gly His Phe Ser Gly Gly Gly Tyr Gly Ala
            180                 185                 190

Leu Met Arg Asn Tyr Gly Leu Ala Ala Asp Asn Ile Ile Asp Ala His
        195                 200                 205

Leu Val Asn Val Asp Gly Lys Val Leu Asp Arg Lys Ser Met Gly Glu
    210                 215                 220

Asp Leu Phe Trp Ala Ile Arg Gly Gly Gly Gly Glu Asn Phe Gly Ile
225                 230                 235                 240

Ile Ala Ala Trp Lys Ile Lys Leu Val Asp Val Pro Ser Lys Ser Thr
                245                 250                 255

Ile Phe Ser Val Lys Lys Asn Met Glu Ile His Gly Leu Val Lys Leu
            260                 265                 270

Phe Asn Lys Trp Gln Asn Ile Ala Tyr Lys Tyr Asp Lys Asp Leu Val
        275                 280                 285

Leu Met Thr His Phe Ile Thr Lys Asn Ile Thr Asp Asn His Gly Lys
    290                 295                 300

Asn Lys Thr Thr Val His Gly Tyr Phe Ser Ser Ile Phe His Gly Gly
305 310 315 320

Val Asp Ser Leu Val Asp Leu Met Asn Lys Ser Phe Pro Glu Leu Gly
325 330 335

Ile Lys Lys Thr Asp Cys Lys Glu Phe Ser Trp Ile Asp Thr Thr Ile
340 345 350

Phe Tyr Ser Gly Val Val Asn Phe Asn Thr Ala Asn Phe Lys Lys Glu
355 360 365

Ile Leu Leu Asp Arg Ser Ala Gly Lys Lys Thr Ala Phe Ser Ile Lys
370 375 380

Leu Asp Tyr Val Lys Lys Pro Ile Pro Glu Thr Ala Met Val Lys Ile
385 390 395 400

Leu Glu Lys Leu Tyr Glu Glu Asp Val Gly Ala Gly Met Tyr Val Leu
405 410 415

Tyr Pro Tyr Gly Gly Ile Met Glu Glu Ile Ser Glu Ser Ala Ile Pro
420 425 430

Phe Pro His Arg Ala Gly Ile Met Tyr Glu Leu Trp Tyr Thr Ala Ser
435 440 445

Trp Glu Lys Gln Glu Asp Asn Glu Lys His Ile Asn Trp Val Arg Ser
450 455 460

Val Tyr Asn Phe Thr Thr Pro Tyr Val Ser Gln Asn Pro Arg Leu Ala
465 470 475 480

Tyr Leu Asn Tyr Arg Asp Leu Asp Leu Gly Lys Thr Asn His Ala Ser
485 490 495

Pro Asn Asn Tyr Thr Gln Ala Arg Ile Trp Gly Glu Lys Tyr Phe Gly
500 505 510

Lys Asn Phe Asn Arg Leu Val Lys Val Lys Thr Lys Val Asp Pro Asn
515 520 525

Asn Phe Phe Arg Asn Glu Gln Ser Ile Pro Pro Leu Pro Pro His His
530 535 540

His
545

<210> SEQ ID NO 3
<211> LENGTH: 385
<212> TYPE: PRT
<213> ORGANISM: Cannabis sativa

<400> SEQUENCE: 3

Met Asn His Leu Arg Ala Glu Gly Pro Ala Ser Val Leu Ala Ile Gly
1 5 10 15

Thr Ala Asn Pro Glu Asn Ile Leu Leu Gln Asp Glu Phe Pro Asp Tyr
20 25 30

Tyr Phe Arg Val Thr Lys Ser Glu His Met Thr Gln Leu Lys Glu Lys
35 40 45

Phe Arg Lys Ile Cys Asp Lys Ser Met Ile Arg Lys Arg Asn Cys Phe
50 55 60

Leu Asn Glu Glu His Leu Lys Gln Asn Pro Arg Leu Val Glu His Glu
65 70 75 80

Met Gln Thr Leu Asp Ala Arg Gln Asp Met Leu Val Val Glu Val Pro
85 90 95

Lys Leu Gly Lys Asp Ala Cys Ala Lys Ala Ile Lys Glu Trp Gly Gln
100 105 110

Pro Lys Ser Lys Ile Thr His Leu Ile Phe Thr Ser Ala Ser Thr Thr

```
        115                 120                 125

Asp Met Pro Gly Ala Asp Tyr His Cys Ala Lys Leu Leu Gly Leu Ser
    130                 135                 140

Pro Ser Val Lys Arg Val Met Met Tyr Gln Leu Gly Cys Tyr Gly Gly
145                 150                 155                 160

Gly Thr Val Leu Arg Ile Ala Lys Asp Ile Ala Glu Asn Asn Lys Gly
                165                 170                 175

Ala Arg Val Leu Ala Val Cys Cys Asp Ile Met Ala Cys Leu Phe Arg
            180                 185                 190

Gly Pro Ser Glu Ser Asp Leu Glu Leu Leu Val Gly Gln Ala Ile Phe
        195                 200                 205

Gly Asp Gly Ala Ala Ala Val Ile Val Gly Ala Glu Pro Asp Glu Ser
    210                 215                 220

Val Gly Glu Arg Pro Ile Phe Glu Leu Val Ser Thr Gly Gln Thr Ile
225                 230                 235                 240

Leu Pro Asn Ser Glu Gly Thr Ile Gly Gly His Ile Arg Glu Ala Gly
                245                 250                 255

Leu Ile Phe Asp Leu His Lys Asp Val Pro Met Leu Ile Ser Asn Asn
            260                 265                 270

Ile Glu Lys Cys Leu Ile Glu Ala Phe Thr Pro Ile Gly Ile Ser Asp
        275                 280                 285

Trp Asn Ser Ile Phe Trp Ile Thr His Pro Gly Gly Lys Ala Ile Leu
    290                 295                 300

Asp Lys Val Glu Glu Lys Leu His Leu Lys Ser Asp Lys Phe Val Asp
305                 310                 315                 320

Ser Arg His Val Leu Ser Glu His Gly Asn Met Ser Ser Ser Thr Val
                325                 330                 335

Leu Phe Val Met Asp Glu Leu Arg Lys Arg Ser Leu Glu Glu Gly Lys
            340                 345                 350

Ser Thr Thr Gly Asp Gly Phe Glu Trp Gly Val Leu Phe Gly Phe Gly
        355                 360                 365

Pro Gly Leu Thr Val Glu Arg Val Val Val Arg Ser Val Pro Ile Lys
    370                 375                 380

Tyr
385


<210> SEQ ID NO 4
<211> LENGTH: 101
<212> TYPE: PRT
<213> ORGANISM: Cannabis sativa

<400> SEQUENCE: 4

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Val Asn
            20                  25                  30

Ile Ile Pro Ala Met Lys Asp Val Tyr Trp Gly Lys Asp Val Thr Gln
        35                  40                  45

Lys Asn Lys Glu Glu Gly Tyr Thr His Ile Val Glu Val Thr Phe Glu
    50                  55                  60

Ser Val Glu Thr Ile Gln Asp Tyr Ile Ile His Pro Ala His Val Gly
65                  70                  75                  80

Phe Gly Asp Val Tyr Arg Ser Phe Trp Glu Lys Leu Leu Ile Phe Asp
                85                  90                  95
```

-continued

```
Tyr Thr Pro Arg Lys
            100


<210> SEQ ID NO 5
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Val Lys His Leu Ile Val Leu Lys Phe Lys Glu Asp Ile Thr
1               5                   10                  15

Glu Ala Gln Lys Asp Glu Phe Phe Lys Thr Tyr Val Asn Leu Val Asn
            20                  25                  30

Ile Ile Pro Ala Met Lys Glu Val Tyr Trp Gly Lys Asp Val Thr Ala
        35                  40                  45

Lys Asn Lys Asp Glu Gly Tyr Thr His Ile Val Glu Val Thr Phe Glu
    50                  55                  60

Ser Val Glu Thr Ile Gln Glu Tyr Ile Ser His Pro Ala His Val Gly
65                  70                  75                  80

Phe Gly Asp Val Tyr Arg Ser Phe Trp Glu Lys Leu Leu Ile Phe Asp
                85                  90                  95

Tyr Thr Pro Thr Lys
            100


<210> SEQ ID NO 6
<211> LENGTH: 305
<212> TYPE: PRT
<213> ORGANISM: Cannabis sativa

<400> SEQUENCE: 6

Met Ser Gly Ala Ala Asp Val Glu Arg Val Tyr Ala Ala Met Glu Glu
1               5                   10                  15

Ala Ala Gly Leu Leu Gly Val Thr Cys Ala Arg Glu Lys Ile Tyr Pro
            20                  25                  30

Leu Leu Thr Glu Phe Gln Asp Thr Leu Thr Asp Gly Val Val Val Phe
        35                  40                  45

Ser Met Ala Ser Gly Arg Arg Ser Thr Glu Leu Asp Phe Ser Ile Ser
    50                  55                  60

Val Pro Thr Ser Gln Gly Asp Pro Tyr Ala Thr Val Val Asp Lys Gly
65                  70                  75                  80

Leu Phe Pro Ala Thr Gly His Pro Val Asp Asp Leu Leu Ala Asp Thr
                85                  90                  95

Gln Lys His Leu Pro Val Ser Met Phe Ala Ile Asp Gly Glu Val Thr
            100                 105                 110

Gly Gly Phe Lys Lys Thr Tyr Ala Phe Phe Pro Thr Asp Asp Met Pro
        115                 120                 125

Gly Val Ala Gln Leu Ser Ala Ile Pro Ser Met Pro Ser Ser Val Ala
    130                 135                 140

Glu Asn Ala Glu Leu Phe Ala Arg Tyr Gly Leu Asp Lys Val Gln Met
145                 150                 155                 160

Thr Ser Met Asp Tyr Lys Lys Arg Gln Val Asn Leu Tyr Phe Ser Glu
                165                 170                 175

Leu Ser Glu Gln Thr Leu Ala Pro Glu Ser Val Leu Ala Leu Val Arg
            180                 185                 190
```

Glu Leu Gly Leu His Val Pro Thr Glu Leu Gly Leu Glu Phe Cys Lys
195 200 205

Arg Ser Phe Ser Val Tyr Pro Thr Leu Asn Trp Asp Thr Gly Lys Ile
210 215 220

Asp Arg Leu Cys Phe Ala Val Ile Ser Thr Asp Pro Thr Leu Val Pro
225 230 235 240

Ser Thr Asp Glu Arg Asp Ile Glu Gln Phe Arg His Tyr Gly Thr Lys
245 250 255

Ala Pro Tyr Ala Tyr Val Gly Glu Asn Arg Thr Leu Val Tyr Gly Leu
260 265 270

Thr Leu Ser Pro Thr Glu Glu Tyr Tyr Lys Leu Gly Ala Tyr Tyr His
275 280 285

Ile Thr Asp Ile Gln Arg Arg Leu Leu Lys Ala Phe Asp Ala Leu Glu
290 295 300

Asp
305

<210> SEQ ID NO 7
<211> LENGTH: 307
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Met Ser Glu Ala Ala Asp Val Glu Arg Val Tyr Ala Ala Met Glu Glu
1 5 10 15

Ala Ala Gly Leu Leu Gly Val Ala Cys Ala Arg Asp Lys Ile Tyr Pro
20 25 30

Leu Leu Ser Thr Phe Gln Asp Thr Leu Val Glu Gly Gly Ser Val Val
35 40 45

Val Phe Ser Met Ala Ser Gly Arg His Ser Thr Glu Leu Asp Phe Ser
50 55 60

Ile Ser Val Pro Thr Ser His Gly Asp Pro Tyr Ala Thr Val Val Glu
65 70 75 80

Lys Gly Leu Phe Pro Ala Thr Gly His Pro Val Asp Asp Leu Leu Ala
85 90 95

Asp Thr Gln Lys His Leu Pro Val Ser Met Phe Ala Ile Asp Gly Glu
100 105 110

Val Thr Gly Gly Phe Lys Lys Thr Tyr Ala Phe Phe Pro Thr Asp Asn
115 120 125

Met Pro Gly Val Ala Glu Leu Ser Ala Ile Pro Ser Met Pro Pro Ala
130 135 140

Val Ala Glu Asn Ala Glu Leu Phe Ala Arg Tyr Gly Leu Asp Lys Val
145 150 155 160

Gln Met Thr Ser Met Asp Tyr Lys Lys Arg Gln Val Asn Leu Tyr Phe
165 170 175

Ser Glu Leu Ser Ala Gln Thr Leu Glu Ala Glu Ser Val Leu Ala Leu
180 185 190

Val Arg Glu Leu Gly Leu His Val Pro Asn Glu Leu Gly Leu Lys Phe
195 200 205

Cys Lys Arg Ser Phe Ser Val Tyr Pro Thr Leu Asn Trp Glu Thr Gly
210 215 220

Lys Ile Asp Arg Leu Cys Phe Ala Val Ile Ser Asn Asp Pro Thr Leu
225 230 235 240

-continued

```
Val Pro Ser Ser Asp Glu Gly Asp Ile Glu Lys Phe His Asn Tyr Ala
                245                 250                 255

Thr Lys Ala Pro Tyr Ala Tyr Val Gly Glu Lys Arg Thr Leu Val Tyr
            260                 265                 270

Gly Leu Thr Leu Ser Pro Lys Glu Glu Tyr Tyr Lys Leu Gly Ala Tyr
        275                 280                 285

Tyr His Ile Thr Asp Val Gln Arg Gly Leu Leu Lys Ala Phe Asp Ser
    290                 295                 300

Leu Glu Asp
305


<210> SEQ ID NO 8
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ser Gly Ala Ala Asp Val Glu Arg Val Tyr Ala Ala Met Glu Glu
1               5                   10                  15

Ala Ala Gly Leu Leu Asp Val Ser Cys Ala Arg Glu Lys Ile Tyr Pro
            20                  25                  30

Leu Leu Thr Val Phe Gln Asp Thr Leu Thr Asp Gly Val Val Val Phe
        35                  40                  45

Ser Met Ala Ser Gly Arg Arg Ser Thr Glu Leu Asp Phe Ser Ile Ser
    50                  55                  60

Val Pro Val Ser Gln Gly Asp Pro Tyr Ala Thr Val Val Arg Glu Gly
65                  70                  75                  80

Leu Phe Arg Ala Thr Gly Ser Pro Val Asp Glu Leu Leu Ala Asp Thr
                85                  90                  95

Val Lys His Leu Pro Val Ser Met Phe Ala Ile Asp Gly Glu Val Thr
            100                 105                 110

Gly Gly Phe Lys Lys Thr Tyr Ala Phe Phe Pro Thr Asp Asp Met Pro
        115                 120                 125

Gly Val Ala Gln Leu Thr Gly Ile Pro Ser Met Pro Ala Ser Val Ala
    130                 135                 140

Glu Asn Ala Glu Leu Phe Ala Arg Tyr Gly Leu Asp Lys Val Gln Met
145                 150                 155                 160

Thr Ser Met Asp Tyr Lys Lys Arg Gln Val Asn Leu Tyr Phe Ser Asp
                165                 170                 175

Leu Lys Gln Glu Tyr Leu Gln Pro Glu Ala Val Val Ala Leu Ala Arg
            180                 185                 190

Glu Leu Gly Leu Gln Val Pro Gly Glu Leu Gly Leu Glu Phe Cys Lys
        195                 200                 205

Arg Ser Phe Ala Val Tyr Pro Thr Leu Asn Trp Asp Thr Gly Lys Ile
    210                 215                 220

Asp Arg Leu Cys Phe Ala Ala Ile Ser Thr Asp Pro Thr Leu Val Pro
225                 230                 235                 240

Ser Thr Asp Glu Arg Asp Ile Glu Met Phe Arg Glu Tyr Ala Thr Lys
                245                 250                 255

Ala Pro Tyr Ala Tyr Val Gly Glu Lys Arg Thr Leu Val Tyr Gly Leu
            260                 265                 270

Thr Leu Ser Pro Thr Glu Glu Tyr Tyr Lys Leu Gly Ala Tyr Tyr His
```

```
        275                 280                 285

Ile Thr Asp Ile Gln Arg Gln Leu Leu Lys Ala Phe Asp Ala Leu Glu
    290                 295                 300

Asp
305


<210> SEQ ID NO 9
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ser Gly Ala Ala Asp Val Glu Arg Val Tyr Ala Ala Met Glu Glu
1               5                   10                  15

Ala Ala Gly Leu Leu Asp Val Ser Cys Ala Arg Glu Lys Ile Tyr Pro
            20                  25                  30

Leu Leu Thr Val Phe Gln Asp Thr Leu Thr Asp Gly Val Val Phe
        35                  40                  45

Ser Met Ala Ser Gly Arg Arg Ser Thr Glu Leu Asp Phe Ser Ile Ser
    50                  55                  60

Val Pro Val Ser Gln Gly Asp Pro Tyr Ala Thr Val Val Lys Glu Gly
65                  70                  75                  80

Leu Phe Arg Ala Thr Gly Ser Pro Val Asp Glu Leu Leu Ala Asp Thr
                85                  90                  95

Val Lys His Leu Pro Val Ser Met Phe Ala Ile Asp Gly Glu Val Thr
            100                 105                 110

Gly Gly Phe Lys Lys Thr Tyr Ala Phe Phe Pro Thr Asp Asp Met Pro
        115                 120                 125

Gly Val Ala Gln Leu Thr Glu Ile Pro Ser Met Pro Ala Ser Val Ala
    130                 135                 140

Glu Asn Ala Glu Leu Phe Ala Arg Tyr Gly Leu Asp Lys Val Gln Met
145                 150                 155                 160

Thr Ser Met Asp Tyr Lys Lys Arg Gln Val Asn Leu Tyr Phe Ser Asp
                165                 170                 175

Leu Lys Gln Glu Tyr Leu Gln Pro Glu Ala Val Val Ala Leu Ala Arg
            180                 185                 190

Glu Leu Gly Leu Gln Val Pro Gly Glu Leu Gly Leu Glu Phe Cys Lys
        195                 200                 205

Arg Ser Phe Ala Val Tyr Pro Thr Leu Asn Trp Asp Thr Gly Lys Ile
    210                 215                 220

Asp Arg Leu Cys Phe Ala Ala Ile Ser Thr Asp Pro Thr Leu Val Pro
225                 230                 235                 240

Ser Thr Asp Glu Arg Asp Ile Glu Met Phe Arg Glu Tyr Ala Thr Lys
                245                 250                 255

Ala Pro Tyr Ala Tyr Val Gly Glu Lys Arg Thr Leu Val Tyr Gly Leu
            260                 265                 270

Thr Leu Ser Ser Thr Glu Glu Tyr Tyr Lys Leu Gly Ala Tyr Tyr His
        275                 280                 285

Ile Thr Asp Ile Gln Arg Gln Leu Leu Lys Ala Phe Asp Ala Leu Glu
    290                 295                 300

Asp
305
```

<210> SEQ ID NO 10
<211> LENGTH: 305
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 10

```
Met Ser Gly Ala Ala Asp Val Glu Arg Val Tyr Ala Ala Met Glu Glu
1               5                   10                  15

Ala Ala Gly Leu Leu Asp Val Ser Cys Ala Arg Glu Lys Ile Tyr Pro
            20                  25                  30

Leu Leu Thr Val Phe Gln Asp Thr Leu Thr Asp Gly Val Val Val Phe
        35                  40                  45

Ser Met Ala Ser Gly Arg Arg Ser Thr Glu Leu Asp Phe Ser Ile Ser
    50                  55                  60

Val Pro Val Ser Gln Gly Asp Pro Tyr Ala Thr Val Val Lys Glu Gly
65                  70                  75                  80

Leu Phe Gln Ala Thr Gly Ser Pro Val Asp Glu Leu Leu Ala Asp Thr
                85                  90                  95

Val Ala His Leu Pro Val Ser Met Phe Ala Ile Asp Gly Glu Val Thr
            100                 105                 110

Gly Gly Phe Lys Lys Thr Tyr Ala Phe Phe Pro Thr Asp Asp Met Pro
        115                 120                 125

Gly Val Ala Gln Leu Ala Ala Ile Pro Ser Met Pro Ala Ser Val Ala
    130                 135                 140

Glu Asn Ala Glu Leu Phe Ala Arg Tyr Gly Leu Asp Lys Val Gln Met
145                 150                 155                 160

Thr Ser Met Asp Tyr Lys Lys Arg Gln Val Asn Leu Tyr Phe Ser Asp
                165                 170                 175

Leu Lys Gln Glu Tyr Leu Gln Pro Glu Ser Val Val Ala Leu Ala Arg
            180                 185                 190

Glu Leu Gly Leu Arg Val Pro Gly Glu Leu Gly Leu Glu Phe Cys Lys
        195                 200                 205

Arg Ser Phe Ala Val Tyr Pro Thr Leu Asn Trp Asp Thr Gly Lys Ile
    210                 215                 220

Asp Arg Leu Cys Phe Ala Ala Ile Ser Thr Asp Pro Thr Leu Val Pro
225                 230                 235                 240

Ser Glu Asp Glu Arg Asp Ile Glu Met Phe Arg Asn Tyr Ala Thr Lys
                245                 250                 255

Ala Pro Tyr Ala Tyr Val Gly Glu Lys Arg Thr Leu Val Tyr Gly Leu
            260                 265                 270

Thr Leu Ser Ser Thr Glu Glu Tyr Tyr Lys Leu Gly Ala Tyr Tyr His
        275                 280                 285

Ile Thr Asp Ile Gln Arg Gln Leu Leu Lys Ala Phe Asp Ala Leu Glu
    290                 295                 300

Asp
305
```

<210> SEQ ID NO 11
<211> LENGTH: 305
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 11

Met Ser Gly Ala Ala Glu Val Glu Arg Val Tyr Ser Ala Met Glu Glu
1 5 10 15

Ala Ala Gly Leu Leu Asp Val Ala Cys Ser Pro Glu Lys Val Arg Pro
20 25 30

Ile Leu Thr Ala Phe Gln Asp Val Leu Ser Asp Gly Val Ile Val Tyr
35 40 45

Ser Met Ala Ser Gly Arg His Ala Thr Glu Leu Asp Phe Ser Ile Ser
50 55 60

Val Pro Ala Asp His Gly Asp Pro Tyr Thr Ala Ala Leu Ala His Gly
65 70 75 80

Leu Ile Pro Glu Thr Asp His Pro Val Gly Asn Leu Leu Ala Asp Thr
85 90 95

Gln Lys Ala Leu Pro Val Ser Met Phe Ala Val Asp Gly Glu Val Thr
100 105 110

Gly Gly Phe Lys Lys Thr Tyr Ala Phe Phe Pro Thr Asp Asp Met Pro
115 120 125

Gly Leu Ala Gln Leu Ile Asp Ile Pro Ser Met Pro Pro Ser Val Ala
130 135 140

Glu Asn Ala Glu Leu Phe Ala Arg Tyr Gly Leu Asp Lys Val Gln Met
145 150 155 160

Thr Ser Leu Asp Tyr Lys Arg Lys Gln Val Asn Leu Tyr Phe Ser Asn
165 170 175

Leu Gln Pro Glu Phe Leu Ala Pro Glu Pro Val Leu Ser Met Val Arg
180 185 190

Glu Met Gly Leu Glu Leu Pro Gly Glu Lys Gly Leu Lys Phe Ala Arg
195 200 205

Arg Ser Phe Ala Ile Tyr Pro Thr Leu Gly Trp Glu Ser Gly Lys Ile
210 215 220

Glu Arg Leu Cys Phe Ala Val Ile Ser Thr Asp Pro Gly Leu Val Pro
225 230 235 240

Ala Pro Asp Glu Ala Asp Arg Ala Leu Phe Ser Thr Tyr Ala Asn Asn
245 250 255

Ala Pro Tyr Ala Tyr Ala Gly Glu Lys Arg Thr Leu Val Tyr Gly Leu
260 265 270

Thr Leu Ser Pro Thr Glu Glu Tyr Tyr Lys Leu Gly Ser Tyr Tyr Gln
275 280 285

Ile Thr Asp Ile Gln Arg Thr Leu Leu Lys Ala Phe Asp Ala Leu Thr
290 295 300

Asp
305

<210> SEQ ID NO 12
<211> LENGTH: 305
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Met Ser Gly Ala Ala Glu Val Glu Arg Val Tyr Ser Ala Met Glu Glu
1 5 10 15

Ser Ala Gly Leu Leu Asp Val Ala Cys Ser Arg Glu Lys Ile Gln Pro
20 25 30

```
Ile Leu Thr Ala Phe Gln Asp Val Leu Ala Asp Gly Val Ile Val Phe
        35                  40                  45

Ser Met Ala Asn Gly Arg His Ala Thr Glu Leu Asp Phe Ser Ile Ser
    50                  55                  60

Val Pro Ala Gly His Gly Asp Pro Tyr Ala Ala Ala Leu Glu His Gly
65                  70                  75                  80

Leu Ile Pro Ala Thr Gly His Pro Val Gly Asp Leu Leu Ala Asp Thr
                85                  90                  95

Gln Lys Ala Leu Pro Val Ser Met Phe Ala Val Asp Gly Glu Val Thr
            100                 105                 110

Ser Gly Phe Lys Lys Thr Tyr Ala Phe Phe Pro Thr Asp Asp Met Pro
        115                 120                 125

Gly Leu Ala Gln Leu Ile Asp Ile Pro Ser Met Pro Pro Ser Val Ala
    130                 135                 140

Glu Asn Ala Glu Leu Phe Gly Arg Tyr Gly Leu Asp Lys Val Gln Met
145                 150                 155                 160

Ile Ser Leu Asp Tyr Lys Lys Asn Gln Val Asn Leu Tyr Phe Ser Asn
                165                 170                 175

Leu Asn Pro Glu Phe Leu Gln Pro Glu Pro Val Gln Ala Met Val Arg
            180                 185                 190

Glu Met Gly Leu Gln Leu Pro Ala Asp Lys Gly Leu Ala Phe Ala Lys
        195                 200                 205

Arg Ser Phe Ala Val Tyr Pro Thr Leu Ser Trp Asp Ser Ala Lys Ile
    210                 215                 220

Glu Arg Leu Cys Phe Ala Val Ile Ser Thr Asp Pro Thr Leu Ala Pro
225                 230                 235                 240

Ala Gln Glu Gln Ala Asp Leu Asp Leu Phe Ser Thr Tyr Ala Asn Asn
                245                 250                 255

Ala Pro Tyr Ala Tyr Ala Gly Glu Lys Arg Thr Leu Val Tyr Gly Leu
            260                 265                 270

Thr Leu Ser Pro Ser Glu Glu Tyr Tyr Lys Leu Gly Ser Tyr Tyr Gln
        275                 280                 285

Ile Ser Asp Ile Gln Arg Lys Leu Leu Lys Ala Phe Asp Ala Leu Thr
    290                 295                 300

Asp
305
```

<210> SEQ ID NO 13
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Met Ser Gly Ala Ala Asp Val Glu Arg Val Tyr Ser Ala Met Glu Glu
1               5                   10                  15

Ala Ala Arg Leu Leu Asp Ile Thr Val Ser Arg Glu Lys Val Arg Pro
            20                  25                  30

Ala Leu Glu Ala Tyr His Glu Val Leu Ala Asp Ala Val Val Val Phe
        35                  40                  45

Ser Met Ala Ser Gly Arg Tyr Ala Thr Glu Leu Asp Phe Ser Ile Ser
    50                  55                  60

Val Pro Ala Glu Ala Gly Asp Pro Tyr Arg Val Ala Leu Ala Lys Gly
```

65 70 75 80

Leu Thr Pro Arg Thr Asp His Pro Val Gly Arg Leu Leu Ala Asp Thr
85 90 95

Gln Glu His Cys Pro Val Ser Met Phe Ala Phe Asp Gly Glu Ile Thr
100 105 110

Gly Gly Phe Lys Lys Thr Tyr Ala Phe Phe Pro Thr Asn Asp Leu Gln
115 120 125

Ser Ala Ser Lys Leu Ala Glu Ile Pro Ser Met Pro Asp Ser Val Lys
130 135 140

Glu Asn Ala Asp Leu Phe Ala Arg Tyr Gly Leu Asp Lys Val Gln Met
145 150 155 160

Thr Ser Ile Asp Tyr Lys Lys Lys Ala Val Asn Leu Tyr Phe Ser Glu
165 170 175

Met Ser Pro Asp Ile Leu Gly Pro Asp Thr Val Arg Ser Met Leu Arg
180 185 190

Asp Met Gly Leu Lys Glu Thr Gly Glu Thr Gly Leu Thr Phe Ala Arg
195 200 205

Arg Ser Phe Ser Val Tyr Pro Thr Leu Asn Trp Glu Thr Gly Arg Ile
210 215 220

Glu Arg Leu Cys Phe Ala Val Ile Ser Arg Asp Pro Thr Leu Ala Pro
225 230 235 240

Ala Glu Arg Ala Glu Asp Leu Ala Lys Phe Ser Lys Tyr Ala Asn Asn
245 250 255

Ala Pro Tyr Ala Tyr Ala Gly Glu Ala Arg Thr Leu Val Tyr Gly Leu
260 265 270

Thr Leu Thr Pro Arg Glu Glu Tyr Tyr Lys Leu Gly Ser Tyr Tyr Gln
275 280 285

Ile Ser Asp Ile Gln Arg Lys Leu Leu Lys Ala Phe Asp Ser Leu Asn
290 295 300

Asp
305

<210> SEQ ID NO 14
<211> LENGTH: 304
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 14

Met Ser Gly Ala Lys Asp Val Glu Arg Val Tyr Ser Ala Met Glu Glu
1 5 10 15

Ala Ala Gly Leu Leu Asn Val Pro Val Ala Arg Asp Lys Ile Trp Pro
20 25 30

Val Leu Thr Ala Tyr Gln Asp Ala Leu Ala Asp Ala Val Ile Val Phe
35 40 45

Ser Met Ala Gly Gly Arg Arg Ser Thr Glu Leu Asp Phe Ser Ile Ser
50 55 60

Val Pro Thr Asp His Gly Asp Pro Phe Thr Thr Ala Leu Glu Arg Gly
65 70 75 80

Leu Thr Glu Lys Glu Asn His Pro Val Asp Asn Leu Leu Ala Glu Leu
85 90 95

Arg Asp Gly Phe Pro Leu Gly Met Tyr Ala Ile Asp Gly Met Val Thr
100 105 110

```
Thr Gly Phe Lys Lys Ala Tyr Ala Ser Phe Pro Thr Asn Glu Pro Gln
        115                 120                 125

Pro Leu Thr Ala Leu Leu Asp Leu Pro Ser Met Pro Glu Ser Ala Arg
    130                 135                 140

Ala Asn Ala Glu Leu Phe Ala Arg Tyr Gly Leu Asp Lys Val Gln Met
145                 150                 155                 160

Val Ser Val Asp Tyr Pro Lys Arg Gln Val Asn Leu Tyr Phe Ser Glu
                165                 170                 175

Leu Lys Ala Asp His Leu Thr Pro Glu Gln Val Lys Ala Thr Ala Ser
            180                 185                 190

Glu Met Gly Leu Val Glu Pro Thr Asp Met Ala Leu Asp Phe Ala Thr
        195                 200                 205

Gly Ser Phe Ala Val Tyr Pro Thr Leu Gly Tyr Asp Ser Asp Val Val
    210                 215                 220

Asp Arg Ile Thr Tyr Ala Val Ile Ser Val Asp Pro Thr Leu Ala Pro
225                 230                 235                 240

Thr Thr Ser Glu Pro Glu Lys Thr Gln Ile Thr Thr Tyr Ala Asn Ser
                245                 250                 255

Ala Pro Tyr Ala Tyr Ala Gly Glu Asn Arg Thr Leu Val Tyr Gly Phe
            260                 265                 270

Thr Leu Thr Ser Lys Glu Glu Tyr Tyr Lys Leu Gly Ser Tyr Tyr Gln
        275                 280                 285

Ile Thr Asp Leu Gln Arg Thr Leu Val Lys Ala Phe Glu Ala Leu Asp
    290                 295                 300


<210> SEQ ID NO 15
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Ser Gly Ala Lys Asp Val Glu Arg Val Tyr Ser Ala Met Glu Glu
1               5                   10                  15

Ala Ala Gly Leu Leu Asn Val Pro Val Ala Arg Asp Lys Ile Trp Pro
            20                  25                  30

Val Leu Thr Ala Tyr Gln Asp Ala Leu Ala Asp Ala Val Ile Val Phe
        35                  40                  45

Ser Met Ala Gly Gly Arg Arg Ser Thr Glu Leu Asp Phe Ser Ile Ser
    50                  55                  60

Val Pro Thr Asp His Gly Asp Pro Phe Thr Thr Ala Leu Glu Arg Gly
65                  70                  75                  80

Leu Thr Glu Lys Glu Asn His Pro Val Asp Asn Leu Leu Ala Glu Leu
                85                  90                  95

Arg Asp Gly Phe Pro Leu Gly Met Tyr Ala Ile Asp Gly Met Val Thr
            100                 105                 110

Thr Gly Phe Lys Lys Ala Tyr Ala Ser Phe Pro Thr Asn Glu Pro Gln
        115                 120                 125

Pro Leu Thr Ala Leu Leu Asp Leu Pro Ser Met Pro Glu Ser Ala Arg
    130                 135                 140

Ala Asn Ala Glu Leu Phe Ala Arg Tyr Gly Leu Asp Lys Val Gln Met
145                 150                 155                 160

Val Ser Val Asp Tyr Pro Lys Arg Gln Val Asn Leu Tyr Phe Ser Asp
                165                 170                 175
```

```
Leu Asn Ala Asp His Leu Thr Pro Glu Glu Val Lys Ser Thr Ala Ser
            180                 185                 190

Glu Met Gly Leu Val Glu Pro Thr Asp Met Ala Leu Asp Phe Ala Thr
        195                 200                 205

Gly Ser Phe Ala Val Tyr Pro Thr Leu Gly Tyr Asp Ser Asp Val Val
    210                 215                 220

Asp Arg Ile Thr Tyr Ala Val Ile Ser Val Asp Pro Thr Leu Ala Pro
225                 230                 235                 240

Thr Thr Ser Glu Pro Glu Lys Thr Gln Ile Thr Thr Tyr Ala Asn Ser
                245                 250                 255

Ala Pro Tyr Ala Tyr Ala Gly Glu Asn Arg Thr Leu Val Tyr Gly Phe
            260                 265                 270

Thr Leu Thr Ser Lys Glu Glu Tyr Tyr Lys Leu Gly Ser Tyr Tyr Gln
        275                 280                 285

Ile Thr Asp Leu Gln Arg Thr Leu Val Lys Ala Phe Glu Ala Leu Asp
    290                 295                 300


<210> SEQ ID NO 16
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Ser Gly Ala Asn Asp Val Glu Arg Val Tyr Ser Ala Met Glu Glu
1               5                   10                  15

Ala Ala Gly Leu Leu Asn Val Pro Val Ala Arg Asp Lys Ile Trp Pro
            20                  25                  30

Val Leu Thr Ala Tyr Gln Asp Ala Leu Ala Asp Ala Val Val Val Phe
        35                  40                  45

Ser Met Ala Gly Gly Arg Arg Ala Thr Glu Leu Asp Phe Ser Ile Ser
    50                  55                  60

Val Pro Thr Asp Leu Gly Asp Pro Phe Thr Thr Ala Leu Arg Arg Gly
65                  70                  75                  80

Leu Thr Glu Lys Thr Asn His Pro Val Asp Asn Leu Leu Ala Glu Leu
                85                  90                  95

Thr Asp Gly Phe Glu Ile Gly Met Tyr Ala Ile Asp Gly Met Val Thr
            100                 105                 110

Thr Gly Phe Lys Lys Thr Tyr Ala Ser Phe Pro Thr Asn Glu Pro Gln
        115                 120                 125

Pro Leu Thr Ala Leu Leu Asp Val Pro Ser Met Pro Glu Ser Ala Arg
    130                 135                 140

Ala Asn Ala Glu Leu Phe Ala Arg Tyr Gly Leu Asp Lys Val Gln Met
145                 150                 155                 160

Val Ser Val Asp Tyr Pro Lys Arg Gln Val Asn Leu Tyr Phe Ser Glu
                165                 170                 175

Leu Asp Thr Asp Tyr Leu Gln Pro Glu His Val Lys Ser Leu Ala Arg
            180                 185                 190

Glu Thr Gly Leu Val Glu Pro Thr Glu Met Gly Leu Asp Phe Ala Ser
        195                 200                 205

Gly Ser Phe Ala Val Tyr Pro Thr Leu Gly Tyr Asp Asn Asp Ile Val
    210                 215                 220

Asp Arg Ile Thr Tyr Ala Val Ile Ser Val Asp Pro Thr Leu Ala Pro
```

```
225                 230                 235                 240

Thr Lys Ser Glu Pro Glu Val Ser Gln Leu Ser Arg Tyr Ala Thr Ser
                245                 250                 255

Ala Pro Tyr Ala Tyr Ala Gly Glu Asn Arg Thr Leu Val Tyr Gly Val
            260                 265                 270

Thr Leu Thr Ser Lys Glu Glu Tyr Tyr Lys Leu Gly Ser Tyr Tyr Gln
        275                 280                 285

Ile Thr Asp Leu Gln Arg Thr Leu Val Lys Ala Phe Glu Ala Leu Asp
    290                 295                 300


<210> SEQ ID NO 17
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Ser Gly Ala Asn Asp Val Glu Arg Val Tyr Ser Ala Met Glu Glu
1               5                   10                  15

Ala Ala Gly Leu Leu Gly Val Pro Val Ala Arg Glu Lys Val Arg Pro
            20                  25                  30

Val Leu Thr Ala Tyr Gln Asp Ala Leu Ala Asp Ala Val Val Val Phe
        35                  40                  45

Ser Met Ala Gly Gly Arg Arg Ala Thr Glu Leu Asp Phe Ser Ile Ser
    50                  55                  60

Val Pro Thr Asp His Gly Asp Pro Phe Thr Thr Ala Leu Gln Arg Gly
65                  70                  75                  80

Leu Thr Glu Lys Thr Gly His Pro Val Asp Asn Leu Leu Ala Glu Leu
                85                  90                  95

Arg Glu Gly Phe Pro Leu Gly Met Tyr Ala Ile Asp Gly Met Val Ser
            100                 105                 110

Thr Gly Phe Lys Lys Thr Tyr Ala Ser Phe Pro Thr Asn Glu Pro Gln
        115                 120                 125

Pro Leu Asp Asp Leu Leu Asp Val Pro Ser Met Pro Ala Ser Ala Arg
    130                 135                 140

Ala Asn Ala Lys Leu Phe Ala Asn Tyr Gly Leu Asp Lys Val Gln Met
145                 150                 155                 160

Val Ser Val Asp Tyr Pro Lys Arg Gln Val Asn Leu Tyr Phe Ser Glu
                165                 170                 175

Leu Asn Thr Asp Tyr Leu Gln Pro Ala Gln Val Lys Ala Leu Ala Ala
            180                 185                 190

Glu Met Gly Leu Ile Glu Pro Ser Glu Leu Gly Leu Glu Phe Ala Lys
        195                 200                 205

Gly Ser Phe Ala Val Tyr Pro Thr Leu Ser Tyr Asp Thr Asp Ala Ser
    210                 215                 220

Asp Arg Leu Cys Leu Ala Val Ile Ser Ser Asp Pro Thr Leu Ala Pro
225                 230                 235                 240

Thr Thr Ser Glu Pro Glu Val Thr Gln Phe Ser Thr Tyr Ala Asn Asn
                245                 250                 255

Ala Pro Tyr Ala Tyr Ala Gly Glu Asn Arg Thr Leu Val Tyr Gly Leu
            260                 265                 270

Thr Leu Thr Pro Lys Glu Glu Tyr Tyr Lys Leu Gly Ser Tyr Tyr Gln
        275                 280                 285
```

-continued

```
Ile Thr Asp Tyr Gln Arg Lys Leu Val Lys Ala Phe Glu Ala Leu Asp
    290                 295                 300


<210> SEQ ID NO 18
<211> LENGTH: 306
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Ser Lys Ala Thr Glu Val Asp Arg Val Tyr Ala Ala Val Glu Lys
1               5                   10                  15

Ala Ala Ala Leu Ala Gly Thr Thr Cys Ala Gly Asp Lys Val Arg Pro
            20                  25                  30

Val Leu Thr Gly His Gln Asp Leu Leu Asp Glu Ala Val Ile Val Phe
        35                  40                  45

Ser Met Thr Ala Ser Gly Ser His Ser Gly Gly Leu Asp Leu Ser Met
    50                  55                  60

Thr Val Pro Ala Glu His Val Asp Pro Tyr Ser Phe Ala Leu Ser Glu
65                  70                  75                  80

Gly Leu Ile Glu Pro Thr Asp His Pro Val Gly Ser Val Ile Ser Asp
                85                  90                  95

Phe Gln Glu Arg Phe Pro Ile Gly Met Tyr Gly Ile Asp Val Asp Val
            100                 105                 110

Ala Gly Gly Phe Lys Lys Ala Tyr Ala Ala Phe Pro Ser Asn Asp Leu
        115                 120                 125

Arg Glu Leu Lys Gln Leu Phe Asp Leu Pro Ser Met Pro Ser Ala Ala
    130                 135                 140

Ala Glu Asn Ala Glu Leu Phe Ala Arg Tyr Gly Leu Asp Arg Val Thr
145                 150                 155                 160

Gly Val Ser Val Asp Tyr Lys Arg His Glu Leu Asn Leu Tyr Cys Asp
                165                 170                 175

Arg Ala Thr Thr Glu Pro Leu Asp Pro Asp Tyr Val Gln Ser Met Leu
            180                 185                 190

Arg Asp Met Gly Leu Lys Glu Ala Ser Glu Gln Gly Leu Glu Phe Ala
        195                 200                 205

Lys Lys Thr Phe Ala Ile Tyr Pro Thr Leu Asn Trp Asp Ser Ser Glu
    210                 215                 220

Ile Val Arg Ile Cys Phe Ala Val Ile Thr Thr Asp Pro Ala Thr Thr
225                 230                 235                 240

Pro Thr Arg Ser Glu Pro Glu Leu Gly Gln Met Trp Glu Tyr Ala Asn
                245                 250                 255

Thr Ala Pro Tyr Ala Tyr Val Gly Glu Gln Arg Ala Leu Val Tyr Gly
            260                 265                 270

Leu Ala Leu Ser Pro Glu Lys Glu Tyr Tyr Lys Leu Gly Ala Tyr Tyr
        275                 280                 285

Gln Ile Ser Asp Tyr Gln Arg Lys Leu Val Lys Ala Phe Asp Ala Leu
    290                 295                 300

Pro Glu
305


<210> SEQ ID NO 19
<211> LENGTH: 378
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 19

Met Cys Val Pro Gly Ser Arg Ala Arg Arg Pro Gly Ser Arg Gly Trp
1               5                   10                  15

Leu Glu Arg Thr Ala Lys Pro Ala Pro Thr Arg Gly Thr Val Gly Ala
            20                  25                  30

Lys Val Arg Ser Gln Thr Trp Glu Arg Arg Ala Pro Gly Ala Thr Thr
        35                  40                  45

Val Thr Cys Pro Val Gln Gly Arg Ser Thr Gly Pro Ile Gln Ala Asp
    50                  55                  60

Ile Gln Asp Arg His Val Gly Asp Ser Met Ser Gly Ala Ala Asp Val
65                  70                  75                  80

Glu Arg Val Tyr Ser Ala Met Glu Arg Ala Ala Gly Leu Leu Asp Leu
                85                  90                  95

Thr Cys Ala Arg Glu Lys Ile Leu Pro Ile Leu Thr Ala Tyr Lys Glu
            100                 105                 110

Ala Leu Ala Asp Ser Val Ile Val Phe Ser Met Ser Gly Gly Asp His
        115                 120                 125

Ser Ala Glu Leu Asp Phe Ser Phe Thr Ile Pro Ser Gly Asp Val Asp
    130                 135                 140

Pro Tyr Ala Phe Gly Pro Ser Thr Gly Ile Pro Thr Glu Thr Asp His
145                 150                 155                 160

Pro Ile Ala Ser Leu Leu Ser Asp Thr Gly Glu Arg Cys Pro Val Ala
                165                 170                 175

Met Tyr Gly Val Asp Gly Glu Val Ser Gly Gly Phe Lys Lys Thr Tyr
            180                 185                 190

Ala Ala Phe Pro Ile Asn Asp Leu Leu Asp Leu Ser Lys Leu Val Ala
        195                 200                 205

Val Pro Ser Met Pro Pro Ala Val Ala Glu Asn Ala Glu Leu Phe Ala
    210                 215                 220

Arg Tyr Gly Leu Asp Lys Val Gln Gly Ile Ser Ile Asp Tyr Gln Arg
225                 230                 235                 240

Lys Gln Val Asn Leu Tyr Cys Gly Asp Ile Pro Ala Glu Ser Leu Glu
                245                 250                 255

Pro Glu Thr Val Arg Ser Met Leu Arg Glu Met Gly Leu Arg Glu Pro
            260                 265                 270

Ser Glu Glu Gly Leu Glu Phe Val Arg Lys Ser Phe Ala Val Tyr Pro
        275                 280                 285

Thr Leu Ser Trp Asp Ser Ser Arg Ile Glu Arg Ile Cys Phe Ala Val
    290                 295                 300

Ile Ser Thr Asp Pro Thr Leu Ala Pro Thr Arg Val Glu Ser Asp Val
305                 310                 315                 320

Ala Leu Phe Ser Lys Tyr Ala Asn Asn Ala Pro Tyr Ala Tyr Ala Gly
                325                 330                 335

Glu Arg Arg Thr Leu Ile Tyr Gly Leu Ala Val Ser Pro Thr Lys Glu
            340                 345                 350

Tyr Ile Lys Leu Gly Ser Tyr Tyr Gln Ile Ser Asp His Gln Arg Lys
        355                 360                 365

Leu Val Lys Ala Phe Asp Ala Leu Glu Asp
    370                 375
```

```
<210> SEQ ID NO 20
<211> LENGTH: 311
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Tyr Gly Gly Thr Glu Val Glu Glu Val Tyr Ser Ala Leu Glu Lys
1               5                   10                  15

Ser Ala Gly Leu Val Gly Val Pro Cys Asn Arg Asp Lys Val Trp Pro
            20                  25                  30

Ala Leu Ser Thr Tyr Gln Asp Ala Leu Gly Glu Ala Val Ile Val Phe
        35                  40                  45

Ser Val Ala Thr Asp Glu Arg His Ala Gly Glu Leu Asp Tyr Thr Ile
    50                  55                  60

Thr Val Pro Thr Gly Gly Ala Asp Pro Tyr Ala Leu Ala Leu Ala Lys
65                  70                  75                  80

Gly Leu Thr Pro Glu Thr Asp His Pro Val Gly Thr Leu Leu Ala Gly
                85                  90                  95

Val Gln Glu Arg Cys Pro Val Ala Gly Tyr Ala Val Asp Cys Gly Val
            100                 105                 110

Val Gly Gly Phe Lys Lys Ile Tyr Ser Phe Phe Pro Gln Asp Asp Leu
        115                 120                 125

Gln Gly Leu Ala Lys Leu Ala Glu Ile Pro Ser Met Pro Arg Ala Leu
    130                 135                 140

Ala Glu Asn Ala Ala Leu Phe Ala Arg His Gly Leu Asp His Lys Val
145                 150                 155                 160

Thr Met Leu Gly Ile Asp Tyr Gln Arg Glu Ser Val Asn Leu Tyr Phe
                165                 170                 175

Gly Lys Leu Pro Glu Glu Cys Leu Gln Pro Asp Ser Ile Arg Ala Ile
            180                 185                 190

Leu Arg Asp Ile Gly Leu Pro Glu Pro Thr Glu Pro Met Leu Glu Phe
        195                 200                 205

Ala Arg Lys Ser Phe Ala Ile Tyr Val Thr Leu Ser Trp Asp Ala Ala
    210                 215                 220

Lys Val Glu Arg Ile Cys Phe Ala Val Pro Pro Gly Arg Asp Leu Ile
225                 230                 235                 240

Thr Leu Asp Pro Ser Ala Leu Pro Ala Arg Ile Ala Pro Glu Ile Glu
                245                 250                 255

His Phe Ala Arg Asn Ser Pro Tyr Ala Tyr Pro Gly Asp Arg Met Leu
            260                 265                 270

Val Tyr Gly Val Thr Trp Ser Pro Glu Glu Glu Tyr Tyr Lys Leu Gly
        275                 280                 285

Ser Tyr Tyr Gln Leu Pro Val Gln Thr Arg Lys Leu Leu Val Ala Phe
    290                 295                 300

Asp Ser Val Lys Asp Gln Glu
305                 310


<210> SEQ ID NO 21
<211> LENGTH: 177
<212> TYPE: PRT
<213> ORGANISM: Unknown
<220> FEATURE:
<223> OTHER INFORMATION: Description of Unknown:
      blc gene product sequence
```

<400> SEQUENCE: 21

```
Met Arg Leu Leu Pro Leu Val Ala Ala Ala Thr Ala Ala Phe Leu Val
1               5                   10                  15

Val Ala Cys Ser Ser Pro Thr Pro Pro Arg Gly Val Thr Val Val Asn
            20                  25                  30

Asn Phe Asp Ala Lys Arg Tyr Leu Gly Thr Trp Tyr Glu Ile Ala Arg
        35                  40                  45

Phe Asp His Arg Phe Glu Arg Gly Leu Glu Lys Val Thr Ala Thr Tyr
    50                  55                  60

Ser Leu Arg Asp Asp Gly Gly Leu Asn Val Ile Asn Lys Gly Tyr Asn
65                  70                  75                  80

Pro Asp Arg Gly Met Trp Gln Gln Ser Glu Gly Lys Ala Tyr Phe Thr
                85                  90                  95

Gly Ala Pro Thr Arg Ala Ala Leu Lys Val Ser Phe Phe Gly Pro Phe
            100                 105                 110

Tyr Gly Gly Tyr Asn Val Ile Ala Leu Asp Arg Glu Tyr Arg His Ala
        115                 120                 125

Leu Val Cys Gly Pro Asp Arg Asp Tyr Leu Trp Ile Leu Ser Arg Thr
    130                 135                 140

Pro Thr Ile Ser Asp Glu Val Lys Gln Glu Met Leu Ala Val Ala Thr
145                 150                 155                 160

Arg Glu Gly Phe Asp Val Ser Lys Phe Ile Trp Val Gln Gln Pro Gly
                165                 170                 175

Ser
```

<210> SEQ ID NO 22
<211> LENGTH: 331
<212> TYPE: PRT
<213> ORGANISM: Unknown
<220> FEATURE:
<223> OTHER INFORMATION: Description of Unknown:
      ybhG gene product sequence

<400> SEQUENCE: 22

```
Met Met Lys Lys Pro Val Val Ile Gly Leu Ala Val Val Val Leu Ala
1               5                   10                  15

Ala Val Val Ala Gly Gly Tyr Trp Trp Tyr Gln Ser Arg Gln Asp Asn
            20                  25                  30

Gly Leu Thr Leu Tyr Gly Asn Val Asp Ile Arg Thr Val Asn Leu Ser
        35                  40                  45

Phe Arg Val Gly Gly Arg Val Glu Ser Leu Ala Val Asp Glu Gly Asp
    50                  55                  60

Ala Ile Lys Ala Gly Gln Val Leu Gly Glu Leu Asp His Lys Pro Tyr
65                  70                  75                  80

Glu Ile Ala Leu Met Gln Ala Lys Ala Gly Val Ser Val Ala Gln Ala
                85                  90                  95

Gln Tyr Asp Leu Met Leu Ala Gly Tyr Arg Asn Glu Glu Ile Ala Gln
            100                 105                 110

Ala Ala Ala Ala Val Lys Gln Ala Gln Ala Ala Tyr Asp Tyr Ala Gln
        115                 120                 125

Phe Tyr Asn Arg Gln Gln Gly Leu Trp Lys Ser Arg Thr Ile Ser Ala
    130                 135                 140

Asn Asp Leu Glu Asn Ala Arg Ser Ser Arg Asp Gln Ala Gln Ala Thr
145                 150                 155                 160

Leu Lys Ser Ala Gln Asp Lys Leu Arg Gln Tyr Arg Ser Gly Asn Arg
```

```
                165                 170                 175

Glu Gln Asp Ile Ala Gln Ala Lys Ala Ser Leu Glu Gln Ala Gln Ala
            180                 185                 190

Gln Leu Ala Gln Ala Glu Leu Asn Leu Gln Asp Ser Thr Leu Ile Ala
        195                 200                 205

Pro Ser Asp Gly Thr Leu Leu Thr Arg Ala Val Glu Pro Gly Thr Val
    210                 215                 220

Leu Asn Glu Gly Gly Thr Val Phe Thr Val Ser Leu Thr Arg Pro Val
225                 230                 235                 240

Trp Val Arg Ala Tyr Val Asp Glu Arg Asn Leu Asp Gln Ala Gln Pro
                245                 250                 255

Gly Arg Lys Val Leu Leu Tyr Thr Asp Gly Arg Pro Asp Lys Pro Tyr
            260                 265                 270

His Gly Gln Ile Gly Phe Val Ser Pro Thr Ala Glu Phe Thr Pro Lys
        275                 280                 285

Thr Val Glu Thr Pro Asp Leu Arg Thr Asp Leu Val Tyr Arg Leu Arg
    290                 295                 300

Ile Val Val Thr Asp Ala Asp Asp Ala Leu Arg Gln Gly Met Pro Val
305                 310                 315                 320

Thr Val Gln Phe Gly Asp Glu Ala Gly His Glu
                325                 330


<210> SEQ ID NO 23
<211> LENGTH: 403
<212> TYPE: PRT
<213> ORGANISM: Unknown
<220> FEATURE:
<223> OTHER INFORMATION: Description of Unknown:
      ydhC gene product sequence

<400> SEQUENCE: 23

Met Gln Pro Gly Lys Arg Phe Leu Val Trp Leu Ala Gly Leu Ser Val
1               5                   10                  15

Leu Gly Phe Leu Ala Thr Asp Met Tyr Leu Pro Ala Phe Ala Ala Ile
            20                  25                  30

Gln Ala Asp Leu Gln Thr Pro Ala Ser Ala Val Ser Ala Ser Leu Ser
        35                  40                  45

Leu Phe Leu Ala Gly Phe Ala Ala Ala Gln Leu Leu Trp Gly Pro Leu
    50                  55                  60

Ser Asp Arg Tyr Gly Arg Lys Pro Val Leu Leu Ile Gly Leu Thr Ile
65                  70                  75                  80

Phe Ala Leu Gly Ser Leu Gly Met Leu Trp Val Glu Asn Ala Ala Thr
                85                  90                  95

Leu Leu Val Leu Arg Phe Val Gln Ala Val Gly Val Cys Ala Ala Ala
            100                 105                 110

Val Ile Trp Gln Ala Leu Val Thr Asp Tyr Tyr Pro Ser Gln Lys Val
        115                 120                 125

Asn Arg Ile Phe Ala Ala Ile Met Pro Leu Val Gly Leu Ser Pro Ala
    130                 135                 140

Leu Ala Pro Leu Leu Gly Ser Trp Leu Leu Val His Phe Ser Trp Gln
145                 150                 155                 160

Ala Ile Phe Ala Thr Leu Phe Ala Ile Thr Val Val Leu Ile Leu Pro
                165                 170                 175

Ile Phe Trp Leu Lys Pro Thr Thr Lys Ala Arg Asn Asn Ser Gln Asp
            180                 185                 190
```

Gly Leu Thr Phe Thr Asp Leu Leu Arg Ser Lys Thr Tyr Arg Gly Asn
195 200 205

Val Leu Ile Tyr Ala Ala Cys Ser Ala Ser Phe Phe Ala Trp Leu Thr
210 215 220

Gly Ser Pro Phe Ile Leu Ser Glu Met Gly Tyr Ser Pro Ala Val Ile
225 230 235 240

Gly Leu Ser Tyr Val Pro Gln Thr Ile Ala Phe Leu Ile Gly Gly Tyr
245 250 255

Gly Cys Arg Ala Ala Leu Gln Lys Trp Gln Gly Lys Gln Leu Leu Pro
260 265 270

Trp Leu Leu Val Leu Phe Ala Val Ser Val Ile Ala Thr Trp Ala Ala
275 280 285

Gly Phe Ile Ser His Val Ser Leu Val Glu Ile Leu Ile Pro Phe Cys
290 295 300

Val Met Ala Ile Ala Asn Gly Ala Ile Tyr Pro Ile Val Val Ala Gln
305 310 315 320

Ala Leu Arg Pro Phe Pro His Ala Thr Gly Arg Ala Ala Ala Leu Gln
325 330 335

Asn Thr Leu Gln Leu Gly Leu Cys Phe Leu Ala Ser Leu Val Val Ser
340 345 350

Trp Leu Ile Ser Ile Ser Thr Pro Leu Leu Thr Thr Thr Ser Val Met
355 360 365

Leu Ser Thr Val Val Leu Val Ala Leu Gly Tyr Met Met Gln Arg Cys
370 375 380

Glu Glu Val Gly Cys Gln Asn His Gly Asn Ala Glu Val Ala His Ser
385 390 395 400

Glu Ser His

<210> SEQ ID NO 24
<211> LENGTH: 183
<212> TYPE: PRT
<213> ORGANISM: Unknown
<220> FEATURE:
<223> OTHER INFORMATION: Description of Unknown:
mlaD gene product sequence

<400> SEQUENCE: 24

Met Gln Thr Lys Lys Asn Glu Ile Trp Val Gly Ile Phe Leu Leu Ala
1 5 10 15

Ala Leu Leu Ala Ala Leu Phe Val Cys Leu Lys Ala Ala Asn Val Thr
20 25 30

Ser Ile Arg Thr Glu Pro Thr Tyr Thr Leu Tyr Ala Thr Phe Asp Asn
35 40 45

Ile Gly Gly Leu Lys Ala Arg Ser Pro Val Ser Ile Gly Gly Val Val
50 55 60

Val Gly Arg Val Ala Asp Ile Thr Leu Asp Pro Lys Thr Tyr Leu Pro
65 70 75 80

Arg Val Thr Leu Glu Ile Glu Gln Arg Tyr Asn His Ile Pro Asp Thr
85 90 95

Ser Ser Leu Ser Ile Arg Thr Ser Gly Leu Leu Gly Glu Gln Tyr Leu
100 105 110

Ala Leu Asn Val Gly Phe Glu Asp Pro Glu Leu Gly Thr Ala Ile Leu
115 120 125

Lys Asp Gly Asp Thr Ile Gln Asp Thr Lys Ser Ala Met Val Leu Glu
130 135 140

```
Asp Leu Ile Gly Gln Phe Leu Tyr Gly Ser Lys Gly Asp Asp Asn Lys
145                 150                 155                 160

Asn Ser Gly Asp Ala Pro Ala Ala Ala Pro Gly Asn Asn Glu Thr Thr
                165                 170                 175

Glu Pro Val Gly Thr Thr Lys
            180


<210> SEQ ID NO 25
<211> LENGTH: 260
<212> TYPE: PRT
<213> ORGANISM: Unknown
<220> FEATURE:
<223> OTHER INFORMATION: Description of Unknown:
      mlaE gene product sequence

<400> SEQUENCE: 25

Met Leu Leu Asn Ala Leu Ala Ser Leu Gly His Lys Gly Ile Lys Thr
1               5                   10                  15

Leu Arg Thr Phe Gly Arg Ala Gly Leu Met Leu Phe Asn Ala Leu Val
            20                  25                  30

Gly Lys Pro Glu Phe Arg Lys His Ala Pro Leu Leu Val Arg Gln Leu
        35                  40                  45

Tyr Asn Val Gly Val Leu Ser Met Leu Ile Ile Val Val Ser Gly Val
    50                  55                  60

Phe Ile Gly Met Val Leu Gly Leu Gln Gly Tyr Leu Val Leu Thr Thr
65                  70                  75                  80

Tyr Ser Ala Glu Thr Ser Leu Gly Met Leu Val Ala Leu Ser Leu Leu
                85                  90                  95

Arg Glu Leu Gly Pro Val Val Ala Ala Leu Leu Phe Ala Gly Arg Ala
            100                 105                 110

Gly Ser Ala Leu Thr Ala Glu Ile Gly Leu Met Arg Ala Thr Glu Gln
        115                 120                 125

Leu Ser Ser Met Glu Met Met Ala Val Asp Pro Leu Arg Arg Val Ile
    130                 135                 140

Ser Pro Arg Phe Trp Ala Gly Val Ile Ser Leu Pro Leu Leu Thr Val
145                 150                 155                 160

Ile Phe Val Ala Val Gly Ile Trp Gly Gly Ser Leu Val Gly Val Ser
                165                 170                 175

Trp Lys Gly Ile Asp Ser Gly Phe Phe Trp Ser Ala Met Gln Asn Ala
            180                 185                 190

Val Asp Trp Arg Met Asp Leu Val Asn Cys Leu Ile Lys Ser Val Val
        195                 200                 205

Phe Ala Ile Thr Val Thr Trp Ile Ser Leu Phe Asn Gly Tyr Asp Ala
    210                 215                 220

Ile Pro Thr Ser Ala Gly Ile Ser Arg Ala Thr Thr Arg Thr Val Val
225                 230                 235                 240

His Ser Ser Leu Ala Val Leu Gly Leu Asp Phe Val Leu Thr Ala Leu
                245                 250                 255

Met Phe Gly Asn
            260


<210> SEQ ID NO 26
<211> LENGTH: 269
<212> TYPE: PRT
<213> ORGANISM: Unknown
<220> FEATURE:
<223> OTHER INFORMATION: Description of Unknown:
      mlaF gene product sequence
```

<400> SEQUENCE: 26

```
Met Glu Gln Ser Val Ala Asn Leu Val Asp Met Arg Asp Val Ser Phe
1               5                   10                  15

Thr Arg Gly Asn Arg Cys Ile Phe Asp Asn Ile Ser Leu Thr Val Pro
            20                  25                  30

Arg Gly Lys Ile Thr Ala Ile Met Gly Pro Ser Gly Ile Gly Lys Thr
        35                  40                  45

Thr Leu Leu Arg Leu Ile Gly Gly Gln Ile Ala Pro Asp His Gly Glu
    50                  55                  60

Ile Leu Phe Asp Gly Glu Asn Ile Pro Ala Met Ser Arg Ser Arg Leu
65                  70                  75                  80

Tyr Thr Val Arg Lys Arg Met Ser Met Leu Phe Gln Ser Gly Ala Leu
                85                  90                  95

Phe Thr Asp Met Asn Val Phe Asp Asn Val Ala Tyr Pro Leu Arg Glu
            100                 105                 110

His Thr Gln Leu Pro Ala Pro Leu Leu His Ser Thr Val Met Met Lys
        115                 120                 125

Leu Glu Ala Val Gly Leu Arg Gly Ala Ala Lys Leu Met Pro Ser Glu
    130                 135                 140

Leu Ser Gly Gly Met Ala Arg Arg Ala Ala Leu Ala Arg Ala Ile Ala
145                 150                 155                 160

Leu Glu Pro Asp Leu Ile Met Phe Asp Glu Pro Phe Val Gly Gln Asp
                165                 170                 175

Pro Ile Thr Met Gly Val Leu Val Lys Leu Ile Ser Glu Leu Asn Ser
            180                 185                 190

Ala Leu Gly Val Thr Cys Val Val Val Ser His Asp Val Pro Glu Val
        195                 200                 205

Leu Ser Ile Ala Asp His Ala Trp Ile Leu Ala Asp Lys Lys Ile Val
    210                 215                 220

Ala His Gly Ser Ala Gln Ala Leu Gln Ala Asn Pro Asp Pro Arg Val
225                 230                 235                 240

Arg Gln Phe Leu Asp Gly Ile Ala Asp Gly Pro Val Pro Phe Arg Tyr
                245                 250                 255

Pro Ala Gly Asp Tyr His Ala Asp Leu Leu Pro Gly Ser
            260                 265
```

<210> SEQ ID NO 27
<211> LENGTH: 385
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Met Asn His Leu Arg Ala Glu Gly Pro Ala Ser Val Leu Ala Ile Gly
1               5                   10                  15

Thr Ala Asn Pro Glu Asn Ile Leu Ile Gln Asp Glu Phe Pro Asp Tyr
            20                  25                  30

Tyr Phe Arg Val Thr Lys Ser Glu His Met Thr Gln Leu Lys Glu Lys
        35                  40                  45

Phe Arg Lys Ile Cys Asp Lys Ser Met Ile Arg Lys Arg Asn Cys Phe
    50                  55                  60

Leu Asn Glu Glu His Leu Lys Gln Asn Pro Arg Leu Val Glu His Glu
65                  70                  75                  80
```

Met Gln Thr Leu Asp Ala Arg Gln Asp Met Leu Val Val Glu Val Pro
85 90 95

Lys Leu Gly Lys Asp Ala Cys Ala Lys Ala Ile Lys Glu Trp Gly Gln
100 105 110

Pro Lys Ser Lys Ile Thr His Leu Ile Phe Thr Ser Ala Ser Thr Thr
115 120 125

Asp Met Pro Gly Ala Asp Tyr His Cys Ala Lys Leu Leu Gly Leu Ser
130 135 140

Pro Ser Val Lys Arg Val Met Met Tyr Gln Leu Gly Cys Tyr Gly Gly
145 150 155 160

Gly Thr Val Leu Arg Ile Ala Lys Asp Ile Ala Glu Asn Asn Lys Gly
165 170 175

Ala Arg Val Leu Ala Val Cys Cys Asp Ile Met Ala Cys Leu Phe Arg
180 185 190

Gly Pro Ser Asp Ser Asp Leu Glu Leu Leu Val Gly Gln Ala Ile Phe
195 200 205

Gly Asp Gly Ala Ala Ala Val Ile Val Gly Ala Glu Pro Asp Glu Ser
210 215 220

Val Gly Glu Arg Pro Ile Phe Glu Leu Val Ser Thr Gly Gln Thr Ile
225 230 235 240

Leu Pro Asn Ser Glu Gly Thr Ile Gly Gly His Ile Arg Glu Ala Gly
245 250 255

Leu Ile Phe Asp Leu His Lys Asp Val Pro Met Leu Ile Ser Asn Asn
260 265 270

Ile Glu Lys Cys Leu Ile Glu Ala Phe Thr Pro Ile Gly Ile Ser Asp
275 280 285

Trp Asn Ser Ile Phe Trp Ile Thr His Pro Gly Gly Lys Ala Ile Leu
290 295 300

Asp Lys Val Glu Glu Lys Leu His Leu Lys Ser Asp Lys Phe Val Asp
305 310 315 320

Ser Arg His Val Leu Ser Glu His Gly Asn Met Ser Ser Ser Thr Val
325 330 335

Leu Phe Val Met Asp Glu Leu Arg Lys Arg Ser Leu Glu Glu Gly Lys
340 345 350

Ser Thr Thr Gly Asp Gly Phe Glu Trp Gly Val Leu Phe Gly Phe Gly
355 360 365

Pro Gly Leu Thr Val Glu Arg Val Val Val Arg Ser Val Pro Ile Lys
370 375 380

Tyr
385

<210> SEQ ID NO 28
<211> LENGTH: 385
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 28

Met Asn His Leu Arg Ala Glu Gly Pro Ala Ser Val Leu Ala Ile Gly
1 5 10 15

Thr Ala Asn Pro Glu Asn Ile Leu Ile Gln Asp Glu Phe Pro Asp Tyr
20 25 30

Tyr Phe Arg Val Thr Lys Ser Glu His Met Thr Gln Leu Lys Glu Lys

```
        35                  40                  45

Phe Arg Lys Ile Cys Asp Lys Ser Met Ile Arg Lys Arg Asn Ile Phe
    50                  55                  60

Leu Asn Glu Glu His Leu Lys Gln Asn Pro Lys Leu Val Glu His Asp
65                  70                  75                  80

Val Gln Thr Leu Asp Ala Arg Gln Asp Met Leu Val Val Glu Val Pro
                85                  90                  95

Lys Leu Gly Lys Asp Ala Cys Ala Lys Ala Ile Lys Glu Trp Gly Gln
            100                 105                 110

Pro Lys Ser Lys Ile Thr His Leu Ile Phe Thr Ser Ala Ser Thr Thr
        115                 120                 125

Asp Met Pro Gly Ala Asp Tyr His Cys Ala Lys Leu Leu Gly Leu Ser
    130                 135                 140

Pro Ser Val Lys Arg Val Met Met Tyr Gln Leu Gly Cys Tyr Gly Gly
145                 150                 155                 160

Gly Thr Val Leu Arg Ile Ala Lys Asp Ile Ala Glu Asn Asn Lys Gly
                165                 170                 175

Ala Arg Val Leu Ala Val Cys Cys Asp Ile Met Ala Cys Leu Phe Arg
            180                 185                 190

Gly Pro Ser Asp Ser Asp Leu Glu Leu Leu Val Gly Gln Ala Ile Phe
        195                 200                 205

Gly Asp Gly Ala Ala Ala Val Ile Val Gly Ala Glu Pro Asp Glu Ser
    210                 215                 220

Val Gly Glu Arg Pro Ile Phe Glu Leu Val Ser Thr Gly Gln Thr Ile
225                 230                 235                 240

Leu Pro Asn Ser Glu Gly Thr Ile Gly Gly His Ile Arg Glu Ala Gly
                245                 250                 255

Leu Ile Phe Asp Leu His Lys Asp Val Pro Met Leu Ile Ser Asn Asn
            260                 265                 270

Ile Glu Lys Cys Leu Ile Glu Ala Phe Thr Pro Ile Gly Ile Ser Asp
        275                 280                 285

Trp Asn Ser Ile Phe Trp Ile Thr His Pro Gly Gly Lys Ala Ile Leu
    290                 295                 300

Asp Lys Val Glu Glu Lys Leu His Leu Lys Ser Asp Lys Phe Val Asp
305                 310                 315                 320

Ser Arg His Val Leu Ser Glu His Gly Asn Met Ser Ser Ser Thr Val
                325                 330                 335

Leu Phe Val Met Asp Glu Leu Arg Lys Arg Ser Leu Glu Glu Gly Lys
            340                 345                 350

Ser Thr Thr Gly Asp Gly Phe Glu Trp Gly Val Leu Phe Gly Phe Gly
        355                 360                 365

Pro Gly Leu Thr Val Glu Arg Val Val Val Arg Ser Val Pro Ile Lys
    370                 375                 380

Tyr
385


<210> SEQ ID NO 29
<211> LENGTH: 385
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29
```

-continued

```
Met Asn His Leu Arg Ala Glu Gly Pro Ala Ser Val Leu Ala Ile Gly
1               5                   10                  15

Thr Ala Asn Pro Glu Asn Ile Leu Ile Gln Asp Glu Phe Pro Asp Tyr
            20                  25                  30

Tyr Phe Arg Val Thr Lys Ser Glu His Met Thr Gln Leu Lys Glu Lys
        35                  40                  45

Phe Arg Lys Ile Cys Asp Lys Ser Met Ile Arg Lys Arg Asn Cys Phe
    50                  55                  60

Leu Asn Glu Glu His Leu Lys Gln Asn Pro Arg Leu Val Glu His Glu
65                  70                  75                  80

Met Gln Thr Leu Asp Ala Arg Gln Asp Met Leu Val Val Glu Val Pro
                85                  90                  95

Lys Leu Gly Lys Asp Ala Cys Ala Lys Ala Ile Lys Glu Trp Gly Gln
            100                 105                 110

Pro Lys Ser Lys Ile Thr His Leu Ile Phe Thr Ser Ala Ser Thr Thr
        115                 120                 125

Asp Met Pro Gly Ala Asp Tyr His Cys Ala Lys Leu Leu Gly Leu Ser
    130                 135                 140

Pro Ser Val Lys Arg Val Met Met Tyr Gln Leu Gly Cys Tyr Gly Gly
145                 150                 155                 160

Gly Thr Val Leu Arg Ile Ala Lys Asp Ile Ala Glu Asn Asn Lys Gly
                165                 170                 175

Ala Arg Val Leu Ala Val Cys Cys Asp Met Thr Ala Cys Leu Phe Arg
            180                 185                 190

Gly Pro Ser Asp Ser Asn Leu Glu Leu Leu Val Gly Gln Ala Ile Phe
        195                 200                 205

Gly Asp Gly Ala Ala Ala Val Ile Val Gly Ala Glu Pro Asp Glu Ser
    210                 215                 220

Val Gly Glu Arg Pro Ile Phe Glu Leu Val Ser Thr Gly Gln Thr Phe
225                 230                 235                 240

Leu Pro Asn Ser Glu Gly Thr Ile Gly Gly His Ile Arg Glu Ala Gly
                245                 250                 255

Leu Met Phe Asp Leu His Lys Asp Val Pro Met Leu Ile Ser Asn Asn
            260                 265                 270

Ile Glu Lys Cys Leu Ile Glu Ala Phe Thr Pro Ile Gly Ile Ser Asp
        275                 280                 285

Trp Asn Ser Ile Phe Trp Ile Thr His Pro Gly Gly Lys Ala Ile Leu
    290                 295                 300

Asp Lys Val Glu Glu Lys Leu His Leu Lys Ser Asp Lys Phe Val Asp
305                 310                 315                 320

Ser Arg His Val Leu Ser Glu His Gly Asn Met Ser Ser Ser Thr Val
                325                 330                 335

Leu Phe Val Met Asp Glu Leu Arg Lys Arg Ser Leu Glu Glu Gly Lys
            340                 345                 350

Ser Thr Thr Gly Asp Gly Phe Glu Trp Gly Val Leu Phe Gly Phe Gly
        355                 360                 365

Pro Gly Leu Thr Val Glu Arg Val Val Leu Arg Ser Val Pro Ile Asn
    370                 375                 380

Tyr
385
```

<210> SEQ ID NO 30
<211> LENGTH: 385
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 30

Met Asn His Leu Arg Ala Glu Gly Pro Ala Ser Val Leu Ala Ile Gly
1               5                   10                  15

Thr Ala Asn Pro Glu Asn Ile Leu Ile Gln Asp Glu Phe Pro Asp Tyr
            20                  25                  30

Tyr Phe Arg Val Thr Lys Ser Glu His Met Thr Gln Leu Lys Glu Lys
        35                  40                  45

Phe Arg Lys Ile Cys Asp Lys Ser Met Ile Arg Lys Arg Asn Cys Phe
    50                  55                  60

Leu Asn Glu Glu His Leu Lys Gln Asn Pro Arg Leu Val Glu His Glu
65                  70                  75                  80

Met Gln Thr Leu Asp Ala Arg Gln Asp Met Leu Val Val Glu Val Pro
                85                  90                  95

Lys Leu Gly Lys Asp Ala Cys Ala Lys Ala Ile Lys Glu Trp Gly Gln
            100                 105                 110

Pro Lys Ser Lys Ile Thr His Leu Ile Phe Thr Ser Ala Ser Thr Thr
        115                 120                 125

Asp Met Pro Gly Ala Asp Tyr His Cys Ala Lys Leu Leu Gly Leu Ser
    130                 135                 140

Pro Ser Val Lys Arg Val Met Met Tyr Gln Leu Gly Cys Tyr Gly Gly
145                 150                 155                 160

Gly Thr Val Leu Arg Ile Ala Lys Asp Ile Ala Glu Asn Asn Lys Gly
                165                 170                 175

Ala Arg Val Leu Ala Val Cys Cys Asp Ile Met Ala Cys Leu Phe Arg
            180                 185                 190

Gly Pro Ser Asp Ser Asp Leu Glu Leu Leu Val Gly Gln Ala Ile Phe
        195                 200                 205

Gly Asp Gly Ala Ala Ala Val Ile Val Gly Ala Glu Pro Asp Glu Ser
    210                 215                 220

Val Gly Glu Arg Pro Ile Phe Glu Leu Val Ser Thr Gly Gln Thr Ile
225                 230                 235                 240

Leu Pro Asn Ser Glu Gly Thr Ile Gly Gly His Ile Arg Glu Ala Gly
                245                 250                 255

Leu Ile Phe Asp Leu His Lys Asp Val Pro Met Leu Ile Ser Asn Asn
            260                 265                 270

Ile Glu Lys Cys Leu Ile Glu Ala Phe Thr Pro Ile Gly Ile Ser Asp
        275                 280                 285

Trp Asn Ser Ile Phe Trp Ile Thr His Pro Gly Gly Lys Ala Ile Leu
    290                 295                 300

Asp Lys Val Glu Glu Lys Leu Asp Leu Lys Lys Glu Lys Phe Val Asp
305                 310                 315                 320

Ser Arg His Val Leu Ser Glu His Gly Asn Met Ser Ser Ser Thr Val
                325                 330                 335

Leu Phe Val Met Asp Glu Leu Arg Lys Arg Ser Leu Glu Glu Gly Lys
            340                 345                 350

Ser Thr Thr Gly Asp Gly Phe Glu Trp Gly Val Leu Phe Gly Phe Gly
        355                 360                 365

Pro Gly Leu Thr Val Glu Arg Val Val Val Arg Ser Val Pro Ile Lys
    370                 375                 380
```

-continued

Tyr
385

<210> SEQ ID NO 31
<211> LENGTH: 385
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 31

```
Met Asn His Leu Arg Ala Glu Gly Pro Ala Ser Val Leu Ala Ile Gly
1               5                   10                  15

Thr Ala Asn Pro Glu Asn Ile Leu Ile Gln Asp Glu Phe Pro Asp Tyr
            20                  25                  30

Tyr Phe Arg Val Thr Lys Ser Glu His Met Thr Gln Leu Lys Glu Lys
        35                  40                  45

Phe Arg Lys Ile Cys Asp Lys Ser Met Ile Arg Lys Arg Asn Cys Phe
    50                  55                  60

Leu Asn Glu Glu His Leu Lys Gln Asn Pro Arg Leu Val Glu His Glu
65                  70                  75                  80

Met Gln Thr Leu Asp Ala Arg Gln Asp Met Leu Val Val Glu Val Pro
                85                  90                  95

Lys Leu Gly Lys Asp Ala Cys Ala Lys Ala Ile Lys Glu Trp Gly Gln
            100                 105                 110

Pro Lys Ser Lys Ile Thr His Leu Ile Phe Thr Ser Ala Ser Thr Thr
        115                 120                 125

Asp Met Pro Gly Ala Asp Tyr His Cys Ala Lys Leu Leu Gly Leu Ser
    130                 135                 140

Pro Ser Val Lys Arg Val Met Met Tyr Gln Leu Gly Cys Tyr Gly Gly
145                 150                 155                 160

Gly Thr Val Leu Arg Ile Ala Lys Asp Ile Ala Glu Asn Asn Lys Gly
                165                 170                 175

Ala Arg Val Leu Ala Val Cys Cys Asp Ile Met Ala Cys Leu Phe Arg
            180                 185                 190

Gly Pro Ser Asp Ser Asp Leu Glu Leu Leu Val Gly Gln Ala Ile Phe
        195                 200                 205

Gly Asp Gly Ala Ala Ala Val Ile Val Gly Ala Glu Pro Asp Glu Ser
    210                 215                 220

Val Gly Glu Arg Pro Ile Phe Glu Leu Val Ser Thr Gly Gln Thr Ile
225                 230                 235                 240

Leu Pro Asn Ser Glu Gly Thr Ile Gly Gly His Ile Arg Glu Ala Gly
                245                 250                 255

Leu Ile Phe Asp Leu His Lys Asp Val Pro Met Leu Ile Ser Asn Asn
            260                 265                 270

Ile Glu Lys Cys Leu Ile Glu Ala Phe Thr Pro Ile Gly Ile Ser Asp
        275                 280                 285

Trp Asn Ser Ile Phe Trp Ile Thr His Pro Gly Gly Lys Ala Ile Leu
    290                 295                 300

Asp Lys Val Glu Glu Lys Leu His Leu Lys Lys Glu Lys Phe Val Asp
305                 310                 315                 320

Ser Arg His Val Leu Ser Glu His Gly Asn Met Ser Ser Ser Thr Val
                325                 330                 335

Leu Phe Val Met Asp Glu Leu Arg Lys Arg Ser Leu Glu Glu Gly Lys
            340                 345                 350
```

Ser Thr Thr Gly Asp Gly Phe Glu Trp Gly Val Leu Phe Gly Phe Gly
355 360 365

Pro Gly Leu Thr Val Glu Thr Val Val Leu Arg Ser Val Pro Ile Asn
370 375 380

Tyr
385

<210> SEQ ID NO 32
<211> LENGTH: 399
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

Met Ala Thr Lys Ser Val Ala Val Glu Glu Met Cys Lys Ala Gln Lys
1 5 10 15

Ala Gly Gly Pro Ala Thr Ile Leu Ala Ile Gly Thr Ala Val Pro Ser
20 25 30

Asn Cys Tyr Tyr Gln Ser Glu Tyr Pro Asp Phe Tyr Phe Arg Val Thr
35 40 45

Lys Ser Asp His Leu Thr Asp Leu Lys Ser Lys Phe Lys Arg Met Cys
50 55 60

Glu Arg Ser Ser Ile Lys Lys Arg Tyr Met His Leu Thr Glu Glu Ile
65 70 75 80

Leu Glu Glu Asn Pro Asn Met Cys Thr Phe Ala Ala Pro Ser Ile Asp
85 90 95

Gly Arg Gln Asp Ile Val Val Lys Glu Ile Pro Lys Leu Ala Lys Glu
100 105 110

Ala Ala Ser Lys Ala Ile Lys Glu Trp Gly Gln Pro Lys Ser Asn Ile
115 120 125

Thr His Leu Val Phe Cys Thr Thr Ser Gly Val Asp Met Pro Gly Cys
130 135 140

Asp Tyr Gln Leu Thr Arg Leu Leu Gly Leu Arg Pro Ser Ile Lys Arg
145 150 155 160

Leu Met Met Tyr Gln Gln Gly Cys His Ala Gly Gly Thr Gly Leu Arg
165 170 175

Leu Ala Lys Asp Leu Ala Glu Asn Asn Lys Gly Ala Arg Val Leu Val
180 185 190

Val Cys Ser Glu Met Thr Val Ile Asn Phe Arg Gly Pro Ser Glu Ala
195 200 205

His Met Asp Ser Leu Val Gly Gln Ser Leu Phe Gly Asp Gly Ala Ser
210 215 220

Ala Val Ile Val Gly Ser Asp Pro Asp Leu Ser Thr Glu His Pro Leu
225 230 235 240

Tyr Gln Ile Met Ser Ala Ser Gln Ile Ile Val Ala Asp Ser Glu Gly
245 250 255

Ala Ile Asp Gly His Leu Arg Gln Glu Gly Leu Thr Phe His Leu Arg
260 265 270

Lys Asp Val Pro Ser Leu Val Ser Asp Asn Ile Glu Asn Thr Leu Val
275 280 285

Glu Ala Phe Thr Pro Ile Leu Met Asp Ser Ile Asp Ser Ile Ile Asp
290 295 300

Trp Asn Ser Ile Phe Trp Ile Ala His Pro Gly Gly Pro Ala Ile Leu

```
305                 310                 315                 320

Asn Gln Val Gln Ala Lys Val Gly Leu Lys Glu Glu Lys Leu Arg Val
                325                 330                 335

Ser Arg His Ile Leu Ser Glu Tyr Gly Asn Met Ser Ser Ala Cys Val
            340                 345                 350

Phe Phe Ile Met Asp Glu Met Arg Lys Arg Ser Met Glu Glu Gly Lys
        355                 360                 365

Gly Thr Thr Gly Glu Gly Leu Glu Trp Gly Val Leu Phe Gly Phe Gly
    370                 375                 380

Pro Gly Phe Thr Val Glu Thr Ile Val Leu His Ser Val Pro Ile
385                 390                 395


<210> SEQ ID NO 33
<211> LENGTH: 399
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Ala Thr Lys Ser Val Ala Val Glu Glu Met Cys Lys Ala Gln Lys
1               5                   10                  15

Ala Gly Gly Pro Ala Thr Ile Leu Ala Ile Gly Thr Ala Val Pro Ser
            20                  25                  30

Asn Cys Tyr Tyr Gln Ser Glu Tyr Pro Asp Phe Tyr Phe Arg Val Thr
        35                  40                  45

Lys Ser Asp His Leu Thr Asp Leu Lys Ser Lys Phe Lys Arg Met Cys
    50                  55                  60

Asp Arg Ser Ser Ile Lys Lys Arg Tyr Met His Leu Thr Glu Glu Ile
65                  70                  75                  80

Leu Lys Glu Asn Pro Asn Met Cys Ser Phe Ala Ala Pro Ser Ile Asp
                85                  90                  95

Gly Arg Gln Asp Ile Val Val Lys Glu Ile Pro Lys Leu Ala Lys Glu
            100                 105                 110

Ala Ala Ser Lys Ala Ile Lys Glu Trp Gly Gln Pro Glu Ser Asn Ile
        115                 120                 125

Thr His Leu Val Phe Cys Thr Thr Ser Gly Val Asp Met Pro Gly Cys
    130                 135                 140

Asp Tyr Gln Leu Thr Arg Leu Leu Gly Leu Arg Pro Ser Ile Lys Arg
145                 150                 155                 160

Leu Met Met Tyr Gln Gln Gly Cys His Ala Gly Gly Thr Gly Leu Arg
                165                 170                 175

Leu Ala Lys Asp Leu Ala Glu Asn Asn Lys Gly Ala Arg Val Leu Val
            180                 185                 190

Val Cys Ser Glu Met Thr Val Ile Asn Phe Arg Gly Pro Ser Glu Ala
        195                 200                 205

His Met Asp Ser Leu Val Gly Gln Ser Leu Phe Gly Asp Gly Ala Ser
    210                 215                 220

Ala Val Ile Val Gly Ser Asp Pro Asp Leu Ser Thr Glu His Pro Leu
225                 230                 235                 240

Tyr Gln Ile Met Ser Ala Ser Gln Ile Ile Val Ala Asp Ser Glu Gly
                245                 250                 255

Val Ile Asp Gly His Leu Arg Gln Glu Gly Leu Thr Phe His Leu Arg
            260                 265                 270
```

```
Lys Asp Val Pro Ser Leu Val Ser Asp Asn Ile Glu Asn Thr Leu Val
        275                 280                 285

Glu Ala Phe Thr Pro Ile Leu Met Asp Ser Ile Asp Ser Ile Ile Asp
    290                 295                 300

Trp Asn Ser Ile Phe Trp Ile Ala His Pro Gly Gly Pro Ala Ile Leu
305                 310                 315                 320

Asn Gln Val Gln Ala Lys Val Gly Leu Lys Glu Glu Lys Leu Arg Val
                325                 330                 335

Ser Arg His Ile Leu Ser Glu Tyr Gly Asn Met Ser Ser Ala Cys Val
            340                 345                 350

Phe Phe Ile Met Asp Glu Met Arg Lys Arg Ser Val Glu Glu Gly Lys
        355                 360                 365

Gly Thr Thr Gly Glu Gly Leu Glu Trp Gly Val Leu Phe Gly Phe Gly
    370                 375                 380

Pro Gly Phe Thr Val Glu Thr Ile Val Leu His Ser Val Pro Ile
385                 390                 395


<210> SEQ ID NO 34
<211> LENGTH: 399
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Ala Thr Lys Ser Val Ala Val Glu Glu Met Cys Lys Ala Gln Lys
1               5                   10                  15

Ala Gly Gly Pro Ala Thr Ile Leu Ala Ile Gly Thr Ala Val Pro Ser
            20                  25                  30

Asn Cys Tyr Tyr Gln Ser Glu Tyr Pro Asp Phe Tyr Phe Arg Val Thr
        35                  40                  45

Lys Ser Asp His Leu Thr Asp Leu Lys Ser Lys Phe Lys Arg Met Cys
    50                  55                  60

Glu Arg Ser Ser Ile Thr Lys Arg Tyr Met His Leu Thr Glu Glu Ile
65                  70                  75                  80

Leu Glu Glu Asn Pro Asn Met Cys Thr Phe Ala Ala Pro Ser Ile Asp
                85                  90                  95

Gly Arg Gln Asp Ile Val Val Lys Glu Ile Pro Lys Leu Ala Lys Glu
            100                 105                 110

Ala Ala Ser Lys Ala Ile Lys Glu Trp Gly Gln Pro Lys Ser Asn Ile
        115                 120                 125

Thr His Leu Val Phe Cys Thr Thr Ser Gly Val Asp Met Pro Gly Cys
    130                 135                 140

Asp Tyr Gln Leu Thr Arg Leu Leu Gly Leu Arg Pro Ser Ile Lys Arg
145                 150                 155                 160

Leu Met Met Tyr Gln Gln Gly Cys His Ala Gly Gly Thr Gly Leu Arg
                165                 170                 175

Leu Ala Lys Asp Leu Ala Glu Asn Asn Lys Gly Ala Arg Val Leu Val
            180                 185                 190

Val Cys Ser Glu Met Thr Val Ile Asn Phe Arg Gly Pro Ser Glu Ala
        195                 200                 205

His Met Asp Ser Leu Val Gly Gln Ser Leu Phe Gly Asp Gly Ala Ser
    210                 215                 220

Ala Val Ile Val Gly Ser Asp Pro Asp Leu Ser Thr Glu His Pro Leu
225                 230                 235                 240
```

Tyr Gln Ile Met Ser Ala Ser Gln Ile Ile Val Ala Asp Ser Glu Gly
245 250 255

Ala Ile Asp Gly His Leu Arg Gln Glu Gly Leu Thr Phe His Leu Arg
260 265 270

Lys Asp Val Pro Ser Leu Val Ser Asp Asn Ile Glu Asn Thr Leu Val
275 280 285

Glu Ala Phe Thr Pro Ile Leu Met Asp Ser Ile Asp Ser Ile Ile Asp
290 295 300

Trp Asn Ser Ile Phe Trp Ile Ala His Pro Gly Gly Pro Ala Ile Leu
305 310 315 320

Asn Gln Val Gln Ala Lys Val Gly Leu Lys Glu Glu Lys Leu Arg Val
325 330 335

Ser Arg His Ile Leu Ser Glu Tyr Gly Asn Met Ser Ser Ala Cys Val
340 345 350

Phe Phe Ile Met Asp Glu Met Arg Lys Arg Ser Val Glu Glu Gly Lys
355 360 365

Gly Thr Thr Gly Glu Gly Leu Glu Trp Gly Val Leu Phe Gly Phe Gly
370 375 380

Pro Gly Phe Thr Val Glu Thr Ile Val Leu His Ser Val Pro Ile
385 390 395

<210> SEQ ID NO 35
<211> LENGTH: 392
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

Met Ser Arg Ser Arg Leu Ile Ala Gln Ala Val Gly Pro Ala Thr Val
1 5 10 15

Leu Ala Met Gly Lys Ala Val Pro Ala Asn Val Phe Glu Gln Ala Thr
20 25 30

Tyr Pro Asp Phe Phe Phe Asn Ile Thr Asn Ser Asn Asp Lys Pro Ala
35 40 45

Leu Lys Ala Lys Phe Gln Arg Ile Cys Asp Lys Ser Gly Ile Lys Lys
50 55 60

Arg His Phe Tyr Leu Asp Gln Lys Ile Leu Glu Ser Asn Pro Ala Met
65 70 75 80

Cys Thr Tyr Met Glu Thr Ser Leu Asn Cys Arg Gln Glu Ile Ala Val
85 90 95

Ala Gln Val Pro Lys Leu Ala Lys Glu Ala Ser Met Asn Ala Ile Lys
100 105 110

Glu Trp Gly Arg Pro Lys Ser Glu Ile Thr His Ile Val Met Ala Thr
115 120 125

Thr Ser Gly Val Asn Met Pro Gly Ala Glu Leu Ala Thr Ala Lys Leu
130 135 140

Leu Gly Leu Arg Pro Asn Val Arg Arg Val Met Met Tyr Gln Gln Gly
145 150 155 160

Cys Phe Ala Gly Ala Thr Val Leu Arg Val Ala Lys Asp Leu Ala Glu
165 170 175

Asn Asn Ala Gly Ala Arg Val Leu Ala Ile Cys Ser Glu Val Thr Ala
180 185 190

Val Thr Phe Arg Ala Pro Ser Glu Thr His Ile Asp Gly Leu Val Gly

```
        195                 200                 205

Ser Ala Leu Phe Gly Asp Gly Ala Ala Ala Val Ile Val Gly Ser Asp
    210                 215                 220

Pro Arg Pro Gly Ile Glu Arg Pro Ile Tyr Glu Met His Trp Ala Gly
225                 230                 235                 240

Glu Met Val Leu Pro Glu Ser Asp Gly Ala Ile Asp Gly His Leu Thr
                245                 250                 255

Glu Ala Gly Leu Val Phe His Leu Leu Lys Asp Val Pro Gly Leu Ile
            260                 265                 270

Thr Lys Asn Ile Gly Gly Phe Leu Lys Asp Thr Lys Asn Leu Val Gly
        275                 280                 285

Ala Ser Ser Trp Asn Glu Leu Phe Trp Ala Val His Pro Gly Gly Pro
    290                 295                 300

Ala Ile Leu Asp Gln Val Glu Ala Lys Leu Glu Leu Glu Lys Gly Lys
305                 310                 315                 320

Phe Gln Ala Ser Arg Asp Ile Leu Ser Asp Tyr Gly Asn Met Ser Ser
                325                 330                 335

Ala Ser Val Leu Phe Val Leu Asp Arg Val Arg Glu Arg Ser Leu Glu
            340                 345                 350

Ser Asn Lys Ser Thr Phe Gly Glu Gly Ser Glu Trp Gly Phe Leu Ile
        355                 360                 365

Gly Phe Gly Pro Gly Leu Thr Val Glu Thr Leu Leu Leu Arg Ala Leu
    370                 375                 380

Pro Leu Gln Gln Ala Glu Arg Val
385                 390
```

<210> SEQ ID NO 36
<211> LENGTH: 1569
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
atggctaacc cgcgtgaaaa ttttcttaag tgtttctcta agcatatccc caataatgtc      60

gcaaacccga agttggtgta tacccagcat gaccaattgt atatgagcat cttaaattca     120

acgattcaaa acttgcgttt tatctctgat actacccccca aaccattggt gatcgtcacg    180

ccgtcaaata attcgcacat tcaagctacg atcttgtgtt caaaaaaggt cgggcttcaa     240

atccgcacgc gctcaggtgg gcatgacgcg gagggtatgt catatatctc acaagtaccc     300

ttcgtcgtgg ttgatctgcg taatatgcac tctattaaga tcgacgtgca tagtcagaca     360

gcttgggtag aggcaggagc aacgctgggc gaagtatact attggattaa tgagaaaaac     420

gagaacctga gttttcctgg agggtactgc cccacagtcg gcgtaggagg acatttctca     480

ggtggtggtt acggagcgtt gatgcgcaac tatggcttag ctgctgacaa tattattgat     540

gctcacttag taaacgttga tggaaaagtg ttggaccgca agtcgatggg ggaagactta     600

ttctgggcta tccgcggagg aggaggtgaa aattttggca tcatcgccgc ttggaagatt     660

aagcttgtgg ctgtcccatc gaagtctacc atcttctcag tgaaaaagaa catggagatc     720

cacggattag tgaaattatt taacaaatgg caaaacatcg catataaata cgacaaggac     780

ttagtactta tgacgcattt catcactaag aacatcaccg acaatcatgg taaaaataaa     840

accaccgttc acggttactt ttctagtatt ttccatgggg gggtggacag tttagtagat     900
```

-continued

```
ttaatgaata agagttttcc cgagctgggc atcaagaaaa ctgattgcaa ggaattcagt    960

tggattgata ctactatctt ctattctgga gtcgtgaact ttaatactgc caattttaaa   1020

aaggagatct tattagatcg ttcagccgga aaaaagactg cgtttagcat taagcttgac   1080

tatgtaaaga aaccaatccc tgaaactgct atggtcaaga tccttgaaaa actgtatgaa   1140

gaagacgtcg gcgccggcat gtatgtactt tacccatatg gaggcatcat ggaagagatc   1200

tctgagagtg caatcccatt cccgcatcgc gctggcatca tgtacgagct gtggtatacg   1260

gcgtcgtggg agaaacagga ggataacgag aagcatatta actgggttcg tagcgtttac   1320

aactttacaa ctccgtacgt cagtcaaaat ccccgtttag cctacttgaa ctaccgcgat   1380

cttgatcttg gtaagactaa tcacgcatcg ccaaacaatt atacccaagc ccgtatctgg   1440

ggggaaaaat acttcggaaa gaacttcaac cgtctggtca aagtaaagac taaagtagat   1500

cccaataatt tcttccgtaa cgaacagagt attcccccct tgcctcccca tcatcatcac   1560

caccactaa                                                            1569
```

<210> SEQ ID NO 37
<211> LENGTH: 299
<212> TYPE: PRT
<213> ORGANISM: Escherichia coli

<400> SEQUENCE: 37

```
Met Asp Phe Pro Gln Gln Leu Glu Ala Cys Val Lys Gln Ala Asn Gln
1               5                   10                  15

Ala Leu Ser Arg Phe Ile Ala Pro Leu Pro Phe Gln Asn Thr Pro Val
            20                  25                  30

Val Glu Thr Met Gln Tyr Gly Ala Leu Leu Gly Gly Lys Arg Leu Arg
        35                  40                  45

Pro Phe Leu Val Tyr Ala Thr Gly His Met Phe Gly Val Ser Thr Asn
    50                  55                  60

Thr Leu Asp Ala Pro Ala Ala Ala Val Glu Cys Ile His Ala Tyr Ser
65                  70                  75                  80

Leu Ile His Asp Asp Leu Pro Ala Met Asp Asp Asp Asp Leu Arg Arg
                85                  90                  95

Gly Leu Pro Thr Cys His Val Lys Phe Gly Glu Ala Asn Ala Ile Leu
            100                 105                 110

Ala Gly Asp Ala Leu Gln Thr Leu Ala Phe Ser Ile Leu Ser Asp Ala
        115                 120                 125

Asp Met Pro Glu Val Ser Asp Arg Asp Arg Ile Ser Met Ile Ser Glu
    130                 135                 140

Leu Ala Ser Ala Ser Gly Ile Ala Gly Met Cys Gly Gly Gln Ala Leu
145                 150                 155                 160

Asp Leu Asp Ala Glu Gly Lys His Val Pro Leu Asp Ala Leu Glu Arg
                165                 170                 175

Ile His Arg His Lys Thr Gly Ala Leu Ile Arg Ala Ala Val Arg Leu
            180                 185                 190

Gly Ala Leu Ser Ala Gly Asp Lys Gly Arg Arg Ala Leu Pro Val Leu
        195                 200                 205

Asp Lys Tyr Ala Glu Ser Ile Gly Leu Ala Phe Gln Val Gln Asp Asp
    210                 215                 220

Ile Leu Asp Val Val Gly Asp Thr Ala Thr Leu Gly Lys Arg Gln Gly
225                 230                 235                 240

Ala Asp Gln Gln Leu Gly Lys Ser Thr Tyr Pro Ala Leu Leu Gly Leu
                245                 250                 255
```

```
Glu Gln Ala Arg Lys Lys Ala Arg Asp Leu Ile Asp Asp Ala Arg Gln
            260                 265                 270

Ser Leu Lys Gln Leu Ala Glu Gln Ser Leu Asp Thr Ser Ala Leu Glu
        275                 280                 285

Ala Leu Ala Asp Tyr Ile Ile Gln Arg Asn Lys
    290                 295


<210> SEQ ID NO 38
<211> LENGTH: 371
<212> TYPE: PRT
<213> ORGANISM: Corynebacterium glutamicum

<400> SEQUENCE: 38

Met Lys Asp Val Ser Leu Ser Ser Phe Asp Ala His Asp Leu Asp Leu
1               5                   10                  15

Asp Lys Phe Pro Glu Val Val Arg Asp Arg Leu Thr Gln Phe Leu Asp
            20                  25                  30

Ala Gln Glu Leu Thr Ile Ala Asp Ile Gly Ala Pro Val Thr Asp Ala
        35                  40                  45

Val Ala His Leu Arg Ser Phe Val Leu Asn Gly Gly Lys Arg Ile Arg
    50                  55                  60

Pro Leu Tyr Ala Trp Ala Gly Phe Leu Ala Ala Gln Gly His Lys Asn
65                  70                  75                  80

Ser Ser Glu Lys Leu Glu Ser Val Leu Asp Ala Ala Ala Ser Leu Glu
                85                  90                  95

Phe Ile Gln Ala Cys Ala Leu Ile His Asp Asp Ile Ile Asp Ser Ser
            100                 105                 110

Asp Thr Arg Arg Gly Ala Pro Thr Val His Arg Ala Val Glu Ala Asp
        115                 120                 125

His Arg Ala Asn Asn Phe Glu Gly Asp Pro Glu His Phe Gly Val Ser
    130                 135                 140

Val Ser Ile Leu Ala Gly Asp Met Ala Leu Val Trp Ala Glu Asp Met
145                 150                 155                 160

Leu Gln Asp Ser Gly Leu Ser Ala Glu Ala Leu Ala Arg Thr Arg Asp
                165                 170                 175

Ala Trp Arg Gly Met Arg Thr Glu Val Ile Gly Gly Gln Leu Leu Asp
            180                 185                 190

Ile Tyr Leu Glu Ser His Ala Asn Glu Ser Val Glu Leu Ala Asp Ser
        195                 200                 205

Val Asn Arg Phe Lys Thr Ala Ala Tyr Thr Ile Ala Arg Pro Leu His
    210                 215                 220

Leu Gly Ala Ser Ile Ala Gly Gly Ser Pro Gln Leu Ile Asp Ala Leu
225                 230                 235                 240

Leu His Tyr Gly His Asp Ile Gly Ile Ala Phe Gln Leu Arg Asp Asp
                245                 250                 255

Leu Leu Gly Val Phe Gly Asp Pro Ala Ile Thr Gly Lys Pro Ala Gly
            260                 265                 270

Asp Asp Ile Arg Glu Gly Lys Arg Thr Val Leu Leu Ala Leu Ala Leu
        275                 280                 285

Gln Arg Ala Asp Lys Gln Ser Pro Glu Ala Ala Thr Ala Ile Arg Ala
    290                 295                 300

Gly Val Gly Lys Val Thr Ser Pro Glu Asp Ile Ala Val Ile Thr Glu
305                 310                 315                 320

His Ile Arg Ala Thr Gly Ala Glu Glu Glu Val Glu Gln Arg Ile Ser
```

```
                325                 330                 335

Gln Leu Thr Glu Ser Gly Leu Ala His Leu Asp Asp Val Asp Ile Pro
            340                 345                 350

Asp Glu Val Arg Ala Gln Leu Arg Ala Leu Ala Ile Arg Ser Thr Glu
        355                 360                 365

Arg Arg Met
    370


<210> SEQ ID NO 39
<211> LENGTH: 371
<212> TYPE: PRT
<213> ORGANISM: Corynebacterium crudilactis

<400> SEQUENCE: 39

Met Lys Asp Val Ser Leu Ser Thr Phe Asp Ala His Asp Leu Asp Leu
1               5                   10                  15

Asn Lys Phe Pro Glu Val Val Arg Asp Arg Leu Thr Arg Phe Leu Asp
            20                  25                  30

Ala Lys Thr Ser Thr Ile Ala Asp Ile Gly Asp Pro Val Thr Glu Ala
        35                  40                  45

Val Ser His Leu Arg Asn Phe Val Leu Asn Gly Gly Lys Arg Ile Arg
    50                  55                  60

Pro Leu Tyr Ala Trp Ala Gly Phe Leu Ala Ala Gln Gly Arg Glu Asn
65                  70                  75                  80

Ser Ser Glu Glu Leu Asp Ala Val Leu Asp Ala Ala Ser Ser Leu Glu
                85                  90                  95

Phe Ile Gln Ala Cys Ala Leu Ile His Asp Asp Ile Ile Asp Ser Ser
            100                 105                 110

Asp Thr Arg Arg Gly Ala Pro Thr Val His Arg Ala Val Glu Ala Asp
        115                 120                 125

His Arg Ala Asn Asn Phe Glu Gly Ala Pro Glu His Phe Gly Val Ser
    130                 135                 140

Val Ala Ile Leu Ala Gly Asp Met Ala Leu Val Trp Ala Glu Asp Met
145                 150                 155                 160

Leu Gln Asp Ser Gly Leu Ser Ala Glu Ala Leu Ala Arg Thr Arg Asp
                165                 170                 175

Ala Trp Arg Gly Met Arg Thr Glu Val Ile Gly Gly Gln Leu Leu Asp
            180                 185                 190

Ile Tyr Leu Glu Ser His Ala Asn Glu Ser Val Glu Leu Ala Asp Ser
        195                 200                 205

Val Asn Arg Phe Lys Thr Ala Ala Tyr Thr Ile Ala Arg Pro Leu His
    210                 215                 220

Leu Gly Ala Ser Ile Ala Gly Gly Ser Pro Glu Leu Ile Asp Ala Leu
225                 230                 235                 240

Leu His Tyr Gly His Asp Ile Gly Ile Ala Phe Gln Leu Arg Asp Asp
                245                 250                 255

Leu Leu Gly Val Phe Gly Asp Pro Gln Ile Thr Gly Lys Pro Ala Gly
            260                 265                 270

Asp Asp Ile Arg Glu Gly Lys Arg Thr Val Leu Leu Ala Leu Ala Leu
        275                 280                 285

Gln Arg Ala Asp Lys Glu Ser Pro Glu Ala Ala Glu Val Ile Arg Ala
    290                 295                 300

Gly Ile Gly Lys Val Thr Thr Pro Glu Asp Ile Ala Arg Ile Ala Ser
305                 310                 315                 320
```

```
His Ile Arg Asp Thr Gly Ala Glu Glu Glu Val Glu Gln Arg Ile Ser
                325                 330                 335

Gln Leu Thr Ser Ser Gly Leu Ala His Leu Asp Asn Val Asp Ile Pro
            340                 345                 350

Asp Ala Val Arg Ile Gln Leu Arg Ala Leu Ala Ile Arg Ser Thr Glu
        355                 360                 365

Arg Arg Met
    370


<210> SEQ ID NO 40
<211> LENGTH: 371
<212> TYPE: PRT
<213> ORGANISM: Corynebacterium glutamicum

<400> SEQUENCE: 40

Met Lys Asp Val Ser Leu Ser Thr Phe Asp Ala His Asp Leu Asp Leu
1               5                   10                  15

Asp Thr Phe Pro Glu Val Val Arg Asp Arg Leu Thr Gln Phe Leu Asp
            20                  25                  30

Ala Gln Ala Thr Thr Ile Ala Gly Ile Gly Asp Pro Val Thr Glu Ala
        35                  40                  45

Val Ser His Leu Arg Ser Phe Val Leu Asn Gly Gly Lys Arg Ile Arg
    50                  55                  60

Pro Leu Tyr Ala Trp Ala Gly Phe Leu Ala Ala Gln Gly Leu Glu Asn
65                  70                  75                  80

Ser Gly Glu Lys Ile Glu Ala Val Leu Asp Ala Ala Ser Ser Leu Glu
                85                  90                  95

Phe Ile Gln Ala Cys Ala Leu Ile His Asp Asp Phe Ile Asp Ser Ser
            100                 105                 110

Asp Thr Arg Arg Gly Ala Pro Thr Val His Arg Ala Val Glu Ala Asn
        115                 120                 125

His Arg Ala His Asn Leu Glu Gly Asp Ser Glu His Phe Gly Glu Ser
    130                 135                 140

Val Ser Ile Leu Ala Gly Asp Met Ala Leu Val Trp Ala Glu Asp Met
145                 150                 155                 160

Leu Gln Asp Ser Gly Leu Ser Ala Glu Ala Leu Ala Arg Thr Arg Asp
                165                 170                 175

Ala Trp Arg Gly Met Arg Thr Glu Val Ile Gly Gly Gln Leu Leu Asp
            180                 185                 190

Ile Tyr Leu Glu Ala His Ala Asn Glu Ala Val Glu Leu Ala Asp Ser
        195                 200                 205

Val Asn Arg Phe Lys Thr Ala Ala Tyr Thr Ile Ala Arg Pro Leu His
    210                 215                 220

Leu Gly Ala Ser Ile Ala Gly Gly Ser Gln Glu Leu Ile Asp Ala Leu
225                 230                 235                 240

Leu His Tyr Gly His Asp Ile Gly Ile Ala Phe Gln Leu Arg Asp Asp
                245                 250                 255

Leu Leu Gly Val Phe Gly Asp Pro Lys Val Thr Gly Lys Pro Ala Gly
            260                 265                 270

Asp Asp Ile Arg Glu Gly Lys Arg Thr Val Leu Leu Ala Leu Ala Leu
        275                 280                 285

Gln Arg Ala Asp Lys Asn Ser Pro Glu Ala Ala Ala Ala Ile Arg Ala
    290                 295                 300

Gly Ile Gly Lys Val Ser Thr Pro Glu Asp Ile Ala Val Ile Ala Lys
305                 310                 315                 320
```

```
His Ile Arg Ala Thr Gly Ala Glu Glu Glu Val Glu Gln Arg Ile Thr
                325                 330                 335

Gln Leu Thr Glu Ser Gly Leu Ala His Leu Asp Asp Val Glu Ile Pro
            340                 345                 350

Asp Glu Val Arg Thr Gln Leu Arg Ala Leu Ala Ile Arg Ser Thr Glu
        355                 360                 365

Arg Arg Met
    370


<210> SEQ ID NO 41
<211> LENGTH: 366
<212> TYPE: PRT
<213> ORGANISM: Corynebacterium deserti

<400> SEQUENCE: 41

Met Ser Thr Phe Asp Ala His Asp Leu Asp Leu Asp Lys Ile Pro Asp
1               5                   10                  15

Val Val Arg Asp Arg Leu Val Ala Phe Leu Asp Ala Lys Ser Ser Thr
            20                  25                  30

Ile Ala Glu Ile Gly Glu Pro Val Thr Asp Ala Val Ser His Leu Arg
        35                  40                  45

Ser Phe Val Leu Asn Gly Gly Lys Arg Ile Arg Pro Leu Tyr Val Trp
    50                  55                  60

Ala Gly Phe Leu Ala Ala Gln Gly Glu Ser Thr Ser Glu Glu Lys Val
65                  70                  75                  80

Glu Ala Val Leu Asp Ala Ala Ala Ser Leu Glu Phe Ile Gln Ala Cys
                85                  90                  95

Ala Leu Ile His Asp Asp Ile Ile Asp Ser Ser Asp Thr Arg Arg Gly
            100                 105                 110

Ala Pro Thr Val His Arg Ala Val Glu Ala Asp His Arg Asp Arg Arg
        115                 120                 125

Phe Glu Gly Asp Pro Lys His Phe Gly Val Ser Val Ser Ile Leu Ala
    130                 135                 140

Gly Asp Met Ala Leu Val Trp Ala Glu Asp Met Leu Gln Asp Ser Gly
145                 150                 155                 160

Leu Thr Ala Glu Ala Leu Ala Arg Thr Arg Asn Ala Trp Arg Gly Met
                165                 170                 175

Arg Thr Glu Val Ile Gly Gly Gln Leu Leu Asp Ile Tyr Leu Glu Ser
            180                 185                 190

His Ala Asn Glu Ser Val Glu Leu Ala Asp Ser Val Asn Arg Phe Lys
        195                 200                 205

Thr Ala Ala Tyr Thr Ile Glu Arg Pro Leu His Leu Gly Ala Ala Ile
    210                 215                 220

Gly Gly Gly Ser Lys Glu Leu Ile Asp Ala Leu Arg Arg Tyr Gly His
225                 230                 235                 240

Asp Ile Gly Ile Ala Phe Gln Leu Arg Asp Asp Leu Leu Gly Val Phe
                245                 250                 255

Gly Asp Pro Ala Ile Thr Gly Lys Pro Ala Gly Asp Asp Ile Arg Glu
            260                 265                 270

Gly Lys Arg Thr Val Leu Leu Ala Leu Ala Leu Gln Arg Ala Asp Glu
        275                 280                 285

Thr Asn Pro Glu Ala Ala Ala Ala Ile Arg Ala Gly Ile Gly Lys Val
    290                 295                 300

Thr Thr Pro Glu Asp Ile Ala Thr Ile Ala Gln Leu Ile Arg Asp Thr
```

```
305                 310                 315                 320

Gly Ala Glu Glu Glu Val Glu Arg Arg Ile Ser Glu Leu Thr Ala Ser
                325                 330                 335

Gly Leu Ser Tyr Leu Asp Arg Val Glu Leu Pro Glu Glu Ile Arg Ala
            340                 345                 350

Gln Leu Arg Ala Leu Ala Ile Arg Ser Thr Glu Arg Arg Met
        355                 360                 365


<210> SEQ ID NO 42
<211> LENGTH: 366
<212> TYPE: PRT
<213> ORGANISM: Corynebacterium callunae

<400> SEQUENCE: 42

Met Ser Thr Leu Asp Ala His Asp Leu Asp Leu Asn Arg Ile Pro Thr
1               5                   10                  15

Val Val His Asp Arg Leu Ser Lys Phe Leu Asp Ser Lys Glu Gly Asp
            20                  25                  30

Ile Ala Ala Ile Gly Thr Pro Val Ser Glu Ala Val Ala Tyr Leu Arg
        35                  40                  45

Ala Phe Val Leu Asn Gly Gly Lys Arg Ile Arg Pro Leu Tyr Thr Trp
    50                  55                  60

Ala Gly Phe Val Ala Ala Gly Gly Leu Glu Asn Asn Thr Glu Lys Leu
65                  70                  75                  80

Glu Ala Val Leu Asp Ala Ala Ala Ser Leu Glu Phe Ile Gln Ala Cys
                85                  90                  95

Ala Leu Ile His Asp Asp Ile Ile Asp Ser Ser Asp Thr Arg Arg Gly
            100                 105                 110

Ala Pro Thr Val His Arg Ala Val Glu Ser Tyr His Arg Glu Asn Asn
        115                 120                 125

Leu Glu Gly Asn Ser Ala His Phe Gly Glu Ser Val Ser Ile Leu Ala
    130                 135                 140

Gly Asp Met Ala Leu Val Trp Ala Glu Asp Met Leu Gln Asp Ser Gly
145                 150                 155                 160

Leu Ser Thr Glu Ala Leu Ala Arg Ser Arg Ala Ala Trp Arg Gly Met
                165                 170                 175

Arg Thr Glu Val Ile Gly Gly Gln Leu Leu Asp Ile Tyr Leu Glu Ala
            180                 185                 190

Gln Ala Asn Glu Ser Val Glu Leu Ala Asn Ser Val Asn Arg Phe Lys
        195                 200                 205

Thr Ala Ala Tyr Thr Ile Glu Arg Pro Leu His Leu Gly Ala Ser Ile
    210                 215                 220

Ala Gly Ala Ser Pro Glu Leu Ile Ser Ala Leu Arg Asn Tyr Gly His
225                 230                 235                 240

Asp Ile Gly Ile Ala Phe Gln Leu Arg Asp Asp Leu Leu Gly Val Phe
                245                 250                 255

Gly Asp Pro Ala Ile Thr Gly Lys Pro Ala Gly Asp Asp Ile Arg Glu
            260                 265                 270

Gly Lys Arg Thr Val Leu Leu Ala Lys Ala Leu Glu Lys Ala Asp Lys
        275                 280                 285

Glu Ser Pro Val Ala Ala Ala Glu Ile Arg Ala Gly Ile Gly Gln Val
    290                 295                 300

Ser Glu Pro Ala Asp Ile Ala Gln Leu Ala Gln Leu Ile Arg Asp Thr
305                 310                 315                 320
```

```
Gly Ala Glu Ala Glu Val Glu Asn Leu Ile Thr Asp Leu Thr Thr Ser
                325                 330                 335

Gly Leu Ala His Leu Glu Ala Val Ser Met Pro Ala Glu Val Lys Glu
            340                 345                 350

Leu Leu Arg Ser Leu Ala Ile Arg Ser Thr Glu Arg Arg Met
        355                 360                 365


<210> SEQ ID NO 43
<211> LENGTH: 366
<212> TYPE: PRT
<213> ORGANISM: Corynebacterium efficiens

<400> SEQUENCE: 43

Met Ser Thr Ala His Asp His Asn Val Asp Leu Asp Gln Ile Pro Asp
1               5                   10                  15

Val Val Arg Glu Arg Leu Thr Arg Phe Leu Asp Asp Arg Ala Ala Asn
            20                  25                  30

Val Val Ala Ile Gly Gly Pro Val Thr Glu Ala Leu Ser Tyr Leu Arg
        35                  40                  45

Asp Phe Val Leu Asn Gly Gly Lys Arg Ile Arg Pro Leu Tyr Val Trp
    50                  55                  60

Ala Gly Phe Val Ala Ala Gln Gly Pro Gly Arg Ser Ser Glu Asp Ile
65                  70                  75                  80

Asn Ala Val Leu Asp Ala Ala Ala Ser Leu Glu Phe Ile Gln Ala Cys
                85                  90                  95

Ala Leu Ile His Asp Asp Ile Ile Asp Ser Ser Asp Thr Arg Arg Gly
            100                 105                 110

Ala Pro Thr Val His Arg Ala Val Glu Ser Met His Gly Ala Val Gly
        115                 120                 125

Leu Glu Gly Asp Ala Ala His Phe Gly Glu Ser Val Ala Ile Leu Ala
    130                 135                 140

Gly Asp Met Ala Leu Val Trp Ala Glu Asp Met Leu Gln Asp Ser Gly
145                 150                 155                 160

Leu Ser Ala Ala Ala Leu Ala Arg Ala Arg Asp Ala Trp Arg Gly Met
                165                 170                 175

Arg Thr Glu Val Ile Gly Gly Gln Leu Leu Asp Ile Tyr Leu Glu Ala
            180                 185                 190

Gln Ala Ser Glu Ser Val Glu Leu Ala Asn Ser Val Asn Arg Phe Lys
        195                 200                 205

Thr Ala Ala Tyr Thr Ile Glu Arg Pro Leu His Leu Gly Ala Ser Leu
    210                 215                 220

Ala Gly Gly Ala Pro Glu Leu Ile Asp Ala Leu Arg Asn Tyr Gly Arg
225                 230                 235                 240

Asp Ile Gly Ile Ala Phe Gln Leu Arg Asp Asp Leu Leu Gly Val Phe
                245                 250                 255

Gly Asp Pro Ala Val Thr Gly Lys Pro Ala Gly Asp Asp Ile Arg Glu
            260                 265                 270

Gly Lys Arg Thr Val Leu Leu Ala Leu Ala Leu Gln Arg Ala Asp Ala
        275                 280                 285

Glu Asp Pro Glu Ala Ala Ala Ala Ile Arg Ser Ala Ile Gly Lys Val
    290                 295                 300

Thr Asp Pro Ala Glu Ile Thr Arg Ile Ala Gly Leu Ile Arg Ala Thr
305                 310                 315                 320

Gly Ala Glu Asp Glu Val Glu Glu His Ile Ser Arg Leu Thr Ala Ser
                325                 330                 335
```

```
Gly Leu Ala His Leu Glu Ile Ala Gly Ile Pro Asp Glu Val Arg Glu
            340                 345                 350

Gln Leu Arg His Leu Ala Ile Arg Ala Thr Glu Arg Arg Met
        355                 360                 365


<210> SEQ ID NO 44
<211> LENGTH: 366
<212> TYPE: PRT
<213> ORGANISM: Corynebacterium sp.

<400> SEQUENCE: 44

Met Ser Ser Phe Asp Ala His Asp Leu Thr Leu Asp Arg Ile Pro Gly
1               5                   10                  15

Val Val Ala Gly Arg Leu Thr Arg Tyr Leu Asp Ser Arg Ala Gly Asp
            20                  25                  30

Ile Ala Val Ile Gly Ala Pro Val Ser Ala Ala Val Glu His Leu Arg
        35                  40                  45

Ser Phe Val Leu Gly Gly Gly Lys Arg Ile Arg Pro Leu Tyr Ala Trp
    50                  55                  60

Ala Gly Phe Leu Ala Ala Gln Gly Pro Gln Arg Ala Glu Glu Arg Leu
65                  70                  75                  80

Glu Ser Val Leu Asp Ala Ala Ser Ser Leu Glu Phe Ile Gln Ala Cys
                85                  90                  95

Ala Leu Leu His Asp Asp Ile Ile Asp Ser Ser Asp Thr Arg Arg Gly
            100                 105                 110

Arg Pro Thr Val His Arg Ala Val Glu Thr Gln His Gly Ser Gln Gly
        115                 120                 125

Leu Gln Gly Asp Ser Ala His Phe Gly Glu Ser Val Ser Ile Leu Val
    130                 135                 140

Gly Asp Met Ala Leu Val Trp Ser Glu Asp Met Phe Gln Asp Ser Gly
145                 150                 155                 160

Leu Ser Ala Pro Ala Leu Ala Arg Ala Arg Glu Pro Trp Arg Ala Met
                165                 170                 175

Arg Thr Glu Val Ile Gly Gly Gln Leu Leu Asp Ile Ser Leu Glu Ala
            180                 185                 190

Thr Thr Asn Glu Ser Val Glu Leu Ala Asp Ala Val Asn Arg Phe Lys
        195                 200                 205

Thr Ala Ala Tyr Thr Ile Glu Arg Pro Leu His Leu Gly Ala Ala Ile
    210                 215                 220

Ala Gly Ala Asp Ala Gly Leu Ile Thr Ala Leu Arg Gly Tyr Gly Arg
225                 230                 235                 240

Asp Ile Gly Val Ala Phe Gln Leu Arg Asp Asp Leu Leu Gly Val Phe
                245                 250                 255

Gly Asp Pro Val Val Thr Gly Lys Pro Ala Gly Asp Asp Leu Arg Glu
            260                 265                 270

Gly Lys Arg Thr Val Leu Leu Ala Leu Ala Leu Lys Leu Ala Asp Ala
        275                 280                 285

His Asn Pro Asp Ser Ala Thr Ala Ile Arg Glu Gly Val Gly Arg Val
    290                 295                 300

Ser Thr Pro Ala Asp Ile Ala Glu Leu Ala Gly Ile Ile Arg Glu Thr
305                 310                 315                 320

Gly Ala Glu Arg Glu Val Glu Glu Arg Ile Thr Arg Leu Thr Arg Ser
                325                 330                 335

Gly Leu Ala Gln Leu Glu Asp Val Gly Leu Pro Ala Asp Val Arg Glu
```

340 345 350

His Leu Glu His Leu Ala Ile Arg Ser Thr Glu Arg Arg Met
355 360 365

<210> SEQ ID NO 45
<211> LENGTH: 367
<212> TYPE: PRT
<213> ORGANISM: Corynebacterium humireducens

<400> SEQUENCE: 45

Met Ser Thr Pro Ser Pro Leu Thr Thr Leu Thr Leu Asp Gln Val Pro
1 5 10 15

Asp Ala Val Arg Glu Glu Leu Thr Arg Phe Ile Asp Asp Arg Arg Arg
20 25 30

Gln Val Ala Ala Ile Gly Gly Pro Val Thr Glu Ala Val Ala His Leu
35 40 45

Glu Ser Phe Val Leu Gly Gly Gly Lys Arg Ile Arg Pro Leu Tyr Ala
50 55 60

Trp Ala Gly Phe Val Gly Gly Gly Gly Leu Glu Arg Ala Ala Glu Asp
65 70 75 80

Pro Ala Ala Met Leu Arg Ala Ala Ala Ser Leu Glu Phe Ile Gln Ala
85 90 95

Cys Ala Leu Ile His Asp Asp Ile Ile Asp Ser Ser Asp Thr Arg Arg
100 105 110

Gly Asn Leu Thr Val His Arg Ala Val Glu Lys Gln His Arg Asp Arg
115 120 125

Ala Trp Ala Gly Asp Pro Ala His Phe Gly Glu Ser Val Ala Ile Leu
130 135 140

Val Gly Asp Leu Ala Leu Val Trp Ala Glu Asp Met Leu Gln Asp Ser
145 150 155 160

Gly Leu Ser Val Ala Ala Leu Gln Arg Ala Arg Asp Pro Trp Arg Gly
165 170 175

Met Arg Thr Glu Val Ile Gly Gly Gln Leu Leu Asp Ile Thr Leu Glu
180 185 190

Ala Thr Ala Asp Glu Asn Ile Glu Leu Ala Asp Ser Val Asn Arg Phe
195 200 205

Lys Thr Ala Ala Tyr Thr Ile Glu Arg Pro Leu His Leu Gly Ala Ala
210 215 220

Ile Ala Gly Ala Asp Gln Ala Thr Ile Asp Ala Phe Arg Gly Tyr Gly
225 230 235 240

His Asp Ile Gly Ile Ala Phe Gln Leu Arg Asp Asp Gln Leu Gly Val
245 250 255

Tyr Gly Asp Pro Ala Val Thr Gly Lys Pro Ala Gly Asp Asp Leu Arg
260 265 270

Glu Gly Lys Arg Thr Val Leu Leu Ala Thr Ala Leu Gln Arg Ala Asp
275 280 285

Asp Arg Asp Pro Ala Ala Ala Ala Glu Leu Arg Ala Gly Val Gly Ala
290 295 300

Thr Asp Asp Pro Ala Gln Ile Ala Arg Leu Ala Gln Ile Ile Ala Asp
305 310 315 320

Thr Gly Ala Val Glu Glu Ile Glu Glu Arg Ile Thr Glu Leu Thr Arg
325 330 335

Ser Gly Leu Ala His Leu Ala Ala Ala Gly Thr Ser Pro Glu Val Thr
340 345 350

```
Ala Thr Leu Thr Asp Leu Ala His Arg Ala Thr Ala Arg Arg His
        355                 360                 365


<210> SEQ ID NO 46
<211> LENGTH: 366
<212> TYPE: PRT
<213> ORGANISM: Corynebacterium halotolerans

<400> SEQUENCE: 46

Met Thr Ser Thr Asp Pro Arg Thr Leu Thr Leu Glu Arg Val Pro Gly
1               5                   10                  15

Ala Ala Arg Asp Ala Leu Ser Glu Phe Phe Asp Ala Arg Arg Gly Gln
            20                  25                  30

Ile Ala Gly Ile Gly Ala Pro Val Thr Asp Ala Val Ala His Leu Glu
        35                  40                  45

Ser Phe Val Leu Gly Gly Gly Lys Arg Ile Arg Pro Leu Tyr Ala Trp
    50                  55                  60

Ala Gly Phe Val Gly Ala Gly Gly Phe Asp Arg Thr Gly Glu Glu Pro
65                  70                  75                  80

Ala Ala Val Leu Lys Ala Ala Ala Ser Leu Glu Phe Ile Gln Ala Cys
                85                  90                  95

Ala Leu Val His Asp Asp Ile Ile Asp Ser Ser Asp Thr Arg Arg Gly
            100                 105                 110

Asn Pro Thr Val His Arg Ala Val Glu Lys Arg His Ala Asp Asn Gly
        115                 120                 125

Trp Leu Gly Asp Ala Ala His Phe Gly Glu Ser Val Ala Ile Leu Val
    130                 135                 140

Gly Asp Leu Ala Leu Val Trp Ala Glu Asp Met Leu Gln Asp Ser Gly
145                 150                 155                 160

Leu Ser Val Asp Ala Leu Arg Arg Ala Arg Glu Pro Trp Arg Ala Met
                165                 170                 175

Arg Thr Glu Val Ile Gly Gly Gln Leu Leu Asp Ile Ser Leu Glu Ala
            180                 185                 190

Ala Ala Asp Glu Arg Val Glu Leu Ala Glu Ser Val Asn Arg Phe Lys
        195                 200                 205

Thr Ala Ala Tyr Thr Ile Glu Arg Pro Leu His Leu Gly Ala Ala Leu
    210                 215                 220

Ala Gly Ala Asp Asp Ala Leu Ile Glu Ala Phe Arg Gly Tyr Gly Arg
225                 230                 235                 240

Asp Ile Gly Met Ala Phe Gln Leu Arg Asp Asp Gln Leu Gly Val Tyr
                245                 250                 255

Gly Asp Pro Ala Val Thr Gly Lys Pro Ala Gly Asp Asp Leu Arg Glu
            260                 265                 270

Gly Lys Arg Thr Val Leu Leu Ala Leu Ala Leu Arg Arg Ala Asp Glu
        275                 280                 285

Arg Asp Pro Ala Ala Ala Ala Glu Leu Arg Arg Gly Val Gly Ala Thr
    290                 295                 300

Gly Asp Pro Ala Thr Leu Ala Arg Leu Ala Glu Ile Ile Arg Ser Thr
305                 310                 315                 320

Gly Ala Val Glu Glu Val Glu Glu Arg Ile Ser Ala Leu Thr Thr Ser
                325                 330                 335

Gly Leu Ala His Leu Asp Ala Ala Gly Thr Ala Pro Glu Val Thr Glu
            340                 345                 350

Thr Leu Arg Ala Leu Ala Val Arg Val Thr Glu Arg Arg Met
        355                 360                 365
```

<210> SEQ ID NO 47
<211> LENGTH: 366
<212> TYPE: PRT
<213> ORGANISM: Corynebacterium marinum

<400> SEQUENCE: 47

```
Met Ser Ser Gln Asp Leu Arg Thr Leu Thr Leu Asp Gln Ile Pro Asp
1               5                   10                  15

Ala Ala Arg Asp Glu Leu Ser Arg Phe Phe Ala Asp Arg Arg Pro Gln
            20                  25                  30

Val Ala Ala Ile Gly Gly Pro Val Thr Asp Ala Val Ala His Leu Glu
        35                  40                  45

Lys Phe Val Leu Gly Gly Gly Lys Arg Ile Arg Pro Leu Tyr Val Trp
    50                  55                  60

Ala Gly Phe Ala Gly Gly Gly Gly Phe Asp Ala Thr Ser Glu Asp Pro
65                  70                  75                  80

Ala Ala Val Leu Arg Ala Ala Ala Ser Leu Glu Phe Ile Gln Ala Cys
                85                  90                  95

Ala Leu Ile His Asp Asp Ile Ile Asp Ala Ser Asp Thr Arg Arg Gly
            100                 105                 110

Asn Pro Thr Val His Arg Ala Val Glu Glu Ala His Arg Thr Ser Gly
        115                 120                 125

Trp Ser Gly Asp Pro Ala His Phe Gly Glu Ser Val Ala Ile Leu Val
    130                 135                 140

Gly Asp Leu Ala Leu Val Trp Ala Glu Asp Met Phe Gln Asp Ser Gly
145                 150                 155                 160

Leu Ser Val Glu Ala Leu Gln Arg Ala Arg Glu Ala Trp Arg Ala Met
                165                 170                 175

Arg Thr Glu Val Ile Gly Gly Gln Leu Leu Asp Ile Ser Leu Glu Ala
            180                 185                 190

Thr Ala Asp Glu Asp Val Glu Leu Ala Asp Ser Val Asn Arg Phe Lys
        195                 200                 205

Thr Ala Ala Tyr Thr Ile Glu Arg Pro Leu His Leu Gly Ala Ser Ile
    210                 215                 220

Ala Gly Ala Asp Asp Lys Thr Ile Glu Ala Phe Arg Gly Tyr Gly Arg
225                 230                 235                 240

Asp Ile Gly Ile Ala Phe Gln Leu Arg Asp Asp Gln Leu Gly Val Tyr
                245                 250                 255

Gly Asp Pro Ala Val Thr Gly Lys Pro Ala Gly Asp Asp Leu Arg Glu
            260                 265                 270

Gly Lys Arg Thr Val Leu Leu Ala Thr Ala Leu Lys Arg Ala Asp Asp
        275                 280                 285

Arg Asp Pro Ala Ala Ala Ala Glu Leu Arg Ala Gly Val Gly Ala Val
    290                 295                 300

Ala Asp Pro Gly Glu Val Ser Arg Leu Ala Asp Ile Ile Ala Gly Thr
305                 310                 315                 320

Gly Ala Val Glu Glu Ile Glu Glu Arg Ile Thr Ala Leu Thr Ala Ser
                325                 330                 335

Gly Leu Ala His Leu Ser Ala Ala His Thr Ser Pro Glu Val Thr Ala
            340                 345                 350

Thr Leu Thr Asp Leu Ala His Arg Ala Thr Ala Arg Arg His
        355                 360                 365
```

-continued

<210> SEQ ID NO 48
<211> LENGTH: 363
<212> TYPE: PRT
<213> ORGANISM: Corynebacterium singulare

<400> SEQUENCE: 48

```
Met Thr Glu Pro Lys Ile Pro Ser Leu Asp Asp Ile Pro Gly Ala Val
1               5                   10                  15

Arg Asp Glu Leu Ala Gln Phe Leu Ala Gly Gln Arg Ser Ala Ile Ala
            20                  25                  30

Ala Ile Gly Gln Pro Val Thr Asn Ala Ile Ser Tyr Leu Glu Ser Phe
        35                  40                  45

Val Leu Asp Gly Gly Lys Arg Ile Arg Pro Leu Tyr Ala Trp Ala Gly
    50                  55                  60

Phe Val Gly Ala Arg Gly Leu Glu Gly Pro Glu Ser Pro Asp Ala Met
65                  70                  75                  80

Leu Arg Ala Ala Ser Ser Leu Glu Phe Ile Gln Ala Cys Ala Leu Ile
                85                  90                  95

His Asp Asp Ile Val Asp Ala Ser Asp Thr Arg Arg Gly Asn Pro Thr
            100                 105                 110

Val His Arg Gly Val Ala Lys Arg His Arg Asp Leu Gly Leu Gly Gly
        115                 120                 125

Asp Ser Asp Phe Phe Gly Gln Ser Leu Ala Ile Leu Ile Gly Asp Met
    130                 135                 140

Ala Leu Val Trp Ala Glu Asp Met Leu Gln Asp Ser Gly Leu Ser Pro
145                 150                 155                 160

Lys Ala Leu Ala Arg Val Arg Asp Pro Trp Arg Gly Met Arg Arg Glu
                165                 170                 175

Val Ile Gly Gly Gln Met Leu Asp Ile Ser Leu Glu Ala Glu Gly Ser
            180                 185                 190

Glu Asp Ala Ser Leu Ala Asp Ser Val Asn Arg Phe Lys Thr Ala Ala
        195                 200                 205

Tyr Thr Ile Glu Arg Pro Leu His Leu Gly Ala Ala Val Ala Gly Ala
    210                 215                 220

Ser Asp Gln Leu Ile Ala Ala Phe Arg Gly Tyr Gly Arg Asp Ile Gly
225                 230                 235                 240

Ile Ala Phe Gln Leu Arg Asp Asp Leu Leu Gly Val Phe Gly Asp Pro
                245                 250                 255

Ala Val Thr Gly Lys Pro Ala Gly Asp Asp Leu Arg Glu Gly Lys Arg
            260                 265                 270

Thr Val Leu Leu Ser Leu Ala Leu Gln Arg Ala Asp Glu Ser Asp Pro
        275                 280                 285

Ala Ala Ala Ala Glu Leu Arg Arg Leu Ile Gly Gln Thr Glu Asp Pro
    290                 295                 300

Gln Glu Ile Ala Arg Met Ala Glu Ile Ile Glu Ala Ser Gly Ala Pro
305                 310                 315                 320

Asp Val Val Glu Gln Arg Ile Ser Asp Leu Thr Arg Ser Gly Leu Ala
                325                 330                 335

His Leu His Asp Ala Pro Val Ser Pro Glu Val Thr Thr Thr Leu Glu
            340                 345                 350

Glu Leu Ala Arg Lys Ser Thr Ala Arg Arg Met
        355                 360
```

<210> SEQ ID NO 49
<211> LENGTH: 363

<212> TYPE: PRT
<213> ORGANISM: Corynebacterium minutissimum

<400> SEQUENCE: 49

Met Thr Glu Pro Lys Ile Pro Thr Leu Asp Asp Ile Pro Ala Ala Val
1               5                   10                  15

Arg Ala Glu Leu Ala Phe Phe Leu Asp Gly Gln Arg Asp Ser Ile Ala
            20                  25                  30

Ala Ile Gly Gln Pro Val Thr His Ala Ile Ser Tyr Leu Glu Ser Phe
        35                  40                  45

Val Leu Asn Gly Gly Lys Arg Ile Arg Pro Leu Tyr Ala Trp Ala Gly
    50                  55                  60

Phe Val Gly Ala His Gly Leu Glu Gly Ser Glu Ser Pro Glu Ala Met
65                  70                  75                  80

Leu Arg Ala Ala Ser Ser Leu Glu Phe Ile Gln Ala Cys Ala Leu Ile
                85                  90                  95

His Asp Asp Ile Val Asp Ala Ser Asp Thr Arg Arg Gly Asn Pro Thr
            100                 105                 110

Val His Arg Gly Val Ala Ala Arg His Arg Glu Leu Glu Leu Asn Gly
        115                 120                 125

Asp Ala Asp Phe Phe Gly Gln Ser Leu Ala Ile Leu Ile Gly Asp Met
    130                 135                 140

Ala Leu Val Trp Ala Glu Asp Met Leu Gln Asp Ser Gly Leu Ser Pro
145                 150                 155                 160

Glu Ala Leu Ala Arg Val Arg Glu Pro Trp Arg Gly Met Arg Arg Glu
                165                 170                 175

Val Ile Gly Gly Gln Met Leu Asp Ile Ser Leu Glu Ala Glu Gly Ser
            180                 185                 190

Glu Asp Ala Ser Leu Ala Asp Ser Val Asn Arg Phe Lys Thr Ala Ala
        195                 200                 205

Tyr Thr Ile Glu Arg Pro Leu His Leu Gly Ala Ala Val Ala Gly Ala
    210                 215                 220

Ser Glu Glu Leu Ile Ala Ala Phe Arg Gly Tyr Gly Arg Asp Ile Gly
225                 230                 235                 240

Ile Ala Phe Gln Leu Arg Asp Asp Leu Leu Gly Val Phe Gly Asp Pro
                245                 250                 255

Ala Ile Thr Gly Lys Pro Ala Gly Asp Asp Leu Arg Glu Gly Lys Arg
            260                 265                 270

Thr Val Leu Leu Ser Leu Ala Leu Gln Arg Thr Asp Ala Thr Asp Pro
        275                 280                 285

Val Ala Ala Ala Glu Leu Arg Arg Leu Ile Gly Gln Thr Glu Asp Pro
    290                 295                 300

Asp Glu Ile Ser Arg Met Ala Glu Ile Ile Ala Glu Ser Gly Ala Pro
305                 310                 315                 320

Asp Val Val Glu Gln Arg Ile Thr Glu Leu Thr Gln Ser Gly Leu Ser
                325                 330                 335

His Leu Tyr Asp Ala His Val Ser Pro Asp Val Thr Ala Thr Leu Glu
            340                 345                 350

Asp Leu Ala Arg Lys Ser Thr Ala Arg Arg Met
        355                 360

<210> SEQ ID NO 50
<211> LENGTH: 360
<212> TYPE: PRT
<213> ORGANISM: Corynebacterium pollutisoli

<400> SEQUENCE: 50

Met Gln Thr Leu Thr Leu Asp Gln Val Pro Ala Ala Ala Arg Asp Glu
1               5                   10                  15

Leu Ala Arg Phe Ile Asp Ser Arg Arg Ala Gln Val Ala Ala Ile Gly
            20                  25                  30

Gly Pro Val Thr Arg Ala Val Ser His Leu Glu Ser Phe Val Leu Asp
        35                  40                  45

Gly Gly Lys Arg Ile Arg Pro Leu Tyr Ala Trp Ala Gly Phe Val Gly
    50                  55                  60

Gly Gly Gly Leu Glu Thr Asp Glu Asp Pro Ala Ala Met Leu Arg Ala
65                  70                  75                  80

Ala Ala Ser Leu Glu Phe Ile Gln Gly Cys Ala Leu Ile His Asp Asp
                85                  90                  95

Ile Ile Asp Ala Ser Asp Thr Arg Arg Gly Asn Pro Thr Val His Arg
            100                 105                 110

Ala Val Glu Lys Val His Gly Asp Asn Gly Trp Ala Gly Asp Pro Ala
        115                 120                 125

His Phe Gly Glu Ser Val Ala Ile Leu Val Gly Asp Leu Ala Leu Val
    130                 135                 140

Trp Ala Glu Asp Met Leu Gln Asp Ser Gly Leu Ser Val Ala Ala Leu
145                 150                 155                 160

Gln Arg Ala Arg Glu Pro Trp Arg Ala Met Arg Thr Glu Val Ile Gly
                165                 170                 175

Gly Gln Leu Leu Asp Ile Ser Leu Glu Ala Thr Gly Asp Glu Asp Ile
            180                 185                 190

Glu Leu Ala Asp Ser Val Asn Arg Phe Lys Thr Ala Ala Tyr Thr Ile
        195                 200                 205

Glu Arg Pro Leu His Leu Gly Ala Ala Ile Ala Gly Ala Asp Gln Ala
    210                 215                 220

Thr Ile Asp Ala Phe Arg Gly Tyr Gly Arg Asp Ile Gly Ile Ala Phe
225                 230                 235                 240

Gln Leu Arg Asp Asp Glu Leu Gly Val Tyr Gly Asp Pro Glu Val Thr
                245                 250                 255

Gly Lys Pro Ala Gly Asp Asp Leu Arg Glu Gly Lys Arg Thr Val Leu
            260                 265                 270

Leu Ala Thr Ala Leu Gln Arg Ala Asp Glu Arg Asp Pro Ala Ala Ala
        275                 280                 285

Ala Glu Leu Arg Arg Gly Ile Gly Thr Thr Ser Asp Pro Ala Glu Ile
    290                 295                 300

Ala Arg Leu Ala Gln Ile Ile Ala Glu Thr Gly Ala Val Glu Ala Leu
305                 310                 315                 320

Glu Glu Arg Ile Ser Ala Leu Thr Ala Ser Gly Leu Ala His Leu Ala
                325                 330                 335

Ala Val Gly Thr Ser Pro Glu Val Thr Ala Thr Leu Thr Asp Leu Ala
            340                 345                 350

His Arg Ala Thr Ala Arg Arg Arg
        355                 360

<210> SEQ ID NO 51
<211> LENGTH: 374
<212> TYPE: PRT
<213> ORGANISM: Corynebacterium lubricantis

<400> SEQUENCE: 51

-continued

```
Met Ser Ala Pro Asp Asn Gln Ala Lys Asp Leu Arg Gln Leu Ser Leu
1               5                   10                  15

Asn Asp Val Pro Glu Glu Ala Gln Lys Leu Leu Ala Gln Phe Phe Asn
            20                  25                  30

Glu Gln Glu Glu Lys Val Ala Gly Ile Gly Arg Pro Val Thr Glu Ala
        35                  40                  45

Val Ser Tyr Leu Arg Asp Phe Val Leu Asn Gly Gly Lys Arg Val Arg
    50                  55                  60

Pro Leu Tyr Gly Trp Ala Gly Phe Val Gly Ala Gly Gly Leu Lys Asn
65                  70                  75                  80

Leu Asn Gly Thr Asn Glu Asp Pro Gln Ala Val Leu Arg Ala Val Ser
                85                  90                  95

Ser Leu Glu Phe Ile Gln Ala Cys Ala Leu Ile His Asp Asp Ile Ile
            100                 105                 110

Asp Ser Ser Asp Thr Arg Arg Gly Asn Pro Thr Val His Arg Ala Val
        115                 120                 125

Glu Ala Ala His Gln Glu Gln Gln Trp Thr Gly Asp Ser Ala His Phe
    130                 135                 140

Gly Glu Ser Thr Ala Ile Leu Val Gly Asp Leu Ala Leu Val Trp Ala
145                 150                 155                 160

Glu Asp Met Trp Arg Tyr Ser Gly Leu Ser His Ala Ala Leu Asp Arg
                165                 170                 175

Ala Ala Glu Pro Trp Arg Ala Met Arg Thr Glu Val Ile Gly Gly Gln
            180                 185                 190

Leu Leu Asp Ile Ser Leu Glu Ala Ser Gly Asp Glu Ser Pro Glu Leu
        195                 200                 205

Ala Asn Ala Val Asn Arg Phe Lys Thr Ala Ala Tyr Thr Ile Glu Arg
    210                 215                 220

Pro Leu His Leu Gly Ala Ala Ile Ala Gly Ala Ser Pro Glu Val Ile
225                 230                 235                 240

Glu Ala Phe Arg Gly Tyr Gly Thr Asp Ile Gly Ile Ala Phe Gln Leu
                245                 250                 255

Arg Asp Asp Leu Leu Gly Val Phe Gly Asp Pro Ser Glu Thr Gly Lys
            260                 265                 270

Pro Ala Gly Asp Asp Leu Arg Glu Gly Lys Arg Thr Val Leu Leu Ala
        275                 280                 285

Thr Ala Leu Gln Arg Ala Asp Lys Ser Asp Pro Ala Ala Ala Ala Gln
    290                 295                 300

Leu Arg Ala Gly Val Gly Thr Glu Thr Asn Pro Glu Lys Ile Ala Glu
305                 310                 315                 320

Leu Ala Ser Ile Ile Ala Ser Thr Gly Ala Val Glu Ser Ile Glu Glu
                325                 330                 335

Gln Ile Ser Thr Leu Thr Val Ser Gly Leu Lys His Leu Thr Asp Ala
            340                 345                 350

Gly Ile Glu Pro Gln Val Thr Glu Asp Leu His Lys Leu Ala Ile Arg
        355                 360                 365

Met Thr Glu Arg Arg Lys
    370
```

<210> SEQ ID NO 52
<211> LENGTH: 371
<212> TYPE: PRT
<213> ORGANISM: Corynebacterium spheniscorum

<400> SEQUENCE: 52

```
Met Asp Thr Pro Val Ser Ala Ser Arg Thr Ala His Thr Thr Pro Asp
1               5                   10                  15

Ile His Gln Ile Pro Asp Ala Val Arg Gly Val Leu Ser Asp Phe Leu
            20                  25                  30

Glu Gly Arg Arg Ser Lys Val Ala Lys Ile Gly Glu Pro Val Thr Arg
        35                  40                  45

Ala Val Ser Tyr Leu Glu Asp Phe Val Leu Gly Gly Gly Lys Arg Ile
    50                  55                  60

Arg Pro Leu Tyr Ala Trp Ala Gly Phe Val Gly Ala Gly Gly Leu Glu
65                  70                  75                  80

Gly Pro Glu Asp Pro Gln Ala Val Leu Arg Ala Val Ser Ser Leu Glu
                85                  90                  95

Phe Ile Gln Ala Cys Ala Leu Ile His Asp Asp Ile Ile Asp Ser Ser
            100                 105                 110

Ala Thr Arg Arg Gly Asn Pro Thr Leu His Arg Ala Val Ala Ser Ala
        115                 120                 125

His Gln Glu Gln Asn Phe Ala Gly Leu Ala Asp His Phe Gly Met Ser
    130                 135                 140

Val Ala Ile Leu Val Gly Asp Met Ala Leu Val Trp Ala Glu Asp Met
145                 150                 155                 160

Leu Arg Asn Ser Gly Val Ser Ala Asp Ala Leu Ala Arg Leu Asn Arg
                165                 170                 175

Pro Trp Ala Gly Met Arg Thr Glu Val Ile Gly Gly Gln Ile Leu Asp
            180                 185                 190

Ile Ser Leu Glu Ala Ser Gly Asp Glu Ser Val Gln Leu Ala Asn Asn
        195                 200                 205

Val Asn Arg Phe Lys Thr Ala Ala Tyr Thr Ile Glu Arg Pro Leu His
    210                 215                 220

Leu Gly Ala Ala Ile Ala Gly Ala Ser Pro Glu Val Ile Arg Ala Phe
225                 230                 235                 240

Arg Gly Tyr Gly Arg Asp Ile Gly Ile Ala Tyr Gln Leu Arg Asp Asp
                245                 250                 255

Leu Leu Gly Val Phe Gly Asp Pro Ala Ile Thr Gly Lys Pro Ala Gly
            260                 265                 270

Asp Asp Leu Arg Glu Gly Lys Arg Thr Val Leu Leu Ala Leu Ala Leu
        275                 280                 285

Glu Arg Ala Asp Ala His Asp Pro Gln Ala Ala Ala Ala Leu Arg Ala
    290                 295                 300

Gly Val Gly His Thr Gln Asp Pro Ala Glu Leu Ala Arg Leu Ala Gln
305                 310                 315                 320

Ile Ile Arg Asp Thr Gly Ala Pro Asp Glu Val Glu Ala Arg Ile Thr
                325                 330                 335

Glu Leu Thr Thr Ser Gly Leu Ala Gln Leu Glu Thr Ala Glu Leu Ser
            340                 345                 350

Pro Thr Val Thr Ser Val Leu Lys Asp Leu Ala Ile Arg Ser Thr Glu
        355                 360                 365

Arg Arg Ser
    370
```

<210> SEQ ID NO 53
<211> LENGTH: 371
<212> TYPE: PRT
<213> ORGANISM: Corynebacterium doosanense

<400> SEQUENCE: 53

Met Ser Ser Gln Ser Thr Pro Gly Pro Arg Pro Asp Pro Ala Thr Ile
1 5 10 15

Asp Ser Ile Pro Asp Ala Ala Arg Ala Gln Leu Ala Ala Tyr Ile Glu
20 25 30

Ala Arg Arg Pro Glu Ile Asp Ala Ile Gly Ala Pro Val Thr Thr Ala
35 40 45

Leu Glu His Leu Ala Asp Phe Val Leu Gly Gly Gly Lys Arg Ile Arg
50 55 60

Pro Leu Tyr Gly Trp Ala Gly Phe Val Gly Ala Gly Gly Leu Glu Asn
65 70 75 80

Ser Ser Glu Asp Pro Glu Ala Val Leu Arg Ala Val Ser Ser Leu Glu
85 90 95

Phe Ile Gln Ala Cys Ala Leu Val His Asp Asp Ile Ile Asp Ser Ser
100 105 110

Glu Thr Arg Arg Gly Arg Pro Thr Val His Arg Ala Val Ala Ala Asp
115 120 125

His Arg Asp Arg Asn His Leu Gly Glu Pro Asp His Tyr Gly Leu Ser
130 135 140

Ala Ala Ile Leu Ile Gly Asp Leu Ala Leu Ala Trp Ala Asp Asp Met
145 150 155 160

Phe Ala Asp Ser Gly Ile Ser Ala Ala Ala Phe Ala Arg Ala Arg Glu
165 170 175

Pro Trp Arg Gly Met Arg Thr Glu Val Ile Gly Gly Gln Leu Leu Asp
180 185 190

Ile Ser Leu Glu Ser Ser Gly Ser Glu Asp Ile Thr Leu Ser Arg Ser
195 200 205

Val Asn Arg Tyr Lys Thr Ala Ala Tyr Thr Ile Glu Arg Pro Leu His
210 215 220

Ile Gly Ala Ala Leu Ala Gly Ala Asp Glu Gln Leu Ile Ser Ser Phe
225 230 235 240

Arg Gly Tyr Gly His Asp Ile Gly Ile Ala Phe Gln Leu Arg Asp Asp
245 250 255

Leu Leu Gly Val Phe Gly Asp Pro Ala Leu Thr Gly Lys Pro Ala Gly
260 265 270

Asp Asp Leu Arg Glu Gly Lys Arg Thr Glu Leu Leu Ser Leu Ala Leu
275 280 285

Ala Asp Ala Asp Arg Ser Asp Pro Ala Ala Ala Ala Glu Leu Arg Ala
290 295 300

Gly Val Gly Thr Val Asp Asp Pro Ala Asp Ile Thr Arg Leu Ala Asp
305 310 315 320

Ile Ile Ala Ser Thr Gly Ala Pro Glu Gln Met Glu Gln Arg Ile Glu
325 330 335

Glu Leu Thr Arg Ser Gly Leu Ala His Leu Asp Arg Val Gln Leu Pro
340 345 350

Glu Ser Val Lys Ser Thr Leu His Ser Leu Ala Ile Arg Ser Thr Glu
355 360 365

Arg Arg Thr
370

<210> SEQ ID NO 54
<211> LENGTH: 361
<212> TYPE: PRT

```
<213> ORGANISM: Corynebacterium flavescens

<400> SEQUENCE: 54

Met His His Thr Pro Asn Leu Asp Glu Ile Pro Gly Ala Val His Gln
1               5                   10                  15

Glu Leu Ser Ala Phe Val Ser Ala Gln Arg Pro Glu Ile Glu Lys Ile
            20                  25                  30

Gly Ala Pro Val Val Asn Ala Thr Ala Phe Leu Glu Ser Phe Val Leu
        35                  40                  45

Gly Gly Gly Lys Arg Ile Arg Pro Leu Tyr Ala Trp Ala Gly Phe Val
    50                  55                  60

Gly Ala Gly Gly Leu Asp Gly Asp Glu Asp Pro Glu Ala Met Leu Arg
65                  70                  75                  80

Ala Ala Ala Ser Leu Glu Phe Ile Gln Ala Ser Ala Leu Ile His Asp
                85                  90                  95

Asp Ile Ile Asp Gly Ser Asp Thr Arg Arg Gly Gln Pro Thr Val His
            100                 105                 110

Arg Gly Val Glu Ala Val His Arg Ser Arg Gln His Leu Gly Asp Pro
        115                 120                 125

Glu Ala Phe Gly Glu Ser Val Ala Ile Leu Val Gly Asp Met Ala Leu
    130                 135                 140

Val Trp Ala Glu Asp Met Phe Gln Asp Ser Gly Leu Ser Phe Gln Ala
145                 150                 155                 160

Leu Arg Arg Ala Arg Asp Pro Trp Arg Gly Met Arg Thr Glu Val Ile
                165                 170                 175

Gly Gly Gln Leu Leu Asp Val Ser Leu Glu Ala Ala Gly Ser Glu Asp
            180                 185                 190

Glu Asn Leu Ala Asn Ser Val Asn Arg Phe Lys Thr Ala Ala Tyr Thr
        195                 200                 205

Ile Glu Arg Pro Leu His Leu Gly Ala Ala Ile Ala Gly Ala Asp Glu
    210                 215                 220

Ala Leu Ile Ala Ala Phe Arg Gly Tyr Gly Arg Asp Ile Gly Val Ala
225                 230                 235                 240

Phe Gln Leu Arg Asp Asp Gln Leu Gly Val Phe Gly Asp Pro Glu Val
                245                 250                 255

Thr Gly Lys Pro Ala Gly Asp Asp Leu Arg Glu Gly Lys Arg Thr Val
            260                 265                 270

Leu Leu Ala Leu Ala Leu Gln Arg Ala Asp Glu Ser Asn Pro Ala Ala
        275                 280                 285

Ala Ala Glu Leu Arg Ala Lys Ile Gly Asn Val Glu Asp Pro Ala Asp
    290                 295                 300

Ile Ala Arg Leu Ala Gln Ile Ile Thr Asp Ser Gly Ala Pro Ala Leu
305                 310                 315                 320

Ile Glu Gln Arg Ile Ala Ala Leu Thr Ser Ser Gly Leu Arg His Leu
                325                 330                 335

Arg Glu Ser Gly Val Ala Pro Glu Val Thr Glu Thr Leu Glu Ala Leu
            340                 345                 350

Ala Leu Lys Ala Thr Ala Arg Arg Ser
        355                 360


<210> SEQ ID NO 55
<211> LENGTH: 363
<212> TYPE: PRT
<213> ORGANISM: Corynebacterium aurimucosum
```

<400> SEQUENCE: 55

Met Thr Thr Pro Gln Ile Pro Ser Leu Asp Asp Ile Pro Val Ala Val
1 5 10 15

Arg Glu Glu Leu Glu Leu Phe Leu Asp Ser Gln Arg Asp Ala Ile Ala
20 25 30

Ser Ile Gly Ser Pro Val Thr Asn Ala Ile Ser Tyr Leu Glu Ser Phe
35 40 45

Val Leu Asp Gly Gly Lys Arg Ile Arg Pro Leu Tyr Ala Trp Ala Gly
50 55 60

Phe Ile Gly Ala His Gly Leu Glu Gly Thr Glu Ser Pro Gln Ala Met
65 70 75 80

Leu Arg Ala Ala Ser Ser Leu Glu Phe Ile Gln Ala Cys Ala Leu Ile
85 90 95

His Asp Asp Ile Val Asp Ala Ser Asp Thr Arg Arg Gly Asn Pro Thr
100 105 110

Val His Arg Gly Val Ala Ala Arg His Arg Glu Leu Gly Leu Ser Gly
115 120 125

Asp Ala Asp Phe Phe Gly Gln Ser Leu Ala Ile Leu Val Gly Asp Met
130 135 140

Ala Leu Val Trp Ala Glu Asp Met Leu Gln Asp Ser Gly Leu Ser Pro
145 150 155 160

Glu Ala Leu Ala Arg Ala Arg Ala Pro Trp Arg Ala Met Arg Arg Glu
165 170 175

Val Ile Gly Gly Gln Met Leu Asp Ile Cys Leu Glu Ala Glu Gly Ser
180 185 190

Glu Asp Ala Thr Leu Ala Asp Ser Val Asn Arg Phe Lys Thr Ala Ala
195 200 205

Tyr Thr Ile Glu Arg Pro Leu His Leu Gly Ala Ala Val Ala Gly Ala
210 215 220

Pro Glu Lys Leu Val Ala Ala Phe Arg Gly Tyr Gly Gln Asp Ile Gly
225 230 235 240

Val Ala Phe Gln Leu Arg Asp Asp Leu Leu Gly Val Phe Gly Asp Pro
245 250 255

Ala Ile Thr Gly Lys Pro Ala Gly Asp Asp Leu Arg Glu Gly Lys Arg
260 265 270

Thr Val Leu Leu Ser Leu Ala Leu Gln Arg Ala Asp Ala Thr Asp Pro
275 280 285

Ala Ala Ala Ser Glu Leu Arg Arg Leu Ile Gly Gln Thr Glu Asp Pro
290 295 300

Ala Asp Ile Ala Arg Met Ala Gln Ile Ile Ala Asp Ser Gly Ala Pro
305 310 315 320

Asp Val Val Glu Gln Arg Ile Ser Asp Leu Thr Arg Ser Gly Leu Asp
325 330 335

His Leu His Asn Ala Gln Val Ala Pro Glu Val Thr Ala Thr Leu Glu
340 345 350

Glu Leu Ala His Lys Ser Thr Ala Arg Arg Met
355 360

<210> SEQ ID NO 56
<211> LENGTH: 366
<212> TYPE: PRT
<213> ORGANISM: Corynebacterium ammoniagenes

<400> SEQUENCE: 56

-continued

```
Met Asn Asn Ser Glu Ala Phe His Gln Leu Pro Ile Ala Glu Val Pro
1               5                   10                  15

Lys His Val Arg Ala Glu Leu Ala Asp Phe Leu Lys Glu Arg Glu Pro
            20                  25                  30

Gln Ile Ala Gln Ile Gly Arg Pro Val Thr Asn Ala Ile Glu His Leu
        35                  40                  45

Glu Arg Phe Ile Leu Gly Gly Gly Lys Arg Ile Arg Pro Leu Tyr Val
    50                  55                  60

Trp Ala Gly Phe Val Ala Ala Asp Gly Leu Leu Gly Asp Glu Asp Pro
65                  70                  75                  80

Gln Ala Val Leu Arg Ala Ala Ser Ser Leu Glu Phe Ile Gln Ser Cys
                85                  90                  95

Ala Leu Ile His Asp Asp Ile Val Asp Ala Ser Asp Thr Arg Arg Gly
            100                 105                 110

Asn Pro Thr Val His Arg Ala Val Glu Ala Glu His Arg Lys Leu Gly
        115                 120                 125

Trp Thr Gly Asp Pro Glu Ala Phe Gly Arg Ser Ala Ala Ile Leu Ile
    130                 135                 140

Gly Asp Met Ser Leu Val Trp Ala Glu Asp Met Leu Leu Asp Ser Gly
145                 150                 155                 160

Leu Ser Gln Ala Ala Leu Gln Arg Thr Arg Glu Pro Trp Arg Ala Met
                165                 170                 175

Arg Thr Glu Val Ile Gly Gly Gln Leu Leu Asp Val Ser Leu Glu Ala
            180                 185                 190

Ala Ala Ile Glu Ser Val Glu Leu Ser Asp Ser Val Asn Arg Phe Lys
        195                 200                 205

Thr Ala Ala Tyr Thr Ile Glu Arg Pro Leu His Leu Gly Ala Ala Ile
    210                 215                 220

Ala Gly Ala Pro Gln Lys Leu Ile Asp Ala Phe Arg Gly Tyr Gly Arg
225                 230                 235                 240

Asp Ile Gly Ile Ala Phe Gln Leu Arg Asp Asp Gln Leu Gly Val Phe
                245                 250                 255

Gly Asp Pro Lys Val Thr Gly Lys Pro Ala Gly Asp Asp Leu Arg Glu
            260                 265                 270

Gly Lys Arg Thr Val Leu Met Ala Ile Ala Leu Gln Arg Ala Asp Glu
        275                 280                 285

Gln Asp Pro Ser Ala Ala Gln Phe Leu Arg Asp Asn Leu Gly Ala Thr
    290                 295                 300

Asp Asp Pro Ser Val Leu Ser Lys Met Ala Gln Met Ile Glu Asp Ser
305                 310                 315                 320

Gly Ala Pro Glu Glu Ile Glu Gln Arg Ile Asp Ala Leu Thr Gln Ser
                325                 330                 335

Gly Leu Glu Tyr Leu Ala Ala Ala Gln Val Asn Ser Glu Val Thr Glu
            340                 345                 350

Leu Leu Arg Ser Leu Ala Ile Gln Ser Thr Ala Arg Ala Lys
        355                 360                 365
```

<210> SEQ ID NO 57
<211> LENGTH: 359
<212> TYPE: PRT
<213> ORGANISM: Corynebacterium kefirresidentii

<400> SEQUENCE: 57

```
Met Gln Asn Ile Pro Glu Leu Ala Asp Ile Pro Gly Ala Val Arg Glu
1               5                   10                  15
```

```
Glu Leu Ala Thr Phe Leu Asp Gln Arg Arg Glu Gln Val Ala Ala Ile
            20                  25                  30

Gly Ala Pro Val Thr Lys Ala Val Ser Phe Leu Glu Ser Phe Val Leu
        35                  40                  45

Asp Gly Gly Lys Arg Val Arg Pro Thr Tyr Ala Trp Ala Gly Tyr Leu
    50                  55                  60

Ala Ala Gly Arg Gly Glu Glu Asp Pro Glu Ala Met Leu Arg Ala Ser
65                  70                  75                  80

Ala Ser Leu Glu Phe Ile Gln Ala Cys Ala Leu Ile His Asp Asp Ile
                85                  90                  95

Ile Asp Ala Ser Asn Thr Arg Arg Gly Asn Pro Thr Val His Arg Gly
            100                 105                 110

Val Glu Lys Leu His Arg Glu Ser Gly Tyr Leu Gly Asp Pro Glu Phe
        115                 120                 125

Phe Gly Thr Ser Val Ala Ile Leu Val Gly Asp Leu Ala Leu Val Tyr
    130                 135                 140

Ala Glu Asp Met Phe Gln Asp Ser Gly Leu Ser Ala Ala Ala Leu His
145                 150                 155                 160

Arg Ala Arg Asn Ala Trp Arg Gly Met Arg Thr Glu Val Ile Gly Gly
                165                 170                 175

Gln Leu Leu Asp Ile Ser Leu Glu Ala Ala Gly Ser Glu Ser Val Glu
            180                 185                 190

Leu Ala Asn Ser Val Asn Arg Tyr Lys Thr Ala Ala Tyr Thr Ile Glu
        195                 200                 205

Arg Pro Leu His Leu Gly Ala Ser Ile Ala Gly Ala Ser Glu Glu Leu
    210                 215                 220

Ile Ala Ala Phe Arg Gly Tyr Gly Gln Asp Ile Gly Ile Ala Tyr Gln
225                 230                 235                 240

Leu Arg Asp Asp Gln Leu Gly Val Phe Gly Asp Pro Ala Val Thr Gly
                245                 250                 255

Lys Pro Ala Gly Asp Asp Leu Arg Glu Gly Lys Arg Thr Glu Leu Leu
            260                 265                 270

Ala Leu Ala Leu Arg Arg Ala Asp Glu Ser Asp Pro Gln Ala Ala Ala
        275                 280                 285

Thr Leu Arg Lys Leu Ile Gly His Thr Ser Asp Pro Gln Glu Leu Ser
    290                 295                 300

Arg Leu Ala Gln Ile Ile Ala Asp Ser Gly Ala Pro Glu Glu Ile Glu
305                 310                 315                 320

Arg Arg Ile Glu Ala Leu Thr Gln Ser Gly Leu Gln His Leu Arg Ala
                325                 330                 335

Ala Arg Val Asp Pro Ala Val Thr Glu Thr Leu Glu Gln Leu Ala Ile
            340                 345                 350

Lys Ala Thr Ala Arg His Lys
        355


<210> SEQ ID NO 58
<211> LENGTH: 363
<212> TYPE: PRT
<213> ORGANISM: Corynebacterium camporealensis

<400> SEQUENCE: 58

Met Thr Phe Pro Asn Val Pro Ser Leu Ala Asp Val Pro Ser Thr Thr
1               5                   10                  15

Gln Glu Leu Leu Ser Glu Phe Leu Glu Ala Arg Arg Pro Gln Val Ala
```

```
            20                  25                  30

Glu Ile Gly Gln Pro Val Thr Gln Ala Thr Gln Phe Leu Glu Asp Phe
        35                  40                  45

Val Leu Gly Gly Gly Lys Arg Ile Arg Pro Leu Tyr Ala Trp Ala Gly
    50                  55                  60

Phe Ile Gly Ala Asp Gly Leu Asp Gly Asp Glu Asp Pro Gln Ala Val
65                  70                  75                  80

Leu Arg Ala Ala Ala Ser Leu Glu Phe Ile Gln Ala Cys Ala Leu Ile
                85                  90                  95

His Asp Asp Ile Ile Asp Ala Ser Asp Thr Arg Arg Gly Asn Pro Thr
            100                 105                 110

Val His Arg Gly Val Ala Ala Leu His Trp Glu Ala Gly Tyr Gln Gly
        115                 120                 125

Ser Pro Glu Phe Phe Gly Gln Ser Val Ala Ile Leu Val Gly Asp Leu
    130                 135                 140

Ala Leu Ala Trp Ser Glu Asp Met Leu Gln Asp Ser Gly Leu Ser Ala
145                 150                 155                 160

Ala Ala Leu Gln Arg Val Arg Glu Pro Trp Arg Ala Met Arg Thr Glu
                165                 170                 175

Val Ile Gly Gly Gln Leu Leu Asp Ile Thr Leu Glu Ala Gln Gly Ser
            180                 185                 190

Glu Ser Val Glu Leu Ala Asp Ala Val Asn Arg Tyr Lys Thr Ala Ala
        195                 200                 205

Tyr Thr Ile Glu Arg Pro Leu His Ile Gly Ala Ala Leu Ala Asp Ala
    210                 215                 220

Pro Ser His Leu Ile Asp Ala Phe Arg Gly Tyr Gly Arg Asp Ile Gly
225                 230                 235                 240

Ile Ala Phe Gln Leu Arg Asp Asp Gln Leu Gly Val Phe Gly Asp Pro
                245                 250                 255

Ser Val Thr Gly Lys Pro Ala Gly Asp Asp Leu Arg Glu Gly Lys Arg
            260                 265                 270

Thr Val Leu Leu Ala Leu Ala Leu Gln Glu Leu Asp Glu Lys Asp Pro
        275                 280                 285

Ser Ala Ala Ala Thr Leu Arg Ala Gly Val Gly Asn Val Ser Glu Pro
    290                 295                 300

Glu Glu Leu Ala Lys Leu Ser Gln Ile Ile Glu Asp Ser Gly Ala Pro
305                 310                 315                 320

Gly Leu Ile Glu Lys Arg Ile Ala Arg Leu Thr Glu Ser Gly Leu Asn
                325                 330                 335

His Leu Arg Ala Ala Asp Val Ser Asp Glu Val Thr Ala Thr Leu Glu
            340                 345                 350

Glu Leu Ala His Lys Ala Thr Ala Arg Arg Ala
        355                 360


<210> SEQ ID NO 59
<211> LENGTH: 359
<212> TYPE: PRT
<213> ORGANISM: Corynebacterium tuberculostearicum

<400> SEQUENCE: 59

Met Gln Asn Ile Pro Glu Leu Ala Asp Ile Pro Gly Ala Val Arg Glu
1               5                   10                  15

Glu Leu Ala Thr Phe Leu Asp Gln Arg Arg Glu Gln Val Ala Ala Ile
            20                  25                  30
```

-continued

Gly Ala Pro Val Thr Lys Ala Val Ser Phe Leu Glu Ser Phe Val Leu
35 40 45

Asp Gly Gly Lys Arg Val Arg Pro Thr Tyr Ala Trp Ala Gly Tyr Leu
50 55 60

Ala Ala Gly Arg Gly Glu Glu Asp Pro Val Ala Met Leu Arg Ala Ala
65 70 75 80

Ala Ser Leu Glu Phe Ile Gln Ala Cys Ala Leu Ile His Asp Asp Ile
85 90 95

Ile Asp Ala Ser Asn Thr Arg Arg Gly Asn Pro Thr Val His Arg Gly
100 105 110

Val Glu Lys Leu His Arg Glu Ser Glu Tyr Leu Gly Asp Pro Glu Phe
115 120 125

Phe Gly Thr Ser Val Ala Ile Leu Val Gly Asp Leu Ala Leu Val Tyr
130 135 140

Ala Glu Asp Met Phe Gln Asp Ser Gly Leu Ser Ala Ala Ala Leu His
145 150 155 160

Arg Ala Arg Ser Pro Trp Arg Gly Met Arg Thr Glu Val Ile Gly Gly
165 170 175

Gln Leu Leu Asp Ile Ser Leu Glu Ala Ala Gly Ser Glu Ser Val Glu
180 185 190

Leu Ala Asn Ser Val Asn Arg Tyr Lys Thr Ala Ala Tyr Thr Ile Glu
195 200 205

Arg Pro Leu His Leu Gly Ala Ala Thr Ala Gly Ala Ser Glu Glu Leu
210 215 220

Ile Ala Ala Phe Arg Gly Tyr Gly His Asp Ile Gly Ile Ala Tyr Gln
225 230 235 240

Leu Arg Asp Asp Gln Leu Gly Val Phe Gly Asp Pro Ala Val Thr Gly
245 250 255

Lys Pro Ala Gly Asp Asp Leu Arg Glu Gly Lys Arg Thr Glu Leu Leu
260 265 270

Ala Leu Ala Leu Gln Arg Ala Asp Glu Ser Asp Pro Gln Ala Ala Ala
275 280 285

Thr Leu Arg Lys Leu Ile Gly Arg Thr Ser Asp Pro Gln Glu Leu Ser
290 295 300

Arg Leu Ala Gln Ile Ile Ala Asp Ser Gly Ala Pro Glu Glu Ile Glu
305 310 315 320

Arg Arg Ile Asp Ala Leu Thr Gln Ser Gly Leu Gln His Leu Arg Ala
325 330 335

Ala Gln Val Asp Pro Ala Val Thr Glu Thr Leu Glu Gln Leu Ala Ile
340 345 350

Lys Ala Thr Ala Arg Arg Lys
355

<210> SEQ ID NO 60
<211> LENGTH: 359
<212> TYPE: PRT
<213> ORGANISM: Corynebacterium pseudogenitalium

<400> SEQUENCE: 60

Met Gln Asn Ile Pro Glu Leu Ala Asp Ile Pro Gly Ala Val Arg Glu
1 5 10 15

Glu Leu Ala Thr Phe Leu Asp Gln Arg Arg Glu Gln Val Ala Ala Ile
20 25 30

Gly Ala Pro Val Thr Lys Ala Val Ser Phe Leu Glu Ser Phe Val Leu
35 40 45

Asp Gly Gly Lys Arg Val Arg Pro Thr Tyr Ala Trp Ala Gly Tyr Leu
    50                  55                  60

Ala Ala Gly Arg Gly Glu Glu Asp Pro Ala Ala Met Leu Arg Ala Ala
65                  70                  75                  80

Ala Ser Leu Glu Phe Ile Gln Ala Cys Ala Leu Ile His Asp Asp Ile
                85                  90                  95

Ile Asp Ala Ser Asn Thr Arg Arg Gly Asn Pro Thr Val His Arg Gly
            100                 105                 110

Val Glu Lys Leu His Arg Glu Ser Glu Tyr Leu Gly Asp Pro Glu Phe
        115                 120                 125

Phe Gly Thr Ser Val Ala Ile Leu Val Gly Asp Leu Ala Leu Val Tyr
    130                 135                 140

Ala Glu Asp Met Phe Gln Asp Ser Gly Leu Ser Ala Ala Ala Leu His
145                 150                 155                 160

Arg Ala Arg Ser Pro Trp Arg Gly Met Arg Thr Glu Val Ile Gly Gly
                165                 170                 175

Gln Leu Leu Asp Ile Ser Leu Glu Ala Ala Gly Ser Glu Ser Val Glu
            180                 185                 190

Leu Ala Asn Ser Val Asn Arg Tyr Lys Thr Ala Ala Tyr Thr Ile Glu
        195                 200                 205

Arg Pro Leu His Leu Gly Ala Ala Ile Ala Gly Ala Ser Glu Glu Leu
    210                 215                 220

Ile Ala Ala Phe Arg Gly Tyr Gly His Asp Ile Gly Ile Ala Tyr Gln
225                 230                 235                 240

Leu Arg Asp Asp Gln Leu Gly Val Phe Gly Asp Pro Ala Val Thr Gly
                245                 250                 255

Lys Pro Ala Gly Asp Asp Leu Arg Glu Gly Lys Arg Thr Glu Leu Leu
            260                 265                 270

Ala Leu Ala Leu His Arg Ala Asp Glu Ser Asp Pro Gln Ala Ala Ala
        275                 280                 285

Thr Leu Arg Lys Leu Ile Gly Arg Thr Ser Asp Pro Gln Glu Leu Ser
    290                 295                 300

Arg Leu Ala Gln Ile Ile Ala Asp Ser Gly Ala Pro Glu Glu Ile Glu
305                 310                 315                 320

Arg Arg Ile Asp Ala Leu Thr Gln Ser Gly Leu Gln His Leu His Ala
                325                 330                 335

Ala Gln Val Asp Pro Ala Val Thr Glu Thr Leu Glu Gln Leu Ala Ile
            340                 345                 350

Lys Ala Thr Ala Arg Arg Lys
        355

<210> SEQ ID NO 61
<211> LENGTH: 422
<212> TYPE: PRT
<213> ORGANISM: Corynebacterium testudinoris

<400> SEQUENCE: 61

Met Arg Ala Arg Ser Leu Phe Ser Pro Leu Pro Ser Arg Tyr Arg Ala
1               5                   10                  15

Trp Trp Lys Ser Gln Leu Arg Ile Leu His Pro Ala Asn Thr Pro Arg
            20                  25                  30

Leu Arg Leu Ser Arg His Leu Thr Gly Tyr Pro Lys Gly His Gln Phe
        35                  40                  45

Leu His Phe Glu Gly Pro Asp Ala Leu Asn Phe Pro Asp Pro Arg Ser

-continued

```
    50                  55                  60

Leu Thr Leu Asp Gln Ile Pro Gly Ala Thr Gln Asp Val Leu Val Glu
65                  70                  75                  80

Phe Leu Arg Ser Arg Glu Gln Gln Ile Ser Ala Ile Gly Gln Pro Val
                85                  90                  95

Thr Glu Ala Val Ser His Leu Glu Ala Phe Val Val Gly Gly Gly Lys
            100                 105                 110

Arg Ile Arg Pro Leu Tyr Ala Trp Ala Gly Phe Val Gly Gly Gly Gly
        115                 120                 125

Leu Thr Asn Gly Lys Glu Asp Pro Tyr Ala Met Leu Lys Ala Ala Ala
    130                 135                 140

Ser Leu Glu Phe Ile Gln Ala Cys Ala Leu Ile His Asp Asp Ile Ile
145                 150                 155                 160

Asp Ala Ser Asp Thr Arg Arg Gly Gln Pro Thr Val His Arg Ala Val
                165                 170                 175

Glu Ala Arg His Ser Ser Ala Gln Trp Val Lys Glu Ser Ala His Phe
            180                 185                 190

Gly Glu Ser Val Ala Ile Leu Val Gly Asp Leu Ala Leu Val Trp Ala
        195                 200                 205

Glu Asp Met Leu Gln Asp Ser Gly Leu Ser Asp Asp Ala Lys Ala Arg
    210                 215                 220

Ala Arg Asp Pro Trp Arg Ala Met Arg Thr Glu Val Ile Gly Gly Gln
225                 230                 235                 240

Leu Leu Asp Ile Tyr Leu Glu Ala Ser Gly Ser Glu Ser Ile Glu Ala
                245                 250                 255

Ala Asp Ala Val Asn Arg Tyr Lys Thr Ala Ala Tyr Thr Ile Glu Arg
            260                 265                 270

Pro Leu His Leu Gly Ala Ala Val Ala Gly Ala Asp Glu Ala Thr Ile
        275                 280                 285

Ala Ala Phe Arg Gly Tyr Gly Arg Asp Ile Gly Ile Ala Tyr Gln Leu
    290                 295                 300

Arg Asp Asp Tyr Leu Gly Val Phe Gly Asp Pro Gly Val Thr Gly Lys
305                 310                 315                 320

Pro Ala Gly Asp Asp Leu Arg Glu Gly Lys Arg Thr Val Leu Leu Ala
                325                 330                 335

Thr Ala Leu Gln Leu Ala Asp Glu His Asp Pro Ser Ala Ala Ala Glu
            340                 345                 350

Leu Arg Thr Lys Ile Gly Thr Thr Thr Asp Leu Ala Glu Val Ala Arg
        355                 360                 365

Leu Thr Glu Ile Ile Ala Ser Thr Gly Ala Val Glu Ala Met Glu Lys
    370                 375                 380

Arg Ile Asp Ala Leu Thr Ala Ser Gly Leu Ala Tyr Leu Asp Ala Ala
385                 390                 395                 400

Gly Thr Ser Pro Glu Val Thr Asp Thr Leu Arg Asp Leu Ala Ile Arg
                405                 410                 415

Ser Thr Phe Arg Arg Ser
            420
```

<210> SEQ ID NO 62
<211> LENGTH: 366
<212> TYPE: PRT
<213> ORGANISM: Corynebacterium stationis

<400> SEQUENCE: 62

-continued

```
Met Asn Asn Ser Glu Asp Phe Ser Gln Leu Pro Ile Ala Glu Ile Pro
1               5                   10                  15

Lys His Val Arg Ala Glu Leu Ser Ser Phe Leu Lys Ala Arg Glu Pro
            20                  25                  30

Gln Leu Ala Gln Ile Gly Lys Pro Val Thr Glu Ala Ile Glu His Leu
        35                  40                  45

Glu Arg Phe Val Leu Asp Gly Gly Lys Arg Ile Arg Pro Leu Tyr Ala
    50                  55                  60

Trp Ala Gly Phe Val Ala Ala Asp Gly Leu Leu Gly Ser Glu Glu Pro
65                  70                  75                  80

Gln Ala Val Leu Arg Ala Ala Ser Ser Leu Glu Phe Ile Gln Ser Cys
                85                  90                  95

Ala Leu Ile His Asp Asp Ile Val Asp Ala Ser Asp Thr Arg Arg Gly
            100                 105                 110

Asn Pro Thr Val His Arg Ala Val Glu Ala Gln His Arg Ala Leu Gly
        115                 120                 125

Trp Thr Gly Asp Ser Ala Asp Phe Gly Arg Ser Ala Ala Ile Leu Ile
    130                 135                 140

Gly Asp Met Ser Leu Val Trp Ala Glu Asp Met Phe Leu Asp Ser Gly
145                 150                 155                 160

Ile Ser Gln Ala Ala Ile Gln Arg Ala Arg Glu Pro Trp Arg Ala Met
                165                 170                 175

Arg Thr Glu Val Ile Gly Gly Gln Leu Leu Asp Val Ser Leu Glu Ala
            180                 185                 190

Ala Ala Ile Glu Ser Val Glu Leu Ser Asp Ser Val Asn Arg Phe Lys
        195                 200                 205

Thr Ala Ala Tyr Thr Ile Glu Arg Pro Leu His Leu Gly Ala Ala Ile
    210                 215                 220

Ala Gly Ala Ser Asp Lys Leu Ile Asp Ala Phe Arg Gly Tyr Gly Arg
225                 230                 235                 240

Asp Ile Gly Ile Ala Phe Gln Leu Arg Asp Asp Gln Leu Gly Val Phe
                245                 250                 255

Gly Asp Pro Gln Val Thr Gly Lys Pro Ala Gly Asp Asp Leu Arg Glu
            260                 265                 270

Gly Lys Arg Thr Val Leu Met Ala Ile Ala Leu Gln Arg Ala Asp Glu
        275                 280                 285

Gln Asp Pro Pro Thr Ala Lys Phe Leu Arg Glu Asn Leu Gly Ala Thr
    290                 295                 300

Asp Asp Pro Ser Val Leu Ser Lys Met Ser Gln Met Ile Glu Asp Ser
305                 310                 315                 320

Gly Ala Ser Glu Glu Ile Glu Gln Arg Ile Asp Ala Leu Thr Gln Ser
                325                 330                 335

Gly Leu Glu Tyr Leu Ala Ala Ala Asn Val Asn Ser Glu Val Thr Glu
            340                 345                 350

Leu Leu Arg Ser Leu Ala Ile Lys Ser Thr Ala Arg Ala Lys
        355                 360                 365
```

<210> SEQ ID NO 63
<211> LENGTH: 366
<212> TYPE: PRT
<213> ORGANISM: Corynebacterium sp.

<400> SEQUENCE: 63

```
Met Asn Asn Ser Glu Asp Phe Ser Gln Leu Pro Ile Ala Glu Ile Pro
1               5                   10                  15
```

```
Lys His Val Arg Ala Glu Leu Ser Ser Phe Leu Lys Ala Arg Glu Pro
            20                  25                  30

Gln Leu Ala Gln Ile Gly Lys Pro Val Thr Glu Ala Ile Glu His Leu
        35                  40                  45

Glu Arg Phe Val Leu Asp Gly Gly Lys Arg Ile Arg Pro Leu Tyr Ala
    50                  55                  60

Trp Ala Gly Phe Val Ala Ala Asp Gly Leu Leu Gly Ser Glu Asp Pro
65                  70                  75                  80

Gln Ala Val Leu Arg Ala Ala Ser Ser Leu Glu Phe Ile Gln Ser Cys
                85                  90                  95

Ala Leu Ile His Asp Asp Ile Val Asp Ala Ser Asp Thr Arg Arg Gly
            100                 105                 110

Asn Pro Thr Val His Arg Ala Val Glu Ala Gln His Arg Ala Leu Gly
        115                 120                 125

Trp Thr Gly Asn Ser Ala Asp Phe Gly Arg Ser Ala Ala Ile Leu Ile
    130                 135                 140

Gly Asp Met Ser Leu Val Trp Ala Glu Asp Met Phe Leu Asp Ser Gly
145                 150                 155                 160

Ile Ser Gln Ala Ala Ile Gln Arg Ala Arg Glu Pro Trp Arg Ala Met
                165                 170                 175

Arg Thr Glu Val Ile Gly Gly Gln Leu Leu Asp Val Ser Leu Glu Ala
            180                 185                 190

Ala Ala Ile Glu Ser Val Glu Leu Ser Asp Ser Val Asn Arg Phe Lys
        195                 200                 205

Thr Ala Ala Tyr Thr Ile Glu Arg Pro Leu His Leu Gly Ala Ala Ile
    210                 215                 220

Ala Gly Ala Ser Asp Lys Leu Ile Asp Ala Phe Arg Gly Tyr Gly Arg
225                 230                 235                 240

Asp Ile Gly Ile Ala Phe Gln Leu Arg Asp Asp Gln Leu Gly Val Phe
                245                 250                 255

Gly Asp Pro Gln Val Thr Gly Lys Pro Ala Gly Asp Asp Leu Arg Glu
            260                 265                 270

Gly Lys Arg Thr Val Leu Met Ala Ile Ala Leu Gln Arg Ala Asp Glu
        275                 280                 285

Gln Asp Pro Ala Ala Ala Lys Phe Leu Arg Glu Asn Leu Gly Ala Thr
    290                 295                 300

Asp Asp Pro Ser Val Leu Ser Lys Met Ser Gln Met Ile Glu Asp Ser
305                 310                 315                 320

Gly Ala Pro Glu Glu Ile Glu Gln Arg Ile Asp Ala Leu Thr Gln Ser
                325                 330                 335

Gly Leu Glu Tyr Leu Ala Ala Ala Asn Val Asn Ser Glu Val Thr Glu
            340                 345                 350

Leu Leu Arg Ser Leu Ala Ile Lys Ser Thr Ala Arg Ala Lys
        355                 360                 365


<210> SEQ ID NO 64
<211> LENGTH: 358
<212> TYPE: PRT
<213> ORGANISM: Corynebacterium sp.

<400> SEQUENCE: 64

Met Thr Leu Asp Gln Ile Pro Glu Ala Thr Thr Lys Leu Leu Ala Glu
1               5                   10                  15

Phe Ile His Ala Arg Ser Glu Gln Val Ala Ala Ile Gly Gly Pro Val
```

```
            20                  25                  30

Ala Glu Ala Val Ser His Leu Glu Ser Phe Ile Leu Asn Gly Gly Lys
        35                  40                  45

Arg Ile Arg Pro Leu Tyr Ala Trp Ala Gly Phe Ile Gly Gly Gly Gly
    50                  55                  60

Leu Thr Asn Thr Asp Glu Asp Pro Leu Ala Met Leu Arg Ala Ala Ala
65                  70                  75                  80

Ser Leu Glu Phe Ile Gln Ala Cys Ala Leu Ile His Asp Asp Ile Ile
                85                  90                  95

Asp Ala Ser Asp Thr Arg Arg Gly Ser Pro Thr Val His Arg Ser Val
            100                 105                 110

Glu Ala Arg His Arg Asp Ala His Trp Ser Gly Ser Ser Ser His Phe
        115                 120                 125

Gly Glu Ser Val Ala Ile Leu Val Gly Asp Leu Ala Leu Val Trp Ala
    130                 135                 140

Glu Asp Met Phe Gln Asp Ser Gly Leu Ser Ser Glu Ala Leu Ala Arg
145                 150                 155                 160

Ala Arg Glu Pro Trp Arg Ala Met Arg Thr Glu Val Ile Gly Gly Gln
                165                 170                 175

Leu Leu Asp Ile Ala Leu Glu Ala Ala Ala Ser Glu Asp Ile Ser Ala
            180                 185                 190

Ala Asp Ser Val Asn Arg Phe Lys Thr Ala Ala Tyr Thr Ile Glu Arg
        195                 200                 205

Pro Leu His Leu Gly Ala Ala Ile Ala Asn Ala Glu Ala Asp Thr Ile
    210                 215                 220

Ser Ala Phe Arg Gly Tyr Gly Gln Asp Ile Gly Val Ala Phe Gln Leu
225                 230                 235                 240

Arg Asp Asp Gln Leu Gly Val Tyr Gly Asp Pro Lys Leu Thr Gly Lys
                245                 250                 255

Pro Ala Gly Asp Asp Leu Arg Glu Gly Lys Arg Thr Val Leu Leu Ala
            260                 265                 270

Thr Ala Leu Arg Leu Ala Asp Ser Ser Asp Pro Ala Ala Ala Ala Ala
        275                 280                 285

Leu Arg Ser Gly Ile Gly Ser Thr Ala Asp Pro Leu Glu Leu Ser His
    290                 295                 300

Leu Ala Asp Leu Ile Ala Gly Thr Gly Ala Val Ala Glu Ile Glu Gln
305                 310                 315                 320

Arg Ile Glu His Leu Thr Glu Ser Gly Leu Ser His Leu Ala Thr Ala
                325                 330                 335

His Thr Ser Ala Glu Val Thr Arg Thr Leu Thr Asp Leu Ala Ile Arg
            340                 345                 350

Ala Thr Ala Arg Arg Ser
        355


<210> SEQ ID NO 65
<211> LENGTH: 359
<212> TYPE: PRT
<213> ORGANISM: Corynebacterium sp.

<400> SEQUENCE: 65

Met Thr Asn Ile Pro Glu Leu Ala Asp Ile Pro Gly Ala Val Arg Glu
1               5                   10                  15

Lys Leu Ala Ile Phe Leu Asp Gln Arg Arg Asp His Val Ala Glu Ile
            20                  25                  30
```

```
Gly Ala Pro Val Ser Thr Ala Met Ser Phe Leu Glu Ser Phe Val Leu
        35                  40                  45

Asp Gly Gly Lys Arg Val Arg Pro Met Tyr Ala Trp Ala Gly Tyr Leu
    50                  55                  60

Ala Ala Gly Arg Gly Ser Glu Ser Pro Glu Ala Met Leu Arg Ala Ala
65                  70                  75                  80

Ser Ser Leu Glu Phe Ile Gln Ala Cys Ala Leu Ile His Asp Asp Ile
                85                  90                  95

Ile Asp Ala Ser Asn Thr Arg Arg Gly Lys Pro Thr Val His Arg Glu
            100                 105                 110

Ala Glu Arg Leu His Arg Glu Ser Asp Phe Leu Gly Asp Pro Glu Phe
        115                 120                 125

Phe Gly Thr Ser Val Ala Ile Leu Val Gly Asp Phe Ala Leu Val Tyr
    130                 135                 140

Ala Glu Asp Met Phe Gln Asp Ser Gly Leu Ser Ser Glu Ala Leu Gln
145                 150                 155                 160

Arg Ala Arg Asp Pro Trp Arg Gly Met Arg Thr Glu Val Leu Gly Gly
                165                 170                 175

Gln Leu Leu Asp Ile Ser Leu Glu Ala Ala Gly Ser Glu Ser Val Ala
            180                 185                 190

Leu Ser Asn Ser Val Asn Arg Tyr Lys Thr Ala Ala Tyr Thr Ile Glu
        195                 200                 205

Arg Pro Leu His Leu Gly Ala Ala Ile Ala Gly Ala Ser Asp Glu Leu
    210                 215                 220

Ile Ser Ala Phe Arg Gly Tyr Gly His Asp Ile Gly Ile Ala Tyr Gln
225                 230                 235                 240

Leu Arg Asp Asp Gln Leu Gly Val Phe Gly Asp Pro Glu Ile Thr Gly
                245                 250                 255

Lys Pro Ala Gly Asp Asp Leu Arg Glu Gly Lys Arg Thr Glu Leu Leu
            260                 265                 270

Ala Leu Ala Leu Gln Arg Ala Asp Glu Arg Asp Pro Ser Ala Ala Ala
        275                 280                 285

Thr Leu Arg Lys Phe Ile Gly Arg Thr Ser Asp Thr Gln Asp Leu Leu
    290                 295                 300

Arg Leu Ser Gln Ile Ile Ala Asp Ser Gly Ala Pro Asp Glu Ile Glu
305                 310                 315                 320

Arg Arg Ile Thr Ala Leu Thr Glu Ser Gly Leu Ala His Leu Arg Ala
                325                 330                 335

Ala Asn Val Asp Pro Gln Ile Thr Glu Thr Leu Glu His Leu Ala Ile
            340                 345                 350

Gln Ala Thr Thr Arg Gln Lys
        355
```

<210> SEQ ID NO 66
<211> LENGTH: 359
<212> TYPE: PRT
<213> ORGANISM: Corynebacterium accolens

<400> SEQUENCE: 66

```
Met Thr Asn Ile Pro Glu Leu Ala Asp Ile Pro Gly Ala Val Arg Glu
1               5                   10                  15

Lys Leu Ala Ile Phe Leu Asp Gln Arg Arg Glu His Val Ala Glu Ile
            20                  25                  30

Gly Ala Pro Val Ser Thr Ala Met Ser Phe Leu Glu Ser Phe Val Leu
        35                  40                  45
```

```
Asp Gly Gly Lys Arg Val Arg Pro Met Tyr Ala Trp Ala Gly Tyr Leu
    50                  55                  60

Ala Ala Gly Arg Gly Ser Glu Ser Pro Glu Ala Met Leu Arg Ala Ala
65                  70                  75                  80

Ser Ser Leu Glu Phe Ile Gln Ala Cys Ala Leu Ile His Asp Asp Ile
                85                  90                  95

Ile Asp Ala Ser Asn Thr Arg Arg Gly Lys Pro Thr Val His Arg Glu
            100                 105                 110

Ala Glu Arg Leu His Arg Glu Ser Asp Phe Leu Gly Asp Pro Glu Phe
        115                 120                 125

Phe Gly Thr Ser Val Ala Ile Leu Val Gly Asp Phe Ala Leu Val Tyr
    130                 135                 140

Ala Glu Asp Met Phe Gln Asp Ser Gly Leu Ser Pro Glu Ala Leu Gln
145                 150                 155                 160

Arg Ala Arg Glu Pro Trp Arg Gly Met Arg Thr Glu Val Leu Gly Gly
                165                 170                 175

Gln Leu Leu Asp Ile Ser Leu Glu Ala Ala Gly Ser Glu Ser Val Ala
            180                 185                 190

Leu Ser Asn Ser Val Asn Arg Tyr Lys Thr Ala Ala Tyr Thr Ile Glu
        195                 200                 205

Arg Pro Leu His Leu Gly Ala Ala Ile Ala Gly Ala Arg Glu Glu Leu
    210                 215                 220

Ile Ser Ala Phe Arg Gly Tyr Gly His Asp Ile Gly Ile Ala Tyr Gln
225                 230                 235                 240

Leu Arg Asp Asp Gln Leu Gly Val Phe Gly Asp Pro Ala Ile Thr Gly
                245                 250                 255

Lys Pro Ala Gly Asp Asp Leu Arg Glu Gly Lys Arg Thr Glu Leu Leu
            260                 265                 270

Ala Leu Ala Leu Gln Arg Ala Asp Glu Arg Asp Pro Ser Ala Ala Ala
        275                 280                 285

Thr Leu Arg Lys Phe Ile Gly Arg Thr Ser Asp Pro Gln Asp Leu Leu
    290                 295                 300

Arg Leu Ser Gln Ile Ile Ala Asp Ser Gly Ala Pro Asp Glu Ile Glu
305                 310                 315                 320

Arg Arg Ile Thr Ala Leu Thr Glu Ser Gly Leu Ala His Leu Arg Ala
                325                 330                 335

Ala Asn Val Asp Pro Gln Ile Thr Glu Thr Leu Glu His Leu Ala Ile
            340                 345                 350

Gln Ala Thr Thr Arg Gln Lys
        355
```

<210> SEQ ID NO 67
<211> LENGTH: 359
<212> TYPE: PRT
<213> ORGANISM: Corynebacterium segmentosum

<400> SEQUENCE: 67

```
Met Thr Asn Ile Pro Glu Leu Ala Asp Ile Pro Gly Ala Val Arg Glu
1               5                   10                  15

Lys Leu Ala Ile Phe Leu Asp Gln Arg Arg Asp His Val Ala Glu Ile
            20                  25                  30

Gly Ala Pro Val Ser Thr Ala Met Ser Phe Leu Glu Ser Phe Val Leu
        35                  40                  45

Asp Gly Gly Lys Arg Val Arg Pro Met Tyr Ala Trp Ala Gly Tyr Leu
```

```
    50                  55                  60

Ala Ala Gly Arg Gly Ser Glu Ser Pro Glu Ala Met Leu Arg Ala Ala
65                  70                  75                  80

Ser Ser Leu Glu Phe Ile Gln Ala Cys Ala Leu Ile His Asp Asp Ile
                85                  90                  95

Ile Asp Ala Ser Asn Thr Arg Arg Gly Lys Pro Thr Val His Arg Gly
            100                 105                 110

Ala Glu Arg Leu His Arg Glu Ser Asp Phe Leu Gly Asp Pro Glu Phe
        115                 120                 125

Phe Gly Thr Ser Val Ala Ile Leu Val Gly Asp Phe Ala Leu Val Tyr
    130                 135                 140

Ala Glu Asp Met Phe Gln Asp Ser Gly Leu Ser Pro Glu Ala Leu Gln
145                 150                 155                 160

Arg Ala Arg Glu Pro Trp Arg Gly Met Arg Thr Glu Val Leu Gly Gly
                165                 170                 175

Gln Leu Leu Asp Ile Ser Leu Glu Ala Ala Gly Ser Glu Ser Val Ala
            180                 185                 190

Leu Ser Asn Ser Val Asn Arg Tyr Lys Thr Ala Ala Tyr Thr Ile Glu
        195                 200                 205

Arg Pro Leu His Leu Gly Ala Ala Ile Ala Gly Ala Ser Glu Glu Leu
    210                 215                 220

Ile Ser Ala Phe Arg Gly Tyr Gly Tyr Asp Ile Gly Ile Ala Tyr Gln
225                 230                 235                 240

Leu Arg Asp Asp Gln Leu Gly Val Phe Gly Asp Pro Ala Ile Thr Gly
                245                 250                 255

Lys Pro Ala Gly Asp Asp Leu Arg Glu Gly Lys Arg Thr Glu Leu Leu
            260                 265                 270

Ala Leu Ala Leu Gln Arg Ala Asp Glu Arg Asp Pro Ser Ala Ala Ala
        275                 280                 285

Thr Leu Arg Lys Phe Ile Gly Arg Thr Ser Asp Thr Gln Asp Leu Leu
    290                 295                 300

Arg Leu Ser Gln Ile Ile Ala Asp Ser Gly Ala Pro Asp Glu Ile Glu
305                 310                 315                 320

Arg Arg Ile Thr Ala Leu Thr Glu Ser Gly Leu Ala His Leu Arg Ala
                325                 330                 335

Ala Asn Val Asp Pro Gln Ile Thr Glu Thr Leu Glu His Leu Ala Val
            340                 345                 350

Gln Ala Thr Thr Arg Gln Lys
        355


<210> SEQ ID NO 68
<211> LENGTH: 359
<212> TYPE: PRT
<213> ORGANISM: Corynebacterium macginleyi

<400> SEQUENCE: 68

Met Thr Asn Ile Pro Glu Leu Ala Asp Ile Pro Gly Ala Val Arg Glu
1               5                   10                  15

Glu Leu Thr Asn Phe Leu Asp Gln Arg Arg Asp His Val Ala Glu Ile
            20                  25                  30

Gly Thr Pro Val Ser Thr Ala Met Ser Leu Leu Glu Ser Phe Ile Leu
        35                  40                  45

Asp Gly Gly Lys Arg Ile Arg Pro Ile Tyr Ala Trp Ala Gly Tyr Leu
    50                  55                  60
```

```
Ala Ala Gly Arg Gly Thr Glu Ser Pro Glu Ala Met Leu Arg Ala Ala
65                  70                  75                  80

Ser Ser Leu Glu Phe Ile Gln Ala Cys Ala Leu Ile His Asp Asp Ile
                85                  90                  95

Ile Asp Ala Ser Asn Thr Arg Arg Gly Lys Pro Thr Val His Arg Lys
            100                 105                 110

Ala Glu Gln Leu His Arg Glu Leu Asp Tyr Leu Gly Asp Pro Glu Phe
        115                 120                 125

Phe Gly Thr Ser Val Ala Ile Leu Val Gly Asp Phe Ala Leu Val Tyr
    130                 135                 140

Ala Glu Asp Met Phe Gln Asp Ser Gly Leu Ser Pro Glu Ala Leu Gln
145                 150                 155                 160

Arg Ala Arg Asp Pro Trp Arg Gly Met Arg Thr Glu Val Leu Gly Gly
                165                 170                 175

Gln Leu Leu Asp Ile Ser Leu Glu Ala Thr Gly Ser Glu Ser Val Ser
            180                 185                 190

Leu Ser Asn Ser Val Asn Arg Tyr Lys Thr Ala Ala Tyr Thr Ile Glu
        195                 200                 205

Arg Pro Leu His Leu Gly Ala Ala Ile Ala Gly Ala Ser Glu Glu Leu
    210                 215                 220

Ile Thr Ala Phe Arg Gly Tyr Gly His Asp Ile Gly Ile Ala Tyr Gln
225                 230                 235                 240

Leu Arg Asp Asp Gln Leu Gly Val Phe Gly Asp Pro Ala Val Thr Gly
                245                 250                 255

Lys Pro Ala Gly Asp Asp Leu Arg Glu Gly Lys Arg Thr Glu Leu Leu
            260                 265                 270

Ala Leu Ala Leu Gln Arg Ala Asp Glu His Asp Pro Ser Ala Ala Ala
        275                 280                 285

Thr Leu Arg Lys Phe Ile Gly Arg Thr Ser Asp Pro Gln Asp Leu Leu
    290                 295                 300

Arg Leu Ser Gln Ile Ile Ala Asp Ser Gly Ala Pro Ala Glu Ile Glu
305                 310                 315                 320

Arg Arg Ile Thr Ala Leu Thr Thr Ser Gly Leu Ala His Leu Arg Ala
                325                 330                 335

Ala Asn Val Asp Ser Gln Ile Thr Lys Thr Leu Glu His Leu Ala Ile
            340                 345                 350

Gln Ala Thr Thr Arg Gln Lys
        355


<210> SEQ ID NO 69
<211> LENGTH: 392
<212> TYPE: PRT
<213> ORGANISM: Pseudomonas aeruginosa

<400> SEQUENCE: 69

Met His His Ser Arg Asp Ala His Thr Ala Ser Pro Val Arg Glu Lys
1               5                   10                  15

Asp Pro Ala Thr Val Ser Arg Ser Thr Thr Ser Pro Gln Phe Asp Ala
            20                  25                  30

Arg Ser Leu Ala Phe Ser Glu Ile Glu Pro Ala Val Glu Gln Lys Leu
        35                  40                  45

Arg Glu Phe Phe Gln Gly Arg Ser Arg Lys Ile Ser Val Ile Gly Glu
    50                  55                  60

Pro Val Ser Arg Ala Val Thr Tyr Leu Glu Asp Phe Val Leu Gly Gly
65                  70                  75                  80
```

```
Gly Lys Arg Ile Arg Pro Ser Tyr Ala Trp Ala Gly Phe Leu Ala Gly
                85                  90                  95

Asn Gly Leu Glu Gly Ala Glu Asp Pro Glu Ala Val Leu Ala Ser Ile
            100                 105                 110

Ser Ser Leu Glu Leu Ile Gln Ala Cys Ala Leu Ile His Asp Asp Ile
        115                 120                 125

Ile Asp Ala Ser Asp Ser Arg Arg Gly Gln Pro Thr Val His Arg Thr
    130                 135                 140

Ala Glu Ala Arg His Arg Asp Asn Ser Trp Asn Gly Asp Ser Ala His
145                 150                 155                 160

Phe Gly Glu Ser Ile Ala Ile Leu Leu Gly Asp Leu Ala Phe Ala Trp
                165                 170                 175

Ala Asp Asp Met Phe Arg Thr Ser Gly Leu Ser Asp Ala Ala Ile Ala
            180                 185                 190

Arg Thr Ser Asn Ala Trp Arg Gly Met Arg Thr Glu Val Ile Gly Gly
        195                 200                 205

Gln Leu Leu Asp Val Phe Leu Glu Ser Ala Gly Ser Glu Ser Ile Glu
    210                 215                 220

Leu Ala Glu Asn Val Asn Arg Phe Lys Thr Ala Ala Tyr Thr Ile Glu
225                 230                 235                 240

Arg Pro Leu His Ile Gly Ala Ala Ile Ala Gly Ala Asp Gly Lys Ile
                245                 250                 255

Val Arg Ala Leu Arg Asp Tyr Gly Arg Asp Ile Gly Val Ala Tyr Gln
            260                 265                 270

Leu Arg Asp Asp Leu Leu Gly Val Phe Gly Asn Pro Ala Val Thr Gly
        275                 280                 285

Lys Pro Ala Gly Asp Asp Leu Arg Glu Gly Lys Arg Thr Val Leu Val
    290                 295                 300

Ala Lys Ala Leu Glu Leu Ala His Ala Ala Asp Asn Ala Asp Ala Val
305                 310                 315                 320

Glu Ser Ile Arg Lys Gly Val Gly Thr Val Thr Glu Pro His Asp Ile
                325                 330                 335

Ala Arg Leu Ala Asp Thr Ile Arg Gln Thr Gly Ala Glu Ala Gly Val
            340                 345                 350

Glu Lys Arg Ile Asp Glu Leu Ala Glu Arg Gly Ile Ser His Leu Cys
        355                 360                 365

Thr Ala Asp Ile Ser Asp Asp Ala Arg Asn Ile Leu Val Ser Leu Ala
    370                 375                 380

Asn Lys Ala Thr Ala Arg Ser Met
385                 390
```

<210> SEQ ID NO 70
<211> LENGTH: 368
<212> TYPE: PRT
<213> ORGANISM: Streptococcus thermophilus

<400> SEQUENCE: 70

```
Met Val Thr His Thr Asp Lys Ser Ser Ile Pro Thr Thr Ala Gln Ile
1               5                   10                  15

Pro Ala Ala Val Glu Arg Glu Leu Glu Leu Phe Phe Thr Glu His Gly
            20                  25                  30

Pro Ser Val Asp Val Ile Gly Pro Pro Val Ser Glu Ala Val Glu His
        35                  40                  45

Leu Arg Thr Phe Val Leu Gly Gly Gly Lys Arg Ile Arg Pro Thr Phe
```

-continued 50 55 60

Gly Trp Val Gly Phe Ile Gly Ala Asn Gly Leu Asp Asn Thr Asp Glu
65 70 75 80

Asp Pro Ala Ala Val Leu Arg Ala Val Ser Ser Leu Glu Leu Ile Gln
85 90 95

Ala Cys Ala Leu Ile His Asp Asp Ile Ile Asp Ala Ser Ala Ser Arg
100 105 110

Arg Gly Asn Pro Thr Val His Val Ala Ala Ala Glu Ser His Arg His
115 120 125

Gln Asn Trp Leu Gly Asn Ser Glu Lys Phe Gly Glu Ser Leu Ala Ile
130 135 140

Leu Val Gly Asp Leu Ala Leu Val Trp Ala Asp Asp Met Trp His His
145 150 155 160

Ser Gly Leu Ser His Ala Ala Leu Asp Arg Ala Ala Glu Pro Trp Arg
165 170 175

Gly Met Arg Thr Glu Val Ile Gly Gly Gln Ile Leu Asp Ile Ser Leu
180 185 190

Glu Ala Ala Gly Cys Glu Asp Glu Glu Leu Ala Asn Ala Val Asn Arg
195 200 205

Phe Lys Thr Ala Ala Tyr Thr Ile Glu Arg Pro Leu His Leu Gly Ala
210 215 220

Ala Ile Ala Gly Ala Asp Asp Asp Thr Ile Ala Ala Leu Arg Gly Tyr
225 230 235 240

Gly His Asp Ile Gly Ile Ala Phe Gln Leu Arg Asp Asp Ile Leu Gly
245 250 255

Val Phe Gly Asp Pro Val Val Thr Gly Lys Pro Ala Gly Asp Asp Leu
260 265 270

Arg Glu Gly Lys Arg Thr Val Leu Tyr Ser Arg Ala Leu Gln Ala Ala
275 280 285

Asp Glu His Asp Pro Ala Ala Ala Gln Arg Leu Arg Asp Gly Ile Gly
290 295 300

Thr Ala Leu Ala Pro Asp Glu Ile Ala Glu Leu Ser Gly Ile Ile Gln
305 310 315 320

Glu Thr Gly Ala Val Asp Asp Val Glu Lys Arg Ile Asp Glu Leu Thr
325 330 335

Glu Ser Gly Leu Glu His Val Arg Arg Ala Ala Leu Ser Pro Glu Ala
340 345 350

Val Glu Thr Leu Glu Thr Leu Ala Ile Lys Ala Thr Ala Arg Arg Met
355 360 365

<210> SEQ ID NO 71
<211> LENGTH: 406
<212> TYPE: PRT
<213> ORGANISM: Nocardia vermiculata

<400> SEQUENCE: 71

Met Arg Ser Pro Gly Arg Arg Tyr Pro Arg Pro Pro Ala Ile Gly Gly
1 5 10 15

Thr Arg Arg Arg Ile Gly Gln Cys Pro Arg Ala Asp Thr Thr Ile Tyr
20 25 30

Leu Glu Val Ala Leu Ser Val Gly Pro Ser Gly Pro Ala Asn Pro Ala
35 40 45

Pro Ser Asp Ser Ala Ala Leu Val His Ala Val Glu Gln Ala Leu Thr
50 55 60

```
Arg Phe Phe Asp Ser Arg Arg Glu Leu Val Ala Glu Leu Gly Pro Val
65                  70                  75                  80

Phe Val Ser Ala Thr Thr Ala Leu Glu Glu Phe Val Leu Arg Gly Gly
                85                  90                  95

Lys Arg Thr Arg Pro Ser Phe Ala Trp Thr Gly Trp Leu Gly Ala Gly
            100                 105                 110

Gly Asp Pro Thr Gly Pro His Ala Glu Ala Val Leu Thr Ala Cys Ser
        115                 120                 125

Ala Leu Glu Leu Val Gln Ala Cys Ala Leu Ile His Asp Asp Ile Ile
    130                 135                 140

Asp Ser Ser Arg Thr Arg Arg Gly Phe Pro Thr Val His Val Asp Phe
145                 150                 155                 160

Glu Asp Arg His Arg Thr Arg Ser Trp Gly Gly Asp Pro Ala His Phe
                165                 170                 175

Gly Ala Ser Val Ala Ile Leu Val Gly Asp Leu Ala Leu Thr Trp Ala
            180                 185                 190

Asp Asp Met Val Ala Ala Ala Gly Leu Asp Pro Ala Ala Arg Ala Arg
        195                 200                 205

Phe Ala Val Val Trp Ala Ala Met Arg Thr Glu Val Met Gly Gly Gln
    210                 215                 220

Leu Leu Asp Val His Gly Glu Ala Gly Ala Asp Asp Ser Val Ala Ala
225                 230                 235                 240

Ala Leu Arg Ile Asn Arg Tyr Lys Thr Ala Ala Tyr Thr Val Glu Arg
                245                 250                 255

Pro Leu His Leu Gly Ala Ala Leu Ala Gly Ala Asp Pro Glu Leu Ile
            260                 265                 270

Ala Ala Tyr Arg Glu Phe Gly Thr Asp Ile Gly Ile Ala Phe Gln Leu
        275                 280                 285

Arg Asp Asp Leu Leu Gly Val Phe Gly Asp Pro Ala Val Thr Gly Lys
    290                 295                 300

Pro Ser Gly Asp Asp Leu Arg Glu Gly Lys Arg Thr Val Leu Val Ala
305                 310                 315                 320

Glu Ala Leu Arg Arg Ala Asp Ser Thr Asp Pro Glu Ala Ala Arg Arg
                325                 330                 335

Leu Arg Thr Cys Leu Gly Thr Asp Leu Asp Ala Glu Gln Val Thr Gly
            340                 345                 350

Leu Arg Glu Ile Ile Thr Asp Leu Gly Ala Val Asp Asp Val Glu Arg
        355                 360                 365

Arg Ile Ser Glu Leu Thr Glu Arg Gly Leu Thr Ala Leu Ala Ser Ser
    370                 375                 380

Ser Val Ala Pro Asp Ala Gly Ala Arg Leu Arg Ala Met Ala Leu Ala
385                 390                 395                 400

Ala Thr Arg Arg Val Ala
                405


<210> SEQ ID NO 72
<211> LENGTH: 383
<212> TYPE: PRT
<213> ORGANISM: Rhodococcus sp.

<400> SEQUENCE: 72

Met Glu Asp Pro Leu Ser Arg Asp Ser Thr Leu Pro Ala Pro Arg Arg
1               5                   10                  15

Thr Ser Asp Pro Asp Pro Val Leu Arg Glu Ala Gly Thr Ala Pro Ile
            20                  25                  30
```

-continued

Ala Leu Val Glu Ser Ala Leu Ala Glu Phe Phe His Ser Arg Arg Glu
35 40 45

Gln Val Ala Arg Val Gly Gly Gly Tyr Val Ser Ala Val Ala Asp Leu
50 55 60

Glu Ala Phe Val Leu Arg Gly Gly Lys Arg Ile Arg Pro Ser Phe Gly
65 70 75 80

Trp Met Ala Trp Leu Gly Ala Gly Gly Asp His Arg Ser Pro Gln Ala
85 90 95

Ala Ser Val Leu Arg Ala Cys Ala Ser Leu Glu Leu Ile Gln Ala Cys
100 105 110

Ala Leu Ile His Asp Asp Ile Ile Asp Ala Ser Leu Thr Arg Arg Gly
115 120 125

Phe Pro Thr Val His Val Gly Phe Thr Ala Arg His Arg Ala Ala Arg
130 135 140

Trp Ser Gly Ser Pro Glu Arg Phe Gly Glu Ser Ala Ala Ile Leu Leu
145 150 155 160

Gly Asp Leu Ala Leu Cys Trp Ala Asp Asp Met Leu Arg Glu Ser Gly
165 170 175

Ile Gly His Asp Ala Met Gly Arg Val Ser Pro Val Trp Ser Ala Met
180 185 190

Arg Thr Glu Val Leu Gly Gly Gln Leu Leu Asp Ile Glu Ala Glu Ala
195 200 205

Gly Leu Asp Glu Ser Val Glu Ala Ala Met Arg Val Asn Arg Tyr Lys
210 215 220

Thr Ala Ala Tyr Thr Val Glu Arg Pro Leu Gln Leu Gly Ala Val Leu
225 230 235 240

Ala Gly Ala Ser Glu Ser Leu Val Asp Ala Tyr Arg Ser Phe Gly Thr
245 250 255

Asp Ile Gly Leu Ala Phe Gln Leu Arg Asp Asp Leu Leu Gly Val Phe
260 265 270

Gly Asp Pro Ala Val Thr Gly Lys Pro Ser Gly Asp Asp Ile Arg Glu
275 280 285

Gly Lys Arg Thr Val Leu Met Ala Val Gly Leu Gln Leu Ala Asp Arg
290 295 300

Asp Arg Pro Glu Ala Gly Ser Leu Leu Arg Ser Ser Leu Gly Val Val
305 310 315 320

Asp Leu Thr Glu Asp Thr Ile Glu Ser Ile Arg Thr Val Leu Ile Glu
325 330 335

Leu Gly Ala Val Ala Asp Val Glu Arg Arg Ile Ser Glu Leu Thr Asp
340 345 350

Arg Ala Leu Asp Thr Leu Lys Ala Ser Ala Val Glu Pro His Ala Ala
355 360 365

Ala Gln Leu Arg Ala Met Ser Ile Ala Ala Thr Gln Arg Thr Tyr
370 375 380

<210> SEQ ID NO 73
<211> LENGTH: 361
<212> TYPE: PRT
<213> ORGANISM: Clostridium paraputrificum

<400> SEQUENCE: 73

Met Ser Pro Leu Asp Val Pro Ala Ala Val Thr Gly Ala Leu Thr Asp
1 5 10 15

Phe Phe Gly Ala Arg Ala Gly Met Val Ala Asp Ile Asp Glu Glu Phe

```
            20                  25                  30

Ser Arg Val Ile Gly Ala Leu Ser Asp Phe Thr Leu Leu Gly Gly Lys
        35                  40                  45

Arg Val Arg Pro Ala Phe Ala Trp Ala Gly Trp Leu Gly Ala Gly Gly
    50                  55                  60

Asp Ala Gly Leu Cys Ala Asp Ala Glu Asp Pro Glu Ala Val Phe Arg
65                  70                  75                  80

Ser Val Cys Ala Leu Glu Phe Ile Gln Ala Cys Ala Leu Ile His Asp
                85                  90                  95

Asp Ile Ile Asp Ala Ser Ala Thr Arg Arg Gly Asn Pro Thr Val His
            100                 105                 110

Lys Val Phe Glu Ser Arg His Arg Asp Asn Gly Trp Arg Gly Asp Ala
        115                 120                 125

Gly His Tyr Gly Gln Ser Val Ala Ile Leu Ala Gly Asp Val Ala Leu
    130                 135                 140

Ala Trp Ala Asp Asp Met Phe His Gly Ser Gly Leu Ser Asp Ala Ala
145                 150                 155                 160

Arg Asn Arg Ala Arg Glu Pro Trp Trp Arg Met Arg Thr Glu Val Leu
                165                 170                 175

Gly Gly Gln Leu Leu Asp Ile Thr Ala Glu Ala Ser Gly Asp Ser Arg
            180                 185                 190

Val Gly Val Ala Glu Lys Val Asn Arg Phe Lys Thr Ala Ala Tyr Thr
        195                 200                 205

Ile Glu Arg Pro Leu His Ile Gly Ala Ala Ile Ala Gly Ala Asp Asp
    210                 215                 220

Ala Ile Val Asp Ala Tyr Arg Glu Phe Gly Leu Asp Ile Gly Ile Ala
225                 230                 235                 240

Phe Gln Leu Arg Asp Asp Gln Leu Gly Val Phe Gly Asp Pro Ala Val
                245                 250                 255

Thr Gly Lys Pro Ala Gly Asp Asp Leu Arg Glu Gly Lys Arg Thr Val
            260                 265                 270

Leu Val Gly Thr Ala Leu Ala Arg Leu Arg Glu Ser Asp Pro Asp Gly
        275                 280                 285

Ala Arg His Leu Asp Asp Lys Leu Gly Arg Val Asp Gly Gln Asp Asp
    290                 295                 300

Val Asp Glu Leu Arg Glu Leu Ile Arg Gly Ser Gly Ala Asp Glu Leu
305                 310                 315                 320

Leu Glu Val Glu Ile Asp Arg Leu Thr Arg Arg Gly Leu Ala Ala Leu
                325                 330                 335

Asp Ser Ala Pro Ile Val Asp Glu Gln Arg Glu Arg Leu Ala Glu Met
            340                 345                 350

Gly Arg Arg Ala Thr Ala Arg Ala Trp
        355                 360


<210> SEQ ID NO 74
<211> LENGTH: 378
<212> TYPE: PRT
<213> ORGANISM: Nocardia cyriacigeorgica

<400> SEQUENCE: 74

Met Glu Val Ile Leu Ser Ala Gly Pro Gly Thr Pro Thr Arg Pro Ser
1               5                   10                  15

Pro Thr Ser Ala Thr Pro Gly Thr Pro Ala Phe Ala Ala Ala Val Glu
            20                  25                  30
```

-continued

```
Gln Ala Leu Thr Ser Phe Phe Ala Thr Arg Arg Glu Thr Val Gly Glu
        35                  40                  45

Leu Gly Pro Ile Phe Val Asp Ala Ala Glu Ala Leu Glu Ser Phe Val
    50                  55                  60

Leu Arg Gly Gly Lys Arg Thr Arg Pro Gly Phe Ala Trp Thr Gly Trp
65                  70                  75                  80

Leu Gly Ala Gly Gly Asp Pro Asp Gly Pro Asp Ala Pro Ala Val Leu
                85                  90                  95

Asn Ala Cys Ala Ala Leu Glu Leu Val Gln Ala Cys Ala Leu Ile His
            100                 105                 110

Asp Asp Ile Ile Asp Ala Ser Arg Thr Arg Arg Arg Phe Pro Thr Val
        115                 120                 125

His Val Asp Phe Glu Gln Arg His Arg Asp Arg Gly Trp Ala Gly Asp
    130                 135                 140

Ala Pro Arg Phe Gly Thr Gly Val Ala Ile Leu Ile Gly Asp Leu Ala
145                 150                 155                 160

Leu Ala Trp Ala Asp Asp Met Val His Ala Ser Gly Leu Asp Pro Arg
                165                 170                 175

Ala Val Ala Arg Phe Ala Thr Val Trp Ala Lys Met Arg Thr Glu Val
            180                 185                 190

Leu Gly Gly Gln Leu Leu Asp Ile His Gly Glu Ala Ser Gly Asp Glu
        195                 200                 205

Ser Val Ala Ala Ala Leu Arg Ile Asn Arg Tyr Lys Thr Ala Ala Tyr
    210                 215                 220

Thr Val Glu Arg Pro Leu His Leu Gly Ala Ala Leu Ala Asp Ala Gly
225                 230                 235                 240

Pro Glu Leu Val Arg Ser Tyr Arg Asp Phe Gly Thr Asp Ile Gly Ile
                245                 250                 255

Ala Phe Gln Leu Arg Asp Asp Leu Leu Gly Val Phe Gly Asp Pro Ser
            260                 265                 270

Val Thr Gly Lys Pro Ser Gly Asp Asp Leu Arg Glu Gly Lys Arg Thr
        275                 280                 285

Val Leu Ile Ala Glu Ala Leu Ala Arg Gly Asp Lys Ala Asp Pro Ala
    290                 295                 300

Ala Ala Glu Leu Leu Arg Thr Lys Val Gly Thr Asp Leu Ser Gly Glu
305                 310                 315                 320

Asp Val Asp Gln Leu Arg Glu Val Leu Val Arg Leu Gly Ala Val Asp
                325                 330                 335

Ala Val Glu Ala Arg Ile Ala Glu Leu Thr Glu Arg Ala Leu Ala Ala
            340                 345                 350

Ile Asp Thr Ser Ser Ala Thr Pro Ala Ala Lys Asp His Leu His Ala
        355                 360                 365

Met Ala Leu Ala Ala Thr Arg Arg Thr Ala
    370                 375
```

<210> SEQ ID NO 75
<211> LENGTH: 374
<212> TYPE: PRT
<213> ORGANISM: Nocardia concava

<400> SEQUENCE: 75

```
Met Lys Glu Ala Pro Leu Ser Ala Gly Pro Gly Thr Pro Thr Arg His
1               5                   10                  15

Pro Val Gly Ala Gly Ser Val Val Ala Ala Val Glu Glu Arg Leu Arg
            20                  25                  30
```

-continued

```
Ala Phe Phe Val Thr Arg Glu Pro Ile Val Glu Pro Leu Gly Pro Val
        35                  40                  45

Phe Val Asp Ala Ala Arg Ala Leu Gln Asp Phe Val Ile Arg Gly Gly
    50                  55                  60

Lys Arg Thr Arg Pro Ser Phe Ala Trp Thr Gly Trp Leu Gly Ala Gly
65                  70                  75                  80

Arg Ser Pro Glu Asp Pro Glu Ala Asp Ala Val Leu Thr Ala Cys Ser
                85                  90                  95

Ala Leu Glu Leu Val Gln Ala Cys Ala Leu Ile His Asp Asp Ile Ile
            100                 105                 110

Asp Ser Ser Arg Thr Arg Arg Gly Phe Pro Thr Val His Val Asp Tyr
        115                 120                 125

Glu Gly Arg His Arg Asp Gln Arg Trp Arg Gly Asp Ala Asp His Tyr
    130                 135                 140

Gly Ile Ser Val Ala Val Leu Ile Gly Asp Leu Ala Leu Ala Trp Ala
145                 150                 155                 160

Asp Asp Met Thr Arg Asp Ala Gly Leu Pro Asp Asp Ala Ala Ala Arg
                165                 170                 175

Phe Ala Pro Val Trp Ala Ala Met Arg Thr Glu Val Leu Gly Gly Gln
            180                 185                 190

Leu Leu Asp Ile His Gly Glu Ser Ala Gly Asp Glu Thr Val Glu Ala
        195                 200                 205

Ala Leu Arg Ile Asn Arg Tyr Lys Thr Ala Ala Tyr Thr Ile Glu Arg
    210                 215                 220

Pro Leu His Met Gly Ala Ala Leu Ala Gly Ala Ser Pro Glu Leu Val
225                 230                 235                 240

Ala Ala Tyr Arg Glu Phe Gly Thr Asp Ile Gly Ile Ala Phe Gln Leu
                245                 250                 255

Arg Asp Asp Leu Leu Gly Val Phe Gly Asp Pro Ala Val Thr Gly Lys
            260                 265                 270

Pro Ser Gly Asp Asp Leu Arg Glu Gly Lys Arg Thr Val Leu Ile Ala
        275                 280                 285

Glu Ala Leu Gln Arg Ala Asp Ile Asp Ala Pro Ala Val Ala Asp Leu
    290                 295                 300

Ile Arg Ser Ser Leu Gly Thr Asp Val Thr Pro Glu Arg Val Thr Glu
305                 310                 315                 320

Leu Arg Thr Ala Leu Thr Glu Leu Gly Ala Val Asp Ala Val Glu Lys
                325                 330                 335

Arg Ile Ser Ser Leu Thr Asp Gln Ala Leu Thr Ala Leu Asp Ala Ser
            340                 345                 350

Thr Ala Thr Pro Glu Ala Lys Arg Gln Leu Arg Ala Met Ala Leu Ala
        355                 360                 365

Ala Thr Ala Arg Thr Tyr
    370
```

<210> SEQ ID NO 76
<211> LENGTH: 383
<212> TYPE: PRT
<213> ORGANISM: Rhodococcus yunnanensis

<400> SEQUENCE: 76

```
Met Glu Asp Pro Leu Ser Gly Asp Leu Thr Ser His Thr Thr Arg Glu
1               5                   10                  15

Ser Thr Glu His Asp Phe Ala Val His Asp Ala Thr Ala Asn Pro Ala
```

```
            20                  25                  30

Thr Leu Val Glu Ser Ala Leu Glu Ala Phe Phe Ala Ser Lys Arg Pro
        35                  40                  45

Gln Val Ala Ala Val Gly Gly Gly Tyr Pro Ala Ala Val Glu Asp Leu
    50                  55                  60

Val Ala Phe Val Leu Arg Gly Gly Lys Arg Ile Arg Pro Ala Phe Ala
65                  70                  75                  80

Trp Thr Ala Trp Leu Gly Ala Gly Gly Asp Arg Ser Ser Thr Ser Ala
                85                  90                  95

Pro Ser Val Leu Arg Ala Cys Ala Ser Leu Glu Leu Ile Gln Ala Cys
            100                 105                 110

Ala Leu Ile His Asp Asp Ile Ile Asp Ala Ser Val Thr Arg Arg Gly
        115                 120                 125

Tyr Pro Thr Val His Ile Gly Phe Ala Asp Arg His Arg Gly Leu Gly
    130                 135                 140

Trp Ser Gly Ser Ala Glu Arg Phe Gly Glu Ser Ala Ala Ile Leu Leu
145                 150                 155                 160

Gly Asp Leu Ala Leu Cys Trp Ala Asp Asp Met Leu Arg Glu Ala Gly
                165                 170                 175

Leu Asp Ser Asp Thr Ala Ala Arg Ile Ser Pro Val Trp Ser Ser Met
            180                 185                 190

Arg Thr Glu Val Leu Gly Gly Gln Leu Leu Asp Ile Glu Ala Glu Ala
        195                 200                 205

Gly Leu Asp Glu Ser Val Asp Ala Ala Met Arg Val Asn Arg Phe Lys
    210                 215                 220

Thr Ala Ala Tyr Thr Val Glu Arg Pro Leu His Leu Gly Ala Leu Leu
225                 230                 235                 240

Ala Gly Ala Pro Ser Glu Leu Val Glu Ser Tyr Arg Ala Phe Gly Ser
                245                 250                 255

Asp Ile Gly Ser Ala Phe Gln Leu Arg Asp Asp Leu Leu Gly Val Phe
            260                 265                 270

Gly Asp Pro Gly Val Thr Gly Lys Pro Ser Gly Asp Asp Ile Arg Glu
        275                 280                 285

Gly Lys Arg Thr Val Leu Met Ala Val Gly Met Gln Leu Ala Asp Arg
    290                 295                 300

Asp Arg Pro Asp Leu Ala Ala Leu Leu Arg Thr Ser Leu Gly Asp Ala
305                 310                 315                 320

Asp Leu Ala Glu Asp Asp Ile Arg Ala Ile Arg Thr Ala Leu Thr Glu
                325                 330                 335

Leu Gly Ala Val Asp Asp Val Glu Arg Arg Ile Thr Glu Leu Thr Glu
            340                 345                 350

Arg Ala Leu Gly Thr Leu Asp Gly Ser Thr Val Glu Pro Gly Ala Ala
        355                 360                 365

Ala Arg Leu Arg Ala Met Ala Val Ser Ala Thr Gln Arg Gln Tyr
    370                 375                 380


<210> SEQ ID NO 77
<211> LENGTH: 691
<212> TYPE: PRT
<213> ORGANISM: Pseudomonas solanacearum

<400> SEQUENCE: 77

Met Gly Val Ser Thr Leu Arg Gly Leu Leu Leu Ala Gly Ser Thr Leu
1               5                   10                  15
```

-continued

```
Gly Ala Val Gly Ala Ala Gly Ala Gln Asp Ser Ala Thr Ala Ala Glu
            20                  25                  30

Pro Ala Asp Val Ala Gln Leu Ala Pro Val Val Val Thr Gly Thr Lys
        35                  40                  45

Leu Asp Ala Ser Gly Gln Thr Ala Asp Ser Ala Thr Ser Val Ala Ser
    50                  55                  60

Gly Ala Arg Leu Gln Ala Ala Gly Val Ala Arg Thr Asp Glu Leu Gly
65                  70                  75                  80

Lys Leu Phe Pro Glu Leu Thr Val Thr Pro Arg Ser Ser Arg Ala Tyr
                85                  90                  95

Thr Leu Phe Gly Met Arg Gly Thr Pro Ser Ser Asp Phe Tyr Ser Pro
            100                 105                 110

Ala Val Thr Val Tyr Val Asp Gly Val Pro Gln Asp Met Ala Tyr Phe
        115                 120                 125

Thr Gln Pro Leu Pro Asp Val Glu Gln Val Glu Val Leu Arg Gly Pro
    130                 135                 140

Gln Gly Thr Leu Tyr Gly Arg Ala Ala Gln Gly Gly Val Ile Asn Ile
145                 150                 155                 160

Val Thr Thr Lys Pro Asn Asn Arg Phe Gly Ala Gln Ala Ser Val Asp
                165                 170                 175

Val Asn Asn Leu Thr Arg Arg Thr Asp Leu Ser Val Arg Gly Pro Leu
            180                 185                 190

Val Lys Asp Leu Leu Tyr Gly Asp Val Ser Ala Tyr Phe Asp Asp Arg
        195                 200                 205

Pro Gly Thr Leu Lys Asn Pro Ala Thr Gly Ala Asp Gln Leu Asp Ser
    210                 215                 220

Gly Arg Glu Ala Leu Gly Arg Ala Arg Leu Arg Trp Thr Pro Arg Asp
225                 230                 235                 240

Thr Asp Leu Asp Ala Thr Leu Ser Val Ser His Asp Arg Tyr Arg Ser
                245                 250                 255

His Glu Glu Tyr Phe Gln Ala Tyr Asp Leu Lys Asp Arg His Ala Ile
            260                 265                 270

Ala Ser Ser Pro Phe Asp Leu Thr Glu Pro Ser Leu Thr Arg Thr Val
        275                 280                 285

Thr Gln Ala Ala Leu Ser Val Asp Tyr Tyr Leu Arg Gly Trp Lys Leu
    290                 295                 300

Ser Ser Val Ser Ala Tyr Gln Asp Arg Arg Leu Glu Arg Val Leu Thr
305                 310                 315                 320

Thr Gly Asn Ala Asp Pro Glu Asn Gln Lys Thr Phe Ser Gln Glu Leu
                325                 330                 335

Arg Val Ala Thr Ser Gly Asp Val Lys Arg Pro Val Asp Gly Val Phe
            340                 345                 350

Gly Leu Tyr Tyr Glu Lys Gln Ala Phe Glu Arg Asp Arg Gly Ile Ala
        355                 360                 365

Val Pro Gly Val Ser Ala Phe Leu Phe Pro Gly Pro Ser Arg Ser Glu
    370                 375                 380

Ser Asn Leu Arg Ser Met Ala Ala Phe Gly Glu Gly Val Trp His Ala
385                 390                 395                 400

Thr Glu Arg Leu Asp Leu Thr Ala Gly Leu Arg Tyr Gly Ile Asp Ser
                405                 410                 415

Ala Asp Ile His Tyr Asn Arg Thr Gly Ala Ala Ala Leu Ser Phe Ala
            420                 425                 430

Gly Asp Lys Thr Phe Arg Ser Leu Thr Pro Lys Val Ser Val Gly Tyr
```

```
        435                 440                 445

Gln Ala Ala Pro Gly Trp Arg Val Tyr Gly Leu Tyr Ser Glu Gly Tyr
    450                 455                 460

Lys Ala Gly Gly Phe Asn Arg Ile Ala Asp Asn Ser Ala Gly Ser Ile
465                 470                 475                 480

Pro Tyr Ser Ala Glu Arg Leu Arg Asn Val Glu Val Gly Phe Gln Ala
                485                 490                 495

Asp Leu Leu Gly Lys Arg Leu Arg Leu Asp Gly Ala Leu Phe His Ser
            500                 505                 510

Arg Thr Ser Asn Leu Gln Ala Gln Val Val Ser Gly Leu Phe Gln Met
        515                 520                 525

Leu Ser Asn Val Gly Asp Ala Arg Ala Thr Gly Val Glu Leu Asn Gly
    530                 535                 540

Thr Trp Leu Ala Thr Pro Asp Leu Thr Leu Arg Ala Gly Gly Ala Trp
545                 550                 555                 560

Thr Thr Ser Lys Ile Tyr Ser Tyr Ser Ala Pro Gln Gly Asn Leu Asp
                565                 570                 575

Leu Thr Gly Lys Arg Val Pro Tyr Val Val Pro Leu Ser Leu Arg Ala
            580                 585                 590

Ser Gly Glu Tyr Arg Phe Arg Pro Gln Gly Met Arg Gly Arg Leu Arg
        595                 600                 605

Trp Asn Val Gly Met Thr Tyr Ser Gly Asp Met Trp Phe Asp Ala Ala
    610                 615                 620

Asn Thr Leu Arg Gln Pro Ala Tyr Ala Leu Leu Asp Thr Ser Leu Ser
625                 630                 635                 640

Trp Asp Ile Asn Lys His Leu Thr Val Val Gly Tyr Val Asp Asn Leu
                645                 650                 655

Thr Asp Arg Ala Val Arg Thr Tyr Ala Phe Ser Leu Gly Thr Phe Gly
            660                 665                 670

Thr Phe Ala Gln Tyr Gly Gln Gly Arg Thr Ile Gly Leu Arg Leu Gln
        675                 680                 685

Ala Arg Leu
    690


<210> SEQ ID NO 78
<211> LENGTH: 517
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Ala Asn Pro Arg Glu Asn Phe Leu Lys Cys Phe Ser Gln Tyr Ile Pro
1               5                   10                  15

Asn Asn Ala Thr Asn Leu Lys Leu Val Tyr Thr Gln Asn Asn Pro Leu
            20                  25                  30

Tyr Met Ser Val Leu Asn Ser Thr Ile His Asn Leu Arg Phe Thr Ser
        35                  40                  45

Asp Thr Thr Pro Lys Pro Leu Val Ile Val Thr Pro Ser His Val Ser
    50                  55                  60

His Ile Gln Gly Thr Ile Leu Cys Ser Lys Lys Val Gly Leu Gln Ile
65                  70                  75                  80

Arg Thr Arg Ser Gly Gly His Asp Ser Glu Gly Met Ser Tyr Ile Ser
                85                  90                  95
```

-continued

```
Gln Val Pro Phe Val Ile Val Asp Leu Arg Asn Met Arg Ser Ile Lys
            100                 105                 110

Ile Asp Val His Ser Gln Thr Ala Trp Val Glu Ala Gly Ala Thr Leu
        115                 120                 125

Gly Glu Val Tyr Tyr Trp Val Asn Glu Lys Asn Glu Asn Leu Ser Leu
    130                 135                 140

Ala Ala Gly Tyr Cys Pro Thr Val Cys Ala Gly Gly His Phe Gly Gly
145                 150                 155                 160

Gly Gly Tyr Gly Pro Leu Met Arg Asn Tyr Gly Leu Ala Ala Asp Asn
                165                 170                 175

Ile Ile Asp Ala His Leu Val Asn Val His Gly Lys Val Leu Asp Arg
            180                 185                 190

Lys Ser Met Gly Glu Asp Leu Phe Trp Ala Leu Arg Gly Gly Gly Ala
        195                 200                 205

Glu Ser Phe Gly Ile Ile Val Ala Trp Lys Ile Arg Leu Val Ala Val
    210                 215                 220

Pro Lys Ser Thr Met Phe Ser Val Lys Lys Ile Met Glu Ile His Glu
225                 230                 235                 240

Leu Val Lys Leu Val Asn Lys Trp Gln Asn Ile Ala Tyr Lys Tyr Asp
                245                 250                 255

Lys Asp Leu Leu Leu Met Thr His Phe Ile Thr Arg Asn Ile Thr Asp
            260                 265                 270

Asn Gln Gly Lys Asn Lys Thr Ala Ile His Thr Tyr Phe Ser Ser Val
        275                 280                 285

Phe Leu Gly Gly Val Asp Ser Leu Val Asp Leu Met Asn Lys Ser Phe
    290                 295                 300

Pro Glu Leu Gly Ile Lys Lys Thr Asp Cys Arg Gln Leu Ser Trp Ile
305                 310                 315                 320

Asp Thr Ile Ile Phe Tyr Ser Gly Val Val Asn Tyr Asp Thr Asp Asn
                325                 330                 335

Phe Asn Lys Glu Ile Leu Leu Asp Arg Ser Ala Gly Gln Asn Gly Ala
            340                 345                 350

Phe Lys Ile Lys Leu Asp Tyr Val Lys Lys Pro Ile Pro Glu Ser Val
        355                 360                 365

Phe Val Gln Ile Leu Glu Lys Leu Tyr Glu Glu Asp Ile Gly Ala Gly
    370                 375                 380

Met Tyr Ala Leu Tyr Pro Tyr Gly Gly Ile Met Asp Glu Ile Ser Glu
385                 390                 395                 400

Ser Ala Ile Pro Phe Pro His Arg Ala Gly Ile Leu Tyr Glu Leu Trp
                405                 410                 415

Tyr Ile Cys Ser Trp Glu Lys Gln Glu Asp Asn Glu Lys His Leu Asn
            420                 425                 430

Trp Ile Arg Asn Ile Tyr Asn Phe Met Thr Pro Tyr Val Ser Lys Asn
        435                 440                 445

Pro Arg Leu Ala Tyr Leu Asn Tyr Arg Asp Leu Asp Ile Gly Ile Asn
    450                 455                 460

Asp Pro Lys Asn Pro Asn Asn Tyr Thr Gln Ala Arg Ile Trp Gly Glu
465                 470                 475                 480

Lys Tyr Phe Gly Lys Asn Phe Asp Arg Leu Val Lys Val Lys Thr Leu
                485                 490                 495

Val Asp Pro Asn Asn Phe Phe Arg Asn Glu Gln Ser Ile Pro Pro Leu
            500                 505                 510

Pro Arg His Arg His
```

515

<210> SEQ ID NO 79
<211> LENGTH: 544
<212> TYPE: PRT
<213> ORGANISM: Cannabis sativa

<400> SEQUENCE: 79

```
Met Lys Cys Ser Thr Phe Ser Phe Trp Phe Val Cys Lys Ile Ile Phe
1               5                   10                  15

Phe Phe Phe Ser Phe Asn Ile Gln Thr Ser Ile Ala Asn Pro Arg Glu
            20                  25                  30

Asn Phe Leu Lys Cys Phe Ser Gln Tyr Ile Pro Asn Asn Ala Thr Asn
        35                  40                  45

Leu Lys Leu Val Tyr Thr Gln Asn Asn Pro Leu Tyr Met Ser Val Leu
    50                  55                  60

Asn Ser Thr Ile His Asn Leu Arg Phe Thr Ser Asp Thr Thr Pro Lys
65                  70                  75                  80

Pro Leu Val Ile Val Thr Pro Ser His Val Ser His Ile Gln Gly Thr
                85                  90                  95

Ile Leu Cys Ser Lys Lys Val Gly Leu Gln Ile Arg Thr Arg Ser Gly
            100                 105                 110

Gly His Asp Ser Glu Gly Met Ser Tyr Ile Ser Gln Val Pro Phe Val
        115                 120                 125

Ile Val Asp Leu Arg Asn Met Arg Ser Ile Lys Ile Asp Val His Ser
    130                 135                 140

Gln Thr Ala Trp Val Glu Ala Gly Ala Thr Leu Gly Glu Val Tyr Tyr
145                 150                 155                 160

Trp Val Asn Glu Lys Asn Glu Asn Leu Ser Leu Ala Ala Gly Tyr Cys
                165                 170                 175

Pro Thr Val Cys Ala Gly Gly His Phe Gly Gly Gly Gly Tyr Gly Pro
            180                 185                 190

Leu Met Arg Asn Tyr Gly Leu Ala Ala Asp Asn Ile Ile Asp Ala His
        195                 200                 205

Leu Val Asn Val His Gly Lys Val Leu Asp Arg Lys Ser Met Gly Glu
    210                 215                 220

Asp Leu Phe Trp Ala Leu Arg Gly Gly Gly Ala Glu Ser Phe Gly Ile
225                 230                 235                 240

Ile Val Ala Trp Lys Ile Arg Leu Val Ala Val Pro Lys Ser Thr Met
                245                 250                 255

Phe Ser Val Lys Lys Ile Met Glu Ile His Glu Leu Val Lys Leu Val
            260                 265                 270

Asn Lys Trp Gln Asn Ile Ala Tyr Lys Tyr Asp Lys Asp Leu Leu Leu
        275                 280                 285

Met Thr His Phe Ile Thr Arg Asn Ile Thr Asp Asn Gln Gly Lys Asn
    290                 295                 300

Lys Thr Ala Ile His Thr Tyr Phe Ser Ser Val Phe Leu Gly Gly Val
305                 310                 315                 320

Asp Ser Leu Val Asp Leu Met Asn Lys Ser Phe Pro Glu Leu Gly Ile
                325                 330                 335

Lys Lys Thr Asp Cys Arg Gln Leu Ser Trp Ile Asp Thr Ile Ile Phe
            340                 345                 350

Tyr Ser Gly Val Val Asn Tyr Asp Thr Asp Asn Phe Asn Lys Glu Ile
        355                 360                 365
```

Leu Leu Asp Arg Ser Ala Gly Gln Asn Gly Ala Phe Lys Ile Lys Leu
    370                 375                 380

Asp Tyr Val Lys Lys Pro Ile Pro Glu Ser Val Phe Val Gln Ile Leu
385                 390                 395                 400

Glu Lys Leu Tyr Glu Glu Asp Ile Gly Ala Gly Met Tyr Ala Leu Tyr
                405                 410                 415

Pro Tyr Gly Gly Ile Met Asp Glu Ile Ser Glu Ser Ala Ile Pro Phe
            420                 425                 430

Pro His Arg Ala Gly Ile Leu Tyr Glu Leu Trp Tyr Ile Cys Ser Trp
        435                 440                 445

Glu Lys Gln Glu Asp Asn Glu Lys His Leu Asn Trp Ile Arg Asn Ile
    450                 455                 460

Tyr Asn Phe Met Thr Pro Tyr Val Ser Lys Asn Pro Arg Leu Ala Tyr
465                 470                 475                 480

Leu Asn Tyr Arg Asp Leu Asp Ile Gly Ile Asn Asp Pro Lys Asn Pro
                485                 490                 495

Asn Asn Tyr Thr Gln Ala Arg Ile Trp Gly Glu Lys Tyr Phe Gly Lys
            500                 505                 510

Asn Phe Asp Arg Leu Val Lys Val Lys Thr Leu Val Asp Pro Asn Asn
        515                 520                 525

Phe Phe Arg Asn Glu Gln Ser Ile Pro Pro Leu Pro Arg His Arg His
    530                 535                 540

<210> SEQ ID NO 80
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Ala Asn Pro Gln Glu Asn Phe Leu Lys Cys Phe Ser Glu Tyr Ile Pro
1               5                   10                  15

Asn Asn Pro Ala Asn Pro Lys Phe Ile Tyr Thr Gln His Asp Gln Leu
            20                  25                  30

Tyr Met Ser Val Leu Asn Ser Thr Ile Gln Asn Leu Arg Phe Thr Ser
        35                  40                  45

Asp Thr Thr Pro Lys Pro Leu Val Ile Val Thr Pro Ser Asn Val Ser
    50                  55                  60

His Ile Gln Ala Ser Ile Leu Cys Ser Lys Lys Val Gly Leu Gln Ile
65                  70                  75                  80

Arg Thr Arg Ser Gly Gly His Asp Ala Glu Gly Leu Ser Tyr Ile Ser
                85                  90                  95

Gln Val Pro Phe Ala Ile Val Asp Leu Arg Asn Met His Thr Val Lys
            100                 105                 110

Val Asp Ile His Ser Gln Thr Ala Trp Val Glu Ala Gly Ala Thr Leu
        115                 120                 125

Gly Glu Val Tyr Tyr Trp Ile Asn Glu Met Asn Glu Asn Phe Ser Phe
    130                 135                 140

Pro Gly Gly Tyr Cys Pro Thr Val Gly Val Gly Gly His Phe Ser Gly
145                 150                 155                 160

Gly Gly Tyr Gly Ala Leu Met Arg Asn Tyr Gly Leu Ala Ala Asp Asn
                165                 170                 175

Ile Ile Asp Ala His Leu Val Asn Val Asp Gly Lys Val Leu Asp Arg
            180                 185                 190

Lys Ser Met Gly Glu Asp Leu Phe Trp Ala Ile Arg Gly Gly Gly Gly
195 200 205

Glu Asn Phe Gly Ile Ile Ala Ala Cys Lys Ile Lys Leu Val Val Val
210 215 220

Pro Ser Lys Ala Thr Ile Phe Ser Val Lys Lys Asn Met Glu Ile His
225 230 235 240

Gly Leu Val Lys Leu Phe Asn Lys Trp Gln Asn Ile Ala Tyr Lys Tyr
245 250 255

Asp Lys Asp Leu Met Leu Thr Thr His Phe Arg Thr Arg Asn Ile Thr
260 265 270

Asp Asn His Gly Lys Asn Lys Thr Thr Val His Gly Tyr Phe Ser Ser
275 280 285

Ile Phe Leu Gly Gly Val Asp Ser Leu Val Asp Leu Met Asn Lys Ser
290 295 300

Phe Pro Glu Leu Gly Ile Lys Lys Thr Asp Cys Lys Glu Leu Ser Trp
305 310 315 320

Ile Asp Thr Thr Ile Phe Tyr Ser Gly Val Val Asn Tyr Asn Thr Ala
325 330 335

Asn Phe Lys Lys Glu Ile Leu Leu Asp Arg Ser Ala Gly Lys Lys Thr
340 345 350

Ala Phe Ser Ile Lys Leu Asp Tyr Val Lys Lys Leu Ile Pro Glu Thr
355 360 365

Ala Met Val Lys Ile Leu Glu Lys Leu Tyr Glu Glu Glu Val Gly Val
370 375 380

Gly Met Tyr Val Leu Tyr Pro Tyr Gly Gly Ile Met Asp Glu Ile Ser
385 390 395 400

Glu Ser Ala Ile Pro Phe Pro His Arg Ala Gly Ile Met Tyr Glu Leu
405 410 415

Trp Tyr Thr Ala Thr Trp Glu Lys Gln Glu Asp Asn Glu Lys His Ile
420 425 430

Asn Trp Val Arg Ser Val Tyr Asn Phe Thr Thr Pro Tyr Val Ser Gln
435 440 445

Asn Pro Arg Leu Ala Tyr Leu Asn Tyr Arg Asp Leu Asp Leu Gly Lys
450 455 460

Thr Asn Pro Glu Ser Pro Asn Asn Tyr Thr Gln Ala Arg Ile Trp Gly
465 470 475 480

Glu Lys Tyr Phe Gly Lys Asn Phe Asn Arg Leu Val Lys Val Lys Thr
485 490 495

Lys Ala Asp Pro Asn Asn Phe Phe Arg Asn Glu Gln Ser Ile Pro Pro
500 505 510

Leu Pro Pro Arg His His
515

<210> SEQ ID NO 81
<211> LENGTH: 545
<212> TYPE: PRT
<213> ORGANISM: Cannabis sativa

<400> SEQUENCE: 81

Met Asn Cys Ser Thr Phe Ser Phe Trp Phe Val Cys Lys Ile Ile Phe
1 5 10 15

Phe Phe Leu Ser Phe Asn Ile Gln Ile Ser Ile Ala Asn Pro Gln Glu
20 25 30

Asn Phe Leu Lys Cys Phe Ser Glu Tyr Ile Pro Asn Asn Pro Ala Asn

-continued

```
        35                  40                  45

Pro Lys Phe Ile Tyr Thr Gln His Asp Gln Leu Tyr Met Ser Val Leu
    50                  55                  60

Asn Ser Thr Ile Gln Asn Leu Arg Phe Thr Ser Asp Thr Thr Pro Lys
65                  70                  75                  80

Pro Leu Val Ile Val Thr Pro Ser Asn Val Ser His Ile Gln Ala Ser
                85                  90                  95

Ile Leu Cys Ser Lys Lys Val Gly Leu Gln Ile Arg Thr Arg Ser Gly
            100                 105                 110

Gly His Asp Ala Glu Gly Leu Ser Tyr Ile Ser Gln Val Pro Phe Ala
        115                 120                 125

Ile Val Asp Leu Arg Asn Met His Thr Val Lys Val Asp Ile His Ser
    130                 135                 140

Gln Thr Ala Trp Val Glu Ala Gly Ala Thr Leu Gly Glu Val Tyr Tyr
145                 150                 155                 160

Trp Ile Asn Glu Met Asn Glu Asn Phe Ser Phe Pro Gly Gly Tyr Cys
                165                 170                 175

Pro Thr Val Gly Val Gly Gly His Phe Ser Gly Gly Gly Tyr Gly Ala
            180                 185                 190

Leu Met Arg Asn Tyr Gly Leu Ala Ala Asp Asn Ile Ile Asp Ala His
        195                 200                 205

Leu Val Asn Val Asp Gly Lys Val Leu Asp Arg Lys Ser Met Gly Glu
    210                 215                 220

Asp Leu Phe Trp Ala Ile Arg Gly Gly Gly Gly Glu Asn Phe Gly Ile
225                 230                 235                 240

Ile Ala Ala Cys Lys Ile Lys Leu Val Val Val Pro Ser Lys Ala Thr
                245                 250                 255

Ile Phe Ser Val Lys Lys Asn Met Glu Ile His Gly Leu Val Lys Leu
            260                 265                 270

Phe Asn Lys Trp Gln Asn Ile Ala Tyr Lys Tyr Asp Lys Asp Leu Met
        275                 280                 285

Leu Thr Thr His Phe Arg Thr Arg Asn Ile Thr Asp Asn His Gly Lys
    290                 295                 300

Asn Lys Thr Thr Val His Gly Tyr Phe Ser Ser Ile Phe Leu Gly Gly
305                 310                 315                 320

Val Asp Ser Leu Val Asp Leu Met Asn Lys Ser Phe Pro Glu Leu Gly
                325                 330                 335

Ile Lys Lys Thr Asp Cys Lys Glu Leu Ser Trp Ile Asp Thr Thr Ile
            340                 345                 350

Phe Tyr Ser Gly Val Val Asn Tyr Asn Thr Ala Asn Phe Lys Lys Glu
        355                 360                 365

Ile Leu Leu Asp Arg Ser Ala Gly Lys Lys Thr Ala Phe Ser Ile Lys
    370                 375                 380

Leu Asp Tyr Val Lys Lys Leu Ile Pro Glu Thr Ala Met Val Lys Ile
385                 390                 395                 400

Leu Glu Lys Leu Tyr Glu Glu Glu Val Gly Val Gly Met Tyr Val Leu
                405                 410                 415

Tyr Pro Tyr Gly Gly Ile Met Asp Glu Ile Ser Glu Ser Ala Ile Pro
            420                 425                 430

Phe Pro His Arg Ala Gly Ile Met Tyr Glu Leu Trp Tyr Thr Ala Thr
        435                 440                 445

Trp Glu Lys Gln Glu Asp Asn Glu Lys His Ile Asn Trp Val Arg Ser
    450                 455                 460
```

-continued

```
Val Tyr Asn Phe Thr Thr Pro Tyr Val Ser Gln Asn Pro Arg Leu Ala
465                 470                 475                 480

Tyr Leu Asn Tyr Arg Asp Leu Asp Leu Gly Lys Thr Asn Pro Glu Ser
                485                 490                 495

Pro Asn Asn Tyr Thr Gln Ala Arg Ile Trp Gly Glu Lys Tyr Phe Gly
            500                 505                 510

Lys Asn Phe Asn Arg Leu Val Lys Val Lys Thr Lys Ala Asp Pro Asn
        515                 520                 525

Asn Phe Phe Arg Asn Glu Gln Ser Ile Pro Pro Leu Pro Pro Arg His
    530                 535                 540

His
545


<210> SEQ ID NO 82
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Ala Asn Pro Arg Glu Asn Phe Leu Lys Cys Phe Ser Lys His Ile Pro
1               5                   10                  15

Asn Asn Val Ala Asn Pro Lys Leu Val Tyr Thr Gln His Asp Gln Leu
            20                  25                  30

Tyr Met Ser Ile Leu Asn Ser Thr Ile Gln Asn Leu Arg Phe Ile Ser
        35                  40                  45

Asp Thr Thr Pro Lys Pro Leu Val Ile Val Thr Pro Ser Asn Asn Ser
    50                  55                  60

His Ile Gln Ala Thr Ile Leu Cys Ser Lys Lys Val Gly Leu Gln Ile
65                  70                  75                  80

Arg Thr Arg Ser Gly Gly His Asp Ala Glu Gly Met Ser Tyr Ile Ser
                85                  90                  95

Gln Val Pro Phe Val Val Val Asp Leu Arg Asn Met His Ser Ile Lys
            100                 105                 110

Ile Asp Val His Ser Gln Thr Ala Trp Val Glu Ala Gly Ala Thr Leu
        115                 120                 125

Gly Glu Val Tyr Tyr Trp Ile Asn Glu Lys Asn Glu Asn Leu Ser Phe
    130                 135                 140

Pro Gly Gly Tyr Cys Pro Thr Val Gly Val Gly Gly His Phe Ser Gly
145                 150                 155                 160

Gly Gly Tyr Gly Ala Leu Met Arg Asn Tyr Gly Leu Ala Ala Asp Asn
                165                 170                 175

Ile Ile Asp Ala His Leu Val Asn Val Asp Gly Lys Val Leu Asp Arg
            180                 185                 190

Lys Ser Met Gly Glu Asp Leu Phe Trp Ala Ile Arg Gly Gly Gly Gly
        195                 200                 205

Glu Asn Phe Gly Ile Ile Ala Ala Trp Lys Ile Lys Leu Val Ala Val
    210                 215                 220

Pro Ser Lys Ser Thr Ile Phe Ser Val Lys Lys Asn Met Glu Ile His
225                 230                 235                 240

Gly Leu Val Lys Leu Phe Asn Lys Trp Gln Asn Ile Ala Tyr Lys Tyr
                245                 250                 255

Asp Lys Asp Leu Val Leu Met Thr His Phe Ile Thr Lys Asn Ile Thr
```

```
            260                 265                 270

Asp Asn His Gly Lys Asn Lys Thr Thr Val His Gly Tyr Phe Ser Ser
        275                 280                 285

Ile Phe His Gly Gly Val Asp Ser Leu Val Asp Leu Met Asn Lys Ser
    290                 295                 300

Phe Pro Glu Leu Gly Ile Lys Lys Thr Asp Cys Lys Glu Phe Ser Trp
305                 310                 315                 320

Ile Asp Thr Thr Ile Phe Tyr Ser Gly Val Val Asn Phe Asn Thr Ala
                325                 330                 335

Asn Phe Lys Lys Glu Ile Leu Leu Asp Arg Ser Ala Gly Lys Lys Thr
            340                 345                 350

Ala Phe Ser Ile Lys Leu Asp Tyr Val Lys Lys Pro Ile Pro Glu Thr
        355                 360                 365

Ala Met Val Lys Ile Leu Glu Lys Leu Tyr Glu Glu Asp Val Gly Ala
    370                 375                 380

Gly Met Tyr Val Leu Tyr Pro Tyr Gly Gly Ile Met Glu Glu Ile Ser
385                 390                 395                 400

Glu Ser Ala Ile Pro Phe Pro His Arg Ala Gly Ile Met Tyr Glu Leu
                405                 410                 415

Trp Tyr Thr Ala Ser Trp Glu Lys Gln Glu Asp Asn Glu Lys His Ile
            420                 425                 430

Asn Trp Val Arg Ser Val Tyr Asn Phe Thr Thr Pro Tyr Val Ser Gln
        435                 440                 445

Asn Pro Arg Leu Ala Tyr Leu Asn Tyr Arg Asp Leu Asp Leu Gly Lys
    450                 455                 460

Thr Asn His Ala Ser Pro Asn Asn Tyr Thr Gln Ala Arg Ile Trp Gly
465                 470                 475                 480

Glu Lys Tyr Phe Gly Lys Asn Phe Asn Arg Leu Val Lys Val Lys Thr
                485                 490                 495

Lys Val Asp Pro Asn Asn Phe Phe Arg Asn Glu Gln Ser Ile Pro Pro
            500                 505                 510

Leu Pro Pro His His His
        515


<210> SEQ ID NO 83
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Ala Asn Pro Arg Glu Asn Phe Leu Lys Cys Phe Ser Gln Tyr Ile
1               5                   10                  15

Pro Asn Asn Ala Thr Asn Leu Lys Leu Val Tyr Thr Gln Asn Asn Pro
            20                  25                  30

Leu Tyr Met Ser Val Leu Asn Ser Thr Ile His Asn Leu Arg Phe Thr
        35                  40                  45

Ser Asp Thr Thr Pro Lys Pro Leu Val Ile Val Thr Pro Ser His Val
    50                  55                  60

Ser His Ile Gln Gly Thr Ile Leu Cys Ser Lys Lys Val Gly Leu Gln
65                  70                  75                  80

Ile Arg Thr Arg Ser Gly Gly His Asp Ser Glu Gly Met Ser Tyr Ile
                85                  90                  95
```

```
Ser Gln Val Pro Phe Val Ile Val Asp Leu Arg Asn Met Arg Ser Ile
            100                 105                 110

Lys Ile Asp Val His Ser Gln Thr Ala Trp Val Glu Ala Gly Ala Thr
        115                 120                 125

Leu Gly Glu Val Tyr Tyr Trp Val Asn Glu Lys Asn Glu Asn Leu Ser
    130                 135                 140

Leu Ala Ala Gly Tyr Cys Pro Thr Val Cys Ala Gly Gly His Phe Gly
145                 150                 155                 160

Gly Gly Gly Tyr Gly Pro Leu Met Arg Asn Tyr Gly Leu Ala Ala Asp
                165                 170                 175

Asn Ile Ile Asp Ala His Leu Val Asn Val His Gly Lys Val Leu Asp
            180                 185                 190

Arg Lys Ser Met Gly Glu Asp Leu Phe Trp Ala Leu Arg Gly Gly Gly
        195                 200                 205

Ala Glu Ser Phe Gly Ile Ile Val Ala Trp Lys Ile Arg Leu Val Ala
    210                 215                 220

Val Pro Lys Ser Thr Met Phe Ser Val Lys Lys Ile Met Glu Ile His
225                 230                 235                 240

Glu Leu Val Lys Leu Val Asn Lys Trp Gln Asn Ile Ala Tyr Lys Tyr
                245                 250                 255

Asp Lys Asp Leu Leu Leu Met Thr His Phe Ile Thr Arg Asn Ile Thr
            260                 265                 270

Asp Asn Gln Gly Lys Asn Lys Thr Ala Ile His Thr Tyr Phe Ser Ser
        275                 280                 285

Val Phe Leu Gly Gly Val Asp Ser Leu Val Asp Leu Met Asn Lys Ser
    290                 295                 300

Phe Pro Glu Leu Gly Ile Lys Lys Thr Asp Cys Arg Gln Leu Ser Trp
305                 310                 315                 320

Ile Asp Thr Ile Ile Phe Tyr Ser Gly Val Val Asn Tyr Asp Thr Asp
                325                 330                 335

Asn Phe Asn Lys Glu Ile Leu Leu Asp Arg Ser Ala Gly Gln Asn Gly
            340                 345                 350

Ala Phe Lys Ile Lys Leu Asp Tyr Val Lys Lys Pro Ile Pro Glu Ser
        355                 360                 365

Val Phe Val Gln Ile Leu Glu Lys Leu Tyr Glu Glu Asp Ile Gly Ala
    370                 375                 380

Gly Met Tyr Ala Leu Tyr Pro Tyr Gly Gly Ile Met Asp Glu Ile Ser
385                 390                 395                 400

Glu Ser Ala Ile Pro Phe Pro His Arg Ala Gly Ile Leu Tyr Glu Leu
                405                 410                 415

Trp Tyr Ile Cys Ser Trp Glu Lys Gln Glu Asp Asn Glu Lys His Leu
            420                 425                 430

Asn Trp Ile Arg Asn Ile Tyr Asn Phe Met Thr Pro Tyr Val Ser Lys
        435                 440                 445

Asn Pro Arg Leu Ala Tyr Leu Asn Tyr Arg Asp Leu Asp Ile Gly Ile
    450                 455                 460

Asn Asp Pro Lys Asn Pro Asn Asn Tyr Thr Gln Ala Arg Ile Trp Gly
465                 470                 475                 480

Glu Lys Tyr Phe Gly Lys Asn Phe Asp Arg Leu Val Lys Val Lys Thr
                485                 490                 495

Leu Val Asp Pro Asn Asn Phe Phe Arg Asn Glu Gln Ser Ile Pro Pro
            500                 505                 510

Leu Pro Arg His Arg His
```

515

<210> SEQ ID NO 84
<211> LENGTH: 519
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 84

Met Ala Asn Pro Gln Glu Asn Phe Leu Lys Cys Phe Ser Glu Tyr Ile
1 5 10 15

Pro Asn Asn Pro Ala Asn Pro Lys Phe Ile Tyr Thr Gln His Asp Gln
20 25 30

Leu Tyr Met Ser Val Leu Asn Ser Thr Ile Gln Asn Leu Arg Phe Thr
35 40 45

Ser Asp Thr Thr Pro Lys Pro Leu Val Ile Val Thr Pro Ser Asn Val
50 55 60

Ser His Ile Gln Ala Ser Ile Leu Cys Ser Lys Lys Val Gly Leu Gln
65 70 75 80

Ile Arg Thr Arg Ser Gly Gly His Asp Ala Glu Gly Leu Ser Tyr Ile
85 90 95

Ser Gln Val Pro Phe Ala Ile Val Asp Leu Arg Asn Met His Thr Val
100 105 110

Lys Val Asp Ile His Ser Gln Thr Ala Trp Val Glu Ala Gly Ala Thr
115 120 125

Leu Gly Glu Val Tyr Tyr Trp Ile Asn Glu Met Asn Glu Asn Phe Ser
130 135 140

Phe Pro Gly Gly Tyr Cys Pro Thr Val Gly Val Gly Gly His Phe Ser
145 150 155 160

Gly Gly Gly Tyr Gly Ala Leu Met Arg Asn Tyr Gly Leu Ala Ala Asp
165 170 175

Asn Ile Ile Asp Ala His Leu Val Asn Val Asp Gly Lys Val Leu Asp
180 185 190

Arg Lys Ser Met Gly Glu Asp Leu Phe Trp Ala Ile Arg Gly Gly Gly
195 200 205

Gly Glu Asn Phe Gly Ile Ile Ala Ala Cys Lys Ile Lys Leu Val Val
210 215 220

Val Pro Ser Lys Ala Thr Ile Phe Ser Val Lys Lys Asn Met Glu Ile
225 230 235 240

His Gly Leu Val Lys Leu Phe Asn Lys Trp Gln Asn Ile Ala Tyr Lys
245 250 255

Tyr Asp Lys Asp Leu Met Leu Thr Thr His Phe Arg Thr Arg Asn Ile
260 265 270

Thr Asp Asn His Gly Lys Asn Lys Thr Thr Val His Gly Tyr Phe Ser
275 280 285

Ser Ile Phe Leu Gly Gly Val Asp Ser Leu Val Asp Leu Met Asn Lys
290 295 300

Ser Phe Pro Glu Leu Gly Ile Lys Lys Thr Asp Cys Lys Glu Leu Ser
305 310 315 320

Trp Ile Asp Thr Thr Ile Phe Tyr Ser Gly Val Val Asn Tyr Asn Thr
325 330 335

Ala Asn Phe Lys Lys Glu Ile Leu Leu Asp Arg Ser Ala Gly Lys Lys
340 345 350

```
Thr Ala Phe Ser Ile Lys Leu Asp Tyr Val Lys Lys Leu Ile Pro Glu
        355                 360                 365

Thr Ala Met Val Lys Ile Leu Glu Lys Leu Tyr Glu Glu Glu Val Gly
    370                 375                 380

Val Gly Met Tyr Val Leu Tyr Pro Tyr Gly Gly Ile Met Asp Glu Ile
385                 390                 395                 400

Ser Glu Ser Ala Ile Pro Phe Pro His Arg Ala Gly Ile Met Tyr Glu
                405                 410                 415

Leu Trp Tyr Thr Ala Thr Trp Glu Lys Gln Glu Asp Asn Glu Lys His
            420                 425                 430

Ile Asn Trp Val Arg Ser Val Tyr Asn Phe Thr Thr Pro Tyr Val Ser
        435                 440                 445

Gln Asn Pro Arg Leu Ala Tyr Leu Asn Tyr Arg Asp Leu Asp Leu Gly
    450                 455                 460

Lys Thr Asn Pro Glu Ser Pro Asn Asn Tyr Thr Gln Ala Arg Ile Trp
465                 470                 475                 480

Gly Glu Lys Tyr Phe Gly Lys Asn Phe Asn Arg Leu Val Lys Val Lys
                485                 490                 495

Thr Lys Ala Asp Pro Asn Asn Phe Phe Arg Asn Glu Gln Ser Ile Pro
            500                 505                 510

Pro Leu Pro Pro Arg His His
        515
```

<210> SEQ ID NO 85
<211> LENGTH: 522
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

```
Met Ala Asn Pro Arg Glu Asn Phe Leu Lys Ala Phe Ser Arg His Ile
1               5                   10                  15

Pro Asn Asn Val Ala Asn Pro Lys Leu Val Tyr Thr Gln His Asp Gln
            20                  25                  30

Leu Tyr Met Ser Ile Leu Asn Ser Thr Ile Gln Asn Leu Arg Phe Ile
        35                  40                  45

Ser Asp Thr Thr Pro Lys Pro Leu Val Ile Val Thr Pro Ser Asp Asp
    50                  55                  60

Ser His Ile Gln Ala Thr Ile Leu Ala Ser Lys Glu Val Gly Leu Gln
65                  70                  75                  80

Ile Arg Thr Arg Ser Gly Gly His Asp Ala Glu Gly Met Ser Tyr Ile
                85                  90                  95

Ser Gln Val Pro Phe Val Val Val Asp Leu Arg Asn Met His Ser Ile
            100                 105                 110

Lys Ile Asp Val His Ser Gln Thr Ala Trp Val Glu Ala Gly Ala Thr
        115                 120                 125

Leu Gly Glu Val Tyr Tyr Trp Ile Asn Glu Lys Asn Glu Asn Leu Ser
    130                 135                 140

Phe Pro Gly Gly Tyr Cys Pro Thr Val Gly Val Gly Gly His Phe Ser
145                 150                 155                 160

Gly Gly Gly Tyr Gly Ala Leu Met Arg Asn Tyr Gly Leu Ala Ala Asp
                165                 170                 175

Asn Ile Ile Asp Ala His Leu Val Asn Val Asp Gly Lys Val Leu Asp
            180                 185                 190
```

-continued

Arg Lys Ser Met Gly Glu Asp Leu Phe Trp Ala Ile Arg Gly Gly Gly
195 200 205

Gly Glu Asn Phe Gly Ile Ile Ala Ala Trp Lys Ile Lys Leu Val Ala
210 215 220

Val Pro Ser Lys Ser Thr Ile Phe Ser Val Lys Lys Asn Met Glu Ile
225 230 235 240

His Gly Leu Val Lys Leu Phe Asn Lys Trp Gln Asn Ile Ala Tyr Lys
245 250 255

Tyr Asp Lys Asp Leu Val Leu Met Thr His Phe Ile Thr Lys Asn Ile
260 265 270

Thr Asp Asn His Gly Lys Asn Lys Thr Thr Val His Gly Tyr Phe Ser
275 280 285

Ser Ile Phe His Gly Gly Val Asp Ser Leu Val Asp Leu Met Asn Lys
290 295 300

Ser Phe Pro Glu Leu Gly Ile Lys Lys Thr Asp Cys Lys Glu Phe Ser
305 310 315 320

Trp Ile Asp Thr Thr Ile Phe Tyr Ser Gly Val Val Asn Phe Asn Thr
325 330 335

Ala Asn Phe Lys Lys Glu Ile Leu Leu Asp Arg Ser Ala Gly Lys Lys
340 345 350

Thr Ala Phe Ser Ile Lys Leu Asp Tyr Val Lys Lys Pro Ile Pro Glu
355 360 365

Thr Ala Met Val Lys Ile Leu Glu Lys Leu Tyr Glu Glu Asp Val Gly
370 375 380

Ala Gly Met Tyr Val Leu Tyr Pro Tyr Gly Gly Ile Met Glu Glu Ile
385 390 395 400

Ser Glu Ser Ala Ile Pro Phe Pro His Arg Ala Gly Ile Met Tyr Glu
405 410 415

Leu Trp Tyr Thr Ala Ser Trp Glu Lys Gln Glu Asp Asn Glu Lys His
420 425 430

Ile Asn Trp Val Arg Ser Val Tyr Asn Phe Thr Thr Pro Tyr Val Ser
435 440 445

Gln Asn Pro Arg Leu Ala Tyr Leu Asn Tyr Arg Asp Leu Asp Leu Gly
450 455 460

Lys Thr Asn His Ala Ser Pro Asn Asn Tyr Thr Gln Ala Arg Ile Trp
465 470 475 480

Gly Glu Lys Tyr Phe Gly Lys Asn Phe Asn Arg Leu Val Lys Val Lys
485 490 495

Thr Lys Val Asp Pro Asn Asn Phe Phe Arg Asn Glu Gln Ser Ile Pro
500 505 510

Pro Leu Pro Pro His His His His His His
515 520

<210> SEQ ID NO 86
<211> LENGTH: 522
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 86

Met Ala Asn Pro Arg Glu Asn Phe Leu Lys Ala Phe Ser Arg His Ile
1 5 10 15

Pro Asn Asn Val Ala Asn Pro Lys Leu Val Tyr Thr Gln His Asp Gln

```
            20                  25                  30

Leu Tyr Met Ser Ile Leu Asn Ser Thr Ile Gln Asn Leu Arg Phe Ile
        35                  40                  45

Ser Asp Thr Thr Pro Lys Pro Leu Val Ile Val Thr Pro Ser Asp Asp
    50                  55                  60

Ser His Ile Gln Ala Thr Ile Leu Ala Ser Lys Glu Val Gly Leu Gln
65                  70                  75                  80

Ile Arg Thr Arg Ser Gly Gly His Asp Ala Glu Gly Met Ser Tyr Ile
                85                  90                  95

Ser Gln Val Pro Phe Val Val Val Asp Leu Arg Asn Met His Ser Ile
            100                 105                 110

Lys Ile Asp Val His Ser Gln Thr Ala Trp Val Glu Ala Gly Ala Thr
        115                 120                 125

Leu Gly Glu Val Tyr Tyr Trp Ile Asn Glu Lys Asn Glu Asn Leu Ser
    130                 135                 140

Phe Pro Gly Gly Tyr Cys Pro Thr Val Gly Val Gly Gly His Phe Ser
145                 150                 155                 160

Gly Gly Gly Tyr Gly Ala Leu Met Arg Asn Tyr Gly Leu Ala Ala Asp
                165                 170                 175

Asn Ile Ile Asp Ala His Leu Val Asn Val Asp Gly Lys Val Leu Asp
            180                 185                 190

Arg Lys Ser Met Gly Glu Asp Leu Phe Trp Ala Ile Arg Gly Gly Gly
        195                 200                 205

Gly Glu Asn Phe Gly Ile Ile Ala Ala Trp Lys Ile Lys Leu Val Ala
    210                 215                 220

Val Pro Ser Lys Ser Thr Ile Phe Ser Val Lys Lys Asn Met Glu Ile
225                 230                 235                 240

His Gly Leu Val Lys Leu Phe Asn Lys Trp Gln Asn Ile Ala Tyr Lys
                245                 250                 255

Tyr Asp Lys Asp Leu Val Leu Met Thr His Phe Ile Thr Lys Asn Ile
            260                 265                 270

Thr Asp Asn His Gly Lys Asn Lys Thr Thr Val His Gly Tyr Phe Ser
        275                 280                 285

Ser Ile Phe His Gly Gly Val Asp Ser Leu Val Asp Leu Met Asn Lys
    290                 295                 300

Ser Phe Pro Glu Leu Gly Ile Lys Lys Thr Asp Cys Lys Glu Phe Ser
305                 310                 315                 320

Trp Ile Asp Thr Thr Ile Phe Tyr Ser Gly Val Val Asn Phe Asn Thr
                325                 330                 335

Ala Asn Phe Lys Lys Glu Ile Leu Leu Asp Arg Ser Ala Gly Lys Lys
            340                 345                 350

Thr Ala Phe Ser Ile Lys Leu Asp Tyr Val Lys Lys Pro Ile Pro Glu
        355                 360                 365

Thr Ala Met Val Lys Ile Leu Glu Lys Leu Tyr Glu Glu Asp Val Gly
    370                 375                 380

Ala Gly Met Tyr Val Leu Tyr Pro Tyr Gly Gly Ile Met Glu Glu Ile
385                 390                 395                 400

Ser Glu Ser Ala Ile Pro Phe Pro His Arg Ala Gly Ile Met Tyr Glu
                405                 410                 415

Leu Trp Tyr Thr Ala Ser Trp Glu Lys Gln Glu Asp Asn Glu Lys His
            420                 425                 430

Ile Asn Trp Val Arg Ser Val Tyr Asn Phe Thr Thr Pro Tyr Val Ser
        435                 440                 445
```

Gln Asn Pro Arg Leu Ala Tyr Leu Asn Tyr Arg Asp Leu Asp Leu Gly
450 455 460

Lys Thr Asn His Ala Ser Pro Asn Asn Tyr Thr Gln Ala Arg Ile Trp
465 470 475 480

Gly Glu Lys Tyr Phe Gly Lys Asn Phe Asn Arg Leu Val Lys Val Lys
485 490 495

Thr Lys Val Asp Pro Asn Asn Phe Phe Arg Asn Glu Gln Ser Ile Pro
500 505 510

Pro Leu Pro Pro His His His His His His
515 520

<210> SEQ ID NO 87
<211> LENGTH: 522
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

Met Ala Asn Pro Arg Glu Asn Phe Leu Lys Ala Phe Ser Arg His Ile
1 5 10 15

Pro Asn Asn Val Ala Asn Pro Lys Leu Val Tyr Thr Gln His Asp Gln
20 25 30

Thr Tyr Met Ser Ile Leu Asn Ser Thr Ile Gln Asn Leu Arg Phe Ile
35 40 45

Ser Asp Thr Thr Pro Lys Pro Leu Val Ile Val Thr Pro Ser Asp Asn
50 55 60

Ser His Ile Gln Ala Thr Ile Leu Ala Ser Lys Glu Val Gly Leu Gln
65 70 75 80

Ile Arg Thr Arg Ser Gly Gly His Asp Ala Glu Gly Met Ser Tyr Ile
85 90 95

Ser Gln Val Pro Phe Val Val Val Asp Leu Arg Asn Met His Ser Ile
100 105 110

Lys Ile Asp Val His Ser Gln Thr Ala Trp Val Glu Ala Gly Ala Thr
115 120 125

Leu Gly Glu Val Tyr Tyr Trp Ile Asn Glu Lys Asn Glu Asn Leu Ser
130 135 140

Phe Pro Gly Gly Tyr Cys Pro Thr Val Gly Val Gly Gly His Phe Ser
145 150 155 160

Gly Gly Gly Tyr Gly Ala Leu Met Arg Asn Tyr Gly Leu Ala Ala Asp
165 170 175

Asn Ile Ile Asp Ala His Leu Val Asn Val Asp Gly Lys Val Leu Asp
180 185 190

Arg Lys Ser Met Gly Glu Asp Leu Phe Trp Ala Ile Arg Gly Gly Gly
195 200 205

Gly Glu Asn Phe Gly Ile Ile Ala Ala Trp Lys Ile Lys Leu Val Ala
210 215 220

Val Pro Ser Lys Ser Thr Ile Phe Ser Val Lys Lys Asn Met Glu Ile
225 230 235 240

His Gly Leu Val Lys Leu Phe Asn Lys Trp Gln Asn Ile Ala Tyr Lys
245 250 255

Tyr Asp Lys Asp Leu Val Leu Met Thr His Phe Ile Thr Lys Asn Ile
260 265 270

Thr Asp Asn His Gly Lys Asn Lys Thr Thr Val His Gly Tyr Phe Ser

```
        275                 280                 285

Ser Ile Phe His Gly Gly Thr Asp Ser Leu Val Asp Leu Met Asn Lys
    290                 295                 300

Ser Phe Pro Glu Leu Gly Ile Lys Lys Thr Asp Cys Lys Glu Phe Ser
305                 310                 315                 320

Trp Ile Asp Thr Thr Ile Phe Tyr Ser Gly Val Val Asn Phe Asn Thr
                325                 330                 335

Ala Asn Phe Lys Lys Glu Ile Leu Leu Asp Arg Ser Ala Gly Lys Lys
            340                 345                 350

Thr Ala Phe Ser Ile Lys Leu Asp Tyr Val Lys Lys Pro Ile Pro Glu
        355                 360                 365

Thr Ala Met Val Lys Ile Leu Glu Lys Leu Tyr Glu Glu Asp Val Gly
    370                 375                 380

Ala Gly Met Tyr Val Leu Tyr Pro Tyr Gly Gly Ile Met Glu Glu Ile
385                 390                 395                 400

Ser Glu Ser Ala Ile Pro Phe Pro His Arg Ala Gly Ile Met Tyr Glu
                405                 410                 415

Leu Trp Tyr Thr Ala Ser Trp Glu Lys Gln Glu Asp Asn Glu Lys His
            420                 425                 430

Ile Asn Trp Val Arg Ser Val Tyr Asn Phe Thr Thr Pro Tyr Val Ser
        435                 440                 445

Gln Asn Pro Arg Leu Ala Tyr Leu Asn Tyr Arg Asp Leu Asp Leu Gly
    450                 455                 460

Lys Thr Asn His Ala Ser Pro Asn Asn Tyr Thr Gln Ala Arg Ile Trp
465                 470                 475                 480

Gly Glu Lys Tyr Phe Gly Lys Asn Phe Asn Arg Leu Val Lys Val Lys
                485                 490                 495

Thr Lys Val Asp Pro Asn Asn Phe Phe Arg Asn Glu Gln Ser Ile Pro
            500                 505                 510

Pro Leu Pro Pro His His His His His His
        515                 520


<210> SEQ ID NO 88
<211> LENGTH: 522
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Ala Asn Pro Arg Glu Asn Phe Leu Lys Ala Phe Ser Arg His Ile
1               5                   10                  15

Pro Asn Asn Val Ala Asn Pro Lys Leu Val Tyr Thr Gln His Asp Gln
            20                  25                  30

Thr Tyr Met Ser Ile Leu Asn Ser Thr Ile Gln Asn Leu Arg Phe Ile
        35                  40                  45

Ser Asp Thr Thr Pro Lys Pro Leu Val Ile Val Thr Pro Ser Asp Asn
    50                  55                  60

Ser His Ile Gln Ala Thr Ile Leu Ala Ser Lys Glu Val Gly Leu Gln
65                  70                  75                  80

Ile Arg Thr Arg Ser Gly Gly His Asp Ala Glu Gly Met Ser Tyr Ile
                85                  90                  95

Ser Gln Val Pro Phe Val Val Val Asp Leu Arg Asn Met His Ser Ile
            100                 105                 110
```

-continued

```
Lys Ile Asp Val His Ser Gln Thr Ala Trp Val Glu Ala Gly Ala Thr
        115                 120                 125

Leu Gly Glu Val Tyr Tyr Trp Ile Asn Glu Lys Asn Glu Asn Leu Ser
    130                 135                 140

Phe Pro Gly Gly Tyr Cys Pro Thr Val Gly Val Gly Gly His Phe Ser
145                 150                 155                 160

Gly Gly Gly Tyr Gly Ala Leu Met Arg Asn Tyr Gly Leu Ala Ala Asp
                165                 170                 175

Asn Ile Ile Asp Ala His Leu Val Asn Val Asp Gly Lys Val Leu Asp
            180                 185                 190

Arg Lys Ser Met Gly Glu Asp Leu Phe Trp Ala Ile Arg Gly Gly Gly
        195                 200                 205

Gly Glu Asn Phe Gly Ile Ile Ala Ala Trp Lys Ile Lys Leu Val Ala
    210                 215                 220

Val Pro Ser Lys Ser Thr Ile Phe Ser Val Lys Lys Asn Met Glu Ile
225                 230                 235                 240

His Gly Leu Val Lys Leu Phe Asn Lys Trp Gln Asn Ile Ala Tyr Lys
                245                 250                 255

Tyr Asp Lys Asp Leu Val Leu Met Thr His Phe Ile Thr Glu Asn Ile
            260                 265                 270

Thr Asp Asn His Gly Lys Asn Lys Thr Thr Val His Gly Tyr Phe Ser
        275                 280                 285

Ser Ile Phe His Gly Gly Val Asp Ser Leu Val Asp Leu Met Asn Lys
    290                 295                 300

Ser Phe Pro Glu Leu Gly Ile Lys Lys Thr Asp Cys Lys Glu Phe Ser
305                 310                 315                 320

Trp Ile Asp Thr Thr Ile Phe Tyr Ser Gly Val Val Asn Phe Asn Thr
                325                 330                 335

Ala Asn Phe Lys Lys Glu Ile Leu Leu Asp Arg Ser Ala Gly Lys Lys
            340                 345                 350

Thr Ala Phe Ser Ile Lys Leu Asp Tyr Val Lys Lys Pro Ile Pro Glu
        355                 360                 365

Thr Ala Met Val Lys Ile Leu Glu Lys Leu Tyr Glu Glu Asp Val Gly
    370                 375                 380

Ala Gly Met Tyr Val Leu Tyr Pro Tyr Gly Gly Ile Met Glu Glu Ile
385                 390                 395                 400

Ser Glu Ser Ala Ile Pro Phe Pro His Arg Ala Gly Ile Met Tyr Glu
                405                 410                 415

Leu Trp Tyr Thr Ala Ser Trp Glu Lys Gln Glu Asp Asn Glu Lys His
            420                 425                 430

Ile Asn Trp Val Arg Ser Val Tyr Asn Phe Thr Thr Pro Tyr Val Ser
        435                 440                 445

Gln Asn Pro Arg Leu Ala Tyr Leu Asn Tyr Arg Asp Leu Asp Leu Gly
    450                 455                 460

Lys Thr Asn His Ala Ser Pro Asn Asn Tyr Thr Gln Ala Arg Ile Trp
465                 470                 475                 480

Gly Glu Lys Tyr Phe Gly Lys Asn Phe Asn Arg Leu Val Lys Val Lys
                485                 490                 495

Thr Lys Val Asp Pro Asn Asn Phe Phe Arg Asn Glu Gln Ser Ile Pro
            500                 505                 510

Pro Leu Pro Pro His His His His His His
        515                 520
```

-continued

```
<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 89

His His His His His His
1               5


<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

His His His His
1
```

CANNABINOID SYNTHASE VARIANTS AND METHODS FOR THEIR USE

SEQUENCE LISTING

The instant application contains a Sequence Listing which has been submitted electronically in ASCII format and is hereby incorporated by reference in its entirety. Said ASCII copy, created on Apr. 13, 2021, is named 0171-0001WO1_SL.txt and is 289,909 bytes in size.

FIELD OF THE INVENTION

The invention relates to a non-natural cannabinoid synthase comprising at least one amino acid variation as compared to a wild type cannabinoid synthase, comprising three alpha helices (αA, αB and αC) where a disulfide bond is not formed between alpha helix αA and alpha helix αC, wherein the non-natural cannabinoid synthase catalyzes the oxidative cyclization of cannabigerolic acid (CBGA) into a cannabinoid. The invention further relates to a non-natural $\Delta^9$-tetrahydrocannabinolic acid synthase (THCAS), cannabidiolic acid synthase (CBDAS), and cannabichromenic acid synthase (CBCAS) comprising at least one amino acid variation as compared to a wild type THCAS, CBDAS, or CBCAS, respectively, comprising three alpha helices (αA, αB and αC) and wherein a disulfide bond is not formed between alpha helix αA and alpha helix αC. The invention also relates to a nucleic acid, expression construct, and engineered cell for making the non-natural THCAS, CBDAS, and/or CBCAS. Also provided are compositions comprising the non-natural THCAS, CBDAS, and/or CBCAS; isolated non-natural THCAS, CBDAS, and/or CBCAS enzymes; methods of making the isolated enzymes; cell extracts comprising cannabinoids; and methods of making cannabinoids.

BACKGROUND

Cannabinoids constitute a varied class of chemicals, typically prenylated polyketides derived from fatty acid and isoprenoid precursors, that bind to cellular cannabinoid receptors. Modulation of these receptors has been associated with different types of physiological processes including pain-sensation, memory, mood, and appetite. Endocannabinoids, which occur in the body, phytocannabinoids, which are found in plants such as *Cannabis*, and synthetic cannabinoids, can have activity on cannabinoid receptors and elicit biological responses.

*Cannabis sativa* produces a variety of phytocannabinoids, for example, cannabigerolic acid (CBGA), which is a precursor of tetrahydrocannabinol (THC), the primary psychoactive compound in *Cannabis*. Additionally, CBGA is also a precursor for $\Delta^9$-tetrahydrocannabinoic acid ($\Delta^9$-THCA), cannabichromenic acid (CBCA), and cannabidiolic acid (CBDA).

$\Delta^9$-tetrahydrocannabinolic acid (THCA) is interchangeably known as $\Delta^1$-tetrahydrocannabinoic acid. THCA has two isoforms, THCA-A and THCA-B, with THCA-A being the predominant isoform in *C. sativa*. Interconversion between the two isoforms of THCA is not yet well-understood. See, e.g., Partland et al., *Cannabis* Cannabinoid Res 2(1):87-95 (2017).

THCA-A has the following structure:

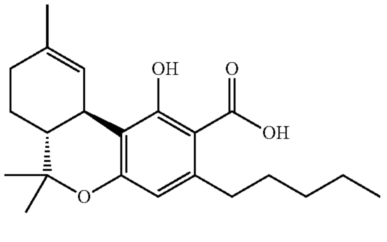 [SMILES: CCCCCc1cc2c(c(O)c1C(=O)O)[C@@H]1C=C(C)CC[C@H]1C(C)(C)O2]

THCA-B has the following structure:

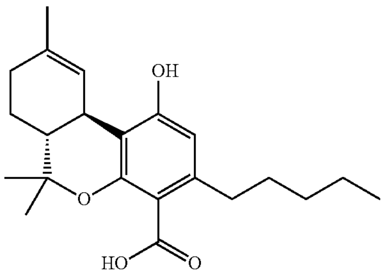 [SMILES: CCCCCc1cc(O)c2c(c1C(=O)O)OC(C)(C)[C@@H]1CCC(C)=C[C@@H]21]

THCA can be converted to THC by non-enzymatic decarboxylation, typically under heat. Studies have shown that THCA may have various therapeutic effects, e.g., anti-inflammatory properties for the treatment of arthritis and lupus, neuroprotective properties for treatment of neurodegenerative diseases, anti-emetic properties for the treatment of nausea and appetite loss, and anti-proliferative properties noted in the studies of prostate cancer. See, e.g., Ruhaak et al., Biol Pharm Bull 34(5):774-778 (2011); Moldzio et al., Phytomedicine 19:819-824 (2012); Baker et al., J Pharm Pharmacol 33(1):369-372 (1981); De Petrocellis et al., Br J Pharmacol 168(1):79-102 (2013); and Verhoeckx et al., Int Immunopharmacol 6(4):656-665 (2006).

In an exemplary cannabinoid biosynthesis pathway for production of THCA, e.g., as found in *C. sativa*, the first enzyme in the pathway is a polyketide synthase, olivetol synthase (OLS), which catalyzes the condensation of hexanoyl-CoA with three molecules of malonyl-CoA to yield 3,5,7-trioxododecanoyl-CoA, which is then converted to olivetolic acid (OA) by the enzyme olivetolic acid cyclase (OAC). Geranyl pyrophosphate (GPP) is produced by geranyl pyrophosphate synthase from isopentyl pyrophosphate (IPP) and dimethylallyl pyrophosphate (DMAPP), which are produced from the mevalonate pathway (MVA), the non-mevalonate, methylerythritol-4-phosphate (MEP) pathway, and/or a non-MVA, non-MEP pathway. A prenyltransferase converts OA and GPP to CBGA, which is then converted to THCA by $\Delta^9$-tetrahydrocannabinolic acid synthase (THCAS). Additionally, cannabidiolic acid synthase (CBDAS) is responsible for the oxidative cyclization of CBGA to cannabidiolic acid (CBDA), and cannabichromenic acid synthase (CBCAS) is responsible for the oxidative cyclization of CBGA to cannabichromenic acid (CBCA).

SUMMARY OF THE INVENTION

The present disclosure relates to a non-natural cannabinoid synthase comprising at least one amino acid variation as compared to a wild type THCAS, comprising three alpha helices (αA, αB and αC) where a disulfide bond is not formed between alpha helix αA and alpha helix αC, wherein the non-natural cannabinoid synthase catalyzes the oxidative cyclization of CBGA into a cannabinoid. The non-natural cannabinoid synthases are advantageous, e.g., because they can be expressed in microbial organisms lacking or having inadequate mechanisms for forming disulfide bonds in the cytoplasm of the microbial organism, e.g., *Escherichia coli.*

In some embodiments, the present disclosure provides a non-natural cannabinoid synthase with 70% or greater identity to any of SEQ ID NOs:1-2 or 78-84 or 85-88, comprising at least one amino acid variation as compared to a wild type cannabinoid synthase, comprising three alpha helices (αA, αB, and αC) and wherein a disulfide bond is not formed between alpha helix αA and alpha helix αC, wherein the non-natural cannabinoid synthase converts cannabigerolic acid (CBGA) into a cannabinoid.

In some embodiments, the non-natural cannabinoid synthase has 80% or greater identity of any of SEQ ID NOs:1-2 or 78-84 or 85-88. In some embodiments, the non-natural cannabinoid synthase has 85% or greater identity of any of SEQ ID NOs:1-2 or 78-84 or 85-88. In some embodiments, the non-natural cannabinoid synthase has 90% or greater identity of any of SEQ ID NOs:1-2 or 78-84 or 85-88. In some embodiments, the non-natural cannabinoid synthase has 95% or greater identity of any of SEQ ID NOs:1-2 or 78-84 or 85-88. In some embodiments, the non-natural cannabinoid synthase has 80% or greater identity to any of SEQ ID NOs:85-88. In some embodiments, the non-natural cannabinoid synthase has 85% or greater identity to any of SEQ ID NOs:85-88. In some embodiments, the non-natural cannabinoid synthase has 90% or greater identity to any of SEQ ID NOs:85-88. In some embodiments, the non-natural cannabinoid synthase has 95% or greater identity to any of SEQ ID NOs:85-88. In some embodiments, the non-natural cannabinoid synthase has 99% or greater identity to any of SEQ ID NOs:85-88.

In some embodiments, the at least one amino acid variation is not within an active site of the non-natural cannabinoid synthase. In some embodiments, the cannabinoid synthase is Δ1-tetrahydrocannabinolic acid synthase (THCAS), cannabidiolic acid synthase (CBDAS), or cannabichromenic acid synthase (CBCAS).

In some embodiments, the disclosure provides a non-natural $\Delta^9$-tetrahydrocannabinolic acid synthase (THCAS) with 80% or greater identity to any of SEQ ID NOs:1, 2, 82, or 85-88, comprising at least one amino acid variation as compared to a wild type THCAS, comprising three alpha helices (αA, αB and αC) and wherein a disulfide bond is not formed between alpha helix αA and alpha helix αC, wherein the non-natural THCAS catalyzes the oxidative cyclization of cannabigerolic acid (CBGA) into $\Delta^9$-tetrahydrocannabinolic acid.

In some embodiments, the THCAS has 80% or greater identity to SEQ ID NO:2. In some embodiments, the variation is a substitution, deletion or insertion. In some embodiments, the non-natural THCAS comprises at least one salt bridge between alpha helix αA and alpha helix αC. In some embodiments, the non-natural THCAS comprises 1-20, 2-20, 3-20, 4-20, 5-20, 10-20, or 15-20 amino acid variations as compared to a wild type THCAS.

In some embodiments, the variation is at position C37, C99, K36, K40, K101, K102, or a combination thereof, wherein the position corresponds to SEQ ID NO:2. In some embodiments, the variation is at position C37, C99, or both, wherein the position corresponds to SEQ ID NO:2.

In some embodiments, the variation in an insertion. In some embodiments, the variation is an insertion of 1 to 10 amino acids. In some embodiments, the variation is an insertion of 1 to 4 amino acids. In some embodiments, the variation is an insertion positioned within 10 amino acids of C37 or C99, wherein the position corresponds to SEQ ID NO:2.

In some embodiments, the variation in a deletion. In some embodiments, the variation is a deletion of 1 to 10 amino acids. In some embodiments, the variation is a deletion of 1 to 4 amino acids. In some embodiments, the variation is a deletion positioned within 10 amino acids of C37 or C99, wherein the position corresponds to SEQ ID NO:2.

In some embodiments, the variation is a substitution. In some embodiments, the non-natural THCAS comprises 1-20, 2-20, 3-20, 4-20, 5-20, 10-20, or 15-20 amino acid substitutions as compared to a wild type THCAS. In some embodiments, the non-natural THCAS comprises a substitution at position C37, wherein the position corresponds to SEQ ID NO:2. In some embodiments, the non-natural THCAS comprises a substitution selected from position C37A, C37D, C37H, C37Y, C37E, C37K, C37N, C37Q, C37T and C37R, wherein the position corresponds to SEQ ID NO:2. In some embodiments, the non-natural THCAS comprises a substitution selected from C37A, C37D, C37E, C37K, C37N, C37Q, and C37R. In some embodiments, the non-natural THCAS comprises a substitution at position C99, wherein the position corresponds to SEQ ID NO:2. In some embodiments, the non-natural THCAS comprises a substitution selected from position C99F, C99A, C99I, C99V, and C99L, wherein the position corresponds to SEQ ID NO:2. In some embodiments, the non-natural THCAS comprises a substitution selected from C99A, C99I, C99V, and C99L. In some embodiments, the non-natural THCAS comprises a substitution at C37 and a substitution at C99. In some embodiments, the non-natural THCAS comprises a substitution selected from C37A, C37Q, C37N, C37E, C37D, C37R, and C37K, and a substitution selected from C99V, C99A, C99I and C99L. In some embodiments, the non-natural THCAS comprises C37D and a substitution selected from C99F, C99V, C99A, C99I, and C99L. In some embodiments, the non-natural THCAS comprises C37Y and a substitution selected from C99A, C99I, C99V, C99L and C99F. In some embodiments, the non-natural THCAS comprises C37K and C99F. In some embodiments, the non-natural THCAS comprises C37H and a substitution selected from C99V, C99L and C99A. In some embodiments, the non-natural THCAS comprises C37N and a substitution selected from C99A, C99F and C99V. In some embodiments, the non-natural THCAS comprises C37Q and a substitution selected from C99I and C99A. In some embodiments, the non-natural THCAS comprises C37R and C99I. In some embodiments, the non-natural THCAS comprises K36, K40, K101, K102, or a combination thereof is independently substituted with a charged amino acid. In some embodiments, the charged amino acid is D, E, or R. In some embodiments, the non-natural THCAS comprises (a) C99V, C99A, C99I or C99L; and (b) C37A, C37Q, C37N, C37E, C37D, C37R or C37K. In some embodiments, the non-natural THCAS comprises K36D, K40E, C37K and K101R.

In some embodiments, the non-natural THCAS comprises at least one amino acid substitution at a position corresponding to SEQ ID NO:2, wherein the substitution is (a) C37D and C99F, (b) C37H, (c) C37Y, (d) C37Y and C99A, (e) C37E and C99F, (f) C37Y and C99I, (g) C37Y and C99V, (h) C37E, (i) C37K and C99F, (j) C37D, (k) C37D and C99V, (l) C37D and C99A, (m) C37H and C99V, (n) C37E and C99V, (o) C37N and C99A, (p) C37N and C99F, (q) C37E and C99A, (r) C37N and C99V, (s) C37Q and C99I, (t) C37T, (u) C37Y and C99L, (v) C37H and C99L, (w) C99F, (x) C37Q, (y) C37N, (z) C37H and C99A, (aa) C37Y and C99F, (bb) C37K, (cc) C37Q and C99A, (dd) C37R and C99I, (ee) C37A and C99V, (ff) C37A and C99A, (gg) C37A and C99I, (hh) C37A and C99L, (ii) C37Q and C99V, (jj) C37Q and C99L, (kk) C37N and C99I, (ll) C37N and C99L, (mm) C37E and C99I, (nn) C37E and C99L, (oo) C37D and C99I, (pp) C37D and C99L, (qq) C37R and C99V, (rr) C37R and C99A, (ss) C37R and C99L, (tt) C37R, (uu) C37K and C99V, (vv) C37K and C99A, (ww) C37K and C99I, or (xx) C37K and C99L, wherein the position corresponds to SEQ ID NO:2.

In some embodiments, K36, K40, K101, K102, or a combination thereof, of the non-natural THCAS is independently substituted with D, E, or R. In some embodiments, the non-natural THCAS comprises K36D, K40E, C37K and K101R.

In some embodiments, the non-natural THCAS position C37 is substituted with K, E, R, or D; position C99 is substituted with F; position K36, K40, K102, or a combination thereof are independently substituted with D, R or E; and position K101 is unsubstituted or is substituted with R, wherein the position corresponds to SEQ ID NO:2. In some embodiments, the non-natural THCAS comprises a substitution selected from K36D, K36R and K36E. In some embodiments, the non-natural THCAS comprises a substitution selected from K40D, K40R, and K40E. In some embodiments, the non-natural THCAS comprises a substitution selected from K102D, K102R and K102E. In some embodiments, the non-natural THCAS comprises at least one amino acid substitution at a position corresponding to SEQ ID NO:2, wherein the substitution is:

| | | | | | | |
|---|---|---|---|---|---|---|
| a. | K36D | C37K | K40D | C99F and | K101R, | |
| b. | K36D | C37K | K40D | C99F | K1101R and | K102R, |
| c. | K36D | C37K | K40E | C99F and | K101R, | |
| d. | K36D | C37K | K40E | C99F | K101R and | K102R, |
| e. | K36R | C37K | K40D | C99F | K101R and | K102R, |
| f. | K36D | C37E | C99F and | K101R, | | |
| g. | K36R | C37E | K40E | C99F | K101R and | K102R, |
| h. | C37E | C99F | K101R and | K102E, | | |
| i. | K36E | C37K | K40E | C99F and | K101R, | |
| j | K36D | C37R | K40D | C99F | K101R and | K102D, |
| k. | K36D | C37K | K40D and | C99F, | | |
| l. | K36R | C37K | K40R | C99F | K101R and | K102E, |
| m. | K36R | C37E | K40D | C99F | K101R and | K102E, |
| n. | K36E | C37R | K40D | C99F and | K101R, | |
| o. | K36D | C37R | K40E | C99F and | K101R, | |
| p. | K36D | C37R | K40D | C99F | K101R and | K102R, |
| q. | K36R | C37R | K40E | C99F | K101R and | K102R, |
| r. | K36D | C37E | K40D | C99F | K101R and | K102R, |
| s. | K36D | C37K | K40E and | C99F, | | |
| t. | K36D | C37R | K40D | C99F | K101R and | K102E, |
| u. | K36D | C37E | K40E | C99F | K101R and | K102R, |
| v. | C37D | C99F | K101R and | K102E, | | |
| w. | K36E | C37E | K40E | C99F | K101R and | K102R, |
| x. | K36R | C37E | C99F | K101R and | K102R, | |
| y. | K36R | C37E | K40D | C99F | K101R and | K102R, |
| z. | K36D | C37D | C99F and | K102E, | | |
| aa. | K36R | C37D | K40D | C99F | K101R and | K102R, |
| bb. | C37D | C99F | K101R and | K102R, | | |
| cc. | K36D | C37D | K40E | C99F | K101R and | K102R, |
| dd. | K36D | C37D | C99F | K101R and | K102D, | |
| ee. | C37E | K40E | C99F | K101R and | K102E, | |
| ff. | K36R | C37E | K40D | C99F and | K101R, | |
| gg. | K36D | C37D | K40R | C99F and | K101R, | |
| hh. | K36D | C37D | C99F | K101R and | K102E, | |
| ii. | K36D | C37K | C99F | K101R and | K102R, or | |
| jj. | K36E | C37R | K40R | C99F | K101R and | K102E. |

In some embodiments, the non-natural THCAS comprises a sequence of any one of SEQ ID NOs:85-88. In some embodiments, the THCAS comprises a substitution at position C37, K40, V46, Q58, L59, N89, N90, C99, K102, K296, V321, V358, K366, K513, N516, N528, H544, or a combination thereof, wherein the position corresponds to SEQ ID NO:2. In some embodiments, the substitution comprises C37A, R40K, V46E, Q58E, L59L, C99A, N89D, N90D, K296E, V321V, V358T, K366D, K513D, N516E, N528T, or H544Y. In some embodiments, the substitution is C37A, K40R, N89D, N90D, C99A, and K102E. In some embodiments, the substitution is C37A, K40R, L59T, N89D, C99A, K102E, and V321T. In some embodiments, the substitution is C37A, K40R, L59T, N89D, C99A, K102E, K296E, V321T, and N516E. In some embodiments, the substitution is C37A, K40R, L59T, N89D, C99A, K102E, and K296E. In some embodiments, the substitution is C37A, K40R, Q58E, L59T, N89D, N90T, C99A, K102E, K296E, V321T, V358T, N516E, and N528T. In some embodiments, the substitution is C37A, K40R, Q58E, L59T, N89D, N90T, C99A, K102E, K296E, V321T, V358T, K366D, N516E, and N528T, In some embodiments, the substitution is C37A, K40R, Q58E, N89D, N90T, C99A, K102E, K296E, V321T, V358T, K366D, N516E, and N528T. In some embodiments, the substitution is C37A, K40R, Q58E, L59T, N89D, N90T, C99A, K102E, K296E, V321T, V358T, K366D, and N516E. In some embodiments, the substitution is C37A, K40R, Q58E, N90T, C99A, K102E, K296E, V321T, V358T, N516E, and N528T. In some embodiments, the substitution is C37A, K40R, Q58E, N89D, N90T, C99A, K102E, K296E, V321T, V358T, K366D, N516E, and N528T. In some embodiments, the substitution is C37A, K40R, Q58E, L59T, N90T, C99A, K102E, K296E, V321T, V358T, K366D, N516E, and N528T.

In some embodiments, the non-natural THCAS comprises SEQ ID NO:86 and further comprises an amino acid substitution selected from: (1) K296E and N516E; (2) V358T and N516E; (3) N90T and N516E; (4) K296E and N528T; (5) K366D and N516E; (6) K296E and V358T; (7) N90T and K296E; (8) T59L and N516E; (9) V358T and N528T; (10) Q58E and K296E; (11) D89N and K296E; (12) N90T and N528T; (13) K366D and N528T; (14) K513D and N516E; (15) Q58E and N516E; (16) Q58E and N90T; (17) Q58E and N528T; (18) D89N and N516E; (19) V358T and H544Y; (20) Q58E and V358T; (21) V358T and K366D; (22) D89N and N90T; (23) V46E and K296E; (24) K296E and H544Y; (25) V46E and N516E; (26) R40K and N516E; (27) T321V and N516E; (28) D89N and N528T; (29) K296E and T321V; (30) K296E and K513D; (31) L59T and N528T; (32) K513D and N528T; (33) K366D and K513D; (34) T59L and V358T; (35) T59L and K366D; (36) D89S and K296E; (37) N90T and T321V; (38) Q58E and H544Y; (39) T59L and K296E; (40) N90T and H544Y; (41) D89S and N516E; (42) Q58E and T321V; (43) T59L and H544Y; (44) V46E and N90T; (45) N90T and K366D; (46) V358T and K513D; (47) T59L and T321V; (48) R40K and K296E; (49) V46E and K366D; (50) T321V and K366D; (51) Q58E and K366D; (52) T321V and N528T; (53) Q58E and L59T; (54) V46E and V358T; (55) K296E; or (56) N516E, wherein the amino acid position corresponds to SEQ ID NO:86.

In some embodiments, the non-natural THCAS comprises SEQ ID NO:88 and further comprises an amino acid substitution selected from Q58E, N90T, V358T, N528T, K366D, or a combination thereof, wherein the amino acid position corresponds to SEQ ID NO:88. In some embodiments, the non-natural THCAS comprises SEQ ID NO:88 and further comprises two amino acid substitutions selected from: (1) Q58E and N90T; (2) Q58E and V358T; (3) Q58E and N528T; (4) Q58E and K366D; (5) N90T and N528T; (6) N90T and K366D; (7) V358T and K366D; (8) K366D and N528T; or (9) V358T and N528T, wherein the amino acid position corresponds to SEQ ID NO:88.

In some embodiments, the non-natural THCAS comprises SEQ ID NO:88 and further comprises three amino acid substitutions selected from: (1) Q58E, N90T, and V358T; (2) Q58E, N90T, and N528T; (3) Q58E, V358T, and N528T; (4) N90T, V358T, and N528T; or (4) V358T, K366D, and N528T, wherein the amino acid position corresponds to SEQ ID NO:88. In some embodiments, the non-natural THCAS comprises SEQ ID NO:88 and further comprises four amino acid substitutions selected from: (1) Q58E, V358T, K366D, and N528T; (2) Q58E, N90T, K366D, and N528T; or (3) N90T, V358T, K366D, and N528T, wherein the amino acid position corresponds to SEQ ID NO:88.

In some embodiments, the non-natural THCAS further catalyzes the oxidative cyclization of CBGA into cannabichromenic acid (CBCA). In some embodiments, the non-natural THCAS catalyzes the oxidative cyclization of CBGA into THCA at about pH 4.0 to about pH 6.0. In some embodiments, the non-natural THCAS catalyzes the oxidative cyclization of CBGA into CBCA at about pH 6.5 to about pH 7.5.

In some embodiments, the disclosure provides a non-natural cannabidiolic acid synthase (CBDAS) with 80% or greater identity to any of SEQ ID NOs:78, 79, or 83, comprising at least one amino acid variation as compared to a wild type CBDAS, comprising three alpha helices (αA, αB, and αC) and wherein a disulfide bond is not formed between alpha helix αA and alpha helix αC, and wherein the non-natural CBDAS catalyzes the oxidative cyclization of cannabigerolic acid (CBGA) into cannabidiolic acid (CBDA).

In some embodiments, the CBDAS has 80% or greater identity to SEQ ID NO:79. In some embodiments, the variation is a substitution, deletion or insertion. In some embodiments, the non-natural CBDAS comprises at least one non-natural salt bridge between alpha helix αA and alpha helix αC in the N-terminal domain. In some embodiments, the non-natural CBDAS comprises 1-20, 2-20, 3-20, 4-20, 5-20, 10-20, or 15-20 amino acid variations as compared to a wild type CBDAS.

In some embodiments, the variation is at position C37, C99, K36, Q40, K101, K102, or a combination thereof, wherein the position corresponds to SEQ ID NO:79. In some embodiments, the variation is at C37, C99, or both, wherein the position corresponds to SEQ ID NO:79.

In some embodiments, the variation is an insertion. In some embodiments, the variation is an insertion of 1 to 10 amino acids. In some embodiments, the variation is an insertion of 1 to 4 amino acids. In some embodiments, the variation is an insertion positioned within 10 amino acids of C37 or C99.

In some embodiments, the variation is a deletion. In some embodiments, the variation is a deletion of 1 to 10 amino acids. In some embodiments, the variation is a deletion of 1 to 4 amino acids. In some embodiments, the variation is a deletion positioned within 10 amino acids of C37 or C99.

In some embodiments, the variation is a substitution. In some embodiments, the non-natural CBDAS comprises 1-20, 2-20, 3-20, 4-20, 5-20, 10-20, or 15-20 amino acid substitutions as compared to a wild type CBDAS. In some embodiments, the non-natural CBDAS comprises a substitution at position C37, wherein the position corresponds to SEQ ID NO:79. In some embodiments, the non-natural CBDAS comprises a substitution selected from position C37A, C37D, C37H, C37Y, C37E, C37K, C37N, C37Q, C37T and C37R, wherein the position corresponds to SEQ ID NO:79. In some embodiments, the non-natural CBDAS comprises a substitution selected from C37A, C37D, C37E, C37K, C37N, C37Q, and C37R. In some embodiments, the non-natural CBDAS comprises a substitution at position C99, wherein the position corresponds to SEQ ID NO:79. In some embodiments, the non-natural CBDAS comprises a substitution selected from position C99F, C99A, C99I, C99V, and C99L wherein the position corresponds to SEQ ID NO:79. In some embodiments, the non-natural CBDAS comprises a substitution selected from C99A, C99I, C99V, and C99L. In some embodiments, the non-natural CBDAS comprises a substitution at C37 and a substitution at C99. In some embodiments, the non-natural CBDAS comprises a substitution selected from C37A, C37Q, C37N, C37E, C37D, C37R, and C37K, and a substitution selected from C99V, C99A, C99I and C99L. In some embodiments, the non-natural CBDAS comprises C37D and a substitution selected from C99F, C99V, C99A, C99I, and C99L. In some embodiments, the non-natural CBDAS comprises C37Y and a substitution selected from C99A, C99I, C99V, C99L and C99F. In some embodiments, the non-natural CBDAS comprises C37K and C99F. In some embodiments, the non-natural CBDAS comprises C37H and a substitution selected from C99V, C99L and C99A. In some embodiments, the non-natural CBDAS comprises C37N and a substitution selected from C99A, C99F and C99V. In some embodiments, the non-natural CBDAS comprises C37Q and a substitution selected from C99I and C99A. In some embodiments, the non-natural CBDAS comprises C37R and C99I. In some embodiments, the non-natural CBDAS comprises K36, Q40, K101, K102, or a combination thereof is independently substituted with a charged amino acid. In some embodiments, the charged amino acid is D, E, or R. In some embodiments, the non-natural CBDAS comprises (a) C99V, C99A, C99I or C99L; and (b) C37A, C37Q, C37N, C37E, C37D, C37R or C37K. In some embodiments, the non-natural CBDAS comprises K36D, C37K, Q40E and K101R.

In some embodiments, the non-natural CBDAS comprises at least one amino acid substitution at a position corresponding to SEQ ID NO:79, wherein the substitution is: (a) C37D and C99F, (b) C37H, (c) C37Y, (d) C37Y and C99A, (e) C37E and C99F, (f) C37Y and C99I, (g) C37Y and C99V, (h) C37E, (i) C37K and C99F, (j) C37D, (k) C37D and C99V, (l) C37D and C99A, (m) C37H and C99V, (n) C37E and C99V, (o) C37N and C99A, (p) C37N and C99F, (q) C37E and C99A, (r) C37N and C99V, (s) C37Q and C99I, (t) C37T, (u) C37Y and C99L, (v) C37H and C99L, (w) C99F, (x) C37Q, (y) C37N, (z) C37H and C99A, (aa) C37Y and C99F, (bb) C37K, (cc) C37Q and C99A, (dd) C37R and C99I, (ee) C37A and C99V, (ff) C37A and C99A, (gg) C37A and C99I, (hh) C37A and C99L, (ii) C37Q and C99V, (jj) C37Q and C99L, (kk) C37N and C99I, (ll) C37N and C99L, (mm) C37E and C99I, (nn) C37E and C99L, (oo) C37D and C99I, (pp) C37D and C99L, (qq) C37R and C99V, (rr) C37R and C99A, (ss) C37R and C99L, (tt) C37R, (uu) C37K and C99V, (vv) C37K and C99A, (ww) C37K and C99I, or (xx) C37K and C99L, wherein the position corresponds to SEQ ID NO:79.

In some embodiments, K36, Q40, K101, K102, or a combination thereof, of the non-natural CBDAS, is independently substituted with D, E, or R. In some embodiments, the non-natural CBDAS comprises K36D, Q40E, C37K and K101R.

In some embodiments, the non-natural CBDAS position C37 is substituted with K, E, R, or D; position C99 is substituted with F; position K36, Q40, K102, or both a combination thereof are independently substituted with D, R or E; and position K101 is unsubstituted or is substituted with R, wherein the position corresponds to SEQ ID NO:79. In some embodiments, the non-natural CBDAS comprises a substitution selected from K36D, K36R and K36E. In some embodiments, the non-natural CBDAS comprises a substitution selected from Q40D, Q40R and Q40E. In some embodiments, the non-natural CBDAS comprises a substitution selected from K102D, K102R and K102E. In some embodiments, the non-natural CBDAS comprises at least one amino acid substitution at a position corresponding to SEQ ID NO:79, wherein the substitution is:

| | | | | | |
|---|---|---|---|---|---|
| a. | K36D | C37K | Q40D | C99F and | K101R, |
| b. | K36D | C37K | Q40D | C99F | K101R and K102R, |
| c. | K36D | C37K | Q40E | C99F and | K101R, |
| d. | K36D | C37K | Q40E | C99F | K101R and K102R, |
| e. | K36R | C37K | Q40D | C99F | K101R and K102R, |
| f. | K36D | C37E | C99F and | K101R, | |
| g. | K36R | C37E | Q40E | C99F | K101R and K102R, |
| h. | C37E | C99F | K101R and | K102E, | |
| i. | K36E | C37K | Q40E | C99F and | K101R, |
| j. | K36D | C37R | Q40D | C99F | K101R and K102D, |
| k. | K36D | C37K | Q40D and | C99F, | |
| l. | K36R | C37K | Q40R | C99F | K101R and K102E, |
| m. | K36R | C37E | Q40D | C99F | K101R and K102E, |
| n. | K36E | C37R | Q40D | C99F and | K101R, |
| o. | K36D | C37R | Q40E | C99F and | K101R, |
| p. | K36D | C37R | Q40D | C99F | K101R and K102R, |
| q. | K36R | C37R | Q40E | C99F | K101R and K102R, |
| r. | K36D | C37E | Q40D | C99F | K101R and K102R, |
| s. | K36D | C37K | Q40E and | C99F, | |
| t. | K36D | C37R | Q40D | C99F | K101R and K102E, |
| u. | K36D | C37E | Q40E | C99F | K101R and K102R, |
| v. | C37D | C99F | K101R and | K102E, | |
| w. | K36E | C37E | Q40E | C99F | K101R and K102R, |
| x. | K36R | C37E | C99F | K101R and | K102R, |
| y. | K36R | C37E | Q40D | C99F | K101R and K102R, |
| z. | K36D | C37D | C99F and | | K102E, |
| aa. | K36R | C37D | Q40D | C99F | |
| bb. | C37D | C99F | K101R and | K102R, | |
| cc. | K36D | C37D | Q40E | C99F | K101R and K102R, |
| dd. | K36D | C37D | C99F | K101R and | K102D, |
| ee. | C37E | Q40E | C99F | K101R and | K102E, |
| ff. | K36R | C37E | Q40D | C99F and | K101R, |
| gg. | K36D | C37D | Q40R | C99F and | K101R, |
| hh. | K36D | C37D | C99F | K101R and | K102E, |
| ii. | K36D | C37K | C99F | K101R and | K102R, or |
| jj. | K36E | C37R | Q40R | C99F | K101R and K102E. |

In some embodiments, the non-natural CBDAS further catalyzes the oxidative cyclization of CBGA into cannabichromenic acid (CBCA). In some embodiments, the non-natural CBDAS catalyzes the oxidative cyclization of CBGA into CBDA at about pH 4.0 to about pH 6.0. In some embodiments, the non-natural CBDAS catalyzes the oxidative cyclization of CBGA into CBCA at about pH 6.5 to about pH 8.0.

In some embodiments, the disclosure provides a non-natural cannabichromenic acid synthase (CBCAS) with 80% or greater identity to any one of SEQ ID NOs:80, 81, or 84 comprising at least one amino acid variation as compared to a wild type CBCAS, comprising three alpha helices (αA, αB, and αC) and wherein a disulfide bond is not formed between alpha helix αA and alpha helix αC, and wherein the non-natural CBCAS catalyzes the oxidative cyclization of cannabigerolic acid (CBGA) into cannabichromenic acid (CBCA).

In some embodiments, the CBCAS has 80% or greater identity to SEQ ID NO:81. 103. In some embodiments, the variation is a substitution, deletion or insertion. In some embodiments, the non-natural CBCAS comprises at least one non-natural salt bridge between the two of the three alpha helices in the N-terminal domain. In some embodiments, the non-natural CBCAS comprises 1-20, 2-20, 3-20, 4-20, 5-20, 10-20, or 15-20 amino acid variations as compared to a wild type CBCAS.

In some embodiments, the variation is at position C37, C99, K36, E40, K101, K102, or a combination thereof, wherein the position corresponds to SEQ ID NO:81. In some embodiments, the variation is at C37, C99, or both, wherein the position corresponds to SEQ ID NO:81.

In some embodiments, the variation is an insertion. In some embodiments, the variation is an insertion of 1 to 10 amino acids. In some embodiments, the variation is an insertion of 1 to 4 amino acids. In some embodiments, the variation is an insertion positioned within 10 amino acids of C37 or C99.

In some embodiments, the variation is a deletion. In some embodiments, the variation is a deletion of 1 to 10 amino acids. In some embodiments, the variation is a deletion of 1 to 4 amino acids. In some embodiments, the variation is a deletion positioned within 10 amino acids of C37 or C99.

In some embodiments, the variation is a substitution. In some embodiments, the non-natural CBCAS comprises 1-20, 2-20, 3-20, 4-20, 5-20, 10-20, or 15-20 amino acid substitutions as compared to a wild type CBCAS. In some embodiments, the non-natural CBCAS comprises a substitution at position C37, wherein the position corresponds to SEQ ID NO:81. In some embodiments, the non-natural CBCAS comprises a substitution selected from position C37A, C37D, C37H, C37Y, C37E, C37K, C37N, C37Q, C37T and C37R, wherein the position corresponds to SEQ ID NO:81. In some embodiments, the non-natural CBCAS comprises a substitution selected from C37A, C37D, C37E, C37K, C37N, C37Q, and C37R. In some embodiments, the non-natural CBCAS comprises a substitution at position C99, wherein the position corresponds to SEQ ID NO:81. In some embodiments, the non-natural CBCAS comprises a substitution selected from position C99F, C99A, C99I, C99V, and C99L wherein the position corresponds to SEQ ID NO:81. In some embodiments, the non-natural CBCAS comprises a substitution selected from C99A, C99I, C99V, and C99L. In some embodiments, the non-natural CBCAS comprises a substitution at C37 and a substitution at C99. In some embodiments, the non-natural CBCAS comprises a substitution selected from C37A, C37Q, C37N, C37E, C37D, C37R, and C37K, and a substitution selected from C99V, C99A, C99I and C99L. In some embodiments, the non-natural CBCAS comprises C37D and a substitution selected from C99F, C99V, C99A, C99I, and C99L. In some embodiments, the non-natural CBCAS comprises C37Y and a substitution selected from C99A, C99I, C99V, C99L and C99F. In some embodiments, the non-natural CBCAS comprises C37K and C99F. In some embodiments, the non-natural CBCAS comprises C37H and a substitution selected from C99V, C99L and C99A. In some embodiments, the non-natural CBCAS comprises C37N and a substitution selected from C99A, C99F and C99V. In some embodiments, the non-natural CBCAS comprises C37Q and a substitution selected from C99I and C99A. In some embodiments, the non-natural CBCAS comprises C37R and C99I. In some embodiments, K36, E40, K101, K102, or a combination thereof, of the non-natural CBCAS is independently substituted with a charged amino acid. In some embodiments, the charged amino acid is D, E, or R. In some embodiments, the non-natural CBCAS comprises (a) C99V, C99A, C99I or C99L; and (b) C37A, C37Q, C37N, C37E, C37D, C37R or C37K. In some embodiments, the non-natural CBCAS comprises K36D, C37K and K101R.

In some embodiments, the non-natural CBCAS comprises at least one amino acid substitution at a position corresponding to SEQ ID NO:81, wherein the substitution is: (a) C37D and C99F, (b) C37H, (c) C37Y, (d) C37Y and C99A, (e) C37E and C99F, (f) C37Y and C99I, (g) C37Y and C99V, (h) C37E, (i) C37K and C99F, (j) C37D, (k) C37D and C99V, (1) C37D and C99A, (m) C37H and C99V, (n) C37E and C99V, (o) C37N and C99A, (p) C37N and C99F, (q) C37E and C99A, (r) C37N and C99V, (s) C37Q and C99I, (t) C37T, (u) C37Y and C99L, (v) C37H and C99L, (w) C99F, (x) C37Q, (y) C37N, (z) C37H and C99A, (aa) C37Y and C99F, (bb) C37K, (cc) C37Q and C99A, (dd) C37R and C99I, (ee) C37A and C99V, (ff) C37A and C99A, (gg) C37A and C99I, (hh) C37A and C99L, (ii) C37Q and C99V, (jj) C37Q and C99L, (kk) C37N and C99I, (ll) C37N and C99L, (mm) C37E and C99I, (nn) C37E and C99L, (oo) C37D and C99I, (pp) C37D and C99L, (qq) C37R and C99V, (rr) C37R and C99A, (ss) C37R and C99L, (tt) C37R, (uu) C37K and C99V, (vv) C37K and C99A, (ww) C37K and C99I, or (xx) C37K and C99L, wherein the position corresponds to SEQ ID NO:81.

In some embodiments, K36, E40, K101, K102, or a combination thereof, of the non-natural CBCAS, is independently substituted with D, E, or R. In some embodiments, the non-natural CBCAS comprises K36D, C37K and K101R.

In some embodiments, the non-natural CBCAS position C37 is substituted with K, E, R, or D; position C99 is substituted with F; position K36, K102, or both are independently substituted with D, R or E; position E40 is substituted with D or R; and position K101 is unsubstituted or is substituted with R, wherein the position corresponds to SEQ ID NO:81. In some embodiments, the non-natural CBCAS comprises a substitution selected from K36D, K36R and K36E. In some embodiments, the non-natural CBCAS comprises a substitution selected from E40D or E40R. In some embodiments, the non-natural CBCAS comprises a substitution selected from K102D, K102R and K102E. In some embodiments, the non-natural CBCAS comprises at least one amino acid substitution at a position corresponding to SEQ ID NO:81, wherein the substitution is:

| | | | | | |
|---|---|---|---|---|---|
| a. | K36D | C37K | E40D | C99F and | K101R, |
| b. | K36D | C37K | E40D | C99F | K101R and K102R, |
| c. | K36D | C37K | C99F and | K101R, | |
| d. | K36D | C37K | C99F | K101R and K102R, | |
| e. | K36R | C37K | E40D | C99F | K101R and K102R, |
| f. | K36D | C37E | C99F and | K101R, | |
| g. | K36R | C37E | C99F | K101R and K102R, | |
| h. | C37E | C99F | K101R and | K102E, | |
| i. | K36E | C37K | C99F and | K101R, | |
| j. | K36D | C37R | E40D | C99F | K101R and K102D, |
| k. | K36D | C37K | E40D and | C99F, | |
| l. | K36R | C37K | E40R | C99F | K101R and K102E, |
| m. | K36R | C37E | E40D | C99F | K101R and K102E, |
| n. | K36E | C37R | E40D | C99F and | K101R, |
| o. | K36D | C37R | C99F and | K101R, | |
| p. | K36D | C37R | E40D | C99F | K101R and K102R, |
| q. | K36R | C37R | C99F | K101R and K102R, | |
| r. | K36D | C37E | E40D | C99F | K101R and K102R, |
| s. | K36D | C37K and | C99F, | | |
| t. | K36D | C37R | E40D | C99F | K101R and K102E, |
| u. | K36D | C37E | C99F | K101R and K102R, | |
| v. | C37D | C99F | K101R and | K102E, | |
| w. | K36E | C37E | C99F | K101R and K102R, | |
| x. | K36R | C37E | C99F | K101R and K102R, | |
| y. | K36R | C37E | E40D | C99F | K101R and K102R, |
| z. | K36D | C37D | C99F and | K102E, | |
| aa. | K36R | C37D | E40D | C99F | K101R and K102R, |

-continued

| | | | | | |
|---|---|---|---|---|---|
| bb. | C37D | C99F | K101R and | K102R, | |
| cc. | K36D | C37D | C99F | K101R and K102R, | |
| dd. | K36D | C37D | C99F | K101R and K102D, | |
| ee. | C37E | C99F | K101R and | K102E, | |
| ff. | K36R | C37E | E40D | C99F and | K101R, |
| gg. | K36D | C37D | E40R | C99F and | K101R, |
| hh. | K36D | C37D | C99F | K101R and K102E, | |
| ii. | K36D | C37K | C99F | K101R and K102R, or | |
| jj. | K36E | C37R | E40R | C99F | K101R and K102E. |

In some embodiments, the at least one amino acid variation of the non-natural THCAS, the non-natural CBDAS, or the non-natural CBCAS, is not within an active site of the non-natural THCAS, CBDAS, or CBCAS. In some embodiments, the active site is within positions 60-75, 105-125, 160-200, 220-250, 280-300, 350-450, 470-490, or 530-540, inclusive, of the non-natural THCAS, CBDAS, or CBCAS, wherein the positions correspond to SEQ ID NOs:2, 79, or 81, respectively.

In some embodiments, the disclosure provides a nucleic acid encoding the non-natural THCAS, the non-natural CBDAS, or the non-natural CBCAS as described herein.

In some embodiments, the disclosure provides an expression construct comprising the nucleic acid as described herein.

In some embodiments, the disclosure provides an engineered cell comprising the non-natural THCAS, the non-natural CBDAS, or the non-natural CBCAS as described herein, the nucleic acid as described herein, the expression construct as described herein, or a combination thereof.

In some embodiments, the engineered cell comprises an enzyme in the olivetolic acid pathway. In some embodiments, the olivetolic acid pathway comprises a natural or non-natural olivetol synthase (OLS). In some embodiments, the engineered cell comprises a non-natural OLS, wherein the non-natural OLS comprises an amino acid variation at position: 125, 126, 185, 187, 190, 204, 209, 210, 211, 249, 250, 257, 259, 331, 332, or a combination thereof, wherein the position corresponds to SEQ ID NO:3. In some embodiments, non-natural OLS comprises an amino acid substitution at position: A125G, A125S, A125T, A125C, A125Y, A125H, A125N, A125Q, A125D, A125E, A125K, A125R, S126G, S126A, D185G, D185G, D185A, D185S, D185P, D185C, D185T, D185N, M187G, M187A, M187S, M187P, M187C, M187T, M187D, M187N, M187E, M187Q, M187H, M187H, M187V, M187L, M187I, M187K, M187R, L190G, L190A, L190S, L190P, L190C, L190T, L190D, L190N, L190E, L190Q, L190H, L190V, L190M, L190I, L190K, L190R, G204A, G204C, G204P, G204V, G204L, G204I, G204M, G204F, G204W, G204S, G204T, G204Y, G204H, G204N, G204Q, G204D, G204E, G204K, G204R, G209A, G209C, G209P, G209V, G209L, G209I, G209M, G209F, G209W, G209S, G209T, G209Y, G209H, G209N, G209Q, G209D, G209E, G209K, G209R, D210A, D210C, D210P, D210V, D210L, D210I, D210M, D210F, D210W, D210S, D210T, D210Y, D210H, D210N, D210Q, D210E, D210K, D210R, G211A, G211C, G211P, G211V, G211L, G211I, G211M, G211F, G211W, G211S, G211T, G211Y, G211H, G211N, G211Q, G211D, G211E, G211K, G211R, G249A, G249C, G249P, G249V, G249L, G249I, G249M, G249F, G249W, G249S, G249T, G249Y, G249H, G249N, G249Q, G249D, G249E, G249K, G249R, G249S, G249T, G249Y, G250A, G250C, G250P, G250V, G250L, G250I, G250M, G250F, G250W, G250S, G250T, G250Y, G250H, G250N, G250Q, G250D, G250E, G250K, G250R, L257V, L257M, L257I, L257K, L257R, L257F, L257Y, L257W, L257S, L257T, L257C, L257H, L257N, L257Q, L257D, L257E, F259G, F259A, F259C, F259P, F259V, F259L, F259I, F259M, F259Y, F259W, F259S, F259T, F259Y, F259H, F259N, F259Q, F259D, F259E, F259K, F259R, M331G, M331A, M331S, M331P, M331C, M331T, M331D, M331N, M331E, M331Q, M331H, M331V, M331L, M331I, M331K, M331R, S332G, S332A, or a combination thereof, wherein the position corresponds to SEQ ID NO:3. In some embodiments, the olivetolic acid pathway comprises a natural or non-natural olivetolic acid cyclase (OAC).

In some embodiments, the non-natural OAC comprises an amino acid variation at position: L9, F23, V59, V61, V66, E67, I69, Q70, I73, I74, V79, G80, F81, G82, D83, R86, W89, L92, I94, V46, T47, Q48, K49, N50, K51, V46, T47, Q48, K49, N50, K51, or a combination thereof, wherein the position corresponds to SEQ ID NO:4. In some embodiments, the non-natural OAC forms a dimer, wherein a first peptide of the dimer comprises an amino acid variation at position: L9, F23, V59, V61, V66, E67, I69, Q70, I73, I74, V79, G80, F81, G82, D83, R86, W89, L92, I94, V46, T47, Q48, K49, N50, K51, or combinations thereof, and a second peptide of the dimer comprises an amino acid variation at position: V46, T47, Q48, K49, N50, K51, or a combination thereof, wherein the position corresponds to SEQ ID NO:4. In some embodiments, the amino acid sequence of the OAC comprises SEQ ID NO:5.

In some embodiments, the engineered cell comprises an enzyme in a geranyl pyrophosphate (GPP) pathway. In some embodiments, the GPP pathway comprises geranyl pyrophosphate synthase (GPPS), farnesyl pyrophosphate synthase, isoprenyl pyrophosphate synthase, geranylgeranyl pyrophosphate synthase, alcohol kinase, alcohol diphosphokinase, phosphate kinase, isopentenyl diphosphate isomerase, geranyl pyrophosphate synthase, or a combination thereof. In some embodiments, the GPP pathway comprises a mevalonate (MVA) pathway, a non-mevalonate (MEP) pathway, an alternative non-MEP, non MVA geranyl pyrophosphate pathway, or a combination of one or more pathways, wherein the alternative non-MEP, non-MVA geranyl pyrophosphate pathway comprises alcohol kinase, alcohol diphosphokinase, phosphate kinase, isopentenyl diphosphate isomerase, geranyl pyrophosphate synthase enzymes, or a combination thereof.

In some embodiments, engineered cell comprises a prenyl transferase. In some embodiments, the prenyltransferase is a natural prenyltransferase or a non-natural prenyltransferase. In some embodiments, the non-natural prenyltransferase comprises at least four amino acid variations at positions corresponding to SEQ ID NO:6 or a corresponding amino acid position in any one of SEQ ID NOs:7-20, the variations selected from:

a. (i) V45I, (ii) Q159S, (iii) S212H, and (iv) Y286V;
b. (i) V45T, (ii) Q159S, (iii) S212H, and (iv) Y286V;
c. (i) F121V, (ii) Q159S, (iii) S212H, and (iv) Y286V;
d. (i) T124K, (ii) Q159S, (iii) S212H, and (iv) Y286V;
e. (i) T124L, (ii) Q159S, (iii) S212H, and (iv) Y286V;
f. (i) Q159S, (ii) M160L, (iii) S212H, and (iv) Y286V;
g. (i) Q159S, (ii) M160L, (iii) S212H, and (iv) Y286V;
h. (i) Q159S, (ii) M160S, (iii) S212H, and (iv) Y286V;
i. (i) Q159S, (ii) Y173D, (iii) S212H, and (iv) Y286V;
j. (i) Q159S, (ii) Y173K, (iii) S212H, and (iv) Y286V;
k. (i) Q159S, (ii) Y173P, (iii) S212H, and (iv) Y286V;
l. (i) Q159S, (ii) Y173Q, (iii) S212H, and (iv) Y286V;
m. (i) Q159S, (ii) Y173Y, (iii) S212H, and (iv) Y286V;
n. (i) Q159S, (ii) S212H, (iii) V213V, and (iv) Y286V;
o. (i) Q159S, (ii) S212H, (iii) A230S, and (iv) Y286V;
p. (i) Q159S, (ii) S212H, (iii) T267P, and (iv) Y286V;
q. (i) Q159S, (ii) S212H, (iii) Y286V, and (iv) Q293H;
r. (i) Q159S, (ii) S212H, (iii) Y286V, and (iv) R294K;
s. (i) Q159S, (ii) S212H, (iii) Y286V, and (iv) L296K;
t. (i) Q159S, (ii) S212H, (iii) Y286V, and (iv) L296L;
u. (i) Q159S, (ii) S212H, (iii) Y286V, and (iv) L296M;
v. (i) Q159S, (ii) S212H, (iii) Y286V, and (iv) L296Q;
w. (i) Q159S, (ii) S212H, (iii) Y286V, and (iv) L296M;
x. (i) Q159S, (ii) S212H, (iii) Y286V, and (iv) F300F; and
y. (i) Q159S, (ii) S212H, (iii) Y286V, and (iv) F300Y.

In some embodiments, the engineered cell comprises one or more of the following modifications: (i) express one or more exogenous nucleic acid sequences or overexpress one or more endogenous genes encoding a protein having an ABC transporter permease activity; (ii) express one or more exogenous nucleic acid sequences or overexpress one or more endogenous genes encoding a protein having an ABC transporter ATP-binding protein activity; (iii) express one or more exogenous nucleic acids sequences or overexpress one or more endogenous genes that encodes a protein that is at least 60% identical to: the blc gene product of SEQ ID NO:21, the ybhG gene product of SEQ ID NO:22, or the ydhC gene product of SEQ ID NO:23; (iv) express one or more exogenous nucleic acids sequences or overexpress one or more endogenous genes that encodes a protein that is at least 60% identical to the mlaD gene product of SEQ ID NO:24, the mlaE gene product of SEQ ID NO:25, or the mlaF gene product of SEQ ID NO:26; (v) express one or more exogenous nucleic acid sequences or overexpress one or more endogenous genes encoding a protein having a siderophore receptor protein activity; (vi) comprise a disruption of or downregulation in the expression of a regulator of expression of one or more endogenous genes encoding a protein having an ABC transporter permease activity, a protein having an ABC transporter ATP-binding protein activity, a blc gene, a ybhG protein, a ydhC protein, a mlaD protein, mlaE protein, mlaF protein, or a protein having a siderophore receptor protein activity; (vii) express an exogenous nucleic acid encoding a multi-domain protein having acetyl-CoA carboxylase activity (MD-ACC); (viii) overexpress one or more endogenous genes encoding acetyl-CoA carboxyltransferase subunit α, biotin carboxyl carrier protein, biotin carboxylase, or acetyl-CoA carboxyltransferase subunit β, or express one or more exogenous genes encoding acetyl-CoA carboxyltransferase, biotin carboxyl carrier protein, or biotin carboxylase; (ix) comprise a disruption of or downregulation in the expression of an endogenous gene encoding a protein having (acyl-carrier-protein) S-malonyltransferase activity, an endogenous gene encoding a protein having 3-hydroxypalmitoykacyl-carrier-protein) dehydratase activity, or both; (x) express an exogenous nucleic acid sequence or overexpress an endogenous gene encoding a protein having fatty acyl-CoA ligase activity, or both; (xi) comprise a disruption of or downregulation in the expression of at least one endogenous gene encoding a protein having acyl-CoA dehydrogenase activity or enoyl-CoA hydratase activity; (xii) comprise a disruption or downregulation in the expression of at least one endogenous gene encoding a protein having acyl-CoA esterase/thioesterase activity; (xiii) comprise a disruption of or downregulation in the expression of at least one endogenous gene encoding a repressor of transcription of one or more genes required for fatty acid beta-oxidation or an upregulator of fatty acid biosynthesis in combination with disruption or downregulation of one or more endogenous genes encoding one or more proteins of fatty acid beta-oxidation pathway; (xiv) express one or more exogenous nucleic acid sequences or overexpress one or more endogenous genes encoding a protein having geranyl pyrophosphate synthase (GPPS), farnesyl pyrophosphate synthase, isoprenyl pyrophosphate synthase, geranylgeranyl pyrophosphate synthase, alcohol kinase, alcohol diphosphokinase, phosphate kinase, isopentenyl diphosphate isomerase, geranyl pyrophosphate synthase, isopentenyl phosphate kinase activity, (iso)prenol diphosphokinase activity, (iso)prenol kinase activity, (iso)prenol diphosphokinase activity, isopentenyl phosphate kinase activity, dimethylallyl phosphate kinase activity, or isopentenyl diphosphate isomerase activity; (xv) express an exogenous nucleic acid sequence or overexpress an endogenous gene encoding a protein having GPP synthase activity; (xvi) express an exogenous nucleic acid sequence encoding an olivetol synthase; (xvii) express an exogenous nucleic acid sequence encoding an olivetolic acid cyclase; (xviii) express an exogenous nucleic acid sequence encoding a prenyltransferase; (xix) express one or more exogenous nucleic acid sequences or overexpressing one or more endogenous genes encoding one or more enzymes of MVA pathway, MEP pathway, or a non-MVA, non-MEP pathway; (xx) express an exogenous nucleic acid sequence or overexpress an endogenous gene encoding a biotin-(acetyl-CoA carboxylase) ligase; (xxi) express an exogenous nucleic acid sequence encoding an isopentenyl-diphosphate delta-isomerase or overexpress an endogenous gene encoding an isopentenyl-diphosphate delta-isomerase; (xxii) express an exogenous nucleic acid sequence encoding a hydroxyethylthiazole kinase or overexpress an endogenous gene encoding a hydroxyethylthiazole kinase; (xxiii) express an exogenous nucleic acid sequence encoding a Type III pantothenate kinase or overexpress an endogenous gene encoding a Type III pantothenate kinase; and (xxiv) comprise a disruption of or downregulation in the expression of at least one endogenous gene encoding a phosphatase selected from the group consisting of ADP-sugar pyrophosphatase, dihydroneopterin triphosphate diphosphatase, pyrimidine deoxynucleotide diphosphatase, pyrimidine pyrophosphate phosphatase, and Nudix hydrolase.

In some embodiments, the engineered cell is selected from bacteria, fungi, yeast, algae, and cyanobacteria. In some embodiments, the bacteria is *Escherichia, Corynebacterium, Bacillus, Ralstonia, Zymomonas*, or *Staphylococcus*. In some embodiments, the bacteria is *Escherichia coli.*

In some embodiments, the disclosure provides a cell extract or cell culture medium comprising cannabigerolic acid (CBGA), tetrahydrocannabivarin (THCV), tetrahydrocannabivarinic acid (THCVA), cannabidivarin (CBDV), cannabidivarinic acid (CBDVA), cannabinol (CBN), cannabinolic acid (CBNA), cannabidiol (CBD), cannabidiolic acid (CBDA), cannabichromene (CBC), cannabichromenic acid (CBCA), cannabigerivarin (CBGV), cannabigerivarinic acid (CBGVA), cannabigerol (CBG), cannabichromevarin (CBCV), cannabichromevarinic acid (CBCVA), tetrahydrocannabinol (THC), tetrahydrocannabinolic acid (THCA), analogs, or derivatives thereof, or a combination thereof derived from the engineered cell as described herein. In some embodiments, the cell extract or cell culture medium further comprises pentyl diacetic acid lactone (PDAL), hexanoyl triacetic acid lactone (HTAL), or lactone analog or derivatives thereof, or a combination thereof, at a concentration of no more than about 50% to about 0.0001% of the cell extract or cell culture medium.

In some embodiments, the disclosure provides a method of making CBGA, CBG, CBGV, CBGVA; CBGOA, THCV, THCVA, CBD, CBDA, CBDV, CBDVA, CBN, CBNA, CBC, CBCA, CBCV, CBCVA, THC, THCA, analogs or derivatives thereof, or combinations thereof, comprising culturing the engineered cell described herein, or isolating CBGA, CBG, CBGV, CBGVA; CBGOA, THCV, THCVA, CBD, CBDA, CBDV, CBDVA, CBN, CBNA, CBC, CBCA, CBCV, CBCVA, THC, THCA, analogs or derivatives thereof from the cell extract or cell culture medium as described herein. In some embodiments, the cannabinoid is THCA, THC, CBDA, CBD, CBCA, CBC, an analog or derivative thereof, or a combination thereof.

In some embodiments, the disclosure provides a method of making THCA or an analog or derivative thereof, comprising contacting CBGA with the non-natural THCAS provided herein, the non-natural CBDAS provided herein, the non-natural CBCAS provided herein, or a combination thereof. In some embodiments, the method comprises contacting CBGA with the non-natural THCAS. In some embodiments, the contacting occurs at pH about 4.0 to about 6.0.

In some embodiments, the disclosure provides a method of making CBDA or an analog or derivative thereof, comprising contacting CBGA with the non-natural THCAS provided herein, the non-natural CBDAS provided herein, the non-natural CBDAS provided herein, the non-natural CBCAS provided herein, or a combination thereof. In some embodiments, the method comprises contacting CBGA with the non-natural CBDAS. In some embodiments, the contacting occurs at pH about 4.0 to about 6.0.

In some embodiments, the disclosure provides a method of making CBCA or an analog or derivative thereof, comprising contacting CBGA with the non-natural THCAS provided herein, the non-natural CBDAS provided herein, the non-natural CBCAS provided herein, or a combination thereof. In some embodiments, the method comprises contacting CBGA with the non-natural CBCAS; or contacting CBGA with the non-natural THCAS or the non-natural CBDAS at pH about 6.5 to about 8.0.

In some embodiments, the non-natural THCAS, the non-natural CBDAS, or the non-natural CBCAS is produced by an engineered cell provided herein.

In some embodiments, the disclosure provides a composition comprising a prenylated aromatic compound or an analog or derivative thereof obtained from the engineered cell as described herein, the cell extract or cell culture medium described herein, or the method of making CBGA, CBG, CBGV, CBGVA; CBGOA, THCV, THCVA, CBD, CBDA, CBDV, CBDVA, CBN, CBNA, CBC, CBCA, CBCV, CBCVA, THC, THCA, analogs or derivatives thereof, or combinations thereof, as described herein. In some embodiments, the prenylated aromatic compound is THCA, THC, THC, CBDA, CBD, CBCA, CBC, an analog or derivative thereof, or a combination thereof.

In some embodiments, the composition comprises THCA, THC, CBDA, CBD, CBCA, CBC, an analog or derivative thereof, or a combination thereof at 10% or greater, 20% or greater, 30% or greater, 40% or greater, 50% or greater, 60% or greater, 70% or greater, 80% or greater, 85% or greater, 90% or greater, 91% or greater, 92% or greater, 93% or greater, 94% or greater, 95% or greater, 96% or greater, 97% or greater, 98% or greater, 99% or greater, 99.2% or greater, 99.4% or greater, 99.5% or greater, 99.6% or greater, 99.7% or greater, 99.8% or greater, or 99.9% or greater of total cannabinoid compound(s) in the composition.

In some embodiments, the composition is a therapeutic or medicinal composition. In some embodiments, the composition is a topical composition. In some embodiments, the composition is an edible composition. In some embodiments, the composition is an oral unit dosage composition.

In some embodiments, the disclosure provides a method of making an isolated non-natural THCAS, an isolated non-natural CBDAS, or an isolated non-natural CBCAS, comprising isolating THCAS, CBDAS, or CBCAS expressed in the engineered cell as described herein. In some embodiments, the disclosure provides an isolated non-natural THCAS, an isolated non-natural CBDAS, or an isolated non-natural CBCAS made by the method described herein.

BRIEF DESCRIPTION OF THE DRAWINGS

The following drawings form part of the present specification and are included to further demonstrate exemplary embodiments of certain aspects of the present invention.

FIG. 8 shows exemplary mevalonate pathway (MVA) and non-mevalonate pathway (MEP) as described in embodiments herein. The abbreviations are AACT: acetoacetyl-CoA thiolase; HMGS: HMG-CoA synthase; HMGR: HMG-CoA reductase; MVK: mevalonate-3-kinase; PMK: Phosphomevalonate kinase; MVD: mevalonate-5-pyrophosphate decarboxylase; DXS: 1-Deoxy-D-xylulose 5-phosphate synthase; DXR: 1-Deoxy-D-xylulose 5-phosphate reductoisomerase; CMS: 2-C-methyl-D-erythritol 4-phosphate cytidylyltransferase; CMK: 4-diphosphocytidyl-2-C-methyl-D-erythritol kinase; MECS: 2-C-methyl-D-erythritol 2,4-cyclodiphosphate synthase; HDS: 4-Hydroxy-3-methyl-but-2-enyl pyrophosphate synthase; DMAP: Dimethylallyl pyrophosphate; HDR: 4-Hydroxy-3-methyl-but-2-enyl pyrophosphate reductase; and IDI: isopentenyl pyrophosphate isomerase.

FIGS. 11A-C show a sequence alignment between amino acid sequences of $\Delta^9$-tetrahydrocannabinolic acid synthase (THCAS), cannabidiolic acid synthase (CBDAS), and cannabichromenic acid synthase (CBCAS) from *C. sativa*, as described in SEQ ID NOs:1, 2, and 78-84.

FIG. 12 shows a structural alignment between the protein structure of THCAS and the predicted structures for CBDAS and CBCAS.

DETAILED DESCRIPTION OF THE INVENTION

Figure 2:
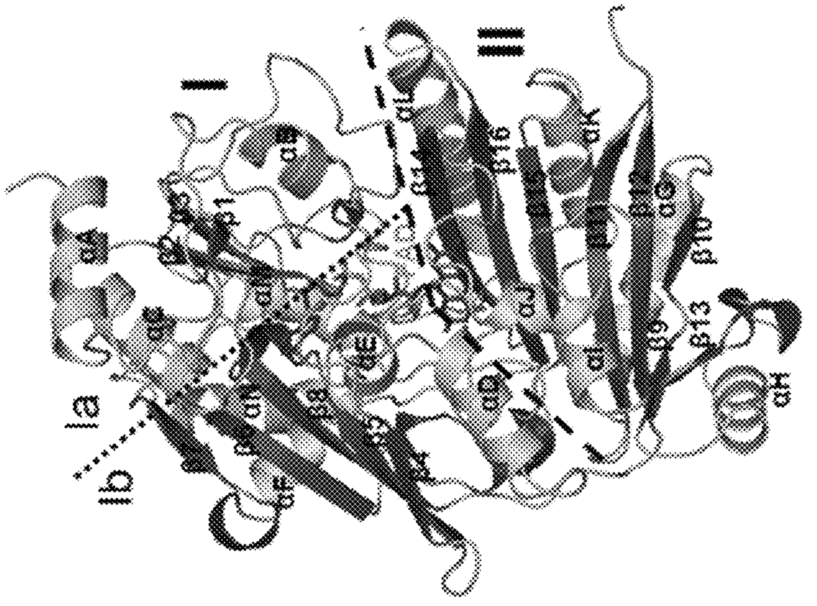
FIG. 2 is reproduced from Shoyama and shows an x-ray crystal structure of wild type THCAS from *C. sativa* with the FAD cofactor. Dashed lines denote subdomains of THCAS, and the α-helices and β-strands are labeled.

Unless otherwise defined herein, scientific and technical terms used in the present disclosure shall have the meanings that are commonly understood by one of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The use of the term "or" in the claims is used to mean "and/or," unless explicitly indicated to refer only to alternatives or the alternatives are mutually exclusive, although the disclosure supports a definition that refers to only alternatives and "and/or."

As used herein, the terms "comprising" (and any variant or form of comprising, such as "comprise" and "comprises"), "having" (and any variant or form of having, such as "have" and "has"), "including" (and any variant or form of including, such as "includes" and "include") or "containing" (and any variant or form of containing, such as "contains" and "contain") are inclusive or open-ended and do not exclude additional, unrecited, elements or method steps.

The use of the term "for example" and its corresponding abbreviation "e.g." means that the specific terms recited are representative examples and embodiments of the disclosure that are not intended to be limited to the specific examples referenced or cited unless explicitly stated otherwise.

As used herein, "about" can mean plus or minus 10% of the provided value. Where ranges are provided, they are inclusive of the boundary values. "About" can additionally or alternately mean either within 10% of the stated value, or within 5% of the stated value, or in some cases within 2.5% of the stated value, or, "about" can mean rounded to the nearest significant digit.

As used herein, "between" is a range inclusive of the ends of the range. For example, a number between x and y explicitly includes the numbers x and y, and any numbers that fall within x and y.

A "nucleic acid," "nucleic acid molecule," "nucleic acid sequence," "nucleotide sequence," "oligonucleotide," or "polynucleotide" means a polymeric compound including covalently linked nucleotides. The term "nucleic acid" includes ribonucleic acid (RNA) and deoxyribonucleic acid (DNA), both of which may be single- or double-stranded. DNA includes, but is not limited to, complementary DNA (cDNA), genomic DNA, plasmid or vector DNA, and synthetic DNA. In some embodiments, the disclosure provides a nucleic acid encoding any one of the polypeptides disclosed herein, e.g., is directed to a polynucleotide encoding THCAS or a variant thereof.

A "gene" refers to an assembly of nucleotides that encode a polypeptide and includes cDNA and genomic DNA nucleic acid molecules. In some embodiments, "gene" also refers to a non-coding nucleic acid fragment that can act as a regulatory sequence preceding (i.e., 5') and following (i.e., 3') the coding sequence.

As used herein, the term "operably linked" means that a polynucleotide of interest, e.g., the polynucleotide encoding a nuclease, is linked to the regulatory element in a manner that allows for expression of the polynucleotide. In some embodiments, the regulatory element is a promoter. In some embodiments, a nucleic acid expressing the polypeptide of interest is operably linked to a promoter on an expression vector.

As used herein, "promoter," "promoter sequence," or "promoter region" refers to a DNA regulatory region or polynucleotide capable of binding RNA polymerase and involved in initiating transcription of a downstream coding or non-coding sequence. In some embodiments, the promoter sequence includes the transcription initiation site and extends upstream to include the minimum number of bases or elements used to initiate transcription at levels detectable above background. In some embodiments, the promoter sequence includes a transcription initiation site, as well as protein binding domains responsible for the binding of RNA polymerase. Eukaryotic promoters typically contain "TATA" boxes and "CAT" boxes. Various promoters, including inducible promoters, may be used to drive expression of the various vectors of the present disclosure.

An "expression vector" or vectors ("an expression construct") can be constructed to include one or more protein of interest-encoding nucleic acids (e.g., nucleic acid encoding a THCAS described herein) operably linked to expression control sequences functional in the host organism. Expression vectors applicable for use in the microbial host organisms provided include, for example, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as *E. coli* and yeast). In some embodiments, the expression vector comprises a nucleic acid encoding a protein described herein, e.g., THCAS.

Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like. When two or more exogenous encoding nucleic acids (e.g., a gene encoding THCAS and an additional gene encoding another enzyme in the THCA biosynthesis pathway such as, e.g., OLS, OAC, prenyltransferase, and/or one or more enzymes for the production of geranyl pyrophosphate as described herein) are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein. The following vectors are provided by way of example; for bacterial host cells: pQE vectors (Qiagen), pBluescript plasmids, pNH vectors, lambda-ZAP vectors (Stratagene); pTrc99a, pKK223-3, pDR540, and pRIT2T (Pharmacia); for eukaryotic host cells: pXT1, pSG5 (Stratagene), pSVK3, pBPV, pMSG, and pSVLSV40 (Pharmacia). However, any other plasmid or other vector may be used so long as it is compatible with the host cell.

The term "host cell" refers to a cell into which a recombinant expression vector has been introduced, or "host cell" may also refer to the progeny of such a cell. Because modifications may occur in succeeding generations, for example, due to mutation or environmental influences, the progeny may not be identical to the parent cell, but are still included within the scope of the term "host cell." In some embodiments, the present disclosure provides a host cell comprising an expression vector that comprises a nucleic acid encoding a THCAS or variant thereof. In some embodiments, the host cell is a bacterial cell, a fungal cell, an algal cell, a cyanobacterial cell, or a plant cell.

A genetic alteration that makes an organism or cell non-natural can include, for example, modifications introducing expressible nucleic acids encoding metabolic polypeptides, other nucleic acid additions, nucleic acid deletions and/or other functional disruption of the organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon.

A host cell, organism, or microorganism engineered to express or overexpress a gene, a nucleic acid, nucleic acid sequence, or nucleic acid molecule, or to overexpress an enzyme or polypeptide has been genetically engineered through recombinant DNA technology to include a gene or nucleic acid sequence that it does not naturally include that encodes the enzyme or polypeptide or to express an endogenous gene at a level that exceeds its level of expression in a non-altered cell. As non-limiting examples, a host cell, organism, or microorganism engineered to express or overexpress a gene, a nucleic acid, nucleic acid sequence, or nucleic acid molecule, or to overexpress an enzyme or polypeptide can have any modifications that affect a coding sequence of a gene, the position of a gene on a chromosome or episome, or regulatory elements associated with a gene. A gene can also be overexpressed by increasing the copy number of a gene in the cell or organism. In some embodiments, overexpression of an endogenous gene comprises replacing the native promoter of the gene with a constitutive promoter that increases expression of the gene relative to expression in a control cell with the native promoter. In some embodiments, the constitutive promoter is heterologous.

Similarly, a host cell, organism, or microorganism engineered to under-express (or to have reduced expression of) a gene, nucleic acid, nucleic acid sequence, or nucleic acid molecule, or to under-express an enzyme or polypeptide can have any modifications that affect a coding sequence of a gene, the position of a gene on a chromosome or episome, or regulatory elements associated with a gene. Specifically included are gene disruptions, which include any insertions, deletions, or sequence mutations into or of the gene or a portion of the gene that affect its expression or the activity of the encoded polypeptide. Gene disruptions include "knockout" mutations that eliminate expression of the gene. Modifications to under-express or down-regulate a gene also include modifications to regulatory regions of the gene that can reduce its expression.

The term "exogenous" is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material that may be introduced on a vehicle such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is naturally present in the host. Similarly, the term when used in reference to expression of an encoding nucleic acid refers to expression of an encoding nucleic acid contained within the microbial organism. The term "heterologous" refers to a molecule or activity derived from a source other than the referenced species, whereas "homologous" refers to a molecule or activity derived from the host microbial organism/species. Accordingly, exogenous expression of an encoding nucleic acid can utilize either or both of a heterologous or homologous encoding nucleic acid.

When used to refer to a genetic regulatory element, such as a promoter, operably linked to a gene, the term "homologous" refers to a regulatory element that is naturally operably linked to the referenced gene. In contrast, a "heterologous" regulatory element is not naturally found operably linked to the referenced gene, regardless of whether the regulatory element is naturally found in the host species.

It is understood that when more than one exogenous nucleic acid is included in a microbial organism, the more than one exogenous nucleic acid(s) refers to the referenced encoding nucleic acid or biosynthetic activity, as discussed above. It is further understood, as disclosed herein, that more than one exogenous nucleic acid(s) can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express at least two, three, four, five, six, seven, eight, nine, ten or more exogenous nucleic acids encoding a desired pathway enzyme or protein. In the case where two or more exogenous nucleic acids encoding a desired activity are introduced into a host microbial organism, it is understood that the two or more exogenous nucleic acids can be introduced as a single nucleic acid, for example, on a single plasmid, on separate plasmids, can be integrated into the host chromosome at a single site or multiple sites, and still be considered as two or more exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

By "exogenous nucleic acid sequence" is meant a nucleic acid that is not naturally-occurring within the cell (e.g., a host cell) or organism. Exogenous nucleic acid sequence may be derived from or identical to a naturally-occurring nucleic acid sequence or it may be a heterologous nucleic acid sequence. For example, a duplication of a naturally-occurring gene is considered to be an exogenous nucleic acid sequence. In some embodiments, the exogenous nucleic acid sequence may be a heterologous nucleic acid sequence.

Genes or nucleic acid sequences can be introduced stably or transiently into a host cell using techniques well known in the art including, but not limited to, conjugation, electroporation, chemical transformation, transduction, transfection, and ultrasound transformation. Optionally, for exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., J Biol Chem 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques known in the art to achieve optimized expression of the proteins.

In general, codon optimization refers to a process of modifying a nucleic acid sequence for enhanced expression in the host cells of interest by replacing at least one codon (e.g., about or more than about 1, 2, 3, 4, 5, 10, 15, 20, 25, or 50 codons) of the native sequence with codons that are more frequently or most frequently used in the genes of that host cell while maintaining the native amino acid sequence.

Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Computer algorithms for codon optimizing a particular sequence for expression in a particular host cell are available and include, e.g., Integrated DNA Technologies' Codon Optimization tool, Entelechon's Codon Usage Table Analysis Tool, GenScript's OptimumGene tool, and the like.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The start of the protein or polypeptide is known as the "N-terminus" (and also referred to as the amino-terminus, $NH_2$-terminus, N-terminal end or amine-terminus), referring to the free amine (—$NH_2$) group of the first amino acid residue of the protein or polypeptide. The end of the protein or polypeptide is known as the "C-terminus" (and also referred to as the carboxy-terminus, carboxyl-terminus, C-terminal end, or COOH-terminus), referring to the free carboxyl group (—COOH) of the last amino acid residue of the protein or polypeptide.

An "amino acid" as used herein refers to a compound including both a carboxyl (—COOH) and amino (—$NH_2$) group. "Amino acid" refers to both natural and unnatural, i.e., synthetic, amino acids. Natural amino acids, with their three-letter and single-letter abbreviations, include: alanine (Ala; A); arginine (Arg, R); asparagine (Asn; N); aspartic acid (Asp; D); cysteine (Cys; C); glutamine (Gln; Q); glutamic acid (Glu; E); glycine (Gly; G); histidine (His; H); isoleucine (Ile; I); leucine (Leu; L); lysine (Lys; K); methionine (Met; M); phenylalanine (Phe; F); proline (Pro; P); serine (Ser; S); threonine (Thr; T); tryptophan (Trp; W); tyrosine (Tyr; Y); and valine (Val; V). Unnatural or synthetic amino acids include a side chain that is distinct from the natural amino acids provided above and may include, e.g., fluorophores, post-translational modifications, metal ion chelators, photocaged and photocross-linking moieties, uniquely reactive functional groups, and NMR, IR, and x-ray crystallographic probes. Exemplary unnatural or synthetic amino acids are provided in, e.g., Mitra et al., Mater Methods 3:204 (2013) and Wals et al., Front Chem 2:15 (2014). Unnatural amino acids may also include naturally-occurring compounds that are not typically incorporated into a protein or polypeptide, such as, e.g., citrulline (Cit), selenocysteine (Sec), and pyrrolysine (Pyl).

As used herein, the terms "non-natural," "non-naturally occurring," "variant," and "mutant" are used interchangeably in the context of an organism, polypeptide, or nucleic acid. The terms "non-natural," "non-naturally occurring," "variant," and "mutant" in this context refer to a polypeptide or nucleic acid sequence having at least one variation or mutation at an amino acid position or nucleic acid position as compared to a wild-type polypeptide or nucleic acid sequence. The at least one variation can be, e.g., an insertion of one or more amino acids or nucleotides, a deletion of one or more amino acids or nucleotides, or a substitution of one or more amino acids or nucleotides. A "variant" protein or polypeptide is also referred to as a "non-natural" protein or polypeptide.

Naturally-occurring organisms, nucleic acids, and polypeptides can be referred to as "wild-type" or "original" or "natural" such as wild type strains of the referenced species, or a wild-type protein or nucleic acid sequence. Likewise, amino acids found in polypeptides of the wild type organism can be referred to as "original" or "natural" with regards to any amino acid position.

An "amino acid substitution" refers to a polypeptide or protein including one or more substitutions of wild-type or naturally occurring amino acid with a different amino acid relative to the wild-type or naturally occurring amino acid at that amino acid residue. The substituted amino acid may be a synthetic or naturally occurring amino acid. In some embodiments, the substituted amino acid is a naturally occurring amino acid selected from the group consisting of: A, R, N, D, C, Q, E, G, H, I, L, K, M, F, P, S, T, W, Y, and V. In some embodiments, the substituted amino acid is an unnaturally or synthetic amino acid. Substitution mutants may be described using an abbreviated system. For example, a substitution mutation in which the fifth (5th) amino acid residue is substituted may be abbreviated as "XSY," wherein "X" is the wild-type or naturally occurring amino acid to be replaced, "5" is the amino acid residue position within the amino acid sequence of the protein or polypeptide, and "Y" is the substituted, or non-wild-type or non-naturally occurring, amino acid.

An "isolated" polypeptide, protein, peptide, or nucleic acid is a molecule that has been removed from its natural environment. It is also understood that "isolated" polypeptides, proteins, peptides, or nucleic acids may be formulated with excipients such as diluents or adjuvants and still be considered isolated. As used herein, "isolated" does not necessarily imply any particular level purity of the polypeptide, protein, peptide, or nucleic acid.

The term "recombinant" when used in reference to a nucleic acid molecule, peptide, polypeptide, or protein means of, or resulting from, a new combination of genetic material that is not known to exist in nature. A recombinant molecule can be produced by any of the techniques available in the field of recombinant technology, including, but not limited to, polymerase chain reaction (PCR), gene splicing (e.g., using restriction endonucleases), and solid-phase synthesis of nucleic acid molecules, peptides, or proteins.

The term "domain" when used in reference to a polypeptide or protein means a distinct functional and/or structural unit in a protein. Domains are sometimes responsible for a particular function or interaction, contributing to the overall role of a protein. Domains may exist in a variety of biological contexts. Similar domains may be found in proteins with different functions. Alternatively, domains with low sequence identity (i.e., less than about 50%, less than about 40%, less than about 30%, less than about 20%, less than about 10%, less than about 5%, or less than about 1% sequence identity) may have the same function.

As used herein, the term "sequence similarity" (% similarity) refers to the degree of identity or correspondence between nucleic acid sequences or amino acid sequences. In the context of polynucleotides, "sequence similarity" may refer to nucleic acid sequences wherein changes in one or more nucleotide bases results in substitution of one or more amino acids, but do not affect the functional properties of the protein encoded by the polynucleotide. "Sequence similarity" may also refer to modifications of the polynucleotide, such as deletion or insertion of one or more nucleotide bases, that do not substantially affect the functional properties of the resulting transcript. It is therefore understood that the present disclosure encompasses more than the specific exemplary sequences. Methods of making nucleotide base substitutions are known, as are methods of determining the retention of biological activity of the encoded polypeptide.

In the context of polypeptides, "sequence similarity" refers to two or more polypeptides wherein greater than about 40% of the amino acids are identical, or greater than about 60% of the amino acids are functionally identical. "Functionally identical" or "functionally similar" amino acids have chemically similar side chains. For example, amino acids can be grouped in the following manner according to functional similarity:

Positively-charged side chains: Arg, His, Lys;

Negatively-charged side chains: Asp, Glu;

Polar, uncharged side chains: Ser, Thr, Asn, Gln;

Hydrophobic side chains: Ala, Val, Ile, Leu, Met, Phe, Tyr, Trp;

Other: Cys, Gly, Pro.

In some embodiments, similar polypeptides of the present disclosure have about 40%, at least about 40%, about 45%, at least about 45%, about 50%, at least about 50%, about 55%, at least about 55%, about 60%, at least about 60%, about 65%, at least about 65%, about 70%, at least about 70%, about 75%, at least about 75%, about 80%, at least about 80%, about 85%, at least about 85%, about 90%, at least about 90%, about 95%, at least about 95%, about 97%, at least about 97%, about 98%, at least about 98%, about 99%, at least about 99%, or about 100% identical amino acids.

In some embodiments, similar polypeptides of the present disclosure have about 60%, at least about 60%, about 65%, at least about 65%, about 70%, at least about 70%, about 75%, at least about 75%, about 80%, at least about 80%, about 85%, at least about 85%, about 90%, at least about 90%, about 95%, at least about 95%, about 97%, at least about 97%, about 98%, at least about 98%, about 99%, at least about 99%, or about 100% functionally identical amino acids.

The "percent identity" (% identity) between two sequences is determined when sequences are aligned for maximum homology, and not including gaps or truncations as set forth in the BLAST parameters. Exemplary parameters for determining relatedness of two or more amino acid sequences using the BLAST algorithm, for example, can be as provided in BLASTP using the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN and the following parameters: Match: 1; mismatch: −2; gap open: 5; gap extension: 2; x_dropoff 50; expect: 10.0; wordsize: 11; filter: off Those skilled in the art will know what modifications can be made to the above parameters to either increase or decrease the stringency of the comparison, for example, for determining the relatedness of two or more sequences. Additional sequences added to a polypeptide sequence, such as but not limited to immunodetection tags, purification tags, localization sequences (presence or absence), etc., do not affect the % identity.

Algorithms known to those skilled in the art, such as Align, BLAST, ClustalW and others compare and determine a raw sequence similarity or identity, and also determine the presence or significance of gaps in the sequence which can be assigned a weight or score. Such algorithms also are known in the art and are similarly applicable for determining nucleotide or amino acid sequence similarity or identity, and can be useful in identifying orthologs of genes of interest. Parameters for sufficient similarity to determine relatedness are computed based on well-known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 45% to 100% sequence identity. Proteins that are unrelated can have an identity which is essentially the same as would be expected to occur by chance if a database of sufficient size is scanned (about 5%).

For example, alignment can be performed using the Needleman-Wunsch algorithm (Needleman, S. & Wunsch, C. "A general method applicable to the search for similarities in the amino acid sequence of two proteins," J Mol Biol 48:443-453(1970)) implemented through the BALIGN tool (balign.sourceforge.net). Default parameters are used for the alignment and BLOSUM62 was used as the scoring matrix. In some cases, it can be useful to use the Basic Local Alignment Search Tool (BLAST) algorithm to understand the sequence identity between an amino acid motif in a template sequence and a target sequence. Therefore, in preferred modes of practice, BLAST is used to identify or understand the identity of a shorter stretch of amino acids (e.g. a sequence motif) between a template and a target protein. BLAST finds similar sequences using a heuristic method that approximates the Smith-Waterman algorithm by locating short matches between the two sequences. The (BLAST) algorithm can identify library sequences that resemble the query sequence above a certain threshold.

A homolog is a gene or genes that are related by vertical descent and are responsible for substantially the same or identical functions in different organisms. Genes are related by vertical descent when, for example, they share sequence similarity of sufficient amount to indicate they are homologous or related by evolution from a common ancestor. Genes that are orthologous can encode proteins with sequence similarity of about 45% to 100% amino acid sequence identity, and more preferably about 60% to 100% amino acid sequence identity. Genes can also be considered orthologs if they share three-dimensional structure but not necessarily sequence similarity, of a sufficient amount to indicate that they have evolved from a common ancestor to the extent that the primary sequence similarity is not identifiable. Paralogs are genes related by duplication within a genome, and can evolve new functions, even if these are related to the original one.

An amino acid position (or simply, amino acid) "corresponding to" an amino acid position in another polypeptide sequence is the position that is aligned with the referenced amino acid position when the polypeptides are aligned for maximum homology, for example, as determined by BLAST which allows for gaps in sequence homology within protein sequences to align related sequences and domains. Alternatively, in some instances, when polypeptide sequences are aligned for maximum homology, a corresponding amino acid may be the nearest amino acid to the identified amino acid that is within the same amino acid biochemical grouping—i.e., the nearest acidic amino acid, the nearest basic amino acid, the nearest aromatic amino acid, etc. to the identified amino acid.

By "substantially identical," with reference to a nucleic acid sequence (e.g., a gene, RNA, or cDNA) or amino acid sequence (e.g., a protein or polypeptide) is meant one that has at least 50%, at least 55%, at least 60%, at least 65%, at least 70%, at least 75%, at least 80%, at least 85%, at least 90%, at least 95%, at least 96%, at least 97% at least 98%, or at least 99% nucleotide or amino acid identity, respectively, to a reference sequence.

As used in the context of proteins, the term "structural similarity" indicates the degree of homology between the overall shape, fold, and/or topology of the proteins. It should be understood that two proteins do not necessarily need to have high sequence similarity to achieve structural similarity. Protein structural similarity is often measured by root mean squared deviation (RMSD), global distance test score (GDT-score), and template modeling score (TM-score); see, e.g., Xu and Zhang, Bioinformatics 26(7):889-895, 2010. Structural similarity can be determined, e.g., by superimposing protein structures obtained from, e.g., x-ray crystallography, NMR spectroscopy, cryogenic electron microscopy (cryo-EM), mass spectrometry, or any combination thereof, and calculating the RMSD, GDT-score, and/or TM-score based on the superimposed structures. In some embodiments, two proteins have substantially similar tertiary structures when the TM-score is greater than about 0.5, greater than about 0.6, greater than about 0.7, greater than about 0.8, or greater than about 0.9. In some embodiments, two proteins have substantially identical tertiary structures when the TM-score is about 1.0. Structurally-similar proteins may also be identified computationally using algorithms such as, e.g., TM-align (Zhang and Skolnick, Nucleic Acids Res 33(7):2302-2309, 2005); DALI (Holm and Sander, J Mol Biol 233(1):123-138, 1993); STRUCTAL (Gerstein and Levitt, Proc Int Conf Intell Syst Mol Biol 4:59-69, 1996); MINRMS (Jewett et al., Bioinformatics 19(5):625-634, 2003); Combinatorial Extension (CE) (Shindyalov and Bourne, Protein Eng 11(9):739-747, 1998); ProtDex (Aung et al., DASFAA 2003, Proceedings); VAST (Gibrat et al., Curr Opin Struct Biol 6:377-385, 1996); LOCK (Singh and Brutlag, Proc Int Conf Intell Syst Mol Biol 5:284-293, 1997); SSM (Krissinel and Henrick, Acta Cryst D60:2256-2268, 2004), and the like.

I. Cannabinoid Synthase

Figure 4:
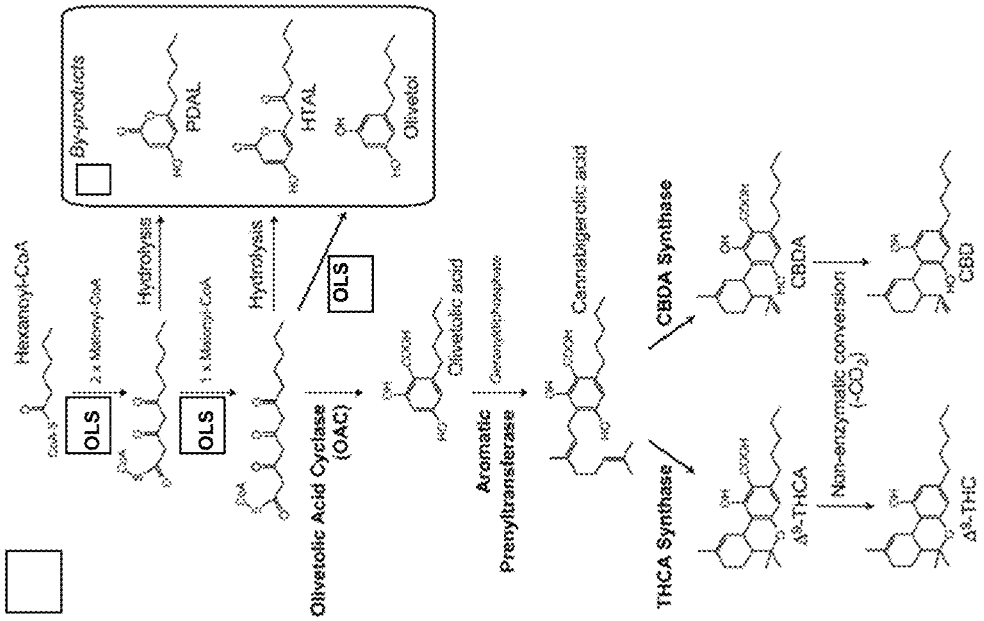
FIG. 4 shows an exemplary cannabinoid biosynthesis pathway as described in embodiments herein. Olivetol synthase (OLS) catalyzes the condensation of hexanoyl-CoA with three molecules of malonyl-CoA to yield 3,5,7-trioxododecanoyl-CoA, which is then converted to olivetolic acid (OA) by the enzyme olivetolic acid cyclase (OAC). A prenyltransferase converts OA and geranyl pyrophosphate (GPP) to CBGA, which is then converted to THCA by $\Delta^9$-tetrahydrocannabinolic acid synthase (THCAS). CBGA can also be converted into cannabidiolic acid (CBDA) by CBDA synthase. Hydrolytic byproducts of the OLS reaction are also shown.

Cannabinoid synthases are enzymes responsible for the biosynthesis of cannabinoids, e.g., cannabinoid compounds described herein. As shown in FIG. 4, cannabinoids can be derived from the condensation product of olivetolic acid (or its base form, olivetolate) and geranylpyrophosphate (GPP). The product of this reaction is cannabigerolate (CBGA), which serves as a "branch" point for cannabinoid biosynthesis. Cannabinoid synthase enzymes can catalyze the cyclization of CBGA to form various cannabinoid cyclization products. Cannabinoid synthases include, e.g., $\Delta^9$-tetrahydrocannabinolic acid synthase (THCAS), cannabidiolic acid synthase (CBDAS), and cannabichromenic acid synthase (CBCAS).

Cannabinoid synthases described herein are expected to perform similar catalytic reactions on the same substrate (e.g., CBGA) utilizing the same cofactor(s) (e.g., FAD), and thus, the polypeptide sequences of these cannabinoid synthases are highly conserved, e.g., at the catalytic, substrate binding, and cofactor binding regions. Moreover, the protein structures of the cannabinoid synthases are expected to be similar.

Cannabinoid synthases described herein can have a certain degree of cross-reactivity in product formation. For example, as described in U.S. Pat. Nos. 9,359,625, 9,526,715, and U.S. Ser. No. 10/081,818, each of THCAS, CBDAS, and CBCAS may be capable of producing THCA, CBDA, and CBCA under certain pH conditions. Thus, cannabinoid synthases described herein are not limited by the cannabinoid specified in their nomenclature (e.g., THCAS is not limited to producing THCA), and it will be understood by one of skill in the art that a particular cannabinoid synthase (e.g., THCAS) is capable of producing more than one cannabinoid. In some embodiments, the reaction products of a cannabinoid synthase can be controlled by modifying the pH of the reaction. For example, THCA is produced by THCAS and CBDA is produced by CBDAS at relatively low pH (e.g., between pH about 4.0 to about 6.0), while CBCA is produced by THCAS and CBDAS at relatively high pH (e.g., between pH about 6.5 to about 8.0).

In some embodiments, the invention provides a non-natural cannabinoid synthase with 70% or greater identity to any of SEQ ID NOs:1-2 or 78-84, comprising at least one amino acid variation as compared to a wild type cannabinoid synthase, comprising three alpha helices (αA, αB, and αC) and wherein a disulfide bond is not formed between alpha helix αA and alpha helix αC, wherein the non-natural cannabinoid synthase converts cannabigerolic acid (CBGA) into a cannabinoid. In some embodiments, the non-natural cannabinoid synthase has 80% or greater identity to any of SEQ ID NOs:1-2 or 78-84 or 85-88. In some embodiments, the non-natural cannabinoid synthase has 85% or greater identity to any of SEQ ID NOs:1-2 or 78-84 or 85-88. In some embodiments, the non-natural cannabinoid synthase has 80% or greater identity to any of SEQ ID NOs:1-2 or 78-84 or 85-88. In some embodiments, the non-natural cannabinoid synthase has 90% or greater identity to any of SEQ ID NOs:1-2 or 78-84 or 85-88. In some embodiments, the non-natural cannabinoid synthase has 85% or greater identity to any of SEQ ID NOs:1-2 or 78-84 or 85-88.

As described herein, a "non-natural" protein or polypeptide refers to a protein or polypeptide sequence having at least one variation at an amino acid position as compared to a wild-type polypeptide or nucleic acid sequence. In some embodiments, the non-natural cannabinoid synthase has at least one variation at an amino acid position as compared to a wild-type cannabinoid synthase.

In some embodiments, the non-natural cannabinoid synthase has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a natural, i.e., wild-type, cannabinoid synthase. The terms "natural" or "wild-type" cannabinoid synthase can refer to any known cannabinoid synthase sequence. For example, a natural cannabinoid synthase can include, but is not limited to, a THCAS sequence from *C. sativa*, a CBDAS sequence from *C. sativa*, and a CBCAS sequence from *C. sativa*, as described in Laverty et al., Genome Res 29(1): 146-156 (2019) and Zager et al., Plant Physiol 180: 1877-1897 (2019).

In some embodiments, the disclosure provides a non-naturally occurring cannabinoid synthase with about 70%, 75%, 80%, 85%, 90%, 95%, 99% or greater identity to at least about 25, 50, 75, 100, 125, 150, 200, 250, 300, 350, 400, 450, 500, or more contiguous amino acids of SEQ ID NOs:1-2 or 78-84 or 85-88, comprising at least one amino acid variation as compared to a wild type cannabinoid synthase, comprising three alpha helices (αA, αB and αC) and wherein a disulfide bond is not formed between alpha helix αA and alpha helix αC, wherein the non-natural cannabinoid synthase catalyzes the oxidative cyclization of cannabigerolic acid (CBGA) into a cannabinoid.

In some embodiments, the non-natural THCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:1. In some embodiments, the non-natural THCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:2. In some embodiments, the non-natural THCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:82. SEQ ID NOs:1, 2, and 82 respectively describe truncated THCAS with an N-terminal methionine (Met), wild-type THCAS, and truncated THCAS without an N-terminal Met.

In some embodiments, the non-natural THCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:85. In some embodiments, the non-natural THCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:86. In some embodiments, the non-natural THCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:87. In some embodiments, the non-natural THCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:88. SEQ ID NOs:85-88 describe truncated THCAS with various amino acid substitutions relative to wild-type THCAS, as described herein.

In some embodiments, the non-natural CBDAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:78. In some embodiments, the non-natural CBDAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:79. In some embodiments, the non-natural CBDAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:83. SEQ ID NOs:78, 79, and 83 respectively describe truncated CBDAS without an N-terminal Met, wild-type CBDAS, and truncated CBDAS with an N-terminal Met.

In some embodiments, the non-natural CBCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:80. In some embodiments, the non-natural CBCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:81. In some embodiments, the non-natural CBCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:84. SEQ ID NOs:80, 81, and 84 respectively describe truncated CBCAS without an N-terminal Met, wild-type CBCAS, and truncated CBCAS with an N-terminal Met.

In some embodiments, the at least one amino acid variation in the non-natural cannabinoid synthase is not in an active site of the non-natural cannabinoid synthase. As used herein, the term "active site" refers to one or more regions in an enzyme that may be important for catalysis, substrate binding, and/or cofactor binding. In some embodiments, the active site of the non-natural cannabinoid synthase comprises amino acid residues involved in binding the substrate, e.g., CBGA. In some embodiments, the active site of the non-natural cannabinoid synthase comprises amino acid residues involved in binding the cofactor, e.g., FAD. In some embodiments, the active site of the non-natural cannabinoid synthase comprises amino acid residues responsible for catalysis, e.g., the cyclization of CBGA.

In some embodiments, the non-natural cannabinoid synthase is $\Delta^9$-tetrahydrocannabinolic acid synthase (THCAS), cannabidiolic acid synthase (CBDAS), or cannabichromenic acid synthase (CBCAS). THCAS, CBDAS, and CBCAS are further described herein.

Figure 1:
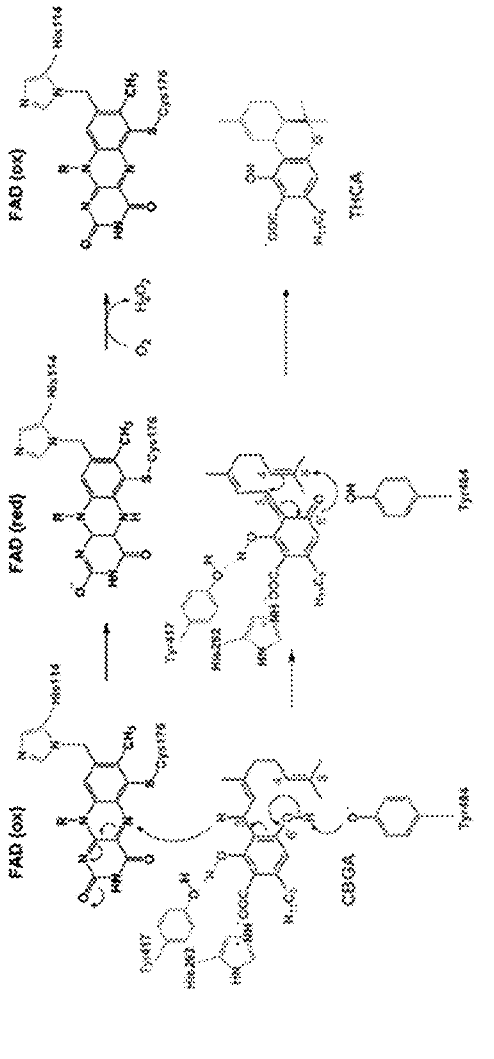
FIG. 1 is adapted from Shoyama et al., J Mol Biol 423:96-105 (2012) ("Shoyama") and shows an exemplary catalysis reaction for the formation of $\Delta^9$-tetrahydrocannabinolic acid (THCA) from cannabigerolic acid (CBGA) by $\Delta^9$-tetrahydrocannabinolic acid synthase (THCAS) utilizing FAD as a cofactor, as described in embodiments herein.

II. THCAS Variants $\Delta^9$-Tetrahydrocannabinolic acid synthase (THCAS) is an enzyme found in *Cannabis sativa* (*C. sativa*) that catalyzes the oxidative cyclization of cannabigerolic acid (CBGA) to $\Delta^9$-tetrahydrocannabinolic acid (THCA) utilizing a FAD cofactor, e.g., as shown in FIG. 1. As used herein, "THCA" refers to either THCA-A isoform or THCA-B isoform, as described herein.

The wild type structure of THCAS is described, e.g., in Shoyama. FIG. 2 shows the structure of THCAS, which comprises two domains, Domain I, Domain II, and a FAD-binding region spanning the two domains (Pfam: PF01565). The FAD-binding comprises amino acids Q69, R108, T109, R110, S111, G112, G113, H114, D115, A116, M119, S120, Y121, L132, A151, G174, Y175, C176, T178, V179, G180, V181, G182, G183, H184, S186, G189, Y190, G235, E236, G239, I240, I241, A242, F381, W444, Y481, N483, Y484, R485, and N533 (amino acid residue numbering with respect to SEQ ID NO:2).

Domain I is further divided into subdomains Ia and Ib. Subdomain Ia includes the region from residue positions 28 to 134 and comprises three α-helices, αA, αB, and αC which surround three β-strands (β1-β3) (amino acid residue numbering with respect to SEQ ID NO:2). As used herein, αA of THCAS includes the amino acid residues Asn29 to Ile42; αB includes the amino acid residues Leu59 to Thr67; and αC includes the amino acid residues Asn89 to Gly 104. In general, a disulfide bond is present between Cys37 in αA and Cys99 in αC of wild-type THCAS. Subdomain Ib includes the region from residue positions 135 to 253 and from 476 to 545 and comprises five antiparallel β-strands (β4-β8) surrounding five α-helices (αD-αF, αM, and αN). Domain II includes the region from residue positions 254 to 475 and comprises eight antiparallel β-strands (β9-β16) surrounding six α-helices (αG-αL).

THCAS further comprises a CBGA binding region. The following amino acid residues may be involved in CBGA binding: A116, G174, Y175, M290, H292, G376, T379, F381, I383, L385, G410, M413, V415, Y417, E442, W444, T446, S448, E450, Y481, L482, N483, and Y484 (amino acid residue numbering with respect to SEQ ID NO: 2).

Figure 9:
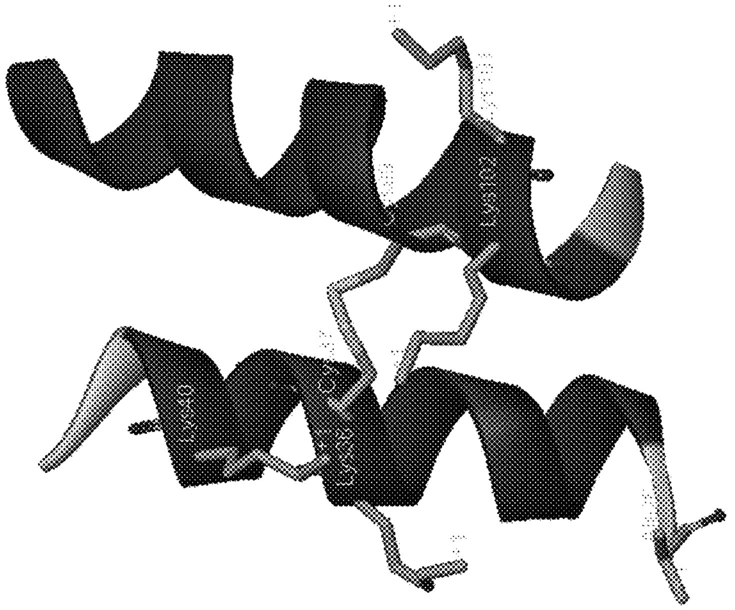
FIG. 9 shows a representation of the αA and αC helices of THCAS as described in embodiments herein. In this representation, a disulfide bond is formed between Cys37 and Cys99. Positively charged residues Lys36, Lys40, Lys101, and Lys102 are also shown.

In some examples, the present disclosure provides non-naturally occurring $\Delta^1$-tetrahydrocannabinolic acid synthase (THCAS) that does not comprise a disulfide bond between alpha helix αA and alpha helix αC, wherein the non-natural THCAS catalyzes the oxidative cyclization of cannabigerolic acid (CBGA) into $\Delta^1$-tetrahydrocannabinolic acid (see, e.g., FIGS. 4 and 9).

In some embodiments, the invention provides a non-natural THCAS with 80% or greater identity to any of SEQ ID NOs:1, 2, 82, or 85-88, comprising at least one amino acid variation as compared to a wild type THCAS, comprising three alpha helices (αA, αB, and αC) and wherein a disulfide bond is not formed between alpha helix αA and alpha helix αC, wherein the non-natural THCAS catalyzes the oxidative cyclization of cannabigerolic acid (CBGA) into $\Delta^9$-tetrahydrocannabinolic acid (THCA). In some embodiments, the invention provides a non-natural THCAS with 90% or greater identity to SEQ ID NOs:1, 2, 82, or 85-88, comprising at least one amino acid variation as compared to a wild type THCAS, comprising three alpha helices (αA, αB, and αC) and wherein a disulfide bond is not formed between alpha helix αA and alpha helix αC, wherein the non-natural THCAS catalyzes the oxidative cyclization of cannabigerolic acid (CBGA) into $\Delta^9$-tetrahydrocannabinolic acid (THCA). In some embodiments, the invention provides a non-natural THCAS with 95% or greater identity to SEQ ID NOs: 1, 2, 82, or 85-88, comprising at least one amino acid variation as compared to a wild type THCAS, comprising three alpha helices (αA, αB, and αC) and wherein a disulfide bond is not formed between alpha helix αA and alpha helix αC, wherein the non-natural THCAS catalyzes the oxidative cyclization of cannabigerolic acid (CBGA) into $\Delta^9$-tetrahydrocannabinolic acid (THCA).

The non-natural THCAS described herein is capable of catalyzing the conversion of CBGA to THCA. In some embodiments, the non-natural THCAS is capable of catalyzing at least one step of the conversion of CBGA to THCA. In some embodiments, the non-natural THCAS has substantially the same amount of activity as wild-type THCAS. The term "substantially" when referring to enzyme activity means that the fragment, truncation, variant, or fusion of THCAS has greater than or about 80%, greater than or about 85%, greater than or about 90%, greater than or about 95%, greater than or about 99%, or about 100% the enzymatic activity of wild-type THCAS. In some embodiments, the non-natural THCAS has greater than or about 80%, greater than or about 85%, greater than or about 90%, greater than or about 95%, greater than or about 99%, or about 100% the enzymatic activity of wild-type THCAS. Encompassed within the definition of "non-natural THCAS" are fragments, truncations, variants, and fusions that are capable of catalyzing the conversion of CBGA to THCA.

In some embodiments, the non-natural THCAS has at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to at least about 25, 50, 75, 100, 125, 150, 200, 250, 300, 350, 400, 450, 500, or more contiguous amino acids of a natural, i.e., wild-type, THCAS and having a cannabinoid synthase activity. In some embodiments, the non-natural THCAS comprises the FAD binding domain (Pfam: PF01565) and a CBGA binding domain.

In some embodiments, the non-natural THCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a natural, i.e., wild-type, THCAS. The term natural THCAS can refer to any known THCAS sequence. For example, a wild-type THCAS sequence can include, but is not limited to, a THCAS sequence from various *Cannabis sativa* plants, as provided in Taura, F., et al., *J. Am. Chem. Soc.* 1995, 117, 9766-9767; Sirikantaramas, S.; et al. *J. Biol. Chem.* 2004, 279, 39767-39774; and Cascini, F., et al., Plants 2019 8(11), 496.

In some embodiments, the non-natural THCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:1. SEQ ID NO:1 discloses a truncated THCAS as compared to wild-type THCAS (SEQ ID NO:2). SEQ ID NO:1 comprises an N-terminal methionine. SEQ ID NO:1 does not comprise an N-terminal leader sequence present in wild-type THCAS. In some embodiments, removal of the leader sequence increases expression of the polypeptide of SEQ ID NO:1 in a host organism, e.g., a bacterial organism such as *E. coli.*

In some embodiments, the non-natural THCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:2. In some embodiments, SEQ ID NO:2 describes a wild-type THCAS. In some embodiments, wild-type THCAS comprises a leader sequence.

In some embodiments, the non-natural THCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:82. SEQ ID NO:82 discloses a truncated THCAS as compared to wild-type THCAS (SEQ ID NO:2). SEQ ID NO:82 does not comprise an N-terminal leader sequence present in wild-type THCAS. SEQ ID NO:82 does not comprise an N-terminal methionine. In some embodiments, removal of the leader sequence increases expression of the polypeptide of SEQ ID NO:82 in a host organism, e.g., a bacterial organism such as *E. coli*. In some embodiments, the N-terminal methionine that is typically present at the start of an expressed polypeptide sequence, e.g., the polypeptide of SEQ ID NO:82, is removed by the host organism, e.g., a bacterial organism such as *E. coli*.

In some embodiments, the non-natural THCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:85. SEQ ID NO:85 does not comprise an N-terminal leader sequence present in wild-type THCAS. SEQ ID NO:85 comprises an N-terminal methionine. SEQ ID NO:85 comprises additional histidine residues at the C-terminus. In some embodiments, C-terminal histidine residues facilitate purification of the non-natural THCAS. SEQ ID NO:85 further comprises C37A, K40R, N89D, N90D, C99A, and K102E substitutions relative to the truncated wild-type THCAS described by SEQ ID NO:2.

In some embodiments, the non-natural THCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:86. SEQ ID NO:86 does not comprise an N-terminal leader sequence present in wild-type THCAS. SEQ ID NO:86 comprises an N-terminal methionine. SEQ ID NO:86 comprises additional histidine residues at the C-terminus. In some embodiments, C-terminal histidine residues facilitate purification of the non-natural THCAS. SEQ ID NO:86 further comprises C37A, K40R, L59T, N89D, C99A, K102E, and V321T substitutions relative to the truncated wild-type THCAS described by SEQ ID NO:2.

In some embodiments, the non-natural THCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:87. SEQ ID NO:87 does not comprise an N-terminal leader sequence present in wild-type THCAS. SEQ ID NO:87 comprises an N-terminal methionine. SEQ ID NO:87 comprises additional histidine residues at the C-terminus. In some embodiments, C-terminal histidine residues facilitate purification of the non-natural THCAS. SEQ ID NO:87 further comprises C37A, K40R, L59T, N89D, C99A, K102E, K296E, V321T, and N516E substitutions relative to the truncated wild-type THCAS described by SEQ ID NO:2.

In some embodiments, the non-natural THCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:88. SEQ ID NO:88 does not comprise an N-terminal leader sequence present in wild-type THCAS. SEQ ID NO:88 comprises an N-terminal methionine. SEQ ID NO:88 comprises additional histidine residues at the C-terminus. In some embodiments, C-terminal histidine residues facilitate purification of the non-natural THCAS. SEQ ID NO:88 further comprises C37A, K40R, L59T, N89D, C99A, K102E, and K296E substitutions relative to the truncated wild-type THCAS described by SEQ ID NO:2.

As used throughout this application, all amino acid positions of the non-natural THCAS described herein are numbered with reference to SEQ ID NO:2, unless otherwise defined. One of skill in the art would understand that alignment methods can be used to determine the appropriate amino acid position number that corresponds to the position referenced in SEQ ID NO:2. An amino acid sequence alignment of SEQ ID NOs:1, 2, and 78-84 is shown in FIGS. 11A-11C. Select amino acids and their corresponding positions in each of SEQ ID NOs:1, 2, and 78-84 are also shown below in Table A. For example, the first amino acid of SEQ ID NO:1 corresponds to the 27$^{th}$ amino acid of SEQ ID NO:2, and thus, the amino acid position of "C37" in SEQ ID NO:2, corresponds to "C11" in SEQ ID NO:1; the amino acid position of "C99" in SEQ ID NO:2, corresponds to "C73" in SEQ ID NO:1, and so on. The first amino acid of SEQ ID NO:82 corresponds to the 28$^{th}$ amino acid of SEQ ID NO:2, and thus, the amino acid position of "C37" in SEQ ID NO:2, corresponds to "C10" in SEQ ID NO:82; the amino acid position of "C99" in SEQ ID NO:2, corresponds to "C72" in SEQ ID NO:82, and so on.

TABLE A

| SEQ ID NO | CORRESPONDING AMINO ACID POSITIONS | | | | | |
|---|---|---|---|---|---|---|
| SEQ1 | K10 | C11 | K14 | C73 | K75 | K76 |
| SEQ2 | K36 | C37 | K40 | C99 | K101 | K102 |
| SEQ78 | K9 | C10 | Q13 | C72 | K74 | K75 |
| SEQ79 | K36 | C37 | Q40 | C99 | K101 | K102 |
| SEQ80 | K9 | C10 | E13 | C72 | K74 | K75 |
| SEQ81 | K36 | C37 | E40 | C99 | K101 | K102 |
| SEQ82 | K9 | C10 | K13 | C72 | K74 | K75 |
| SEQ83 | K10 | C11 | Q14 | C73 | K75 | K76 |
| SEQ84 | K10 | C11 | E14 | C73 | K75 | K76 |

As described herein, a "non-natural" protein or polypeptide refers to a protein or polypeptide sequence having at least one variation at an amino acid position as compared to a wild-type polypeptide or nucleic acid sequence. In some embodiments, the non-natural THCAS has at least one variation at an amino acid position as compared to a wild-type THCAS.

Figure 3:
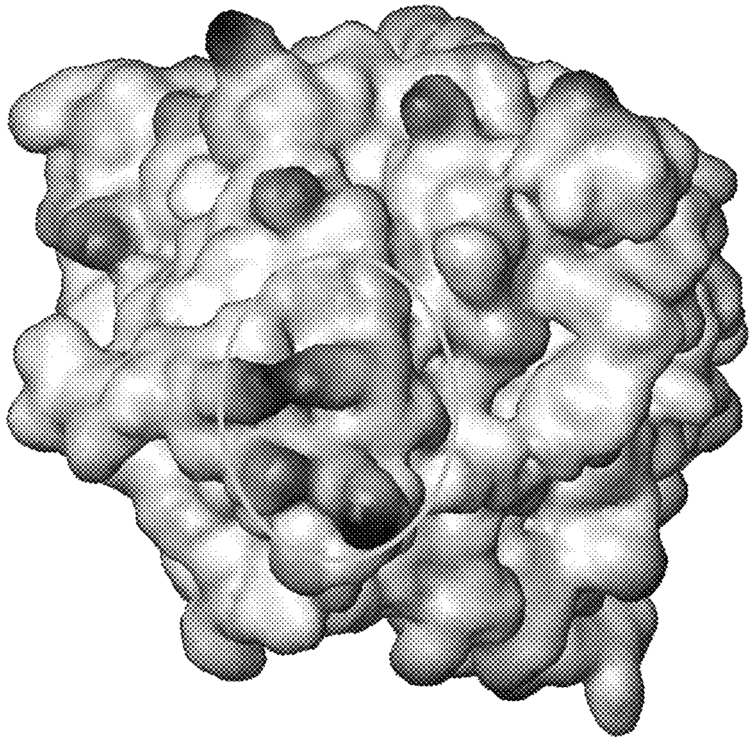
FIG. 3 shows a molecular surface map of wild-type THCAS as described in embodiments herein. The region encircled by the ellipse indicates a cluster of positively-charged amino acid residues.

In some embodiments, the non-natural THCAS comprises three alpha helices, αA, αB, and αC, as described for wild-type THCAS, i.e., αA includes the amino acid residues Asn29 to Ile42; αB includes the amino acid residues Leu59 to Thr67; and αC includes the amino acid residues Asn89 to Gly 104 (amino acid residue numbering with respect to SEQ ID NO:2). In some embodiments, the non-natural THCAS does not comprise a disulfide bond between αA and αC present in wild-type THCAS. In some embodiments, the at least one amino acid variation in the non-natural THCAS disrupts the disulfide bond between αA and αC in wild-type THCAS. In the context of a protein or polypeptide, a disulfide bond (sometimes called an "S—S bond" or "disulfide bridge") refers to a bond between two cysteine residues, typically formed through oxidation of the thiol groups on the cysteines. Disulfide bonds can play an important role in the folding and stability of proteins, and in general, disruption of a disulfide bond in a protein structure can lead to loss of the protein's structure and result in protein misfolding, aggregation, and/or loss of function, e.g. enzymatic activity. As seen in FIG. 3, the molecular surface of THCAS mapped with residue charges shows that a cluster of positive charges are present inside the ellipse that circles portions of αA and αC. Without being bound by theory, it is contemplated that the positively charged amino acids in this cluster repel one another, and that the disulfide bond between C37 of αA and C99 of αC holds the two alpha helices together and overcomes the repulsion between the positive charges.

In some embodiments, the disulfide bond between αA and αC stabilizes the tertiary structure of wild-type THCAS. Proteins comprising disulfide bonds, e.g., endogenous to plants, can be unstable in bacterial host cells as the disulfide bonds are often disrupted due to the reducing environment in the bacterial cells. In some embodiments, wild-type THCAS comprising a disulfide bond between αA and αC is substantially unstable in a bacterial cell, e.g., an *E. coli* cell. As used herein, "unstable" THCAS can refer to THCAS polypeptides that are non-functional, denatured, and/or degraded rapidly, resulting in THCAS activity that is greatly reduced relative to the activity found in its native host cell, e.g., *Cannabis sativa* plants. In some embodiments, the THCAS activity is 50% less, 60% less, 70% less, 80% less, or 90% less than the expected activity from the activity found in the native host cell, based on the expression parameters such as, e.g., vector, culture medium, induction agent, temperature, and/or time; "substantially unstable" THCAS can also mean less than 70%, less than 60%, less than 50%, less than 40%, less than 30%, less than 20%, less than 10%, less than 5%, or less than 1% of the total amount of THCAS isolated from the host cell is soluble.

In some embodiments, the non-natural THCAS described herein does not comprise the disulfide bond between αA and αC and has a substantially similar tertiary structure as wild-type THCAS. In some embodiments, the non-natural THCAS that does not comprise the disulfide bond between αA and αC has a substantially identical tertiary structure as wild-type THCAS comprising the disulfide bond between αA and αC. Methods of determining structural similarity between two proteins are described herein and includes, e.g., TM-scoring. In some embodiments, the TM-score for the non-natural THCAS that does not comprise the disulfide bond between αA and αC and the wild-type THCAS comprising the disulfide bond between αA and αC is greater than about 0.5, greater than about 0.6, greater than about 0.7, greater than about 0.8, greater than about 0.9, or about 1.0.

In some embodiments, the non-natural THCAS comprises one or more amino acid variations to keep αA and αC in proximity comparable to the distance of a disulfide bond. In some embodiments, αA and αC in the non-natural THCAS are 1 to about 5 Å, about 1.5 to about 4.5 Å, about 2 to about 4 Å, or about 2.5 to about 3.5 Å from one another at their closest amino acid residues. In some embodiments, the non-natural THCAS comprises one or more amino acid variations that removes a hydrophobic residue or replaces the hydrophobic residue with a neutral or hydrophilic residue in αA and/or αC. Examples of hydrophobic, neutral, and hydrophilic residues are described herein. In some embodiments, reducing the number of hydrophobic residues in αA and/or αC, reduces the repulsion between αA and αC. In some embodiments, the non-natural THCAS comprises one or more amino acid variations to overcome the repulsion between the positive charges in αA and αC. In some embodiments, the non-natural THCAS that does not comprise the disulfide bond between αA and αC comprises at least one salt bridge between αA and αC. In the context of a protein or polypeptide, a salt bridge (also called "ion pairing") refers to a combination of two non-covalent interactions: hydrogen bonding and ionic bonding, that can contribute to the stability of a protein structure. Salt bridges can be formed, for example, between anionic amino acid side chains (such as the carboxylate ($RCOO^-$) of aspartic acid or glutamic acid) and cationic amino acid side chains (such as the ammonium ($RNH_3^+$) of lysine or the guanidium ($RNHC(NH_2)_2^+$) of arginine). Additional amino acid residues with ionizable side chains that can form salt bridges include, e.g., histidine, tyrosine, threonine, serine, glutamine, asparagine, lysine, and cysteine. In addition to salt bridges, van der Waals interaction can also contribute to the stability of a protein structure, e.g., between two α-helices. For example, van der Waals forces can exist between the non-polar, aliphatic amino acids such as Gly, Ala, Val, Leu, Ile, Pro, and aromatic amino acids such as Phe, Tyr, and Trp.

In some embodiments, the at least one amino acid variation in the non-natural THCAS is a substitution of one or more cysteines forming the disulfide bond between αA and αC in wild-type THCAS, thereby disrupting the disulfide bond. In some embodiments, the at least one amino acid variation in the non-natural THCAS is a deletion of one or more cysteines forming the disulfide bond between αA and αC in wild-type THCAS, thereby disrupting the disulfide bond. In some embodiments, the at least one amino acid variation in the non-natural THCAS is an insertion near one or more cysteines forming the disulfide bond between αA and αC in wild-type THCAS, thereby disrupting the disulfide bond. In some embodiments, the at least one amino acid variation in the non-natural THCAS replaces the disulfide bond between αA and αC of wild-type THCAS with a salt bridge. In some embodiments, the non-natural THCAS comprising a salt bridge and no disulfide bond between αA and αC has improved expression, e.g., improved yield and/or solubility, in a bacterial cell (e.g., *E. coli*), compared with the expression of a THCAS comprising a disulfide bond between αA and αC.

In some embodiments, the non-natural THCAS comprises 1 to 100, 1 to 90, 1 to 80, 1 to 70, 1 to 60, 1 to 50, 1 to 40, 1 to 30, 1 to 25, 1 to 20, 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, or 19 to 20 amino acid variations as compared to a wild-type THCAS. In some embodiments, the non-natural THCAS comprises about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, or about 100 amino acid variations as compared to a wild-type THCAS.

In some embodiments, the amino acid variation in the non-natural THCAS is in αA, αC, or both. In some embodiments, the amino acid variation is at position C37, C99, K36, K40, K101, K102, or a combination thereof, wherein the position corresponds to SEQ ID NO:2. In some embodiments, the amino acid variation is at position C37, C99, or both, wherein the amino acid position corresponds to SEQ ID NO:2.

In some embodiments, the amino acid variation in the non-natural THCAS is an amino acid substitution, deletion, or insertion. In some embodiments, the variation is a substitution of one or more amino acids in a wild-type THCAS polypeptide sequence. In some embodiments, the variation is a deletion of one or more amino acids in a wild-type THCAS polypeptide sequence. In some embodiments, the variation is an insertion of one or more amino acids in a wild-type THCAS polypeptide sequence.

In some embodiments, the disulfide bond which occurs in wild-type THCAS can be disrupted by the insertion of one or more amino acids. In some embodiments, the insertion of one or more amino acids results in formation of a salt bridge. In some embodiments, the variation is an insertion of 1 to 20, 1 to 15, 1 to 10, 1 to 9, 1 to 8, 1 to 7, 1 to 6, 1 to 5, 1 to 4, 1 to 3, or 1 to 2 amino acids. In some embodiments, the variation is an insertion of about 1, about 2, about 3, about 4, about 5, about 6, about 7, about 8, about 9, about 10, about 11, about 12, about 13, about 14, about 15, about 16, about 17, about 18, about 19, or about 20 amino acids. In some embodiments, the insertion is positioned within about 20 amino acids of C37 or C99. It will be understood that when referring to amino acid positions herein, "within" n number of amino acids expressly specifically includes n and all numbers between 0 and n. For example, an insertion position within 10 amino acids of X means that the insertion is 1, 2, 3, 4, 5, 6, 7, 8, 9, or 10 amino acids from the specified position X. In some embodiments, the insertion is positioned within about 10, within about 9, within about 8, within about 7, within about 6, within about 5, within about 4, within about 3, within about 2, or within about 1 amino acids of C37. In some embodiments, the insertion is within about 10, within about 9, within about 8, within about 7, within about 6, within about 5, within about 4, within about 3, within about 2, or within about 1 amino acids of C99. In some embodiments, the insertion is sufficient to disrupt the disulfide bond between αA and αC.

In some embodiments, the disulfide bond which occurs in wild-type THCAS can be disrupted by the deletion of one or more amino acids. In some embodiments, the deletion of one or more amino acids results in formation of a salt bridge. In some embodiments, the variation is a deletion of 1 to 20, 1 to 15, 1 to 10, 1 to 9, 1 to 8, 1 to 7, 1 to 6, 1 to 5, 1 to 4, 1 to 3, or 1 to 2 amino acids. In some embodiments, the variation is an deletion of about 1, about 2, about 3, about 4, about 5, about 6, about 7, about 8, about 9, about 10, about 11, about 12, about 13, about 14, about 15, about 16, about 17, about 18, about 19, or about 20 amino acids. In some embodiments, the deletion is within about 20 amino acids of C37 or C99. In some embodiments, the deletion is within about 10, within about 9, within about 8, within about 7, within about 6, within about 5, within about 4, within about 3, within about 2, or within about 1 amino acids of C37. In some embodiments, the deletion is within about 10, within about 9, within about 8, within about 7, within about 6, within about 5, within about 4, within about 3, within about 2, or within about 1 amino acids of C99. In some embodiments, the deletion is sufficient to disrupt the disulfide bond between C37 of αA and C99 of αC.

In some embodiments, the disulfide bond which occurs in wild-type THCAS can be disrupted on the substitution of one or more amino acids. In some embodiments, the substitution of one or more amino acids results in formation of a salt bridge. In some embodiments, the variation is a substitution. In some embodiments, the non-natural THCAS comprises 1 to 50, 1 to 40, 1 to 30, 1 to 25, 1 to 20, 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, or 19 to 20 amino acid substitutions as compared to a wild-type THCAS. In some embodiments, the non-natural THCAS comprises about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, or about 50 amino acid substitutions as compared to a wild-type THCAS.

In some embodiments, the non-natural THCAS comprises an amino acid substitution at position C37, C99, K36, K40, K101, K102, or any combination thereof, wherein the position corresponds to SEQ ID NO:2.

In some embodiments, the non-natural THCAS comprises a substitution at position C37, wherein the position corresponds to SEQ ID NO:2. In some embodiments, the substitution is selected from position C37A, C37D, C37H, C37Y, C37E, C37K, C37N, C37Q, C37T and C37R, wherein the position corresponds to SEQ ID NO:2. In some embodiments, the substitution is selected from position C37A, C37D, C37E, C37K, C37N, C37Q, and C37R, wherein the position corresponds to SEQ ID NO:2.

In some embodiments, the non-natural THCAS comprises a substitution at position C99, wherein the position corresponds to SEQ ID NO:2. In some embodiments, the substitution is selected from position C99F, C99A, C99I, C99V, and C99L, wherein the position corresponds to SEQ ID NO:2. In some embodiments, the substitution is selected from position C99A, C99I, C99V, and C99L, wherein the position corresponds to SEQ ID NO:2.

In some embodiments, the non-natural THCAS comprises a substitution at C37 and a substitution at C99. In some embodiments, the non-natural THCAS comprises a substitution selected from C37A, C37D, C37H, C37Y, C37E, C37K, C37N, C37Q, C37T and C37R and a substitution selected from C99A, C99I, C99V, C99L, and C99F. In some embodiments, the non-natural THCAS comprises a substitution selected from C37A, C37D, C37E, C37K, C37N, C37Q, and C37R and a substitution selected from C99A, C99I, C99V, and C99L.

In some embodiments, the non-natural THCAS comprises C37A and a substitution selected from C99F, C99A, C99I, C99V, and C99L. In some embodiments, the non-natural THCAS comprises C37D and a substitution selected from C99F, C99A, C99I, C99V, and C99L. In some embodiments, the non-natural THCAS comprises C37H and a substitution selected from C99F, C99A, C99I, C99V, and C99L. In some embodiments, the non-natural THCAS comprises C37Y and a substitution selected from C99F, C99A, C99I, C99V, and C99L. In some embodiments, the non-natural THCAS comprises C37E and a substitution selected from C99F, C99A, C99I, C99V, and C99L. In some embodiments, the non-natural THCAS comprises C37K and a substitution selected from C99F, C99A, C99I, C99V, and C99L. In some embodiments, the non-natural THCAS comprises C37N and a substitution selected from C99F, C99A, C99I, C99V, and C99L. In some embodiments, the non-natural THCAS comprises C37Q and a substitution selected from C99F, C99A, C99I, C99V, and C99L. In some embodiments, the non-natural THCAS comprises C37T and a substitution selected from C99F, C99A, C99I, C99V, and C99L. In some embodiments, the non-natural THCAS comprises C37R and a substitution selected from C99F, C99A, C99I, C99V, and C99L.

In some embodiments, the non-natural THCAS comprises C37A and a substitution selected from C99A, C99I, C99V, and C99L. In some embodiments, the non-natural THCAS comprises C37D and a substitution selected from C99A, C99I, C99V, and C99L. In some embodiments, the non-natural THCAS comprises C37E and a substitution selected from C99A, C99I, C99V, and C99L. In some embodiments, the non-natural THCAS comprises C37K and a substitution selected from C99A, C99I, C99V, and C99L. In some embodiments, the non-natural THCAS comprises C37N and a substitution selected from C99A, C99I, C99V, and C99L. In some embodiments, the non-natural THCAS comprises C37Q and a substitution selected from C99A, C99I, C99V, and C99L. In some embodiments, the non-natural THCAS comprises C37R and a substitution selected from C99A, C99I, C99V, and C99L. In some embodiments, the amino acid substitutions described herein stabilize the structure of the non-natural THCAS.

In some embodiments, the non-natural THCAS comprises C37D. In some embodiments, the non-natural THCAS comprises C99F. In some embodiments, the non-natural THCAS comprises C37D and a substitution selected from C99F, C99V, C99A, C99I, and C99L. In some embodiments, the non-natural THCAS comprises C37Y. In some embodiments, the non-natural THCAS comprises C37Y and a substitution selected from C99A, C99I, C99V, C99L, and C99F. In some embodiments, the non-natural THCAS comprises C37K and C99F. In some embodiments, the non-natural THCAS comprises C37K. In some embodiments, the non-natural THCAS comprises C37H. In some embodiments, the non-natural THCAS comprises C37H and a substitution selected from C99V, C99L, and C99A. In some embodiments, the non-natural THCAS comprises C37N. In some embodiments, the non-natural THCAS comprises C37N and a substitution selected from C99A, C99F and C99V. In some embodiments, the non-natural THCAS comprises C37Q. In some embodiments, the non-natural THCAS comprises C37Q and a substitution selected from C99I and C99A. In some embodiments, the non-natural THCAS comprises C37R. In some embodiments, the non-natural THCAS comprises C37R and C99I.

In some embodiments, the non-natural THCAS comprises at least one amino acid substitution corresponding to SEQ ID NO:2, wherein the substitution is:

(a) C37D and C99F;
(b) C37H;
(c) C37Y;
(d) C37Y and C99A;
(e) C37Y and C99V;
(f) C37E and C99F;
(g) C37Y and C99I;
(h) C37E;
(i) C37K and C99F;
(j) C37D;
(k) C37D and C99V;
(l) C37D and C99A;
(m) C37H and C99V;
(n) C37E and C99V;
(o) C37N and C99A;
(p) C37N and C99F;
(q) C37E and C99A;
(r) C37N and C99V;
(s) C37Q and C99I;
(t) C37T;
(u) C37Y and C99L;
(v) C37H and C99L;
(w) C99F;
(x) C37Q;
(y) C37N;
(z) C37H and C99A;
(aa) C37Y and C99F;
(bb) C37K;
(cc) C37Q and C99A;
(dd) C37R and C99I;
(ee) C37A and C99V;
(ff) C37A and C99A;
(gg) C37A and C99I;
(hh) C37A and C99L;
(ii) C37Q and C99V;
(jj) C37Q and C99L;
(kk) C37N and C99I;
(ll) C37N and C99L;
(mm) C37E and C99I;
(nn) C37E and C99L;
(oo) C37D and C99I;
(pp) C37D and C99L;
(qq) C37R and C99V;
(rr) C37R and C99A;
(ss) C37R and C99L;
(tt) C37R;
(uu) C37K and C99V;
(vv) C37K and C99A;
(ww) C37K and C99I; or
(xx) C37K and C99L.

In some embodiments, the at least one amino acid variation in the non-natural THCAS is a substitution of one or more positively-charged residues in αA and αC in wild-type THCAS, thereby reducing the charge repulsion, forming a salt bridge, and/or increasing van der Waals interaction between αA and αC as described herein. In some embodiments, the at least one amino acid variation in the non-natural THCAS is a deletion of one or more positively-charged residues, or a deletion of one or more amino acids near (e.g., within 1 to 10 amino acids, within 1 to 5 amino acids, within 1 to 4 amino acids, within 1 to 3 amino acids, or within 1 to 2 amino acids) of one or more positively-charged residues in αA and αC in wild-type THCAS and reduces their charge repulsion, forms a salt bridge, and/or increases van der Waals interaction between αA and αC as described herein. In some embodiments, the at least one amino acid variation in the non-natural THCAS is an insertion of one or more amino acids near (e.g., within 1 to 10 amino acids, within 1 to 5 amino acids, within 1 to 4 amino acids, within 1 to 3 amino acids, or within 1 to 2 amino acids) of one or more positively-charged residues in αA and αC in wild-type THCAS and reduces their charge repulsion, forms a salt bridge, and/or increases van der Waals interaction between αA and αC as described herein.

In some embodiments, the at least one amino acid variation, e.g., an insertion, deletion, or substitution in the non-natural THCAS provides resistance to protease degradation. For example, the amino acid variation can disrupt a protease target sequence and/or a protease binding site, or the amino acid variation can recruit a protease inhibitor. Protein variants for increasing protease resistance is further discussed, e.g., in Ahmad et al., Protein Sci 21(3):433-446 (2012) and Heard et al., J Med Chem 56(21):8339-8351 (2013).

In some embodiments, the non-natural THCAS comprises a substitution at K36, K40, K101, K102, or a combination thereof. In some embodiments, the non-natural THCAS comprises a substitution of K36, K40, K101, K102, or a combination thereof, with a charged amino acid. Charged amino acids are described herein. In some embodiments, the charged amino acid is D, E, or R. In some embodiments, K36, K40, K101, K102, or a combination thereof, is independently substituted with D, E, or R. In some embodiments, the non-natural THCA comprises K36D. In some embodiments, the non-natural THCA comprises K36E. In some embodiments, the non-natural THCA comprises K36R. In some embodiments, the non-natural THCA comprises K40D. In some embodiments, the non-natural THCA comprises K40E. In some embodiments, the non-natural THCA comprises K40R. In some embodiments, the non-natural THCA comprises K101D. In some embodiments, the non-natural THCA comprises K101E. In some embodiments, the non-natural THCA comprises K101R. In some embodiments, the non-natural THCA comprises K102D. In some embodiments, the non-natural THCA comprises K102E. In some embodiments, the non-natural THCA comprises K102R.

In some embodiments, the non-natural THCAS comprises: a substitution of K36, K40, K101, K102, or a combination thereof, with a charged amino acid; a substitution selected from C37A, C37D, C37H, C37Y, C37E, C37K, C37N, C37Q, C37T and C37R; a substitution selected from C99A, C99I, C99V, C99L, and C99F; or any combination thereof. In some embodiments, the non-natural THCAS comprises: a substitution of K36, K40, K101, K102, or a combination thereof, with a charged amino acid; a substitution selected from C37A, C37D, C37E, C37K, C37N, C37Q, and C37R; a substitution selected from C99A, C99I, C99V, and C99L; or any combination thereof.

In some embodiments, the non-natural THCAS comprises: a substitution selected from C37A, C37D, C37E, C37K, C37N, C37Q, and C37R; a substitution selected from C99A, C99I, C99V, and C99L; a substitution selected from K36D, K36E, and K36R; a substitution selected from K40D, K40E, K40R; a substitution selected from K101D, K101E, K101R; a substitution selected from K102D, K102E, and K102R; or any combination thereof.

In some embodiments, the non-natural THCAS comprises K36D; a substitution selected from C37A, C37D, C37E, C37K, C37N, C37Q, and C37R; and a substitution selected from C99A, C99I, C99V, and C99L. In some embodiments, the non-natural THCAS comprises K36E; a substitution selected from C37A, C37D, C37E, C37K, C37N, C37Q, and C37R; and a substitution selected from C99A, C99I, C99V, and C99L. In some embodiments, the non-natural THCAS comprises K36R; a substitution selected from C37A, C37D, C37E, C37K, C37N, C37Q, and C37R; and a substitution selected from C99A, C99I, C99V, and C99L.

In some embodiments, the non-natural THCAS comprises K40D; a substitution selected from C37A, C37D, C37E, C37K, C37N, C37Q, and C37R; and a substitution selected from C99A, C99I, C99V, and C99L. In some embodiments, the non-natural THCAS comprises K40E; a substitution selected from C37A, C37D, C37E, C37K, C37N, C37Q, and C37R; and a substitution selected from C99A, C99I, C99V, and C99L. In some embodiments, the non-natural THCAS comprises K40R; a substitution selected from C37A, C37D, C37E, C37K, C37N, C37Q, and C37R; and a substitution selected from C99A, C99I, C99V, and C99L.

In some embodiments, the non-natural THCAS comprises K101D; a substitution selected from C37A, C37D, C37E, C37K, C37N, C37Q, and C37R; and a substitution selected from C99A, C99I, C99V, and C99L. In some embodiments, the non-natural THCAS comprises K101E; a substitution selected from C37A, C37D, C37E, C37K, C37N, C37Q, and C37R; and a substitution selected from C99A, C99I, C99V, and C99L. In some embodiments, the non-natural THCAS comprises K101R; a substitution selected from C37A, C37D, C37E, C37K, C37N, C37Q, and C37R; and a substitution selected from C99A, C99I, C99V, and C99L.

In some embodiments, the non-natural THCAS comprises K102D; a substitution selected from C37A, C37D, C37E, C37K, C37N, C37Q, and C37R; and a substitution selected from C99A, C99I, C99V, and C99L. In some embodiments, the non-natural THCAS comprises K102E; a substitution selected from C37A, C37D, C37E, C37K, C37N, C37Q, and C37R; and a substitution selected from C99A, C99I, C99V, and C99L. In some embodiments, the non-natural THCAS comprises K102R; a substitution selected from C37A, C37D, C37E, C37K, C37N, C37Q, and C37R; and a substitution selected from C99A, C99I, C99V, and C99L.

In some embodiments, the non-natural THCAS comprises C37A and one or more substitutions selected from K36D, K36E, K36R, K40D, K40E, K40R, K101D, K101E, K101R, K102D, K102E, and K102R. In some embodiments, the non-natural THCAS comprises C37D and one or more substitutions selected from K36D, K36E, K36R, K40D, K40E, K40R, K101D, K101E, K101R, K102D, K102E, and K102R. In some embodiments, the non-natural THCAS comprises C37E and one or more substitutions selected from K36D, K36E, K36R, K40D, K40E, K40R, K101D, K101E, K101R, K102D, K102E, and K102R. In some embodiments, the non-natural THCAS comprises C37K and one or more substitutions selected from K36D, K36E, K36R, K40D, K40E, K40R, K101D, K101E, K101R, K102D, K102E, and K102R. In some embodiments, the non-natural THCAS comprises C37N and one or more substitutions selected from K36D, K36E, K36R, K40D, K40E, K40R, K101D, K101E, K101R, K102D, K102E, and K102R. In some embodiments, the non-natural THCAS comprises C37Q and one or more substitutions selected from K36D, K36E, K36R, K40D, K40E, K40R, K101D, K101E, K101R, K102D, K102E, and K102R. In some embodiments, the non-natural THCAS comprises C37R and one or more substitutions selected from K36D, K36E, K36R, K40D, K40E, K40R, K101D, K101E, K101R, K102D, K102E, and K102R.

In some embodiments, the non-natural THCAS comprises: a substitution selected from (a) C37D and C99F; (b) C37H; (c) C37Y; (d) C37Y and C99A; (e) C37Y and C99V; (f) C37E and C99F; (g) C37Y and C99I; (h) C37E; (i) C37K and C99F; (j) C37D; (k) C37D and C99V; (1) C37D and C99A; (m) C37H and C99V; (n) C37E and C99V; (o) C37N and C99A; (p) C37N and C99F; (q) C37E and C99A; (r) C37N and C99V; (s) C37Q and C99I; (t) C37T; (u) C37Y and C99L; (v) C37H and C99L; (w) C99F; (x) C37Q; (y) C37N; (z) C37H and C99A; (aa) C37Y and C99F; (bb) C37K; (cc) C37Q and C99A; (dd) C37R and C99I; (ee) C37A and C99V; (ff) C37A and C99A; (gg) C37A and C99I; (hh) C37A and C99L; (ii) C37Q and C99V; (jj) C37Q and C99L; (kk) C37N and C99I; (ll) C37N and C99L; (mm) C37E and C99I; (nn) C37E and C99L; (oo) C37D and C99I; (pp) C37D and C99L; (qq) C37R and C99V; (rr) C37R and C99A; (ss) C37R and C99L; (tt) C37R; (uu) C37K and C99V; (vv) C37K and C99A; (ww) C37K and C99I; and (xx) C37K and C99L; and one or more substitutions selected from K36D, K36E, K36R, K40D, K40E, K40R, K101D, K101E, K101R, K102D, K102E, and K102R.

In some embodiments, the non-natural THCAS comprises position C37 substituted with D, E, R, or K; position C99 substituted with F; position K36, K40, K102, or a combination thereof independently substituted with D, E, or R; and position K101 unsubstituted or substituted with R, wherein the position corresponds to SEQ ID NO:2. In some embodiments, the non-natural THCAS comprises C37 substituted with D, E, R, or K; C99 substituted with F; and K36 substituted with D, E, or R. In some embodiments, the non-natural THCAS comprises C37 substituted with D, E, R, or K; C99 substituted with F; and K40 substituted with D, E, or R. In some embodiments, the non-natural THCAS comprises C37 substituted with D, E, R, or K; C99 substituted with F; and K102 substituted with D, E, or R. In some embodiments, the non-natural THCAS comprises C37 substituted with D, E, R, or K; C99 substituted with F; and K101 substituted with R. In some embodiments, the non-natural THCAS comprises C37K, K36D, K40E, and K101R. In some embodiments, the amino acid substitutions described herein stabilize the structure of the non-natural THCAS.

In some embodiments, the non-natural THCAS comprises at least one substitution at a position corresponding to SEQ ID NO:2, wherein the substitution is:

(a) K36D, C37K, K40D, C99F, and K101R;

(b) K36D, C37K, K40D, C99F, K101R and K102R;

(c) K36D, C37K, K40E, C99F, and K101R;
(d) K36D, C37K, K40E, C99F, K101R and K102R;
(e) K36R, C37K, K40D, C99F, K101R and K102R;
(f) K36D, C37E, C99F, and K101R;
(g) K36R, C37E, K40E, C99F, K101R, and K102R;
(h) C37E, C99F, K101R, and K102E;
(i) K36E, C37K, K40E, C99F, and K101R;
(j) K36D, C37R, K40D, C99F, K101R, and K102D;
(k) K36D, C37K, K40D, and C99F;
(l) K36R, C37K, K40R, C99F, K101R, and K102E;
(m) K36R, C37E, K40D, C99F, K101R, and K102E;
(n) K36E, C37R, K40D, C99F, and K101R;
(o) K36D, C37R, K40E, C99F, and K101R;
(p) K36D, C37R, K40D, C99F, K101R, and K102R;
(q) K36R, C37R, K40E, C99F, K101R, and K102R;
(r) K36D, C37E, K40D, C99F, K101R, and K102R;
(s) K36D, C37K, K40E, and C99F;
(t) K36D, C37R, K40D, C99F, K101R, and K102E;
(u) K36D, C37E, K40E, C99F, K101R, and K102R;
(v) C37D, C99F, K101R, and K102E;
(w) K36E, C37E, K40E, C99F, K101R, and K102R;
(x) K36R, C37E, C99F, K101R, and K102R;
(y) K36R, C37E, K40D, C99F, K101R, and K102R;
(z) K36D, C37D, C99F, and K102E;
(aa) K36R, C37D, K40D, C99F, K101R, and K102R;
(bb) C37D, C99F, K101R, and K102R;
(cc) K36D, C37D, K40E, C99F, K101R, and K102R;
(dd) K36D, C37D, C99F, K101R, and K102D;
(ee) C37E, K40E, C99F, K101R, and K102E;
(ff) K36R, C37E, K40D, C99F, and K101R;
(gg) K36D, C37D, K40R, C99F, and K101R;
(hh) K36D, C37D, C99F, K101R, and K102E;
(ii) K36D, C37K, C99F, K101R, and K102R; or
(jj) K36E, C37R, K40R, C99F, K101R, and K102E.

In some embodiments, the non-natural THCAS comprises at least one amino acid substitution at position C37, K40, V46, Q58, L59, N89, N90, C99, K102, K296, V321, V358, K366, K513, N516, N528, H544, or a combination thereof, wherein the amino acid position corresponds to SEQ ID NO:2. In some embodiments, the non-natural THCAS comprises at least one amino acid substitution at position C37, C99, and one or more of K40, V46, Q58, L59, N89, N90, K102, K296, V321, V358, K366, K513, N516, N528, and H544, wherein the amino acid position corresponds to SEQ ID NO:2. In some embodiments, the substitution is C37A, K40R, V46E, Q58E, L59T, N89D, N90D, N90T, C99A, K102E, K296E, V321T, V358T, K366D, K513D, N516E, N528T, H544Y, or a combination thereof. In some embodiments, the non-natural THCAS comprises at least one amino acid substitution at position C37, C99, and one or more of K40, L59, N89, N90, K102, K296, V321, and N516, wherein the amino acid position corresponds to SEQ ID NO:2. In some embodiments, the substitution is C37A, K40R, L59T, N89D, N90D, C99A, K102E, K296E, V321T, N516E, or a combination thereof. In some embodiments, the substitution is C37A, K40R, N89D, N90D, C99A, and K102E. In some embodiments, the substitution is C37A, K40R, L59T, N89D, C99A, K102E, and V321T. In some embodiments, the substitution is C37A, K40R, L59T, N89D, C99A, K102E, K296E, V321T, and N516E. In some embodiments, the substitution is C37A, K40R, L59T, N89D, C99A, K102E, and K296E. In some embodiments, the substitution is C37A, K40R, Q58E, L59T, N89D, N90T, C99A, K102E, K296E, V321T, V358T, N516E, and N528T.

In some embodiments, the non-natural THCAS comprises:

1) C37A, K40R, L59T, N89D, C99A, K102E, V321T, K296E and N516E;
2) C37A, K40R, L59T, N89D, C99A, K102E, V321T, V358T and N516E;
3) C37A, K40R, L59T, N89D, C99A, K102E, V321T, N90T and N516E;
4) C37A, K40R, L59T, N89D, C99A, K102E, V321T, K296E and N528T;
5) C37A, K40R, L59T, N89D, C99A, K102E, V321T, K366D and N516E;
6) C37A, K40R, L59T, N89D, C99A, K102E, V321T, K296E and V358T;
7) C37A, K40R, L59T, N89D, C99A, K102E, V321T, N90T and K296E;
8) C37A, K40R, N89D, C99A, K102E, V321T, and N516E;
9) C37A, K40R, L59T, N89D, C99A, K102E, V321T, V358T and N528T;
10) C37A, K40R, L59T, N89D, C99A, K102E, V321T, Q58E and K296E;
11) C37A, K40R, L59T, C99A, K102E, V321T, and K296E;
12) C37A, K40R, L59T, N89D, C99A, K102E, V321T, N90T and N528T;
13) C37A, K40R, L59T, N89D, C99A, K102E, V321T, K366D and N528T;
14) C37A, K40R, L59T, N89D, C99A, K102E, V321T, K513D and N516E;
15) C37A, K40R, L59T, N89D, C99A, K102E, V321T, Q58E and N516E;
16) C37A, K40R, L59T, N89D, C99A, K102E, V321T, Q58E and N90T;
17) C37A, K40R, L59T, N89D, C99A, K102E, V321T, Q58E and N528T;
18) C37A, K40R, L59T, C99A, K102E, V321T, and N516E;
19) C37A, K40R, L59T, N89D, C99A, K102E, V321T, V358T and H544Y;
20) C37A, K40R, L59T, N89D, C99A, K102E, V321T, Q58E and V358T;
21) C37A, K40R, L59T, N89D, C99A, K102E, V321T, V358T and K366D;
22) C37A, K40R, L59T, C99A, K102E, V321T, and N90T;
23) C37A, K40R, L59T, N89D, C99A, K102E, V321T, V46E and K296E;
24) C37A, K40R, L59T, N89D, C99A, K102E, V321T, K296E and H544Y;
25) C37A, K40R, L59T, N89D, C99A, K102E, V321T, V46E and N516E;
26) C37A, L59T, N89D, C99A, K102E, V321T, and N516E;
27) C37A, K40R, L59T, N89D, C99A, K102E, and N516E;
28) C37A, K40R, L59T, C99A, K102E, V321T, and N528T;
29) C37A, K40R, L59T, N89D, C99A, K102E, and K296E;
30) C37A, K40R, L59T, N89D, C99A, K102E, V321T, K296E and K513D;
31) C37A, K40R, N89D, C99A, K102E, V321T, and N528T;
32) C37A, K40R, L59T, N89D, C99A, K102E, V321T, K513D and N528T;
33) C37A, K40R, L59T, N89D, C99A, K102E, V321T, K366D and K513D;

34) C37A, K40R, N89D, C99A, K102E, V321T, and V358T;
35) C37A, K40R, N89D, C99A, K102E, V321T, and K366D;
36) C37A, K40R, L59T, C99A, K102E, V321T, N89S and K296E;
37) C37A, K40R, L59T, N89D, C99A, K102E, and N90T;
38) C37A, K40R, L59T, N89D, C99A, K102E, V321T, Q58E and H544Y;
39) C37A, K40R, N89D, C99A, K102E, V321T, and K296E;
40) C37A, K40R, L59T, N89D, C99A, K102E, V321T, N90T and H544Y;
41) C37A, K40R, L59T, C99A, K102E, V321T, N89S and N516E;
42) C37A, K40R, L59T, N89D, C99A, K102E, and Q58E;
43) C37A, K40R, N89D, C99A, K102E, V321T, and H544Y;
44) C37A, K40R, L59T, N89D, C99A, K102E, V321T, V46E and N90T;
45) C37A, K40R, L59T, N89D, C99A, K102E, V321T, N90T and K366D;
46) C37A, K40R, L59T, N89D, C99A, K102E, V321T, V358T and K513D;
47) C37A, K40R, N89D, C99A, K102E, V321T, and T321V;
48) C37A, L59T, N89D, C99A, K102E, V321T, and K296E;
49) C37A, K40R, L59T, N89D, C99A, K102E, V321T, V46E and K366D;
50) C37A, K40R, L59T, N89D, C99A, K102E, and K366D;
51) C37A, K40R, L59T, N89D, C99A, K102E, V321T, Q58E and K366D;
52) C37A, K40R, L59T, N89D, C99A, K102E, and N528T;
53) C37A, K40R, N89D, C99A, K102E, V321T, and Q58E;
54) C37A, K40R, L59T, N89D, C99A, K102E, V321T, V46E and V358T;
55) K296E; or
56) N516E, wherein the amino acid position corresponds to SEQ ID NO:2.

In some embodiments, the non-natural THCAS comprises an amino acid substitution at C37, K40, L59, N89, C99, K102, K296, and any one of: Q58, N90, V358, N528, and K366, wherein the amino acid position corresponds to SEQ ID NO:2. In some embodiments, the non-natural THCAS comprises C37A, K40E, L59T, N89D, C99A, K102E, K296E, and any one of: Q58E, N90T, V358T, N528T, and K366D, wherein the amino acid position corresponds to SEQ ID NO:2.

In some embodiments, the non-natural THCAS comprises an amino acid substitution at C37, K40, L59, N89, C99, K102, K296, and two substitutions at: (1) Q58 and N90; (2) Q58 and V358; (3) Q58 and N528; (4) Q58 and K366; (5) N90 and N528; (6) N90 and K366; (7) V358 and K366; (8) K366 and N528; or (9) V358 and N528, wherein the amino acid position corresponds to SEQ ID NO:2. In some embodiments, the non-natural THCAS comprises C37A, K40E, L59T, N89D, C99A, K102E, K296E, and two substitutions selected from: (1) Q58E and N90T; (2) Q58E and V358T; (3) Q58E and N528T; (4) Q58E and K366D; (5) N90T and N528T; (6) N90T and K366D; (7) V358T and K366D; (8) K366D and N528T; or (9) V358T and N528T.

In some embodiments, the non-natural THCAS comprises an amino acid substitution at C37, K40, L59, N89, C99, K102, K296, and three substitutions at: (1) Q58, N90, and V358; (2) Q58, N90, and N528; (3) Q58, V358, and N528; (4) N90, V358, and N528; or (5) V358, K366, and N528, wherein the amino acid position corresponds to SEQ ID NO:2. In some embodiments, the non-natural THCAS comprises C37A, K40E, L59T, N89D, C99A, K102E, K296E, and three substitutions selected from: (1) Q58E, N90T, and V358T; (2) Q58E, N90T, and N528T; (3) Q58E, V358T, and N528T; (4) N90T, V358T, and N528T; or (5) V358T, K366D, and N528T, wherein the amino acid position corresponds to SEQ ID NO:2.

In some embodiments, the non-natural THCAS comprises an amino acid substitution at C37, K40, L59, N89, C99, K102, K296, and four substitutions at: (1) Q58, V358, K366, and N528; (2) Q58, N90, K366, and N528; or (3) N90, V358, K366, and N528, wherein the amino acid position corresponds to SEQ ID NO:2. In some embodiments, the non-natural THCAS comprises C37A, K40E, L59T, N89D, C99A, K102E, K296E, and four substitutions selected from: (1) Q58E, V358T, K366D, and N528T; (2) Q58E, N90T, K366D, and N528T; or (3) N90T, V358T, K366D, and N528T, wherein the amino acid position corresponds to SEQ ID NO:2.

In some embodiments, the non-natural THCAS comprises SEQ ID NO:86 and further comprises an amino acid substitution selected from:

1) K296E and N516E;
2) V358T and N516E;
3) N90T and N516E;
4) K296E and N528T;
5) K366D and N516E;
6) K296E and V358T;
7) N90T and K296E;
8) T59L and N516E;
9) V358T and N528T;
10) Q58E and K296E;
11) D89N and K296E;
12) N90T and N528T;
13) K366D and N528T;
14) K513D and N516E;
15) Q58E and N516E;
16) Q58E and N90T;
17) Q58E and N528T;
18) D89N and N516E;
19) V358T and H544Y;
20) Q58E and V358T;
21) V358T and K366D;
22) D89N and N90T;
23) V46E and K296E;
24) K296E and H544Y;
25) V46E and N516E;
26) R40K and N516E;
27) T321V and N516E;
28) D89N and N528T;
29) K296E and T321V;
30) K296E and K513D;
31) T59L and N528T;
32) K513D and N528T;
33) K366D and K513D;
34) T59L and V358T;
35) T59L and K366D;
36) D89S and K296E;
37) N90T and T321V;

38) Q58E and H544Y;
39) T59L and K296E;
40) N90T and H544Y;
41) D89S and N516E;
42) Q58E and T321V;
43) T59L and H544Y;
44) V46E and N90T;
45) N90T and K366D;
46) V358T and K513D;
47) T59L and T321V;
48) R40K and K296E;
49) V46E and K366D;
50) T321V and K366D;
51) Q58E and K366D;
52) T321V and N528T;
53) Q58E and T59L;
54) V46E and V358T;
55) K296E; or
56) N516E, wherein the amino acid position corresponds to SEQ ID NO:86.

In some embodiments, the non-natural THCAS comprises SEQ ID NO:88 and further comprises an amino acid substitution at position Q58, N90, V358, N528, K366, or a combination thereof, wherein the amino acid position corresponds to SEQ ID NO:88. In some embodiments, the non-natural THCAS comprises SEQ ID NO:88 and further comprises an amino acid substitution selected from Q58E, N90T, V358T, N528T, K366D, or a combination thereof, wherein the amino acid position corresponds to SEQ ID NO:88.

In some embodiments, the non-natural THCAS comprises SEQ ID NO:88 and further comprises two amino acid substitutions at positions: (1) Q58 and N90; (2) Q58 and V358; (3) Q58 and N528; (4) Q58 and K366; (5) N90 and N528; (6) N90 and K366; (7) V358 and K366; (8) K366 and N528; or (9) V358 and N528, wherein the amino acid position corresponds to SEQ ID NO:88. In some embodiments, the non-natural THCAS comprises SEQ ID NO:88 and further comprises two amino acid substitutions selected from: (1) Q58E and N90T; (2) Q58E and V358T; (3) Q58E and N528T; (4) Q58E and K366D; (5) N90T and N528T; (6) N90T and K366D; (7) V358T and K366D; (8) K366D and N528T; or (9) V358T and N528T, wherein the amino acid position corresponds to SEQ ID NO:88.

In some embodiments, the non-natural THCAS comprises SEQ ID NO:88 and further comprises three amino acid substitution at positions: (1) Q58, N90, and V358; (2) Q58, N90, and N528; (3) Q58, V358, and N528; (4) N90, V358, and N528; or (5) V358, K366, and N528, wherein the amino acid position corresponds to SEQ ID NO:88. In some embodiments, the non-natural THCAS comprises SEQ ID NO:88 and further comprises three amino acid substitutions selected from: (1) Q58E, N90T, and V358T; (2) Q58E, N90T, and N528T; (3) Q58E, V358T, and N528T; (4) N90T, V358T, and N528T; or (5) V358T, K366D, and N528T, wherein the amino acid position corresponds to SEQ ID NO:88.

In some embodiments, the non-natural THCAS comprises SEQ ID NO:88 and further comprises four amino acid substitutions at positions: (1) Q58, V358, K366, and N528; (2) Q58, N90, K366, and N528; or (3) N90, V358, K366, and N528, wherein the amino acid position corresponds to SEQ ID NO:88. In some embodiments, the non-natural THCAS comprises SEQ ID NO:88 and further comprises four amino acid substitutions selected from: (1) Q58E, V358T, K366D, and N528T; (2) Q58E, N90T, K366D, and N528T; or (3) N90T, V358T, K366D, and N528T, wherein the amino acid position corresponds to SEQ ID NO:88.

In some embodiments, the non-natural THCAS comprises the amino acid substitutions C37A, K40R, N89D, N90D, C99A, and K102E, wherein the amino acid position corresponds to SEQ ID NO:2. In some embodiments, the non-natural THCAS comprises the amino acid substitutions C37A, K40R, L59T, N89D, C99A, K102E, and V321T, wherein the amino acid position corresponds to SEQ ID NO:2. In some embodiments, the non-natural THCAS comprises the amino acid substitutions C37A, K40R, L59T, N89D, C99A, K102E, K296E, V321T, and N516E, wherein the amino acid position corresponds to SEQ ID NO:2. In some embodiments, the non-natural THCAS comprises the amino acid substitutions C37A, K40R, L59T, N89D, C99A, K102E, and K296E, wherein the amino acid position corresponds to SEQ ID NO:2.

In some embodiments, the non-natural THCAS comprises C37A, K40R, Q58E, L59T, N89D, N90T, C99A, K102E, K296E, V321T, V358T, N516E, and N528T, wherein the amino acid position corresponds to SEQ ID NO:2. In some embodiments, the non-natural THCAS comprises:

1) C37A, K40R, Q58E, L59T, N89D, N90T, C99A, K102E, K296E, V321T, V358T, K366D, N516E, and N528T;
2) C37A, K40R, Q58E, N89D, N90T, C99A, K102E, K296E, V321T, V358T, N516E, and N528T;
3) C37A, K40R, Q58E, L59T, N89D, N90T, C99A, K102E, K296E, V321T, V358T, K366D, and N516E;
4) C37A, K40R, Q58E, N90T, C99A, K102E, K296E, V321T, V358T, N516E, and N528T;
5) C37A, K40R, Q58E, N89D, N90T, C99A, K102E, K296E, V321T, V358T, K366D, N516E, and N528T; or
6) C37A, K40R, Q58E, L59T, N90T, C99A, K102E, K296E, V321T, V358T, K366D, N516E, and N528T, wherein the amino acid position corresponds to SEQ ID NO:2.

In some embodiments, the at least one amino acid variation is not within an active site of the non-natural THCAS. As described herein, "active site" refers to a region in an enzyme that may be important for catalysis, substrate binding, and/or cofactor binding. In some embodiments, the active site of a natural or non-natural THCAS comprises amino acid residues involved in CBGA binding, FAD binding, and/or cyclization of CBGA. In some embodiments, the active site of the non-natural THCAS comprises amino acid residues involved in FAD binding. In some embodiments, the active site of the non-natural THCAS comprises amino acid residues involved in FAD binding. In some embodiments, the active site of the non-natural THCAS comprises amino acid residues Q69, R108, T109, R110, S111, G112, G113, H114, D115, A116, M119, S120, Y121, L132, A151, G174, Y175, C176, T178, V179, G180, V181, G182, G183, H184, S186, G189, Y190, G235, E236, G239, I240, I241, A242, F381, W444, Y481, N483, Y484, R485, N533, A116, G174, Y175, M290, H292, G376, T379, F381, I383, L385, G410, M413, V415, Y417, E442, W444, T446, S448, E450, Y481, L482, N483, Y484, or a combination thereof (amino acid residue numbering with respect to SEQ ID NO:2). In some embodiments, the active site of the non-natural THCAS is within positions 60-75, 105-125, 160-200, 220-250, 280-300, 350-450, 470-490, or 530-540, inclusive, of the THCAS, wherein the position corresponds to SEQ ID NO:2.

In some embodiments, the non-natural THCAS further comprises an affinity tag, a purification tag, a solubility tag, or a combination thereof. For example, at least 1, at least 2, at least 3, at least 4, at least 5, or at least 6 histidine residues can be appended to the C-terminus of the non-natural THCAS of any of SEQ ID NOs:1, 2, 82, or 85-88 to provide a 6×His tag (SEQ ID NO: 89) for affinity purification by Ni-NTA. Affinity tags, purification tags, and solubility tags, and method of tagging proteins are known to one of ordinary skill in the art and described, e.g., in Kimple et al. (2013), Curr Protoc Protein Sci 73: Unit-9.9.

In some embodiments, the non-natural THCAS described herein is capable of catalyzing the oxidative cyclization of CBGA to THCA. In some embodiments, the non-natural THCAS described herein has substantially the same catalytic activity as a wild-type THCAS. In some embodiments, the non-natural THCAS described herein has at least about 70%, at least about 75%, at least about 80%, at least about 85%, at least about 90%, at least about 95%, at least or about 99%, or at least about 100% of the catalytic activity of a wild-type THCAS produced from its native host organism. In some embodiments, the non-natural THCAS catalyzes the oxidative cyclization of CBGA to THCA at pH greater than about 3.5 and less than pH about 6.5, less than about 6.0, less than about 5.5, less than about 5.0, less than about 4.5, or less than about 4.0. In some embodiments, the non-natural THCAS catalyzes the oxidative cyclization of CBGA to THCA at about pH 4.0 to about pH 6.0. In some embodiments, the non-natural THCAS catalyzes the oxidative cyclization of CBGA to THCA at about pH 4.0, about pH 4.1, about pH 4.2, about pH 4.3, about pH 4.4, about pH 4.5, about pH 4.6, about pH 4.7, about pH 4.8, about pH 4.9, about pH 5.0, about pH 5.1, about pH 5.2, about pH 5.3, about pH 5.4, about pH 5.5, about pH 5.6, about pH 5.7, about pH 5.8, about pH 5.9, or about 6.0.

In some embodiments, the non-natural THCAS described herein further catalyzes the oxidative cyclization of CBGA into cannabidiolic acid (CBDA), cannabichromenic acid (CBCA), or both. As described herein, cannabinoid synthases such as THCAS are capable of producing more than one cannabinoid. In some embodiments, the non-natural THCAS is capable of catalyzing the oxidative cyclization of CBGA to CBDA. In some embodiments, the non-natural THCAS is capable of catalyzing the oxidative cyclization of CBGA into CBCA. In some embodiments, the non-natural THCAS catalyzes the oxidative cyclization of CBGA into CBCA at pH less than 8.0 and greater than about 6.5, greater than about 7.0, or greater than about 7.5. In some embodiments, the non-natural THCAS catalyzes the oxidative cyclization of CBGA to CBCA at about pH 6.5 to about pH 8.0. In some embodiments, the non-natural THCAS catalyzes the oxidative cyclization of CBGA to CBCA at about pH about pH 6.5, about pH 6.6, about pH 6.7, about pH 6.8, about pH 6.9, about pH 7.0, about pH 7.1, about pH 7.2, about pH 7.3, about pH 7.4, about pH 7.5, about pH 7.6, about pH 7.7, about pH 7.8, about pH 7.9, or about pH 8.0.

In some embodiments, the invention further provides a nucleic acid encoding the non-natural THCAS described herein. In some embodiments, the nucleic acid comprises a polynucleotide sequence with at least 70%, at least 75%, at least 80%, at least 85%, at least 90%, at least 95%, at least 96%, at least 97%, at least 98%, at least 99%, or 100% sequence identity to SEQ ID NO:36. In some embodiments, the nucleic acid encoding the non-natural THCAS is 100% identical to SEQ ID NO:36.

In some embodiments, the nucleic acid encoding the non-natural THCAS is codon optimized. An example of a codon optimized sequence is, in one instance, a sequence optimized for expression in a bacterial host cell, e.g., *E. coli.* In some embodiments, one or more codons (e.g., about or more than about 1, 2, 3, 4, 5, 10, 15, 20, 25, 50, or all codons) in a nucleic acid sequence encoding the non-natural THCAS described herein corresponds to the most frequently used codon for a particular amino acid in the bacterial host cell.

In some embodiments, the invention provides an expression construct comprising the nucleic acid encoding the non-natural THCAS described herein. Expression constructs are described herein. In some embodiments, the expression construct comprises the nucleic acid encoding the non-natural THCAS operably linked to a regulatory element. In some embodiments, the regulatory element is a bacterial regulatory element. Non-limiting examples of expression vectors are provided herein and include, e.g., pQE vectors (Qiagen), pBluescript plasmids, pNH vectors, lambda-ZAP vectors (Stratagene); pTrc99a, pKK223-3, pDR540, and pRIT2T (Pharmacia).

In some embodiments, the invention provides an engineered cell comprising the non-natural THCAS described herein, the nucleic acid encoding the non-natural THCAS, the expression construct comprising the nucleic acid, or a combination thereof. In some embodiments, the invention provides a method of making an isolated non-natural THCAS comprising isolating THCAS expressed in the engineered cell provided herein. In some embodiments, the invention provides an isolated THCAS, wherein the isolated THCAS is expressed and isolated from the engineered cell.

III. CBDAS Variants

Cannabidiolic acid synthase (CBDAS) is an enzyme found in *Cannabis sativa* (*C. sativa*) that catalyzes the oxidative cyclization of cannabigerolic acid (CBGA) to cannabidiolic acid (CBDA) utilizing a FAD cofactor.

The protein structure of CBDAS is predicted to be highly similar to that of THCAS, as described herein. FIG. 11 shows a sequence alignment between THCAS and CBDAS. CBDAS likely comprises two domains, Domain I and Domain II. CBDAS is also predicted to have a FAD-binding domain comprising amino acids H69, R108, T109, R110, S111, G112, G113, H114, D115, S116, M11, S120, Y121, L132, A151, G174, Y175, C176, T178, V179, C180, A181, G182, G183, H184, G189, Y190, A235, E236, G239, I240, I241, V242, F380, W443, Y480, N482, Y483, and N532 (amino acid residue numbering with respect to SEQ ID NO:79).

CBDAS further comprises a CBGA binding domain. The following amino acid residues may be involved in CBGA binding: S116, G174, Y175, M291, H293, G377, G380, F382, K384, L386, G411, M414, A416, Y418, E443, W445, I447, S449, E45I, Y482, L483, N484, and Y485 (amino acid residue numbering with respect to SEQ ID NO:79).

Domain I of CBDAS can likely be further divided into subdomains Ia and Ib, similar to THCAS. Based on structural alignments, subdomain Ia likely includes the region from amino acid residue positions 28 to 134 and comprises three α-helices, αA, αB, and αC which surround three β-strands (β1-β3) (amino acid residue numbering with respect to SEQ ID NO:79). As used herein, αA of CBDAS includes the amino acid residues Asn29 to Ile42; αB includes the amino acid residues Leu59 to Thr67; and αC include the amino acid residues His89 to Gly 104. A disulfide bond likely is present between Cys37 in αA and Cys99 in αC of wild-type CBDAS. Subdomain IIb of CBDAS likely includes the region from residue positions 135 to 252 and from 475 to 544 and likely comprises five β-strands (β4-β8) surrounding five α-helices (αD-αF, αM, and αN). Domain II likely includes the region from positions 253 to 474 and likely comprises eight β strands (β9-β16) surrounding six α-helices (αG-αL).

In some examples, the present disclosure provides non-naturally occurring cannabidiolic acid synthase (CBDAS) that does not comprise a disulfide bond between alpha helix αA and alpha helix αC, wherein the non-natural CBDAS catalyzes the oxidative cyclization of cannabigerolic acid (CBGA) into cannabidiolic acid (CBDA) (see, e.g., FIGS. 4 and 9).

In some embodiments, the invention provides a non-natural CBDAS with 80% or greater identity to SEQ ID NOs:78, 79, or 83, comprising at least one amino acid variation as compared to a wild type CBDAS, comprising three alpha helices (αA, αB, and αC) and wherein a disulfide bond is not formed between alpha helix αA and alpha helix αC, wherein the non-natural CBDAS catalyzes the oxidative cyclization of cannabigerolic acid (CBGA) into cannabidiolic acid (CBDA). In some embodiments, the invention provides a non-natural CBDAS with 90% or greater identity to SEQ ID NOs:78, 79, or 83, comprising at least one amino acid variation as compared to a wild type CBDAS, comprising three alpha helices (αA, αB, and αC) and wherein a disulfide bond is not formed between alpha helix αA and alpha helix αC, wherein the non-natural CBDAS catalyzes the oxidative cyclization of cannabigerolic acid (CBGA) into cannabidiolic acid (CBDA). In some embodiments, the invention provides a non-natural CBDAS with 95% or greater identity to SEQ ID NOs:78, 79, or 83, comprising at least one amino acid variation as compared to a wild type CBDAS, comprising three alpha helices (αA, αB, and αC) and wherein a disulfide bond is not formed between alpha helix αA and alpha helix αC, wherein the non-natural CBDAS catalyzes the oxidative cyclization of cannabigerolic acid (CBGA) into cannabidiolic acid (CBDA).

The non-natural CBDAS described herein is capable of catalyzing the conversion of CBGA to CBDA. In some embodiments, the non-natural CBDAS is capable of catalyzing at least one step of the conversion of CBGA to CBDA. In some embodiments, the non-natural CBDAS has substantially the same amount of activity as wild-type CBDAS. In some embodiments, the non-natural CBDAS with substantially the same amount of activity as wild-type CBDAS, has greater than or about 80%, greater than or about 85%, greater than or about 90%, greater than or about 95%, greater than or about 99%, or about 100% the enzymatic activity of wild-type CBDAS. In some embodiments, the non-natural CBDAS has greater than or about 80%, greater than or about 85%, greater than or about 90%, greater than or about 95%, greater than or about 99%, or about 100% the enzymatic activity of wild-type CBDAS. Encompassed within the definition of "non-natural CBDAS" are fragments, truncations, variants, and fusions that are capable of catalyzing the conversion of CBGA to CBDA.

In some embodiments, the non-natural CBDAS has at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to at least about 25, 50, 75, 100, 125, 150, 200, 250, 300, 350, 400, 450, 500, or more contiguous amino acids of a natural, i.e., wild-type, CBDAS and having a cannabinoid synthase activity. In some embodiments, the non-natural CBDAS comprises the FAD binding domain (Pfam: PF01565) and a CBGA binding domain.

In some embodiments, the non-natural CBDAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a natural, i.e., wild-type, CBDAS. The term natural CBDAS can refer to any known CBDAS sequence. For example, a wild-type CBDAS sequence can include, but is not limited to, a CBDAS sequence from various *Cannabis sativa* plants, as provided in Taura et al. *J. Biol. Chem* 271: 17411-17416 (1996); Taura et al., *FEBS Lett* 581(16): 2929-2934 (2007); and Allen et al., *J. Forensic Investigation* 4(1): 7 (2016).

In some embodiments, the non-natural CBDAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:78. SEQ ID NO:78 discloses a truncated CBDAS as compared to wild-type CBDAS (SEQ ID NO:79). SEQ ID NO:78 does not comprise an N-terminal leader sequence present in wild-type CBDAS. SEQ ID NO:78 does not comprise an N-terminal methionine. In some embodiments, removal of the leader sequence increases expression of the polypeptide of SEQ ID NO:78 in a host organism, e.g., a bacterial organism such as *E. coli*. In some embodiments, the N-terminal methionine that is typically present at the start of an expressed polypeptide sequence, e.g., the polypeptide of SEQ ID NO:83, is removed by the host organism, e.g., a bacterial organism such as *E. coli.*

In some embodiments, the non-natural CBDAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:79. In some embodiments, SEQ ID NO:79 describes a wild-type CBDAS. In some embodiments, wild-type CBDAS comprises a leader sequence.

In some embodiments, the non-natural CBDAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:83. SEQ ID NO:83 discloses a truncated CBDAS as compared to wild-type CBDAS (SEQ ID NO:79). SEQ ID NO:83 comprises an N-terminal methionine. SEQ ID NO:83 does not comprise an N-terminal leader sequence present in wild-type CBDAS. In some embodiments, removal of the leader sequence increases expression of the polypeptide of SEQ ID NO:83 in a host organism, e.g., a bacterial organism such as *E. coli.*

As used throughout this application, all amino acid positions of the non-natural CBDAS described herein are numbered with reference to SEQ ID NO:79, unless otherwise defined. One of skill in the art would understand that alignment methods can be used to determine the appropriate amino acid position number that corresponds to the position referenced in SEQ ID NO:79. As described herein, an amino acid sequence alignment of SEQ ID NOs:1, 2, and 78-84 is shown in FIGS. 11A-11C. Select amino acids and their corresponding positions in each of SEQ ID NOs:1, 2, and 78-84 are also shown in Table A herein. For example, the first amino acid of SEQ ID NO:78 corresponds to the 28$^{th}$ amino acid of SEQ ID NO:79, and thus, the amino acid position of "C37" in SEQ ID NO:79, corresponds to "C10" in SEQ ID NO:78; the amino acid position of "C99" in SEQ ID NO:79, corresponds to "C72" in SEQ ID NO:78, and so on. The first amino acid of SEQ ID NO:83 corresponds to the $27^{th}$ amino acid of SEQ ID NO:79, and thus, the amino acid position of "C37" in SEQ ID NO:79, corresponds to "C11" in SEQ ID NO:78; the amino acid position of "C99" in SEQ ID NO:79, corresponds to "C73" in SEQ ID NO:78, and so on.

TABLE A

| SEQ ID NO | CORRESPONDING AMINO ACID POSITIONS | | | | | |
|---|---|---|---|---|---|---|
| SEQ1 | K10 | C11 | K14 | C73 | K75 | K76 |
| SEQ2 | K36 | C37 | K40 | C99 | K101 | K102 |
| SEQ78 | K9 | C10 | Q13 | C72 | K74 | K75 |
| SEQ79 | K36 | C37 | Q40 | C99 | K101 | K102 |
| SEQ80 | K9 | C10 | E13 | C72 | K74 | K75 |
| SEQ81 | K36 | C37 | E40 | C99 | K101 | K102 |
| SEQ82 | K9 | C10 | K13 | C72 | K74 | K75 |
| SEQ83 | K10 | C11 | Q14 | C73 | K75 | K76 |
| SEQ84 | K10 | C11 | E14 | C73 | K75 | K76 |

As described herein, a "non-natural" protein or polypeptide refers to a protein or polypeptide sequence having at least one variation at an amino acid position as compared to a wild-type polypeptide or nucleic acid sequence. In some embodiments, the non-natural CBDAS has at least one variation at an amino acid position as compared to a wild-type CBDAS.

In some embodiments, the non-natural CBDAS comprises three alpha helices, αA, αB, and αC, as described for wild-type CBDAS, i.e., αA includes the amino acid residues Asn29 to Ile42; αB includes the amino acid residues Leu59 to Thr67; and αC includes the amino acid residues His89 to Gly 104 (amino acid residue numbering with respect to SEQ ID NO:79). In some embodiments, the non-natural CBDAS does not comprise a disulfide bond between αA and αC present in wild-type CBDAS. In some embodiments, the at least one amino acid variation in the non-natural CBDAS disrupts the disulfide bond between αA and αC in wild-type CBDAS. Disulfide bonds are described herein. As seen from the sequence alignment between THCAS and CBDAS in FIG. 11, the positively-charged amino acid residues present in THCAS in αA and αC are also present in CBDAS. Thus, a disulfide bond between C37 of αA and C99 of αC would likely hold the two alpha helices together and overcome repulsion between the positive charges.

In some embodiments, the disulfide bond between αA and αC stabilizes the tertiary structure of wild-type CBDAS. As described herein, proteins comprising disulfide bonds, e.g., endogenous to plants, can be unstable in bacterial host cells as the disulfide bonds are often disrupted due to the reducing environment in the bacterial cells. In some embodiments, wild-type CBDAS comprising a disulfide bond between αA and αC is substantially unstable in a bacterial cell, e.g., an *E. coli* cell. As used herein, "unstable" CBDAS can refer to CBDAS polypeptides that are non-functional, denatured, and/or degraded rapidly, resulting in CBDAS activity that is greatly reduced relative to the activity found in its native host cell, e.g., *C. sativa* plants. In some embodiments, the CBDAS activity is 50% less, 60% less, 70% less, 80% less, or 90% less than the expected activity from the activity found in the native host cell, based on the expression parameters such as, e.g., vector, culture medium, induction agent, temperature, and/or time; "substantially unstable" CBDAS can also mean less than 70%, less than 60%, less than 50%, less than 40%, less than 30%, less than 20%, less than 10%, less than 5%, or less than 1% of the total amount of CBDAS isolated from the host cell is soluble.

In some embodiments, the non-natural CBDAS described herein does not comprise the disulfide bond between αA and αC and has a substantially similar tertiary structure as wild-type CBDAS. In some embodiments, the non-natural CBDAS that does not comprise the disulfide bond between αA and αC has a substantially identical tertiary structure as wild-type CBDAS comprising the disulfide bond between αA and αC. Methods of determining structural similarity between two proteins are described herein and includes, e.g., TM-scoring. In some embodiments, the TM-score for the non-natural CBDAS that does not comprise the disulfide bond between αA and αC and the wild-type CBDAS comprising the disulfide bond between αA and αC is greater than about 0.5, greater than about 0.6, greater than about 0.7, greater than about 0.8, greater than about 0.9, or about 1.0.

In some embodiments, the non-natural CBDAS comprises one or more amino acid variations to keep αA and αC in proximity comparable to the distance of a disulfide bond. In some embodiments, αA and αC in the non-natural CBDAS are 1 to about 5 Å, about 1.5 to about 4.5 Å, about 2 to about 4 Å, or about 2.5 to about 3.5 Å from one another at their closest amino acid residues. In some embodiments, the non-natural CBDAS comprises one or more amino acid variations that removes a hydrophobic residue or replaces the hydrophobic residue with a neutral or hydrophilic residue in αA and/or αC. Examples of hydrophobic, neutral, and hydrophilic residues are described herein. In some embodiments, reducing the number of hydrophobic residues in αA and/or αC, reduces the repulsion between αA and αC. In some embodiments, the non-natural CBDAS comprises one or more amino acid variations to overcome the repulsion between the positive charges in αA and αC. In some embodiments, the non-natural CBDAS that does not comprise the disulfide bond between αA and αC comprises at least one salt bridge between αA and αC. Salt bridges are further described herein. In addition to salt bridges, van der Waals interaction can also contribute to the stability of a protein structure, e.g., between two α-helices. Van der Waals interactions are further described herein.

In some embodiments, the at least one amino acid variation in the non-natural CBDAS is a substitution of one or more cysteines forming the disulfide bond between αA and αC in wild-type CBDAS, thereby disrupting the disulfide bond. In some embodiments, the at least one amino acid variation in the non-natural CBDAS is a deletion of one or more cysteines forming the disulfide bond between αA and αC in wild-type CBDAS, thereby disrupting the disulfide bond. In some embodiments, the at least one amino acid variation in the non-natural CBDAS is an insertion near one or more cysteines forming the disulfide bond between αA and αC in wild-type CBDAS, thereby disrupting the disulfide bond. In some embodiments, the at least one amino acid variation in the non-natural CBDAS replaces the disulfide bond between αA and αC of wild-type CBDAS with a salt bridge. In some embodiments, the non-natural CBDAS comprising a salt bridge and no disulfide bond between αA and αC has improved expression, e.g., improved yield and/or solubility, in a bacterial cell (e.g., *E. coli*), compared with the expression of a CBDAS comprising a disulfide bond between αA and αC.

In some embodiments, the non-natural CBDAS comprises 1 to 100, 1 to 90, 1 to 80, 1 to 70, 1 to 60, 1 to 50, 1 to 40, 1 to 30, 1 to 25, 1 to 20, 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, or 19 to 20 amino acid variations as compared to a wild-type CBDAS. In some embodiments, the non-natural CBDAS comprises about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, or about 100 amino acid variations as compared to a wild-type CBDAS.

In some embodiments, the amino acid variation in the non-natural CBDAS is in αA, αC, or both. In some embodiments, the amino acid variation is at position C37, C99, K36, Q40, K101, K102, or a combination thereof, wherein the position corresponds to SEQ ID NO:79. In some embodiments, the amino acid variation is at position C37, C99, or both, wherein the amino acid position corresponds to SEQ ID NO:79.

In some embodiments, the amino acid variation in the non-natural CBDAS is an amino acid substitution, deletion, or insertion. In some embodiments, the variation is a substitution of one or more amino acids in a wild-type CBDAS polypeptide sequence. In some embodiments, the variation is a deletion of one or more amino acids in a wild-type CBDAS polypeptide sequence. In some embodiments, the variation is an insertion of one or more amino acids in a wild-type CBDAS polypeptide sequence.

In some embodiments, the disulfide bond which occurs in wild-type CBDAS can be disrupted by the insertion of one or more amino acids. In some embodiments, the insertion of one or more amino acids results in formation of a salt bridge. In some embodiments, the variation is an insertion of 1 to 20, 1 to 15, 1 to 10, 1 to 9, 1 to 8, 1 to 7, 1 to 6, 1 to 5, 1 to 4, 1 to 3, or 1 to 2 amino acids. In some embodiments, the variation is an insertion of about 1, about 2, about 3, about 4, about 5, about 6, about 7, about 8, about 9, about 10, about 11, about 12, about 13, about 14, about 15, about 16, about 17, about 18, about 19, or about 20 amino acids. In some embodiments, the insertion is positioned within about 20 amino acids of C37 or C99. It will be understood that when referring to amino acid positions herein, "within" n number of amino acids expressly specifically includes n and all numbers between 0 and n. For example, an insertion position within 10 amino acids of X means that the insertion is 1, 2, 3, 4, 5, 6, 7, 8, 9, or 10 amino acids from the specified position X. In some embodiments, the insertion is positioned within about 10, within about 9, within about 8, within about 7, within about 6, within about 5, within about 4, within about 3, within about 2, or within about 1 amino acids of C37. In some embodiments, the insertion is within about 10, within about 9, within about 8, within about 7, within about 6, within about 5, within about 4, within about 3, within about 2, or within about 1 amino acids of C99. In some embodiments, the insertion is sufficient to disrupt the disulfide bond between αA and αC.

In some embodiments, the disulfide bond which occurs in wild-type CBDAS can be disrupted by the deletion of one or more amino acids. In some embodiments, the deletion of one or more amino acids results in formation of a salt bridge. In some embodiments, the variation is a deletion of 1 to 20, 1 to 15, 1 to 10, 1 to 9, 1 to 8, 1 to 7, 1 to 6, 1 to 5, 1 to 4, 1 to 3, or 1 to 2 amino acids. In some embodiments, the variation is an deletion of about 1, about 2, about 3, about 4, about 5, about 6, about 7, about 8, about 9, about 10, about 11, about 12, about 13, about 14, about 15, about 16, about 17, about 18, about 19, or about 20 amino acids. In some embodiments, the deletion is within about 20 amino acids of C37 or C99. In some embodiments, the deletion is within about 10, within about 9, within about 8, within about 7, within about 6, within about 5, within about 4, within about 3, within about 2, or within about 1 amino acids of C37. In some embodiments, the deletion is within about 10, within about 9, within about 8, within about 7, within about 6, within about 5, within about 4, within about 3, within about 2, or within about 1 amino acids of C99. In some embodiments, the deletion is sufficient to disrupt the disulfide bond between C37 of αA and C99 of αC.

In some embodiments, the disulfide bond which occurs in wild-type CBDAS can be disrupted on the substitution of one or more amino acids. In some embodiments, the substitution of one or more amino acids results in formation of a salt bridge. In some embodiments, the variation is a substitution. In some embodiments, the non-natural CBDAS comprises 1 to 50, 1 to 40, 1 to 30, 1 to 25, 1 to 20, 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, or 19 to 20 amino acid substitutions as compared to a wild-type CBDAS. In some embodiments, the non-natural CBDAS comprises about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, or about 50 amino acid substitutions as compared to a wild-type CBDAS.

In some embodiments, the non-natural CBDAS comprises an amino acid substitution at position C37, C99, K36, Q40, K101, K102, or any combination thereof, wherein the position corresponds to SEQ ID NO:79.

In some embodiments, the non-natural CBDAS comprises a substitution at position C37, wherein the position corresponds to SEQ ID NO:79. In some embodiments, the substitution is selected from position C37A, C37D, C37H, C37Y, C37E, C37K, C37N, C37Q, C37T and C37R, wherein the position corresponds to SEQ ID NO:79. In some embodiments, the substitution is selected from position C37A, C37D, C37E, C37K, C37N, C37Q, and C37R, wherein the position corresponds to SEQ ID NO:79.

In some embodiments, the non-natural CBDAS comprises a substitution at position C99, wherein the position corresponds to SEQ ID NO:79. In some embodiments, the substitution is selected from position C99F, C99A, C99I, C99V, and C99L, wherein the position corresponds to SEQ ID NO:79. In some embodiments, the substitution is selected from position C99A, C99I, C99V, and C99L, wherein the position corresponds to SEQ ID NO:79.

In some embodiments, the non-natural CBDAS comprises a substitution at C37 and a substitution at C99. In some embodiments, the non-natural CBDAS comprises a substitution selected from C37A, C37D, C37H, C37Y, C37E, C37K, C37N, C37Q, C37T and C37R and a substitution selected from C99A, C99I, C99V, C99L, and C99F. In some embodiments, the non-natural CBDAS comprises a substitution selected from C37A, C37D, C37E, C37K, C37N, C37Q, and C37R and a substitution selected from C99A, C99I, C99V, and C99L.

In some embodiments, the non-natural CBDAS comprises C37A and a substitution selected from C99F, C99A, C99I, C99V, and C99L. In some embodiments, the non-natural CBDAS comprises C37D and a substitution selected from C99F, C99A, C99I, C99V, and C99L. In some embodiments, the non-natural CBDAS comprises C37H and a substitution selected from C99F, C99A, C99I, C99V, and C99L. In some embodiments, the non-natural CBDAS comprises C37Y and a substitution selected from C99F, C99A, C99I, C99V, and C99L. In some embodiments, the non-natural CBDAS comprises C37E and a substitution selected from C99F, C99A, C99I, C99V, and C99L. In some embodiments, the non-natural CBDAS comprises C37K and a substitution selected from C99F, C99A, C99I, C99V, and C99L. In some embodiments, the non-natural CBDAS comprises C37N and a substitution selected from C99F, C99A, C99I, C99V, and C99L. In some embodiments, the non-natural CBDAS comprises C37Q and a substitution selected from C99F, C99A, C99I, C99V, and C99L. In some embodiments, the non-natural CBDAS comprises C37T and a substitution selected from C99F, C99A, C99I, C99V, and C99L. In some embodiments, the non-natural CBDAS comprises C37R and a substitution selected from C99F, C99A, C99I, C99V, and C99L.

In some embodiments, the non-natural CBDAS comprises C37A and a substitution selected from C99A, C99I, C99V, and C99L. In some embodiments, the non-natural CBDAS comprises C37D and a substitution selected from C99A, C99I, C99V, and C99L. In some embodiments, the non-natural CBDAS comprises C37E and a substitution selected from C99A, C99I, C99V, and C99L. In some embodiments, the non-natural CBDAS comprises C37K and a substitution selected from C99A, C99I, C99V, and C99L. In some embodiments, the non-natural CBDAS comprises C37N and a substitution selected from C99A, C99I, C99V, and C99L. In some embodiments, the non-natural CBDAS comprises C37Q and a substitution selected from C99A, C99I, C99V, and C99L. In some embodiments, the non-natural CBDAS comprises C37R and a substitution selected from C99A, C99I, C99V, and C99L. In some embodiments, the amino acid substitutions described herein stabilize the structure of the non-natural CBDAS.

In some embodiments, the non-natural CBDAS comprises C37D. In some embodiments, the non-natural CBDAS comprises C99F. In some embodiments, the non-natural CBDAS comprises C37D and a substitution selected from C99F, C99V, C99A, C99I, and C99L. In some embodiments, the non-natural CBDAS comprises C37Y. In some embodiments, the non-natural CBDAS comprises C37Y and a substitution selected from C99A, C99I, C99V, C99L, and C99F. In some embodiments, the non-natural CBDAS comprises C37K and C99F. In some embodiments, the non-natural CBDAS comprises C37K. In some embodiments, the non-natural CBDAS comprises C37H. In some embodiments, the non-natural CBDAS comprises C37H and a substitution selected from C99V, C99L, and C99A. In some embodiments, the non-natural CBDAS comprises C37N. In some embodiments, the non-natural CBDAS comprises C37N and a substitution selected from C99A, C99F and C99V. In some embodiments, the non-natural CBDAS comprises C37Q. In some embodiments, the non-natural CBDAS comprises C37Q and a substitution selected from C99I and C99A. In some embodiments, the non-natural CBDAS comprises C37R. In some embodiments, the non-natural CBDAS comprises C37R and C99I.

In some embodiments, the non-natural CBDAS comprises at least one amino acid substitution corresponding to SEQ ID NO:79, wherein the substitution is:

(a) C37D and C99F;
(b) C37H;
(c) C37Y;
(d) C37Y and C99A;
(e) C37Y and C99V;
(f) C37E and C99F;
(g) C37Y and C99I;
(h) C37E;
(i) C37K and C99F;
(j) C37D;
(k) C37D and C99V;
(l) C37D and C99A;
(m) C37H and C99V;
(n) C37E and C99V;
(o) C37N and C99A;
(p) C37N and C99F;
(q) C37E and C99A;
(r) C37N and C99V;
(s) C37Q and C99I;
(t) C37T;
(u) C37Y and C99L;
(v) C37H and C99L;
(w) C99F;
(x) C37Q;
(y) C37N;
(z) C37H and C99A;
(aa) C37Y and C99F;
(bb) C37K;
(cc) C37Q and C99A;
(dd) C37R and C99I;
(ee) C37A and C99V;
(ff) C37A and C99A;
(gg) C37A and C99I;
(hh) C37A and C99L;
(ii) C37Q and C99V;
(jj) C37Q and C99L;
(kk) C37N and C99I;
(ll) C37N and C99L;
(mm) C37E and C99I;
(nn) C37E and C99L;
(oo) C37D and C99I;
(pp) C37D and C99L;
(qq) C37R and C99V;
(rr) C37R and C99A;
(ss) C37R and C99L;
(tt) C37R;
(uu) C37K and C99V;
(vv) C37K and C99A;
(ww) C37K and C99I; or
(xx) C37K and C99L.

In some embodiments, the at least one amino acid variation in the non-natural CBDAS is a substitution of one or more positively-charged residues in αA and αC in wild-type CBDAS, thereby reducing the charge repulsion, forming a salt bridge, and/or increasing van der Waals interaction between αA and αC as described herein. In some embodiments, the at least one amino acid variation in the non-natural CBDAS is a deletion of one or more positively-charged residues, or a deletion of one or more amino acids near (e.g., within 1 to 10 amino acids, within 1 to 5 amino acids, within 1 to 4 amino acids, within 1 to 3 amino acids, or within 1 to 2 amino acids) of one or more positively-charged residues in αA and αC in wild-type CBDAS and reduces their charge repulsion, forms a salt bridge, and/or increases van der Waals interaction between αA and αC as described herein. In some embodiments, the at least one amino acid variation in the non-natural CBDAS is an insertion of one or more amino acids near (e.g., within 1 to 10 amino acids, within 1 to 5 amino acids, within 1 to 4 amino acids, within 1 to 3 amino acids, or within 1 to 2 amino acids) of one or more positively-charged residues in αA and αC in wild-type CBDAS and reduces their charge repulsion, forms a salt bridge, and/or increases van der Waals interaction between αA and αC as described herein.

In some embodiments, the at least one amino acid variation, e.g., an insertion, deletion, or substitution in the non-natural CBDAS provides resistance to protease degradation. For example, the amino acid variation can disrupt a protease target sequence and/or a protease binding site, or the amino acid variation can recruit a protease inhibitor. Protein variants for increasing protease resistance is further discussed, e.g., in Ahmad et al., Protein Sci 21(3):433-446 (2012) and Heard et al., J Med Chem 56(21):8339-8351 (2013).

In some embodiments, the non-natural CBDAS comprises a substitution at K36, Q40, K101, K102, or a combination thereof. In some embodiments, the non-natural CBDAS comprises a substitution of K36, Q40, K101, K102, or a combination thereof, with a charged amino acid. Charged amino acids are described herein. In some embodiments, the charged amino acid is D, E, or R. In some embodiments, K36, Q40, K101, K102, or a combination thereof, is independently substituted with D, E, or R. In some embodiments, the non-natural CBDA comprises K36D. In some embodiments, the non-natural CBDA comprises K36E. In some embodiments, the non-natural CBDA comprises K36R. In some embodiments, the non-natural CBDA comprises Q40D. In some embodiments, the non-natural CBDA comprises Q40E. In some embodiments, the non-natural CBDA comprises Q40R. In some embodiments, the non-natural CBDA comprises K101D. In some embodiments, the non-natural CBDA comprises K101E. In some embodiments, the non-natural CBDA comprises K101R. In some embodiments, the non-natural CBDA comprises K102D. In some embodiments, the non-natural CBDA comprises K102E. In some embodiments, the non-natural CBDA comprises K102R.

In some embodiments, the non-natural CBDAS comprises: a substitution of K36, Q40, K101, K102, or a combination thereof, with a charged amino acid; a substitution selected from C37A, C37D, C37H, C37Y, C37E, C37K, C37N, C37Q, C37T and C37R; a substitution selected from C99A, C99I, C99V, C99L, and C99F; or any combination thereof. In some embodiments, the non-natural CBDAS comprises: a substitution of K36, Q40, K101, K102, or a combination thereof, with a charged amino acid; a substitution selected from C37A, C37D, C37E, C37K, C37N, C37Q, and C37R; a substitution selected from C99A, C99I, C99V, and C99L; or any combination thereof.

In some embodiments, the non-natural CBDAS comprises: a substitution selected from C37A, C37D, C37E, C37K, C37N, C37Q, and C37R; a substitution selected from C99A, C99I, C99V, and C99L; a substitution selected from K36D, K36E, and K36R; a substitution selected from Q40D, Q40E, Q40R; a substitution selected from K101D, K101E, K101R; a substitution selected from K102D, K102E, and K102R; or any combination thereof.

In some embodiments, the non-natural CBDAS comprises K36D; a substitution selected from C37A, C37D, C37E, C37K, C37N, C37Q, and C37R; and a substitution selected from C99A, C99I, C99V, and C99L. In some embodiments, the non-natural CBDAS comprises K36E; a substitution selected from C37A, C37D, C37E, C37K, C37N, C37Q, and C37R; and a substitution selected from C99A, C99I, C99V, and C99L. In some embodiments, the non-natural CBDAS comprises K36R; a substitution selected from C37A, C37D, C37E, C37K, C37N, C37Q, and C37R; and a substitution selected from C99A, C99I, C99V, and C99L.

In some embodiments, the non-natural CBDAS comprises Q40D; a substitution selected from C37A, C37D, C37E, C37K, C37N, C37Q, and C37R; and a substitution selected from C99A, C99I, C99V, and C99L. In some embodiments, the non-natural CBDAS comprises Q40E; a substitution selected from C37A, C37D, C37E, C37K, C37N, C37Q, and C37R; and a substitution selected from C99A, C99I, C99V, and C99L. In some embodiments, the non-natural CBDAS comprises Q40R; a substitution selected from C37A, C37D, C37E, C37K, C37N, C37Q, and C37R; and a substitution selected from C99A, C99I, C99V, and C99L.

In some embodiments, the non-natural CBDAS comprises K101D; a substitution selected from C37A, C37D, C37E, C37K, C37N, C37Q, and C37R; and a substitution selected from C99A, C99I, C99V, and C99L. In some embodiments, the non-natural CBDAS comprises K101E; a substitution selected from C37A, C37D, C37E, C37K, C37N, C37Q, and C37R; and a substitution selected from C99A, C99I, C99V, and C99L. In some embodiments, the non-natural CBDAS comprises K101R; a substitution selected from C37A, C37D, C37E, C37K, C37N, C37Q, and C37R; and a substitution selected from C99A, C99I, C99V, and C99L.

In some embodiments, the non-natural CBDAS comprises K102D; a substitution selected from C37A, C37D, C37E, C37K, C37N, C37Q, and C37R; and a substitution selected from C99A, C99I, C99V, and C99L. In some embodiments, the non-natural CBDAS comprises K102E; a substitution selected from C37A, C37D, C37E, C37K, C37N, C37Q, and C37R; and a substitution selected from C99A, C99I, C99V, and C99L. In some embodiments, the non-natural CBDAS comprises K102R; a substitution selected from C37A, C37D, C37E, C37K, C37N, C37Q, and C37R; and a substitution selected from C99A, C99I, C99V, and C99L.

In some embodiments, the non-natural CBDAS comprises C37A and one or more substitutions selected from K36D, K36E, K36R, Q40D, Q40E, Q40R, K101D, K101E, K101R, K102D, K102E, and K102R. In some embodiments, the non-natural CBDAS comprises C37D and one or more substitutions selected from K36D, K36E, K36R, Q40D, Q40E, Q40R, K101D, K101E, K101R, K102D, K102E, and K102R. In some embodiments, the non-natural CBDAS comprises C37E and one or more substitutions selected from K36D, K36E, K36R, Q40D, Q40E, Q40R, K101D, K101E, K101R, K102D, K102E, and K102R. In some embodiments, the non-natural CBDAS comprises C37K and one or more substitutions selected from K36D, K36E, K36R, Q40D, Q40E, Q40R, K101D, K101E, K101R, K102D, K102E, and K102R. In some embodiments, the non-natural CBDAS comprises C37N and one or more substitutions selected from K36D, K36E, K36R, Q40D, Q40E, Q40R, K101D, K101E, K101R, K102D, K102E, and K102R. In some embodiments, the non-natural CBDAS comprises C37Q and one or more substitutions selected from K36D, K36E, K36R, Q40D, Q40E, Q40R, K101D, K101E, K101R, K102D, K102E, and K102R. In some embodiments, the non-natural CBDAS comprises C37R and one or more substitutions selected from K36D, K36E, K36R, Q40D, Q40E, Q40R, K101D, K101E, K101R, K102D, K102E, and K102R.

In some embodiments, the non-natural CBDAS comprises: a substitution selected from (a) C37D and C99F; (b) C37H; (c) C37Y; (d) C37Y and C99A; (e) C37Y and C99V; (f) C37E and C99F; (g) C37Y and C99I; (h) C37E; (i) C37K and C99F; (j) C37D; (k) C37D and C99V; (1) C37D and C99A; (m) C37H and C99V; (n) C37E and C99V; (o) C37N and C99A; (p) C37N and C99F; (q) C37E and C99A; (r) C37N and C99V; (s) C37Q and C99I; (t) C37T; (u) C37Y and C99L; (v) C37H and C99L; (w) C99F; (x) C37Q; (y) C37N; (z) C37H and C99A; (aa) C37Y and C99F; (bb) C37K; (cc) C37Q and C99A; (dd) C37R and C99I; (ee) C37A and C99V; (ff) C37A and C99A; (gg) C37A and C99I;

(hh) C37A and C99L; (ii) C37Q and C99V; (jj) C37Q and C99L; (kk) C37N and C99I; (ll) C37N and C99L; (mm) C37E and C99I; (nn) C37E and C99L; (oo) C37D and C99I; (pp) C37D and C99L; (qq) C37R and C99V; (rr) C37R and C99A; (ss) C37R and C99L; (tt) C37R; (uu) C37K and C99V; (vv) C37K and C99A; (ww) C37K and C99I; and (xx) C37K and C99L; and one or more substitutions selected from K36D, K36E, K36R, Q40D, Q40E, Q40R, K101D, K101E, K101R, K102D, K102E, and K102R.

In some embodiments, the non-natural CBDAS comprises position C37 substituted with D, E, R, or K; position C99 substituted with F; position K36, Q40, K102, or a combination thereof independently substituted with D, E, or R; and position K101 unsubstituted or substituted with R, wherein the position corresponds to SEQ ID NO:79. In some embodiments, the non-natural CBDAS comprises C37 substituted with D, E, R, or K; C99 substituted with F; and K36 substituted with D, E, or R. In some embodiments, the non-natural CBDAS comprises C37 substituted with D, E, R, or K; C99 substituted with F; and Q40 substituted with D, E, or R. In some embodiments, the non-natural CBDAS comprises C37 substituted with D, E, R, or K; C99 substituted with F; and K102 substituted with D, E, or R. In some embodiments, the non-natural CBDAS comprises C37 substituted with D, E, R, or K; C99 substituted with F; and K101 substituted with R. In some embodiments, the non-natural CBDAS comprises C37K, K36D, Q40E, and K101R. In some embodiments, the amino acid substitutions described herein stabilize the structure of the non-natural CBDAS.

In some embodiments, the non-natural CBDAS comprises at least one substitution at a position corresponding to SEQ ID NO:79, wherein the substitution is:

(a) K36D, C37K, Q40D, C99F, and K101R;
(b) K36D, C37K, Q40D, C99F, K101R and K102R;
(c) K36D, C37K, Q40E, C99F, and K101R;
(d) K36D, C37K, Q40E, C99F, K101R and K102R;
(e) K36R, C37K, Q40D, C99F, K101R and K102R;
(f) K36D, C37E, C99F, and K101R;
(g) K36R, C37E, Q40E, C99F, K101R, and K102R;
(h) C37E, C99F, K101R, and K102E;
(i) K36E, C37K, Q40E, C99F, and K101R;
(j) K36D, C37R, Q40D, C99F, K101R, and K102D;
(k) K36D, C37K, Q40D, and C99F;
(l) K36R, C37K, Q40R, C99F, K101R, and K102E;
(m) K36R, C37E, Q40D, C99F, K101R, and K102E;
(n) K36E, C37R, Q40D, C99F, and K101R;
(o) K36D, C37R, Q40E, C99F, and K101R;
(p) K36D, C37R, Q40D, C99F, K101R, and K102R;
(q) K36R, C37R, Q40E, C99F, K101R, and K102R;
(r) K36D, C37E, Q40D, C99F, K101R, and K102R;
(s) K36D, C37K, Q40E, and C99F;
(t) K36D, C37R, Q40D, C99F, K101R, and K102E;
(u) K36D, C37E, Q40E, C99F, K101R, and K102R;
(v) C37D, C99F, K101R, and K102E;
(w) K36E, C37E, Q40E, C99F, K101R, and K102R;
(x) K36R, C37E, C99F, K101R, and K102R;
(y) K36R, C37E, Q40D, C99F, K101R, and K102R;
(z) K36D, C37D, C99F, and K102E;
(aa) K36R, C37D, Q40D, C99F, K101R, and K102R;
(bb) C37D, C99F, K101R, and K102R;
(cc) K36D, C37D, Q40E, C99F, K101R, and K102R;
(dd) K36D, C37D, C99F, K101R, and K102D;
(ee) C37E, Q40E, C99F, K101R, and K102E;
(ff) K36R, C37E, Q40D, C99F, and K101R;
(gg) K36D, C37D, Q40R, C99F, and K101R;
(hh) K36D, C37D, C99F, K101R, and K102E;
(ii) K36D, C37K, C99F, K101R, and K102R; or
(jj) K36E, C37R, Q40R, C99F, K101R, and K102E.

In some embodiments, the non-natural CBDAS comprises at least one amino acid substitution at position C37, Q40, A46, P58, L59, H89, V90, C99, K102, R295, V320, V357, N365, K512, D515, N527, R543, or a combination thereof, wherein the position corresponds to SEQ ID NO:79. In some embodiments, the non-natural CBDAS comprises at least one amino acid substitution at position C37, C99, and one or more of Q40, A46, P58, L59, H89, V90, K102, R295, V320, V357, N365, K512, D515, N527, and R543, wherein the amino acid position corresponds to SEQ ID NO:79. In some embodiments, the substitution is C37A, Q40R, A46E, P58E, L59T, H89D, V90D, C99A, K102E, R295E, V320T, V357T, N365D, K512D, D515E, N527T, R543Y, or a combination thereof. In some embodiments, the non-natural CBDAS comprises at least one amino acid substitution at position C37, C99, and one or more of Q40, L59, H89, V90, K102, R295, V320, and D515, wherein the amino acid position corresponds to SEQ ID NO:79. In some embodiments, the substitution is C37A, Q40R, L59T, H89D, V90D, C99A, K102E, R295E, V320T, D515E, or a combination thereof. In some embodiments, the substitution is C37A, Q40R, H89D, V90D, C99A, and K102E. In some embodiments, the substitution is C37A, Q40R, L59T, H89D, C99A, K102E, and V320T. In some embodiments, the substitution is C37A, Q40R, L59T, H89D, C99A, K102E, R295E, V320T, and D515E. In some embodiments, the substitution is C37A, Q40R, L59T, H89D, C99A, K102E, and R295E. In some embodiments, the substitution is C37A, Q40R, P58E, L59T, H89D, V90T, C99A, K102E, R295E, V320T, V357T, D515E, and N527T.

In some embodiments, the non-natural CBDAS comprises:

1) C37A, Q40R, L59T, H89D, C99A, K102E, V320T, R295E and D515E;
2) C37A, Q40R, L59T, H89D, C99A, K102E, V320T, V357T and D515E;
3) C37A, Q40R, L59T, H89D, C99A, K102E, V320T, V90T and D515E;
4) C37A, Q40R, L59T, H89D, C99A, K102E, V320T, R295E and N527T;
5) C37A, Q40R, L59T, H89D, C99A, K102E, V320T, N365D and D515E;
6) C37A, Q40R, L59T, H89D, C99A, K102E, V320T, R295E and V357T;
7) C37A, Q40R, L59T, H89D, C99A, K102E, V320T, V90T and R295E;
8) C37A, Q40R, H89D, C99A, K102E, V320T, and D515E;
9) C37A, Q40R, L59T, H89D, C99A, K102E, V320T, V357T and N527T;
10) C37A, Q40R, L59T, H89D, C99A, K102E, V320T, P58E and R295E;
11) C37A, Q40R, L59T, C99A, K102E, V320T, and R295E;
12) C37A, Q40R, L59T, H89D, C99A, K102E, V320T, V90T and N527T;
13) C37A, Q40R, L59T, H89D, C99A, K102E, V320T, N365D and N527T;
14) C37A, Q40R, L59T, H89D, C99A, K102E, V320T, K512D and D515E;
15) C37A, Q40R, L59T, H89D, C99A, K102E, V320T, P58E and D515E;
16) C37A, Q40R, L59T, H89D, C99A, K102E, V320T, P58E and V90T;
17) C37A, Q40R, L59T, H89D, C99A, K102E, V320T, P58E and N527T;

18) C37A, Q40R, L59T, C99A, K102E, V320T, and D515E;
19) C37A, Q40R, L59T, H89D, C99A, K102E, V320T, V357T and R543Y;
20) C37A, Q40R, L59T, H89D, C99A, K102E, V320T, P58E and V357T;
21) C37A, Q40R, L59T, H89D, C99A, K102E, V320T, V357T and N365D;
22) C37A, Q40R, L59T, C99A, K102E, V320T, and V90T;
23) C37A, Q40R, L59T, H89D, C99A, K102E, V320T, A46E and R295E;
24) C37A, Q40R, L59T, H89D, C99A, K102E, V320T, R295E and R543Y;
25) C37A, Q40R, L59T, H89D, C99A, K102E, V320T, A46E and D515E;
26) C37A, L59T, H89D, C99A, K102E, V320T, and D515E;
27) C37A, Q40R, L59T, H89D, C99A, K102E, and D515E;
28) C37A, Q40R, L59T, K102E, V320T, and N527T;
29) C37A, Q40R, L59T, H89D, C99A, K102E, and R295E;
30) C37A, Q40R, L59T, H89D, C99A, K102E, V320T, R295E and K512D;
31) C37A, Q40R, H89D, C99A, K102E, V320T, and N527T;
32) C37A, Q40R, L59T, H89D, C99A, K102E, V320T, K512D and N527T;
33) C37A, Q40R, L59T, H89D, C99A, K102E, V320T, N365D and K512D;
34) C37A, Q40R, H89D, C99A, K102E, V320T, and V357T;
35) C37A, Q40R, H89D, C99A, K102E, V320T, and N365D;
36) C37A, Q40R, L59T, C99A, K102E, V320T, H89S and R295E;
37) C37A, Q40R, L59T, H89D, C99A, K102E, and V90T;
38) C37A, Q40R, L59T, H89D, C99A, K102E, V320T, P58E and R543Y;
39) C37A, Q40R, H89D, C99A, K102E, V320T, and R295E;
40) C37A, Q40R, L59T, H89D, C99A, K102E, V320T, V90T and R543Y;
41) C37A, Q40R, L59T, C99A, K102E, V320T, H89S and D515E;
42) C37A, Q40R, L59T, H89D, C99A, K102E, and P58E;
43) C37A, Q40R, H89D, C99A, K102E, V320T, and R543Y;
44) C37A, Q40R, L59T, H89D, C99A, K102E, V320T, A46E and V90T;
45) C37A, Q40R, L59T, H89D, C99A, K102E, V320T, V90T and N365D;
46) C37A, Q40R, L59T, H89D, C99A, K102E, V320T, V357T and K512D;
47) C37A, Q40R, H89D, C99A, and K102E;
48) C37A, L59T, H89D, C99A, K102E, V320T, and R295E;
49) C37A, Q40R, L59T, H89D, C99A, K102E, V320T, A46E and N365D;
50) C37A, Q40R, L59T, H89D, C99A, K102E, and N365D;
51) C37A, Q40R, L59T, H89D, C99A, K102E, V320T, P58E and N365D;
52) C37A, Q40R, L59T, H89D, C99A, K102E, and N527T;
53) C37A, Q40R, H89D, C99A, K102E, V320T, and P58E;
54) C37A, Q40R, L59T, H89D, C99A, K102E, V320T, A46E and V357T;
55) R295E; or
56) D515E, wherein the amino acid position corresponds to SEQ ID NO:79.

In some embodiments, the non-natural CBDAS comprises an amino acid substitution at C37, C99, Q40, L59, V90, C99, K102, R295, and any one of: P58, V90, V357, N527, and N365, wherein the amino acid position corresponds to SEQ ID NO:79. In some embodiments, the non-natural CBDAS comprises C37A, Q40R, L59T, V90D, C99A, K102E, R295E, and any one of: P58E, V90T, V357T, N527T, and N365D.

In some embodiments, the non-natural CBDAS comprises an amino acid substitution at C37, C99, Q40, L59, V90, C99, K102, R295, and two substitutions at: (1) P58 and V90; (2) P58 and V357; (3) P58 and N527; (4) P58 and N365; (5) V90 and N527; (6) V90 and N365; (7) V357 and N365; (8) N365 and N527; or V357 and N527, wherein the amino acid position corresponds to SEQ ID NO:79. In some embodiments, the non-natural CBDAS comprises C37A, Q40R, L59T, V90D, C99A, K102E, R295E, and two substitutions selected from: (1) P58E and V90T; (2) P58E and V357T; (3) P58E and N527T; (4) P58E and N365D; (5) V90T and N527T; (6) V90T and N365D; (7) V357T and N365D; (8) N365D and N527T; or (9) V357T and N527T.

In some embodiments, the non-natural CBDAS comprises an amino acid substitution at C37, C99, Q40, L59, V90, C99, K102, R295, and three substitutions at: (1) P58, V90, and V357; (2) P58, V90, and N527; (3) P58, V357, and N527; (4) V90, V357, and N527; or (5) V357, N365, and N527, wherein the amino acid position corresponds to SEQ ID NO:79. In some embodiments, the non-natural CBDAS comprises C37A, Q40R, L59T, V90D, C99A, K102E, R295E, and three substitutions selected from: (1) P58E, V90T, and V357T; (2) P58E, V90T, and N527T; (3) P58E, V357T, and N527T; (4) V90T, V357T, and N527T; or (5) V357T, N365D, and N527T.

In some embodiments, the non-natural CBDAS comprises an amino acid substitution at C37, C99, Q40, L59, V90, C99, K102, R295, and four substitutions at: (1) P58E, V357T, N365D, and N527T; (2) P58E, V90T, N365D, and N527T; or (3) V90T, V357T, N365D, and N527T, wherein the amino acid position corresponds to SEQ ID NO:79. In some embodiments, the non-natural CBDAS comprises C37A, Q40R, L59T, V90D, C99A, K102E, R295E, and four substitutions selected from: (1) P58E, V357T, N365D, and N527T; (2) P58E, V90T, N365D, and N527T; or (3) V90T, V357T, N365D, and N527T.

In some embodiments, the non-natural CBDAS comprises the amino acid substitutions C37A, Q40R, V90D, V90D, C99A, and K102E, wherein the amino acid position corresponds to SEQ ID NO:79. In some embodiments, the non-natural CBDAS comprises the amino acid substitutions C37A, Q40R, L59T, V90D, C99A, K102E, and V321T, wherein the amino acid position corresponds to SEQ ID NO:79. In some embodiments, the non-natural CBDAS comprises the amino acid substitutions C37A, Q40R, L59T, V90D, C99A, K102E, R295E, V321T, and N516E, wherein the amino acid position corresponds to SEQ ID NO:79. In some embodiments, the non-natural CBDAS comprises the amino acid substitutions C37A, Q40R, L59T, V90D, C99A, K102E, and R295E, wherein the amino acid position corresponds to SEQ ID NO:79.

In some embodiments, non-natural CBDAS comprises C37A, Q40R, P58E, L59T, H89D, V90T, C99A, K102E, R295E, V320T, V357T, D515E, and N527T, wherein the amino acid position corresponds to SEQ ID NO:79. In some embodiments, the non-natural CBDAS comprises:

1) C37A, Q40R, P58E, L59T, H89D, V90T, C99A, K102E, R295E, V320T, V357T, N365D, D515E, and N527T;
2) C37A, Q40R, P58E, H89D, V90T, C99A, K102E, R295E, V320T, V357T, D515E, and N527T;
3) C37A, Q40R, P58E, L59T, H89D, V90T, C99A, K102E, R295E, V320T, V357T, N365D, and D515E;
4) C37A, Q40R, P58E, V90T, C99A, K102E, R295E, V320T, V357T, D515E, and N527T;
5) C37A, Q40R, P58E, H89D, V90T, C99A, K102E, R295E, V320T, V357T, N365D, D515E, and N527T; or
6) C37A, Q40R, P58E, L59T, V90T, C99A, K102E, R295E, V320T, V357T, N365D, D515E, and N527T, wherein the amino acid position corresponds to SEQ ID NO:79.

In some embodiments, the at least one amino acid variation is not within an active site of the non-natural CBDAS. As described herein, "active site" refers to a region in an enzyme that may be important for catalysis, substrate binding, and/or cofactor binding. In some embodiments, the active site of a natural or non-natural CBDAS comprises amino acid residues involved in CBGA binding, FAD binding, and/or cyclization of CBGA. In some embodiments, the active site of the non-natural CBDAS comprises amino acid residues involved in FAD binding. In some embodiments, the active site of the non-natural CBDAS comprises amino acid residues involved in FAD binding. In some embodiments, the active site of the non-natural CBDAS comprises amino acid residues H69, R108, T109, R110, S111, G112, G113, H114, D115, S116, M11, S120, Y121, L132, A151, G174, Y175, C176, T178, V179, C180, A181, G182, G183, H184, G189, Y190, A235, E236, G239, I240, I241, V242, F380, W443, Y480, N482, Y483, N532, S116, G174, Y175, M291, H293, G377, G380, F382, K384, L386, G411, M414, A416, Y418, E443, W445, I447, S449, E45I, Y482, L483, N484, Y485, or a combination thereof (amino acid residue numbering with respect to SEQ ID NO:79). In some embodiments, the active site of the non-natural CBDAS is within positions 60-75, 105-125, 160-200, 220-250, 280-300, 350-450, 470-490, or 530-540, inclusive, of the CBDAS, wherein the position corresponds to SEQ ID NO:79.

In some embodiments, the non-natural CBDAS further comprises an affinity tag, a purification tag, a solubility tag, or a combination thereof. For example, at least 1, at least 2, at least 3, at least 4, at least 5, or at least 6 histidine residues can be appended to the C-terminus of the non-natural CBDAS of any of SEQ ID NOs:78, 79, or 83 to provide a 6×His tag (SEQ ID NO: 89) for affinity purification by Ni-NTA. Affinity tags, purification tags, and solubility tags, and method of tagging proteins are known to one of ordinary skill in the art and described, e.g., in Kimple et al. (2013), Curr Protoc Protein Sci 73: Unit-9.9.

In some embodiments, the non-natural CBDAS described herein is capable of catalyzing the oxidative cyclization of CBGA to CBDA. In some embodiments, the non-natural CBDAS described herein has substantially the same catalytic activity as a wild-type CBDAS. In some embodiments, the non-natural CBDAS described herein has at least about 70%, at least about 75%, at least about 80%, at least about 85%, at least about 90%, at least about 95%, at least or about 99%, or at least about 100% of the catalytic activity of a wild-type CBDAS produced from its native host organism.

In some embodiments, the non-natural CBDAS catalyzes the oxidative cyclization of CBGA to CBDA at pH greater than about 3.5 and less than pH about 6.5, less than about 6.0, less than about 5.5, less than about 5.0, less than about 4.5, or less than about 4.0. In some embodiments, the non-natural CBDAS catalyzes the oxidative cyclization of CBGA to CBDA at about pH 4.0 to about pH 6.0. In some embodiments, the non-natural CBDAS catalyzes the oxidative cyclization of CBGA to CBDA at about pH 4.0, about pH 4.1, about pH 4.2, about pH 4.3, about pH 4.4, about pH 4.5, about pH 4.6, about pH 4.7, about pH 4.8, about pH 4.9, about pH 5.0, about pH 5.1, about pH 5.2, about pH 5.3, about pH 5.4, about pH 5.5, about pH 5.6, about pH 5.7, about pH 5.8, about pH 5.9, or about 6.0.

In some embodiments, the non-natural CBDAS described herein further catalyzes the oxidative cyclization of CBGA into $\Delta^9$-tetrahydrocannabinolic acid (THCA), cannabichromenic acid (CBCA), or both. As described herein, cannabinoid synthases such as CBDAS are capable of producing more than one cannabinoid. In some embodiments, the non-natural CBDAS is capable of catalyzing the oxidative cyclization of CBGA to THCA. In some embodiments, the non-natural CBDAS is capable of catalyzing the oxidative cyclization of CBGA into CBCA. In some embodiments, the non-natural CBDAS catalyzes the oxidative cyclization of CBGA into CBCA at pH less than 8.0 and greater than about 6.5, greater than about 7.0, or greater than about 7.5. In some embodiments, the non-natural CBDAS catalyzes the oxidative cyclization of CBGA to CBCA at about pH 6.5 to about pH 8.0. In some embodiments, the non-natural CBDAS catalyzes the oxidative cyclization of CBGA to CBCA at about pH about pH 6.5, about pH 6.6, about pH 6.7, about pH 6.8, about pH 6.9, about pH 7.0, about pH 7.1, about pH 7.2, about pH 7.3, about pH 7.4, about pH 7.5, about pH 7.6, about pH 7.7, about pH 7.8, about pH 7.9, or about pH 8.0.

In some embodiments, the invention further provides a nucleic acid encoding the non-natural CBDAS described herein. In some embodiments, the nucleic acid comprises a polynucleotide sequence capable of encoding a polypeptide with at least 70%, at least 75%, at least 80%, at least 85%, at least 90%, at least 95%, at least 96%, at least 97%, at least 98%, at least 99%, or 100% sequence identity to SEQ ID NO:78 or 79.

In some embodiments, the nucleic acid encoding the non-natural CBDAS is codon optimized. An example of a codon optimized sequence is, in one instance, a sequence optimized for expression in a bacterial host cell, e.g., *E. coli*. In some embodiments, one or more codons (e.g., about or more than about 1, 2, 3, 4, 5, 10, 15, 20, 25, 50, or all codons) in a nucleic acid sequence encoding the non-natural CBDAS described herein corresponds to the most frequently used codon for a particular amino acid in the bacterial host cell.

In some embodiments, the invention provides an expression construct comprising the nucleic acid encoding the non-natural CBDAS described herein. Expression constructs are described herein. In some embodiments, the expression construct comprises the nucleic acid encoding the non-natural CBDAS operably linked to a regulatory element. In some embodiments, the regulatory element is a bacterial regulatory element. Non-limiting examples of expression vectors are provided herein and include, e.g., pQE vectors (Qiagen), pBluescript plasmids, pNH vectors, lambda-ZAP vectors (Stratagene); pTrc99a, pKK223-3, pDR540, and pRIT2T (Pharmacia).

In some embodiments, the invention provides an engineered cell comprising the non-natural CBDAS described herein, the nucleic acid encoding the non-natural CBDAS, the expression construct comprising the nucleic acid, or a combination thereof. In some embodiments, the invention provides a method of making an isolated non-natural CBDAS comprising isolating CBDAS expressed in the engineered cell provided herein. In some embodiments, the invention provides an isolated CBDAS, wherein the isolated CBDAS is expressed and isolated from the engineered cell.

IV. CBCAS Variants

Cannabidiolic acid synthase (CBCAS) is an enzyme found in *Cannabis sativa* (*C. sativa*) that catalyzes the oxidative cyclization of cannabigerolic acid (CBGA) to cannabichromenic acid (CBCA) utilizing a FAD cofactor.

The protein structure of CBCAS is predicted to be highly similar to that of THCAS, as described herein. FIG. 11 shows a sequence alignment between THCAS and CBCAS. CBCAS likely comprises two domains, Domain I and Domain II. CBCAS is also predicted to have a FAD-binding domain comprising amino acids CBCAS (40 residues): CBCAS: Q69, R108, T109, R110, S111, G112, G113, H114, D115, A116, L119, S120, Y121, L132, A151, G174, Y175, C176, T178, V179, G180, V181, G182, G183, H184, S186, G189, Y190, G235, E236, G239, I240, I241, A242, F381, W444, Y481, N483, Y484, and N533 (amino acid residue numbering with respect to SEQ ID NO:81).

CBCAS further comprises a CBGA binding domain. The following amino acid residues may be involved in CBGA binding: A116, G174, Y175, T290, H292, G376, T379, F381, I383, L385, G410, M413, V415, Y417, E442, W444, T446, T448, E450, Y481, L482, N483, and Y484 (amino acid residue numbering with respect to SEQ ID NO:81).

Domain I of CBCAS can likely be further divided into subdomains Ia and Ib, similar to THCAS. Based on structural alignments, subdomain Ia likely includes the region from amino acid residue positions 28 to 134 and comprises three α-helices, αA, αB, and αC which surround three β-strands (β1-β3) (amino acid residue numbering with respect to SEQ ID NO:81). As used herein, αA of CBCAS includes the amino acid residues Asn29 to Ile42; αB includes the amino acid residues Leu59 to Thr67; and αC include the amino acid residues Asn89 to Gly 104. A disulfide bond likely is present between Cys37 in αA and Cys99 in αC of wild-type CBCAS. Subdomain IIb of CBCAS likely includes the region from residue positions 135 to 253 and from 476 to 545 and likely comprises five β-strands (β4-β8) surrounding five α-helices (αD-αF, αM, and αN). Domain II likely includes the region from positions 254 to 475 and likely comprises eight β strands (β9-β16) surrounding six α-helices (αG-αL).

In some examples, the present disclosure provides non-naturally occurring cannabichromenic acid synthase (CBCAS) that does not comprise a disulfide bond between alpha helix αA and alpha helix αC, wherein the non-natural CBCAS catalyzes the oxidative cyclization of cannabigerolic acid (CBGA) into cannabichromenic acid (CBCA) (see, e.g., FIG. 9).

In some embodiments, the invention provides a non-natural CBCAS with 80% or greater identity to SEQ ID NOs:80, 81, or 84, comprising at least one amino acid variation as compared to a wild type CBCAS, comprising three alpha helices (αA, αB, and αC) and wherein a disulfide bond is not formed between alpha helix αA and alpha helix αC, wherein the non-natural CBCAS catalyzes the oxidative cyclization of cannabigerolic acid (CBGA) into cannabidiolic acid (CBCA). In some embodiments, the invention provides a non-natural CBCAS with 90% or greater identity to SEQ ID NOs:80, 81, or 84, comprising at least one amino acid variation as compared to a wild type CBCAS, comprising three alpha helices (αA, αB, and αC) and wherein a disulfide bond is not formed between alpha helix αA and alpha helix αC, wherein the non-natural CBCAS catalyzes the oxidative cyclization of cannabigerolic acid (CBGA) into cannabidiolic acid (CBCA). In some embodiments, the invention provides a non-natural CBCAS with 95% or greater identity to SEQ ID NOs:80, 81, or 84, comprising at least one amino acid variation as compared to a wild type CBCAS, comprising three alpha helices (αA, αB, and αC) and wherein a disulfide bond is not formed between alpha helix αA and alpha helix αC, wherein the non-natural CBCAS catalyzes the oxidative cyclization of cannabigerolic acid (CBGA) into cannabidiolic acid (CBCA).

The non-natural CBCAS described herein is capable of catalyzing the conversion of CBGA to CBCA. In some embodiments, the non-natural CBCAS is capable of catalyzing at least one step of the conversion of CBGA to CBCA. In some embodiments, the non-natural CBCAS has substantially the same amount of activity as wild-type CBCAS. In some embodiments, the non-natural CBCAS with substantially the same amount of activity as wild-type CBCAS, has greater than or about 80%, greater than or about 85%, greater than or about 90%, greater than or about 95%, greater than or about 99%, or about 100% the enzymatic activity of wild-type CBCAS. In some embodiments, the non-natural CBCAS has greater than or about 80%, greater than or about 85%, greater than or about 90%, greater than or about 95%, greater than or about 99%, or about 100% the enzymatic activity of wild-type CBCAS. Encompassed within the definition of "non-natural CBCAS" are fragments, truncations, variants, and fusions that are capable of catalyzing the conversion of CBGA to CBCA.

In some embodiments, the non-natural CBCAS has at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% sequence identity to at least about 25, 50, 75, 100, 125, 150, 200, 250, 300, 350, 400, 450, 500, or more contiguous amino acids of a natural, i.e., wild-type, CBCAS and having a cannabinoid synthase activity. In some embodiments, the non-natural CBCAS comprises the FAD binding domain (Pfam: PF01565) and a CBGA binding domain.

In some embodiments, the non-natural CBCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a natural, i.e., wild-type, CBCAS. The term natural CBCAS can refer to any known CBCAS sequence. For example, a wild-type CBCAS sequence can include, but is not limited to, a CBCAS sequence from various *Cannabis sativa* plants, as provided in Laverty et al., Genome Res 29(1): 146-156; McKernan et al., bioRxiv 2020.01.03.894428; and US 2017/0211049.

In some embodiments, the non-natural CBCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:80. SEQ ID NO:80 discloses a truncated CBCAS as compared to wild-type CBCAS (SEQ ID NO:81). SEQ ID NO:80 does not comprise an N-terminal leader sequence present in wild-type CBCAS. SEQ ID NO:80 does not comprise an N-terminal methionine. In some embodiments, removal of the leader sequence increases expression of the polypeptide of SEQ ID NO:80 in a host organism, e.g., a bacterial organism such as *E. coli*. In some embodiments, the N-terminal methionine that is typically present at the start of an expressed polypeptide sequence, e.g., the polypeptide of SEQ ID NO:83, is removed by the host organism, e.g., a bacterial organism such as *E. coli*.

In some embodiments, the non-natural CBCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:81. In some embodiments, SEQ ID NO:81 describes a wild-type CBCAS. In some embodiments, wild-type CBCAS comprises a leader sequence.

In some embodiments, the non-natural CBCAS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:84. SEQ ID NO:84 discloses a truncated CBCAS as compared to wild-type CBCAS (SEQ ID NO:81). SEQ ID NO:84 comprises an N-terminal methionine. SEQ ID NO:84 does not comprise an N-terminal leader sequence present in wild-type CBCAS. In some embodiments, removal of the leader sequence increases expression of the polypeptide of SEQ ID NO:80 in a host organism, e.g., a bacterial organism such as *E. coli*. In some embodiments, the N-terminal methionine that is typically present at the start of an expressed polypeptide sequence, e.g., the polypeptide of SEQ ID NO:83, is removed by the host organism, e.g., a bacterial organism such as *E. coli*.

As used throughout this application, all amino acid positions of the non-natural CBCAS described herein are numbered with reference to SEQ ID NO:81, unless otherwise defined. One of skill in the art would understand that alignment methods can be used to determine the appropriate amino acid position number that corresponds to the position referenced in SEQ ID NO:81. As described herein, an amino acid sequence alignment of SEQ ID NOs:1, 2, and 78-84 is shown in FIGS. 11A-11C. Select amino acids and their corresponding positions in each of SEQ ID NOs:1, 2, and 78-84 are also shown in Table A herein. For example, the first amino acid of SEQ ID NO:80 corresponds to the 28$^{th}$ amino acid of SEQ ID NO:81, and thus, the amino acid position of "C37" in SEQ ID NO:81, corresponds to "C10" in SEQ ID NO:80; the amino acid position of "C99" in SEQ ID NO:81, corresponds to "C72" in SEQ ID NO:80, and so on. The first amino acid of SEQ ID NO:84 corresponds to the 27$^{th}$ amino acid of SEQ ID NO:81, and thus, the amino acid position of "C37" in SEQ ID NO:81, corresponds to "C11" in SEQ ID NO:84; the amino acid position of "C99" in SEQ ID NO:81, corresponds to "C73" in SEQ ID NO:84, and so on.

TABLE A

| SEQ ID NO | CORRESPONDING AMINO ACID POSITIONS | | | | | |
|---|---|---|---|---|---|---|
| SEQ1 | K10 | C11 | K14 | C73 | K75 | K76 |
| SEQ2 | K36 | C37 | K40 | C99 | K101 | K102 |

TABLE A-continued

| SEQ ID NO | CORRESPONDING AMINO ACID POSITIONS | | | | | |
|---|---|---|---|---|---|---|
| SEQ78 | K9 | C10 | Q13 | C72 | K74 | K75 |
| SEQ79 | K36 | C37 | Q40 | C99 | K101 | K102 |
| SEQ80 | K9 | C10 | E13 | C72 | K74 | K75 |
| SEQ81 | K36 | C37 | E40 | C99 | K101 | K102 |
| SEQ82 | K9 | C10 | K13 | C72 | K74 | K75 |
| SEQ83 | K10 | C11 | Q14 | C73 | K75 | K76 |
| SEQ84 | K10 | C11 | E14 | C73 | K75 | K76 |

As described herein, a "non-natural" protein or polypeptide refers to a protein or polypeptide sequence having at least one variation at an amino acid position as compared to a wild-type polypeptide or nucleic acid sequence. In some embodiments, the non-natural CBCAS has at least one variation at an amino acid position as compared to a wild-type CBCAS.

In some embodiments, the non-natural CBCAS comprises three alpha helices, αA, αB, and αC, as described for wild-type CBCAS, i.e., αA includes the amino acid residues Asn29 to Ile42; αB includes the amino acid residues Leu59 to Thr67; and αC includes the amino acid residues Asn89 to Gly 104 (amino acid residue numbering with respect to SEQ ID NO:81). In some embodiments, the non-natural CBCAS does not comprise a disulfide bond between αA and αC present in wild-type CBCAS. In some embodiments, the at least one amino acid variation in the non-natural CBCAS disrupts the disulfide bond between αA and αC in wild-type CBCAS. Disulfide bonds are described herein. As seen from the sequence alignment between THCAS and CBCAS in FIG. 11, the positively-charged amino acid residues present in THCAS in αA and αC are also present in CBCAS. Thus, a disulfide bond between C37 of αA and C99 of αC would likely hold the two alpha helices together and overcome repulsion between the positive charges.

In some embodiments, the disulfide bond between αA and αC stabilizes the tertiary structure of wild-type CBCAS. As described herein, proteins comprising disulfide bonds, e.g., endogenous to plants, can be unstable in bacterial host cells as the disulfide bonds are often disrupted due to the reducing environment in the bacterial cells. In some embodiments, wild-type CBCAS comprising a disulfide bond between αA and αC is substantially unstable in a bacterial cell, e.g., an *E. coli* cell. As used herein, "unstable" CBCAS can refer to CBCAS polypeptides that are non-functional, denatured, and/or degraded rapidly, resulting in CBCAS activity that is greatly reduced relative to the activity found in its native host cell, e.g., *C. sativa* plants. In some embodiments, the CBCAS activity is 50% less, 60% less, 70% less, 80% less, or 90% less than the expected activity from the activity found in the native host cell, based on the expression parameters such as, e.g., vector, culture medium, induction agent, temperature, and/or time; "substantially unstable" CBCAS can also mean less than 70%, less than 60%, less than 50%, less than 40%, less than 30%, less than 20%, less than 10%, less than 5%, or less than 1% of the total amount of CBCAS isolated from the host cell is soluble.

In some embodiments, the non-natural CBCAS described herein does not comprise the disulfide bond between αA and αC and has a substantially similar tertiary structure as wild-type CBCAS. In some embodiments, the non-natural CBCAS that does not comprise the disulfide bond between αA and αC has a substantially identical tertiary structure as wild-type CBCAS comprising the disulfide bond between αA and αC. Methods of determining structural similarity between two proteins are described herein and includes, e.g., TM-scoring. In some embodiments, the TM-score for the non-natural CBCAS that does not comprise the disulfide bond between αA and αC and the wild-type CBCAS comprising the disulfide bond between αA and αC is greater than about 0.5, greater than about 0.6, greater than about 0.7, greater than about 0.8, greater than about 0.9, or about 1.0.

In some embodiments, the non-natural CBCAS comprises one or more amino acid variations to keep αA and αC in proximity comparable to the distance of a disulfide bond. In some embodiments, αA and αC in the non-natural CBCAS are 1 to about 5 Å, about 1.5 to about 4.5 Å, about 2 to about 4 Å, or about 2.5 to about 3.5 Å from one another at their closest amino acid residues. In some embodiments, the non-natural CBCAS comprises one or more amino acid variations to overcome the repulsion between the positive charges in αA and αC. In some embodiments, the non-natural CBCAS that does not comprise the disulfide bond between αA and αC comprises at least one salt bridge between αA and αC. Salt bridges are further described herein. In addition to salt bridges, van der Waals interaction can also contribute to the stability of a protein structure, e.g., between two α-helices. Van der Waals interactions are further described herein.

In some embodiments, the at least one amino acid variation in the non-natural CBCAS is a substitution of one or more cysteines forming the disulfide bond between αA and αC in wild-type CBCAS, thereby disrupting the disulfide bond. In some embodiments, the at least one amino acid variation in the non-natural CBCAS is a deletion of one or more cysteines forming the disulfide bond between αA and αC in wild-type CBCAS, thereby disrupting the disulfide bond. In some embodiments, the at least one amino acid variation in the non-natural CBCAS is an insertion near one or more cysteines forming the disulfide bond between αA and αC in wild-type CBCAS, thereby disrupting the disulfide bond. In some embodiments, the at least one amino acid variation in the non-natural CBCAS replaces the disulfide bond between αA and αC of wild-type CBCAS with a salt bridge. In some embodiments, the non-natural CBCAS comprising a salt bridge and no disulfide bond between αA and αC has improved expression, e.g., improved yield and/or solubility, in a bacterial cell (e.g., *E. coli*), compared with the expression of a CBCAS comprising a disulfide bond between αA and αC.

In some embodiments, the non-natural CBCAS comprises 1 to 100, 1 to 90, 1 to 80, 1 to 70, 1 to 60, 1 to 50, 1 to 40, 1 to 30, 1 to 25, 1 to 20, 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, or 19 to 20 amino acid variations as compared to a wild-type CBCAS. In some embodiments, the non-natural CBCAS comprises about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, or about 100 amino acid variations as compared to a wild-type CBCAS.

In some embodiments, the amino acid variation in the non-natural CBCAS is in αA, αC, or both. In some embodiments, the amino acid variation is at position C37, C99, K36, E40, K101, K102, or a combination thereof, wherein the position corresponds to SEQ ID NO:81. In some embodiments, the amino acid variation is at position C37, C99, or both, wherein the amino acid position corresponds to SEQ ID NO:81.

In some embodiments, the amino acid variation in the non-natural CBCAS is an amino acid substitution, deletion, or insertion. In some embodiments, the variation is a substitution of one or more amino acids in a wild-type CBCAS polypeptide sequence. In some embodiments, the variation is a deletion of one or more amino acids in a wild-type CBCAS polypeptide sequence. In some embodiments, the variation is an insertion of one or more amino acids in a wild-type CBCAS polypeptide sequence.

In some embodiments, the disulfide bond which occurs in wild-type CBCAS can be disrupted by the insertion of one or more amino acids. In some embodiments, the insertion of one or more amino acids results in formation of a salt bridge. In some embodiments, the variation is an insertion of 1 to 20, 1 to 15, 1 to 10, 1 to 9, 1 to 8, 1 to 7, 1 to 6, 1 to 5, 1 to 4, 1 to 3, or 1 to 2 amino acids. In some embodiments, the variation is an insertion of about 1, about 2, about 3, about 4, about 5, about 6, about 7, about 8, about 9, about 10, about 11, about 12, about 13, about 14, about 15, about 16, about 17, about 18, about 19, or about 20 amino acids. In some embodiments, the insertion is positioned within about 20 amino acids of C37 or C99. It will be understood that when referring to amino acid positions herein, "within" n number of amino acids expressly specifically includes n and all numbers between 0 and n. For example, an insertion position within 10 amino acids of X means that the insertion is 1, 2, 3, 4, 5, 6, 7, 8, 9, or 10 amino acids from the specified position X. In some embodiments, the insertion is positioned within about 10, within about 9, within about 8, within about 7, within about 6, within about 5, within about 4, within about 3, within about 2, or within about 1 amino acids of C37. In some embodiments, the insertion is within about 10, within about 9, within about 8, within about 7, within about 6, within about 5, within about 4, within about 3, within about 2, or within about 1 amino acids of C99. In some embodiments, the insertion is sufficient to disrupt the disulfide bond between αA and αC.

In some embodiments, the disulfide bond which occurs in wild-type CBCAS can be disrupted by the deletion of one or more amino acids. In some embodiments, the deletion of one or more amino acids results in formation of a salt bridge. In some embodiments, the variation is a deletion of 1 to 20, 1 to 15, 1 to 10, 1 to 9, 1 to 8, 1 to 7, 1 to 6, 1 to 5, 1 to 4, 1 to 3, or 1 to 2 amino acids. In some embodiments, the variation is an deletion of about 1, about 2, about 3, about 4, about 5, about 6, about 7, about 8, about 9, about 10, about 11, about 12, about 13, about 14, about 15, about 16, about 17, about 18, about 19, or about 20 amino acids. In some embodiments, the deletion is within about 20 amino acids of C37 or C99. In some embodiments, the deletion is within about 10, within about 9, within about 8, within about 7, within about 6, within about 5, within about 4, within about 3, within about 2, or within about 1 amino acids of C37. In some embodiments, the deletion is within about 10, within about 9, within about 8, within about 7, within about 6, within about 5, within about 4, within about 3, within about 2, or within about 1 amino acids of C99. In some embodiments, the deletion is sufficient to disrupt the disulfide bond between C37 of αA and C99 of αC.

In some embodiments, the disulfide bond which occurs in wild-type CBCAS can be disrupted on the substitution of one or more amino acids. In some embodiments, the substitution of one or more amino acids results in formation of a salt bridge. In some embodiments, the variation is a substitution. In some embodiments, the non-natural CBCAS comprises 1 to 50, 1 to 40, 1 to 30, 1 to 25, 1 to 20, 2 to 20, 3 to 20, 4 to 20, 5 to 20, 6 to 20, 7 to 20, 8 to 20, 9 to 20, 10 to 20, 11 to 20, 12 to 20, 13 to 20, 14 to 20, 15 to 20, 16 to 20, 17 to 20, 18 to 20, or 19 to 20 amino acid substitutions as compared to a wild-type CBCAS. In some embodiments, the non-natural CBCAS comprises about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, or about 50 amino acid substitutions as compared to a wild-type CBCAS.

In some embodiments, the non-natural CBCAS comprises an amino acid substitution at position C37, C99, K36, E40, K101, K102, or any combination thereof, wherein the position corresponds to SEQ ID NO:81.

In some embodiments, the non-natural CBCAS comprises a substitution at position C37, wherein the position corresponds to SEQ ID NO:81. In some embodiments, the substitution is selected from position C37A, C37D, C37H, C37Y, C37E, C37K, C37N, C37Q, C37T and C37R, wherein the position corresponds to SEQ ID NO:81. In some embodiments, the substitution is selected from position C37A, C37D, C37E, C37K, C37N, C37Q, and C37R, wherein the position corresponds to SEQ ID NO:81.

In some embodiments, the non-natural CBCAS comprises a substitution at position C99, wherein the position corresponds to SEQ ID NO:81. In some embodiments, the substitution is selected from position C99F, C99A, C99I, C99V, and C99L, wherein the position corresponds to SEQ ID NO:81. In some embodiments, the substitution is selected from position C99A, C99I, C99V, and C99L, wherein the position corresponds to SEQ ID NO:81.

In some embodiments, the non-natural CBCAS comprises a substitution at C37 and a substitution at C99. In some embodiments, the non-natural CBCAS comprises a substitution selected from C37A, C37D, C37H, C37Y, C37E, C37K, C37N, C37Q, C37T and C37R and a substitution selected from C99A, C99I, C99V, C99L, and C99F. In some embodiments, the non-natural CBCAS comprises a substitution selected from C37A, C37D, C37E, C37K, C37N, C37Q, and C37R and a substitution selected from C99A, C99I, C99V, and C99L.

In some embodiments, the non-natural CBCAS comprises C37A and a substitution selected from C99F, C99A, C99I, C99V, and C99L. In some embodiments, the non-natural CBCAS comprises C37D and a substitution selected from C99F, C99A, C99I, C99V, and C99L. In some embodiments, the non-natural CBCAS comprises C37H and a substitution selected from C99F, C99A, C99I, C99V, and C99L. In some embodiments, the non-natural CBCAS comprises C37Y and a substitution selected from C99F, C99A, C99I, C99V, and C99L. In some embodiments, the non-natural CBCAS comprises C37E and a substitution selected from C99F, C99A, C99I, C99V, and C99L. In some embodiments, the non-natural CBCAS comprises C37K and a substitution selected from C99F, C99A, C99I, C99V, and C99L. In some embodiments, the non-natural CBCAS comprises C37N and a substitution selected from C99F, C99A, C99I, C99V, and C99L. In some embodiments, the non-natural CBCAS comprises C37Q and a substitution selected from C99F, C99A, C99I, C99V, and C99L. In some embodiments, the non-natural CBCAS comprises C37T and a substitution selected from C99F, C99A, C99I, C99V, and C99L. In some embodiments, the non-natural CBCAS comprises C37R and a substitution selected from C99F, C99A, C99I, C99V, and C99L.

In some embodiments, the non-natural CBCAS comprises C37A and a substitution selected from C99A, C99I, C99V, and C99L. In some embodiments, the non-natural CBCAS comprises C37D and a substitution selected from C99A, C99I, C99V, and C99L. In some embodiments, the non-natural CBCAS comprises C37E and a substitution selected from C99A, C99I, C99V, and C99L. In some embodiments, the non-natural CBCAS comprises C37K and a substitution selected from C99A, C99I, C99V, and C99L. In some embodiments, the non-natural CBCAS comprises C37N and a substitution selected from C99A, C99I, C99V, and C99L. In some embodiments, the non-natural CBCAS comprises C37Q and a substitution selected from C99A, C99I, C99V, and C99L. In some embodiments, the non-natural CBCAS comprises C37R and a substitution selected from C99A, C99I, C99V, and C99L. In some embodiments, the amino acid substitutions described herein stabilize the structure of the non-natural CBCAS.

In some embodiments, the non-natural CBCAS comprises C37D. In some embodiments, the non-natural CBCAS comprises C99F. In some embodiments, the non-natural CBCAS comprises C37D and a substitution selected from C99F, C99V, C99A, C99I, and C99L. In some embodiments, the non-natural CBCAS comprises C37Y. In some embodiments, the non-natural CBCAS comprises C37Y and a substitution selected from C99A, C99I, C99V, C99L, and C99F. In some embodiments, the non-natural CBCAS comprises C37K and C99F. In some embodiments, the non-natural CBCAS comprises C37K. In some embodiments, the non-natural CBCAS comprises C37H. In some embodiments, the non-natural CBCAS comprises C37H and a substitution selected from C99V, C99L, and C99A. In some embodiments, the non-natural CBCAS comprises C37N. In some embodiments, the non-natural CBCAS comprises C37N and a substitution selected from C99A, C99F and C99V. In some embodiments, the non-natural CBCAS comprises C37Q. In some embodiments, the non-natural CBCAS comprises C37Q and a substitution selected from C99I and C99A. In some embodiments, the non-natural CBCAS comprises C37R. In some embodiments, the non-natural CBCAS comprises C37R and C99I.

In some embodiments, the non-natural CBCAS comprises at least one amino acid substitution corresponding to SEQ ID NO:81, wherein the substitution is:

(a) C37D and C99F;
(b) C37H;
(c) C37Y;
(d) C37Y and C99A;
(e) C37Y and C99V;
(f) C37E and C99F;
(g) C37Y and C99I;
(h) C37E;
(i) C37K and C99F;
(j) C37D;
(k) C37D and C99V;
(l) C37D and C99A;
(m) C37H and C99V;
(n) C37E and C99V;
(o) C37N and C99A;
(p) C37N and C99F;
(q) C37E and C99A;
(r) C37N and C99V;
(s) C37Q and C99I;
(t) C37T;
(u) C37Y and C99L;
(v) C37H and C99L;
(w) C99F;

(x) C37Q;
(y) C37N;
(z) C37H and C99A;
(aa) C37Y and C99F;
(bb) C37K;
(cc) C37Q and C99A;
(dd) C37R and C99I;
(ee) C37A and C99V;
(ff) C37A and C99A;
(gg) C37A and C99I;
(hh) C37A and C99L;
(ii) C37Q and C99V;
(jj) C37Q and C99L;
(kk) C37N and C99I;
(ll) C37N and C99L;
(mm) C37E and C99I;
(nn) C37E and C99L;
(oo) C37D and C99I;
(pp) C37D and C99L;
(qq) C37R and C99V;
(rr) C37R and C99A;
(ss) C37R and C99L;
(tt) C37R;
(uu) C37K and C99V;
(vv) C37K and C99A;
(ww) C37K and C99I; or
(xx) C37K and C99L.

In some embodiments, the at least one amino acid variation in the non-natural CBCAS is a substitution of one or more positively-charged residues in αA and αC in wild-type CBCAS, thereby reducing the charge repulsion, forming a salt bridge, and/or increasing van der Waals interaction between αA and αC as described herein. In some embodiments, the at least one amino acid variation in the non-natural CBCAS is a deletion of one or more positively-charged residues, or a deletion of one or more amino acids near (e.g., within 1 to 10 amino acids, within 1 to 5 amino acids, within 1 to 4 amino acids, within 1 to 3 amino acids, or within 1 to 2 amino acids) of one or more positively-charged residues in αA and αC in wild-type CBCAS and reduces their charge repulsion, forms a salt bridge, and/or increases van der Waals interaction between αA and αC as described herein. In some embodiments, the at least one amino acid variation in the non-natural CBCAS is an insertion of one or more amino acids near (e.g., within 1 to 10 amino acids, within 1 to 5 amino acids, within 1 to 4 amino acids, within 1 to 3 amino acids, or within 1 to 2 amino acids) of one or more positively-charged residues in αA and αC in wild-type CBCAS and reduces their charge repulsion, forms a salt bridge, and/or increases van der Waals interaction between αA and αC as described herein.

In some embodiments, the at least one amino acid variation, e.g., an insertion, deletion, or substitution in the non-natural CBCAS provides resistance to protease degradation. For example, the amino acid variation can disrupt a protease target sequence and/or a protease binding site, or the amino acid variation can recruit a protease inhibitor. Protein variants for increasing protease resistance is further discussed, e.g., in Ahmad et al., Protein Sci 21(3):433-446 (2012) and Heard et al., J Med Chem 56(21):8339-8351 (2013).

In some embodiments, the non-natural CBCAS comprises a substitution at K36, E40, K101, K102, or a combination thereof. In some embodiments, the non-natural CBCAS comprises a substitution of K36, E40, K101, K102, or a combination thereof, with a charged amino acid. Charged amino acids are described herein. In some embodiments, the charged amino acid is D, E, or R. In some embodiments, K36, E40, K101, K102, or a combination thereof, is independently substituted with D, E, or R. In some embodiments, the non-natural CBCA comprises K36D. In some embodiments, the non-natural CBCA comprises K36E. In some embodiments, the non-natural CBCA comprises K36R. In some embodiments, the non-natural CBCA comprises E40D. In some embodiments, the non-natural CBCA comprises E40R. In some embodiments, the non-natural CBCA comprises K101D. In some embodiments, the non-natural CBCA comprises K101E. In some embodiments, the non-natural CBCA comprises K101R. In some embodiments, the non-natural CBCA comprises K102D. In some embodiments, the non-natural CBCA comprises K102E. In some embodiments, the non-natural CBCA comprises K102R.

In some embodiments, the non-natural CBCAS comprises: a substitution of K36, E40, K101, K102, or a combination thereof, with a charged amino acid; a substitution selected from C37A, C37D, C37H, C37Y, C37E, C37K, C37N, C37Q, C37T and C37R; a substitution selected from C99A, C99I, C99V, C99L, and C99F; or any combination thereof. In some embodiments, the non-natural CBCAS comprises: a substitution of K36, E40, K101, K102, or a combination thereof, with a charged amino acid; a substitution selected from C37A, C37D, C37E, C37K, C37N, C37Q, and C37R; a substitution selected from C99A, C99I, C99V, and C99L; or any combination thereof.

In some embodiments, the non-natural CBCAS comprises: a substitution selected from C37A, C37D, C37E, C37K, C37N, C37Q, and C37R; a substitution selected from C99A, C99I, C99V, and C99L; a substitution selected from K36D, K36E, and K36R; a substitution selected from E40D and E40R; a substitution selected from K101D, K101E, K101R; a substitution selected from K102D, K102E, and K102R; or any combination thereof.

In some embodiments, the non-natural CBCAS comprises K36D; a substitution selected from C37A, C37D, C37E, C37K, C37N, C37Q, and C37R; and a substitution selected from C99A, C99I, C99V, and C99L. In some embodiments, the non-natural CBCAS comprises K36E; a substitution selected from C37A, C37D, C37E, C37K, C37N, C37Q, and C37R; and a substitution selected from C99A, C99I, C99V, and C99L. In some embodiments, the non-natural CBCAS comprises K36R; a substitution selected from C37A, C37D, C37E, C37K, C37N, C37Q, and C37R; and a substitution selected from C99A, C99I, C99V, and C99L.

In some embodiments, the non-natural CBCAS comprises E40D; a substitution selected from C37A, C37D, C37E, C37K, C37N, C37Q, and C37R; and a substitution selected from C99A, C99I, C99V, and C99L. In some embodiments, the non-natural CBCAS comprises E40R; a substitution selected from C37A, C37D, C37E, C37K, C37N, C37Q, and C37R; and a substitution selected from C99A, C99I, C99V, and C99L.

In some embodiments, the non-natural CBCAS comprises K101D; a substitution selected from C37A, C37D, C37E, C37K, C37N, C37Q, and C37R; and a substitution selected from C99A, C99I, C99V, and C99L. In some embodiments, the non-natural CBCAS comprises K101E; a substitution selected from C37A, C37D, C37E, C37K, C37N, C37Q, and C37R; and a substitution selected from C99A, C99I, C99V, and C99L. In some embodiments, the non-natural CBCAS comprises K101R; a substitution selected from C37A, C37D, C37E, C37K, C37N, C37Q, and C37R; and a substitution selected from C99A, C99I, C99V, and C99L.

In some embodiments, the non-natural CBCAS comprises K102D; a substitution selected from C37A, C37D, C37E, C37K, C37N, C37Q, and C37R; and a substitution selected from C99A, C99I, C99V, and C99L. In some embodiments, the non-natural CBCAS comprises K102E; a substitution selected from C37A, C37D, C37E, C37K, C37N, C37Q, and C37R; and a substitution selected from C99A, C99I, C99V, and C99L. In some embodiments, the non-natural CBCAS comprises K102R; a substitution selected from C37A, C37D, C37E, C37K, C37N, C37Q, and C37R; and a substitution selected from C99A, C99I, C99V, and C99L.

In some embodiments, the non-natural CBCAS comprises C37A and one or more substitutions selected from K36D, K36E, K36R, E40D, E40R, K101D, K101E, K101R, K102D, K102E, and K102R. In some embodiments, the non-natural CBCAS comprises C37D and one or more substitutions selected from K36D, K36E, K36R, E40D, E40R, K101D, K101E, K101R, K102D, K102E, and K102R. In some embodiments, the non-natural CBCAS comprises C37E and one or more substitutions selected from K36D, K36E, K36R, E40D, E40R, K101D, K101E, K101R, K102D, K102E, and K102R. In some embodiments, the non-natural CBCAS comprises C37K and one or more substitutions selected from K36D, K36E, K36R, E40D, E40R, K101D, K101E, K101R, K102D, K102E, and K102R. In some embodiments, the non-natural CBCAS comprises C37N and one or more substitutions selected from K36D, K36E, K36R, E40D, E40R, K101D, K101E, K101R, K102D, K102E, and K102R. In some embodiments, the non-natural CBCAS comprises C37Q and one or more substitutions selected from K36D, K36E, K36R, E40D, E40R, K101D, K101E, K101R, K102D, K102E, and K102R. In some embodiments, the non-natural CBCAS comprises C37R and one or more substitutions selected from K36D, K36E, K36R, E40D, E40R, K101D, K101E, K101R, K102D, K102E, and K102R.

In some embodiments, the non-natural CBCAS comprises: a substitution selected from (a) C37D and C99F; (b) C37H; (c) C37Y; (d) C37Y and C99A; (e) C37Y and C99V; (f) C37E and C99F; (g) C37Y and C99I; (h) C37E; (i) C37K and C99F; (j) C37D; (k) C37D and C99V; (l) C37D and C99A; (m) C37H and C99V; (n) C37E and C99V; (o) C37N and C99A; (p) C37N and C99F; (q) C37E and C99A; (r) C37N and C99V; (s) C37Q and C99I; (t) C37T; (u) C37Y and C99L; (v) C37H and C99L; (w) C99F; (x) C37Q; (y) C37N; (z) C37H and C99A; (aa) C37Y and C99F; (bb) C37K; (cc) C37Q and C99A; (dd) C37R and C99I; (ee) C37A and C99V; (ff) C37A and C99A; (gg) C37A and C99I; (hh) C37A and C99L; (ii) C37Q and C99V; (jj) C37Q and C99L; (kk) C37N and C99I; (ll) C37N and C99L; (mm) C37E and C99I; (nn) C37E and C99L; (oo) C37D and C99I; (pp) C37D and C99L; (qq) C37R and C99V; (rr) C37R and C99A; (ss) C37R and C99L; (tt) C37R; (uu) C37K and C99V; (vv) C37K and C99A; (ww) C37K and C99I; and (xx) C37K and C99L; and one or more substitutions selected from K36D, K36E, K36R, E40D, E40R, K101D, K101E, K101R, K102D, K102E, and K102R.

In some embodiments, the non-natural CBCAS comprises position C37 substituted with D, E, R, or K; position C99 substituted with F; position K36, K102, or both are independently substituted with D, E, or R; position E40 is substituted with D or R; and position K101 unsubstituted or substituted with R, wherein the position corresponds to SEQ ID NO:81. In some embodiments, the non-natural CBCAS comprises C37 substituted with D, E, R, or K; C99 substituted with F; and K36 substituted with D, E, or R. In some embodiments, the non-natural CBCAS comprises C37 substituted with D, E, R, or K; C99 substituted with F; and E40 substituted with D or R. In some embodiments, the non-natural CBCAS comprises C37 substituted with D, E, R, or K; C99 substituted with F; and K102 substituted with D, E, or R. In some embodiments, the non-natural CBCAS comprises C37 substituted with D, E, R, or K; C99 substituted with F; and K101 substituted with R. In some embodiments, the non-natural CBCAS comprises C37K, K36D, and K101R. In some embodiments, the amino acid substitutions described herein stabilize the structure of the non-natural CBCAS.

In some embodiments, the non-natural CBCAS comprises at least one substitution at a position corresponding to SEQ ID NO:81, wherein the substitution is:

(a) K36D, C37K, E40D, C99F, and K101R;
(b) K36D, C37K, E40D, C99F, K101R and K102R;
(c) K36D, C37K, C99F, and K101R;
(d) K36D, C37K, C99F, K101R and K102R;
(e) K36R, C37K, E40D, C99F, K101R and K102R;
(f) K36D, C37E, C99F, and K101R;
(g) K36R, C37E, C99F, K101R, and K102R;
(h) C37E, C99F, K101R, and K102E;
(i) K36E, C37K, C99F, and K101R;
(j) K36D, C37R, E40D, C99F, K101R, and K102D;
(k) K36D, C37K, E40D, and C99F;
(l) K36R, C37K, E40R, C99F, K101R, and K102E;
(m) K36R, C37E, E40D, C99F, K101R, and K102E;
(n) K36E, C37R, E40D, C99F, and K101R;
(o) K36D, C37R, C99F, and K101R;
(p) K36D, C37R, E40D, C99F, K101R, and K102R;
(q) K36R, C37R, C99F, K101R, and K102R;
(r) K36D, C37E, E40D, C99F, K101R, and K102R;
(s) K36D, C37K, and C99F;
(t) K36D, C37R, E40D, C99F, K101R, and K102E;
(u) K36D, C37E, C99F, K101R, and K102R;
(v) C37D, C99F, K101R, and K102E;
(w) K36E, C37E, C99F, K101R, and K102R;
(x) K36R, C37E, C99F, K101R, and K102R;
(y) K36R, C37E, E40D, C99F, K101R, and K102R;
(z) K36D, C37D, C99F, and K102E;
(aa) K36R, C37D, E40D, C99F, K101R, and K102R;
(bb) C37D, C99F, K101R, and K102R;
(cc) K36D, C37D, C99F, K101R, and K102R;
(dd) K36D, C37D, C99F, K101R, and K102D;
(ee) C37E, C99F, K101R, and K102E;
(ff) K36R, C37E, E40D, C99F, and K101R;
(gg) K36D, C37D, E40R, C99F, and K101R;
(hh) K36D, C37D, C99F, K101R, and K102E;
(ii) K36D, C37K, C99F, K101R, and K102R; or
(jj) K36E, C37R, E40R, C99F, K101R, and K102E.

In some embodiments, the non-natural CBCAS comprises at least one amino acid substitution at position C37, E40, V46, Q58, L59, N89, V90, C99, K102, R296, V321, V358, K366, K513, N516, N528, H544, or a combination thereof, wherein the amino acid position corresponds to SEQ ID NO:81. In some embodiments, the non-natural CBCAS comprises at least one amino acid substitution at position C37, C99, and one or more of E40, V46, Q58, L59, N89, V90, K102, R296, V321, V358, K366, K513, N516, N528, and H544, wherein the amino acid position corresponds to SEQ ID NO:81. In some embodiments, the substitution is C37A, E40R, V46E, Q58E, L59T, N89D, V90D, C99A, K102E, R296E, V321T, V358T, K366D, K513D, N516E, N528T, H544Y, or a combination thereof. In some embodiments, the non-natural CBCAS comprises at least one amino acid substitution at position C37, C99, and one or more of E40, L59, N89, V90, K102, R296, V321, and N516, wherein the amino acid position corresponds to SEQ ID NO:81. In some embodiments, the substitution is C37A, E40R, L59T, N89D, V90D, K102E, R296E, V321T, N516E, or a combination thereof. In some embodiments, the substitution is C37A, E40R, N89D, V90D, C99A, and K102E. In some embodiments, the substitution is C37A, E40R, L59T, N89D, C99A, K102E, and V321T. In some embodiments, the substitution is C37A, E40R, L59T, N89D, C99A, K102E, R296E, V321T, and N516E. In some embodiments, the substitution is C37A, E40R, L59T, N89D, C99A, K102E, and R296E. In some embodiments, the substitution comprises C37A, E40R, Q58E, L59T, N89D, V90T, C99A, K102E, R296E, V321T, V358T, N516E, and N528T.

In some embodiments, the non-natural CBCAS comprises:

1) C37A, E40R, L59T, N89D, C99A, K102E, V321T, R296E and N516E;
2) C37A, E40R, L59T, N89D, C99A, K102E, V321T, V358T and N516E;
3) C37A, E40R, L59T, N89D, C99A, K102E, V321T, V90D and N516E;
4) C37A, E40R, L59T, N89D, C99A, K102E, V321T, R296E and N528T;
5) C37A, E40R, L59T, N89D, C99A, K102E, V321T, K366D and N516E;
6) C37A, E40R, L59T, N89D, C99A, K102E, V321T, R296E and V358T;
7) C37A, E40R, L59T, N89D, C99A, K102E, V321T, V90D and R296E;
8) C37A, E40R, N89D, C99A, K102E, V321T, and N516E;
9) C37A, E40R, L59T, N89D, C99A, K102E, V321T, V358T and N528T;
10) C37A, E40R, L59T, N89D, C99A, K102E, V321T, Q58E and R296E;
11) C37A, E40R, L59T, C99A, K102E, V321T, and R296E;
12) C37A, E40R, L59T, N89D, C99A, K102E, V321T, V90D and N528T;
13) C37A, E40R, L59T, N89D, C99A, K102E, V321T, K366D and N528T;
14) C37A, E40R, L59T, N89D, C99A, K102E, V321T, K513D and N516E;
15) C37A, E40R, L59T, N89D, C99A, K102E, V321T, Q58E and N516E;
16) C37A, E40R, L59T, N89D, C99A, K102E, V321T, Q58E and V90D;
17) C37A, E40R, L59T, N89D, C99A, K102E, V321T, Q58E and N528T;
18) C37A, E40R, L59T, C99A, K102E, V321T, and N516E;
19) C37A, E40R, L59T, N89D, C99A, K102E, V321T, V358T and H544Y;
20) C37A, E40R, L59T, N89D, C99A, K102E, V321T, Q58E and V358T;
21) C37A, E40R, L59T, N89D, C99A, K102E, V321T, V358T and K366D;
22) C37A, E40R, L59T, C99A, K102E, V321T, and V90D;
23) C37A, E40R, L59T, N89D, C99A, K102E, V321T, V46E and R296E;
24) C37A, E40R, L59T, N89D, C99A, K102E, V321T, R296E and H544Y;
25) C37A, E40R, L59T, N89D, C99A, K102E, V321T, V46E and N516E;
26) C37A, L59T, N89D, C99A, K102E, V321T, and N516E;
27) C37A, E40R, L59T, N89D, C99A, K102E, and N516E;
28) C37A, E40R, L59T, C99A, K102E, V321T, and N528T;
29) C37A, E40R, L59T, N89D, C99A, K102E, and R296E;
30) C37A, E40R, L59T, N89D, C99A, K102E, V321T, R296E and K513D;
31) C37A, E40R, N89D, C99A, K102E, V321T, and N528T;
32) C37A, E40R, L59T, N89D, C99A, K102E, V321T, K513D and N528T;
33) C37A, E40R, L59T, N89D, C99A, K102E, V321T, K366D and K513D;
34) C37A, E40R, N89D, C99A, K102E, V321T, and V358T;
35) C37A, E40R, N89D, C99A, K102E, V321T, and K366D;
36) C37A, E40R, L59T, C99A, K102E, V321T, N89S and R296E;
37) C37A, E40R, L59T, N89D, C99A, K102E, and V90T;
38) C37A, E40R, L59T, N89D, C99A, K102E, V321T, Q58E and H544Y;
39) C37A, E40R, N89D, C99A, K102E, V321T, and R296E;
40) C37A, E40R, L59T, N89D, C99A, K102E, V321T, V90D and H544Y;
41) C37A, E40R, L59T, C99A, K102E, V321T, N89S and N516E;
42) C37A, E40R, L59T, N89D, C99A, K102E, and Q58E;
43) C37A, E40R, N89D, C99A, K102E, V321T, and H544Y;
44) C37A, E40R, L59T, N89D, C99A, K102E, V321T, V46E and V90T;
45) C37A, E40R, L59T, N89D, C99A, K102E, V321T, V90T and K366D;
46) C37A, E40R, L59T, N89D, C99A, K102E, V321T, V358T and K513D;
47) C37A, E40R, N89D, C99A, and K102E;
48) C37A, L59T, N89D, C99A, K102E, V321T, and R296E;
49) C37A, E40R, L59T, N89D, C99A, K102E, V321T, V46E and K366D;
50) C37A, E40R, L59T, N89D, C99A, K102E, and K366D;
51) C37A, E40R, L59T, N89D, C99A, K102E, V321T, Q58E and K366D;
52) C37A, E40R, L59T, N89D, C99A, K102E, and N528T;
53) C37A, E40R, N89D, C99A, K102E, V321T, and Q58E;
54) C37A, E40R, L59T, N89D, C99A, K102E, V321T, V46E and V358T;
55) R296E; or
56) N516E;

wherein the amino acid position corresponds to SEQ ID NO:81.

In some embodiments, the non-natural CBCAS comprises an amino acid substitution at C37, C99, E40, L59, N89, C99, K102, R296, and any one of: Q58, V90, V358, N528, and K366, wherein the amino acid position corresponds to SEQ ID NO:81. In some embodiments, the non-natural CBCAS comprises C37A, E40R, L59T, N89D, C99A, K102E, R296E, and any one of: Q58E, V90T, V358T, N528T, and K366D, wherein the amino acid position corresponds to SEQ ID NO:81.

In some embodiments, the non-natural CBCAS comprises an amino acid substitution at C37, C99, E40, L59, N89, C99, K102, R296, and two substitutions at: (1) Q58 and V90; (2)

Q58 and V358; (3) Q58 and N528; (4) Q58 and K366; (5) V90 and N528; (6) V90 and K366; (7) V358 and K366; (8) K366 and N528; or (9) V358 and N528, wherein the amino acid position corresponds to SEQ ID NO:81. In some embodiments, the non-natural CBCAS comprises C37A, E40R, L59T, N89D, C99A, K102E, R296E, and two substitutions selected from: (1) Q58E and V90T; (2) Q58E and V358T; (3) Q58E and N528T; (4) Q58E and K366D; (5) V90T and N528T; (6) V90T and K366D; (7) V358T and K366D; (8) K366D and N528T; or (9) V358T and N528T, wherein the amino acid position corresponds to SEQ ID NO:81.

In some embodiments, the non-natural CBCAS comprises an amino acid substitution at C37, C99, E40, L59, N89, C99, K102, R296, and three substitutions at: (1) Q58, V90, and V358; (2) Q58, V90, and N528; (3) Q58, V358, and N528; (4) V90, V358, and N528; or (5) V358, K366, and N528, wherein the amino acid position corresponds to SEQ ID NO:81. In some embodiments, the non-natural CBCAS comprises C37A, E40R, L59T, N89D, C99A, K102E, R296E, and three substitutions selected from: (1) Q58E, V90T, and V358T; (2) Q58E, V90T, and N528T; (3) Q58E, V358T, and N528T; (4) V90T, V358T, and N528T; or (5) V358T, K366D, and N528T, wherein the amino acid position corresponds to SEQ ID NO:81.

In some embodiments, the non-natural CBCAS comprises an amino acid substitution at C37, C99, E40, L59, N89, C99, K102, R296, and four substitutions at: (1) Q58E, V358T, K366D, and N528T; (2) Q58E, V90T, K366D, and N528T; or (3) V90T, V358T, K366D, and N528T, wherein the amino acid position corresponds to SEQ ID NO:81. In some embodiments, the non-natural CBCAS comprises C37A, E40R, L59T, N89D, C99A, K102E, R296E, and four substitutions selected from: (1) Q58E, V358T, K366D, and N528T; (2) Q58E, V90T, K366D, and N528T; or (3) V90T, V358T, K366D, and N528T, wherein the amino acid position corresponds to SEQ ID NO:81.

In some embodiments, the non-natural CBCAS comprises C37A, E40R, Q58E, L59T, N89D, V90T, C99A, K102E, R296E, V321T, V358T, N516E, and N528T, wherein the amino acid position corresponds to SEQ ID NO:81. In some embodiments, the non-natural CBCAS comprises:

1) C37A, E40R, Q58E, L59T, N89D, V90T, C99A, K102E, R296E, V321T, V358T, K366D, N516E, and N528T;
2) C37A, E40R, Q58E, N89D, V90T, C99A, K102E, R296E, V321T, V358T, N516E, and N528T;
3) C37A, E40R, Q58E, L59T, N89D, V90T, C99A, K102E, R296E, V321T, V358T, K366D, and N516E;
4) C37A, E40R, Q58E, V90T, C99A, K102E, R296E, V321T, V358T, N516E, and N528T;
5) C37A, E40R, Q58E, N89D, V90T, C99A, K102E, R296E, V321T, V358T, K366D, N516E, and N528T; or
6) C37A, E40R, Q58E, L59T, V90T, C99A, K102E, R296E, V321T, V358T, K366D, N516E, and N528T, wherein the amino acid position corresponds to SEQ ID NO:81.

In some embodiments, the non-natural CBCAS comprises the amino acid substitutions C37A, E40R, N89D, V90D, C99A, and K102E, wherein the amino acid position corresponds to SEQ ID NO:81. In some embodiments, the non-natural CBCAS comprises the amino acid substitutions C37A, E40R, L59T, N89D, C99A, K102E, and V321T, wherein the amino acid position corresponds to SEQ ID NO:81. In some embodiments, the non-natural CBCAS comprises the amino acid substitutions C37A, E40R, L59T, N89D, C99A, K102E, R296E, V321T, and N516E, wherein the amino acid position corresponds to SEQ ID NO:81. In some embodiments, the non-natural CBCAS comprises the amino acid substitutions C37A, E40R, L59T, N89D, C99A, K102E, and R296E, wherein the amino acid position corresponds to SEQ ID NO:81.

In some embodiments, the at least one amino acid variation is not within an active site of the non-natural CBCAS. As described herein, "active site" refers to a region in an enzyme that may be important for catalysis, substrate binding, and/or cofactor binding. In some embodiments, the active site of a natural or non-natural CBCAS comprises amino acid residues involved in CBGA binding, FAD binding, and/or cyclization of CBGA. In some embodiments, the active site of the non-natural CBCAS comprises amino acid residues involved in FAD binding. In some embodiments, the active site of the non-natural CBCAS comprises amino acid residues involved in FAD binding. In some embodiments, the active site of the non-natural CBCAS comprises amino acid residues Q69, R108, T109, R110, S111, G112, G113, H114, D115, A116, L119, S120, Y121, L132, A151, G174, Y175, C176, T178, V179, G180, V181, G182, G183, H184, S186, G189, Y190, G235, E236, G239, I240, I241, A242, F381, W444, Y481, N483, Y484, N533, A116, G174, Y175, T290, H292, G376, T379, F381, I383, L385, G410, M413, V415, Y417, E442, W444, T446, T448, E450, Y481, L482, N483, Y484, or a combination thereof (amino acid residue numbering with respect to SEQ ID NO:81). In some embodiments, the active site of the non-natural CBCAS is within positions 60-75, 105-125, 160-200, 220-250, 280-300, 350-450, 470-490, or 530-540, inclusive, of the CBCAS, wherein the position corresponds to SEQ ID NO:81.

In some embodiments, the non-natural CBCAS further comprises an affinity tag, a purification tag, a solubility tag, or a combination thereof. For example, at least 1, at least 2, at least 3, at least 4, at least 5, or at least 6 histidine residues can be appended to the C-terminus of the non-natural CBCAS of any of SEQ ID NOs: 80, 81, or 84 to provide a 6×His tag (SEQ ID NO: 89) for affinity purification by Ni-NTA. Affinity tags, purification tags, and solubility tags, and method of tagging proteins are known to one of ordinary skill in the art and described, e.g., in Kimple et al. (2013), Curr Protoc Protein Sci 73: Unit-9.9.

In some embodiments, the non-natural CBCAS described herein is capable of catalyzing the oxidative cyclization of CBGA to CBCA. In some embodiments, the non-natural CBCAS described herein has substantially the same catalytic activity as a wild-type CBCAS. In some embodiments, the non-natural CBCAS described herein has at least about 70%, at least about 75%, at least about 80%, at least about 85%, at least about 90%, at least about 95%, at least or about 99%, or at least about 100% of the catalytic activity of a wild-type CBCAS produced from its native host organism.

In some embodiments, the non-natural CBCAS described herein further catalyzes the oxidative cyclization of CBGA into $\Delta^9$-tetrahydrocannabinolic acid (THCA), cannabichromenic acid (CBCA), or both. As described herein, cannabinoid synthases such as CBCAS are capable of producing more than one cannabinoid. In some embodiments, the non-natural CBCAS is capable of catalyzing the oxidative cyclization of CBGA to THCA. In some embodiments, the non-natural CBCAS is capable of catalyzing the oxidative cyclization of CBGA into CBDA.

In some embodiments, the invention further provides a nucleic acid encoding the non-natural CBCAS described herein. In some embodiments, the nucleic acid comprises a polynucleotide sequence with at least 70%, at least 75%, at least 80%, at least 85%, at least 90%, at least 95%, at least 96%, at least 97%, at least 98%, at least 99%, or 100% sequence identity to SEQ ID NO:83. In some embodiments, the nucleic acid encoding the non-natural CBCAS is 100% identical to SEQ ID NO:83.

In some embodiments, the nucleic acid encoding the non-natural CBCAS is codon optimized. An example of a codon optimized sequence is, in one instance, a sequence optimized for expression in a bacterial host cell, e.g., *E. coli*. In some embodiments, one or more codons (e.g., about or more than about 1, 2, 3, 4, 5, 10, 15, 20, 25, 50, or all codons) in a nucleic acid sequence encoding the non-natural CBCAS described herein corresponds to the most frequently used codon for a particular amino acid in the bacterial host cell.

In some embodiments, the invention provides an expression construct comprising the nucleic acid encoding the non-natural CBCAS described herein. Expression constructs are described herein. In some embodiments, the expression construct comprises the nucleic acid encoding the non-natural CBCAS operably linked to a regulatory element. In some embodiments, the regulatory element is a bacterial regulatory element. Non-limiting examples of expression vectors are provided herein and include, e.g., pQE vectors (Qiagen), pBluescript plasmids, pNH vectors, lambda-ZAP vectors (Stratagene); pTrc99a, pKK223-3, pDR540, and pRIT2T (Pharmacia).

In some embodiments, the invention provides an engineered cell comprising the non-natural CBCAS described herein, the nucleic acid encoding the non-natural CBCAS, the expression construct comprising the nucleic acid, or a combination thereof. In some embodiments, the invention provides a method of making an isolated non-natural CBCAS comprising isolating CBCAS expressed in the engineered cell provided herein. In some embodiments, the invention provides an isolated CBCAS, wherein the isolated CBCAS is expressed and isolated from the engineered cell.

V. OLS

In some embodiments, the engineered cell of the invention further comprises an enzyme in the olivetolic acid pathway. In some embodiments, the olivetolic acid pathway comprises a natural or non-natural olivetol synthase (OLS).

In some embodiments, THCAS, CBDAS, and CBCAS catalyzes the conversion of cannabigerolic acid (CBGA) to $\Delta^9$-tetrahydrocannabinoic acid (THCA), cannabidiolic acid (CBDA), or cannabichromenic acid (CBCA). In some embodiments, CBGA is produced from olivetolic acid (OA) and geranyldiphosphate (GPP). In some embodiments, the engineered cells of the invention have higher levels of available CBGA, GPP, and/or OA (and derivatives or analogs thereof) as compared to a naturally-occurring, non-engineered cell for increased production of THCA, CBDA, and/or CBCA.

As illustrated in FIG. 4, intracellular hexanoyl-CoA (Hex-CoA) can be combined with 3x malonyl-CoA (Mal-CoA) by olivetol synthase (OLS; also called 3,5,7-trioxododecanoyl-CoA synthase and tetraketide synthase, EC 2.3.1.206) or variant thereof, to form a tetraketide (e.g., 3,5,7-trioxododecanoyl-CoA), which is subsequently converted to OA by olivetolic acid cyclase (OAC; EC 4.4.1.26) or variant thereof. Although the metabolic pathway is illustrated with reference to certain precursors and intermediates, it is understood that analogs may be substituted in essentially the same reactions. For example, it is understood that Hex-CoA analogs, including other acyl-CoA, can be used in place of Hex-CoA. Exemplary analogs include, but are not limited to, acetyl-CoA, propionyl-CoA, butyryl-CoA, pentanoyl-CoA, heptanoyl-CoA, octanoyl-CoA, nonanoyl-CoA, decanoyl-CoA, generally any C2-Cao acyl-CoA, and an aromatic acid CoA, e.g., benzoic, chorismic, phenylacetic, and phenoxyacetic acid-CoA.

The precursors Mal-CoA and Hex-CoA (or other acyl-CoA described herein) can be a limiting factor in the production of OA or OA analogs. In embodiments, the invention provides methods of increasing the production and availability of precursors Mal-CoA and Hex-CoA (or other acyl-CoA described herein), e.g., by increasing the precursor production, and/or by limiting precursor metabolism through competing (e.g., non-OA producing pathways). For example, as shown in FIG. 4, the tri- and tetraketides produced by OLS can be hydrolyzed into various byproducts such as, e.g., pentyl diacetic lactone (PDAL), hexanoyl triacetic acid lactone (HTAL), or olivetol. In some embodiments, the engineered cells of the invention have increased production of one or more precursors (e.g., Mal-CoA, Hex-CoA, OA, and/or CBGA) of THCA, CBDA, and/or CBCA. In some embodiments, the engineered cells of the invention have limited precursor metabolism through competing (non-OA-producing) pathways.

In some embodiments, the engineered cells of the invention have increased production of OA precursors, e.g., Mal-CoA and/or acyl-CoA (such as, e.g., Hex-CoA or any other acyl-CoA described herein). In some embodiments, the non-natural OLS preferentially catalyzes the condensation of Mal-CoA and acyl-CoA (such as, e.g., Hex-CoA or any other acyl-CoA described herein) to form a polyketide (such as, e.g., 3,5,7-trioxododecanoyl-CoA and 3,5,7-trioxododecanoate and their analogs) over PDAL, HTAL, or other lactone analogs compared with a wild-type OLS.

In some embodiments, the engineered cells express an exogenous (e.g., a heterologous) or overexpress an exogenous or endogenous OLS. In some embodiments, the OLS is a natural OLS, e.g., a wild-type OLS. In some embodiments, the OLS is a non-natural OLS. In some embodiments, the OLS comprises one or more amino acid substitutions relative to a wild-type OLS. In some embodiments, the one or more amino acid substitutions in the non-natural OLS increases the activity of the OLS as compared to a wild-type OLS.

Olivetol synthase (OLS) belongs to plant type III polyketide synthases (PKS), which are a group of condensing enzymes that catalyze the initial key reactions in the biosynthesis of a myriad of secondary metabolites. All of the plant type III polyketide synthases that have been characterized are homodimeric proteins. Each monomer of the dimeric protein contains its own active site and catalyzes the sequential condensation of starter CoA molecule and one acyl unit from malonyl-CoA, independently. Each condensation step is associated with one decarboxylation step. OLS enzymes are classified as EC:2.3.1.206 under the Enzyme Commission nomenclature. OLS enzymes have structural similarities with plant type III PKS enzymes. The OLS enzyme comprises conserved Cys157-His297-Asn330 catalytic triad, and the "gatekeeper" Phe208 corresponding to the amino acid positions of SEQ ID NO:3. These amino acid residues are conserved for all other OLS homologs corresponding to SEQ ID NOs:26-35.

In some embodiments, the OLS has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to any one of SEQ ID NOs:3 or 26-35. In some embodiments, the non-natural OLS comprises an amino acid variations at position: 125, 126, 185, 187, 190, 204, 209, 210, 211, 249, 250, 257, 259, 331, 332, or a combination thereof, wherein the position corresponds to SEQ ID NO:3.

Although the amino acid positions of OLS described herein are with reference to the corresponding amino acid sequence of SEQ ID NO:3, it is understood that the amino acid sequence of a non-natural OLS can include an amino acid variation at an equivalent position corresponding to a variant of SEQ ID NO:3, e.g., SEQ ID NOs:27-36. One of skill in the art would understand that alignment methods can be used to align variations of SEQ ID NO:3 (e.g., OLS variants, e.g., corresponding to SEQ ID NOs:27-36) to identify the position in the OLS variant that corresponds to a position in SEQ ID NO:3.

In some embodiments, the non-natural OLS comprises an amino acid substitution according to Table 1.

TABLE 1

Substitutions of Olivetol Synthase

| Position | Substitution |
|---|---|
| A125 | G, S, T, C, Y, H, N, Q, D, E, K, R |
| S126 | G, A |
| D185 | G, A, S, P, C, T, N |
| M187 | G, A, S, P, C, T, D, N, E, Q, H, V, L, I, K, R |
| L190 | G, A, S, P, C, T, D, N, E, Q, H, V, M, I, K, R |
| G204 | A, C, P, V, L, I, M, F, W |
| G209 | A, C, P, V |
| D210 | A, C, P, V |
| G211 | A, C, P, V |
| G249 | A, C, P, V, L, I, M, F, W, S, T, Y, H, N, Q, D, E, K, R |
| G250 | A, C, P, V, L, I, M, F, W, S, T, Y, H, N, Q, D, E, K, R |
| L257 | V, M, I, K, R, F, Y, W, S, T, C, H, N, Q, D, E |
| F259 | G, A, C, P, V, L, I, M, Y, W, S, T, Y, H, N, Q, D, E, K, R |
| M331 | G, A, S, P, C, T, D, N, E, Q, H, V, L, I, K, R |
| S332 | G, A |

In some embodiments, the non-natural OLS comprises an amino acid variant at position: A125, S126, D185, M187, L190, G204, G209, D210, G211, G249, G250, L257, F259, M331, S332, or a combination thereof, wherein the position corresponds to SEQ ID NO:3.

In some embodiments, the non-natural OLS comprises an amino acid substitution at position: A125G, A125S, A125T, A125C, A125Y, A125H, A125N, A125Q, A125D, A125E, A125K, A125R, S126G, S126A, D185G, D185G, D185A, D185S, D185P, D185C, D185T, D185N, M187G, M187A, M187S, M187P, M187C, M187T, M187D, M187N, M187E, M187Q, M187H, M187H, M187V, M187L, M187I, M187K, M187R, L190G, L190A, L190S, L190P, L190C, L190T, L190D, L190N, L190E, L190Q, L190H, L190V, L190M, L190I, L190K, L190R, G204A, G204C, G204P, G204V, G204L, G204I, G204M, G204F, G204W, G204S, G204T, G204Y, G204H, G204N, G204Q, G204D, G204E, G204K, G204R, G209A, G209C, G209P, G209V, G209L, G209I, G209M, G209F, G209W, G209S, G209T, G209Y, G209H, G209N, G209Q, G209D, G209E, G209K, G209R, D210A, D210C, D210P, D210V, D210L, D210I, D210M, D210F, D210W, D210S, D210T, D210Y, D210H, D210N, D210Q, D210E, D210K, D210R, G211A, G211C, G211P, G211V, G211L, G211I, G211M, G211F, G211W, G211S, G211T, G211Y, G211H, G211N, G211Q, G211D, G211E, G211K, G211R, G249A, G249C, G249P, G249V, G249L, G249I, G249M, G249F, G249W, G249S, G249T, G249Y, G249H, G249N, G249Q, G249D, G249E, G249K, G249R, G249S, G249T, G249Y, G250A, G250C, G250P, G250V, G250L, G250I, G250M, G250F, G250W, G250S, G250T, G250Y, G250H, G250N, G250Q, G250D, G250E, G250K, G250R, L257V, L257M, L257I, L257K, L257R, L257F, L257Y, L257W, L257S, L257T, L257C, L257H, L257N, L257Q, L257D, L257E, F259G, F259A, F259C, F259P, F259V, F259L, F259I, F259M, F259Y, F259W, F259S, F259T, F259Y, F259H, F259N, F259Q, F259D, F259E, F259K, F259R, M331G, M331A, M331S, M331P, M331C, M331T, M331D, M331N, M331E, M331Q, M331H, M331V, M331L, M331I, M331K, M331R, S332G, S332A, or a combination thereof, wherein the position corresponds to SEQ ID NO:3.

In some embodiments, the invention provides a composition comprising a non-natural cannabinoid synthase (e.g., the non-natural THCAS, CBDAS, and/or CBCAS described herein) and a non-natural OLS described herein. In some embodiments, the invention provides an engineered cell comprising a non-natural cannabinoid synthase (e.g., THCAS, CBDAS, and/or CBCAS) and a non-natural OLS. In some embodiments, the invention provides one or more nucleic acids encoding a non-natural cannabinoid synthase (e.g., the non-natural THCAS, CBDAS, and/or CBCAS) and a non-natural OLS. In some embodiments, the invention provides an expression construct comprising the one or more nucleic acids. In some embodiments, the invention provides an engineered cell comprising the one or more nucleic acids. In some embodiments, the invention provides an engineered cell comprising the expression construct. In some embodiments, the expression construct comprises a single expression vector. In some embodiments, the expression construct comprises more than one expression vector. In some embodiments, the engineered cell is capable of expressing THCAS, CBDAS, and/or CBCAS. In some embodiments, the engineered cell is capable of producing THCA, CBDA, and/or CBCA.

VI. OAC

In some embodiments, the engineered cell of the invention further comprises an enzyme in the olivetolic acid pathway. In some embodiments, the olivetolic acid pathway comprises a natural or non-natural olivetolic acid cyclase (OAC). In some embodiments, the polyketide produced from OLS, e.g., a natural or non-natural OLS described herein, is converted to olivetolic acid and its analogs by OAC.

Olivetolic acid cyclase (OAC) is a dimeric α+β barrel (DABB) protein that is similar to DABB-type polyketide cyclase enzymes from *Streptomyces* and to stress-responsive proteins in plants. OAC is classified under #C:4.4.1.26 under the Enzyme Commission nomenclature. OAC is a homodimeric protein with conformational differences between monomers A and B. See, e.g., Yang et al., FEBS J 283(6): 1088-1106 (2016).

In some embodiments, the OAC has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:4. In some embodiments, the OAC has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:5. In some embodiments, the amino acid sequence of the non-natural OAC comprises SEQ ID NO:5.

Although the amino acid positions of OAC described herein are with reference to the corresponding amino acid sequence of SEQ ID NO:4, it is understood that the amino acid sequence of a non-natural OAC can include an amino acid variation at an equivalent position corresponding to a variant of SEQ ID NO:4, e.g., SEQ ID NO:5. One of the skill in the art would understand that alignment methods can be used to align variations of SEQ ID NO:4 (i.e., OAC variants) to identify the position in the OAC variant that corresponds to a position in SEQ ID NO:4.

In some embodiments, the non-natural OAC comprises an amino acid substitution according to Tables 2 and 3.

TABLE 2

Substitutions of Olivetolic Acid Cyclase

| Position | Mutation |
|---|---|
| H5 | G, A, C, P, V, L, I, M, F, Y, W |
| I7 | G, A, C, P, V, L, M, F, Y, W |
| L9 | G, A, C, P, V, I, M, F, Y, W |
| F23 | G, A, C, P, V, L, I, M, Y, W |
| F24 | G, A, C, P, V, L, I, M, Y, W |
| Y27 | G, A, C, P, V, L, I, M, F, W |
| V59 | G, A, C, P, L, I, M, F, Y, W |
| V61 | G, A, C, P, L, I, M, F, Y, W |
| V66 | G, A, C, P, L, I, M, F, Y, W |
| E67 | G, A, C, P, V, L, I, M, F, Y, W |
| I69 | G, A, C, P, V, L, M, F, Y, W |
| Q70 | S, T, H, N, D, E, R, K, Y |
| I73 | G, A, C, P, V, L, M, F, Y, W |
| I74 | G, A, C, P, V, L, M, F, Y, W |
| V79 | G, A, C, P, L, I, M, F, Y, W |
| G80 | A, C, P, V, L, I, M, F, Y, W |
| F81 | G, A, C, P, V, L, I, M, Y, W |
| G82 | A, C, P, V, L, I, M, F, Y, W |
| D83 | S, T, H, Q, N, E, R, K, Y |
| R86 | S, T, H, Q, N, D, E, K, Y |
| W89 | G, A, C, P, V, L, I, M, F, Y |
| L92 | G, A, C, P, V, I, M, F, Y, W |
| I94 | G, A, C, P, V, L, M, F, Y, W |
| D96 | S, T, H, Q, N, E, R, K, Y |
| V46* | G, A, C, P, L, I, M, F, Y, W |
| T47* | S, H, Q, N, D, E, R, K, Y |
| Q48* | S, T, H, N, D, E, R, K, Y |
| K49* | S, T, H, Q, N, D, E, R, Y |
| N50* | G, A, C, P, V, L, I, M, F, Y, W |
| K51* | S, T, H, Q, N, D, E, R, Y |

*: amino acid residues from chain B of the OAC dimer and corresponding to SEQ ID NO: 4

TABLE 3

Substitutions of Olivetolic Acid Cyclase

| Position | Analogs with larger, hydrophobic starter molecules | Analogs with smaller, hydrophobic starter molecules | Analogs with polar or charged starter molecules |
|---|---|---|---|
| H5 | G, A, C, P, V | V, M, F, Y, W, Q, E, K, R | S, T, Y, N, Q, D, E, K, R |
| I7 | G, A, C, P, V, L, M | L, M, F, Y, W, K, R | S, T, Y, H, N, Q, D, E, K, R |
| L9 | G, A, C, P, V, I, M | I, M, F, Y, W, K, R | S, T, Y, H, N, Q, D, E, K, R |
| F23 | G, A, C, P, V, L, I, M, Y, W, S, T, H, N, Q, D, E, K, R | Y, W | S, T, Y, H, N, Q, D, E, K, R |
| F24 | G, A, C, P, V, L, I, M, Y, W, S, T, H, N, Q, D, E, K, R | Y, W | S, T, Y, H, N, Q, D, E, K, R |
| Y27 | G, A, C, P, V, L, I, M, F, W, S, T, H, N, Q, D, E, K, R | F, W | S, T, H, N, Q, D, E, K, R |
| V59 | G, A, C, P | M, F, Y, W, H, Q, E, K, R | S, T, Y, H, N, Q, D, E, K, R |
| V61 | G, A, C, P | M, F, Y, W, H, Q, E, K, R | S, T, Y, H, N, Q, D, E, K, R |

TABLE 3-continued

Substitutions of Olivetolic Acid Cyclase

| Position | Analogs with larger, hydrophobic starter molecules | Analogs with smaller, hydrophobic starter molecules | Analogs with polar or charged starter molecules |
|---|---|---|---|
| G80 | A, C, P, V | A, C, P, V, L, I, M, F, Y, W, S, T, H, N, Q, D, E, K, R | S, T, Y, H, N, Q, D, E, K, R |
| F81 | G, A, C, P, V, L, I, M, Y, W, S, T, H, N, Q, D, E, K, R | Y, W | S, T, Y, H, N, Q, D, E, K, R |
| G82 | A, C, P, V | A, C, P, V, L, I, M, F, Y, W, S, T, H, N, Q, D, E, K, R | S, T, Y, H, N, Q, D, E, K, R |
| W89 | G, A, C, P, V, L, I, M, F, Y, W, S, T, H, N, Q, D, E, K, R | F, Y | S, T, Y, H, N, Q, D, E, K, R |
| L92 | G, A, C, P, V, I, M | I, M, F, Y, W, K, R | S, T, Y, H, N, Q, D, E, K, R |
| I94 | G, A, C, P, V, L, M | L, M, F, Y, W, K, R | S, T, Y, H, N, Q, D, E, K, R |

In some embodiments, the non-natural OAC comprises an amino acid variant at position: L9, F23, V59, V61, V66, E67, I69, Q70, I73, I74, V79, G80, F81, G82, D83, R86, W89, L92, or I94, V46, T47, Q48, K49, N50, K51, V46, T47, Q48, K49, N50, K51, or a combination thereof, wherein the position corresponds to SEQ ID NO:4. In some embodiments, the amino acid variant is in a first peptide (e.g., a first monomer) of an OAC dimer. In some embodiments, the amino acid variant is in a second peptide (e.g., a second monomer) of an OAC dimer.

In some embodiments, the non-natural OAC forms a dimer, wherein a first peptide of the dimer (e.g., a first monomer) of the dimer comprises an amino acid variation at position H5, I7, L9, F23, F24, Y27, V59, V61, V66, E67, I69, Q70, I73, I74, V79, G80, F81, G82, D83, R86, W89, L92, I94, D96, V46, T47, Q48, K49, N50, K51, or combination thereof, and wherein a second peptide (e.g., a second monomer) of the dimer comprises an amino acid variation at position V46, T47, Q48, K49, N50, K51, or combination thereof, wherein the position corresponds to SEQ ID NO:4. In some embodiments, the non-natural OAC forms a dimer, wherein a first peptide of the dimer comprises an amino acid variation at position: L9, F23, V59, V61, V66, E67, I69, Q70, I73, I74, V79, G80, F81, G82, D83, R86, W89, L92, I94, V46, T47, Q48, K49, N50, K51, or combination thereof, and a second peptide of the dimer comprises an amino acid variation at position: V46, T47, Q48, K49, N50, K51, or combination thereof, wherein the position corresponds to SEQ ID NO:4.

In some embodiments, the non-natural OAC has an amino acid variation at position: H5$X^1$, wherein $X^1$ is selected from G, A, C, P, V, L, I, M, F, Y, W, Q, E, K, R, S, T, Y, N, Q, D, E, K, and R; I7$X^2$, wherein $X^2$ is selected from G, A, C, P, V, L, M, F, Y, W, K, R, S, T, H, N, Q, D, and E; L9$X^3$, wherein $X^3$ is selected from G, A, C, P, V, I, M, F, Y, W, K, R, S, T, Y, H, N, Q, D, E, K, and R; F23$X^4$, wherein $X^4$ is selected from G, A, C, P, V, L, I, M, Y, W, S, T, H, N, Q, D, E, K, and R; F24$X^5$, wherein $X^5$ is selected from G, A, C, P, V, I, M, Y, S, T, H, N, Q, D, E, K, R, and W; Y27$X^6$, wherein $X^6$ is selected from G, A, C, P, V, L, I, M, F, W, S, T, H, N, Q, D, E, K, and R; V59$X^7$, wherein $X^7$ is selected from G, A, C, P, L, I, M, F, Y, W, H, Q, E, K, and R; V61$X^8$, wherein $X^8$ is selected from G, A, C, P, L, I, M, F, Y, W, H, Q, E, K, R, S, T, N, and D; V66$X^{9}$, wherein $X^{9}$ is selected from G, A, C, P, L, I, M, F, Y, and W; E67$X^{10}$, wherein $X^{10}$ is selected from G, A, C, P, V, L, I, M, F, Y, and W; I69$X^{11}$, wherein $X^{11}$ is selected from G, A, C, P, V, L, M, F, Y, and W; Q70$X^{12}$, wherein $X^{12}$ is selected from S, T, H, N, D, E, R, K, and Y; I73$X^{13}$, wherein $X^{13}$ is selected from G, A, C, P, V, L, M, F, Y, and W; I74$X^{14}$, wherein $X^{14}$ is selected from G, A, C, P, V, L, M, F, Y, and W; V79$X^{15}$, wherein $X^{15}$ is selected from G, A, C, P, L, I, M, F, Y, and W; G80$X^{16}$, wherein $X^{16}$ is selected from A, C, P, V, L, I, M, F, Y, W, S, T, H, N, Q, D, E, K, and R; F81$X^{17}$, wherein $X^{17}$ is selected from G, A, C, P, V, L, I, M, Y, W, S, T, H, N, Q, D, E, R, and K; G82$X^{18}$, wherein $X^{18}$ is selected from A, C, P, V, L, I, M, F, Y, W, S, T, H, N, Q, E, K, and R; D83$X^{19}$, wherein $X^{19}$ is selected from S, T, H, Q, N, E, R, K, and Y; R86$X^{20}$, wherein $X^{20}$ is selected from S, T, H, Q, N, D, E, K, and Y; W89$X^{21}$, wherein $X^{21}$ is selected from G, A, C, P, V, L, I, M, F, Y, W, S, T, H, N, Q, D, E, K, and R; L92$X^{22}$, wherein $X^{22}$ is selected from G, A, C, P, V, I, M, F, Y, and W; I94$X^{23}$, wherein $X^{23}$ is selected from G, A, C, P, V, L, M, F, Y, W, K, R, S, T, Y, H, N, Q, D, and E; D96$X^{24}$, wherein $X^{24}$ is selected from S, T, H, Q, N, E, R, K, and Y; V46$X^{25}$, wherein $X^{25}$ is selected from G, A, C, P, L, I, M, F, Y, and W; T47$X^{26}$, wherein $X^{26}$ is selected from S, H, Q, N, D, E, R, K, and Y; Q48$X^{27}$, wherein $X^{27}$ is selected from S, T, H, N, D, E, R, K, and Y; K49$X^{28}$, wherein $X^{28}$ is selected from S, T, H, Q, N, D, E, R, and Y; N50$X^{29}$, wherein $X^{29}$ is selected from G, A, C, P, V, L, I, M, F, Y, and W; and K51$X^{30}$, wherein $X^{30}$ is selected from S, T, H, Q, N, D, E, R, and Y; V46*$X^{31}$, wherein $X^{31}$ is selected from G, A, C, P, L, I, M, F, Y, and W; T47*$X^{32}$, wherein $X^{32}$ is selected from S, H, Q, N, D, E, R, K, and Y; Q48*$X^{33}$, wherein $X^{33}$ is selected from S, T, H, N, D, E, R, K, and Y; K49*$X^{34}$, wherein $X^{34}$ is selected from S, T, H, Q, N, D, E, R, and Y; N50*$X^{35}$, wherein $X^{35}$ is selected from G, A, C, P, V, L, I, M, F, Y, and W; K51*$X^{36}$, wherein $X^{36}$ is selected from S, T, H, Q, N, D, E, R, and Y; or a combination thereof; wherein position corresponds to SEQ ID NO: 4 and wherein the "*" indicates amino acid residues from a second peptide of a OAC dimer (e.g., monomer B) and corresponding to SEQ ID NO:4. In some embodiments, the non-natural OAC comprises more than one amino acid variations. In some embodiments, the non-natural OAC is not a single variant of K4A, H5A, H5L, H5Q, H5S, H5N, H5D, I7L, I7F, L9A, L9W, K12A, F23A, F23I, F23W, F23L, F24L, F24W, F24A, Y27F, Y27M, Y27W, V28F, V29M, K38A, V40F, D45A, H57A, V59M, V59A, V59F, Y72F, H75A, H78A, H78N, H78Q, H78S, H78D, or D96A, and wherein the "*" indicates amino acid residues from chain B of OAC dimer and corresponding to SEQ ID NO:4.

In some embodiments, the non-natural OAC is capable of producing olivetolic acid at a faster rate compared with wild-type OAC. In some embodiments, the non-natural OAC has increased affinity for a polyketide substrate (e.g., a tri- or tetraketide produced from OLS, such as a 3,5,7-trioxoacyl-CoA or 3,5,7-trioxocarboxylate, e.g., 3,5,7-trioxododecanoyl-CoA and 3,5,7-trioxododecanoate and their analogs) compared with wild-type OAC. In some embodiments, the rate of formation of olivetolic acid from 3,5,7-trioxoacyl-CoA or 3,5,7-trioxocarboxylate by a non-natural OAC is about 1.2 times to about 300 times, about 1.5 times to about 200 times, or about 2 times to about 30 times as compared to a wild-type OAC. In some embodiments, the rate of formation of olivetolic acid from 3,5,7-trioxoacyl-CoA or 3,5,7-trioxocarboxylate can be determined in an in vitro enzymatic reaction using a purified non-natural OAC. In some embodiments, the 3,5,7-trioxoacyl-CoA or 3,5,7-trioxocarboxylate is produced by OLS from an acyl-CoA and malonyl-CoA. Methods of determining enzyme kinetics and product formation rate are known in the field.

In some embodiments, the polyketide produced from OLS, e.g., a natural or non-natural OLS described herein, is converted to olivetolic acid and its analogs by olivetolic acid cyclase (OAC). In some embodiments, a non-natural OLS with an amino acid variant as described herein is enzymatically capable of at least about 1.1, 1.2, 1.5, 2, 3, 4, 5, 6, 7, 8, 9, 10, 12, 15, 20, or greater rate of formation of OA and/or olivetol from Mal-CoA and Hex-CoA in the presence of excess OAC enzyme, as compared to the wild type OLS.

In some embodiments, the OAC is present in molar excess of OLS in the engineered cell. In some embodiments, the molar ratio of OLS to OAC is about 1:1.1, 1:1.2, 1:1.5, 1:1.8, 1:2, 1:3, 1:4, 1:5, 1:10, 1:20, 1:25, 1:50, 1:75, 1:100, 1:125, 1:150, 1:200, 1:250, 1:300, 1:350, 1:400, 1:450, 1:500, 1:1000, 1:1250, 1:1500, 1:2000, 1:2500, 1:5000, 1:7500, 1:10,000, or 1 to more than 10,000. In some embodiments, the molar ratio of OLS to OAC is about 1000:1, 500:1, 100:1, 10:1, 5:1, 2.5:1. 1.5:1, 1.2:1. 1.1:1, 1:1, or less than 1 to 1. In some embodiments, the enzyme turnover rate of the OAC is greater than OLS. As used herein, "turnover rate" refers to the rate at which an enzyme can catalyze a reaction (e.g., turn substrate into product). In some embodiments, the higher turnover rate of OAC compared to OLS provides a greater rate of formation of OA than olivetol.

In some embodiments, the total byproducts (e.g., olivetol, analogs of olivetol, PDAL, HTAL, and other lactone analogs) of the non-natural OLS reaction products in the presence of molar excess of OAC, are in an amount (w/w) of less than about 50%, 45%, 40%, 35%, 30%, 25%, 20%, 15%, 12.5%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.05%, 0.025%, or 0.01% of the total weight of the products formed by the combination of individual OLS and OAC enzyme reactions.

In some embodiments, the invention provides a composition comprising a non-natural cannabinoid synthase (e.g., the non-natural THCAS, CBDAS, and/or CBCAS described herein) and one or both of a non-natural OLS described herein and a non-natural OAC described herein. In some embodiments, the invention provides an engineered cell comprising a non-natural cannabinoid synthase (e.g., the non-natural THCAS, CBDAS, and/or CBCAS) and one or both of a non-natural OLS and a non-natural OAC. In some embodiments, the invention provides one or more nucleic acids encoding a non-natural cannabinoid synthase (e.g., the non-natural THCAS, CBDAS, and/or CBCAS) and one or both of a non-natural OLS and a non-natural OAC. In some embodiments, the invention provides an expression construct comprising the one or more nucleic acids. In some embodiments, the invention provides an engineered cell comprising the one or more nucleic acids. In some embodiments, the invention provides an engineered cell comprising the expression construct. In some embodiments, the expression construct comprises a single expression vector. In some embodiments, the expression construct comprises more than one expression vector. In some embodiments, the engineered cell is capable of expressing THCAS, CBDAS, and/or CBCAS. In some embodiments, the engineered cell is capable of producing THCA, CBDA, and/or CBCA.

VII. GPP

In some embodiments, the engineered cell of the invention further comprises an enzyme for producing geranyl pyrophosphate (GPP). In some embodiments, the engineered cell comprising the non-natural cannabinoid synthase (e.g., the non-natural THCAS, CBDAS, and/or CBCAS described herein), the nucleic acid encoding the non-natural cannabinoid synthase (e.g., the non-natural THCAS, CBDAS, and/or CBCAS), the expression construct comprising the nucleic acid, or a combination thereof, further comprises an enzyme in a geranyl pyrophosphate (GPP) pathway. In some embodiments, the GPP pathway comprises a mevalonate (MVA) pathway, a non-mevalonate (MEP) pathway, an alternative non-MEP, non-MVA geranyl pyrophosphate pathway, or a combination of one or more pathways. In some embodiments, the GPP pathway comprises geranyl pyrophosphate synthase (GPPS), farnesyl pyrophosphate synthase, isoprenyl pyrophosphate synthase, geranylgeranyl pyrophosphate synthase, alcohol kinase, alcohol diphosphokinase, phosphate kinase, isopentenyl diphosphate isomerase, geranyl pyrophosphate synthase, or a combination thereof. In some embodiments, the alternative non-MEP, non-MVA geranyl pyrophosphate pathway comprises alcohol kinase, alcohol diphosphokinase, phosphate kinase, isopentenyl disphosphate isomerase, geranyl pyrophosphate synthase, or a combination thereof.

Figure 5:
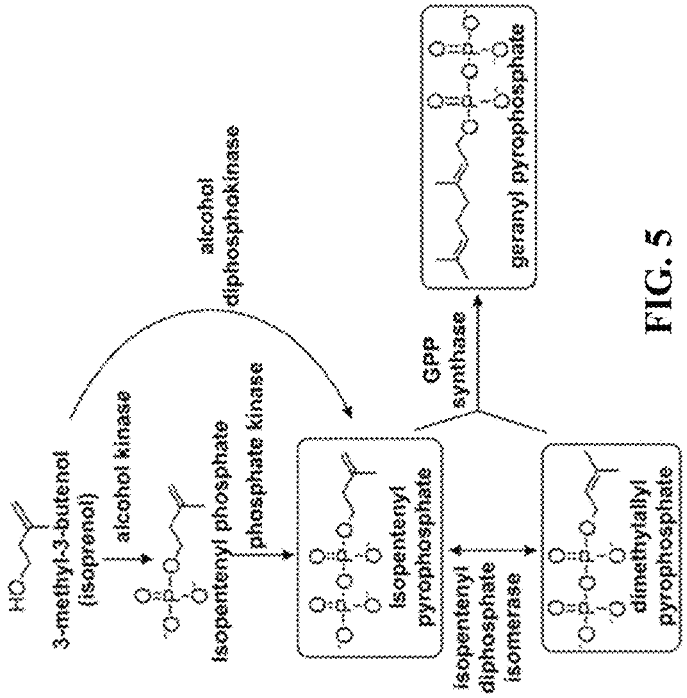
FIG. 5 shows exemplary pathways of forming geranyl pyrophosphate from isoprenol, as described in embodiments herein.
Figure 10:
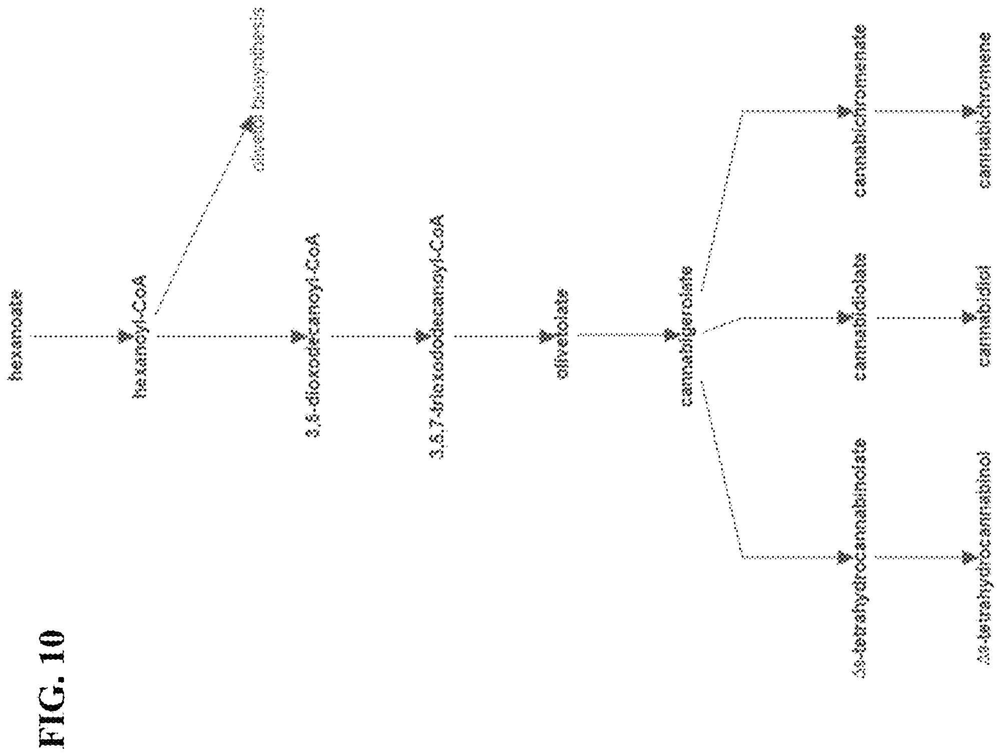
FIG. 10 shows exemplary cannabinoid biosynthesis pathways as described in embodiments herein. Hexanoate is converted to CBGA via several intermediates, including hexanoyl-CoA, 3,5-dioxodecanoyl-CoA, 3,5,7-trioxododecanoyl-CoA, and olivetolate as described in embodiments herein. $\Delta^9$-tetrahydrocannabinolic acid synthase (THCAS) can convert CBGA to THCA, which decarboxylates to $\Delta^9$-tetrahydrocannabinol (THC). Cannabidiolic acid synthase (CBDAS) can convert CBGA to CBDA, which decarboxylaets into cannabidiol (CBD.) Cannabichromenic acid synthase (CBCAS) can convert CBGA to cannabichromenate (CBCA), which decarboxylates to cannabichromene (CBC).

GPP and its precursors may be produced from several pathways within a host cell, including the mevalonate pathway (MVA) or a non-mevalonate, methylerythritol-4-phosphate (MEP) pathway (also known as the deoxyxylulose-5-phosphate pathway), which produce isopentenyl pyrophosphate (IPP) and dimethylallyl pyrophosphate (DMAPP), which are isomerized by isopentenyl-diphosphate delta-isomerase (IDI) and converted to geranyl pyrophosphate (GPP) using geranyl pyrophosphate synthase. Prenyltransferase can convert GPP and olivetolic acid (OA) into cannabigerolic acid (CBGA), which can then be converted into THCA, CBDA, and/or CBCA by THCAS, CBDAS, and/or CBCAS, e.g., a non-natural THCAS, CBDAS, and/or CBCAS of the invention. Exemplary MVA and MEP pathways are shown in FIG. 5. In some embodiments, GPP is produced using a MVA pathway, e.g., as shown in FIG. 5. In some embodiments, GPP is produced using a MEP pathway, e.g., as shown in FIG. 5. In some embodiments, expression of an exogenous (e.g., heterologous) or overexpression of an exogenous or endogenous gene that encodes any one or more of the enzymes in the MVA and/or MEP pathways increases the production of GPP and, ultimately, THCA, CBDA, and/or CBCA. In some embodiments, the MVA pathway enzyme is acetoacetyl-CoA thiolase (AACT); HMG-CoA synthase (HMGS); HMG-CoA reductase (HMGR); mevalonate-3-kinase (MVK); phosphomevalonate kinase (PMK); mevalonate-5-pyrophosphate decarboxylase (MVD); 4-hydroxy-3-methyl-but-2-enyl pyrophosphate reductase (HDR); isopentenyl pyrophosphate isomerase (IDI), or geranyl pyrophosphate GPP synthase. In some embodiments, the MEP pathway enzyme is 1-deoxy-D-xylulose 5-phosphate synthase (DXS), 1-deoxy-D-xylulose 5-phosphate reductoisomerase (DXR); 2-C-methyl-D-erythritol 4-phosphate cytidylyltransferase (CMS); 4-diphosphocytidyl-2-C-methyl-D-erythritol kinase (CMK); 2-C-methyl-D-erythritol 2,4-cyclodiphosphate synthase (MECS); 4-hydroxy-3-methyl-but-2-enyl pyrophosphate synthase (HDS); 4-hydroxy-3-methyl-but-2-enyl pyrophosphate reductase (HDR); isopentenyl pyrophosphate isomerase (IDI), or geranyl pyrophosphate GPP synthase.

Figure 6:
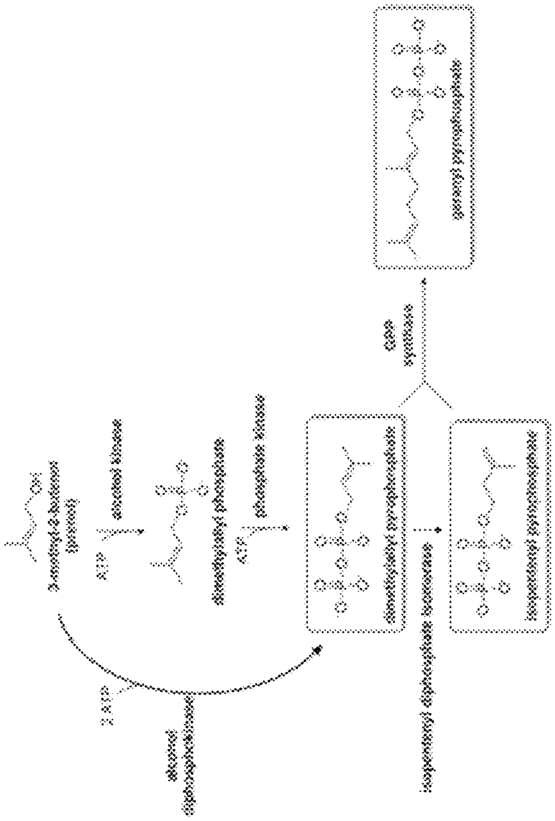
FIG. 6 shows exemplary pathways of forming geranyl pyrophosphate from prenol, as described in embodiments herein.
Figure 7:
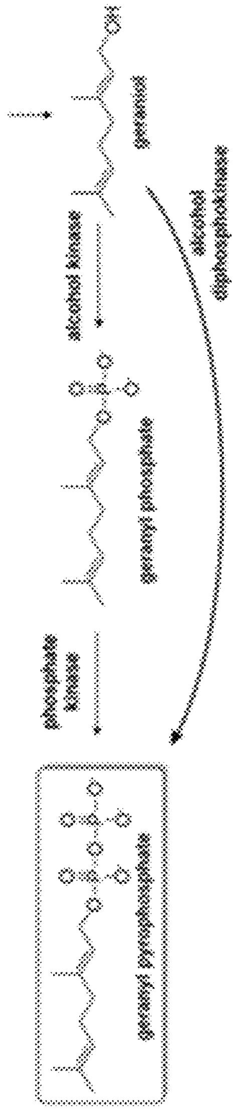
FIG. 7 shows an exemplary pathway of forming geranyl pyrophosphate from geraniol, as described in embodiments herein.

In some embodiments, GPP is produced using an alternative non-MVA, non-MEP pathway. Exemplary pathways for GPP production with isoprenol, prenol, and geraniol as precursors are shown in FIGS. 5, 6, and 7, respectively. As shown in FIG. 5, isoprenol is phosphorylated to isopentenyl phosphate (IP) by alcohol kinase then to IPP by phosphate kinase, or isoprenol is directly phosphorylated to IPP by alcohol diphosphokinase. Similarly, as shown in FIG. 6, prenol is phosphorylated to dimethylallyl phosphate (DMAP) by alcohol kinase then to DMAPP by phosphate kinase, or prenol is directly phosphorylated to DMAPP by alcohol diphosphokinase. GPP can also be formed directly from geraniol, e.g., as shown in FIG. 7. Two phosphate groups can be added directly to geraniol via alcohol (geraniol) diphosphokinase, or geraniol can be phosphorylated sequentially with alcohol (geraniol) kinase and phosphate kinase. In some embodiments, expression of an exogenous (e.g., heterologous) or overexpression of an exogenous or endogenous gene that encodes any one or more of the enzymes in a non-MVA, non-MEP pathways increases the production of GPP and, ultimately, THCA, CBDA, and/or CBCA. In some embodiments, the non-MVA, non-MEP pathway enzyme is alcohol kinase, alcohol diphosphokinase, phosphate kinase, isopentenyl diphosphate isomerase, or geranyl pyrophosphate (GPP) synthase.

In some embodiments, the engineered cell comprising an enzyme in the GPP pathway, e.g., GPP synthase, retains endogenous expression of its native GPP pathway enzyme. In some embodiments, the engineered cell comprising an enzyme in the GPP pathway, e.g., GPP synthase, overexpresses an endogenous or exogenous GPP pathway enzyme. In some embodiments, the engineered cell comprising an enzyme in the GPP pathway, e.g., GPP synthase, has reduced or eliminated expression of its native GPP pathway enzyme. GPP synthases are in the EC 2.5.1.- (e.g., EC 2.5.1.1) class, according the Enzyme Commission nomenclature. Non-limiting examples of GPP synthases include *E. coli* IspA (NP 414955, SEQ ID NO:37) and *C. glutamicum* IdsA (WP 011014931.1, SEQ ID NO:38). In some embodiments, the GPP synthase has at least at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:37 or SEQ ID NO:38 and has the enzymatic activity of EC 2.5.1.-. Other GPP synthases that may be expressed or overexpressed in the engineered cells described herein include those provided in Table 4. Further GPP pathway enzymes are described, e.g., in US 2019/0352679 and include, e.g., alcohol kinase, alcohol diphosphokinase, and phosphate kinase, which can produce GPP from geraniol.

TABLE 4

GPP Synthase Enzymes

| Species | GenBank Accession No. | SEQ ID NO: |
|---|---|---|
| *Corynebacterium crudilactis* | WP_074025495.1 | 39 |
| *Corynebacterium glutamicum* | WP_096457048.1 | 40 |
| *Corynebacterium deserti* | WP_053545301.1 | 41 |
| *Corynebacterium callunae* | WP_015651699.1 | 42 |
| *Corynebacterium efficiens* | WP_006768068.1 | 43 |
| *Corynebacterium* sp. *Marseille*-P2417 | WP_080794061.1 | 44 |
| *Corynebacterium humireducens* | WP_040086238.1 | 45 |
| *Corynebacterium halotolerans* | WP_015401326.1 | 46 |
| *Corynebacterium marinum* | WP_042621772.1 | 47 |
| *Corynebacterium singulare* | WP_042531577.1 | 48 |
| *Corynebacterium minutissimum* | WP_115022907.1 | 49 |
| *Corynebacterium pollutisoli* | WP_143337494.1 | 50 |
| *Corynebacterium lubricantis* | WP_018297093.1 | 51 |
| *Corynebacterium spheniscorum* | WP_092284621.1 | 52 |
| *Corynebacterium doosanense* | WP_018020857.1 | 53 |

TABLE 4-continued

| GPP Synthase Enzymes | | |
|---|---|---|
| Species | GenBank Accession No. | SEQ ID NO: |
| *Corynebacterium flavescens* | WP_075731219.1 | 54 |
| *Corynebacterium aurimucosum* | WP_143334899.1 | 55 |
| *Corynebacterium ammoniagenes* | WP_003845210.1 | 56 |
| *Corynebacterium kefirresidentii* | WP_086587718.1 | 57 |
| *Corynebacterium camporealensis* | WP_035105251.1 | 58 |
| *Corynebacterium tuberculostearicum* | WP_005328932.1 | 59 |
| *Corynebacterium pseudogenitalium* | WP_005324491.1 | 60 |
| *Corynebacterium testudinoris* | WP_083985528.1 | 61 |
| *Corynebacterium stationis* | WP_066793135.1 | 62 |
| *Corynebacterium* sp. J010B-136 | WP_105324112.1 | 63 |
| *Corynebacterium* sp. CCUG 69366 | WP_123047545.1 | 64 |
| *Corynebacterium* sp. KPL1818 | WP_023030480.1 | 65 |
| *Corynebacterium accolens* | WP_005283903.1 | 66 |
| *Corynebacterium segmentosum* | WP_126319428.1 | 67 |
| *Corynebacterium macginleyi* | WP_121911356.1 | 68 |
| *Pseudomonas aeruginosa* | SQG59150.1 | 69 |
| *Streptococcus thermophilus* | VDG63248.1 | 70 |
| *Nocardia vermiculata* | WP_084473733.1 | 71 |
| *Rhodococcus* sp. 1168 | WP_088945631.1 | 72 |
| *Clostridium paraputrificum* | WP_113570111.1 | 73 |
| *Nocardia cyriacigeorgica* | WP_036535265.1 | 74 |
| *Nocardia concava* | WP_040806894.1 | 75 |
| *Rhodococcus yunnanensis* | WP_072806331.1 | 76 |

In some embodiments, the GPP pathway comprises geranyl pyrophosphate (GPP) synthase, farnesyl pyrophosphate synthase, isoprenyl pyrophosphate synthase, geranylgeranyl pyrophosphate synthase, alcohol kinase, alcohol diphosphokinase, phosphate kinase, isopentenyl diphosphate isomerase, geranyl pyrophosphate synthase, or a combination thereof. Farnesyl pyrophosphate synthase, isoprenyl pyrophosphate synthase, and geranylgeranyl pyrophosphate synthase also belong to the EC 2.5.1.-enzyme class and have similar activity as GPP synthase.

In some embodiments, the invention provides a composition comprising a non-natural cannabinoid synthase (e.g., the non-natural THCAS, CBDAS, and/or CBCAS described herein) and one or more of a non-natural OLS described herein, a non-natural OAC described herein, and a GPP pathway enzyme, wherein the GPP pathway enzyme comprises geranyl pyrophosphate (GPP) synthase, farnesyl pyrophosphate synthase, isoprenyl pyrophosphate synthase, geranylgeranyl pyrophosphate synthase, alcohol kinase, alcohol diphosphokinase, phosphate kinase, isopentenyl diphosphate isomerase, geranyl pyrophosphate synthase, or a combination thereof. In some embodiments, the invention provides an engineered cell comprising a non-natural cannabinoid synthase (e.g., the non-natural THCAS, CBDAS, and/or CBCAS) and one or more of a non-natural OLS, a non-natural OAC, and a GPP pathway enzyme described herein. In some embodiments, the invention provides one or more nucleic acids encoding a non-natural cannabinoid synthase (e.g., the non-natural THCAS, CBDAS, and/or CBCAS) and one or more of a non-natural OLS, a non-natural OAC, and a GPP pathway enzyme. In some embodiments, the invention provides an expression construct comprising the one or more nucleic acids. In some embodiments, the invention provides an engineered cell comprising the one or more nucleic acids. In some embodiments, the invention provides an engineered cell comprising the expression construct. In some embodiments, the expression construct comprises a single expression vector. In some embodiments, the expression construct comprises more than one expression vector. In some embodiments, the engineered cell is capable of expressing THCAS, CBDAS, and/or CBCAS. In some embodiments, the engineered cell is capable of producing THCA, CBDA, and/or CBCA.

VIII. Prenyltransferase

In some embodiments, the engineered cell of the invention further comprises a prenyltransferase. In some embodiments, the prenyltransferase is a natural (e.g., wild-type) prenyltransferase or a non-natural prenyltransferase.

In general, the conversion of olivetolic acid (OA) to cannabigerolic acid (CGBA) is performed by a prenyltransferase. In *C. sativa*, prenyltransferase is a transmembrane protein belonging to the UbiA superfamily of membrane proteins. Other prenyltransferases, e.g., aromatic prenyltransferases such as NphB from *Streptomyces*, which are non-transmembrane and soluble, can also catalyze conversion of OA to CBGA.

In some embodiments, the prenyltransferase has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to any one of SEQ ID NOs:6-20. In some embodiments, the prenyltransferase is a non-natural prenyltransferase comprising at least 1, at least 2, at least 3, at least 4, at least 5, at least 6, at least 7, at least 8, at least 9, or at least 10 amino acid variations at positions corresponding to SEQ ID NO:6, or a corresponding amino acid position in any one of SEQ ID NOs:7-20.

Although the amino acid positions of prenyltransferase described herein are with reference to the corresponding amino acid sequence of SEQ ID NO:6, it is understood that the amino acid sequence of a non-natural prenyltransferase can include an amino acid variation at an equivalent position corresponding to a variant of SEQ ID NO:6, e.g., SEQ ID NOs:7-20. One of the skill in the art would understand that alignment methods can be used to align variations of SEQ ID NO:6 (i.e., prenyltransferase variants) to identify the position in the prenyltransferase variant that corresponds to a position in SEQ ID NO:6. In some embodiments, SEQ ID NO:6 corresponds to the amino acid sequence of *Streptomyces antibioticus* AQJ23_4042 prenyltransferase.

In some embodiments, the non-natural prenyltransferase comprises one or more (e.g., 2, 3, 4, 5, 6, 7, 8, 9, 10, or more) amino acid substitutions at positions V45, F121, T124, Q159, M160, Y173, S212, V213, A230, T267, Y286, Q293, R294, L296, F300, or a combination thereof, wherein the position corresponds to SEQ ID NO:6.

In some embodiments, the non-natural prenyltransferase comprises at least four amino acid variations at positions corresponding to SEQ ID NO:6 or a corresponding amino acid position in any one of SEQ ID NOs:7-20, the variations selected from:

a. (i) V45I, (ii) Q159S, (iii) S212H, and (iv) Y286V;
b. (i) V45T, (ii) Q159S, (iii) S212H, and (iv) Y286V;
c. (i) F121V, (ii) Q159S, (iii) S212H, and (iv) Y286V;
d. (i) T124K, (ii) Q159S, (iii) S212H, and (iv) Y286V;
e. (i) T124L, (ii) Q159S, (iii) S212H, and (iv) Y286V;
f. (i) Q159S, (ii) M160L, (iii) S212H, and (iv) Y286V;
g. (i) Q159S, (ii) M160L, (iii) S212H, and (iv) Y286V;
h. (i) Q159S, (ii) M160S, (iii) S212H, and (iv) Y286V;
i. (i) Q159S, (ii) Y173D, (iii) S212H, and (iv) Y286V;
j. (i) Q159S, (ii) Y173K, (iii) S212H, and (iv) Y286V;
k. (i) Q159S, (ii) Y173P, (iii) S212H, and (iv) Y286V;
l. (i) Q159S, (ii) Y173Q, (iii) S212H, and (iv) Y286V;
m. (i) Q159S, (ii) Y173Y, (iii) S212H, and (iv) Y286V;
n. (i) Q159S, (ii) S212H, (iii) V213V, and (iv) Y286V;
o. (i) Q159S, (ii) S212H, (iii) A230S, and (iv) Y286V;
p. (i) Q159S, (ii) S212H, (iii) T267P, and (iv) Y286V;

q. (i) Q159S, (ii) S212H, (iii) Y286V, and (iv) Q293H;
r. (i) Q159S, (ii) S212H, (iii) Y286V, and (iv) R294K;
s. (i) Q159S, (ii) S212H, (iii) Y286V, and (iv) L296K;
t. (i) Q159S, (ii) S212H, (iii) Y286V, and (iv) L296L;
u. (i) Q159S, (ii) S212H, (iii) Y286V, and (iv) L296M;
v. (i) Q159S, (ii) S212H, (iii) Y286V, and (iv) L296Q;
w. (i) Q159S, (ii) S212H, (iii) Y286V, and (iv) L296M;
x. (i) Q159S, (ii) S212H, (iii) Y286V, and (iv) F300F; and
y. (i) Q159S, (ii) S212H, (iii) Y286V, and (iv) F300Y.

In some embodiments, the non-natural prenyltransferase comprising an amino acid variant as described herein is capable of a greater rate of formation of CBGA from GPP and OA, as compared with wild-type prenyltransferase. In some embodiments, the rate of formation of CBGA from GPP and OA is about 1.5 times to about 750 times, about 5 times to about 750 times, or about 10 times to about 750 times as compared with wild-type prenyltransferase, as determined using an in vitro enzymatic reaction using purified prenyltransferase.

In some embodiments, the non-natural prenyltransferase comprising an amino acid variant as described herein provides a rate of formation of CBGA of greater than about 0.005 μM CBGA/min/μM enzyme, greater than about 0.010 μM CBGA/min/μM enzyme, greater than about 0.020 μM CBGA/min/μM enzyme, greater than about 0.050 μM CBGA/min/μM enzyme, greater than about 0.100 μM CBGA/min/μM enzyme, greater than about 0.250 μM CBGA/min/μM enzyme, or greater than about 0.500 μM CBGA/min/μM enzyme. In some embodiments, the non-natural prenyltransferase comprising an amino acid variant as described herein provides a rate of formation of CBGA of about 0.005 to about 1.50 μM CBGA/min/μM enzyme, or about 0.010 to about 1.250 μM CBGA/min/μM enzyme, or about 0.020 to about 1.0 μM CBGA/min/μM enzyme.

In some embodiments, the invention provides a composition comprising a non-natural cannabinoid synthase (e.g., the non-natural THCAS, CBDAS, and/or CBCAS described herein) and one or more of a non-natural OLS described herein, a non-natural OAC described herein, a GPP pathway enzyme described herein, and a non-natural prenyltransferase described herein. In some embodiments, the invention provides an engineered cell comprising a non-natural cannabinoid synthase (e.g., the non-natural THCAS, CBDAS, and/or CBCAS) and one or more of a non-natural OLS, a non-natural OAC, a GPP pathway enzyme, and a non-natural prenyltransferase. In some embodiments, the invention provides one or more nucleic acids encoding a non-natural cannabinoid synthase (e.g., the non-natural THCAS, CBDAS, and/or CBCAS) and one or more of a non-natural OLS, a non-natural OAC, a GPP pathway enzyme, and a non-natural prenyltransferase. In some embodiments, the invention provides an expression construct comprising the one or more nucleic acids. In some embodiments, the invention provides an engineered cell comprising the one or more nucleic acids. In some embodiments, the invention provides an engineered cell comprising the expression construct. In some embodiments, the expression construct comprises a single expression vector. In some embodiments, the expression construct comprises more than one expression vector. In some embodiments, the engineered cell is capable of expressing THCAS, CBDAS, and/or CBCAS. In some embodiments, the engineered cell is capable of producing THCA, CBDA, and/or CBCA.

IX. Additional Strain Modifications

In some embodiments, the engineered cell of the invention further comprises a modification that facilitates the production of a cannabinoid, e.g., THCA, CBDA, and/or CBCA or a precursor thereof. In some embodiments, the modification increases production of a cannabinoid, in the engineered cell compared with a cell not comprising the modification. In some embodiments, the modification increases efflux of a cannabinoid in the engineered cell compared with a cell not comprising the modification. In some embodiments, the modification comprises expressing or upregulating the expression of an endogenous gene that facilitates production of a cannabinoid. In some embodiments, the modification comprises introducing and/or overexpression an exogenous and/or heterologous gene that facilitates production of a cannabinoid. In some embodiments, the modification comprises downregulating, disrupting, or deleting an endogenous gene that hinders production of a cannabinoid. In some embodiments, the cannabinoid is THCA. In some embodiments, the cannabinoid is CBDA. In some embodiments, the cannabinoid is CBCA. Expression and/or overexpression of endogenous and exogenous genes, and downregulation, disruption and/or deletion of endogenous genes are described in embodiments herein.

In some embodiments, the engineered cell of the invention comprises one or more of the following modifications:

(i) express one or more exogenous nucleic acid sequences or overexpress one or more endogenous genes encoding a protein having an ABC transporter permease activity;

(ii) express one or more exogenous nucleic acid sequences or overexpress one or more endogenous genes encoding a protein having an ABC transporter ATP-binding protein activity;

(iii) express one or more exogenous nucleic acids sequences or overexpress one or more endogenous genes that encodes a protein that is at least 60% identical to: the blc gene product of SEQ ID NO: 147, ybhG gene product of SEQ ID NO: 116, or the ydhC gene product of SEQ ID NO: 148;

(iv) express one or more exogenous nucleic acids sequences or overexpress one or more endogenous genes that encodes a protein that is at least 60% identical to the mlaD gene product of SEQ ID NO: 149, the mlaE gene product of SEQ ID NO: 150, or the mlaF gene product of SEQ ID NO: 151;

(v) express one or more exogenous nucleic acid sequences or overexpress one or more endogenous genes encoding a protein having a siderophore receptor protein activity or overexpress one or more endogenous genes encoding a protein having a siderophore receptor protein activity;

(vi) comprise a disruption of or downregulation in the expression of a regulator of expression of one or more endogenous genes encoding a protein having an ABC transporter permease activity, a protein having an ABC transporter ATP-binding protein activity, a blc gene, a ybhG protein, a ydhC protein, a mlaD protein, mlaE protein, mlaF protein, or a protein having a siderophore receptor protein activity;

(vii) express an exogenous nucleic acid encoding a multi-domain protein having acetyl-CoA carboxylase activity (MD-ACC);

(viii) overexpress one or more endogenous genes encoding acetyl-CoA carboxyltransferase subunit α, biotin carboxyl carrier protein, biotin carboxylase, or acetyl-CoA carboxyltransferase subunit β, or express one or more exogenous genes encoding acetyl-CoA carboxyltransferase, biotin carboxyl carrier protein, or biotin carboxylase activities;

(ix) disruption of or downregulation in the expression of an endogenous gene encoding a protein having (acyl-carrier-protein) S-malonyltransferase activity, an endogenous gene encoding a protein having 3-hydroxypalmitoyl-(acyl-carrier-protein) dehydratase activity, or both;

(x) express an exogenous nucleic acid sequence or overexpress an endogenous gene encoding a protein having fatty acyl-CoA ligase activity, or both;

(xi) disruption of or downregulation in the expression of at least one endogenous gene encoding a protein having acyl-CoA dehydrogenase activity or enoyl-CoA hydratase activity;

(xii) a disruption or downregulation in the expression of at least one endogenous gene encoding a protein having acyl-CoA esterase/thioesterase activity;

(xiii) disruption of or downregulation in the expression of at least one endogenous gene encoding a repressor of transcription of one or more genes required for fatty acid beta-oxidation or an upregulator of fatty acid biosynthesis in combination with disruption or downregulation of one or more endogenous genes encoding one or more proteins of fatty acid beta-oxidation pathway;

(xiv) express an exogenous nucleic acid sequence or overexpress an endogenous gene encoding a protein having geranyl pyrophosphate synthase (GPPS), farnesyl pyrophosphate synthase, isoprenyl pyrophosphate synthase, geranylgeranyl pyrophosphate synthase, alcohol kinase, alcohol diphosphokinase, phosphate kinase, isopentenyl diphosphate isomerase, geranyl pyrophosphate synthase, prenol kinase activity, prenol diphosphokinase activity, isoprenol kinase activity, isoprenol diphosphokinase activity, dimethylallyl phosphate kinase activity, isopentenyl phosphate kinase activity, or isopentenyl diphosphate isomerase activity;

(xv) express an exogenous nucleic acid sequence or overexpress an endogenous gene encoding a protein having GPP synthase activity;

(xvi) express an exogenous nucleic acid sequence encoding an olivetol synthase;

(xvii) express an exogenous nucleic acid sequence encoding an olivetolic acid cyclase;

(xviii) express an exogenous nucleic acid sequence encoding a prenyltransferase;

(xix) express one or more exogenous nucleic acid sequences or overexpressing one or more endogenous genes encoding one or more enzymes of MVA pathway, MEP pathway, or a non-MVA, non-MEP pathway;

(xx) express an exogenous nucleic acid sequence or overexpress an endogenous gene encoding a biotin-(acetyl-CoA carboxylase) ligase;

(xxi) overexpress an endogenous gene encoding a isopentenyl-diphosphate delta-isomerase or express an exogenous nucleic acid sequence encoding a isopentenyl-diphosphate delta-isomerase;

(xxii) overexpress an endogenous genes encoding a hydroxyethylthiazole kinase or express an exogenous nucleic acid sequence encoding a hydroxyethylthiazole kinase or both;

(xxiii) express an exogenous nucleic acid sequence encoding a Type III pantothenate kinase or overexpress an endogenous gene encoding a Type III pantothenate kinase; and (xxiv) a disruption of or downregulation in the expression of at least one endogenous gene encoding a phosphatase selected from the group consisting of ADP-sugar pyrophosphatase, dihydroneopterin triphosphate diphosphatase, pyrimidine deoxynucleotide diphosphatase, pyrimidine pyrophosphate phosphatase, and Nudix hydrolase.

In some embodiments, the engineered cell expresses one or more exogenous nucleic acid sequences or overexpresses one or more endogenous genes encoding a protein having ABC transporter permease activity or ABC transporter ATP-binding protein activity. In some embodiments, the engineered cell comprises an ABC transporter permease. In some embodiments, the protein having ABC transporter permease activity has an enzyme activity of EC 7.6.2.2. In some embodiments, the engineered cell comprises an ABC transporter ATP-binding protein. In some embodiments, ABC transporter permease and/or ABC transporter ATP-binding protein are capable of affecting cannabinoid (or derivatives thereof) efflux from the cell. In some embodiments, the gene encoding the ABC transporter permease is selected from a ybhS gene, a ybhR gene, and a ybhG gene. In some embodiments, the gene encoding the ABC transporter ATP-binding protein is ybhF.

In some embodiments, the engineered cell expresses one or more exogenous nucleic acids sequences or overexpresses one or more endogenous genes that encodes a protein that is at least 60% identical to: the blc gene product of SEQ ID NO:21, the ybhG gene product of SEQ ID NO:22, or the ydhC gene product of SEQ ID NO:23. In some embodiments, the engineered cell expresses one or more exogenous nucleic acids sequences or overexpress one or more endogenous genes that encodes a protein that is at least 60%, at least 70%, at least 80%, at least 90%, at least 95%, or about 100% identical to: the blc gene product of SEQ ID NO:21, the ybhG gene product of SEQ ID NO:22, or the ydhC gene product of SEQ ID NO:23. In some embodiments, the blc and ydhC genes each encodes a protein involved in cannabinoid efflux. In some embodiments, the ybhG gene encodes a protein involved in cannabinoid transport.

In some embodiments, the engineered cell expresses one or more exogenous nucleic acids sequences or overexpresses one or more endogenous genes that encodes a protein that is at least 60% identical to the mlaD gene product of SEQ ID NO:24, the mlaE gene product of SEQ ID NO:25, or the mlaF gene product of SEQ ID NO:26. In some embodiments, the engineered cell expresses one or more exogenous nucleic acids sequences or overexpress one or more endogenous genes that encodes a protein that is at least 60%, at least 70%, at least 80%, at least 90%, at least 95%, or about 100% identical to the mlaD gene product of SEQ ID NO:24, the mlaE gene product of SEQ ID NO:25, or the mlaF gene product of SEQ ID NO:26. In some embodiments, the mlaD, mlaE, and mlaF genes each encodes a protein involved in cannabinoid efflux.

In some embodiments, the engineered cell expresses one or more exogenous nucleic acid sequences or overexpresses one or more endogenous genes encoding a protein having a siderophore receptor protein activity. In some embodiments, the protein having siderophore receptor protein activity is at least 60%, at least 70%, at least 80%, at least 90%, at least 95%, or about 100% identical to the protein encoded by UniProt protein sequence Q8XYF1 (SEQ ID NO:77).

In some embodiments, the engineered cell comprises a disruption of or downregulation in the expression of a regulator of expression of one or more endogenous genes encoding a protein having an ABC transporter permease activity, a protein having an ABC transporter ATP-binding protein activity, a blc gene, a ybhG protein, a ydhC protein, a mlaD protein, mlaE protein, mlaF protein, or a protein having a siderophore receptor protein activity. These proteins are described in embodiments herein.

In some embodiments, the engineered cell expresses an exogenous nucleic acid encoding a multi-domain protein having acetyl-CoA carboxylase activity (MD-ACC). In some embodiments, the multi-domain protein having acetyl-CoA carboxylase activity is derived from *Mucor* spp, *Rhizopus* spp. *Aspergillus* spp., *Saccharomyces* spp., or *Yarrowia* spp. Non-limiting examples of fungal ACC proteins are described in Table 5.

TABLE 5

Fungal Acetyl-CoA Carboxylases

| Species | GenBank Accession No. |
|---|---|
| *Mucor circinelloides f. circinelloides* 1006PhL | EPB82652.1 |
| *Amylomyces rouxii* | ABQ28729.1 |
| *Mucor circinelloides f. lusitanicus* CBS 277.49 | OAD07937.1 |
| *Mucor ambiguus* | GAN08941.1 |
| *Parasitella parasitica* | CEP09288.1 |
| *Rhizopus stolonifer* | RCI05537.1 |
| *Choanephora cucurbitarum* | OBZ91864.1 |
| *Rhizopus delemar* RA 99-880 | EIE80272.1 |
| *Rhizopus microsporus* ATCC 52813 | XP_023470433.1 |
| *Rhizopus microsporus* | ORE23244.1 |
| *Rhizopus microspores* | CEG63811.1 |
| *Rhizopus azygosporus* | RCH96152.1 |
| *Rhizopus microspores* | CEI99071.1 |
| *Absidia repens* | ORZ25473.1 |
| *Absidia glauca* | SAL97607.1 |
| *Phycomyces blakesleeanus* NRRL 1555(−) | XP_018296012.1 |
| *Hesseltinella vesiculosa* | ORX57605.1 |
| *Rhizopus stolonifera* | EPB82652.2 |
| *Lichtheimia ramose* | ABQ28729.2 |
| *Lichtheimia ramose* | OAD07937.2 |
| *Lichtheimia corymbifera* JMRC:FSU:9682 | GAN08941.2 |
| *Absidia glauca* | CEP09288.2 |
| *Syncephalastrum racemosum* | RCI05537.2 |
| *Mucor circinelloides f. circinelloides* 1006PhL | OBZ91864.2 |
| *Mucor circinelloides f. lusitanicus* CBS 277.49 | EIE80272.2 |
| *Mucor ambiguous* | XP_023470433.2 |
| *Lichtheimia corymbifera* JMRC:FSU:9682 | ORE23244.2 |
| *Bifiguratus adelaidae* | CEG63811.2 |
| *Endogone* sp. FLAS-F59071 | RCH96152.2 |
| *Glomus cerebriforme* | CEI99071.2 |
| *Jimgerdemannia flammicorona* | ORZ25473.2 |
| *Lobosporangium transversal* | SAL97607.2 |
| *Rhizophagus irregularis* | XP_018296012.2 |
| *Rhizophagus irregularis* | ORX57605.2 |
| *Rhizophagus irregularis* | EPB82652.3 |
| *Rhizophagus irregularis* | ABQ28729.3 |
| *Mortierella elongata* AG-77 | OAD07937.3 |
| *Mortierella verticillata* NRRL 6337 | GAN08941.3 |
| *Diversispora epigaea* | CEP09288.3 |
| *Rhizophagus irregularis* | RCI05537.3 |
| *Rhizophagus clarus* | OBZ91864.3 |
| *Basidiobolus meristosporus* CBS 931.73 | EIE80272.3 |
| *Gigaspora rosea* | XP_023470433.3 |
| *Rhizophagus irregularis* | ORE23244.3 |
| *Rhizophagus diaphanus* [*Rhizophagus* sp. MUCL 43196] | CEG63811.3 |
| *Basidiobolus meristosporus* CBS 931.73 | RCH96152.3 |
| *Saitoella complicata* NRRL Y-17804 | CEI99071.3 |
| *Saitoella complicata* NRRL Y-17804 | ORZ25473.3 |
| *Basidiobolus meristosporus* CBS 931.73 | SAL97607.3 |
| *Coleophoma cylindrospora* | XP_018296012.3 |
| *Dactylellina haptotyla* CBS 200.50 | ORX57605.3 |
| *Pyronema omphalodes* CBS 100304 | EPB82652.4 |
| *Aspergillus fischeri* NRRL 181 | ABQ28729.4 |
| *Coleophoma crateriformis* | OAD07937.4 |
| *Aspergillus turcosus* | GAN08941.4 |
| *Aspergillus lentulus* | CEP09288.4 |
| *Byssochlamys spectabilis* | RCI05537.4 |
| *Aspergillus fumigatus* A1163 | OBZ91864.4 |
| *Aspergillus udagawae* | EIE80272.4 |
| *Aspergillus thermomutatus* | XP_023470433.4 |
| *Aspergillus fumigatus* Af293 | ORE23244.4 |
| *Botrytis tulipae* | CEG63811.4 |
| *Morchella conica* CCBAS932 | RCH96152.4 |
| *Botrytis cinerea* B05.10 | CEI99071.4 |
| *Aspergillus fumigatus* var. RP-2014 | ORZ25473.4 |
| *Botrytis galanthina* | SAL97607.4 |
| *Botrytis elliptica* | XP_018296012.4 |
| *Byssochlamys spectabilis* No. 5 | ORX57605.4 |
| *Xylona heveae* TC161 | EPB82652.5 |
| *Botrytis cinerea* BcDW1 | ABQ28729.5 |
| *Phialocephala scopiformis* | OAD07937.5 |
| *Sclerotinia sclerotiorum* 1980 UF-70 | GAN08941.5 |
| *Amorphotheca resinae* ATCC 22711 | CEP09288.5 |
| *Aspergillus oryzae* RIB40 | RCI05537.5 |
| *Aspergillus parasiticus* SU-1 | OBZ91864.5 |
| *Phialocephala subalpine* | EIE80272.5 |
| *Rutstroemia* sp. NJR-2017a WRK4 | XP_023470433.5 |
| *Rutstroemia* sp. NJR-2017a BVV2 | ORE23244.5 |
| *Aspergillus costaricaensis* CBS 115574 | CEG63811.5 |
| *Pezoloma ericae* | RCH96152.5 |
| *Aspergillus brasiliensis* CBS 101740 | CEI99071.5 |
| *Aspergillus vadensis* CBS 113365 | ORZ25473.5 |
| *Aspergillus heteromorphus* CBS 117.55 | SAL97607.5 |
| *Aspergillus piperis* CBS 112811 | XP_018296012.5 |
| *Rutstroemia* sp. NJR-2017a BBW | ORX57605.5 |
| *Drechslerella stenobrocha* 248 | EPB82652.6 |
| *Botrytis hyacinthi* | ABQ28729.6 |
| *Aspergillus bombycis* | OAD07937.6 |
| *Glonium stellatum* | GAN08941.6 |
| *Botryotinia convolute* | CEP09288.6 |
| *Aspergillus clavatus* NRRL 1 | RCI05537.6 |
| *Aspergillus neoniger* CBS 115656 | OBZ91864.6 |
| *Erysiphe pulchra* | EIE80272.6 |
| *Penicillium chrysogenum* | XP_023470433.6 |
| *Penicillium rubens* Wisconsin 54-1255 | ORE23244.6 |
| *Botrytis paeoniae* | CEG63811.6 |
| *Glarea lozoyensis* ATCC 20868 | RCH96152.6 |
| *Aspergillus eucalypticola* CBS 122712 | CEI99071.6 |
| *Pseudogymnoascus* sp. VKM F-4515 (FW-2607) | ORZ25473.6 |
| *Aspergillus niger* CBS 513.88 | SAL97607.6 |
| *Saccharomyces cerevisiae* | AAA20073 |
| *Yarrowia lipolytica* | VBB85319 |

In some embodiments, the engineered cell overexpresses one or more endogenous genes encoding acetyl-CoA carboxyltransferase subunit α, biotin carboxyl carrier protein, biotin carboxylase, or acetyl-CoA carboxyltransferase subunit β, or expresses one or more exogenous genes encoding acetyl-CoA carboxyltransferase, biotin carboxyl carrier protein, or biotin carboxylase. In some embodiments, the acetyl-CoA carboxyltransferase, biotin carboxyl carrier protein, and biotin carboxylase form an acetyl-CoA carboxylase as described herein. In some embodiments, the acetyl-CoA carboxyltransferase comprises binding sites for carboxybiotin and acetyl-CoA. In some embodiments, the biotin carboxyl carrier protein comprises a biotin binding site. In some embodiments, the biotin carboxylase comprises an ATP binding site.

In some embodiments, the engineered cell comprises a disruption of or downregulation in the expression of an endogenous gene encoding a protein having (acyl-carrier-protein) S-malonyltransferase activity, an endogenous gene encoding a protein having 3-hydroxypalmitoyl-(acyl-carrier-protein) dehydratase activity, or both. In some embodiments, the protein having acyl-carrier-protein) S-malonyltransferase activity has an enzymatic activity of EC 2.3.1.39. In some embodiments, the protein having the (acyl-carrier-protein) S-malonyltransferase activity is encoded by the fabD gene. In some embodiments, the protein having 3-hydroxypalmitoyl-(acyl-carrier-protein) dehydratase activity has an enzymatic activity of EC 4.2.1.59. In some embodiments, the protein having 3-hydroxypalmitoyl-(acyl-carrier-protein) dehydratase activity is encoded by the fabZ gene.

In some embodiments, the engineered cell expresses an exogenous nucleic acid sequence or overexpresses an endogenous gene encoding a protein having fatty acyl-CoA ligase activity, or both. In some embodiments, the protein having fatty acyl-CoA ligase activity has an enzymatic activity of EC 6.2.1.3. In some embodiments, the protein having fatty acyl-CoA ligase activity is encoded by the fadD gene or homologs or variants thereof. In some embodiments, the engineered cell has increased levels of acyl-CoA than a control cell that does not express an exogenous nucleic acid sequence or overexpress an endogenous gene encoding a protein having fatty acyl-CoA ligase activity.

In some embodiments, the engineered cell comprises a disruption of or downregulation in the expression of at least one endogenous gene encoding a protein having acyl-CoA dehydrogenase activity or enoyl-CoA hydratase activity. In some embodiments, the protein having acyl-CoA dehydrogenase activity has an enzymatic activity of EC 1.3.8.1. In some embodiments, the gene encoding a protein having acyl-CoA dehydrogenase activity is a fadE gene. In some embodiments, the protein having enoyl-CoA hydratase activity has an enzymatic activity of EC 4.2.1.17. In some embodiments, the protein having enoyl-CoA hydratase activity is encoded by the fadB gene.

In some embodiments, the engineered cell comprises a disruption or downregulation in the expression of at least one endogenous gene encoding a protein having acyl-CoA esterase/thioesterase activity. In some embodiments, the protein having acyl-CoA esterase/thioesterase activity has an enzymatic activity of EC 3.1.2.20. In some embodiments, the protein having acyl-CoA esterase/thioesterase activity is encoded by the tesB gene, vciA gene, ybgC gene, tesA gene, ydil gene, or fadM gene. In some embodiments, the engineered cell has increased levels of acyl-CoA than a control cell that does not comprise a disruption or downregulation in the expression of at least one endogenous gene encoding a protein having acyl-CoA esterase/thioesterase activity.

In some embodiments, the engineered cell comprises a disruption of or downregulation in the expression of at least one endogenous gene encoding a repressor of transcription of one or more genes required for fatty acid beta-oxidation or an upregulator of fatty acid biosynthesis in combination with disruption or downregulation of one or more endogenous genes encoding one or more proteins of fatty acid beta-oxidation pathway. In some embodiments, the repressor of transcription of one or more genes required for fatty acid beta-oxidation or upregulator of fatty acid biosynthesis is encoded by the fadR gene. In some embodiments, the engineered cell comprising an attenuated or no fadR expression or deleted fadR has increased levels of acyl-CoA than a control cell that does not have attenuation of fadR expression or deletion of fadR.

In some embodiments, the engineered cell expresses one or more exogenous nucleic acid sequences or overexpresses one or more endogenous genes encoding a protein having geranyl pyrophosphate synthase (GPPS), farnesyl pyrophosphate synthase, isoprenyl pyrophosphate synthase, geranylgeranyl pyrophosphate synthase, alcohol kinase, alcohol diphosphokinase, phosphate kinase, isopentenyl diphosphate isomerase, geranyl pyrophosphate synthase, isopentenyl phosphate kinase activity, isoprenol diphosphokinase activity, prenol kinase activity, prenol diphosphokinase activity, dimethylallyl phosphate kinase activity, or isopentenyl diphosphate isomerase activity. Geranyl pyrophosphate synthase (GPPS), farnesyl pyrophosphate synthase, isoprenyl pyrophosphate synthase, geranylgeranyl pyrophosphate synthase, alcohol kinase, alcohol diphosphokinase, phosphate kinase, isopentenyl diphosphate isomerase, geranyl pyrophosphate synthase, isopentenyl phosphate kinase, isoprenol diphosphokinase, prenol kinase, prenol diphosphokinase, dimethylallyl phosphate kinase, and isopentenyl diphosphate isomerase relate to geranyl pyrophosphate (GPP) biosynthesis and are described in embodiments herein.

In some embodiments, the engineered cell expresses an exogenous nucleic acid sequence or overexpresses an endogenous gene encoding a protein having GPP synthase activity. In some embodiments, the engineered cell expresses an exogenous nucleic acid sequence encoding an olivetol synthase (OLS). In some embodiments, the engineered cell expresses an exogenous nucleic acid sequence encoding an olivetolic acid cyclase (OAC). In some embodiments, the engineered cell expresses an exogenous nucleic acid sequence encoding a prenyltransferase. In some embodiments, the engineered cell expresses one or more exogenous nucleic acid sequences or overexpressing one or more endogenous genes encoding one or more enzymes of MVA pathway, MEP pathway, or a non-MVA, non-MEP pathway. GPP synthase, OLS, OAC, prenyltransferase, and the MVA, MEP, and non-MVA non-MEP pathways are described in embodiments herein.

In some embodiments, the engineered cell expresses an exogenous nucleic acid sequence or overexpresses an endogenous gene encoding a biotin-(acetyl-CoA carboxylase) ligase. In some embodiments, the biotin-(acetyl-CoA) carboxylase ligase has an enzymatic activity of EC 6.3.4.15. In some embodiments, the biotin-(acetyl-CoA) carboxylase ligase is encoded by the BirA gene.

In some embodiments, the engineered cell expresses an exogenous nucleic acid sequence encoding an isopentenyl-diphosphate delta-isomerase or overexpresses an endogenous gene encoding an isopentenyl-diphosphate delta-isomerase. Isopentenyl-diphosphate delta-isomerase (IDI) catalyzes the isomerization of isopentenyl pyrophosphate (IPP) and dimethylallyl pyrophosphate (DMAPP) and is described in embodiments herein.

In some embodiments, the engineered cell expresses an exogenous nucleic acid sequence encoding a hydroxyethylthiazole kinase or overexpresses an endogenous genes encoding a hydroxyethylthiazole kinase or both. In some embodiments, the hydroxyethylthiazole kinase has an enzyme activity of EC 2.7.1.50. In some embodiments, the hydroxyethylthiazole kinase is encoded by the thiM gene.

In some embodiments, the engineered cell expresses an exogenous nucleic acid sequence encoding a Type III pantothenate kinase or overexpresses an endogenous gene encoding a Type III pantothenate kinase has an enzyme activity of EC 2.7.1.33. In some embodiments, the Type III pantothenate kinase is encoded by the coaX gene. In some embodiments, the engineered cell has increased levels of acyl-CoA (e.g., alkanoyl-CoA, acetyl-CoA, or malonyl-CoA) than a control cell that does not express an exogenous nucleic acid sequence or overexpress an endogenous gene encoding the Type III pantothenate kinase.

In some embodiments, the engineered cell comprises a disruption of or downregulation in the expression of at least one endogenous gene encoding a phosphatase selected from the group consisting of ADP-sugar pyrophosphatase, dihydroneopterin triphosphate diphosphatase, pyrimidine deoxynucleotide diphosphatase, pyrimidine pyrophosphate phosphatase, and Nudix hydrolase. In some embodiments, the phosphatase has an enzyme activity of EC 3.6.1.-. In some embodiments, the phosphatase catalyzes the hydrolytic breakdown of ADP-glucose linked to glycogen biosynthesis. In some embodiments, the ADP-sugar pyrophosphatase is encoded by the aspP gene. In some embodiments, the dihydroneopterin triphosphate diphosphatase is encoded by the nudB gene. In some embodiments, the pyrimidine deoxynucleotide diphosphatase is encoded by the nudI gene. In some embodiments, the Nudix hydrolase is Dcp2, ADP-ribose diphosphatase, MutT, ADPRase, Ap4A hydrolase, or RppH. Nudix hydrolases are further described, e.g., in Mildvan et al., Arch Biochem Biophys 433(1):129-143 (2005).

In some embodiments, the engineered cell comprises an enzyme capable of converting an acyl-CoA (e.g., hexanoyl-CoA) to a triketide or a tetraketide. In some embodiments, the enzyme capable of converting an acyl-CoA to a triketide or a tetraketide is OLS, as described herein. In some embodiments, the enzyme capable of converting an acyl-CoA to a triketide or a tetraketide is a thiolase. Thiolases are enzymes that catalyze Claisen condensation of acyl-CoAs with acetyl-CoA to generate beta-ketoacyl-CoAs elongated by two carbons. An exemplary thiolase is acetyl-CoA acetyltransferases (ACAT), which converts acetyl-CoA to acetoacetyl-CoA. In some embodiments, the thiolase is capable of converting hexanoyl-CoA to 3,5,7-trioxododecanoyl-CoA.

In some embodiments, the invention provides a composition comprising a non-natural cannabinoid synthase (e.g., the non-natural THCAS, CBDAS, and/or CBCAS) described herein and one or more of a non-natural OLS described herein, a non-natural OAC described herein, a GPP pathway enzyme described herein, a non-natural prenyltransferase described herein, and an additional modification, wherein the additional modification is one or more of the following:

(i) express one or more exogenous nucleic acid sequences or overexpress one or more endogenous genes encoding a protein having an ABC transporter permease activity;

(ii) express one or more exogenous nucleic acid sequences or overexpress one or more endogenous genes encoding a protein having an ABC transporter ATP-binding protein activity;

(iii) express one or more exogenous nucleic acids sequences or overexpress one or more endogenous genes that encodes a protein that is at least 60% identical to: the blc gene product of SEQ ID NO: 147, ybhG gene product of SEQ ID NO: 116, or the ydhC gene product of SEQ ID NO: 148;

(iv) express one or more exogenous nucleic acids sequences or overexpress one or more endogenous genes that encodes a protein that is at least 60% identical to the mlaD gene product of SEQ ID NO: 149, the mlaE gene product of SEQ ID NO: 150, or the mlaF gene product of SEQ ID NO: 151;

(v) express one or more exogenous nucleic acid sequences or overexpress one or more endogenous genes encoding a protein having a siderophore receptor protein activity or overexpress one or more endogenous genes encoding a protein having a siderophore receptor protein activity;

(vi) comprise a disruption of or downregulation in the expression of a regulator of expression of one or more endogenous genes encoding a protein having an ABC transporter permease activity, a protein having an ABC transporter ATP-binding protein activity, a blc gene, a ybhG protein, a ydhC protein, a mlaD protein, mlaE protein, mlaF protein, or a protein having a siderophore receptor protein activity;

(vii) express an exogenous nucleic acid encoding a multi-domain protein having acetyl-CoA carboxylase activity (MD-ACC);

(viii) overexpress one or more endogenous genes encoding acetyl-CoA carboxyltransferase subunit α, biotin carboxyl carrier protein, biotin carboxylase, or acetyl-CoA carboxyltransferase subunit β, or express one or more exogenous genes encoding acetyl-CoA carboxyltransferase, biotin carboxyl carrier protein, or biotin carboxylase activities;

(ix) disruption of or downregulation in the expression of an endogenous gene encoding a protein having (acyl-carrier-protein) S-malonyltransferase activity, an endogenous gene encoding a protein having 3-hydroxypalmitoyl-(acyl-carrier-protein) dehydratase activity, or both;

(x) express an exogenous nucleic acid sequence or overexpress an endogenous gene encoding a protein having fatty acyl-CoA ligase activity, or both;

(xi) disruption of or downregulation in the expression of at least one endogenous gene encoding a protein having acyl-CoA dehydrogenase activity or enoyl-CoA hydratase activity;

(xii) a disruption or downregulation in the expression of at least one endogenous gene encoding a protein having acyl-CoA esterase/thioesterase activity;

(xiii) disruption of or downregulation in the expression of at least one endogenous gene encoding a repressor of transcription of one or more genes required for fatty acid beta-oxidation or an upregulator of fatty acid biosynthesis in combination with disruption or downregulation of one or more endogenous genes encoding one or more proteins of fatty acid beta-oxidation pathway;

(xxv) express an exogenous nucleic acid sequence or overexpress an endogenous gene encoding a protein having geranyl pyrophosphate synthase (GPPS), farnesyl pyrophosphate synthase, isoprenyl pyrophosphate synthase, geranylgeranyl pyrophosphate synthase, alcohol kinase, alcohol diphosphokinase, phosphate kinase, isopentenyl diphosphate isomerase, geranyl pyrophosphate synthase, prenol kinase activity, prenol diphosphokinase activity, isoprenol kinase activity, isoprenol diphosphokinase activity, dimethylallyl phosphate kinase activity, isopentenyl phosphate kinase activity, or isopentenyl diphosphate isomerase activity;

(xiv) express an exogenous nucleic acid sequence or overexpress an endogenous gene encoding a protein having GPP synthase activity;

(xv) express an exogenous nucleic acid sequence encoding an olivetol synthase;

(xvi) express an exogenous nucleic acid sequence encoding an olivetolic acid cyclase;

(xvii) express an exogenous nucleic acid sequence encoding a prenyltransferase;

(xviii) express one or more exogenous nucleic acid sequences or overexpressing one or more endogenous genes encoding one or more enzymes of MVA pathway, MEP pathway, or a non-MVA, non-MEP pathway;

(xix) express an exogenous nucleic acid sequence or overexpress an endogenous gene encoding a biotin-(acetyl-CoA carboxylase) ligase;

(xx) overexpress an endogenous gene encoding a isopentenyl-diphosphate delta-isomerase or express an exogenous nucleic acid sequence encoding a isopentenyl-diphosphate delta-isomerase;

(xxi) overexpress an endogenous genes encoding a hydroxyethylthiazole kinase or express an exogenous nucleic acid sequence encoding a hydroxyethylthiazole kinase or both;

(xxii) express an exogenous nucleic acid sequence encoding a Type III pantothenate kinase or overexpress an endogenous gene encoding a Type III pantothenate kinase; and (xxiii) a disruption of or downregulation in the expression of at least one endogenous gene encoding a phosphatase selected from the group consisting of ADP-sugar pyrophosphatase, dihydroneopterin triphosphate diphosphatase, pyrimidine deoxynucleotide diphosphatase, pyrimidine pyrophosphate phosphatase, and Nudix hydrolase.

In some embodiments, the invention provides an engineered cell comprising a non-natural cannabinoid synthase (e.g., the non-natural THCAS, CBDAS, and/or CBCAS) and one or more of a non-natural OLS, a non-natural OAC, a GPP pathway enzyme, a non-natural prenyltransferase, and an additional modification described herein. In some embodiments, the invention provides one or more nucleic acids encoding a non-natural cannabinoid synthase (e.g., the non-natural THCAS, CBDAS, and/or CBCAS) and one or more of a non-natural OLS, a non-natural OAC, a GPP pathway enzyme, a non-natural prenyltransferase, and an additional modification. In some embodiments, the invention provides an expression construct comprising the one or more nucleic acids. In some embodiments, the invention provides an engineered cell comprising the one or more nucleic acids. In some embodiments, the invention provides an engineered cell comprising the expression construct. In some embodiments, the expression construct comprises a single expression vector. In some embodiments, the expression construct comprises more than one expression vector. In some embodiments, the engineered cell is capable of expressing THCAS, CBDAS, and/or CBCAS. In some embodiments, the engineered cell is capable of producing THCA, CBDA, and/or CBCA.

X. Host Cells

A variety of microorganisms may be suitable as the engineered cell described herein. Such organisms include both prokaryotic and eukaryotic organisms including, but not limited to, bacteria, including archaea and eubacteria, and eukaryotes, including yeast, plant, and insect. Nonlimiting examples of suitable microbial hosts for the bio-production of a cannabinoid include, but are not limited to, any Gram negative organisms, more particularly a member of the family Enterobacteriaceae, such as *E. coli*, or *Oligotropha carboxidovorans*, or a *Pseudomononas* sp.; any Gram positive microorganism, for example *Bacillus subtilis, Lactobaccilus* sp. or *Lactococcus* sp.; a yeast, for example *Saccharomyces cerevisiae, Pichia pastoris* or *Pichia stipitis*; and other groups or microbial species. In some embodiments, the microbial host is a member of the genera *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula*, or *Saccharomyces*. In some embodiments, the microbial host is *Oligotropha carboxidovorans* (such as strain OM5), *Escherichia coli, Alcaligenes eutrophus* (*Cupriavidus necator*), *Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Bacillus subtilis* or *Saccharomyces cerevisiae.*

Further exemplary species are reported in U.S. Pat. No. 9,657,316 and include, for example, *Escherichia coli, Saccharomyces cerevisiae, Saccharomyces kluyveri, Candida boidinii, Clostridium kluyveri, Clostridium acetobutylicum, Clostridium beijerinckii, Clostridium saccharoperbutylacetonicum, Clostridium perfringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculosis, Porphyromonas gingivalis, Arabidopsis thaliana, Thermus thermophilus, Pseudomonas* species, including *Pseudomonas aeruginosa, Pseudomonas putida, Pseudomonas stutzeri, Pseudomonas fluorescens, Homo sapiens, Oryctolagus cuniculus, Rhodobacter spaeroides, Thermoanaerobacter brockii, Metallosphaera sedula, Leuconostoc mesenteroides, Chloroflexus aurantiacus, Roseiflexus castenholzii, Erythrobacter, Simmondsia chinensis, Acinetobacter* species, including *Acinetobacter calcoaceticus* and *Acinetobacter baylyi, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salinarum, Geobacillus stearothermophilus, Aeropyrum pernix, Sus scrofa, Caenorhabditis elegans, Corynebacterium glutamicum, Acidaminococcus fermentans, Lactococcus lactis, Lactobacillus plantarum, Streptococcus thermophilus, Enterobacter aerogenes, Candida, Aspergillus terreus, Pedicoccus pentosaceus, Zymomonas mobilus, Acetobacter pasteurians, Kluyveromyces lactis, Eubacterium barkeri, Bacteroides capillosus, Anaerotruncus colihominis, Natranaerobius thermophilusm, Campylobacter jejuni, Haemophilus influenzae, Serratia marcescens, Citrobacter amalonaticus, Myxococcus xanthus, Fusobacterium nuleatum, Penicillium chrysogenum*, marine gamma proteobacterium, butyrate-producing bacterium, *Nocardia iowensis, Nocardia farcinica, Streptomyces griseus, Schizosaccharomyces pombe, Geobacillus thermoglucosidasius, Salmonella typhimurium, Vibrio cholera, Heliobacter pylori, Nicotiana tabacum, Oryza sativa, Haloferax mediterranei, Agrobacterium tumefaciens, Achromobacter denitrificans, Fusobacterium nucleatum, Streptomyces clavuligenus, Acinetobacter baumanii, Mus musculus, Lachancea kluyveri, Trichomonas vaginalis, Trypanosoma brucei, Pseudomonas stutzeri, Bradyrhizobium japonicum, Mesorhizobium loti, Bos taurus, Nicotiana glutinosa, Vibrio vulnificus, Selenomonas ruminantium, Vibrio parahaemolyticus, Archaeoglobus fulgidus, Haloarcula marismortui, Pyrobaculum aerophilum, Mycobacterium smegmatis* MC2 155, *Mycobacterium avium* subsp. *paratuberculosis* K-10, *Mycobacterium marinum* M, *Tsukamurella paurometabola* DSM 20162, Cyanobium PCC7001, *Dictyostelium discoideum* AX4, as well as other exemplary species disclosed herein or available as source organisms for corresponding genes.

In some embodiments, the engineered cell is selected from bacteria, fungi, yeast, algae, and cyanobacteria. In some embodiments, the bacteria is *Escherichia, Corynebacterium, Bacillus, Ralstonia, Zymomonas*, or *Staphylococcus*. In some embodiments, the bacteria is *Escherichia coli.*

In some embodiments, the engineered cell is an organism selected from *Acinetobacter baumannii* Naval-82, *Acinetobacter* sp. ADP1, *Acinetobacter* sp. strain M-1, *Actinobacillus succinogenes* 130Z, *Allochromatium vinosum* DSM 180, *Amycolatopsis methanolica, Arabidopsis thaliana, Atopobium parvulum* DSM 20469, *Azotobacter vinelandii* DJ, *Bacillus alcalophilus* ATCC 27647, *Bacillus azotoformans* LMG 9581, *Bacillus coagulans* 36D1, *Bacillus megaterium, Bacillus methanolicus* MGA3, *Bacillus methanolicus* PB1, *Bacillus methanolicus* PB-1, *Bacillus selenitireducens* MLS10, *Bacillus smithii, Bacillus subtilis, Burkholderia cenocepacia, Burkholderia cepacia, Burkholderia multivorans, Burkholderia pyrrocinia, Burkholderia stabilis, Burkholderia thailandensis* E264, Burkholderiales bacterium Joshi_001, Butyrate-producing bacterium L2-50, *Campylobacter jejuni, Candida albicans, Candida boidinii, Candida methylica, Carboxydothermus hydrogenoformans, Carboxydothermus* hydrogenoformans Z-2901, *Caulobacter* sp. AP07, *Chloroflexus aggregans* DSM 9485, *Chloroflexus aurantiacus* J-10-fl, *Citrobacter freundii, Citrobacter koseri* ATCC BAA-895, *Citrobacter youngae, Clostridium, Clostridium acetobutylicum, Clostridium acetobutylicum* ATCC 824, *Clostridium acidurici, Clostridium aminobutyricum, Clostridium asparagiforme* DSM 15981, *Clostridium beijerinckii, Clostridium beijerinckii* NCIMB 8052, *Clostridium bolteae* ATCC BAA-613, *Clostridium carboxidivorans* P7, *Clostridium cellulovorans* 743B, *Clostridium difficile, Clostridium hiranonis* DSM 13275, *Clostridium hylemonae* DSM 15053, *Clostridium kluyveri, Clostridium kluyveri* DSM 555, *Clostridium ljungdahli, Clostridium ljungdahlii* DSM 13528, *Clostridium methylpentosum* DSM 5476, *Clostridium pasteurianum, Clostridium pasteurianum* DSM 525, *Clostridium perfringens, Clostridium perfringens* ATCC 13124, *Clostridium perfringens* str. 13, *Clostridium phytofermentans* ISDg, *Clostridium saccharobutylicum, Clostridium saccharoperbutylacetonicum, Clostridium saccharoperbutylacetonicum* N1-4, *Clostridium tetani, Corynebacterium glutamicum* ATCC 14067, *Corynebacterium glutamicum* R, *Corynebacterium* sp. U-96, *Corynebacterium variabile, Cupriavidus* necator N-1, Cyanobium PCC7001, *Desulfatibacillum alkenivorans* AK-01, *Desulfitobacterium hafniense, Desulfitobacterium metallireducens* DSM 15288, *Desulfotomaculum reducens* MI-1, *Desulfovibrio africanus* str. Walvis Bay, *Desulfovibrio fructosovorans* JJ, *Desulfovibrio vulgaris* str. Hildenborough, *Desulfovibrio vulgaris* str. 'Miyazaki F', *Dictyostelium discoideum* AX4, *Escherichia coli, Escherichia coli* K-12, *Escherichia coli* K-12 MG1655, *Eubacterium hallii* DSM 3353, *Flavobacterium frigoris, Fusobacterium nucleatum* subsp. *polymorphum* ATCC 10953, *Geobacillus* sp. Y4.1MC1, *Geobacillus themodenitrificans* NG80-2, *Geobacter bemidjiensis* Ben), *Geobacter sulfurreducens, Geobacter sulfurreducens* PCA, *Geobacillus stearothermophilus* DSM 2334, *Haemophilus influenzae, Helicobacter pylori, Homo sapiens, Hydrogenobacter thermophilus, Hydrogenobacter thermophilus* TK-6, *Hyphomicrobium denitrificans* ATCC 51888, *Hyphomicrobium zavarzinii, Klebsiella pneumoniae, Klebsiella pneumoniae* subsp. *pneumoniae* MGH 78578, *Lactobacillus brevis* ATCC 367, *Leuconostoc mesenteroides, Lysinibacillus fusiformis, Lysinibacillus sphaericus, Mesorhizobium loti* MAFF303099, *Metallosphaera sedula, Methanosarcina acetivorans, Methanosarcina acetivorans* C2A, *Methanosarcina barkeri, Methanosarcina mazei* Tuc01, *Methylobacter marinus, Methylobacterium extorquens, Methylobacterium extorquens* AM1, *Methylococcus capsulatas, Methylomonas aminofaciens, Moorella thermoacetica, Mycobacter* sp. strain JC1 DSM 3803, *Mycobacterium avium* subsp. *paratuberculosis* K-10, *Mycobacterium bovis* BCG, *Mycobacterium gastri, Mycobacterium marinum* M, *Mycobacterium smegmatis, Mycobacterium smegmatis* MC2 155, *Mycobacterium tuberculosis, Nitrosopumilus salaria* BD31, *Nitrososphaera gargensis* Ga9.2, *Nocardia farcinica* IFM 10152, *Nocardia iowensis* (sp. NRRL 5646), *Nostoc* sp. PCC 7120, *Ogataea angusta, Ogataea parapolymorpha* DL-1 (*Hansenula polymorpha* DL-1), *Paenibacillus peoriae* KCTC 3763, *Paracoccus denitrificans, Penicillium chrysogenum, Photobacterium profundum* 3TCK, *Phytofermentans* ISDg, *Pichia pastoris, Picrophilus torridus* DSM9790, *Porphyromonas gingivalis, Porphyromonas gingivalis* W83, *Pseudomonas aeruginosa* PA01, *Pseudomonas denitrificans, Pseudomonas knackmussii, Pseudomonas putida, Pseudomonas* sp, *Pseudomonas syringae* pv. *syringae* B728a, *Pyrobaculum islandicum* DSM 4184, *Pyrococcus abyssi, Pyrococcus furiosus, Pyrococcus horikoshii* OT3, *Ralstonia eutropha, Ralstonia eutropha* H16, *Rhodobacter capsulatus, Rhodobacter sphaeroides, Rhodobacter sphaeroides* ATCC 17025, *Rhodopseudomonas palustris, Rhodopseudomonas palustris* CGA009, *Rhodopseudomonas palustris* DX-1, *Rhodospirillum rubrum, Rhodospirillum rubrum* ATCC 11170, *Ruminococcus obeum* ATCC 29174, *Saccharomyces cerevisiae, Saccharomyces cerevisiae* S288c, *Salmonella enterica, Salmonella enterica* subsp. *enterica* serovar *Typhimurium* str. LT2, *Salmonella enterica typhimurium, Salmonella typhimurium, Schizosaccharomyces pombe, Sebaldella termitidis* ATCC 33386, *Shewanella oneidensis* MR-1, *Sinorhizobium meliloti* 1021, *Streptomyces coelicolor, Streptomyces griseus* subsp. *griseus* NBRC 13350, *Sulfolobus acidocalarius, Sulfolobus solfataricus* P-2, *Synechocystis* str. PCC 6803, *Syntrophobacter fumaroxidans, Thauera aromatica, Thermoanaerobacter* sp. X514, *Thermococcus kodakaraensis, Thermococcus litoralis, Thermoplasma acidophilum, Thermoproteus neutrophilus, Thermotoga maritima, Thiocapsa roseopersicina, Tolumonas auensis* DSM 9187, *Trichomonas vaginalis* G3, *Trypanosoma brucei, Tsukamurella paurometabola* DSM 20162, *Vibrio cholera, Vibrio harveyi* ATCC BAA-1116, *Xanthobacter autotrophicus* Py2, *Yersinia intermedia*, and *Zea mays*.

Algae that can be engineered for cannabinoid production include, but are not limited to, unicellular and multicellular algae. Examples of such algae can include a species of rhodophyte, chlorophyte, heterokontophyte (including diatoms), tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta.

Microalgae (single-celled algae) produce natural oils that can contain the synthesized cannabinoids. Specific species that are considered for cannabinoid production include, but are not limited to, *Neochloris oleoabundans, Scenedesmus dimorphus, Euglena gracilis, Phaeodactylum tricornutum, Pleurochrysis carterae, Prymnesium parvum, Tetraselmis chui, Nannochloropsis gaditiana. Dunaliella sauna. Dunaliella tertiolecta, Chlorella vulgaris, Chlorella variabilis*, and *Chlamydomonas reinhardtii*. Additional or alternate algal sources can include one or more microalgae of the *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrsosphaera, Cricosphaera, Crypthecodinium, Cryptomonas, Cyclotella, Dunaliella, Ellipsoidon, Emiliania. Eremospha-*

*era, Ernodesmius, Euglena, Franceia, Fragilaria, Gloeolhamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus. Platymonas, Pleurochrsis, Pleurococcus, Prototheca, Pseudochlorella, Pyramimonas, Pvrobotrys, Scenedesmus, Skeletonema, Spyrogyra, Stichococcus, Tetraselmis, Thalassiosira, Viridiella*, and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylcoccopsis, Dermocarpella, Fischerella, Fremyella, Geitleria, Geitlerinema, Gloeobacter, Gloeocapsa, Gloeothece, Halospirulina, Ivengariella, Leptolyngbya, Limnothrix, Lyngbya, Microcoleus, Microcystis, Mxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scvtonema, Spirulina, Stanieria, Starria, Stigonema, Symploca, Synechococcus, Svnechocystis, Tolipothrix, Trichodesmium. Tychonema*, and *Xenococcus* species.

The host cell may be genetically modified for a recombinant production system, e.g., to produce THCA, CBDA, and/or CBCA as described herein. The mode of gene transfer technology may be by electroporation, conjugation, transduction or natural transformation.

To genetically modify a host cell of the invention, one or more heterologous nucleic acids disclosed herein is introduced stably or transiently into a host cell, using established techniques. Such techniques may include, but are not limited to, electroporation, calcium phosphate precipitation, DEAE-dextran mediated transfection, liposome-mediated transfection, particle bombardment, and the like. For stable transformation, a heterologous nucleic acid will generally further include a selectable marker, e.g., any of several well-known selectable markers such as neomycin resistance, ampicillin resistance, tetracycline resistance, chloramphenicol resistance, kanamycin resistance, hygromycin resistance, G418 resistance, bleomycin resistance, zeocin resistance, and the like. A broad range of plasmids and drug resistance markers are available and described in embodiments herein. The cloning vectors are tailored to the host organisms based on the nature of antibiotic resistance markers that can function in that host cell. In some embodiments, the host cell is genetically modified using CRISPR/Cas9 to produce the engineered cell of the invention.

XI. Fermentation

In some embodiments, the invention provides a method of producing a cannabinoid or precursor thereof, e.g., THCA, CBDA, and/or CBCA, as described herein, comprising incubating a culture of an engineered cell provided herein to provide the cannabinoid. In some embodiments, the method further comprises recovering the cannabinoid, e.g., THCA, CBDA, and/or CBCA from the cell, the cell extract, the culture medium, the whole culture, or a combination thereof.

In some embodiments, the culture of the engineered cells further comprises at least one carbon source. In embodiments where the cells are heterotrophic cells, the culture medium comprises at least one carbon source that is also an energy source. In some embodiments, the culture medium comprises one, two, three, or more carbon sources that are not primary energy sources. Nonlimiting examples of feed molecules that can be included in the culture medium include acetate, malonate, oxaloacetate, aspartate, glutamate, beta-alanine, alpha-alanine, hexanoate, hexanol, prenol, isoprenol, and geraniol. Further examples of compounds that can be provided in the culture medium include, without limitation, biotin, thiamine, pantotheine, and 4-phosphopantetheine.

In some embodiments, acetate is provided in the culture medium. In some embodiments, acetate and hexanoate are provided in the culture medium. In some embodiments, malonate and hexanoate are provided in the culture medium. In some embodiments, the culture medium comprises prenol, isoprenol, and/or geraniol. In some embodiments, the culture medium comprises aspartate, hexanoate, and prenol, isoprenol, and/or geraniol.

Depending on the desired microorganism or strain to be used, the appropriate culture medium may be used. For example, descriptions of various culture media may be found in "Manual of Methods for General Bacteriology" of the American Society for Bacteriology (Washington D.C., USA, 1981). As used here, culture medium, or simply "medium" as it relates to the growth source refers to the starting medium be it in a solid or liquid form. "Cultured medium" as used herein refers to medium (e.g. liquid medium) containing microbes that have been fermentatively grown and can include other cellular biomass. The medium generally includes one or more carbon sources, nitrogen sources, inorganic salts, vitamins and/or trace elements. "Whole culture" as used herein refers to cultured cells plus the culture medium in which they are cultured. "Cell extract" as used herein refers to a lysate of the cultured cells, which may include the culture medium and which may be crude (unpurified), purified or partially purified. Methods of purifying cell lysates are known to the skilled artisan and described in embodiments herein.

Exemplary carbon sources include sugar carbons such as sucrose, glucose, galactose, fructose, mannose, isomaltose, xylose, maltose, arabinose, cellobiose and 3-, 4-, or 5-oligomers thereof. Other carbon sources include carbon sources such as methanol, ethanol, glycerol, formate and fatty acids. Still other carbon sources include carbon sources from gas such as synthesis gas, waste gas, methane, CO, $CO_2$ and any mixture of CO, $CO_2$ with $H_2$. Other carbon sources can include renewal feedstocks and biomass. Exemplary renewal feedstocks include cellulosic biomass, hemicellulosic biomass and lignin feedstocks.

In some embodiments, culture conditions include aerobic, microaerobic, anaerobic or substantially anaerobic growth or maintenance conditions. Exemplary aerobic, microaerobic, and anaerobic conditions have been described previously and are known in the art. Exemplary anaerobic conditions for fermentation processes are described, for example, in U.S. Patent Publication No. 2009/0047719. Any of these conditions can be employed with the microbial organisms described herein as well as other anaerobic conditions known in the field. The culture conditions can include, for example, liquid culture procedures as well as fermentation and other large scale culture procedures. Useful yields of the products can be obtained under aerobic, microaerobic, anaerobic or substantially anaerobic culture conditions.

In some embodiments, the engineered cell is sustained, cultured or fermented under aerobic, microaerobic, anaerobic or substantially anaerobic conditions. Briefly, anaerobic conditions refer to an environment devoid of oxygen. Conditions include, for example, a culture, batch fermentation or continuous fermentation such that the dissolved oxygen concentration in the medium remains between 0 and 10% of saturation, or higher. Substantially anaerobic conditions also include growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions can be scaled up and grown continuously for manufacturing cannabinoid product. Exemplary growth procedures include, for example, fed-batch fermentation and batch separation; fed-batch fermentation and continuous separation, or continuous fermentation and continuous separation. Fermentation procedures can be particularly useful for the biosynthetic production of commercial quantities of cannabinoids, e.g., THCA, CBDA, and/or CBCA. Generally, and as with non-continuous culture procedures, the continuous and/or near-continuous production of cannabinoid product can include culturing a cannabinoid-producing organism with sufficient nutrients and medium to sustain and/or nearly sustain growth in an exponential phase. Continuous culture under such conditions can include, for example, 1 day, 2, 3, 4, 5, 6 or 7 days or more. Additionally, continuous culture can include 1 week, 2, 3, 4 or 5 or more weeks and up to several months. Alternatively, the desired microorganism can be cultured for hours, if suitable for a particular application. It is to be understood that the continuous and/or near-continuous culture conditions also can include all time intervals in between these exemplary periods. It is further understood that the time of culturing the microbial organism is for a sufficient period of time to produce a sufficient amount of product for a desired purpose.

Fermentation procedures are known to the skilled artisan. Briefly, fermentation for the biosynthetic production of a cannabinoid, e.g., THCA, CBDA, and/or CBCA, can be utilized in, for example, fed-batch fermentation and batch separation; fed-batch fermentation and continuous separation, or continuous fermentation and continuous separation. Examples of batch and continuous fermentation procedures are known in the field. Typically cells are grown at a temperature in the range of about 25° C. to about 40° C. in an appropriate medium, as well as up to 70° C. for thermophilic microorganisms.

The culture medium at the start of fermentation may have a pH of about 4 to about 7. The pH may be less than 11, less than 10, less than 9, or less than 8. In some embodiments, the pH is at least 2, at least 3, at least 4, at least 5, at least 6, or at least 7. In some embodiments, the pH of the medium is about 6 to about 9.5; 6 to about 9, about 6 to 8 or about 8 to 9.

In some embodiments, upon completion of the cultivation period, the fermenter contents are passed through a cell separation unit, for example, a centrifuge, filtration unit, and the like, to remove cells and cell debris. In embodiments where the desired product is expressed intracellularly, the cells are lysed or disrupted enzymatically or chemically prior to or after separation of cells from the fermentation broth, as desired, in order to release additional product. The fermentation broth can be transferred to a product separations unit. Isolation of product can be performed by standard separations procedures employed in the art to separate a desired product from dilute aqueous solutions. Such methods include, but are not limited to, liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, and the like) to provide an organic solution of the product, if appropriate, standard distillation methods, and the like, depending on the chemical characteristics of the product of the fermentation process.

Suitable purification and/or assays to test a cannabinoid, e.g., THCA, CBDA, and/or CBCA, produced by the methods herein can be performed using known methods. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., Biotechnol. Bioeng. 90:775-779 (2005)), or other suitable assay and detection methods well known in the art. The individual enzyme or protein activities from the exogenous DNA sequences can also be assayed using methods known in the art.

Cannabinoids can be separated from other components in the culture using a variety of methods well known in the art. Such separation methods include, for example, extraction procedures as well as methods that include liquid-liquid extraction, pervaporation, evaporation, filtration, membrane filtration (including reverse osmosis, nanofiltration, ultrafiltration, and microfiltration), membrane filtration with diafiltration, membrane separation, reverse osmosis, electrodialysis, distillation, extractive distillation, reactive distillation, azeotropic distillation, crystallization and recrystallization, centrifugation, extractive filtration, ion exchange chromatography, size exclusion chromatography, adsorption chromatography, carbon adsorption, hydrogenation, and ultrafiltration. For example, the amount of cannabinoid or other product(s), including a polyketide, produced in a bio-production media generally can be determined using any of methods such as, for example, high performance liquid chromatography (HPLC), gas chromatography (GC), GC/Mass Spectroscopy (MS), or spectrometry.

In some embodiments, the cell extract or cell culture medium described herein comprises a cannabinoid. Exemplary cannabinoids include, but are not limited to, cannabichromene (CBC) type (e.g. cannabichromenic acid), cannabigerol (CBG) type (e.g. cannabigerolic acid), cannabidiol (CBD) type (e.g. cannabidiolic acid), $\Delta^9$-trans-tetrahydrocannabinol ($\Delta^9$-THC) type (e.g. $\Delta^9$-tetrahydrocannabinolic acid), $\Delta^8$-trans-tetrahydrocannabinol ($\Delta^8$-THC) type, cannabicyclol (CBL) type, cannabielsoin (CBE) type, cannabinol (CBN) type, cannabinodiol (CBND) type, cannabitriol (CBT) type, cannabigerolic acid (CBGA), cannabigerolic acid monomethylether (CBGAM), cannabigerol (CBG), cannabigerol monomethylether (CBGM), cannabigerovarinic acid (CBGVA), cannabigerovarin (CBGV), cannabichromenic acid (CBCA), cannabichromene (CBC), cannabichromevarinic acid (CBCVA), cannabichromevarin (CBCV), cannabidiolic acid (CBDA), cannabidiol (CBD), cannabidiol monomethylether (CBDM), cannabidiol-C4 (CBD-C4), cannabidivarinic acid (CBDVA), cannabidivarin (CBDV), cannabidiorcol (CBD-C1), $\Delta^9$-tetrahydrocannabinolic acid A (THCA-A), $\Delta^9$-tetrahydrocannabinolic acid B (THCA-B), $\Delta^9$-tetrahydrocannabinol (THC), $\Delta^9$-tetrahydrocannabinolic acid-C4 (THCA-C4), $\Delta^9$-tetrahydrocannabinol-C4 (THC-C4), $\Delta^9$-tetrahydrocannabivarinic acid (THCVA), $\Delta^9$-tetrahydrocannabivarin (THCV), $\Delta^9$-tetrahydrocannabiorcolic acid (THCA-C1), $\Delta^9$-tetrahydrocannabiorcol (THC-C1), $\Delta^7$-cis-iso-tetrahydrocannabivarin, $\Delta^8$-tetrahydrocannabinolic acid ($\Delta^8$-THCA), $\Delta^8$-tetrahydrocannabinol ($\Delta^8$-THC), cannabicyclolic acid (CBLA), cannabicyclol (CBL), cannabicyclovarin (CBLV), cannabielsoic acid A (CBEA-A), cannabielsoic acid B (CBEA-B), cannabielsoin (CBE), cannabielsoic acid, cannabicitranic acid, cannabinolic acid (CBNA), cannabinol (CBN), cannabinol methylether (CBNM), cannabinol-C4, (CBN-C4), cannabivarin (CBV), cannabinol-C2 (CNB-C2), cannabiorcol (CBN-C1), cannabinodiol (CBND), cannabinodivarin (CBVD), cannabitriol (CBT), 10-ethyoxy-9-hydroxy-delta-6a-tetrahydrocannabinol, 8,9-dihydroxyl-delta-6a-tetrahydrocannabinol, cannabitriolvarin (CBTVE), dehydrocannabifuran (DCBF), cannabifuran (CBF), cannabichromanon (CBCN), cannabicitran (CBT), 10-oxo-delta-6a-tetrahydrocannabinol (OTHC), $\Delta^9$-cis-tetrahydrocannabinol (cis-THC), 3,4,5,6-tetrahydro-7-hydroxy-alpha-alpha-2-trimethyl-9-n-propyl-2,6-methano-2H-1-benzoxocin-5-methanol (OH-iso-HHCV), cannabiripsol (CBR), and trihydroxy-$\Delta^9$-tetrahydrocannabinol (triOH-THC).

In some embodiments, the invention provides a cell extract or cell culture medium comprising cannabigerolic acid (CBGA), tetrahydrocannabivarin (THCV), tetrahydrocannabivarinic acid (THCVA), cannabidivarin (CBDV), cannabidivarinic acid (CBDVA), cannabinol (CBN), cannabinolic acid (CBNA), cannabidiol (CBD), cannabidiolic acid (CBDA), cannabichromene (CBC), cannabichromenic acid (CBCA), cannabigerivarin (CBGV), cannabigerivarinic acid (CBGVA), cannabigerol (CBG), cannabichromevarin (CBCV), cannabichromevarinic acid (CBCVA), tetrahydrocannabinol (THC), tetrahydrocannabinolic acid (THCA), analogs, or derivatives thereof, or a combination thereof derived from the engineered cell described herein. In some embodiments, the cell extract or cell culture medium comprises one or both of THCA-A and THCA-B, or an analog or derivative thereof. In some embodiments, the analog or derivative of THCA comprises tetrahydrocannabinolic acid-C4 (THCA-C4).

In some embodiments, the cell extract or cell culture medium derived from the engineered cell comprises reduced amounts of pentyl diacetic acid lactone (PDAL), hexanoyl triacetic acid lactone (HTAL), or lactone analog or derivatives thereof, compared with a cell not comprising the modifications described herein. In some embodiments, the cell extract or cell culture medium comprises pentyl diacetic acid lactone (PDAL), hexanoyl triacetic acid lactone (HTAL), or lactone analog or derivatives thereof, or combination thereof, at a concentration of no more than about 50% to about 0.0001% of the cell extract or cell culture medium. In some embodiments, the cell extract or cell culture medium comprises PDAL, HTAL, or lactone analog or derivatives thereof, or combination thereof, at a concentration of no more than about 45% to about 0.001%, or about 40% to about 0.005%, or about 35% to about 0.01%, or about 30% to about 0.05%, or about 25% to about 0.1%, or about 20% to about 0.5%, or about 15% to about 1%, or about 10% to about 5% of the cell extract or cell culture medium. In some embodiments, the cell extract or cell culture medium comprises PDAL, HTAL, or lactone analog or derivatives thereof, or combination thereof, at a concentration of no more than about 0.0001%, about 0.0005%, about 0.001%, about 0.005%, about 0.01%, about 0.05%, about 0.1%, about 0.5%, about 1%, about 2%, about 5%, about 7%, about 10%, about 12%, about 15%, about 17%, about 20%, about 22%, about 25%, about 27%, about 30%, about 32%, about 35%, about 37%, about 40%, about 42%, about 45%, about 47%, or about 50% of the cell extract or cell culture medium. In some embodiments, the reduced amounts of PDAL, HTAL, or lactone analog or derivatives thereof leads to increased flux for the biosynthesis of a cannabinoid, e.g., THCA, CBDA, and/or CBCA.

XII. Method of Making or Isolating

In some embodiments, the invention provides a method of making a cannabinoid selected from CBGA, CBG, CBGV, CBGVA; CBGOA, THCV, THCVA, CBD, CBDA, CBDV, CBDVA, CBN, CBNA, CBC, CBCA, CBCV, CBCVA, THC, THCA, analogs or derivatives thereof, or combinations thereof, comprising culturing the engineered cell as described herein, or isolating CBGA, CBG, CBGV, CBGVA; CBGOA, THCV, THCVA, CBD, CBDA, CBDV, CBDVA, CBN, CBNA, CBC, CBCA, CBCV, CBCVA, THC, THCA, analogs or derivatives thereof from the cell extract or cell culture medium as described herein. In some embodiments, the cannabinoid is THCA, THC, CBDA, CBD, CBCA, CBC, an analog or derivative thereof, or a combination thereof.

In some embodiments, the invention provides a method of making THCA, CBDA, and/or CBCA or analogs or derivatives thereof, comprising culturing the engineered cell comprising the non-natural THCAS, CBDAS, and/or CBCAS described herein, the nucleic acid encoding the non-natural THCAS, CBDAS, and/or CBCAS, the expression construct comprising the nucleic acid, or a combination thereof. In some embodiments, the invention provides a method of isolating THCA, CBDA, and/or CBCA or analogs or derivatives thereof from the cell extract or cell culture medium of the engineered cell.

Methods of culturing cells, e.g., the engineered cell of the invention, are provided herein. Methods of isolating a cannabinoid, e.g., THCA, CBDA, or CBCA, are also provided herein. In some embodiments, the isolating comprises liquid-liquid extraction, pervaporation, evaporation, filtration, membrane filtration (including reverse osmosis, nanofiltration, ultrafiltration, and microfiltration), membrane filtration with diafiltration, membrane separation, reverse osmosis, electrodialysis, distillation, extractive distillation, reactive distillation, azeotropic distillation, crystallization and recrystallization, centrifugation, extractive filtration, ion exchange chromatography, size exclusion chromatography, adsorption chromatography, carbon adsorption, hydrogenation, ultrafiltration, or combination thereof.

In some embodiments, the invention provides an in vitro method of making THCA, CBDA, and/or CBCA. In some embodiments, the invention provides a method of making THCA, CBDA, and/or CBCA or an analog or derivative thereof, comprising contacting CBGA with a non-natural THCAS, CBDAS, and/or CBCAS provided herein.

In some embodiments, the invention provides a method of making THCA or an analog or derivative thereof, comprising contacting CBGA with the non-natural THCAS provided herein, the non-natural CBDAS provided herein, the non-natural CBCAS provided herein, or a combination thereof. In some embodiments, the method comprises contacting CBGA with the non-natural THCAS. In some embodiments, the contacting occurs at pH about 4.0 to about 6.0. In some embodiments, the contacting occurs at pH greater than about 3.5 and less than pH about 6.5, less than about 6.0, less than about 5.5, less than about 5.0, less than about 4.5, or less than about 4.0. In some embodiments, the contacting occurs at about pH 4.0, about pH 4.1, about pH 4.2, about pH 4.3, about pH 4.4, about pH 4.5, about pH 4.6, about pH 4.7, about pH 4.8, about pH 4.9, about pH 5.0, about pH 5.1, about pH 5.2, about pH 5.3, about pH 5.4, about pH 5.5, about pH 5.6, about pH 5.7, about pH 5.8, about pH 5.9, or about 6.0. The pH-dependency of THCA biosynthesis by THCAS is described herein.

In some embodiments, the disclosure provides a method of making CBDA or an analog or derivative thereof, comprising contacting CBGA with the non-natural THCAS provided herein, the non-natural CBDAS provided herein, the non-natural CBDAS provided herein, the non-natural CBCAS provided herein, or a combination thereof. In some embodiments, the method comprises contacting CBGA with the non-natural CBDAS. In some embodiments, the contacting occurs at pH about 4.0 to about 6.0. In some embodiments, the contacting occurs at pH greater than about 3.5 and less than pH about 6.5, less than about 6.0, less than about 5.5, less than about 5.0, less than about 4.5, or less than about 4.0. In some embodiments, the contacting occurs at about pH 4.0, about pH 4.1, about pH 4.2, about pH 4.3, about pH 4.4, about pH 4.5, about pH 4.6, about pH 4.7, about pH 4.8, about pH 4.9, about pH 5.0, about pH 5.1, about pH 5.2, about pH 5.3, about pH 5.4, about pH 5.5, about pH 5.6, about pH 5.7, about pH 5.8, about pH 5.9, or about 6.0. The pH-dependency of CBDA biosynthesis by CBDAS is described herein.

In some embodiments, the disclosure provides a method of making CBCA or an analog or derivative thereof, comprising contacting CBGA with the non-natural THCAS provided herein, the non-natural CBDAS provided herein, the non-natural CBCAS provided herein, or a combination thereof. In some embodiments, the method comprises contacting CBGA with the non-natural CBCAS; or contacting CBGA with the non-natural THCAS or the non-natural CBDAS at pH about 6.5 to about 8.0. In some embodiments, the CBCA is made by contacting CBGA with the non-natural THCAS or CBDAS at pH less than 8.0 and greater than about 6.5, greater than about 7.0, or greater than about 7.5. In some embodiments, the contacting occurs at about pH about pH 6.5, about pH 6.6, about pH 6.7, about pH 6.8, about pH 6.9, about pH 7.0, about pH 7.1, about pH 7.2, about pH 7.3, about pH 7.4, about pH 7.5, about pH 7.6, about pH 7.7, about pH 7.8, about pH 7.9, or about pH 8.0.

In some embodiments, the non-natural THCAS, CBDAS, and/or CBCAS is produced by an engineered cell, e.g., as described herein. In some embodiments, the non-natural THCAS, CBDAS, and/or CBCAS is overexpressed, e.g., on an exogenous nucleic acid such as a plasmid by an inducible or constitutive promoter, in an engineered cell then isolated from the engineered cell. Methods of isolating proteins from cells are known in the art. For example, the cells can be lysed to form a crude lysate, and the crude lysate can be further purified using filtration, centrifugation, chromatography, buffer exchange, or a combination thereof. The cell lysate is considered partially purified when about 10% to about 60%, or about 20% to about 50%, or about 30% to about 50% of the total proteins in the lysate is the desired protein of interest, e.g., THCAS, CBDAS, and/or CBCAS. A protein can also be isolated from the cell lysate as a purified protein when greater than 60%, greater than 70%, greater than 80%, greater than 90%, greater than 95%, or greater than 99% of total proteins in the lysate is the desired protein of interest, e.g., THCAS, CBDAS, and/or CBCAS. In some embodiments, the crude lysate comprising THCAS, CBDAS, and/or CBCAS is capable of converting CBGA to THCA, CBDA, and/or CBCA. In some embodiments, the CBGA is contacted with crude cell lysate comprising the non-natural THCAS, CBDAS, and/or CBCAS to form THCA, CBDA, and/or CBCA. In some embodiments, a partially purified lysate comprising THCAS, CBDAS, and/or CBCAS is capable of converting CBGA to THCA, CBDA, and/or CBCA. In some embodiments, the CBGA is contacted with partially purified lysate comprising the non-natural THCAS, CBDAS, and/or CBCAS to form THCA, CBDA, and/or CBCA. In some embodiments, a purified THCAS, CBDAS, and/or CBCAS protein is capable of converting CBGA to THCA, CBDA, and/or CBCA. In some embodiments, the CBGA is contacted with purified THCAS, CBDAS, and/or CBCAS to form THCA, CBDA, and/or CBCA.

XIII. Compositions

In some embodiments, the invention provides a composition comprising a prenylated aromatic compound or a derivative thereof obtained from the engineered cell, cell extract or cell culture medium, or method described herein. In some embodiments, the prenylated aromatic compound is CBGA, CBG, CBGV, CBGVA; CBGOA, THCV, THCVA, CBD, CBDA, CBDV, CBDVA, CBN, CBNA, CBC, CBCA, CBCV, CBCVA, THC, or THCA. In some embodiments, the prenylated aromatic compound is THCA, THC, CBDA, CBD, CBCA, CBC, an analog, derivative, or combination thereof.

In some embodiments, the composition comprises THCA, THC, an analog, derivative, or combination thereof at 10% or greater, 20% or greater, 30% or greater, 40% or greater, 50% or greater, 60% or greater, 70% or greater, 80% or greater, 85% or greater, 90% or greater, 91% or greater, 92% or greater, 93% or greater, 94% or greater, 95% or greater, 96% or greater, 97% or greater, 98% or greater, 99% or greater, 99.2% or greater, 99.4% or greater, 99.5% or greater, 99.6% or greater, 99.7% or greater, 99.8% or greater, or 99.9% or greater of total cannabinoid compound(s) in the composition.

In some embodiments, the composition comprises CBDA, CBD, an analog, derivative, or combination thereof at 10% or greater, 20% or greater, 30% or greater, 40% or greater, 50% or greater, 60% or greater, 70% or greater, 80% or greater, 85% or greater, 90% or greater, 91% or greater, 92% or greater, 93% or greater, 94% or greater, 95% or greater, 96% or greater, 97% or greater, 98% or greater, 99% or greater, 99.2% or greater, 99.4% or greater, 99.5% or greater, 99.6% or greater, 99.7% or greater, 99.8% or greater, or 99.9% or greater of total cannabinoid compound(s) in the composition.

In some embodiments, the composition comprises CBCA, CBC, an analog, derivative, or combination thereof at 10% or greater, 20% or greater, 30% or greater, 40% or greater, 50% or greater, 60% or greater, 70% or greater, 80% or greater, 85% or greater, 90% or greater, 91% or greater, 92% or greater, 93% or greater, 94% or greater, 95% or greater, 96% or greater, 97% or greater, 98% or greater, 99% or greater, 99.2% or greater, 99.4% or greater, 99.5% or greater, 99.6% or greater, 99.7% or greater, 99.8% or greater, or 99.9% or greater of total cannabinoid compound(s) in the composition.

In some embodiments, the composition is a therapeutic or medicinal composition. In some embodiments, the composition further comprises a pharmaceutically acceptable excipient. In some embodiments, the composition is a topical composition. In some embodiments, the composition is in the form of a cream, a lotion, a paste, or an ointment.

In some embodiments, the composition is an edible composition. In some embodiments, the composition is provided in a food or beverage product. In some embodiments, the composition is an oral unit dosage composition. In some embodiments, the composition is provided in a tablet or a capsule.

All references cited herein, including patents, patent applications, papers, textbooks and the like, and the references cited therein, to the extent that they are not already, are hereby incorporated herein by reference in their entirety.

EXAMPLES

Example 1. Amino Acid Substitutions in THCAS

As used throughout Example 1, the amino acid numbering indicated is shown relative to SEQ ID NO:2. As described previously, SEQ ID NO:2 corresponds to wild-type THCAS.

The structure of THCAS revealed that the area surrounding the disulfide bond between Cys37 in αA and Cys99 in αC is heavily positively-charged with four positive residues: Lys36, Lys40, Lys101, and Lys102, as shown in FIGS. 3 and 8. The Calculate Mutation Energy (Stability) protocol from Discovery Studio 2019 (Dassault Systemes BIOVIA, San Diego, CA 92121) was used to predict beneficial mutations to stabilize the structure of THCAS. In predicting mutations for Cys37 and Cys99 of THCAS, all 20 amino acids were considered as mutation targets. In predicting mutations for Lys36, Cys37, Lys40, Lys101, and Lys102, four charged residues (Asp, Glu, Lys, Arg) were considered as mutation targets.

Table 6 shows the predicted stabilizing energy of selected amino acid substitutions at C37, C99, or both, as described herein, with higher absolute values indicating greater stabilization effect:

TABLE 6

| Mutation | Stabilizing Energy (kcal/mol) |
|---|---|
| CYS37 -> ASP, CYS99 -> PHE | −5.2 |
| CYS37 -> HIS | −4.87 |
| CYS37 -> TYR | −4.6 |
| CYS37 -> TYR, CYS99 -> ALA | −4.03 |
| CYS37 -> GLU, CYS99 -> PHE | −3.81 |
| CYS37 -> TYR, CYS99 -> ILE | −3.54 |
| CYS37 -> TYR, CYS99 -> VAL | −3.47 |
| CYS37 -> GLU | −3.27 |
| CYS37 -> LYS, CYS99 -> PHE | −2.91 |
| CYS37 -> ASP | −2.9 |
| CYS37 -> ASP, CYS99 -> VAL | −2.84 |
| CYS37 -> ASP, CYS99 -> ALA | −2.65 |
| CYS37 -> HIS, CYS99 -> VAL | −2.64 |
| CYS37 -> GLU, CYS99 -> VAL | −2.41 |
| CYS37 -> ASN, CYS99 -> ALA | −2.28 |
| CYS37 -> ASN, CYS99 -> PHE | −2.2 |
| CYS37 -> GLU, CYS99 -> ALA | −2.16 |
| CYS37 -> ASN, CYS99 -> VAL | −1.92 |
| CYS37 -> GLN, CYS99 -> ILE | −1.59 |
| CYS37 -> THR | −1.41 |
| CYS37 -> TYR, CYS99 -> LEU | −1.09 |
| CYS37 -> HIS, CYS99 -> LEU | −1.07 |
| CYS37 -> CYS, CYS99 -> PHE | −1.01 |
| CYS37 -> GLN | −1 |
| CYS37 -> ASN | −0.82 |
| CYS37 -> HIS, CYS99 -> ALA | −0.81 |
| CYS37 -> TYR, CYS99 -> PHE | −0.78 |
| CYS37 -> LYS | −0.74 |
| CYS37 -> GLN, CYS99 -> ALA | −0.68 |
| CYS37 -> ARG, CYS99 -> ILE | −0.6 |

Table 7 shows the predicted stabilizing energy of selected amino acids described herein (e.g., C37, C99, K36, K40, K101, K102, or combination thereof), with higher absolute values indicating greater stabilization effect:

TABLE 7

| Mutation | Energy (kcal/mol) |
|---|---|
| LYS36 -> ASP, CYS37 -> LYS, LYS40 -> ASP, CYS99 -> PHE, LYS101 -> ARG, LYS102 -> LYS | −35.17 |
| LYS36 -> ASP, CYS37 -> LYS, LYS40 -> ASP, CYS99 -> PHE, LYS101 -> ARG, LYS102 -> ARG | −34.54 |
| LYS36 -> ASP, CYS37 -> LYS, LYS40 -> GLU, CYS99 -> PHE, LYS101 -> ARG, LYS102 -> LYS | −34.26 |
| LYS36 -> ASP, CYS37 -> LYS, LYS40 -> GLU, CYS99 -> PHE, LYS101 -> ARG, LYS102 -> ARG | −33.08 |
| LYS36 -> ARG, CYS37 -> LYS, LYS40 -> ASP, CYS99 -> PHE, LYS101 -> ARG, LYS102 -> ARG | −32.46 |
| LYS36 -> ASP, CYS37 -> GLU, LYS40 -> LYS, CYS99 -> PHE, LYS101 -> ARG, LYS102 -> LYS | −32.41 |
| LYS36 -> ARG, CYS37 -> GLU, LYS40 -> GLU, CYS99 -> PHE, LYS101 -> ARG, LYS102 -> ARG | −32.23 |
| LYS36 -> LYS, CYS37 -> GLU, LYS40 -> LYS, CYS99 -> PHE, LYS101 -> ARG, LYS102 -> GLU | −31.75 |
| LYS36 -> GLU, CYS37 -> LYS, LYS40 -> GLU, CYS99 -> PHE, LYS101 -> ARG, LYS102 -> LYS | −31.64 |
| LYS36 -> ASP, CYS37 -> ARG, LYS40 -> ASP, CYS99 -> PHE, LYS101 -> ARG, LYS102 -> ASP | −31.52 |
| LYS36 -> ASP, CYS37 -> LYS, LYS40 -> ASP, CYS99 -> PHE, LYS101 -> LYS, LYS102 -> LYS | −31.26 |
| LYS36 -> ARG, CYS37 -> LYS, LYS40 -> ARG, CYS99 -> PHE, LYS101 -> ARG, LYS102 -> GLU | −31.12 |
| LYS36 -> ARG, CYS37 -> GLU, LYS40 -> ASP, CYS99 -> PHE, LYS101 -> ARG, LYS102 -> GLU | −30.77 |
| LYS36 -> GLU, CYS37 -> ARG, LYS40 -> ASP, CYS99 -> PHE, LYS101 -> ARG, LYS102 -> LYS | −30.76 |
| LYS36 -> ASP, CYS37 -> ARG, LYS40 -> GLU, CYS99 -> PHE, LYS101 -> ARG, LYS102 -> LYS | −30.68 |
| LYS36 -> ASP, CYS37 -> ARG, LYS40 -> ASP, CYS99 -> PHE, LYS101 -> ARG, LYS102 -> ARG | −30.56 |
| LYS36 -> ARG, CYS37 -> ARG, LYS40 -> GLU, CYS99 -> PHE, LYS101 -> ARG, LYS102 -> ARG | −30.23 |
| LYS36 -> ASP, CYS37 -> GLU, LYS40 -> ASP, CYS99 -> PHE, LYS101 -> ARG, LYS102 -> ARG | −30.08 |
| LYS36 -> ASP, CYS37 -> LYS, LYS40 -> GLU, CYS99 -> PHE, LYS101 -> LYS, LYS102 -> LYS | −29.86 |
| LYS36 -> ASP, CYS37 -> ARG, LYS40 -> ASP, CYS99 -> PHE, LYS101 -> ARG, LYS102 -> GLU | −29.76 |
| LYS36 -> ASP, CYS37 -> GLU, LYS40 -> GLU, CYS99 -> PHE, LYS101 -> ARG, LYS102 -> ARG | −29.66 |
| LYS36 -> LYS, CYS37 -> ASP, LYS40 -> LYS, CYS99 -> PHE, LYS101 -> ARG, LYS102 -> GLU | −29.65 |
| LYS36 -> GLU, CYS37 -> GLU, LYS40 -> GLU, CYS99 -> PHE, LYS101 -> ARG, LYS102 -> ARG | −29.64 |
| LYS36 -> ARG, CYS37 -> GLU, LYS40 -> LYS, CYS99 -> PHE, LYS101 -> ARG, LYS102 -> ARG | −29.6 |
| LYS36 -> ARG, CYS37 -> GLU, LYS40 -> ASP, CYS99 -> PHE, LYS101 -> ARG, LYS102 -> ARG | −29.34 |
| LYS36 -> ASP, CYS37 -> ASP, LYS40 -> LYS, CYS99 -> PHE, LYS101 -> LYS, LYS102 -> GLU | −29.29 |
| LYS36 -> ARG, CYS37 -> ASP, LYS40 -> ASP, CYS99 -> PHE, LYS101 -> ARG, LYS102 -> ARG | −29.28 |
| LYS36 -> LYS, CYS37 -> ASP, LYS40 -> LYS, CYS99 -> PHE, LYS101 -> ARG, LYS102 -> ARG | −29.28 |
| LYS36 -> ASP, CYS37 -> ASP, LYS40 -> GLU, CYS99 -> PHE, LYS101 -> ARG, LYS102 -> ARG | −29.23 |
| LYS36 -> ASP, CYS37 -> ASP, LYS40 -> LYS, CYS99 -> PHE, LYS101 -> ARG, LYS102 -> ASP | −29.19 |
| LYS36 -> LYS, CYS37 -> GLU, LYS40 -> GLU, CYS99 -> PHE, LYS101 -> ARG, LYS102 -> GLU | −29.16 |
| LYS36 -> ARG, CYS37 -> GLU, LYS40 -> ASP, CYS99 -> PHE, LYS101 -> ARG, LYS102 -> LYS | −29.16 |
| LYS36 -> ASP, CYS37 -> ASP, LYS40 -> ARG, CYS99 -> PHE, LYS101 -> ARG, LYS102 -> LYS | −28.91 |
| LYS36 -> ASP, CYS37 -> ASP, LYS40 -> LYS, CYS99 -> PHE, LYS101 -> ARG, LYS102 -> GLU | −28.85 |
| LYS36 -> ASP, CYS37 -> LYS, LYS40 -> LYS, CYS99 -> PHE, LYS101 -> ARG, LYS102 -> ARG | −28.83 |
| LYS36 -> GLU, CYS37 -> ARG, LYS40 -> ARG, CYS99 -> PHE, LYS101 -> ARG, LYS102 -> GLU | −28.78 |

Example 2. Mutant Library Construction

Variants of THCAS can be constructed as libraries on plasmids by single-site and multi-site (combinatorial) mutagenesis methods, using specific primers at the positions undergoing mutagenesis, amplifying fragments via PCR, and circularizing the plasmids via Gibson ligation. THCAs variants were constructed on a vector backbone closely related to pET28a. DNA bases that encode histidine residues were added to the C-terminus of all THCAS sequences to facilitate protein purification using nickel column methods. Plasmids were transformed into *E. coli* cells closely related to BL21(DE3), and transformants were selected by plating on antibiotic containing kanamycin. In some cases, *E. coli* cells may have a second plasmid that can express chaperones to help facilitate correct protein folding of THCAS. For example, the chaperone expression plasmid pGro7, from TAKARA BIO, may be in the *E. coli* cells along with the plasmid that expresses the THCAS proteins.

Cell Culture for Screening Homologs and Mutant Libraries

From both mutant library transformants and control transformants, single colonies can be picked for growth into 96-well plates using Luria Bertani (LB) growth medium with suitable antibiotic. Following overnight growth, cultures can be sub-cultured into fresh medium of LB with 1% arabinose and antibiotic. After 4 hours growth, gene expression may be induced by addition of IPTG, and cells can be pelleted after overnight growth at 30° C., and media discarded. Cells pellets can be stored at −20° C. until ready for assay. Number of samples screened can be approximately three times oversampling based on calculation of total possible variants.

Example 3. Activity Assay

An activity assay for THCAS can be performed in 25 μL volume containing cell extract or purified synthase and 200 μM CBGA. Reactions can be incubated at 30-50° C. and 600 rpm in a thermoshaker, and time points at 0, 5, 10, 15, 30, 60 minutes up to 48 hours can be taken. The assay can be stopped by the addition of 225 ul 75% acetonitrile acidified with 0.1% formic acid. After extensive mixing and centrifugation (10 min, 4700 rpm, 4° C.), 50 μL of each sample can be analyzed by LCMS, e.g., as described in Lange et al., J. Biotechnol 211:68-76 (2015).

Example 4. Expression and Activity of *C. sativa* THCAS and Variants in *E. coli*

As used throughout Example 4, the amino acid numbering indicated is shown relative to SEQ ID NO:1. As described previously, the first amino acid of SEQ ID NO:1 corresponds to the 27$^{th}$ amino acid of SEQ ID NO:2.

The THCAS gene from *C. sativa* was codon optimized for expression in *E. coli*. The twenty-six amino acids at the N-terminus of the wild-type *C. sativa* THCAS protein, which encode a “leader peptide,” were removed. Additionally, four histidine residues (SEQ ID NO: 90) were added to the C-terminus of the THCAS protein to facilitate purification of the THCAS protein from crude lysate using a nickel-affinity column. This construct is designated as the “C construct.” The amino acid sequence of the C construct is identical to SEQ ID NO:1, except with three additional His residues at the C-terminus.

Amino acid variants of the THCAS were designed to increase the stability of the protein between alpha helix αA and alpha helix αC. Additionally, variants were designed on the surface of the protein to reduce the size and number of hydrophobic patches and to reduce the number of positively charged residues. The variants with their designated construct names are listed in Table 8.

TABLE 8

| Variant Construct | SEQ ID NO: | THCAS Mutations from THCAS C Construct |
|---|---|---|
| AH | 85 | C11A, K14R, N63D, N64D, C73A, K76E |
| AR | 86 | C11A, K14R, L33T, N63D, C73A, K76E, V295T |
| AS | 87 | C11A, K14R, L33T, N63D, C73A, K76E, K270E, V295T, N490E |
| AT | 88 | C11A, K14R, L33T, N63D, C73A, K76E, K270E |
| AV | | C11A, K14R, Q32E, L33T, N63D, N64T, C73A, K76E, K270E, V295T, V332T, N490E, N502T |

The constructs were expressed in *E. coli* cells as follows: An overnight culture of *E. coli* BL21(DE3) cells containing a sequence-verified plasmid with a THCAS variant was grown in 0.5 mL of LB media overnight at 35° C. The following day, 10 μL of the overnight culture was added to 1000 μL of LB media containing 100 μg/mL of carbenicillin in a 96-depp well plate and allowed to grow at room temperature for 24 hours. The THCAS protein was expressed constitutively during *E. coli* culture. Following the expression, OD of the cultures were measured, and the cultures were ten transferred to 96 well plates. Cell pellets were collected by centrifugation at 4000×g for 10 minutes, then resuspended to OD600=40 in 100 mM phosphate buffer pH 8.0 with 300 mM KCl and protease inhibitor cocktail. 4 μL of the whole cell suspension was mixed with 20 μL of 240 μM CBGA in 100 mM Na-Citrate buffer, pH 5.0 with 0.1% TRITON X-100 in a 96 well plate. The plate was then sealed and incubated at 37° C. for 24 hours, and the reactions were quenched with 376 μL of 75% acetonitrile solution containing 0.1% formic acid and 1.2 μM diclofenac and 2 μM ibuprofen as internal standards. Precipitated protein and cell debris were removed by vacuum filtration using a 0.2 μM 96-well filter plate (PALL). The flow-through was directly injected into an HPLC/MS system for analysis. Cannabinoid products were identified by retention time to authentic cannabinoid standards and quantified by relative peak area versus peak area of known concentrations of cannabinoid standards.

No conversion of CBGA to THCA by the C construct was detected using the HPLC assay. The AH construct showed low but detectable conversion of CBGA to THCA. The AR construct showed approximately 5-fold higher CBGA conversion over the AH construct. The AS construct and AT construct, which included additional mutations based on the AR construct, showed 10-fold and 2.5-fold improvement in CBGA conversion over the AR construct, respectively. Results in Table 9 show the improvement in THCA production over the AR construct with the addition of the K270E or N490E mutation. Results in Table 10 show the improvement in THCA production over the AR construct with two additional mutations.

TABLE 9

| Variant | [THCA] μM | Fold-improvement Over AR Construct |
|---|---|---|
| AR Construct | 0.01 | — |
| AR + K270E | 0.02 | 3.16 |
| AR + N490E | 0.01 | 1.24 |

TABLE 10

| Variant | [THCA] μM | Fold-improvement Over C Construct (No Substitutions) |
|---|---|---|
| AR | 0.01 | — |
| AR + K270E, N490E (AS construct) | 0.10 | 13.22 |
| AR + V332T, N490E | 0.08 | 10.06 |
| AR + N64T, N490E | 0.08 | 9.96 |
| AR + K270E, N502T | 0.06 | 7.22 |
| AR + K340D, N490E | 0.05 | 6.59 |
| AR + K270E, V332T | 0.05 | 5.83 |
| AR + N64T, K270E | 0.04 | 4.99 |
| AR + T33L, N490E | 0.04 | 4.73 |
| AR + V332T, N502T | 0.04 | 4.59 |
| AR + Q32E, K270E | 0.04 | 4.58 |
| AR + D63N, K270E | 0.03 | 4.45 |
| AR + N64T, N502T | 0.03 | 4.36 |
| AR + K340D, N502T | 0.03 | 3.95 |
| AR + K487D, N490E | 0.03 | 3.93 |
| AR + Q32E, N490E | 0.03 | 3.67 |
| AR + Q32E, N64T | 0.03 | 3.62 |
| AR + Q32E, N502T | 0.03 | 3.58 |
| AR + D63N, N490E | 0.03 | 3.58 |
| AR + V332T, H518Y | 0.03 | 3.46 |
| AR + Q32E, V332T | 0.03 | 3.44 |
| AR + V332T, K340D | 0.03 | 3.40 |
| AR + D63N, N64T | 0.02 | 3.03 |
| AR + V20E, K270E | 0.02 | 2.83 |
| AR + K270E, H518Y | 0.02 | 2.81 |
| AR + V20E, N490E | 0.02 | 2.64 |
| AR + R14K, N490E | 0.02 | 2.62 |
| AR + T295V, N490E | 0.02 | 2.58 |
| AR + D63N, N502T | 0.02 | 2.52 |
| AR + K270E, T295V (AT construct) | 0.02 | 2.42 |
| AR + K270E, K487D | 0.02 | 2.31 |
| AR + T33L, N502T | 0.02 | 2.20 |
| AR + K487D, N502T | 0.02 | 2.15 |
| AR + K340D, K487D | 0.02 | 2.11 |
| AR + T33L, V332T | 0.02 | 2.07 |
| AR + T33L, K340D | 0.02 | 2.00 |
| AR + D63S, K270E | 0.02 | 2.00 |
| AR + N64T, T295V | 0.02 | 2.00 |
| AR + Q32E, H518Y | 0.01 | 1.91 |
| AR + T33L, K270E | 0.01 | 1.85 |
| AR + N64T, H518Y | 0.01 | 1.83 |
| AR + D63S, N490E | 0.01 | 1.80 |
| AR + Q32E, T295V | 0.01 | 1.71 |
| AR + T33L, H518Y | 0.01 | 1.70 |
| AR + V20E, N64T | 0.01 | 1.66 |
| AR + N64T, K340D | 0.01 | 1.65 |
| AR + V332T, K487D | 0.01 | 1.65 |
| AR + T33L, T295V | 0.01 | 1.54 |
| AR + R14K, K270E | 0.01 | 1.43 |
| AR + V20E, K340D | 0.01 | 1.40 |
| AR + T295V, K340D | 0.01 | 1.36 |
| AR + Q32E, K340D | 0.01 | 1.35 |
| AR + T295V, N502T | 0.01 | 1.25 |
| AR + Q32E, T33L | 0.01 | 1.21 |
| AR + V20E, V332T | 0.01 | 1.21 |

Additional mutants were designed based on the AT construct and tested. Results are shown in Table 11. The results show that the several of the additional mutants had 5-fold improvement in THCA production over the AT construct.

TABLE 11

| | Variant | [THCA] μM | Fold-improvement Over AT Construct |
|---|---|---|---|
| Control Constructs | AR | 0.01 | — |
| | AS | 0.09 | — |
| | AT | 0.02 | — |
| AT + 1 additional mutation | Q32E | 0.05 | 2.19 |
| | N64T | 0.04 | 1.76 |
| | V332T | 0.03 | 1.40 |
| | N502T | 0.03 | 1.25 |
| | K340D | 0.03 | 1.18 |
| AT + 2 additional mutations | Q32E, N64T | 0.07 | 3.23 |
| | Q32E, V332T | 0.07 | 3.01 |
| | Q32E, N502T | 0.06 | 2.83 |
| | Q32E, K340D | 0.06 | 2.80 |
| | N64T, N502T | 0.06 | 2.59 |
| | N64T, K340D | 0.04 | 1.86 |
| | V332T, K340D | 0.04 | 1.68 |
| | K340D, N502T | 0.04 | 1.58 |
| | V332T, N502T | 0.04 | 1.58 |
| AT + 3 additional mutations | Q32E, N64T, V332T | 0.12 | 5.15 |
| | Q32E, N64T, N502T | 0.11 | 5.00 |
| | Q32E, V332T, N502T | 0.09 | 3.88 |
| | N64T, V332T, N502T | 0.08 | 3.34 |
| | V332T, K340D, N502T | 0.05 | 2.34 |
| AT + 4 additional mutations | Q32E, V332T, K340D, N502T | 0.11 | 4.96 |
| | Q32E, N64T, K340D, N502T | 0.09 | 4.15 |
| | N64T, V332T, K340D, N502T | 0.09 | 4.08 |

The AV construct was designed based on the AS construct with the additional mutations Q32E, N64T, V332T, and N502T. The AV construct showed improvement in THCA production as compared to the AS construct, as shown in Table 12. Further variants of the AV construct were produced and tested. The results in Table 12 show that the additional mutants had further improvement in THCA production over the AS and AV constructs.

TABLE 12

| | Variant | [THCA] μM | Fold-improvement Over AT Construct |
|---|---|---|---|
| Control Constructs | AS | 0.07 | — |
| | AV | 0.44 | 1.00 |
| AV + 1 additional mutation | K340D | 0.48 | 1.11 |
| | T33L | 0.46 | 1.07 |
| AV + 2 additional mutations | K340D, T502N | 0.66 | 1.52 |
| | T33L, D63N | 0.58 | 1.33 |
| | T33L, K340D | 0.54 | 1.24 |
| | D63N, K340D | 0.50 | 1.15 |

All references cited herein, including patents, patent applications, papers, textbooks and the like, and the references cited therein, to the extent that they are not already, are hereby incorporated herein by reference in their entirety.

SEQUENCES

SEQ ID NO: 1 Amino acid sequence of N-terminal truncation of *C. sativa* THCAS

MANPRENFLKCFSKHIPNNVANPKLVYTQHDQLYMSILNSTIQNLRFISDTTPKPLVIVTPSNNSHIQATILCSKKV

GLQIRTRSGGHDAEGMSYISQVPFVVVDLRNMHSIKIDVHSQTAWVEAGATLGEVYYWINEKNENLSFPGGYCPTVG

-continued

SEQUENCES

VGGHFSGGGYGALMRNYGLAADNIIDAHLVNVDGKVLDRKSMGEDLFWAIRGGGGENFGIIAAWKIKLVAVPSKSTI
FSVKKNMEIHGLVKLFNKWQNIAYKYDKDLVLMTHFITKNITDNHGKNKTTVHGYFSSIFHGGVDSLVDLMNKSFPE
LGIKKTDCKEFSWIDTTIFYSGVVNFNTANFKKEILLDRSAGKKTAFSIKLDYVKKPIPETAMVKILEKLYEEDVGA
GMYVLYPYGGIMEEISESAIPFPHRAGIMYELWYTASWEKQEDNEKHINWVRSVYNFTTPYVSQNPRLAYLNYRDLD
LGKTNHASPNNYTQARIWGEKYFGKNFNRLVKVKTKVDPNNFFRNEQSIPPLPPHHH

SEQ ID NO: 2 Amino acid sequence of wild-type *C. sativa* THCAS
MNCSAFSFWFVCKIIFFFLSFHIQISIANPRENFLKCFSKHIPNNVANPKLVYTQHDQLYMSILNSTIQNLRFISDT
TPKPLVIVTPSNNSHIQATILCSKKVGLQIRTRSGGHDAEGMSYISQVPFVVVDLRNMHSIKIDVHSQTAWVEAGAT
LGEVYYWINEKNENLSFPGGYCPTVGVGGHFSGGGYGALMRNYGLAADNIIDAHLVNVDGKVLDRKSMGEDLFWAIR
GGGGENFGIIAAWKIKLVDVPSKSTIFSVKKNMEIHGLVKLFNKWQNIAYKYDKDLVLMTHFITKNITDNHGKNKTT
VHGYFSSIFHGGVDSLVDLMNKSFPELGIKKTDCKEFSWIDTTIFYSGVVNFNTANFKKEILLDRSAGKKTAFSIKL
DYVKKPIPETAMVKILEKLYEEDVGAGMYVLYPYGGIMEEISESAIPFPHRAGIMYELWYTASWEKQEDNEKHINWV
RSVYNFTTPYVSQNPRLAYLNYRDLDLGKTNHASPNNYTQARIWGEKYFGKNFNRLVKVKTKVDPNNFFRNEQSIPP
LPPHHH SEQ ID NO: 3 Wild-type OLS
MNHLRAEGPASVLAIGTANPENILLQDEFPDYYFRVTKSEHMTQLKEKFRKICDKSMIRKRNCFLNEEHLKQNPRLV
EHEMQTLDARQDMLVVEVPKLGKDACAKAIKEWGQPKSKITHLIFTSASTTDMPGADYHCAKLLGLSPSVKRVMMYQ
LGCYGGGTVLRIAKDIAENNKGARVLAVCCDIMACLFRGPSESDLELLVGQAIFGDGAAAVIVGAEPDESVGERPIF
ELVSTGQTILPNSEGTIGGHIREAGLIFDLHKDVPMLISNNIEKCLIEAFTPIGISDWNSIFWITHPGGKAILDKVE
EKLHLKSDKFVDSRHVLSEHGNMSSSTVLFVMDELRKRSLEEGKSTTGDGFEWGVLFGFGPGLTVERVVVRSVPIKY SEQ ID NO: 4 Wild-type OAC
MAVKHLIVLKFKDEITEAQKEEFFKTYVNLVNIIPAMKDVYWGKDVTQKNKEEGYTHIVEVTFESVETIQDYIIHPA
HVGFGDVYRSFWEKLLIFDYTPRK SEQ ID NO: 5 Variant OAC
MAVKHLIVLKFKEDITEAQKDEFFKTYVNLVNIIPAMKEVYWGKDVTAKNKDEGYTHIVEVTFESVETIQEYISHPA
HVGFGDVYRSFWEKLLIFDYTPTK SEQ ID NO: 6 Wild-type PT
MSGAADVERVYAAMEEAAGLLGVTCAREKIYPLLTEFQDTLTDGVVVFSMASGRRSTELDFSISVPTSQGDPYATVV
DKGLFPATGHPVDDLLADTQKHLPVSMFAIDGEVTGGFKKTYAFFPTDDMPGVAQLSAIPSMPSSVAENAELFARYG
LDKVQMTSMDYKKRQVNLYFSELSEQTLAPESVLALVRELGLHVPTELGLEFCKRSFSVYPTLNWDTGKIDRLCFAV
ISTDPTLVPSTDERDIEQFRHYGTKAPYAYVGENRTLVYGLTLSPTEEYYKLGAYYHITDIQRRLLKAFDALED SEQ ID NO: 7 Variant PT
MSEAADVERVYAAMEEAAGLLGVACARDKIYPLLSTFQDTLVEGGSVVVFSMASGRHSTE
LDFSISVPTSHGDPYATVVEKGLFPATGHPVDDLLADTQKHLPVSMFAIDGEVTGGFKKT
YAFFPTDNMPGVAELSAIPSMPPAVAENAELFARYGLDKVQMTSMDYKKRQVNLYFSELS
AQTLEAESVLALVRELGLHVPNELGLKFCKRSFSVYPTLNWETGKIDRLCFAVISNDPTL
VPSSDEGDIEKFHNYATKAPYAYVGEKRTLVYGLTLSPKEEYYKLGAYYHITDVQRGLLK
AFDSLED SEQ ID NO: 8 Variant PT
MSGAADVERVYAAMEEAAGLLDVSCAREKIYPLLTVFQDTLTDGVVVFSMASGRRSTELD
FSISVPVSQGDPYATVVREGLFRATGSPVDELLADTVKHLPVSMFAIDGEVTGGFKKTYA
FFPTDDMPGVAQLTGIPSMPASVAENAELFARYGLDKVQMTSMDYKKRQVNLYFSDLKQE
YLQPEAVVALARELGLQVPGELGLEFCKRSFAVYPTLNWDTGKIDRLCFAAISTDPTLVP
STDERDIEMFREYATKAPYAYVGEKRTLVYGLTLSPTEEYYKLGAYYHITDIQRQLLKAF
DALED SEQ ID NO: 9 Variant PT
MSGAADVERVYAAMEEAAGLLDVSCAREKIYPLLTVFQDTLTDGVVVFSMASGRRSTELD
FSISVPVSQGDPYATVVKEGLFRATGSPVDELLADTVKHLPVSMFAIDGEVTGGFKKTYA
FFPTDDMPGVAQLTEIPSMPASVAENAELFARYGLDKVQMTSMDYKKRQVNLYFSDLKQE
YLQPEAVVALARELGLQVPGELGLEFCKRSFAVYPTLNWDTGKIDRLCFAAISTDPTLVP
STDERDIEMFREYATKAPYAYVGEKRTLVYGLTLSSTEEYYKLGAYYHITDIQRQLLKAF
DALED SEQ ID NO: 10 Variant PT
MSGAADVERVYAAMEEAAGLLDVSCAREKIYPLLTVFQDTLTDGVVVFSMASGRRSTELD
FSISVPVSQGDPYATVVKEGLFQATGSPVDELLADTVAHLPVSMFAIDGEVTGGFKKTYA
FFPTDDMPGVAQLAAIPSMPASVAENAELFARYGLDKVQMTSMDYKKRQVNLYFSDLKQE
YLQPESVVALARELGLRVPGELGLEFCKRSFAVYPTLNWDTGKIDRLCFAAISTDPTLVP
SEDERDIEMFRNYATKAPYAYVGEKRTLVYGLTLSSTEEYYKLGAYYHITDIQRQLLKAF
DALED SEQ ID NO: 11 Variant PT
MSGAAEVERVYSAMEEAAGLLDVACSPEKVRPILTAFQDVLSDGVIVYSMASGRHATELD
FSISVPADHGDPYTAALAHGLIPETDHPVGNLLADTQKALPVSMFAVDGEVTGGFKKTYA
FFPTDDMPGLAQLIDIPSMPPSVAENAELFARYGLDKVQMTSLDYKRKQVNLYFSNLQPE
FLAPEPVLSMVREMGLELPGEKGLKFARRSFAIYPTLGWESGKIERLCFAVISTDPGLVP
APDEADRALFSTYANNAPYAYAGEKRTLVYGLTLSPTEEYYKLGSYYQITDIQRTLLKAF
DALTD -continued

| SEQUENCES |
|---|
| SEQ ID NO: 12 Variant PT<br>MSGAAEVERVYSAMEESAGLLDVACSREKIQPILTAFQDVLADGVIVFSMANGRHATELD<br>FSISVPAGHGDPYAAALEHGLIPATGHPVGDLLADTQKALPVSMFAVDGEVTSGFKKTYA<br>FFPTDDMPGLAQLIDIPSMPPSVAENAELFGRYGLDKVQMISLDYKKNQVNLYFSNLNPE<br>FLQPEPVQAMVREMGLQLPADKGLAFAKRSFAVYPTLSWDSAKIERLCFAVISTDPTLAP<br>AQEQADLDLFSTYANNAPYAYAGEKRTLVYGLTLSPSEEYYKLGSYYQISDIQRKLLKAF<br>DALTD |
| SEQ ID NO: 13 Variant PT<br>MSGAADVERVYSAMEEAARLLDITVSREKVRPALEAYHEVLADAVVVFSMASGRYATELD<br>FSISVPAEAGDPYRVALAKGLTPRTDHPVGRLLADTQEHCPVSMFAFDGEITGGFKKTYA<br>FFPTNDLQSASKLAEIPSMPDSVKENADLFARYGLDKVQMTSIDYKKKAVNLYFSEMSPD<br>ILGPDTVRSMLRDMGLKETGETGLTFARRSFSVYPTLNWETGRIERLCFAVISRDPTLAP<br>AERAEDLAKFSKYANNAPYAYAGEARTLVYGLTLTPREEYYKLGSYYQISDIQRKLLKAF<br>DSLND |
| SEQ ID NO: 14 Variant PT<br>MSGAKDVERVYSAMEEAAGLLNVPVARDKIWPVLTAYQDALADAVIVFSMAGGRRSTELD<br>FSISVPTDHGDPFTTALERGLTEKENHPVDNLLAELRDGFPLGMYAIDGMVTTGFKKAYA<br>SFPTNEPQPLTALLDLPSMPESARANAELFARYGLDKVQMVSVDYPKRQVNLYFSELKAD<br>HLTPEQVKATASEMGLVEPTDMALDFATGSFAVYPTLGYDSDVVDRITYAVISVDPTLAP<br>TTSEPEKTQITTYANSAPYAYAGENRTLVYGFTLTSKEEYYKLGSYYQITDLQRTLVKAF<br>EALD |
| SEQ ID NO: 15 Variant PT<br>MSGAKDVERVYSAMEEAAGLLNVPVARDKIWPVLTAYQDALADAVIVFSMAGGRRSTELD<br>FSISVPTDHGDPFTTALERGLTEKENHPVDNLLAELRDGFPLGMYAIDGMVTTGFKKAYA<br>SFPTNEPQPLTALLDLPSMPESARANAELFARYGLDKVQMVSVDYPKRQVNLYFSDLNAD<br>HLTPEEVKSTASEMGLVEPTDMALDFATGSFAVYPTLGYDSDVVDRITYAVISVDPTLAP<br>TTSEPEKTQITTYANSAPYAYAGENRTLVYGFTLTSKEEYYKLGSYYQITDLQRTLVKAF<br>EALD |
| SEQ ID NO: 16 Variant PT<br>MSGANDVERVYSAMEEAAGLLNVPVARDKIWPVLTAYQDALADAVVVFSMAGGRRATELD<br>FSISVPTDLGDPFTTALRRGLTEKTNHPVDNLLAELTDGFEIGMYAIDGMVTTGFKKTYA<br>SFPTNEPQPLTALLDVPSMPESARANAELFARYGLDKVQMVSVDYPKRQVNLYFSELDTD<br>YLQPEHVKSLARETGLVEPTEMGLDFASGSFAVYPTLGYDNDIVDRITYAVISVDPTLAP<br>TKSEPEVSQLSRYATSAPYAYAGENRTLVYGVTLTSKEEYYKLGSYYQITDLQRTLVKAF<br>EALD |
| SEQ ID NO: 17 Variant PT<br>MSGANDVERVYSAMEEAAGLLGVPVAREKVRPVLTAYQDALADAVVVFSMAGGRRATELD<br>FSISVPTDHGDPFTTALQRGLTEKTGHPVDNLLAELREGFPLGMYAIDGMVSTGFKKTYA<br>SFPTNEPQPLDDLLDVPSMPASARANAKLFANYGLDKVQMVSVDYPKRQVNLYFSELNTD<br>YLQPAQVKALAAEMGLIEPSELGLEFAKGSFAVYPTLSYDTDASDRLCLAVISSDPTLAP<br>TTSEPEVTQFSTYANNAPYAYAGENRTLVYGLTLTPKEEYYKLGSYYQITDYQRKLVKAF<br>EALD |
| SEQ ID NO: 18 Variant PT<br>MSKATEVDRVYTUWEKAAALAGTTCAGDKVRPVLTGHQDLLDEAVIVFSMTASGSHSGGL<br>DLSMTVPAEHVDPYSFALSEGLIEPTDHPVGSVISDFQERFPIGMYGIDVDVAGGFKKAY<br>AAFPSNDLRELKQLFDLPSMPSAAAENAELFARYGLDRVTGVSVDYKRHELNLYCDRATT<br>EPLDPDYVQSMLRDMGLKEASEQGLEFAKKTFAIYPTLNWDSSEIVRICFAVITTDPATT<br>PTRSEPELGQMWEYANTAPYAYVGEQRALVYGLALSPEKEYYKLGAYYQISDYQRKLVKA<br>FDALPE |
| SEQ ID NO: 19 Variant PT<br>MCVPGSRARRPGSRGWLERTAKPAPTRGTVGAKVRSQTWERRAPGATTVTCPVQGRSTGP<br>IQADIQDRHVGDSMSGAADVERVYSAMERAAGLLDLTCAREKILPILTAYKEALADSVIV<br>FSMSGGDHSAELDFSFTIPSGDVDPYAFGPSTGIPTETDHPIASLLSDTGERCPVAMYGV<br>DGEVSGGFKKTYAAFPINDLLDLSKLVAVPSMPPAVAENAELFARYGLDKVQGISIDYQR<br>KQVNLYCGDIPAESLEPETVRSMLREMGLREPSEEGLEFVRKSFAVYPTLSWDSSRIERI<br>CFAVISTDPTLAPTRVESDVALFSKYANNAPYAYAGERRTLIYGLAVSPTKEYIKLGSYY<br>QISDHQRKLVKAFDALED |
| SEQ ID NO: 20 Variant PT<br>MYGGTEVEEVYSALEKSAGLVGVPCNRDKVWPALSTYQDALGEAVIVFSVATDERHAGEL<br>DYTITVPTGGADPYALALAKGLTPETDHPVGTLLAGVQERCPVAGYAVDCGWGGFKKIY<br>SFFPODDLQGLAKLAEIPSMPRALAENAALFARHGLDHKVTMLGIDYORESVNLYFGKLP<br>EECLQPDSIRAILRDIGLPEPTEPMLEFARKSFAIYVTLSWDAAKVERICFAVPPGRDLI<br>TLDPSALPARIAPEIEHFARNSPYAYPGDRMLVYGVTWSPEEEYYKLGSYYQLPVQTRKL<br>LVAFDSVKDQE |
| SEQ ID NO: 21 blc gene product<br>1 mrllplvaaa taaflvvacs sptpprgvtv vnnfdakryl gtwyeiarfd hrferglekv<br>61 tatyslrddg glnvinkgyn pdrgmwqqse gkayftgapt raalkvsffg pfyggynvia |

-continued

SEQUENCES 121 ldreyrhalv cgpdrdylwi lsrtptisde vkqemlavat regfdvskfi wvqqpgs

SEQ ID NO: 22 ybhG gene product
1 mmkkpvvigl avvvlaavva ggywwyqsrq dngltlygnv dirtvnlsfr vggrveslav 61 degdaikagq vlgeldhkpy eialmqakag vsvaqaqydl mlagyrneei aqaaaavkqa 121 qaaydyaqf ynrqqglwks rtisandlen arssrdqaqa tlksaqdklr qyrsgnreqd 181 iaqakasleq aqaqlaqael nlqdstliap adgtlltrav epgtvlnegg tvftvsltrp 241 vwvrayvder nldqaqpgrk vllytdgrpd kpyhgqigfv sptaeftpkt vetpdlrtdl 301 vyrlrivvtd addalrqgmp vtvqfgdeag he SEQ ID NO: 23 ydhC gene product
1 mqpgkrflvw laglsvlgfl atdmylpafa aiqadlqtpa savsaslslf lagfaaaqll 61 wgplsdrygr kpvlliglti falgslgmlw venaatllvl rfvqavgvca aaviwqalvt 121 dyypsqkvnr ifaaimplvg lspalapllg swllvhfswq aifatlfait vvlilpifwl 181 kpttkarnns qdgltftdll rsktyrgnvl iyaacsasff awltgspfil semgyspavi 241 glsyvpqtia fliggygcra alqkwqgkql lpwllvlfav sviatwaagf ishvslveil 301 ipfcvmaian gaiypivvaq alrpfphatg raaalqntlq lglcflaslv vswlisistp 361 llttsvmls tvvlvalgym mqrceevgcq nhgnaevahs esh SEQ ID NO: 24 mlaD gene product
1 mqtkkneiwv gifllaalla alfvclkaan vtsirtepty tlyatfdnig glkarspvsi 61 ggvvvgrvad itldpktylp rvtleieqry nhipdtssls irtsgllgeq ylalnvgfed 121 pelgtailkd gdtiqdtksa mvledligqf lygskgddnk nsgdapaaap gnnettepvg 181 ttk SEQ ID NO: 25 mlaE gene product
1 mllnalaslg hkgiktlrtf graglmlfna lvgkpefrkh apllvrqlyn vgvlsmliiv 61 vsgvfigmvl glqgylvltt ysaetslgml valsllrelg pvvaallfag ragsaltaei 121 glmrateqls smemmavdpl rrvisprfwa gvislplltv ifvavgiwgg slvgvswkgi 181 dsgffwsamq navdwrmdlv ncliksvvfa itvtwislfn gydaiptsag israttrtvv 241 hsslavlgld fvltalmfgn SEQ ID NO: 26 mlaF gene product
1 meqsvanlvd mrdvsftrgn rcifdnislt vprgkitaim gpsgigkttl lrliggqiap 61 dhgeilfdge nipamsrsrl ytvrkrmsml fqsgalftdm nvfdnvaypl rehtqlpapl 121 lhstvmmkle avglrgaakl mpselsggma rraalaraia lepdlimfde pfvgqdpitm 181 gvlvklisel nsalgvtcvv vshdvpevls iadhawilad kkivahgsaq alqanpdprv 241 rqfldgiadg pvpfrypagd yhadllpgs SEQ ID NO: 27 Variant OLS
MNHLRAEGPASVLAIGTANPENILIQDEFPDYYFRVTKSEHMTQLKEKFRKICDKSMIRKRNCFLNEEHLKQNPRLV
EHEMQTLDARQDMLVVEVPKLGKDACAKAIKEWGQPKSKITHLIFTSASTTDMPGADYHCAKLLGLSPSVKRVMMYQ
LGCYGGGTVLRIAKDIAENNKGARVLAVCCDIMACLFRGPSDSDLELLVGQAIFGDGAAAVIVGAEPDESVGERPIF
ELVSTGQTILPNSEGTIGGHIREAGLIFDLHKDVPMLISNNIEKCLIEAFTPIGISDWNSIFWITHPGGKAILDKVE
EKLHLKSDKFVDSRHVLSEHGNMSSSTVLFVMDELRKRSLEEGKSTTGDGFEWGVLFGFGPGLTVERVVVRSVPIKY SEQ ID NO: 28 Variant OLS
MNHLRAEGPASVLAIGTANPENILIQDEFPDYYFRVTKSEHMTQLKEKFRKICDKSMIRKRNIFLNEEHLKQNPKLV
EHDVOTLDARQDMLVVEVPKLGKDACAKAIKEWGQPKSKITHLIFTSASTTDMPGADYHCAKLLGLSPSVKRVMMYQ
LGCYGGGTVLRIAKDIAENNKGARVLAVCCDIMACLFRGPSDSDLELLVGQAIFGDGAAAVIVGAEPDESVGERPIF
ELVSTGQTILPNSEGTIGGHIREAGLIFDLHKDVPMLISNNIEKCLIEAFTPIGISDWNSIFWITHPGGKAILDKVE
EKLHLKSDKFVDSRHVLSEHGNMSSSTVLFVMDELRKRSLEEGKSTTGDGFEWGVLFGFGPGLTVERVVVRSVPIKY -continued

| SEQUENCES |
| --- |

SEQ ID NO: 29 Variant OLS
MNHLRAEGPASVLAIGTANPENILIQDEFPDYYFRVTKSEHMTQLKEKFRKICDKSMIRKRNCFLNEEHLKQNPRLV
EHEMQTLDARQDMLVVEVPKLGKDACAKAIKEWGQPKSKITHLIFTSASTTDMPGADYHCAKLLGLSPSVKRVMMYQ
LGCYGGGTVLRIAKDIAENNKGARVLAVCCDMTACLFRGPSDSNLELLVGQAIFGDGAAAVIVGAEPDESVGERPIF
ELVSTGQTFLPNSEGTIGGHIREAGLMFDLHKDVPMLISNNIEKCLIEAFTPIGISDWNSIFWITHPGGKAILDKVE
EKLHLKSDKFVDSRHVLSEHGNMSSSTVLFVMDELRKRSLEEGKSTTGDGFEWGVLFGFGPGLTVERVVLRSVPINY SEQ ID NO: 30 Variant OLS
MNHLRAEGPASVLAIGTANPENILIQDEFPDYYFRVTKSEHMTQLKEKFRKICDKSMIRKRNCFLNEEHLKQNPRLV
EHEMQTLDARQDMLVVEVPKLGKDACAKAIKEWGQPKSKITHLIFTSASTTDMPGADYHCAKLLGLSPSVKRVMMYQ
LGCYGGGTVLRIAKDIAENNKGARVLAVCCDIMACLFRGPSDSDLELLVGQAIFGDGAAAVIVGAEPDESVGERPIF
ELVSTGQTILPNSEGTIGGHIREAGLIFDLHKDVPMLISNNIEKCLIEAFTPIGISDWNSIFWITHPGGKAILDKVE
EKLDLKKEKFVDSRHVLSEHGNMSSSTVLFVMDELRKRSLEEGKSTTGDGFEWGVLFGFGPGLTVERVVVRSVPIKY SEQ ID NO: 31 Variant OLS
MNHLRAEGPASVLAIGTANPENILIQDEFPDYYFRVTKSEHMTQLKEKFRKICDKSMIRKRNCFLNEEHLKQNPRLV
EHEMQTLDARQDMLVVEVPKLGKDACAKAIKEWGQPKSKITHLIFTSASTTDMPGADYHCAKLLGLSPSVKRVMMYQ
LGCYGGGTVLRIAKDIAENNKGARVLAVCCDIMACLFRGPSDSDLELLVGQAIFGDGAAAVIVGAEPDESVGERPIF
ELVSTGQTILPNSEGTIGGHIREAGLIFDLHKDVPMLISNNIEKCLIEAFTPIGISDWNSIFWITHPGGKAILDKVE
EKLHLKKEKFVDSRHVLSEHGNMSSSTVLFVMDELRKRSLEEGKSTTGDGFEWGVLFGFGPGLTVETVVLRSVPINY SEQ ID NO: 32 Variant OLS
MATKSVAVEEMCKAQKAGGPATILAIGTAVPSNCYYQSEYPDFYFRVTKSDHLTDLKSKFKRMCERSSIKKRYMHLT
EEILEENPNMCTFAAPSIDGRQDIVVKEIPKLAKEAASKAIKEWGQPKSNITHLVFCTTSGVDMPGCDYQLTRLLGL
RPSIKRLMMYQQGCHAGGTGLRLAKDLAENNKGARVLVVCSEMTVINFRGPSEAHMDSLVGQSLFGDGASAVIVGSD
PDLSTEHPLYQIMSASQIIVADSEGAIDGHLRQEGLTFHLRKDVPSLVSDNIENTLVEAFTPILMDSIDSIIDWNSI
FWIAHPGGPAILNQVQAKVGLKEEKLRVSRHILSEYGNMSSACVFFIMDEMRKRSMEEGKGTTGEGLEWGVLFGFGP
GFTVETIVLHSVPI SEQ ID NO: 33 Variant OLS
MATKSVAVEEMCKAQKAGGPATILAIGTAVPSNCYYQSEYPDFYFRVTKSDHLTDLKSKFKRMCDRSSIKKRYMHLT
EEILKENPNMCSFAAPSIDGRQDIVVKEIPKLAKEAASKAIKEWGQPESNITHLVFCTTSGVDMPGCDYQLTRLLGL
RPSIKRLMMYQQGCHAGGTGLRLAKDLAENNKGARVLVVCSEMTVINFRGPSEAHMDSLVGQSLFGDGASAVIVGSD
PDLSTEHPLYQIMSASQIIVADSEGVIDGHLRQEGLTFHLRKDVPSLVSDNIENTLVEAFTPILMDSIDSIIDWNSI
FWIAHPGGPAILNQVQAKVGLKEEKLRVSRHILSEYGNMSSACVFFIMDEMRKRSVEEGKGTTGEGLEWGVLFGFGP
GFTVETIVLHSVPI SEQ ID NO: 34 Variant OLS
MATKSVAVEEMCKAQKAGGPATILAIGTAVPSNCYYQSEYPDFYFRVTKSDHLTDLKSKFKRMCERSSITKRYMHLT
EEILEENPNMCTFAAPSIDGRQDIVVKEIPKLAKEAASKAIKEWGQPKSNITHLVFCTTSGVDMPGCDYQLTRLLGL
RPSIKRLMMYQQGCHAGGTGLRLAKDLAENNKGARVLVVCSEMTVINFRGPSEAHMDSLVGQSLFGDGASAVIVGSD
PDLSTEHPLYQIMSASQIIVADSEGAIDGHLRQEGLTFHLRKDVPSLVSDNIENTLVEAFTPILMDSIDSIIDWNSI
FWIAHPGGPAILNQVQAKVGLKEEKLRVSRHILSEYGNMSSACVFFIMDEMRKRSVEEGKGTTGEGLEWGVLFGFGP
GFTVETIVLHSVPI SEQ ID NO: 35 Variant OLS
MSRSRLIAQAVGPATVLAMGKAVPANVFEQATYPDFFFNITNSNDKPALKAKFQRICDKSGIKKRHFYLDQKILESN
PAMCTYMETSLNCRQEIAVAQVPKLAKEASMNAIKEWGRPKSEITHIVMATTSGVNMPGAELATAKLLGLRPNVRRV
MMYQQGCFAGATVLRVAKDLAENNAGARVLAICSEVTAVTFRAPSETHIDGLVGSALFGDGAAAVIVGSDPRPGIER
PIYEMHWAGEMVLPESDGAIDGHLTEAGLVFHLLKDVPGLITKNIGGFLKDTKNLVGASSWNELFWAVHPGGPAILD
QVEAKLELEKGKFQASRDILSDYGNMSSASVLFVLDRVRERSLESNKSTFGEGSEWGFLIGFGPGLTVETLLLRALP
LQQAERV SEQ ID NO: 36 Nucleotide sequence capable of encoding SEQ ID NO: 1
ATGGCTAACCCGCGTGAAAATTTTCTTAAGTGTTTCTCTAAGCATATCCCCAATAATGTCGCAAACCCGAAGTTGGT
GTATACCCAGCATGACCAATTGTATATGAGCATCTTAAATTCAACGATTCAAAACTTGCGTTTTATCTCTGATACTA
CCCCCAAACCATTGGTGATCGTCACGCCGTCAAATAATTCGCACATTCAAGCTACGATCTTGTGTTCAAAAAAGGTC
GGGCTTCAAATCCGCACGCGCTCAGGTGGGCATGACGCGGAGGGTATGTCATATATCTCACAAGTACCCTTCGTCGT
GGTTGATCTGCGTAATATGCACTCTATTAAGATCGACGTGCATAGTCAGACAGCTTGGGTAGAGGCAGGAGCAACGC
TGGGCGAAGTATACTATTGGATTAATGAGAAAAACGAGAACCTGAGTTTTCCTGGAGGGTACTGCCCCACAGTCGGC
GTAGGAGGACATTTCTCAGGTGGTGGTTACGGAGCGTTGATGCGCAACTATGGCTTAGCTGCTGACAATATTATTGA
TGCTCACTTAGTAAACGTTGATGGAAAAGTGTTGGACCGCAAGTCGATGGGGGAAGACTTATTCTGGGCTATCCGCG
GAGGAGGAGGTGAAAATTTTGGCATCATCGCCGCTTGGAAGATTAAGCTTGTGGCTGTCCCATCGAAGTCTACCATC
TTCTCAGTGAAAAAGAACATGGAGATCCACGGATTAGTGAAATTATTTAACAAATGGCAAAACATCGCATATAAATA
CGACAAGGACTTAGTACTTATGACGCATTTCATCACTAAGAACATCACCGACAATCATGGTAAAAATAAAACCACCG
TTCACGGTTACTTTTCTAGTATTTTCCATGGGGGGGTGGACAGTTTAGTAGATTTAATGAATAAGAGTTTTCCCGAG
CTGGGCATCAAGAAAACTGATTGCAAGGAATTCAGTTGGATTGATACTACTATCTTCTATTCTGGAGTCGTGAACTT
TAATACTGCCAATTTTAAAAAGGAGATCTTATTAGATCGTTCAGCCGGAAAAAAGACTGCGTTTAGCATTAAGCTTG
ACTATGTAAAGAAACCAATCCCTGAAACTGCTATGGTCAAGATCCTTGAAAAACTGTATGAAGAAGACGTCGGCGCC
GGCATGTATGTACTTTACCCATATGGAGGCATCATGGAAGAGATCTCTGAGAGTGCAATCCCATTCCCGCATCGCGC
TGGCATCATGTACGAGCTGTGGTATACGGCGTCGTGGGAGAAACAGGAGGATAACGAGAAGCATATTAACTGGGTTC
GTAGCGTTTACAACTTTACAACTCCGTACGTCAGTCAAAATCCCCGTTTAGCCTACTTGAACTACCGCGATCTTGAT
CTTGGTAAGACTAATCACGCATCGCCAAACAATTATACCCAAGCCCGTATCTGGGGGGAAAAATACTTCGGAAAGAA
CTTCAACCGTCTGGTCAAAGTAAAGACTAAAGTAGATCCCAATAATTTCTTCCGTAACGAACAGAGTATTCCCCCCT
TGCCTCCCCATCATCATCACCACCACTAA -continued

| SEQUENCES |
|---|

SEQ ID NO: 37 *E. coli* IspA
1 mdfpqqleac vkqanqalsr fiaplpfqnt pvvetmqyga llggkrlrpf lvyatghmfg 61 vstntldapa aavecihays lihddlpamd dddlrrglpt chvkfgeana ilagdalqtl 121 afsilsdadm pevsdrdris miselasasg iagmcggqal dldaegkhvp ldalerihrh 181 ktgaliraav rlgalsagdk grralpvldk yaesiglafq vqddildvvg dtatlgkrqg 241 adqqlgksty pallgleqar kkardlidda rqslkqlaeq sldtsaleal adyiiqrnk SEQ ID NO: 38 *C. glutamicum* IdsA
1 mkdvslssfd ahdldldkfp evvrdrltqf ldaqeltiad igapvttava hlrsfvlngg 61 krirplyawa gflaaqghkn sseklesvld aaaslefiqa calihddiid ssdtrrgapt 121 vhraveadhr annfegdpeh fgvsvsilag dmalvwaedm lqdsglsaea lartrdawrg 181 mrteviggql ldiyleshan esveladsvn rfktaaytia rplhlgasia ggspqlidal 241 lhyghdigia fqlrddllgv fgdpaitgkp agddiregkr tvllalalqr adkqspeaat 301 airagvgkvt spediavite hiratgaeee veqrisqlte sglahlddvd ipdevraqlr 361 alairsterr m SEQ ID NO: 39 GPPS
1 mkdvslstfd ahdldlnkfp evvrdrltrf ldaktstiad igdpvteavs hlrnfvlngg 61 krirplyawa gflaaqgren sseeldavid aasslefiqa calihddiid ssdtrrgapt 121 vhraveadhr annfegapeh fgvsvailag dmalvwaedm lqdsglsaea lartrdawrg 181 mrteviggql ldiyleshan esveladsvn rfktaaytia rplhlgasia ggspelidal 241 lhyghdigia fqlrddllgv fgdpqitgkp agddiregkr tvllalalqr adkespeaae 301 viragigkvt tpediarias hirdtgaeee veqrisqlts sglahldnvd ipdavriqlr 361 alairsterr m SEQ ID NO: 40 GPPS
1 mkdvslstfd ahdldldtfp evvrdrltqf ldaqattiag igdpvteavs hlrsfvlngg 61 krirplyawa gflaaqglen sgekieavld aasslefiqa calihddfid ssdtrrgapt 121 vhraveanhr ahnlegdseh fgesvsilag dmalvwaedm lqdsglsaea lartrdawrg 181 mrteviggql ldiyleahan eaveladsvn rfktaaytia rplhlgasia ggsqelidal 241 lhyghdigia fqlrddllgv fgdpkvtgkp agddiregkr tvllalalqr adknspeaaa 301 airagigkvs tpediaviak hiratgaeee veqritqlte sglahlddve ipdevrtqlr 361 alairsterr m SEQ ID NO: 41 GPPS
1 mstfdahdld ldkipdvvrd rlvafldaks stiaeigepv tdavshlrsk vlnggkrirp 61 lyvwagflaa qgestseekv eavldaaasl efiqacalih ddiidssdtr rgaptvhrav 121 eadhrdrrfe gdpkhfgvsv silagdmalv waedmlqdsg ltaealartr nawrgmrtev 181 iggqlldiyl eshanesvel adsvnrfkta aytierplhl gaaigggske lidairrygh 241 digiafqlrd dllgvfgdpa itgkpagddi regkrtvlla lalqradetn peaaaairag 301 igkvttpedi atiaqlirdt gaeeeverri seltasglsy ldrvelpeei raqlralair 361 sterrm SEQ ID NO: 42 GPPS
1 mstldahdld lnriptvvhd rlskfldske gdiaaigtpv seavaylraf vlnggkrirp 61 lytwagfvaa gglenntekl eavldaaasl efiqaealih ddiidssdtr rgaptvhrav 121 esyhrennle gnsahfgesv silagdmalv waedmlqdsg lstealarsr aawrgmrtev -continued

SEQUENCES 181 iggqlldiyl eaqanesvel ansvnrfkta aytierplhl gasiagaspe lisalrnygh 241 digiafqlrd dllgvfgdpa itgkpagddi regkrtvlla kalekadkes pvaaaeirag 301 igqvsepadi aqlaqlirdt gaeaevenli tdlttsglah leavsmpaev kellrslair 361 sterrm SEQ ID NO: 43 GPPS
1 mstahdhnvd ldqipdvvre rltrflddra anvvaiggpv tealsylrdf vlnggkrirp 61 lyvwagfvaa qgpgrssedi navldaaasl efiqaealih ddiidssdtr rgaptvhrav 121 esmhgavgle gdaahfgesv ailagdmalv waedmlqdsg lsaaalarar dawrgmrtev 181 iggqlldiyl eaqasesvel ansvnrfkta aytierplhl gaslaggape lidairnygr 241 digiafqlrd dllgvfgdpa vtgkpagddi regkrtvlla lalqradaed peaaaairsa 301 igkvtdpaei triaglirat gaedeveehi srltasglah leiagipdev reqlrhlair 361 aterrm SEQ ID NO: 44 GPPS
1 mssfdahdlt ldripgvvag rltryldsra gdiavigapv saavehlrsf vlgggkrirp 61 lyawagflaa qgpqraeerl esvldaassl efiqaeallh ddiidssdtr rgrptvhrav 121 etqhgsqglq gdsahfgesv silvgdmalv wsedmfqdsg lsapalarar epwramrtev 181 iggqlldisl eattnesvel adavnrfkta aytierplhl gaaiagadag litalrgygr 241 digvafqlrd dllgvfgdpv vtgkpagddi regkrtvlla lalkladahn pdsataireg 301 vgrvstpadi aelagiiret gaereveeri trltrsglaq ledvglpadv rehlehlair 361 sterrm SEQ ID NO: 45 GPPS
1 mstpspltt1 tldqvpdavr eeltrfiddr rrqvaaiggp vteavahles fvlgggkrir 61 plyawagfvg gggleraaed paamlraaas lefiqaeali hddiidssdt rrgnltvhra 121 vekqhrdraw agdpahfges vailvgdlal vwaedmlqds glsvaalqra rdpwrgmrte 181 viggqlldit leatadenie ladsvnrfkt aaytierplh lgaaiagadq atidafrgyg 241 hdigiafqlr ddqlgvygdp avtgkpagdd lregkrtvll atalqraddr dpaaaaelra 301 gvgatddpaq iarlaqiiad tgaveeieer iteltrsgla hlaaagtspe vtatltdlah 361 ratarrh SEQ ID NO: 46 GPPS
1 mtstdprtlt lervpgaard alseffdarr gqiagigapv tdavahlesf vlgggkrirp 61 lyawagfvga ggfdrtgeep aavlkaaasl efiqacalvh ddiidssdtr rgnptvhrav 121 ekrhadngwl gdaahfgesv ailvgdlalv waedmlqdsg lsvdalrrar epwramrtev 181 iggqlldisl eaaadervel aesvnrfkta aytierplhl gaalagadda lieafrgygr 241 digmafqlrd dqlgvygdpa vtgkpagddi regkrtvlla lalrraderd paaaaelrrg 301 vgatgdpatl arlaeiirst gaveeveeri salttsglah ldaagtapev tetlralavr 361 vterrm SEQ ID NO: 47 GPPS
1 mssqdlrtlt ldqipdaard elsrffadrr pqvaaiggpv tdavahlekf vlgggkrirp 61 lyvwagfagg ggfdatsedp aavlraaasl efiqaealih ddiidasdtr rgnptvhrav 121 eeahrtsgws gdpahfgesv ailvgdlalv waedmfqdsg lsvealqrar eawramrtev 181 iggqlldisl eatadedvel adsvnrfkta aytierplhl gasiagaddk tieafrgygr -continued

| SEQUENCES |
|---|
| 241 digiafqlrd dqlgvygdpa vtgkpagddl regkrtvlla talkraddrd paaaaelrag |
| 301 vgavadpgev srladiiagt gaveeieeri taltasglah lsaahtspev tatltdlahr |
| 361 atarrh |
| SEQ ID NO: 48 GPPS |
| 1 mtepkipsld dipgavrdel aqflagqrsa iaaigqpvtn aisylesfvl dggkrirply |
| 61 awagfvgarg legpespdam lraasslefi qacalihddi vdasdtrrgn ptvhrgvakr |
| 121 hrdlglggds dffgqslail igdmalvwae dmlqdsglsp kalarvrdpw rgmrrevigg |
| 181 qmldisleae gsedaslads vnrfktaayt ierplhlgaa vagasdqlia afrgygrdig |
| 241 iafqlrddll gvfgdpavtg kpagddlreg krtvllslal qradesdpaa aaelrrligq |
| 301 tedpqeiarm aeiieasgap dvveqrisdl trsglahlhd apvspevttt leelarksta |
| 361 rrm |
| SEQ ID NO: 49 GPPS |
| 1 mtepkiptld dipaavrael affidgqrds iaaigqpvth aisylesfvl nggkrirply |
| 61 awagfvgahg legsespeam lraasslefi qacalihddi vdasdtrrgn ptvhrgvaar |
| 121 hrelelngda dffgqslail igdmalvwae dmlqdsglsp ealarvrepw rgmrrevigg |
| 181 qmldisleae gsedaslads vnrfktaayt ierplhlgaa vagaseelia afrgygrdig |
| 241 iafqlrddll gvfgdpaitg kpagddlreg krtvllslal grtdatdpva aaelrrligq |
| 301 tedpdeisrm aeiiaesgap dvveqritel tqsglshlyd ahvspdvtat ledlarksta |
| 361 rrm |
| SEQ ID NO: 50 GPPS |
| 1 mqtltldqvp aaardelarf idsrraqvaa iggpvtravs hlesfvldgg krirplyawa |
| 61 gfvgggglet dedpaamlra aaslefiqgc alihddiida sdtrrgnptv hravekvhgd |
| 121 ngwagdpahf gesvailvgd lalvwaedml qdsglsvaal grarepwram rteviggqll |
| 181 disleatgde dieladsvnr fktaaytier plhlgaaiag adqatidafr gygrdigiaf |
| 241 qlrddelgvy gdpevtgkpa gddlregkrt vllatalqra derdpaaaae lrrgigttsd |
| 301 paeiarlaqi iaetgaveal eerisaltas glahlaavgt spevtatltd lahratarrr |
| SEQ ID NO: 51 GPPS |
| 1 msapdnqakd lrqlslndvp eeaqkllaqf fneqeekvag igrpvteavs ylrdfvlngg |
| 61 krvrplygwa gfvgagglkn lngtnedpqa vlravsslef iqacalihdd iidssdtrrg |
| 121 nptvhravea ahqeqqwtgd sahfgestai lvgdlalvwa edmwrysgls haaldraaep |
| 181 wramrtevig gqlldislea sgdespelan avnrfktaay tierplhlga aiagaspevi |
| 241 eafrgygtdi giafqlrddl lgvfgdpset gkpagddlre gkrtvllata lqradksdpa |
| 301 aaaqlragvg tetnpekiae lasiiastga vesieeqist ltvsglkhlt dagiepqvte |
| 361 dlhklairmt errk |
| SEQ ID NO: 52 GPPS |
| 1 mdtpvsasrt ahttpdihqi pdavrgvlsd flegrrskva kigepvtrav syledfvlgg |
| 61 gkrirplyaw agfvgaggle gpedpqavlr avsslefiqa calihddiid ssatrrgnpt |
| 121 lhravasahq eqnfagladh fgmsvailvg dmalvwaedm lrnsgvsada larlnrpwag |
| 181 mrteviggqi ldisleasgd esvqlannvn rfktaaytie rplhlgaaia gaspeviraf |
| 241 rgygrdigia yqlrddllgv fgdpaitgkp agddlregkr tvllalaler adahdpqaaa |

-continued

| SEQUENCES |
|---|

301 alragvghtq dpaelarlaq iirdtgapde veariteltt sglaqletae lsptvtsvlk 361 dlairsterr s SEQ ID NO: 53 GPPS
1 mssqstpgpr pdpatidsip daaraqlaay iearrpeida igapvttale hladfvlggg 61 krirplygwa gfvgagglen ssedpeavlr avsslefiqa calvhddiid ssetrrgrpt 121 vhravaadhr drnhlgepdh yglsaailig dlalawaddm fadsgisaaa fararepwrg 181 mrteviggql ldislessgs editlsrsvn ryktaaytie rplhigaala gadeqlissf 241 rgyghdigia fqlrddllgv fgdpaitgkp agddlregkr tellslalad adrsdpaaaa 301 elragvgtvd dpaditrlad iiastgapeq meqrieeltr sglahldrvg ipesvkstlh 361 slairsterr t SEQ ID NO: 54 GPPS
1 mhhtpnldei pgavhqelsa fvsaqrpeie kigapvvnat aflesfvlgg gkrirplyaw 61 agfvgaggld gdedpeamlr aaaslefiqa salihddiid gsdtrrgqpt vhrgveavhr 121 srqhlgdpea fgesvailvg dmalvwaedm fqdsglsfqa lrrardpwrg mrteviggql 181 ldvsleaags edenlansvn rfktaaytie rplhlgaaia gadealiaaf rgygrdigva 241 fqlrddqlgv fgdpevtgkp agddlregkr tvllalalqr adesnpaaaa elrakignve 301 dpadiarlaq iitdsgapal ieqriaalts sglrhlresg vapevtetle alalkatarr 361 s SEQ ID NO: 55 GPPS
1 mttpqipsld dipvavreel elfldsqrda iasigspvtn aisylesfvl dggkrirply 61 awagfigahg legtespqam lraasslefi qacalihddi vdasdtrrgn ptvhrgvaar 121 hrelglsgda dffgqslail vgdmalvwae dmlqdsglsp ealararapw ramrrevigg 181 qmldicleae gsedatlads vnrfktaayt ierplhlgaa vagapeklva afrgygqdig 241 vafqlrddll gvfgdpaitg kpagddlreg krtvilslal qradatdpaa aselrrligq 301 tedpadiarm aqiiadsgap dvveqrisdl trsgldhlhn aqvapevtat leelahksta 361 rrm SEQ ID NO: 56 GPPS
1 mnnseafhql piaevpkhvr aeladfIker epqiaqigrp vtnaiehler filgggkrir 61 plyvwagfva adgllgdedp qavlraassl efiqscalih ddivdasdtr rgnptvhrav 121 eaehrklgwt gdpeafgrsa ailigdmslv waedmlldsg lsqaalqrtr epwramrtev 181 iggqlldvsl eaaaiesvel sdsvnrfkta aytierplhl gaaiagapqk lidafrgygr 241 digiafqlrd dqlgvfgdpk vtgkpagddl regkrtvlma ialqradeqd psaaqflrdn 301 lgatddpsvl skmaqmieds gapeeieqri daltqsgley laaaqvnsev tellrslaiq 361 starak SEQ ID NO: 57 GPPS
1 mqnipeladi pgavreelat fldqrreqva aigapvtkav sflesfvidg gkrvrptyaw 61 agylaagrge edpeamlras aslefiqaca lihddiidas ntrrgnptvh rgveklhres 121 gylgdpeffg tsvailvgdl alvyaedmfq dsglsaaalh rarnawrgmr teviggqlld 181 isleaagses velansvnry ktaaytierp lhlgasiaga seeliaafrg ygqdigiayq 241 lrddqlgvfg dpavtgkpag ddlregkrte llalalrrad esdpqaaatl rklightsdp 301 qelsrlaqii adsgapeeie rriealtqsg lqhlraarvd pavtetleql aikatarhk -continued

| SEQUENCES |
|---|

SEQ ID NO: 58 GPPS
1 mtfpnvpsla dvpsttqell seflearrpq vaeigqpvtq atqfledfvl gggkrirply 61 awagfigadg ldgdedpqav lraaaslefi qacalihddi idasdtrrgn ptvhrgvaal 121 hweagyqgsp effgqsvail vgdlalawse dmlqdsglsa aalqrvrepw ramrtevigg 181 qllditleaq gsesvelada vnryktaayt ierplhigaa ladapshlid afrgygrdig 241 iafqlrddql gvfgdpsvtg kpagddlreg krtvllalal qeldekdpsa aatlragvgn 301 vsepeelakl sqiiedsgap gliekriarl tesglnhlra advsdevtat leelahkata 361 rra SEQ ID NO: 59 GPPS
1 mqnipeladi pgavreelat fldqrreqva aigapvtkav sflesfvldg gkrvrptyaw 61 agylaagrge edpvamlraa aslefiqaca lihddiidas ntrrgnptvh rgveklhres 121 eylgdpeffg tsvailvgdl alvyaedmfq dsglsaaalh rarspwrgmr teviggqlld 181 isleaagses velansvnry ktaaytierp lhlgaataga seeliaafrg yghdigiayq 241 lrddqlgvfg dpavtgkpag ddlregkrte llalalqrad esdpqaaatl rkligrtsdp 301 qelsrlaqii adsgapeeie rridaltqsg lqhlraaqvd pavtetleql aikatarrk SEQ ID NO: 60 GPPS
1 mqnipeladi pgavreelat fldqrreqva aigapvtkav sflesfvidg gkrvrptyaw 61 agylaagrge edpaamlraa aslefiqaca lihddiidas ntrrgnptvh rgveklhres 121 eylgdpeffg tsvailvgdl alvyaedmfq dsglsaaalh rarspwrgmr teviggqlld 181 isleaagses velansvnry ktaaytierp lhlgaaiaga seeliaafrg yghdigiayq 241 lrddqlgvfg dpavtgkpag ddlregkrte llalalhrad esdpqaaatl rkligrtsdp 301 qelsrlaqii adsgapeeie SEQ ID NO: 61 GPPS
1 mrarslfspl psryrawwks qlrilhpant prlrlsrhlt gypkghqflh fegpdalnfp 61 dprsltldqi pgatqdvlve flrsreqqis aigqpvteav shleafvvgg gkrirplyaw 121 agfvggggltngkedpyaml kaaaslefiq acalihddii dasdtrrgqp tvhravearh 181 ssaqwvkesa hfgesvailv gdlalvwaed mlqdsglsdd akarardpwr amrteviggq 241 lldiyleasg sesieaadav nryktaayti erplhlgaav agadeatiaa frgygrdigi 301 ayqlrddylg vfgdpgvtgk pagddlregk rtvllatalq ladehdpsaa aelrtkigtt 361 tdlaevarlt eiiastgave amekridalt asglayldaa gtspevtdtl rdlairstfr 421 rs SEQ ID NO: 62 GPPS
1 mnnsedfsql piaeipkhvr aelssfIkar epqlaqigkp vteaiehler fvldggkrir 61 plyawagfva adgllgseep qavlraassl efiqscalih ddivdasdtr rgnptvhrav 121 eaqhralgwt gdsadfgrsa ailigdmslv waedmfldsg isqaaiqrar epwramrtev 181 iggqlldvsl eaaaiesvel sdsvnrfkta aytierplhl gaaiagasdk lidafrgygr 241 digiafqlrd dqlgvfgdpq vtgkpagddl regkrtvlma ialqradeqd pptakflren 301 lgatddpsvl skmsqmieds gaseeieqri daltqsgley laaanvnsev tellrslaik 361 starak SEQ ID NO: 63 GPPS
1 mnnsedfsql piaeipkhvr aelssflkar epqlaqigkp vteaiehler fvldggkrir -continued

| SEQUENCES |
|---|

```
 61    plyawagfva adgllgsedp qavlraassl efiqscalih ddivdasdtr rgnptvhrav

121    eaqhralgwt gnsadfgrsa ailigdmslv waedmfldsg isqaaiqrar epwramrtev

181    iggqlldvsl eaaaiesvel sdsvnrfkta aytierplhl gaaiagasdk lidafrgygr

241    digiafqlrd dqlgvfgdpq vtgkpagddl regkrtvlma ialqradeqd paaakflren

301    lgatddpsvl skmsqmieds gapeeieqri daltqsgley laaanvnsev tellrslaik

361    starak

SEQ ID NO: 64 GPPS
  1    mtldqipeat tkllaefiha rseqvaaigg pvaeavshle sfilnggkri rplyawagfi

 61    gggglltntde dplamlraaa slefiqacal ihddiidasd trrgsptvhr svearhrdah

121    wsgssshfge svailvgdla lvwaedmfqd sglssealar arepwramrt eviggqlldi

181    aleaaasedi saadsvnrfk taaytierpl hlgaaianae adtisafrgy gqdigvafql

241    rddqlgvygd pkltgkpagd dlregkrtvl latalrlads sdpaaaaalr sgigstadpl

301    elshladlia gtgavaeieq riehltesgl shlatahtsa evtrtltdla iratarrs

SEQ ID NO: 65 GPPS
  1    mtnipeladi pgavreklai fldqrrdhva eigapvstam sflesfvidg gkrvrpmyaw

 61    agylaagrgs espeamlraa sslefiqaca lihddiidas ntrrgkptvh reaerlhres

121    dflgdpeffg tsvailvgdf alvyaedmfq dsglssealq rardpwrgmr tevlggqlld

181    isleaagses valsnsvnry ktaaytierp lhlgaaiaga sdelisafrg yghdigiayq

241    lrddqlgvfg dpeitgkpag ddlregkrte llalalqrad erdpsaaatl rkfigrtsdt

301    qdllrlsqii adsgapdeie rritaltesg lahlraanvd pqitetlehl aiqattrqk

SEQ ID NO: 66 GPPS
  1    mtnipeladi pgavreklai fldqrrehva eigapvstam sflesfvidg gkrvrpmyaw

 61    agylaagrgs espeamlraa sslefiqaca lihddiidas ntrrgkptvh reaerlhres

121    dflgdpeffg tsvailvgdf alvyaedmfq dsglspealq rarepwrgmr tevlggqlld

181    isleaagses valsnsvnry ktaaytierp lhlgaaiaga reelisafrg yghdigiayq

241    lrddqlgvfg dpaitgkpag ddlregkrte llalalqrad erdpsaaatl rkfigrtsdp

301    qdllrlsqii adsgapdeie rritaltesg lahlraanvd pqitetlehl aiqattrqk

SEQ ID NO: 67 GPPS
  1    mtnipeladi pgavreklai fldqrrdhva eigapvstam sflesfvidg gkrvrpmyaw

 61    agylaagrgs espeamlraa sslefiqaca lihddiidas ntrrgkptvh rgaerlhres

121    dflgdpeffg tsvailvgdf alvyaedmfq dsglspealq rarepwrgmr tevlggqlld

181    isleaagses valsnsvnry ktaaytierp lhlgaaiaga seelisafrg ygydigiayq

241    lrddqlgvfg dpaitgkpag ddlregkrte llalalqrad erdpsaaatl rkfigrtsdt

301    qdllrlsqii adsgapdeie rritaltesg lahlraanvd pqitetlehl avqattrqk

SEQ ID NO: 68 GPPS
  1    mtnipeladi pgavreeltn fldqrrdhva eigtpvstam sllesfildg gkrirpiyaw

 61    agylaagrgt espeamlraa sslefiqaca lihddiidas ntrrgkptvh rkaeqlhrel

121    dylgdpeffg tsvailvgdf alvyaedmfq dsglspealq rardpwrgmr tevlggqlld

181    isleatgses vslsnsvnry ktaaytierp lhlgaaiaga seelitafrg yghdigiayq

241    lrddqlgvfg dpavtgkpag ddlregkrte llalalqrad ehdpsaaatl rkfigrtsdp

301    qdllrlsqii adsgapaeie rritalttsg lahlraanvd sqitktlehl aiqattrqk
```

-continued

| SEQUENCES |
|---|

SEQ ID NO: 69 GPPS
1 mhhsrdahta spvrekdpat vsrsttspqf darslafsei epaveqklre ffqgrsrkis
61 vigepvsrav tyledfvlgg gkrirpsyaw agflagngle gaedpeavla sissleliqa
121 calihddiid asdsrrgqpt vhrtaearhr dnswngdsah fgesiaillg dlafawaddm
181 frtsglsdaa iartsnawrg mrteviggql ldvflesags esielaenvn rfktaaytie
241 rplhigaaia gadgkivral rdygrdigva yqlrddllgv fgnpavtgkp agddlregkr
301 tvlvakalel ahaadnadav esirkgvgtv tephdiarla dtirqtgaea gvekridela
361 ergishlcta disddarnil vslankatar sm SEQ ID NO: 70 GPPS
1 mvthtdkssi pttaqipaav erelelffte hgpsvdvigp pvseavehlr tfvlgggkri
61 rptfgwvgfi gangldntde dpaavlravs sleliqacal ihddiidasa srrgnptvhv
121 aaaeshrhqn wlgnsekfge slailvgdla lvwaddmwhh sglshaaldr aaepwrgmrt
181 eviggqildi sleaagcede elanavnrfk taaytierpl hlgaaiagad ddtiaalrgy
241 ghdigiafql rddilgvfgd pvvtgkpagd dlregkrtvl ysralqaade hdpaaaqrlr
301 dgigtalapd eiaelsgiiq etgavddvek rideltesgl ehvrraalsp eavetletla
361 ikatarrm SEQ ID NO: 71 GPPS
1 mrspgrrypr ppaiggtrrr igqcpradtt iylevalsvg psgpanpaps dsaalvhave
61 qaltrffdsr relvaelgpv fvsattalee fvlrggkrtr psfawtgwlg aggdptgpha
121 eavltacsal elvqacalih ddiidssrtr rgfptvhvdf edrhrtrswg gdpahfgasv
181 ailvgdlalt waddmvaaag ldpaararfa vvwaamrtev mggqlldvhg eagaddsvaa
241 alrinrykta aytverplhl gaalagadpe liaayrefgt digiafqlrd dllgvfgdpa
301 vtgkpsgddl regkrtvlva ealrradstd peaarrlrtc lgtdldaeqv tglreiitdl
361 gavddverri seltergl ta lasssvapda garlramala atrrva SEQ ID NO: 72 GPPS
1 medplsrdst lpaprrtsdp dpvlreagta pialvesala effhsrreqv arvgggyvsa
61 vadleafvlr ggkrirpsfg wmawlgaggd hrspqaasvl racasleliq acalihddii
121 dasltrrgfp tvhvgftarh raarwsgspe rfgesaaill gdlalcwadd mlresgighd
181 amgrvspvws amrtevlggq lldieaeagl desveaamrv nryktaaytv erplqlgavl
241 agaseslvda yrsfgtdigl afqlrddllg vfgdpavtgk psgddiregk rtvlmavglq
301 ladrdrpeag sllrsslgvv dltedtiesi rtvlielgav adverrisel tdraldtlka
361 savephaaaq lramsiaatq rty SEQ ID NO: 73 GPPS
1 mspldvpaav tgaltdffga ragmvadide efsrvigals dftllggkrv rpafawagwl
61 gaggdaglca daedpeavfr svcalefiqa calihddiid asatrrgnpt vhkvfesrhr
121 dngwrgdagh ygqsvailag dvalawaddm fhgsglsdaa rnrarepwwr mrteviggql
181 lditaeasgd srvgvaekvn rfktaaytie rplhigaaia gaddaivday refgldigia
241 fqlrddqlgv fgdpavtgkp agddlregkr tvlvgtalar lresdpdgar hlddklgrvd
301 gqddvdelre lirgsgadel leveidrltr rglaaldsap ivdeqrerla emgrratara
361 w SEQ ID NO: 74 GPPS
1 mevilsagpg tptrpsptsa tpgtpafaaa veqaltsffa trretvgelg pifvdaaeal -continued

SEQUENCES 61 esfvlrggkr trpgfawtgw lgaggdpdgp dapavlnaca alelvqacal ihddiidasr 121 trrrfptvhv dfeqrhrdrg wagdaprfgt gvailigdla lawaddmvha sgldpravar 181 fatvwakmrt evlggqlldi hgeasgdesv aaalrinryk taaytverpi hlgaaladag 241 pelvrsyrdf gtdigiafql rddllgvfgd psvtgkpsgd dlregkrtvl iaealargdk 301 adpaaaellr tkvgtdlsge dvdqlrevlv rlgavdavea riaelteral aaidtssatp 361 aakdhlhama laatrrta SEQ ID NO: 75 GPPS
1 mkeaplsagp gtptrhpvga gsvvaaveer lraffvtrep iveplgpvfv daaralqdfv 61 irggkrtrps fawtgwlgag rspedpeada vltacsalel vqacalihdd iidssrtrrg 121 fptvhvdyeg rhrdqrwrgd adhygisvav ligdlalawa ddmtrdaglp ddaaarfapv 181 waamrtevlg gqlldihges agdetveaal rinryktaay tierplhmga alagaspelv 241 aayrefgtdi giafqlrddl lgvfgdpavt gkpsgddlre gkrtvliaea lqradidapa 301 vadlirsslg tdvtpervte lrtaltelga vdavekriss ltdqaltald astatpeakr 361 qlramalaat arty SEQ ID NO: 76 GPPS
1 medplsgdlt shttresteh dfavhdatan patlvesale affaskrpqv aavgggypaa 61 vedlvafvlr ggkrirpafa wtawlgaggd rsstsapsvl racasleliq acalihddii 121 dasvtrrgyp tvhigfadrh rglgwsgsae rfgesaaill gdlalcwadd mlreagldsd 181 taarispvws smrtevlggq lldieaeagl desvdaamrv nrfktaaytv erplhlgall 241 agapselves yrafgsdigs afqlrddllg vfgdpgvtgk psgddiregk rtvlmavgmq 301 ladrdrpdla allrtslgda dlaeddirai rtaltelgav ddverritel teralgtldg 361 stvepgaaar lramavsatq rqy SEQ ID NO: 77 UniProt Q8XYF1
1 mgvstlrgll lagstlgavg aagaqdsata aepadvaqla pvvvtgtkld asgqtadsat 61 svasgarlqa agvartdelg klfpeltvtp rssraytlfg mrgtpssdfy spavtvyvdg 121 vpqdmayftq plpdveqvev lrgpqgtlyg raaqggvini vttkpnnrfg aqasvdvnnl 181 trrtdlsvrg plvkdllygd vsayfddrpg tlknpatgad qldsgrealg rarlrwtprd 241 tdldatlsvs hdryrsheey fqaydlkdrh aiasspfdlt epsltrtvtq aalsvdyylr 301 gwklssvsay qdrrlervlt tgnadpenqk tfsqelrvat sgdvkrpvdg vfglyyekqa 361 ferdrgiavp gvsaflfpgp srsesnlrsm aafgegvwha terldltagl rygidsadih 421 ynrtgaaals fagdktfrsl tpkvsvgyqa apgwrvygly segykaggfn riadnsagsi 481 pysaerlrnv evgfqadllg krlrldgalf hsrtsnlqaq vvsglfqmls nvgdaratgv 541 elngtwlatp dltlraggaw ttskiysysa pqgnldltgk rvpyvvplsl rasgeyrfrp 601 qgmrgrlrwn vgmtysgdmw fdaantlrqp ayalldtsls wdinkhltvv gyvdnltdra 661 vrtyafslgt fgtfaqygqg rtiglrlqar l SEQ ID NO: 78 Amino acid sequence of N-terminal truncation of *C. sativa*
CBDAS without N-terminal methionine
ANP RENFLKCFSQ YIPNNATNLK
LVYTQNNPLY MSVLNSTIHN LRFTSDTTPK PLVIVTPSHV SHIQGTILCS
KKVGLQIRTR SGGHDSEGMS YISQVPFVIV DLRNMRSIKI DVHSQTAWVE
AGATLGEVYY WVNEKNENLS LAAGYCPTVC AGGHFGGGGY GPLMRNYGLA
ADNIIDAHLV NVHGKVLDRK SMGEDLFWAL RGGGAESFGI IVAWKIRLVA
VP KSTMFSV KKIMEIHELV KLVNKWQNIA YKYDKDLLLM THFITRNITD
NQGKNKTAIH TYFSSVFLGG VDSLVDLMNK SFPELGIKKT DCRQLSWIDT -continued

| SEQUENCES |
|---|

IIFYSGVVNY DTDNFNKEIL LDRSAGQNGA FKIKLDYVKK PIPESVFVQI
LEKLYEEDIG AGMYALYPYG GIMDEISESA IPFPHRAGIL YELWYICSWE
KQEDNEKHLN WIRNIYNFMT PYVSKNPRLA YLNYRDLDIG INDPKNPNNY
TQARIWGEKY FGKNFDRLVK VKTLVDPNNF FRNEQSIPPL PRHRH

SEQ ID NO: 79 Amino acid sequence of wild-type *C. sativa* CBDAS
MKCSTFSFWF VCKIIFFFFS FNIQTSIANP RENFLKCFSQ YIPNNATNLK
LVYTQNNPLY MSVLNSTIHN LRFTSDTTPK PLVIVTPSHV SHIQGTILCS
KKVGLQIRTR SGGHDSEGMS YISQVPFVIV DLRNMRSIKI DVHSQTAWVE
AGATLGEVYY WVNEKNENLS LAAGYCPTVC AGGHFGGGGY GPLMRNYGLA
ADNIIDAHLV NVHGKVLDRK SMGEDLFWAL RGGGAESFGI IVAWKIRLVA
VP KSTMFSV KKIMEIHELV KLVNKWQNIA YKYDKDLLLM THFITRNITD
NQGKNKTAIH TYFSSVFLGG VDSLVDLMNK SFPELGIKKT DCRQLSWIDT
IIFYSGVVNY DTDNFNKEIL LDRSAGQNGA FKIKLDYVKK PIPESVFVQI
LEKLYEEDIG AGMYALYPYG GIMDEISESA IPFPHRAGIL YELWYICSWE
KQEDNEKHLN WIRNIYNFMT PYVSKNPRLA YLNYRDLDIG INDPKNPNNY
TQARIWGEKY FGKNFDRLVK VKTLVDPNNF FRNEQSIPPL PRHRH SEQ ID NO: 80 Amino acid sequence of N-terminal truncation of *C. sativa*
CBCAS without N-terminal methionine
ANP QENFLKCFSE YIPNNPANPK
FIYTQHDQLY MSVLNSTIQN LRFTSDTTPK PLVIVTPSNV SHIQASILCS
KKVGLQIRTR SGGHDAEGLS YISQVPFAIV DLRNMHTVKV DIHSQTAWVE
AGATLGEVYY WINEMNENFS FPGGYCPTVG VGGHFSGGGY GALMRNYGLA
ADNIIDAHLV NVDGKVLDRK SMGEDLFWAI RGGGGENFGI IAACKIKLVV
VPSKATIFSV KKNMEIHGLV KLFNKWQNIA YKYDKDLMLT THFRTRNITD
NHGKNKTTVH GYFSSIFLGG VDSLVDLMNK SFPELGIKKT DCKELSWIDT
TIFYSGVVNY NTANFKKEIL LDRSAGKKTA FSIKLDYVKK LIPETAMVKI
LEKLYEEEVG VGMYVLYPYG GIMDEISESA IPFPHRAGIM YELWYTATWE
KQEDNEKHIN WVRSVYNFTT PYVSQNPRLA YLNYRDLDLG KTNPESPNNY
TQARIWGEKY FGKNFNRLVK VKTKADPNNF FRNEQSIPPL PPRHH SEQ ID NO: 81 Amino acid sequence of wild-type *C. sativa* CBCAS
MNCSTFSFWF VCKIIFFFLS FNIQISIANP QENFLKCFSE YIPNNPANPK
FIYTQHDQLY MSVLNSTIQN LRFTSDTTPK PLVIVTPSNV SHIQASILCS
KKVGLQIRTR SGGHDAEGLS YISQVPFAIV DLRNMHTVKV DIHSQTAWVE
AGATLGEVYY WINEMNENFS FPGGYCPTVG VGGHFSGGGY GALMRNYGLA
ADNIIDAHLV NVDGKVLDRK SMGEDLFWAI RGGGGENFGI IAACKIKLVV
VPSKATIFSV KKNMEIHGLV KLFNKWQNIA YKYDKDLMLT THFRTRNITD
NHGKNKTTVH GYFSSIFLGG VDSLVDLMNK SFPELGIKKT DCKELSWIDT
TIFYSGVVNY NTANFKKEIL LDRSAGKKTA FSIKLDYVKK LIPETAMVKI
LEKLYEEEVG VGMYVLYPYG GIMDEISESA IPFPHRAGIM YELWYTATWE
KQEDNEKHIN WVRSVYNFTT PYVSQNPRLA YLNYRDLDLG KTNPESPNNY
TQARIWGEKY FGKNFNRLVK VKTKADPNNF FRNEQSIPPL PPRHH SEQ ID NO: 82 Amino acid sequence of N-terminal truncation of *C. sativa*
THCAS without N-terminal methionine
ANPRENFLKCFSKHIPNNVANPKLVYTQHDQLYMSILNSTIQNLRFISDTTPKPLVIVTPSNNSHIQATILCSKKVG
LQIRTRSGGHDAEGMSYISQVPFVVVDLRNMHSIKIDVHSQTAWVEAGATLGEVYYWINEKNENLSFPGGYCPTVGV
GGHFSGGGYGALMRNYGLAADNIIDAHLVNVDGKVLDRKSMGEDLFWAIRGGGGENFGIIAAWKIKLVAVPSKSTIF
SVKKNMEIHGLVKLFNKWQNIAYKYDKDLVLMTHFITKNITDNHGKNKTTVHGYFSSIFHGGVDSLVDLMNKSFPEL
GIKKTDCKEFSWIDTTIFYSGVVNFNTANFKKEILLDRSAGKKTAFSIKLDYVKKPIPETAMVKILEKLYEEDVGAG
MYVLYPYGGIMEEISESAIPFPHRAGIMYELWYTASWEKQEDNEKHINWVRSVYNFTTPYVSQNPRLAYLNYRDLDL
GKTNHASPNNYTQARIWGEKYFGKNFNRLVKVKTKVDPNNFFRNEQSIPPLPPHHH SEQ ID NO: 83 Amino acid sequence of N-terminal truncation of *C. sativa*
CBDAS with N-terminal methionine
MANP RENFLKCFSQ YIPNNATNLK
LVYTQNNPLY MSVLNSTIHN LRFTSDTTPK PLVIVTPSHV SHIQGTILCS
KKVGLQIRTR SGGHDSEGMS YISQVPFVIV DLRNMRSIKI DVHSQTAWVE
AGATLGEVYY WVNEKNENLS LAAGYCPTVC AGGHFGGGGY GPLMRNYGLA
ADNIIDAHLV NVHGKVLDRK SMGEDLFWAL RGGGAESFGI IVAWKIRLVA
VP KSTMFSV KKIMEIHELV KLVNKWQNIA YKYDKDLLLM THFITRNITD
NQGKNKTAIH TYFSSVFLGG VDSLVDLMNK SFPELGIKKT DCRQLSWIDT
IIFYSGVVNY DTDNFNKEIL LDRSAGQNGA FKIKLDYVKK PIPESVFVQI
LEKLYEEDIG AGMYALYPYG GIMDEISESA IPFPHRAGIL YELWYICSWE
KQEDNEKHLN WIRNIYNFMT PYVSKNPRLA YLNYRDLDIG INDPKNPNNY
TQARIWGEKY FGKNFDRLVK VKTLVDPNNF FRNEQSIPPL PRHRH SEQ ID NO: 84 Amino acid sequence of N-terminal truncation of *C. sativa*
CBCAS with N-terminal methionine
MANP QENFLKCFSE YIPNNPANPK
FIYTQHDQLY MSVLNSTIQN LRFTSDTTPK PLVIVTPSNV SHIQASILCS
KKVGLQIRTR SGGHDAEGLS YISQVPFAIV DLRNMHTVKV DIHSQTAWVE
AGATLGEVYY WINEMNENFS FPGGYCPTVG VGGHFSGGGY GALMRNYGLA
ADNIIDAHLV NVDGKVLDRK SMGEDLFWAI RGGGGENFGI IAACKIKLVV
VPSKATIFSV KKNMEIHGLV KLFNKWQNIA YKYDKDLMLT THFRTRNITD -continued

SEQUENCES

NHGKNKTTVH GYFSSIFLGG VDSLVDLMNK SFPELGIKKT DCKELSWIDT
TIFYSGVVNY NTANFKKEIL LDRSAGKKTA FSIKLDYVKK LIPETAMVKI
LEKLYEEEVG VGMYVLYPYG GIMDEISESA IPFPHRAGIM YELWYTATWE
KQEDNEKHIN WVRSVYNFTT PYVSQNPRLA YLNYRDLDLG KTNPESPNNY
TQARIWGEKY FGKNFNRLVK VKTKADPNNF FRNEQSIPPL PPRHH

SEQ ID NO: 85 Amino acid sequence of N-terminal truncation of *C. sativa* THCAS with N-terminal methionine and with C11A, K14R, N63D, N64D, C73A, K76E mutations (amino acid numbering relative to N-terminal truncation of wild-type C. sativa THCAS)
MANPRENFLKAFSRHIPNNVANPKLVYTQHDQLYMSILNSTIQNLRFISDTTPKPLVIVTPSDDSHIQATILASKEV
GLQIRTRSGGHDAEGMSYISQVPFVVVDLRNMHSIKIDVHSQTAWVEAGATLGEVYYWINEKNENLSFPGGYCPTVG
VGGHFSGGGYGALMRNYGLAADNIIDAHLVNVDGKVLDRKSMGEDLFWAIRGGGGENFGIIAAWKIKLVAVPSKSTI
FSVKKNMEIHGLVKLFNKWQNIAYKYDKDLVLMTHFITKNITDNHGKNKTTVHGYFSSIFHGGVDSLVDLMNKSFPE
LGIKKTDCKEFSWIDTTIFYSGVVNFNTANFKKEILLDRSAGKKTAFSIKLDYVKKPIPETAMVKILEKLYEEDVGA
GMYVLYPYGGIMEEISESAIPFPHRAGIMYELWYTASWEKQEDNEKHINWVRSVYNFTTPYVSQNPRLAYLNYRDLD
LGKTNHASPNNYTQARIWGEKYFGKNFNRLVKVKTKVDPNNFFRNEQSIPPLPPHHHHHH SEQ ID NO: 86 Amino acid sequence of N-terminal truncation of *C. sativa* THCAS with N-terminal methionine and with C11A, K14R, L33T, N63D, C73A, K76E, V295T mutations (amino acid numbering relative to N-terminal truncation of wild-type *C. sativa* THCAS)
MANPRENFLKAFSRHIPNNVANPKLVYTQHDQLYMSILNSTIQNLRFISDTTPKPLVIVTPSDDSHIQATILASKEV
GLQIRTRSGGHDAEGMSYISQVPFVVVDLRNMHSIKIDVHSQTAWVEAGATLGEVYYWINEKNENLSFPGGYCPTVG
VGGHFSGGGYGALMRNYGLAADNIIDAHLVNVDGKVLDRKSMGEDLFWAIRGGGGENFGIIAAWKIKLVAVPSKSTI
FSVKKNMEIHGLVKLFNKWQNIAYKYDKDLVLMTHFITKNITDNHGKNKTTVHGYFSSIFHGGVDSLVDLMNKSFPE
LGIKKTDCKEFSWIDTTIFYSGVVNFNTANFKKEILLDRSAGKKTAFSIKLDYVKKPIPETAMVKILEKLYEEDVGA
GMYVLYPYGGIMEEISESAIPFPHRAGIMYELWYTASWEKQEDNEKHINWVRSVYNFTTPYVSQNPRLAYLNYRDLD
LGKTNHASPNNYTQARIWGEKYFGKNFNRLVKVKTKVDPNNFFRNEQSIPPLPPHHHHHH SEQ ID NO: 87 Amino acid sequence of N-terminal truncation of *C. sativa* THCAS with N-terminal methionine and with C11A, K14R, L33T, N63D, C73A, K76E, K270E, V295T, N490E mutations (amino acid numbering relative to N-terminal truncation of wild-type *C. sativa* THCAS)
MANPRENFLKAFSRHIPNNVANPKLVYTQHDQTYMSILNSTIQNLRFISDTTPKPLVIVTPSDNSHIQATILASKEV
GLQIRTRSGGHDAEGMSYISQVPFVVVDLRNMHSIKIDVHSQTAWVEAGATLGEVYYWINEKNENLSFPGGYCPTVG
VGGHFSGGGYGALMRNYGLAADNIIDAHLVNVDGKVLDRKSMGEDLFWAIRGGGGENFGIIAAWKIKLVAVPSKSTI
FSVKKNMEIHGLVKLFNKWQNIAYKYDKDLVLMTHFITKNITDNHGKNKTTVHGYFSSIFHGGTDSLVDLMNKSFPE
LGIKKTDCKEFSWIDTTIFYSGVVNFNTANFKKEILLDRSAGKKTAFSIKLDYVKKPIPETAMVKILEKLYEEDVGA
GMYVLYPYGGIMEEISESAIPFPHRAGIMYELWYTASWEKQEDNEKHINWVRSVYNFTTPYVSQNPRLAYLNYRDLD
LGKTNHASPNNYTQARIWGEKYFGKNFNRLVKVKTKVDPNNFFRNEQSIPPLPPHHHHHH SEQ ID NO: 88 Amino acid sequence of N-terminal truncation of *C. sativa* THCAS with N-terminal methionine and with C11A, K14R, L33T, N63D, C73A, K76E, K270E mutations (amino acid numbering relative to N-terminal truncation of wild-type *C. sativa* THCAS)
MANPRENFLKAFSRHIPNNVANPKLVYTQHDQTYMSILNSTIQNLRFISDTTPKPLVIVTPSDNSHIQATILASKEV
GLQIRTRSGGHDAEGMSYISQVPFVVVDLRNMHSIKIDVHSQTAWVEAGATLGEVYYWINEKNENLSFPGGYCPTVG
VGGHFSGGGYGALMRNYGLAADNIIDAHLVNVDGKVLDRKSMGEDLFWAIRGGGGENFGIIAAWKIKLVAVPSKSTI
FSVKKNMEIHGLVKLFNKWQNIAYKYDKDLVLMTHFITENITDNHGKNKTTVHGYFSSIFHGGVDSLVDLMNKSFPE
LGIKKTDCKEFSWIDTTIFYSGVVNFNTANFKKEILLDRSAGKKTAFSIKLDYVKKPIPETAMVKILEKLYEEDVGA
GMYVLYPYGGIMEEISESAIPFPHRAGIMYELWYTASWEKQEDNEKHINWVRSVYNFTTPYVSQNPRLAYLNYRDLD
LGKTNHASPNNYTQARIWGEKYFGKNFNRLVKVKTKVDPNNFFRNEQSIPPLPPHHHHHH

What is claimed is:

1. A non-natural cannabinoid synthase comprising 95% or greater identity to SEQ ID NO: 1 and comprises C11A, K14R, L33T, N63D, C73A, K76E, K270E, V295T, and N490E substitutions as compared to a wild type cannabinoid synthase, wherein amino acid numbering is relative to SEQ ID NO:1, wherein the non-natural cannabinoid synthase comprises three alpha helices (αA, αB, and αC) and wherein a disulfide bond is not formed between alpha helix αA and alpha helix αC, wherein the non-natural cannabinoid synthase converts cannabigerolic acid (CBGA) into a cannabinoid, and wherein the cannabinoid synthase is Δ9-tetrahydrocannabinolic acid synthase (THCAS), cannabidiolic acid synthase (CBDAS), or cannabichromenic acid synthase (CBCAS).

2. The non-natural cannabinoid synthase of claim 1, wherein the cannabinoid synthase is THCAS, and wherein the THCAS catalyzes oxidative cyclization of CBGA to into Δ9-tetrahydrocannabinolic acid (THCA).

3. The non-natural cannabinoid synthase of claim 2, wherein the THCAS comprises alpha helices αA and αC, and wherein the THCAS comprises at least one salt bridge between alpha helix αA and alpha helix αC.

4. The non-natural cannabinoid synthase of claim 2, further comprising a substitution at amino acid position K10, K75, or both, wherein amino acid numbering is relative to SEQ ID NO: 1.

5. The non-natural cannabinoid synthase of claim 2, further comprising a substitution at amino acid positions V20, Q32, N64, V332, K340, K487, N502, H518, or a combination thereof, wherein the position corresponds to SEQ ID NO: 1.

6. The non-natural cannabinoid synthase of claim 2, wherein the THCAS catalyzes the oxidative cyclization of CBGA into THCA at about pH 4.0 to about pH 6.0.

7. The non-natural cannabinoid synthase of claim 2, wherein the THCAS further catalyzes the oxidative cyclization of CBGA into cannabichromenic acid (CBCA).

8. A nucleic acid encoding the non-natural cannabinoid synthase of claim 1.

9. An engineered cell comprising the non-natural cannabinoid synthase of claim 1, optionally wherein:

(a) the cell further comprises an enzyme in an olivetolic acid pathway, an enzyme in a geranyl pyrophosphate (GPP) pathway, or combination thereof;

(b) the cell is bacteria, fungi, yeast, algae, or cyanobacteria, further optionally wherein the cell is a bacterial cell selected from *Escherichia, Corynebacterium, Bacillus, Ralstonia, Zymomonas*, and *Staphylococcus;*

(c) the cell comprises one or more of a modification selected from:

(i) express one or more exogenous nucleic acid sequences or overexpress one or more endogenous genes encoding a protein having an ABC transporter permease activity;

(ii) express one or more exogenous nucleic acid sequences or overexpress one or more endogenous genes encoding a protein having an ABC transporter ATP-binding protein activity;

(iii) express one or more exogenous nucleic acids sequences or overexpress one or more endogenous genes that encodes a protein that is at least 60% identical to: the blc gene product of SEQ ID NO:21, the ybhG gene product of SEQ ID NO:22, or the ydhC gene product of SEQ ID NO:23;

(iv) express one or more exogenous nucleic acids sequences or overexpress one or more endogenous genes that encodes a protein that is at least 60% identical to the mlaD gene product of SEQ ID NO:24, the mlaE gene product of SEQ ID NO:25, or the mlaF gene product of SEQ ID NO:26;

(v) express one or more exogenous nucleic acid sequences or overexpress one or more endogenous genes encoding a protein having a siderophore receptor protein activity;

(vi) comprise a disruption of or downregulation in the expression of a regulator of expression of one or more endogenous genes encoding a protein having an ABC transporter permease activity, a protein having an ABC transporter ATP-binding protein activity, a blc gene, a ybhG protein, a ydhC protein, a mlaD protein, mlaE protein, mlaF protein, or a protein having a siderophore receptor protein activity;

(vii) express an exogenous nucleic acid encoding a multi-domain protein having acetyl-CoA carboxylase activity (MD-ACC);

(viii) overexpress one or more endogenous genes encoding acetyl-CoA carboxyltransferase subunit α, biotin carboxyl carrier protein, biotin carboxylase, or acetyl-CoA carboxyltransferase subunit β, or express one or more exogenous genes encoding acetyl-CoA carboxyltransferase, biotin carboxyl carrier protein, or biotin carboxylase;

(ix) comprise a disruption of or downregulation in the expression of an endogenous gene encoding a protein having (acyl-carrier-protein) S-malonyltransferase activity, an endogenous gene encoding a protein having 3-hydroxypalmitoyl-(acyl-carrier-protein) dehydratase activity, or both;

(x) express an exogenous nucleic acid sequence or overexpress an endogenous gene encoding a protein having fatty acyl-CoA ligase activity, or both;

(xi) comprise a disruption of or downregulation in the expression of at least one endogenous gene encoding a protein having acyl-CoA dehydrogenase activity or enoyl-CoA hydratase activity;

(xii) comprise a disruption or downregulation in the expression of at least one endogenous gene encoding a protein having acyl-CoA esterase/thioesterase activity;

(xiii) comprise a disruption of or downregulation in the expression of at least one endogenous gene encoding a repressor of transcription of one or more genes required for fatty acid beta-oxidation or an upregulator of fatty acid biosynthesis in combination with disruption or downregulation of one or more endogenous genes encoding one or more proteins of fatty acid beta-oxidation pathway;

(xiv) express one or more exogenous nucleic acid sequences or overexpress one or more endogenous genes encoding a protein having geranyl pyrophosphate synthase (GPPS), farnesyl pyrophosphate synthase, isoprenyl pyrophosphate synthase, geranylgeranyl pyrophosphate synthase, alcohol kinase, alcohol diphosphokinase, phosphate kinase, isopentenyl diphosphate isomerase, geranyl pyrophosphate synthase, isopentenyl phosphate kinase activity, isoprenol diphosphokinase activity, prenol kinase activity, prenol diphosphokinase activity, dimethylallyl phosphate kinase activity, or isopentenyl diphosphate isomerase activity;

(xv) express an exogenous nucleic acid sequence or overexpress an endogenous gene encoding a protein having GPP synthase activity;

(xvi) express an exogenous nucleic acid sequence encoding an olivetol synthase;

(xvii) express an exogenous nucleic acid sequence encoding an olivetolic acid cyclase;

(xviii) express an exogenous nucleic acid sequence encoding a prenyltransferase;

(xix) express one or more exogenous nucleic acid sequences or overexpressing one or more endogenous genes encoding one or more enzymes of MVA pathway, MEP pathway, or a non-MVA, non-MEP pathway;

(xx) express an exogenous nucleic acid sequence or overexpress an endogenous gene encoding a biotin-(acetyl-CoA carboxylase) ligase;

(xxi) express an exogenous nucleic acid sequence encoding an isopentenyl-diphosphate delta-isomerase or overexpress an endogenous gene encoding an isopentenyl-diphosphate delta-isomerase;

(xxii) express an exogenous nucleic acid sequence encoding a hydroxyethylthiazole kinase or overexpress an endogenous genes encoding a hydroxyethylthiazole kinase;

(xxiii) express an exogenous nucleic acid sequence encoding a Type III pantothenate kinase or overexpress an endogenous gene encoding a Type III pantothenate kinase; and (xxiv) comprise a disruption of or downregulation in the expression of at least one endogenous gene encoding a phosphatase selected from the group consisting of ADP-sugar pyrophosphatase, dihydroneopterin triphosphate diphosphatase, pyrimidine deoxynucleotide diphosphatase, pyrimidine pyrophosphate phosphatase, and Nudix hydrolase;

(d) any combination of (a)-(c).

10. A method of making THCA, CBDA, or CBCA, comprising contacting CBGA with the non-natural cannabinoid synthase of claim 1, optionally wherein the contacting is at about pH 4.0 to about pH 6.0.

11. A composition comprising a cannabinoid obtained from the engineered cell of claim 9.

12. A method of making an isolated cannabinoid synthase, comprising isolating a cannabinoid synthase expressed in the engineered cell of claim 9.

13. The non-natural cannabinoid synthase of claim 5, wherein the substitution at V20 is V20E, the substitution at Q32 is Q32E, the substitution at N64 is N64D, the substitution at V332 is V332T, the substitution is K340 is K340D, the substitution at K487 is K487D, the substitution at N502 is N502T, and the substitution at H518 is H518Y.

14. The non-natural cannabinoid synthase of claim 5, comprising the substitutions:

1) C11A, K14R, Q32E, L33T, N63D, N64T, C73A, K76E, K270E, V295T, V332T, N490E, and N502T;

2) C11A, K14R, Q32E, L33T, N63D, N64T, C73A, K76E, K270E, V295T, V332T, K340D, N490E, and N502T; or 3) C11A, K14R, Q32E, L33T, N63D, N64T, C73A, K76E, K270E, V295T, V332T, K340D, and N490E.

15. The non-natural cannabinoid synthase of claim 7, wherein the oxidative cyclization of CBGA into CBCA is at about pH 6.5 to about pH 8.0.

* * * * *